US012234447B2

United States Patent
Seth et al.

(10) Patent No.: US 12,234,447 B2
(45) Date of Patent: *Feb. 25, 2025

(54) MODIFIED COMPOUNDS AND USES THEREOF

(71) Applicant: Ionis Pharmaceuticals, Inc., Carlsbad, CA (US)

(72) Inventors: Punit P. Seth, Carlsbad, CA (US); Michael Oestergaard, Carlsbad, CA (US); Michael T. Migawa, Carlsbad, CA (US); Xue-Hai Liang, Del Mar, CA (US); Wen Shen, Carlsbad, CA (US); Stanley T. Crooke, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/697,577

(22) Filed: Mar. 17, 2022

(65) Prior Publication Data

US 2023/0068063 A1 Mar. 2, 2023

Related U.S. Application Data

(63) Continuation of application No. 16/968,701, filed as application No. PCT/US2019/017725 on Feb. 12, 2019, now Pat. No. 11,332,733.

(51) Int. Cl.
| | |
|---|---|
| *C07H 21/04* | (2006.01) |
| *C12N 15/10* | (2006.01) |
| *C12N 15/113* | (2010.01) |

(52) U.S. Cl.
CPC ............ *C12N 15/10* (2013.01); *C12N 15/113* (2013.01); *C12N 2310/315* (2013.01); *C12N 2310/3231* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. | |
| 4,751,219 A | 6/1988 | Kempen | |
| 4,845,205 A | 7/1989 | Huynh Dinh et al. | |
| 5,034,506 A | 7/1991 | Summerton et al. | |
| 5,130,302 A | 7/1992 | Spielvogel et al. | |
| 5,134,066 A | 7/1992 | Rogers et al. | |
| 5,166,315 A | 11/1992 | Summerton et al. | |
| 5,175,273 A | 12/1992 | Bischofberger et al. | |
| 5,185,444 A | 12/1993 | Summerton et al. | |
| 5,367,066 A | 11/1994 | Urdea et al. | |
| 5,432,272 A | 7/1995 | Benner | |
| 5,434,257 A | 7/1995 | Matteucci | |
| 5,457,187 A | 10/1995 | Gmelner et al. | |
| 5,457,191 A | 10/1995 | Cook et al. | |
| 5,459,255 A | 10/1995 | Cook et al. | |
| 5,484,908 A | 1/1996 | Froehler et al. | |
| 5,502,177 A | 3/1996 | Matteucci et al. | |
| 5,525,711 A | 6/1996 | Hawkins et al. | |
| 5,552,540 A | 9/1996 | Haralambidis | |
| 5,587,469 A | 12/1996 | Cook et al. | |
| 5,587,470 A | 12/1996 | Cook et al. | |
| 5,594,121 A | 1/1997 | Froehler et al. | |
| 5,596,091 A | 1/1997 | Switzer | |
| 5,614,617 A | 3/1997 | Cook et al. | |
| 5,645,985 A | 7/1997 | Froehler et al. | |
| 5,681,941 A | 10/1997 | Cook et al. | |
| 5,698,685 A | 12/1997 | Summerton et al. | |
| 5,750,692 A | 5/1998 | Cook et al. | |
| 5,763,588 A | 6/1998 | Matteucci et al. | |
| 5,808,027 A | 9/1998 | Cook et al. | |
| 5,811,534 A | 9/1998 | Cook et al. | |
| 5,830,653 A | 11/1998 | Froehler et al. | |
| 5,948,903 A | 9/1999 | Cook et al. | |
| 5,994,517 A | 11/1999 | Ts'O | |
| 6,005,096 A | 12/1999 | Matteucci et al. | |
| 6,166,199 A | 12/2000 | Cook et al. | |
| 6,268,490 B1 | 7/2001 | Imanishi et al. | |
| 6,300,319 B1 | 10/2001 | Manoharan | |
| 6,383,812 B1 | 5/2002 | Chen et al. | |
| 6,525,031 B2 | 2/2003 | Manoharan | |
| 6,525,191 B1 | 2/2003 | Ramasamy | |

(Continued)

FOREIGN PATENT DOCUMENTS

| | | |
|---|---|---|
| WO | WO 1994/022890 | 10/1994 |
| WO | WO/1997/020563 | 6/1997 |

(Continued)

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Biessen et al., "Novel hepatotrophic prodrugs of the antiviral nucleoside 9-(2-phosphonylmethoxyethyl)adenine with improved pharmacokinetics and antiviral activity" FASEB J. (2000) 14(12):1784-1792.

Biessen et al., "Synthesis of Cluster Galactosides with High Affinity for the Hepatic Asialoglycoprotein Receptor" J Med Chem (1995) 38(9):1538-1546.

(Continued)

*Primary Examiner* — Kimberly Chong
(74) *Attorney, Agent, or Firm* — McNeill PLLC

(57) ABSTRACT

The present disclosure provides oligomeric compound comprising a modified oligonucleotide having a central region comprising one or more modifications. In certain embodiments, the present disclosure provides oligomeric compounds having an improved therapeutic index or an increased maximum tolerated dose.

21 Claims, No Drawings

Specification includes a Sequence Listing.

(56) References Cited

U.S. PATENT DOCUMENTS

| | | |
|---|---|---|
| 6,620,916 B1 | 9/2003 | Takahara et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 6,908,903 B1 | 6/2005 | Theodore et al. |
| 7,034,133 B2 | 4/2006 | Wengel et al. |
| 7,053,207 B2 | 5/2006 | Wengel et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,582,744 B2 | 9/2009 | Manoharan et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,851,615 B2 | 12/2010 | Manoharan et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,137,695 B2 | 3/2012 | Rozema et al. |
| 8,153,365 B2 | 4/2012 | Wengel et al. |
| 8,158,601 B2 | 4/2012 | Chen et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,313,772 B2 | 11/2012 | Rozema et al. |
| 8,344,125 B2 | 1/2013 | Manoharan et al. |
| 8,349,308 B2 | 1/2013 | Yurkovetskiy et al. |
| 8,404,862 B2 | 3/2013 | Manoharan et al. |
| 8,435,491 B2 | 5/2013 | Wang et al. |
| 8,440,803 B2 | 5/2013 | Swayze et al. |
| 8,450,467 B2 | 5/2013 | Manoharan et al. |
| 8,501,805 B2 | 8/2013 | Seth et al. |
| 8,501,930 B2 | 8/2013 | Rozema et al. |
| 8,530,640 B2 | 9/2013 | Seth et al. |
| 8,541,548 B2 | 9/2013 | Rozema |
| 8,546,556 B2 | 10/2013 | Seth et al. |
| 8,552,163 B2 | 10/2013 | Lee et al. |
| RE44,779 E | 2/2014 | Imanishi et al. |
| 8,642,752 B2 | 2/2014 | Swayze et al. |
| 8,796,437 B2 | 8/2014 | Swayze et al. |
| 8,957,200 B2 | 2/2015 | Seth et al. |
| 9,005,906 B2 | 4/2015 | Swayze et al. |
| 9,012,421 B2 | 4/2015 | Migawa et al. |
| 9,175,291 B2 | 11/2015 | MacLeod et al. |
| 9,523,094 B2 | 12/2016 | Hung |
| 9,550,988 B2 | 1/2017 | Swayze |
| 9,695,418 B2 | 7/2017 | Seth et al. |
| 9,752,142 B2 | 9/2017 | Oestergaard et al. |
| 9,914,922 B2 | 3/2018 | Freier et al. |
| 9,926,556 B2 | 3/2018 | Wan et al. |
| 10,017,764 B2 | 7/2018 | Freier et al. |
| 10,202,599 B2 | 2/2019 | Seth et al. |
| 10,415,038 B2 | 9/2019 | Guo et al. |
| 10,426,789 B2 | 10/2019 | Murray et al. |
| 11,149,264 B2 | 10/2021 | Seth et al. |
| 2003/0077829 A1 | 4/2003 | Maclachlan |
| 2003/0119724 A1 | 6/2003 | Ts'o et al. |
| 2003/0158403 A1 | 8/2003 | Manoharan et al. |
| 2003/0175906 A1 | 9/2003 | Manoharan et al. |
| 2005/0164235 A1 | 7/2005 | Manoharan et al. |
| 2006/0148740 A1 | 7/2006 | Platenburg et al. |
| 2006/0183886 A1 | 8/2006 | Ts'o et al. |
| 2008/0039618 A1 | 2/2008 | Allerson et al. |
| 2008/0108801 A1 | 5/2008 | Manoharan et al. |
| 2008/0206869 A1 | 8/2008 | Smith et al. |
| 2008/0281041 A1 | 11/2008 | Rozema et al. |
| 2008/0281044 A1 | 11/2008 | Monahan et al. |
| 2009/0203132 A1 | 8/2009 | Swayze et al. |
| 2009/0203135 A1 | 8/2009 | Forst et al. |
| 2009/0286973 A1 | 11/2009 | Manoharan et al. |
| 2010/0240730 A1 | 9/2010 | Beigelman et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0207799 A1 | 8/2011 | Rozema et al. |
| 2011/0269814 A1 | 11/2011 | Manoharan et al. |
| 2012/0035115 A1 | 2/2012 | Manoharan et al. |
| 2012/0095075 A1 | 4/2012 | Manoharan et al. |
| 2012/0101148 A1 | 4/2012 | Aking et al. |
| 2012/0128760 A1 | 5/2012 | Manoharan et al. |
| 2012/0136042 A1 | 5/2012 | Manoharan et al. |
| 2012/0157509 A1 | 6/2012 | Hadwiger et al. |
| 2012/0165393 A1 | 6/2012 | Rozema et al. |
| 2012/0230938 A1 | 9/2012 | Rozema et al. |
| 2013/0004427 A1 | 1/2013 | El-Sayed et al. |
| 2013/0109817 A1 | 5/2013 | Yurkovetskiy et al. |
| 2013/0121954 A1 | 5/2013 | Wakefield et al. |
| 2013/0178512 A1 | 7/2013 | Manoharan et al. |
| 2013/0203836 A1 | 8/2013 | Rajeev et al. |
| 2013/0236968 A1 | 9/2013 | Manoharan et al. |
| 2014/0107330 A1 | 4/2014 | Freier et al. |
| 2014/0303235 A1* | 10/2014 | Oestergaard ......... C12N 15/113 435/375 |
| 2014/0309279 A1 | 10/2014 | Oestergaard et al. |
| 2014/0323707 A1 | 10/2014 | Seth et al. |
| 2015/0051389 A1 | 2/2015 | Swayze et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0276208 A1 | 10/2015 | Oestergaard et al. |
| 2016/0138014 A1 | 5/2016 | Kordasiewicz et al. |
| 2016/0160280 A1 | 6/2016 | Burel |
| 2016/0186175 A1 | 6/2016 | Seth et al. |
| 2017/0044526 A1 | 2/2017 | Wan et al. |
| 2017/0191064 A1 | 7/2017 | Costa et al. |
| 2017/0327824 A1 | 11/2017 | Oestergaard et al. |
| 2018/0002701 A1 | 1/2018 | Iacone et al. |
| 2018/0023081 A1 | 1/2018 | Hagedorn et al. |
| 2018/0161356 A1 | 6/2018 | Olson et al. |
| 2018/0273577 A1 | 9/2018 | Revenko et al. |
| 2019/0055564 A1 | 2/2019 | Sanchez et al. |
| 2019/0111073 A1* | 4/2019 | Kammler ............. C12N 15/113 |
| 2019/0265230 A1 | 8/2019 | Gubler et al. |
| 2019/0383797 A1 | 12/2019 | Olson et al. |
| 2020/0010831 A1 | 1/2020 | Hagedorn et al. |
| 2020/0109451 A1 | 4/2020 | Gubler et al. |
| 2020/0354720 A1 | 11/2020 | Olson et al. |
| 2020/0362337 A1 | 11/2020 | Dodart et al. |
| 2020/0362347 A1 | 11/2020 | Olson et al. |
| 2020/0385727 A1 | 12/2020 | Moller et al. |
| 2021/0017513 A1 | 1/2021 | Seth et al. |
| 2021/0261945 A1 | 8/2021 | Seth et al. |

FOREIGN PATENT DOCUMENTS

| | | |
|---|---|---|
| WO | WO/1997/046098 | 12/1997 |
| WO | WO/1998/013381 | 4/1998 |
| WO | WO/1999/014226 | 3/1999 |
| WO | WO/2002/043771 | 6/2002 |
| WO | WO/2004/024757 | 3/2004 |
| WO | WO/2004/101619 | 11/2004 |
| WO | WO/2004/106356 | 12/2004 |
| WO | WO/2007/134181 | 11/2007 |
| WO | WO/2008/098788 | 8/2008 |
| WO | WO/2008/101157 | 8/2008 |
| WO | WO/2009/082607 | 7/2009 |
| WO | WO/2009/126933 | 10/2009 |
| WO | WO/2009/134487 | 11/2009 |

(56) References Cited

FOREIGN PATENT DOCUMENTS

| | | |
|---|---|---|
| WO | WO/2010/054406 | 5/2010 |
| WO | WO/2010/088537 | 8/2010 |
| WO | WO/2010/129709 | 11/2010 |
| WO | WO/2010/144740 | 12/2010 |
| WO | WO/2010/148013 | 12/2010 |
| WO | WO/2011/038356 | 3/2011 |
| WO | WO/2011/100131 | 8/2011 |
| WO | WO/2011/120053 | 9/2011 |
| WO | WO/2011/133876 | 10/2011 |
| WO | WO/2011/163121 | 12/2011 |
| WO | WO/2012/037254 | 3/2012 |
| WO | WO/2012/068187 | 5/2012 |
| WO | WO/2012/083046 | 6/2012 |
| WO | WO/2012/083185 | 6/2012 |
| WO | WO/2012/089352 | 7/2012 |
| WO | WO/2012/089602 | 7/2012 |
| WO | WO 2012/170347 | 12/2012 |
| WO | WO/2012/177947 | 12/2012 |
| WO | WO 2013/022966 | 2/2013 |
| WO | WO 2013/022967 | 2/2013 |
| WO | WO 2013/022984 | 2/2013 |
| WO | WO 2013/022990 | 2/2013 |
| WO | WO/2013/033230 | 3/2013 |
| WO | WO/2013/075035 | 5/2013 |
| WO | WO/2013/165816 | 11/2013 |
| WO | WO/2013/166121 | 11/2013 |
| WO | WO 2014/059341 | 4/2014 |
| WO | WO/2014/179620 | 11/2014 |
| WO | WO 2015/021457 | 2/2015 |
| WO | WO/2015/106128 | 7/2015 |
| WO | WO/2017/015555 | 1/2017 |
| WO | WO 2018/165564 | 9/2018 |
| WO | WO 2019/032607 | 2/2019 |
| WO | WO 2019/032612 | 2/2019 |
| WO | WO 2019/138057 | 7/2019 |
| WO | WO 2019/157531 | 8/2019 |
| WO | WO 2019/169219 | 9/2019 |
| WO | WO 2019/200172 | 10/2019 |
| WO | WO 2019/245957 | 12/2019 |
| WO | WO 2020/160336 | 8/2020 |
| WO | WO 2020/201339 | 10/2020 |
| WO | WO 2020/219983 | 10/2020 |
| WO | WO 2020/227691 | 11/2020 |

OTHER PUBLICATIONS

Biessen et al., "The cholesterol derivative of a triantennary galactoside with high affinity for the hepatic asialoglycoprotein receptor: a potent cholesterol lowering agent" J Med Chem (1995) 38(11):1846-1852.

Braasch et al., "Novel Antisense and Peptide Nucleic Acid Strategies for Controlling Gene Expression" Biochemistry (2002) 41(14):4503-4510.

Burel et al., "Hepatotoxicity of high affinity gapmer antisense oligonucleotides is mediated by Rnase H1 dependent promiscuous reduction of very long pre-mRNA transcripts" Nucleic Acids Research (2015) 44(5): 2093-2109.

Connolly et al., "Binding and endocytosis of cluster glycosides by rabbit hepatocytes. Evidence for a short-circuit pathway that does not lead to degradation." J Biol Chem (1982) 257(2):939-945.

Crooke et al., "Pharmacokinetic Properties of Several Novel Oligonucleotide Analogs in mice" J. Pharmacol. Exp. Ther. (1996) 277(2):923-937.

Crooke S.T., Ed., "Antisense Drug Technology, Second Edition" CRC Press (2008) 163-166 and 442-443.

Dieckmann, et al. "A Sensitive In Vitro Approach to Assess the Hybridization-Dependent Toxic Potential of High Affinity Gapmer Oligonucleotides" Molecular Therapy: Nucleic Acids (2018) 10: 45-54.

Detmer et al., "Substrates for Investigation of DNA Polymerase Function: Synthesis and Properties of 4'-C-Alkylated Oligonucleotides" European J. Org. Chem (2003) 10:1837-1846.

Duff et al., "Intrabody tissue-specific delivery of antisense conjugates in animals: ligand-linker-antisense oligomer conjugates." Methods Enzymol (2000) 313:297-321.

Englisch et al., "Chemically Modified Oligonucleotides as Probes and Inhibitors" Agnew Chem. Int. Ed. Engl. (1991) 30:613-629.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

International Search Report for PCT/US2019/017725 dated Apr. 15, 2019.

Jayaprakash et al., "Non-Nucleoside Building Blocks for Copper-Assisted and Copper-Free Click Chemistry for the Efficient Synthesis of RNA Conjugates" Org Lett (2010) 12:5410-5413.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259: 327-330.

Kasuya et al., "Ribonuclease H1-dependent hepatotoxicity caused by locked nucleic acid-modified gapmer antisense oligonucleotides" Scientific Reports (2016) 6:30377, 1-12.

Kato et al., "N-acetylgalactosamine incorporation into a peptide containing consecutive threonine residues by UDP-N-acetyl-D-galactosaminide:polypeptide N-acetylgalactosaminyltransferases" Glycobiol (2001) 11:821-829.

Khorev et al., "Trivalent, Gal/GalNAc-containing ligands designed for the asialoglycoprotein receptor." Bioorg Med Chem (2008) 16:5216-5231.

Kim et al., "Oligomeric glycopeptidomimetics bearing the cancer related TN-antigen" Tetrahedron Lett (1997) 38:3487-3490.

Kornilova et al., "Development of a fluorescence polarization binding assay for asialoglycoprotein receptor" Analyt Biochem (2012) 425:43-46.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kroschwitz, "Polynucleotides" Concise Encyclopedia of Polymer Science and Engineering (1990) John Wiley & Sons, NY pp. 858-859.

Kumar et al., "The first analogues of LNA (locked nucleic acids): phosphorothioate-LNA and 2'-thio-LNA" Bioorg Med Chem Lett. (1998) 8:2219-2222.

Kumar et al., "Design, synthesis, biophysical and primer extension studies of novel acyclic butyl nucleic acid (BuNA)" Org. Biomol. Chem. (2013) 11:5853-5865.

Lee et al., "New synthetic cluster ligands for galactose/N-acetylgalactosamine-specific lectin of mammalian liver" Biochem (1984) 23:4255-4261.

Lee et al., "Facile Synthesis of a High-Affinity Ligand for Mammalian Hepatic Lectin Containing Three Terminal N-Acetylgalactosamine Residues" Bioconjug Chem (1997) 8(5):762-765.

Lee et al., "Protein microarrays to study carbohydrate-recognition events" Bioorg Med Chem Lett (2006) 16(19):5132-5135.

Lee et al., "New and more efficient multivalent glyco-ligands for asialoglycoprotein receptor of mammalian hepatocytes" Bioorg Med Chem (2011) 19(8):2494-2500.

Lee et al., "Preparation of cluster glycosides of N-acetylgalactosamine that have subnanomolar binding constants towards the mammalian hepatic Gal/GalNAc-specific receptor" Glycoconjugate J (1987) 4(4):317-328.

Lee et al., "Synthesis of Multivalent Neoglyconjugates of MUC1 by the Conjugation of Carbohydrate-Centered, Triazole-Linked Glycoclusters to MUC1 Peptides Using Click Chemistry" J Org Chem (2012) 77:7564-7571.

Lee et al., "Synthesis of peptide-based trivalent scaffold for preparation of cluster glycosides." Methods Enzymol (2003) 362:38-43.

(56) References Cited

OTHER PUBLICATIONS

Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Maier et al., "Synthesis of Antisense Oligonucleotides Conjugated to a Multivalent Carbohydrate Cluster for Cellular Targeting," Bioconjugate Chemistry (2003) 14, 18-29.
Maierhofer et al., "Probing multivalent carbohydrate-lectin interactions by an enzyme-linked lectin assay employing covalently immobilized carbohydrates" Bioorg Med Chem (2007) 15(24):7661-7676.
Manoharan et al., "Chemical Modifications to Improve Uptake and Bioavailability of Antisense Oligonucleotides" Ann. N.Y. Acad. Sci. (1992) 660: 306-309.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Cholic Acid-Oligonucleotide Conjugates for Antisense Applications" Bioorg. Med. Chem. Lett. (1994) 4:1053-1060.
Manoharan et al., "Oligonucleotide Conjugates: Alteration of the Pharmacokinetic Properties of Antisense Agents" Nucleosides & Nucleotides (1995) 14(3-5):969-973.
Manoharan et al., "Lipidic Nucleic Acids" Tetrahedron Lett. (1995) 36(21):3651-3654.
Manoharan, "Oligonucleotide conjugates as potential antisense drugs with improved uptake, biodistribution, targeted delivery, and mechanism of action." Antisense Nucleic Acid Drug Dev (2002) 12(2):103-128.
Merwin et al., "Targeted Delivery of DNA Using YEE(GalNAcAH)3, a Synthetic Glycopeptide Ligand for the Asialoglycoprotein Receptor" Bioconjug Chem (1994) 5(6):612-620.
Migawa et al., "Site-specific replacement of phosphorothioate with alkyl phosphonate linkages enhances the therapeutic profile of gapmer ASOs by modulating interactions with cellular proteins" Nucleic Acids Research (2019) 47(11): 5465-6479.
Mishra et al., "Improved leishmanicidal effect of phosphorotioate antisense oligonucleotides by LDL-mediated delivery" Biochim. Biophys. Acta (1995) 1264:229-237.
Morvan et al., "Sugar modified oligonucleotides. III (1). Synthesis, nuclease resistance and base pairing properties of α- and β-L-octathymidylates" Biochem Biophys Res Commun. (1990) 172(2):537-543.
Nishina et al., "Chimeric Antisense Oligonucleotide Conjugated to α-Tocopherol" Molecular Therapy Nucleic Acids (2015) 4(1):e220.
Nishina et al., "Efficient in vivo delivery of siRNA to the liver by conjugation of alpha-tocopherol." Molecular Therapy (2008) 16(4):734-740.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Oestergaard et al., "Rational design of antisense oligonucleotides targeting single nucleotide polymorphisms for potent and allele selective suppression of mutant Huntingtin in the CNS" Nucleic Acids Research (2013) 41(21): 9634-9650.
Oka et al., "An Oxazapholidine Approach for the Stereocontrolled Synthesis of Oligonucleoside Phosphorothioates" JACS (2003) 125(27):8307-8317.
Pavia et al., "Synthetic TN glycopeptide related to human glycophorin AM. High-field proton and carbon-13 nuclear magnetic resonance study." Int J Pep Protein Res. (1983) 22(5):539-548.
Pujol et al., "A sulfur tripod glycoconjugate that releases a high-affinity copper chelator in hepatocytes." Angew Chemie Int Ed Engl. (2012) 51(30):7445-7448.
Rajur et al., "Covalent Protein-Oligonucleotide Conjugates for Efficient Delivery of Antisense Molecules" Bioconjug Chem. (1997) 8(6):935-940.
Rensen et al., "Design and Synthesis of Novel N-Acetylgalactosamine-Terminated Glycolipids for Targeting of Lipoproteins to the Hepatic Asiaglycoprotein Receptor," J. Med. Chem. (2004) 47:5798-5808.
Rensen et al., "Stimulation of liver-directed cholesterol flux in mice by novel N-acetylgalactosamine- terminated glycolipids with high affinity for the asialoglycoprotein receptor." Arterioscler Thromb Vasc Biol. (2006) 26(1):169-175.
Rensen et al., "Determination of the Upper Size Limit for Uptake and Processing of Ligands by the Asialoglycoprotein Receptor on Hepatocytesin Vitro and in Vivo" J Biol Chem. (2001) 276:37577-37584.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi, Chapter 15, Antisense Research and Applications, Crooke and Lebleu ed., CRC Press (1993).
Sato et al., "Glycoinsulins: Dendritic Sialyloligosaccharide-Displaying Insulins Showing a Prolonged Blood-Sugar-Lowering Activity" J Am Chem Soc. (2004) 126(43):14013-14022.
Shea et al., "Synthesis, hybridization properties and antiviral activity of lipid-oligodeoxynucleotide conjugates" Nucl. Acids Res. (1990) 18(13):3777-3783.
Shen et al., "Chemical modification of PS-ASO therapeutics reduces cellular protein-binding and improves the therapeutic index", Nature Biotechnology (2019) 37(6): 640-650.
Singh et al., "LNA (locked nucleic acids): synthesis and high-affinity nucleic acid recognition" Chem. Commun. (1998) 4: 455-456.
Singh et al., "Synthesis of 2'-amino-LNA: A novel conformationally restricted high-affinity oligonucleotide analogue with a handle" J. Org. Chem. (1998) 63: 10035-10039.
Sliedregt et al., "Design and Synthesis of Novel Amphiphilic Dendritic Galactosides for Selective Targeting of Liposomes to the Hepatic Asialoglycoprotein Receptor" J Med Chem. (1999) 42(4):609-618.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Tomiya et al., "Liver-targeting of primaquine-(poly-γ-glutamic acid) and its degradation in rat hepatocytes" Bioorg Med Chem. (2013) 21(17):5275-5281.
Toyokuni et al., "Synthetic vaccines: I. Synthesis of multivalent Tn antigen cluster-lysyllysine conjugates" Tetrahedron Lett. (1990) 31(19):2673-2676.
Valentijn et al., "Solid-phase synthesis of lysine-based cluster galactosides with high affinity for the asialoglycoprotein Receptor" Tetrahedron (1997) 53:759-770.
Van Rossenberg et al., "Stable polyplexes based on arginine-containing oligopeptides for in vivo gene delivery." Gene Ther. (2004) 11(5):457-464.
Wan et al. "Synthesis, biophysical properties and biological activity of second generation antisense oligonucleotides containing chiral phosphorothioate linkages" Nucleic Acids Res. (2014) 42:13456-13468.
Wang et al., "Cytotoxic and Mutagenic Properties of C3'-Epimeric Lesions of 2'-Deoxyribonucleosides in *Escherichia coli* Cells" Biochemistry (2017) 56(29): 3725-3732.
Westerlind et al., "Ligands of the asialoglycoprotein receptor for targeted gene delivery, part 1: Synthesis of and binding studies with biotinylated cluster glycosides containing N-acetylgalactosamine." Glycoconj J. (2004) 21(5):227-241.
Zhou et al., "Fine Tuning of Electrostatics around the Internucleotidic Phosphate through Incorporation of Modified 2',4'-Carbocyclic-

(56) References Cited

OTHER PUBLICATIONS

LNAs and -ENAs Leads to Significant Modulation of Antisense Properties" J. Org. Chem. (2009) 74:118-134.

* cited by examiner

SEQUENCE LISTING

<160> NUMBER OF SEQ ID NOS: 154

<210> SEQ ID NO 1
<211> LENGTH: 14836
<212> TYPE: DNA
<213> ORGANISM: Mus musculus

<400> SEQUENCE: 1

```
cctcccccgt gtctccccac acccgggttg gggttgtttt ggttgaccag agtggaacac      60
aacgatctat tggcagggct gaacaccaat gggtctattt gtaaagcgcc aatgaccact     120
ttctgaagca gggttttagg gagcgggggcc ttagggaact ctttggtcct ttttagaaca     180
ctggactttc ttctggaaag gcaggaaaca ctgaagttta agaagttgtt tccagcttcc     240
attaactgaa cacacattaa aaccaagcac agagaatcag gacgtttcgc gggagtgaga     300
cccagtcatt tctcctccgt ttccattctg cagggtgaga gttgtaatca cccacccact     360
attcgtacca tccacccacc cccagtcgag agaatagggg tacagagggg aggtggcaaa     420
gaaaattcac gatactgagt atctctggga gacctgtttg gtctctttgc tcggtagcgc     480
agccctacgt tagaatgcat cttcccggga atgactgtag tgagactttg gctgggaatc     540
caagttattc taactgtaga ttggtccacg ttgccctaag cctagcagtc cactgcggca     600
cagacaccct ggacatgagg tgggtcagct taagttcctg gcacgaaaga aagggtactc     660
tgcaactttt tggatgcggc gaaacagact gtttcgtctc tcaggttctt atttcacggc     720
ttgtgccttt gacagcccct tagtttctct atctgcagga tgggagcatt aagctctacg     780
acccagcctc tttacaattc aggtccaaag agcccgccca agttggggac tgggaagatc     840
aaaggtctca gcacccagcg gagccgcgga cactgagggc gccaagaagg gggtgggtag     900
gtagggaact ggaagggcgg ctgctccgca ggggatgcgc gtcagagacc ccagccacac     960
tccaggcccc cccttgatg agccccgccc cgccccgcct ggttttcgcc tctaaagcgc    1020
ccagcgctcg cctcccgctg ccgcactttc actctcggtc cacctcggtg tcctcttgct    1080
gtccagctct gcagcctccg gcgcgccctc ccgcccacgc catggacgcc aaggtcgtcg    1140
ccgtgctggc cctggtgctg gccgcgctct gcatcagtga cggtgagtgc aatccgcggc    1200
cgggccgggg aaaggctcgc agctctgcgc cggagctcct tcgggtccgc ggttcctctg    1260
cccgcgccga agtcgcggag aaagaactcg gtcggcgccg ttcactacaa gcgaacttgg    1320
ggcagtccac tttgcagggc gcactccacc cgggtgccct ttccgtgtc ccacgggtcg    1380
```

```
caccgaggtt ttgtgctctg cgaagtgcgg ccataggacc tagagagggc tgcaggggag    1440
gacccgcagg attgttgggc aagagtgggt tcggcgcgga atggaagcgt gggcgattgt    1500
gtccggggct tgggccccgg agcgcgccag ctgcactcag ctagtgtcta ccggcgccca    1560
gatgtttcca gaggcgaagg gcagcgcggt cccggagttg accgtgcaag aggttcactc    1620
gggtggtgcg tgtgtcagca aactctcaaa gaccggtcaa gtagctcgaa gtgcatggct    1680
tggctatagg ttcagtggtg aggctgagtt tcgtcccctg cgggtgtagc gtgttctctt    1740
acagcaccct cgagggcctc agggccacca gcagcgcagc gcagctcttg aactcgcgct    1800
gccagccagg gccgcgcttc tgcacagttc gttggtccgt agcgacgcgg acctgagcac    1860
gcgtctcttc actgcccctt tttcttctta cccgggtcac tagacaaagg ctcagcagtt    1920
acccaagcta tatgcacacc tctccccaac ccccaaacac acctgcaaac gggcgctttt    1980
gtagccagcc ccggagtcct cagctctgga atgagagctg cagcggagtt cagtctccca    2040
gacccagggt ggtgtcttct ttcactggga aagggctttc attttgtttt cttttttga    2100 cactgaagag aaaactctca gcgctgttac aagacaccgt tgctgcaaaa caaacaaac     2160 cattgcctct gaacacaaaa caaaatccta ctagtcgatc ccctgccttc ctccgcagtg    2220
gtgtttcctg gagagaactg agggacagtc ggggctcttg gtgagactga gctctaaatg    2280
ctgcccaagt acaccaactc gttcgtttgg gttcttttcccc tgtgacaacg ggtacggga    2340 atggttggag ttgcctagtc cgagggaaat gttctgtaaa agaatagtca gttgctgatc    2400
ggagtagtaa aaaaaagaa atgaaaggca gtttcgattt ttttttttt ttttttttt      2460 tttttttgtta ccgagaacac ccgggaggct gagccttccc actggtcccc cagtgccccg    2520
tcatggagca cattgatttg gcattaata attgaatgag ctggtgatgt tgcaagggtc     2580
acagcctctg gcaagttagg tatgggggcaa gaatgtagga ctcaggtcct caaggttgga    2640
gtgcaattat ccagagtaaa agttgtctca ccctcaacat attctgaccc taggaagagt    2700
cggattgttg acagtgtctg gatcagacct gttctctagg caggacccca ttgtgctgcc    2760
cgaatgaact ttttttacctc ctagtgcctg tgtgccctct gatcttacac agccctcaag    2820
ttgcagcacg gctaaccttg ctgtggttcc tgtcttttcc catcagctac tccaactcag    2880
aagctagata gtagacaccg gaggcttctt tggttaaacc cagagcagca ggcttgccag    2940
gcttgttaga ttgaatggac ccctggttcc ctaagccaag ctctctagat tcccaagtcc    3000
agggtggcag cagagctgga ttagacttgt gtctgtacct gaagtctggt tttcctatgc    3060
tttagagtct aaagacacta cccttcctgg ggcatgcatc ccttagctaa ataatgcttg    3120
cagaagaaga taatcccatc atatatttaa ttcggtccac ttctccagct gcttcccaaa    3180
ggcagtgaac ttcagaatac ccagaagtct cctggaactc taaataagca aacttaaaat    3240
cctggggcta actattctca gtcatacttt taaactttgg tgaaaagacc cataaattga    3300
aacatttggg gatgctcagt agagctagga taaaaccctg ttgttggggg agcagctaca    3360
aatccagcag tcctcagggt ttgcaattct agacttaaag ggtggttctt aaggggggt     3420 tctaaaggag ccccttgcta atttacacta atgagtgtca attatagcat tttgcaaatt    3480
ggtgaattgg caaacaaagc tggtaatagg atccaggagg cctaggcatc caggtagtga    3540
ccataaaagc cacggttgac cccagctttt gggaaaagct ggatagaagg taaatccggg    3600
tcctcccctc tggattcttt tgtgattttcc agggcttagg ataggtgag tgggaggagg    3660 gaaaactgca ggtggtagaa gtgaagcccc ccacctccag gcctgcacca gagggccaca    3720
agggagccca gaactctgcc accccacttc tcctgggtcc ttttgtcctt tagaggctga    3780
```

```
gcccagtcag atctcactgt gatccctggc cgaggggatg gtctttgcaa gaaactttct   3840
gtaaccattc ctgctgatgt tcctgagtct tccccacaag agccaccaaa ccccctgcac   3900
caggcagata atgactggcc ccacttttct ctctacacct cctctaggta aaccagtcag   3960
cctgagctac cgatgcccct gccggttctt cgagagccac atcgccagag ccaacgtcaa   4020
gcatctgaaa atcctcaaca ctccaaactg tgcccttcag attgtgtaag tcctagccgc   4080
catcccccaa agaggagcat ggtatagaag cctcggactt ggcataacta ggggcagctg   4140
ttaccaccac caccacgggg acactgatat gccatcagac atgggtttca aaggatactt   4200
ttgttcccca gagccctgat gtcctcagtg tttctcactc ttgctttcca agctgtttct   4260
tgcagcacag tgggccgcct ctctacagaa aaagccatgg acttgatgga ggtcagccct   4320
cagctgacag ttgggtctgt cttgtcagtt tcaaggttct ggtgtccaaa gttaatcctt   4380
tctcacatag aaaaaaaaat tacaagaccc ggatggcacg ggggggggg gggttcagtt   4440 ttactcactt gcactcactt gctcagaggt cattttgtt ttagagttttt agagtttgct   4500 ggagtgtgat ggtagctgcc agtatttgat ttaaatttac ctgggaaata agaaaagccc   4560
aaaaaaggta taaatgatgt gaatatctca ctcagagtct ggtagacttg gcagagatgt   4620
gtcctgtgct agtctgtcct gctcactgcc ccccagcagg ggttcccatc ctcgggagac   4680
tcaacactaa caacagtata aggatgcagc agctggagca atgctagcct gacggctttg   4740
tcacccaacg gtgactgctt cagactttct gtgctcatca gccttcctct ccagcctccg   4800
ctgctgtgtt atgtacagta ggcttttagag acctagatga tgaatattat ttttgctgtt   4860
ttgattaaaa tacaatactc tcccgagaaa gggatttttaa agatgatgag tttacgtttg   4920
aataggctgt gctggtgcac tgtcccggga agggcccttg aacttagagg gtcaaataca   4980
actattgatt ctgggtgatc actaagttaa taaatggcag gatccagact gacacccctg   5040
atccctgttg aagttacatc cctctgaacg actggtcaac tgcagggcag cctgcttgaa   5100
gagggttacc tgtccctagg acactgaaca ggcatttgtt tttcctagaa gacagttcac   5160
cagctggaga ggagtcgtct cccgtagttt ctgtttggtt gcttttggtt tttgtttggt   5220 tttggtttt taattatctg gcatccagga cttgatggaa aataaccaga gctaagctca   5280
ccggttcatc tgcccattag gaagttctag ggatgggaga agaacacgg cgtcaattaa   5340 caaatccaca aagctaagac cttgaagcat tctgtgaact tgtaaacgcg ctcaggcaac   5400
cattggacaa tttgtctaga ctgctccttg cccaccctgaa ctgccctgtt cctcccttc   5460 tggactcctg ccgtcttcct ccagagctac ctttaaggtt gtcccatgta ctatcaaggt   5520
gctctgtcaa aagttcttag gctgcttctg gcactctcca gaattttcca agacctcccc   5580
cccaccatga tatcagtcat ccgcgccttc tgggtggttc ttcctccaca cccttttggc   5640
actttgactc ctgtgggata ttcgtccttc cttttccttt agctttcctc acttgccaag   5700
ctccaacttg gccagaagct caaatgcctc cactgtggtc tcttctctgt gtccctggg   5760 agacatcctt agcacgtccc taactctgcg gtggtggtcc caacacgatt caagtgctat   5820
gtcttccaaa actgaagctt ccgggagcag cagctgggcc ctgcagtgag gacctttagc   5880
tgggtgtgtt gggtgagccc acaggatcgc tttctcccgc ttggctgtac agcgtctctc   5940
cccttgtgtt ttggcagtgc acggctgaag aacaacaaca gacaagtgtg cattgacccg   6000
aaattaaagt ggatccaaga gtacctggag aaagctttaa acaagtaagc acaacagccc   6060
aaaggacttt ccagtagacc cccgaggaag gctgacatcc gtgggagatg caagggcagt   6120
```

```
ggtgggagg agggcctgaa ccctggccag gatggccggc gggacagcac tgactggggt    6180
catgctaagg tttgccagca taaagacact ccgccatagc atatggtacg atattgcagc    6240
ttatattcat ccctgccctc gcccgtgcac aatggagctt ttataactgg ggttttttcta   6300
aggaattgta ttaccctaac cagttagctt catccccatt ctcctcatcc tcatcttcat    6360
tttaaaaagc agtgattact tcaagggctg tattcagttt gctttggagc ttctctttgc    6420
cctggggcct ctgggcacag ttatagacgg tggctttgca gggagcccta gagagaaacc    6480
ttccaccaga gcagagtccg aggaacgctg cagggcttgt cctgcagggg gcgctcctcg    6540
acagatgcct tgtcctgagt caacacaaga tccggcagag ggaggctcct ttatccagtt    6600
cagtgccagg gtcgggaagc ttcctttaga agtgatccct gaagctgtgc tcagagaccc    6660
tttcctagcc gttcctgctc tctgcttgcc tccaaacgca tgcttcatct gacttccgct    6720
tctcacctct gtagcctgac ggaccaatgc tgcaatggaa gggaggagag tgatgtgggg    6780
tgccccctcc ctctcttccc tttgcttttcc tctcacttgg gcccttttgtg agattttttct   6840
ttggcctcct gtagaatgga gccagaccat cctggataat gtgagaacat gcctagattt    6900
acccacaaaa cacaagtctg agaattaatc ataaacggaa gtttaaatga ggatttggac    6960
tttggtaatt gtccctgagt cctatatatt tcaacagtgg ctctatgggc tctgatcgaa    7020
tatcagtgat gaaaataata ataataataa taataacgaa taagccagaa tcttgccatg    7080
aagccacagt ggggattctg ggttccaatc agaaatggag acaagataaa acttgcatac    7140
attcttatga tcacagacgg ccctggtggt ttttggtaac tatttacaag gcattttttt    7200
acatatattt ttgtgcactt tttatgtttc tttggaagac aaatgtattt cagaatatat    7260
ttgtagtcaa ttcatatatt tgaagtggag ccatagtaat gccagtagat atctctatga    7320
tcttgagcta ctggcaactt gtaaagaaat atatatgaca tataaatgta ttgtagcttt    7380
ccggtgtcag ccacggtgta ttttttccact tggaatgaaa ttgtatcaac tgtgacatta    7440
tatgcactag caataaaatg ctaattgttt catgctgtaa acctcctacc gtatgtggga    7500
atttatttac ctgaaataaa atctactagt tgttagatgg agtgcacata catttctgaa    7560
gatggagaaa acaggtgtg cctgctgatc aggtgctgtg ggctgccctg cagtcctggt    7620
gagcgacaga cactgaggca ggcttgtctc atgaacaggc tgcctctgca gtgaaagttt    7680
ttgtgtatttt ttttttaaccc aagctagttt tctaatgaat aatacttgac tcactaattt   7740
cccctcctcc tccttctcct cagttctcct aacatcctca tgtgatcccc agactcaact    7800
ccagtaatat caagctttcc tattttccca tgtaaaaaaa tcccatgact ctgggccatg    7860
ttaatatcag gcttttgtgg gaacaggtgg cctcacccca taaatcatta aataccattc    7920
agcttgaatc attttaatgt gacagtcaca aaccagttgc tctaataaaa actctgctaa    7980
ccatccttct ccttagctct ctagaacaat ctcagttatc cctagggatg ctccccagca    8040
tccagaaaag agaagtggga tcaatcatcc tgcctttctc cccctcctct cttgagggc    8100
tgcctgagcc cgtggcctcc acctcccctg ctttgtataa tttgaaatgc agatttgtag    8160
tgaaggcaga gttcacctct gcattgaaag ggaaggcagg cccagagctt ccttccctgc    8220
cctctgagat gtgcatttat gtctcaggat ggatgagctt tggtaggaat gctcaaaacc    8280
aggaccagcc agacaaactg gcagtccctg taagcggttc ccgggtcata gggttagggc    8340
accctgtttt aactttgggg tggggaaagt atctggtttt ctttgataaa ttgcttgtga    8400
accacatttg ccaagtggcc tccaggcctc aaactcaaag accgagctaa atcgactcgg    8460
aaggcaatgc tgaatgaaga ttgtgggaac tgagatagat acactcctct atgttgcaat    8520
```

| | |
|---|---|
| gtgattaatg gttctactaa ttttatctaa gggggcgcag agaagaaaaa gtggggaaaa | 8580 |
| aagaaaagat aggaaaaaag aagcgacaga agaagagaaa ggctgcccag aaaaggaaaa | 8640 |
| actagttccc cgcttcctgc cgatggaccg cagtgcgctc tgctctggcg ctttgtaact | 8700 |
| cgctcctccc tcttcggggg cagaccccac actccgggca ggtgctcaaa cctgacggta | 8760 |
| aactcttccc tcttcggggg cagaccccat accccggggc gggtgcttag gctttcctgc | 8820 |
| cctggtggcc acaccagctg ctgtatttat gtgcttcata aggccctgct ctgtctgcta | 8880 |
| aagctatgaa gaaagatgtg cagagactgg ggtggagact aagccaaaga ggagctgcct | 8940 |
| agcctggcag cattgccccg agctgagccc ccttggccag gacttcacaa ggctcacacc | 9000 |
| tacaatccca tgaaggccag ggtggtctgc ttagccagga aagggcaagt gccttcccct | 9060 |
| cggccacact gccccttgtg gccttctcgg gacatgtggt aactgacttg ctctcaggcc | 9120 |
| cacccgcagc ttttccaaat acctgcagcc ttcagccctg ctgccctgcc tgtgggagca | 9180 |
| gctttgactc cagtccagaa gggtttctgc agactgtgtt gggtgagacg cagaaaggat | 9240 |
| gaaatctcag aacacatgtc agctgcttct caggaaatct tttctttgga caattcactt | 9300 |
| tagagtcttt aaacgggtct ctcgtgggga ggatagatgt gctctggaac tttctgaagg | 9360 |
| accagcagct tcagggactc ttagtctgtc cttccccact tttggtccca acatccctgg | 9420 |
| gatggtgtgc tgtctgggca ccacggtctc catcctcact cctgagagat ttctgccttc | 9480 |
| tgtgagttgg gttaaagctc tggaattatc tactatccca atccactacc ctcacctggc | 9540 |
| aatatttgtc tgtttttgtt tgttgtttg tttgttttg tcttttgcca gtttgaatta | 9600 |
| gaaggcaagg ctctgatttt agtagtgttt tggaaaagga cttttttctt caccttcctc | 9660 |
| tttgcctcat gtgtacacac acacacacat cttgtacccc agacctctgg gtataatttt | 9720 |
| cataattggt gcagaaagaa gaaatgatct gaagatgtgt taaatggatt gcaggggaag | 9780 |
| gaaggcccag ggccctgtgt gtcatgccct cttgggttcc taagttctat gttccttaga | 9840 |
| ggttctagca ttaaacagat aaagcccttc atggtcctgg ctgaggaaga gtcttgctag | 9900 |
| ggggattcag ggaagacccg tgttaccagc tcttacccct tatctggaca gctctccctac | 9960 |
| cctgtatctt ctcctcagat ctgaggatag caggctggac tattggtggg cacctttcaa | 10020 |
| gcccagggct actgtttgtc ctgtggcagc cggctacagt ctcgtctgag tggcctcatc | 10080 |
| tggacccttc ctgttattaa taaaacgctt ctggaggcca gatctgtgct caagccatag | 10140 |
| ttctgcttag aaagggatgc cccacccttaa ccggacactg ggaagaactg ttggcccta | 10200 |
| gaaaccaaag gccaaactga ggctgccctg agttggaaga ccactttctg aaatgcccat | 10260 |
| ggactctgcc tcccaaccat tcgtctctca ctccctagcag agctgtctgt gcagactgtt | 10320 |
| tcttaggagg cacagcaagc tccagggaac cctctgtgct tatgaagctc gtctggtggg | 10380 |
| caaccccagc ccactggaca gagtcctcat ggaaatgcct gggaagctga tttcatctaa | 10440 |
| ggatggggttg aagtaggatg tgctcctgcg acttctcagg caggtgagag gggtagtcct | 10500 |
| tacactgtct agcataaacg ccttccggaa ggacctgcag ctccagagac cacctcctga | 10560 |
| gcaccaagac ctcttctggt ggtgtggaac cagccaagag atttcaagga agagtgatta | 10620 |
| tttgatgaat gctatgggaa tggcctcttc tcttggagtt ctgaggcctg gggatgccca | 10680 |
| ggaacactgg gcacctgctg ctgttagggc caatgcatag tctcagcacc ggtgtcctaa | 10740 |
| ggttaaggcg gtgcgccttg tcatgtgctc cttgtaccat gccatctgtg ccagtgtgtg | 10800 |
| tctgcctcac cctgtgcttg acatgttcac ccatcttctc tgcttcccgc caccatccag | 10860 |

```
atcctcagcg gccgcccggg ctgtgccctt ccctgctctc ccgctctctc aggcctcgga    10920
aggaagatcg gtggctgcga gctgaactaa ggagtagggc ctgtggctca gcgctaggcc    10980
acgcacgcag catcccaggc atgtggtgag aaactgcctt aatgtgtctc ctctgttctt    11040
gtcaacagga ggctcaagat gtgagaggtg tgagtcagac gcccgaggaa cttacaggag    11100
gagcctaggt ctgaagtcag tgttagggaa gggcccatag ccacttcctc tgctcctgag    11160
cagggctgaa gccgtttgca agggacttgc tttgcacagt tttgctgtac tttcacattt    11220
tattatgtag caagatacat ggtgattttt tttttttca tttagcctga ttttccaacg    11280
tcattggtga caggccaagg ccactatgtt atttcctttg ttctggtatc cttcccttgg    11340
aggaccttct ctgagtagtg gctccccagg tttgtccttt gagctgaggc aggaggctca    11400
cccattcttc tgaataggaa ctgggtgttc ccacccccca aggactgcag ggctttccca    11460
agctgaggca ggaacgtgag gccagggaag agtgagcttc accctcatcc cacgctgtcc    11520
tcctcaaccc accatgctca tcattctgtc tcatccatcc atccatccat ccattcatcg    11580
ccatgtgtcc gcaagactgt ctccatgacc ctgaaaaagg actctcgaga tgaaatcctt    11640
tattcaaatg ggacagcaag aaggaaaagc caatgtctgg tgtctctccc ccgcccccta    11700
ccctgcgcgc atctatgtct tgtttggaat attgtctctt caaccccctg ttcatgtcct    11760
tctcactcat gatcgatgtc ttgtctgtgc actgtctcta acccaaatgc aaaggctgag    11820
tgtgaggtga tggcccccgag gtccaggttg tagtcatgga aagagccctg ctgtctccct    11880
tctcaggggg cccatttttag acacacaaag cccaagaaaa ggtggtttgc aacagtgctt    11940
agctcgagcc tccatatttc cataactgtt agcttaaaac tgtggggttt taccttcctg    12000
gaaccaaatg cattcttctg ttgaggagta acaggtctca attcttttca attaattta    12060 aaagtcaatc actaagagca tcggcttttgg gccctgatgg gcaggcattt ccctggaaag    12120
ggggtgaact acctacctct cctcaagaca gccgaagggt gggattggtg ccgctctggg    12180
aagcgtggcc ccaggagttt tgtcctctgc agttttttaat gcaagttcac tgccactttg    12240
acaaaagccc aattagaagc cagtctctag ttccttaaac aaaacagaca gagtaaggaa    12300
aggaaggagg gtggcagcca gctggctgga cactcgagaa agacggggaa gtaagctaca    12360
gaaagatagt cttcaaaaac aggtgtttga gagtgaatac tctgtagaat tgttagtggg    12420
gtgtgtgtgg tggtggtggg gggatttcta caaaatagtc ctttaagttg agtttacagc    12480
agatgaaaaa tccaaccagc aaaattttga tcaaatttga acaaaaaccc aaaaacctaa    12540
aactgttgag caggttgcga tgaggagcac agggctagct gcagagctgg atcctcagga    12600
ggatagcgaa ttattttcaa ccctggaata gaaaccacac actggcttgc tgtgcaccag    12660
ccactttgca tctaatccaa gctttgaagg gtgttgcttg ggaggaaaca aatacagcct    12720
tccatcttca ctccagttag ggatcctttc aaagtctcct tcacagtgag gaaaagaga    12780 agggtagaaa cttagggag ccggatttgt gtatcaattc ctccgctgac agtcagtttc    12840
tagatggaga cagcctgctt aaagcaaatc cgaatttaaa taggacattt acatcggaaa    12900
agtctctccc taccttaatc ccccattctc ttgctttcaa aatacaagca cagcagtcct    12960 tgaatgctg ttgacccagg gcacctagct gtccctgctg gtcctgggc tgccagaatt    13020 cccttgggcg ccaagcaacc tgccaggtag ccagtccctc tgttacaagc ctttgcatct    13080
ggatagggaa aggggtggag acatacagtc tgctttgtgt tgaaaccag atttgtaccc    13140 tgtgttata cactgctgct ggctcccgag gacagtggga ctttagcaag gaagtgcagc    13200
cgaggggtaa agagccctct ggttcattgc ctgatcggct ttgagagagg gtttggaggg    13260
```

```
caaggggctg cattcctctg agggacttgg cctgaggcct ttcgggcctc tccagtgggt    13320
tctgtttatc ctctcatggg tgattatctc agtggtgtca ccaggggctt cctcccagaa    13380
gtcagtcatc cccaggccgt gcacccttttt cagctggatg agagccaggg atgcattctc    13440
tccaaacagc taccctggcc cattttaagg taatctcatt cttcaaaatg ttccatagaa    13500
tcctccaaat tcccccagca gacttctacc ctcgccaagt tcccaaaacc cactcagcaa    13560
agttgccaac ctcgacgggc tagcagtgtc taagcagcga tgggttcagt gttgtgtgtg    13620
gtgaatactg tattttgttt cagttctgtc tcccagataa tgtgaaaacg tccaggaga    13680 aggcagcttc ctatatgcag cgtgtgcttt cttattctta tttttaatat atgcagtta    13740 tttgagaagc catttctact ttgaagtcat tatcgatgaa agtgatgtat cttcacctac    13800
cattttccta ataaagttct gtattcaaat atagctgcca agcatcctca gtgaatgtta    13860
ccatgtggaa ttttccacac ttggttttac cccctcaaac ctgactctga ccgtgcagtc    13920
ttagcagaag agcttagcag gtcctagtgt tcactcttgg tctaactgct ggtgtcagaa    13980
gatctctaca gggagaggtg ttccattttc tccacatgac ctggattgct ccttagaggt    14040
cagacagcct tgcactgtac aaggcaatgg cttagggtaa agtcccagga gttttcccta    14100
cagtcccaag aatttggaag aggaaggccc acactacaca tgcaggtcat ggtggaaggt    14160
gacagaggaa ggactctgtc cctgtaagac agctggaaac cacaatattc tgcatgttcc    14220
tatcctgggt gaggacgcta atggaagtca aaggggaatt tgctaactgc tgttggccag    14280
cttcctccaa gaatcctgct tccccaacag acagagcctt tgtctcttat agtttggtct    14340
tcagattctc tttatcccac attcagccat ttttgtaaaa gagaggctag caccagctcc    14400
aaatatccaa atctgcagtg tttgagatct cactgcgcct cctccatacc aacacatttg    14460
ccattactta tagggtagtt ttcatgtgag ttctaagttg attaacacac aagaattaga    14520
agggtgggag gctctaggaa aggcactgtg ggactatttg actgcatggg tgtgaaaatg    14580
taaggaacag gcaagagctt ggatcccatt ctctctgccc acattgtgac ttgagatata    14640
ctaattgctc ttggggggtct cagtcatata ccatccataa cagagttaaa ctgagagaga    14700
tacaggatca gctagaatga aaagcccacc ccatgcttcc agaaagtccc ctctttatac    14760
ctcctgtgat atgaactaga ggaaaagcaa ttgactttgc ttctcaaaca gcctacggca    14820
aagccctgtg agtttg                                                    14836

<210> SEQ ID NO 2
<211> LENGTH: 25001
<212> TYPE: DNA
<213> ORGANISM: Mus musculus

<400> SEQUENCE: 2
aagggtttct ttggcttaca cttttcttat tgttgttcat tattgaagga agtcaggaca      60
ggaattcaaa caagtcagga tcaaggaggc aggagctgat gcagaggcca tggagggatg     120
ttacttacta gcttacaccc ccccccccccc cccggcttgc tcagctttct tttttttttt     180
tttttttttt tttttttttag atattttcta atttacattt caaatgctac cctgaaagtc     240
ccctatacca tcccccacca ctgctcccca acccaccacc tcctgcttcc tggccctggc     300
attcctctgt attgttgctc agctttctta tagaacccag gaccaccagc ccaggaatga     360
caccacccat agtaggctgt gccttcctcc actgatcacc aacggagaaa tatgggcaac     420
agcttgccca taggatgggt cactagttgg gttggttact gttgggccat tccctcagtc     480
```

```
tctgctccat cccccatctc tacatttctt gtagacagaa tcaattttgg gtcaaaagtt    540
ttgcaggcag gttgttgtcc ctcttacatt tctcatggag gcatttcctc aacttatttc    600
ctctctctga tgtctccagc tcatgtcaag ttgacacagt tgttcgggac ccacatgaag    660
accaagctgt tcatctgcta catgtgtggg gaggcctagg tccaacccgt gtatgctgtg    720
gtagttcagt ctctgagagc caaaacagtc caggttagtt gactctattg atcttccttt    780
ggagttccat cccctttggg gccctcaatc cttcccacaa ctctaccatc agagtcccca    840
agcttcatcc actgtttggc tgtgggtctc tgcatccgtc tgagtcagct gctgggtgga    900
gcctctcaga ggacaggctt tctagactcc tgtctgcaag catagcatta atagcatcag    960
ggattggtgc ttgcccatag gatggatcac tagttgggtt ggttactgtt ggccattccc    1020
tcagtctctg ctccatcccc catctctaca tttcttatag acagaatcaa ttttgggtca    1080
aaagttttgc aggcaggttg ttgtccctct tgctccactg aggttcctgc ctagctacat    1140
gaggtagcct ctttaggttt gatatcctca atgctgtgaa tcccaactaa gatcaccccc    1200
cattcattcc tggtgtctcc cctatctcag gtctcagata tgccttcaag atgccccccc    1260
cccacctctc cacctctgcc agctgcagat ttccattcat tctcatggcc atctggctat    1320
ctctcctgtt cctccccata cctggtcctg aaccccttc accccactcc ccatccctc     1380 tcccacccag ttccttttcct ccatcttcct cctatgactc ttttattccc tcttctaaat    1440
aagattcaag catcctcgct tggacattcc ttcttattta gcttctttgg gtctgtggag    1500
tggagcgtga gtattccaac ttctaaggca cacagacaac ctcagattct ccagcccttt    1560
gtgtgtgttg cttatttgaa caaacgggtg aaagaaaaca cacaaagttg gcgtgttgaa    1620
agagttagtc gatcttctgg ggtaggtttc agtacagaga ccaaagggac attctcagac    1680
actagacaca ctatgcaaag acaggatgtc acatgacaaa ggataacggc acaagtaaac    1740
atttaagcaa cagtgttcca taccggctca cgtagaaaaa ggacaagact ataggaaaga    1800
aagcaaacac tccgccgagg actacagcaa agacagaaag tatctgcagg tacggcttca    1860
aaaggagcat ttctctcagc aacttatatc tgttaatgcc ctgtcttctg gaataagggc    1920
ttagttttta tcagtagaga gagattgatt tttaagatgt atctgatttt acattgtaga    1980
tctccttagt cacccctgt agtaaactaa ggaaaacttc cgtggaggga gaggggaaga     2040
ttagtaactc gtagtgagta agaattctct ttcaagaaaa agattcaaga gcaatacaag    2100
gcctagatat gaaggtgtgt gtgtgtgtgt gtgtgtgtgt gtgtgtgtgt cttaacagcc    2160
tgttcagaat ttagtaggtc acatacactt acaagtaatg aagacaatat attaatgaat    2220
ttgcagtaat ttttgttttt agaaatagaa actgttgtaa ggaggataat cattcagagc    2280
tctttgatat gtatcactca cattcacata catgcataca cacagagaga gagaaagaga    2340
gatacagaga tagacagaga gagaacccaa aaatgtaaag agaggaaatg agttgaaaga    2400
aaaaatggga aactgggtta gggagggtt cagatgacag tgactggggg ctttcagagt     2460
tgggagtgag gcagcgatgg agagagggca gggaggaggg agtgtccatt gtgacctctg    2520
cagaactctg actagactga gcagctcaca ccgtgttgga gctgtcctaa cactaccaag    2580 gggacgggg agaccccatg aacaccacct agggagttgc tcctttcatt ctgtgtaaag     2640
tctgatgtct tcaaacttgt tgtaaatta tactctgttc taaaaacagt gacattcttc      2700
tctttgtagg atgacctcat tacatcaggt gttatatttt atcttttttg cctcagtttc    2760
tagtggtaag ttgctgtatt tattttcccc taacataata tttttttatta cttgagagtt    2820 tcatacaatg caccctgatc acactcactt tccattcctt ctaagttcac cctcccactc    2880
```

```
ttgagccctg ccagctcact ccccccttct tgaaaaaaaa tcatcaagtc aatcaatttg   2940
tgttgagaat atatactcgt tgggaatgtg atcaaactcc caatggtcag ccccttaaag   3000
aaaagtgagt cttttcctc ccccacttct ctccccactc ccttacccag ttggaagcca    3060
tcaactgtga agagttatac ttcagcatct ttactacaat tttaaaggac tctcttcagt   3120
atttaagtat ggcttagaaa tagctcattc cttgacctgt aatgtaggaa acagcctaag   3180
tccacaaaaa gaaattacac ttcagacccc atatattgtg gaataattcc atgctgtgaa   3240
ctccagggaa ggaaatagag tcgtttattt tccagtgaaa gctccccttt aatacatcaa   3300
agaaagaaag agatttaaat atagaattac aaagagtctt cacctatatc atctgaatgc   3360
tagtaatatc tgtctataga gttgcatctc tatctaccta cacaacacat tgccatgatt   3420
cctaggagca agattagaaa gagaagactc gactcacctc attgattatt attccataag   3480
ggattcagtc tagtatctct ctctgtctct gtctctctgt ctctgtctct gtctctctct   3540
gtctccgtct ctctctctct ctctttctct ctctctctct ctctcacg cacacacaca    3600 cacacacaca cacacacaca cacactcacc aattcctgac tgaaaatgtt atagaaaaat   3660
taatgtgtgg cttacacatt tggttaattt accccttgca attatgcttc cattctacat   3720
tacatccagt aaatacattg cttaccattc agtagaatga aatgggaagt tacctcacca   3780
atactgatct taacaactta gtgtaagcac ttcttaaaat aatttattta tgttatattg   3840
aatgcctgag actgccattg acatattaag catagttagt tctttttggt gtgacacatg   3900
tgaacagtag cagatctaaa ataaaataaa catatgtaac atattaaatt atacagatta   3960
tagcttaatt tttctttgtg attagattga ttttcaggtt attccttcat tatcaatgtt   4020
ttgaaatccc attgttattt gtactgtctt gttcagtact gttttgacat gttgttgttg   4080
ttgttgttgt tgttgttgtt tgacacagag tttctatgtg tagccctggc tgtcctggag   4140
cttgatttgt agaccaagct gacctcaaac tcagagatct gcctgcctct acctccaagg   4200
gctgggattg aaggtgtgca ccatcatcgc tcggcagcct gtcttaacat cttaaacact   4260
gagttcaata actgtgtcga ttcacaagga cattctgaga attataagac ttttttgctt   4320
atgaatatat atatgcaaat gtaactgaca aaatattatc cattgtggtt gtatcacact   4380
taaaaatctc agagccgaga aagttggggc aagatgatta aaagttcgag gacaggatgg   4440
gctacataac aaggttctgt ctcaaattgg ctataccaaa ccgtccaaca catattttaa   4500
agaaaaataa atgggaggct agagagatgg ctcagtagtt aagagcactt agtgctcttg   4560
catgggatca gttcaattct cagcgcccat gttagatagt tcacaacttc ctatgactct   4620
aacttccagg aatacagcac cctcttctgg cttctgtagg tacacacaca cacacacaca   4680
cacagacggc atacgtacat acatacatac atacatacat acatacatac atgcctacat   4740
acacatgtac atgcatacac aataaaaaag ttttttaaat cttttttttt aaagaaagaa   4800
aattaaaaga ccaattacat tggcatattt tggccaagtt tgcttaattc taggaacaag   4860
gagttacttt aatctaagaa aaacaatcaa tggatgcaat gtagatccaa aggaagtgaa   4920
agaagagagt cctacagaga tttgtcattt gtcttcctgc tatcgggcag agaaccagca   4980
agagagaaac gtgggcattt gaagcccact cagccgtgtc atagcacaag ttgggtcttc   5040
accaatggac agaaggttaa acaaaatata atatcacagt atgcacatgc aacacaaaac   5100
aggatattac tcagcgtgtg aggaagaaaa ttctccctca tactggggca tagctgagcc   5160
ttcgtggttt tatactcaac gaaatgagtc atttacaaat gaacacatga ctgaacccct   5220
```

-continued

```
aacgtttggt tcccagagat gccgatttca ggaaaacaaa agaccgaaga gaactgacca    5280
ggggctaatg ctaatgacta tttaatgggt acaagttttc agttggaaaa gctgaaggaa    5340
ttctagaata gtggtggaaa ttgtacctaa ggtacatact tcattccaca actctagaga    5400
cctgaaaagg gccggagtga caaactttat gtcatatata ttttgccata gaagaacaaa    5460
attaaaataa tctaacacat cgaagatttt aaagattttc ataataaaat agtttagcaa    5520
actcagaact ttcccaatga ctaagtagta ctgtaaaaca acaacaacta gaaaaacatt    5580
caaaccaaaa gttttcaaga aatctcatat gtaatggtga ctgaaatagt gtttccctga    5640
ggtactgggg taaggcagga gtatccacaa cttggctcct gtgaatagga acaaggaac     5700
agagagatgc aagcatcttc aaaaagttgt cataggatcc atcatggaca ttccaggagg    5760
ggttcagttc tacttttagt tttctgtgac atctcattac aggttttgat ttttcccc      5820
catagcttcg ccagcatgga aatttattca caagtaccaa gtcagggagt ctgcctatgt    5880
gtccatcaat agatgaatgc aaagagcaaa cactggatgt aggcacagtg caggggcag     5940
ggaggggtgg catgttctgc atttagctaa aatggttgtt ttagttttta ctaattcttc    6000
aagaatgcca tataccatat tttgctaatt tttacctcga ctccccaaac tccatccaga    6060
accccccatt ctgtacccac ctaactctgt gttctccctg tttcatttgg ccacagtgag    6120
gaatgaaatc gtgccatttg tgtaacaatg gctgtgactg ggcatcatca ttattcagtg    6180
agataagtca gattgaagaa gataaatatc ccattttctc aaatttgtgg attctagacc    6240
ttatatggat acataaaatc cagtgtgtgt gtgtgtgtgt gtgtgtgtgt gtgtgtgtgt    6300
gtgtgtgtgc ttgagtgaca cactctaggc tccagagtct aggggaatga cagagactag    6360
aaggaaagag ggaaacgaaa agatatgaag aataaaatata gtcgaagcac atgatacatg    6420
cctatgatat tatgatgtat acacacctat gcaggtgtcc catgaagccc cctgctatgc    6480
aacgaatacg tgtcaataaa tgtgttgaga gactatctac tgtcacttcc cttaaacatt    6540
atattagaga tcctgtgtag cacagtaggg aaggtcgaag gacctaagag tcaggagaaa    6600
gatggaaatt aactgactct tcccataaat gtggttatgt acatagaaaa attcaaagta    6660
atgaatgcac tgattatttc aggcagatca gcaaggagtt tacaaactcg atggacccccc    6720
gggagtggag gcacacactt gtaatctcat gactcaggag gcagagggca catcagagac    6780
cctaactcca gctcttccgt tcaaaatctt caatatacaa acagtagcca actctcgcca    6840
gtactaggaa ctgtactgag attatgaaag tcaatattat aggttaaatg attcaagtag    6900
tggctacatc ctaatcaaaa ctgcacattt attaatcctt taaaaatcaa ttcaacttat    6960
caaatcctgg tgttgtgctt gataagaaca ttttaatgtg ttatgatggc ttaatagtaa    7020
aatgttgcat ttcttagagt taacaggtaa actgtgaggt gggaatagac tgccaattag    7080
ctggaaacag acgcagtatg gtttggtggg agacaacact gaacttggaa aaagaagtcg    7140
gatctctatg tagctcctgg gatacttgcc tgtagtggag aaaaccatgt tcccctaccaa   7200
gtctctgctg aattttggaa atggatctgt agtgaggttg ctcttcctcc ccacaaatcc    7260
cttccgaggc cccatggacg cagcggagcc tatccttgga ataactttc taaaggcatg    7320
gactaaaaat ataggggtt gctggggaaa ttaattatat tgaaatatga gtagctaaag    7380
tggaaaatac tcagtacaga attagttgtg gctcggagtt aacaccttac atgacattag    7440
tggcatgccc aaaactgaat agaaataacc aacaaattat cgacaaatca taatgatgtt    7500
atatctcatc atcacataca tgacaaatac taatcatgtt aattgattac attaataata    7560
caggtatgta tgtaccacat tttggttagg gaatcaatga aaaaccacat gaggtttttt    7620
```

```
tgagctcgtt ggttatctag gtcctacaag cctcatagga gggttttgag actgctatgc   7680
acctacaatc ctctcaagac atgactgatg ctgttacag tagtctatat ttgagttaaa   7740
ttttattctt ctggaagtac ttccacgtga gtctggtaat gttttcaagt tataaagaga   7800
aatgggctag caacacctct ccatgggcat gtatggctgc atgaagtaat cttttattca   7860
gtcactaggc aacctactgt gtgaattatt agctatctct tctagcaaca gagcactttt   7920
gaatttttat gcattttggc ttttaaaaa ctaaagctga tgtaaggttt tcgctaaata   7980
gaactcagta agtttccct ggtaaatgtt ggtcatgaga ccattttaa tgttcgcatg   8040 acatcataca agggcccctc agtcttggct tttagtttgt ggtagtgtca aaacaataaa   8100
tgaacgtaaa cacagcacac ccttgctgac cccctagagg ggtttcatgg ggaccgtgtt   8160
cttcttgccg gtcaacagct gagaaatcac tgagttgctc ctgcagcctt cccaagacaa   8220
tcactcataa atgtgacaac acggagggcc cccatgttgt ttgtgattta tagttccatc   8280
tggggctgtt cactgaagag cgttgcccga tctgatgtcc gaggtcaggc atatttagca   8340 ctgactttt aacaaaccat gtaacgaggt aagtgcccac caacatctgc agtaatgtgc   8400
gcccgcgtgt ttttttcttc acagaatgcg ttactaaggt cttcaaagac atcagctttc   8460
aaggaggtga cctgagtact gttttcacac cgagcgccac atactgccgc ttggtctgca   8520
ctcaccaccc acggtgcttg ctcttcacgt tcatggctga gtcatcttcg gatgatccta   8580
ccaaatggta acagtttctg tttctctgaa gaggaactga tttccagtgc cagttactca   8640
ccaatgcaga ttccttaca accccacttt tgtcatttta caaaagggga tgttagtggc   8700
tggaaagtga gtttccttcc acggaaatac taaatattac aggaaggata gcgcttaggc   8760
atattggtgg aaaaccgtaa taactcctgg gacctcaatc ttaaagtcac gtttttgctc   8820
ttcatccatg gtttgtctta cattctttt ctgtcgtggc tattggctaa caatggtggg   8880
gttatctaga gcttccttct aacctttcaa ttaggggaa aatgtttaaa aagctacttt   8940
aaaaattatt acaacaattt tctacccct ccaatatcct gtcatattat gtggctttct   9000
cggctcccat cagtggttca ataaggcatg cagactttta tataaaactt aaggcccttc   9060
attggggcag gcagactctc agctctcttc tctaatctta gatcgtctgc caagtagcta   9120
atgatttatc tcgtttccat tccttttccct atctgcctct gaatctccca cctctgcttt   9180
agttctctct ctctctctct ctctctctct ctctctctcc ctctctctct   9240
ctctctctct ctctctctct ctctctctcc ccctctctct gtcccacccc cagaagtccc   9300
acccttgtac ttcccgtccc actttaggca atatgagtgg gtgaggaagg acaagcactt   9360
acaaatcaga agctggtgat gggccataga catgacgata ccaaacatct gccagaactt   9420
agctctttgc cagtacagta atcaacaatt gcacaattga agtacagag acacgcctta   9480 atacaatata aggaaggtca tcgcaacact gtcatatttg ctttacctac ctgtatatgg   9540
tcacagataa atactgaaag tgagtttaaa atatcatcga cctgcatatc taaatacttc   9600
aacatgaatt tcccaataag gaaactgtaa gaagcccaac aaagttaaac atacttgaaa   9660
tgttaatttt agctgttaat taaattctca tcaaatttca caggttccta tggctgtttt   9720
tccctctcta tcttattttt aaaatattgc atccatttct gtctctatgc taagcttgaa   9780
attttaatat ataaccttta atgcaaaatt aagctgccaa tatctttgtt attgctgttt   9840
tctcagatgg ttacatattg ctgtcaacat taaatattct tctgaaatct agaacagaga   9900
tcggcaagac aggaataaaa ctttaggctt tgttgaacca aatgcaaaaa gaacattctg   9960
```

```
tgtttctaac actgttttag aatgtaacca tgtgtgggct ggagggattg ctcagtggtt    10020
aagtttgctg gctgctcttc taaagggccc taggtttgtt accccaactt acagagattt    10080
gcaatcattg gtaactccag ctctagatgc catcttctgc ctttctcatg catgtgatca    10140
cacacacaca cacacacaca cacacacaca cagagagaga gagagagaga gagagagaga    10200
gagagagaga gagacagaga gagacagaga cagacagaga gacagagaca gagacagagg    10260
cagaggcaga gagagagaca gagagaggca gaggcacaga ctgagagaga gtgtgtgttt    10320
aaaatttaaa atgtagccat gtaaaaaata gaaaaccatt tctatctcaa ggataacaca    10380
aaaatggcag attttaagca acattttagc aataggttaa agtccttcca ttcttattca    10440
tgtcctgttg gaaaggaggg ccgtgtgtgt tcttttagat gtagggatgt tgtaataaaa    10500
aacaaagtca aatcttgcta attaaacatt tgttttggca ggaaacccag tcgtttgtct    10560
ccttctcttt gaccttagga tcccctcttt gaaagcatga attcctgctg aataatgtta    10620
ttttcatttt attttactat tttattttt aaaaagaac aggtttgcct gcatcctgaa    10680
ggacagcgtc acagaaatat tgccaatggt aaacatgaca ggcgcgatct ctggatattc    10740
cttcaagcaa tgccctcagc aattaagtag taagattttt tttatcaaat acaattaaaa    10800
ctagccatta gagtatatac gtgtaatcgt ttcagataca ggtttgtggc tataaaataa    10860
aatactacca cctaggacta aacttcccac caaggaacca tcttcctatg tagagtagag    10920
gacacagttt tctcccttcc tctccccata agcacactgt ctcgctttac catttcttag    10980
cctcataaag gcatgtcagc acctcagttc ttattattgc acacgaaagc cctcgttata    11040
aaagctaatt caaatcaaga ggagaaatgc agactgaagt ggcacatgtt ttaatagtgg    11100
aacgggcact tttcagtaag ttaaggggtg aaccagttgg tcagtgcggt ttgaggtcag    11160
aaagtcaaaa ttcaaattca caagctttct atttgttaaa aaaattttt atttatttta    11220 tatgcattgg tgttttgcct ccatgtgtgt ttgcgtgagc gtgtcagatc ccctgaaact    11280
agagttacac acagttgtga gctgccatgt gggtgttggg aattggaccc aggacctctg    11340
gtagagcagc cagtggtttg aatcgctgag tcccctctcc agtctcaaat gtacaagctt    11400
aaagcggttc cagtctaaga ggcacattgg cttcctcgga atacctccta gtggaagtgg    11460
gaatcacagc tgagtgaaac aaaacataga acttccacgg gagagtgggc gagaagcgag    11520
cagtttccac gcgagagggc cagcagcgaa agcagcgtac tgtagttgcc cctcgcttct    11580
ggtgacgcct agattctccg cctttatttc cagcttgcag caaagatgtg tacgtgaacc    11640
tagacatgaa gggcatgaac tataacagct ctgtcgtgaa gaatgctcga gaatgccagg    11700
agagatgcac agacgatgcc cactgccagt ttttcacata cgcaacaggg tattttccca    11760
gtgtggacca tcggtgagtg agcgggagtc cgagccgctg gatataagcc tgcccaggga    11820
aagaaaaccg ctggttccgt aggtatttc atcaatttga agcctaaact tctttttta    11880 aaccccaaga tatttgcata acaacaatca ctgttttgtc atgaaaaggt catagcgtgt    11940
ctaacacaca tttacgacat attcaaattt cagaactgga ggatggctcg gtgggtgcgt    12000
aaacacactg cttatgcagg gaccctgagt ttggatccca gcatgcacat aaaagccaga    12060
tatgggtgtg tatgccttta accccagtgc ttgggacatg ggcacgggac agagggagga    12120
tggttggagc tcactggtta gctccaggcc tttattatta ttattattat taaatattgt    12180
ctttatttac atttcaaatg ttatctcctt tccctgcccc cccccaacc ccctctccca    12240 tcccctccc atttctacta ggttgtttac ccacacacca acccactcct gcctccctgc    12300
cctggcattc ccctacactg gggcatagag ccttcacagg accaagggac tctcctccca    12360
```

```
ttgatgcctg acaagaacat tctctttagc tccaggctta gggagagatc ctgtctggag    12420
gggaaaagac agagaggtca tagggcagga actctaacac cccccccca cttggacttc    12480 ctattctcac ttgcataccc acaccccac accccacaca caccatatac aatacataca    12540
gcgtggcctc acagattctg tgtatgttgt aaagcataca caagcttacc ctatctaact    12600
tcaaaaggca ttacattttc acgcttgtgg ttctgagagc tcggtttgct tggccatgct    12660
cttcccagtc taacaaatgt cctaacctaa aaatcatcaa aacttaaagt tgtttctct    12720 atctacctac atgtacagtt ctgtcccta cccaagacga agtcattgga acccatgtgc    12780
aaagttttct cctgtttgat gtgggattcc aaactcctcc aaggaagaaa tctgttatat    12840
aaactaacga gagggaatga ctaaatctgc atcttcagtt taaattgttg ttagaaaagt    12900
atatgacttg ttctttaca acatttaa ttttgtgtgt gtgtgtgtat gtttatgtat    12960
gtgtgtgcct gtgcgtttag acacacacgt gtgcagataa ctatatagcc agaagagaca    13020
tctctcaatc tctcaaggtt catttttaga cttaggaatc tttgacatta tctagatttg    13080
cacagtaaac aacaggtatg tggtagttgg attttaacat tggctattcc tacttcactt    13140
tccataattc tggggggaa aagatgaatg ggaagtgaaa cattaaagat gtcttttaga    13200
atgaataata aaaaaatgga aagtagcctt ctatggctct ctttagctct cctcagagga    13260
catgttttat gtcttagact tcacagaatg ccaactgcag gctaggaaaa tgttcctagg    13320
gcttacacaa aagcgtattt ggagggctaa cgtgaacccg ttcacacaac cacctcacac    13380
cacatcaggt cttctgtgtt gtcctctcac tgatgagata acattattcc tgagtccaca    13440
gagcctccct gtggttagaa gagctgccag gactcatgca gccacctggc tctgcaggtg    13500
aacactcctg ggcagttcct ctgttattac agtcatttcc cccctgcgga ccgtaacttc    13560
ttatcctctc gtgttttat acacttggaa agaacaatat tttgccattt tgtttgtat    13620 tcagtaaaat gtgtcttttg aagtacaccc gaacggggac gccaaccaca ataacgaagc    13680
tcaatggcgt ggtatctgga ttttcactga agtcctgtgg actttcaaac ttgggtaact    13740
atcatttttc tcaatgagat attggtacca ttaagcctga gtgaagcaga gactatgtgc    13800
aatgggtcta actttaaaaa cagctgatgg ttatacatga agcgaaccca gtaacctttt    13860
actgtcttca aagtgaaatg gttcactatg tcctggaaag catttccttc ttaaatttca    13920
aatttgttct ttttataaac aacaacaaca acaacaacaa cagcataaat aaataaataa    13980
ataaataaat aaataaataa ataaataaat aaataaggtc ttcggatgaa ctttccattt    14040
ataatacaat ttacaaaccc tgtctgggat gtctatgatt ttgctggtgc ccctgccttc    14100
ctaacacagt ttcttcctt ggacagcttg tatcagggac attttcccta acacggtgct    14160
ggcagacctt aacattgaca gcgtggtggc cccagatgct tttgtctgtc gtcgcatctg    14220
cacgcatcac cccacttgtt tgttcttcac attctttcc caagcatggc cgaaagaatc    14280
tcagaggtaa ggcgttgtca ttaagggtca tctggtcttt ttaaaaaac ggccaataaa    14340 aatgtgctgc acaatcaaga taggaaacgt ctaggcagca ggacacttct ggactccttg    14400
agatagattt gaattgcgga aaggaatggt accagcagga ggaaagactg ggaccacgga    14460
caatagggca aggttcaaaa gtgttttgaa aagttcttag tgcattaca atttacgaaa    14520 cgcgacttgg tgattcaaga agcaatgtta ggatgaggtt gctattaaat gcttctctga    14580 gctacctta tttgctatac ttgtaccaag tggtctttct ctttgctata ttttatctga    14640
tttattcata cactcccttt ggtcctttag acatctttgt ctccttaaaa cctctgaaag    14700
```

-continued

```
tggattacca agcacacgca ttacaaagag ccacgcccctt tcgggcttca gtctccagca    14760
ctgcaggcac agtgtcccag gtaaacaatg caggctgtcc ctctctctga gctccacagc    14820
cccaaggaac tggatggctg tgaaggctac acacttcaaa cctggcgtgt gctttgttgt    14880
ctagtattct gccatccgtc cttttacaac gacactgatt tcttgggaga agagctggac    14940
atcgtcgatg tgaaaggcca agaaacctgt cagaaaacgt gtaccaataa cgcccgctgc    15000
cagttcttta cctactatcc atcgcacaga ctgtgcaatg agaggaagta aggcacaagt    15060
taggtggatg ctcttggagc atctccttgt aggatgagtt ttgcttacag agttttgttt    15120
tcagccgcag gggcagatgt tacctaaagc tttcctccaa tggatctcca acgagaatac    15180
ttcatgggag gggaggcatc tctggatact cactgaggct gtgcaaaatg gataatggtg    15240
aatacttgaa aaaatacaac tgaaggggaa tagtcaacct aacgttgcta gtctactaca    15300
cgaggctagt ctacaacaac catagagaga tggagacagc agcacaagga ggttgaggca    15360
ggagaatcag aaatttaata ccagattgga ttaaaaggca aaatcctgta taaaaaatga    15420
caacaaaata gacatggaag agagaacaaa gttaacaaat ttggaggttt tcccttacat    15480
atatgtatgt catatatata tatatactta tatatatatg tatatgtgta tgaatatgta    15540
tatgtatata tgtcatttca agtggcattt cctgtagaga cagacccaga gggccaattt    15600
ttgttttcaa gaagtgtttt ttttaattat cagagattaa actattaaac agtccattaa    15660
ataaattatt cattttcttc ccacttaata tttcagtgag ccatgattag atgctatgat    15720
atatgatatg atatatacac acacacatat ataatatatc tctcatatat atatatatat    15780
atatatatat atatatatat atatatatat acatacacat acatacacac atgcatatat    15840
ataattccag atgttaagct atcctgtaaa ttgtgatgag atttcatcaa taaagtgtga    15900
ccctaattac tcctcgtgaa agtttcaaaa gtataaaacc tttttcatca gatcatttgc    15960
tattctagaa ggtgactcta tccttagttt cagaggacct gatttacagc acattgagat    16020
gttttatccc aacaactgca gtgccctaaa cagaaaacat gccttcctag aattcactgg    16080
tttgatagca atctctgggt ggcctgagcc tcttaagaca gttaattaag ttatagttca    16140
tacacactgt gttttgctca tgataaactt acctaataag aaggaacatt caagacaagt    16200
attgtcttaa ttctacttct tcatggtaga aggggcaact agaaagacgg ctaagtcatg    16260
tgagcatgct ttaaaaactg ggatccagaa cagatagctt gatacactga agattacatt    16320
tctcacccac ttctgccttc attatgtttg tctctgttga atttatagcc tggtctgtac    16380
aggtgacaga atggatcagt tgtagattga cagaagagaa aatgtggagg gtaataaacc    16440
tgtctgcctt ctcatgcata gagaagtggt tacactgtac aatattgggc tacaatactt    16500
acctttatgc aagagagaag atcgaactca gttgttttc gtatttactc tgttgttggt    16560
ctctaatgta acttgacttc ctaaagacac ctagcaatgg acaccactaa aagaagtatt    16620
tcttcatccc caatgcaaag ttgagcacta aagttttca gcattctgtt caagttgatg    16680
gagcagacat cgagatagaa cttttctga aggcttgcat tgggcttact gataatgtgt    16740
cctacttact gcttgcctgt taactttcta aaggttacct ttctgctgat ggactgaaag    16800
gtttctgagg gatttctcag aagcctttca ggacgaggga cattgaagcc taggtaactg    16860
ctaaccacac tctctctgtt gtagtgtgca caactaaaat caacccagat gtggtaggag    16920
gagctgcgtc tgttcacggt gagtggccat ggcaggtgac tctgcacatc agccagggac    16980
acctgtgtgg aggctccatc attggaaacc aatggatact gacagcagct cattgtttct    17040
ctgggtgagt attattgcta ttctcctggg attgccatca tgaaggtgaa atctgggact    17100
```

```
atcataagag tcaataaaca ctttgaaaat gtaaatgatc ctgtttccta aattaattct   17160
ctctgtgtgg gcagggacga tggtgtagaa gagaccagtc ctcatcattt ggccacaata   17220
gaacagggc aggagcagag cagattgccc acctctgcct tttcattcaa acgcaaatta   17280
tttccattgt cttcctgatg gtgcctggtg gcgaagcaca gggccagagt gaagcttaca   17340
atcctcagct ctctgaatcc tggttaccct agtctctctt tctctgcctc cgaatgctta   17400
gagttcagca cacaccatca gaccagatcc ccgcacttag cattgctttt cgatattggc   17460
caaatgtgaa catcttagcc ggggaagtgt gtatctcgag gaaattcggt tgagtgaaac   17520
cttttctgtgc tacttttagt gcctctgttg cttccagaca caggtttaga ggctaatcgt   17580
tttgttaatt ttttccatg catggatgca ttatgcacat aattcaatgc tacacttgag   17640
atcaatagtc ccctttgcaa gcacatatga aaaacacag aaagtcccag tgacttttct   17700
ttaaattctg cccaagacaa ggttgagact aatacccaac tctcctgagc ttggagatgt   17760
gctgggggagt agaaagacca tttatttaaa gtgtccaata ttagtgcaag aactaatcca   17820
gtgatttcac tgtagaggaa atatgtgact aaaagttttg agaataaaat cacttttttt   17880
accacctaaa ggtagaaaca gacacagagt ataaataact gtgaaacaca aatatttgga   17940
aattgcctag tgatagattt tttttttccat tctgtttgtt ccttaggata gagacaccta   18000
aaaagctgcg tgtctacggt ggcattgtaa atcaatcaga aataaatgaa gggactgctt   18060
tcttcagggt tcaagaaatg ataattcatg atcagtatac gacagcagaa agtgggtatg   18120
atattgccct gttaaaactg gaatcagcca tgaattacac aggtatatat atagagagag   18180
agagttttag gtgacctaga taaaacattc acgttaggag actcacagtc tcatctatgg   18240
ggtctaatca acagacagac aaggaaggtc tgaaaagatg gcctcactct gttgagacag   18300
agagtttgcc ttagaatact agattagcga tccatactta tctccttgta ctaaggtcaa   18360
atctaagtgg atcaaggaac ttcacataaa accagagaca ctgaaactta tagaggagaa   18420
agtggggaaa agccttgaag atatgggcac aggggaaaaa ttcctgaaca gaacagcaat   18480
ggcttgtgct gtaagattga gaattgacaa atgggaccta atgaaactcc aaagtttctg   18540
caaggcaaaa gataccgtca ataagacaaa aagaccacca acagattggg aaaggatctt   18600
tacctatccc aaatcagata ggggactaat atccaacata tataaagaac tcaagaaggt   18660
ggacttcaga aaatcaaata accccattaa aaaatgggc tcagaactga acaaagaatt   18720
ctcacctgag gaataccgaa tggcagagaa gcacctgaaa aaatgttcaa catccttaat   18780
catcagggaa atgcaaatca aaacaaccct gagattccac ctcacaccag tcagaatggc   18840
taagatcaaa aattcaggtg acagcagatg ctgtcgtgga tgtggagaaa gaggaacact   18900
cctccattgt tggtgggatt gcaggcttgt acaaccactc tggaaatcag tctggcggtt   18960
cctcagaaaa ttggacatag tactaccgga ggatccagca atacctctcc tgggcatata   19020
tccagaagat gccccaactg gtaagaagga cacgtgctcc actatgttca tagcagcctt   19080
atttataata gccagaagct ggaaagaacc cagatgcccc tcaacagagg aatggataca   19140
gaaaatgtgg tacatctaca caatggagta ctactcagct attaaaaaga atgaatttat   19200
gaaattccta ggcaaatgga tggacctgga ggcatcatc ctgagtgagg taacacattc   19260
acaaaggaac tcacacaata tgtactcact gataagtgga tattagccca aaacctagga   19320
tacccaagat ataagataca acttgctaaa cacatgaaac tcaagaaaaa tgaagactga   19380
agtgtggaca ctatgcccct ccttagaagt gggaacaaaa cacccatgga aggagctaca   19440
```

```
gagacaaagt ttggagctga gacgaaagga tagaccatgt agagactgcc atatccaggg    19500
atccacccca taatcagcat ccaaacgctg acacctttgc atacactagc aagattttat    19560
cgaaaggacc cagatgtagc tgtctcttgt gagactatgt cggggcctag caaacacaga    19620
agtggatgct cacagtcagc taatggatgg atcacagggc tctcaatgga ggagctagag    19680
aaagtaccca aggagctaaa gggatctgca acccaatagg tggaacaaca ttatgaacta    19740
accagtaccc tggagctctt gactctagct gcatatgtat caaagatag cctagtcggc     19800 catcactgga aagagaggcc cattggacat gcaaacttta tatgcccag ttcagggaa      19860 cgccagggcc aaaaggagg agagggtggg taggggagtg ggggtgggtg ggtatggggg     19920
acttttggta tagcattgga aatgtaaatg agctaaatac ctaataaaaa tggaaaaaaa    19980
attaaaaaaa aagaatacta gattagactt tgagagtgca gacggagaga cttgccttca    20040
ggcttcttca ggtacataga atgacatcgt tttataaaat accgaagcaa taagaataat    20100
gattgatatt ttgctttagt aacaaagggc ttgacagcac agttgagcaa atgctacaga    20160
atattaaacc acattaaaaa tgaaaggtgg tgtaaagagg gcctgtctta ccctttcccct   20220 tgtcccttct gcttgggaca tttcatatgt gccactgaac acatgacatg aaacacatga    20280 gaaaagata acgaatatca taagaaaga gagcatgatt aatgtcaggt gagataacac      20340 cctttctgg gacaaatgat tggctttctt tctgcttcgg tcagcttttc gctactgtga     20400
caaaatgcct gatgtaacca ccctgtaaga aagaaaggtg atatgggctc tcttgatgtc    20460
agaggcttca gcctgcagtt gtgtgtgtgt gtgtggggggg gggggtcca ctgctttgta    20520 gcccttggta agaaatgtgc agaggagcaa attttcacct cctggatgct gggaagcatt    20580
aatgaaggga cggggctcct gatagcccct tcaaaggccc accctcaatg acgtcacttc    20640
cttcctacac cttccccccc aacacacaca cacacacaca cacacacaca cacacacaca    20700
cacattctcc attatctcta agtagtgtca caggctggga tggagtcttt gaacatgggc    20760
ctttggggag acacctcaga tccaaaccgt agtggcctct gatgactaaa ctgtgatttt    20820
caaaattaga ttttcagcgg ccaatatgcc tgccttccaa aggagataga aacgcagtgc    20880
acacagaatg ctgggtgact ggatgggggt acacagcact aagaggtaac aaaccatgcc    20940
ttctatctct gctttattct gaagtcaaag aacagagctt aaccattgcc tctgttttct    21000
atctagtcat atggcccaaa cgtgagtcaa gtcacctact caataacagg aagactgata    21060
acaaagatca atacatctga tcagaaacgt taaatatgat taaacccctc taaagaccat    21120
tttaactgga gacttttagt ttgggaccta acactctatg taaaagttct agcctggttt    21180
ctaattattt tgtctgaaaa gaaattctac ttagtgtcag ttaattttga acttaataac    21240
attaatgaaa ttatgtacac aatagtagaa acaatgtctt ctttatactc catacttaca    21300
aaaattactt atgaatcaag cttagtaata ccacccccc ccaggatttg tatgtacaat     21360
tttggctttt aaatataatt gtatataaac ctatagtaat tattcctcta aaacactaat    21420
atgacccttt tcaggtgaag tacaaagtac tcttcagaaa gccaaggttc cattggtgtc    21480
aaatgaagaa tgtcagacaa gatacagaag acacaaaata accaataaga tgatctgtgc    21540
aggctacaaa gaaggaggga aggatacgtg caaggtaagg cagtctcaag caatcagtca    21600
tgccagattg aagtgagagc ttaatgcatt tgtacaaacc actgtaccat tgagcagtgt    21660
ccgagtgtgc ttcctgttgc tgtgataaaa cactgaccaa acacaactca gggaaggaaa    21720
gggtttatca agcttacagg ttacacagtc caccatagcg aaagtcaag gtaggcagga     21780 actgcagtag agacggtgga ggagtgctac ttcctggctt ctgtttagtc ttgtgttccc    21840
```

```
tacttttctt ttgtgacaat gtggttaaca attagcagtg gagaaagttc cccacagtcc  21900
aggctgatgg cagaggtgcc tcagctgtgt tccctcttcc caggtgtgtg aggttgacaa  21960
ctcagattag ccatcgcaag cagatcactt ggtgggttta ttttaggtaa actaaactct  22020
acaggaggaa ggaaagctgg ataaaggaga acaattggat gtttggatgc ttgtgagagg  22080
gccagaatat tatgtaaaat tgctgtgagc aatacttact taactcagga aatgcctacc  22140
atgatcccgg catgtgtctt cttttctcc  cccttgaca gggagattct ggagggcccc  22200
tgtcctgcaa atacaatggg gtctggcact tggtgggcat cacaagctgg ggtgaaggct  22260
gtggtcagaa ggagagaccg ggggtctaca cgaacgtggc caagtacgtg gactggattc  22320
tggagaaaac tcaaacagtc tgaaagagtt caactggtat cactttgtgg ccctggaaga  22380
ttattccata gaaatgagct tgacgtctct gatgaagaca ctgggatact gactcttcca  22440
ctgtaaccaa ttgaatggcc ttgatgtacg taagaacacc cagaaagaaa actattattt  22500
tcagaattcc tgatctggga gaaccactgg ttgttttctg catccagcta ctactcaagg  22560
aaacaaatac agcaaggaga ttttaaaaat aaaaacacat cagatatata aggaaaatat  22620
caagtaaggg tgctgtctgc ctttttagtc tctgtgacaa atacctaaag tagttcacaa  22680
aaggaaaaat ttcttttgca cacctttcct caggtttcag cctacgatct ggttggctgg  22740
ccccattgct ttagcctgag gtgaggcaga accatatatc cataggaggc tgtggagaag  22800
gagtctgctc agttcatggt aggcaggaag caaatggaaa caggaatgta ttggggacac  22860
gaatggtcct tcaagaatat actgtcaatc atttacttct tccagagaca tcctgctccc  22920
taacctccct ttccttccca gataacacct ctgtcctagc tggccccaag agatcaggta  22980
gaaaggcaga ggaaaccata taagagttg  ttaagtgcaa aatcaaaacc agaaggaatg  23040
cagacaggag ctcaaaatgt ccatttataa gaatcttttt ttttctctgc ctatatgaat  23100
cccctcctg  tataaaggac tgactcaatt cagtgatggg ttttgagaag tctgtttgtg  23160
tgtgtgtgtg tgtgtgtgcg cgcgcgcgtg tgtgtgtgtc tgtctgtctg tgcacattca  23220
tgtttaggta tgtgcaggta cctggtgggg gcgatcaacc ttgcattatt tctcatgtgc  23280
catctacct  agcttttcaa agacagagtg tcttactggg attggagact tgggctaagc  23340
tagctatcta gcaagtccag ggaccattct gtctctacct ccccaaactg aaattaagaa  23400
gacatgccat ggtgcttaat ttaaacctct ctctgtcttt gtctctgtct ctgtctctgt  23460
ctctgtctct gtctctgtct cgctctctct ccttcctcct tctctccctc ccactctctc  23520
tttgggtgtg cacgtgcgca tgtgcaagtc atagtgtgtg tgcagggcag tggaccatct  23580
tcaggagtca atgctctcct tccatcatgt aaggtccagg gatggacatt aggtgttcag  23640
atttggtgac aaatgtctgt accttcttag ccacgtcaca agccagctgt tccgatttcc  23700
tacagatgct gggaatcaaa tctgagtcct cggggttgcc tggcaagcat cattactgac  23760
tgagctctcc agtggccttg tcagtcttct ctctgcattt tcccaaactg gcttggacaa  23820
gcaccattgc aggtgttaag tgcacacttc ctaatttcca catgggccga gtataggagg  23880
agcaattttc caggaagtgg tcccttgaag acacaccgta ctgatttgct tgcctcggaa  23940
agtatctcag cgtagcctgc actctttttg cagtgttagg ggaaagtaca ggtggatgga  24000
gataaggaag acaagccaaa acctaccaag atctgccagt gagtgggagt ttacaaagct  24060
gagtaatgaa tgtgctggac ggaaatgtgt gttgaaatcg tacatactac ggggggggg  24120
gggggggtgg ataatttggg agcaaatgtg gtttcaatag aggctgcagc ctcctcaaac  24180
```

| | |
|---|---|
| agttctctgt attctgagta cctgactttt gtcctcacat ggggcaataa tgtagtattt | 24240 |
| ggactttgtc cccgtacttt tcagtcagcg ttgataacta tacaagttgt ccaaatgaaa | 24300 |
| agtatttatt gtgcccaatt atgtcagagt gtcttgttga gcttggggaa ctgaagcgcc | 24360 |
| agccaataaa ttatgaaggt ttcataaggt tttctgttga tttagtacga accgaagaga | 24420 |
| ggagctgcac aaaatctata ctttcaaaca aagatgacca tgacacaaag ggttctaaga | 24480 |
| aatgacaacg aagaagagtt agcagaagct aagagagtgg catggaaagg aagtggcccc | 24540 |
| aagcaagaca aagcaaagac agcaaacaag caaaagccag agatcgatgt cactgaaatg | 24600 |
| gcacgagcag gctggattca aaatgcttct agagtaagac agaattgaca tcaaatgggg | 24660 |
| tcacaacttc acaacccatg aacaagcagc gccttttata acctatttat tacatttcac | 24720 |
| ataggaaatc ttttataacc tatttattac atttcacata ggaaattgag gaggcattgc | 24780 |
| tgtcttctct gagaagtatt taaggaatgt tttcgtctta attttttttc agaacaagtg | 24840 |
| caacatctta attctgaata tctagtacct agaaaatgct atgagctata aggaataaga | 24900 |
| aattacgctg agcagattca catctccaca ccaacaagct gcgaatctgt atactttctg | 24960 |
| gcacttttct cacttaatct tctctctcct ggagctagct c | 25001 |

<210> SEQ ID NO 3
<211> LENGTH: 74000
<212> TYPE: DNA
<213> ORGANISM: Mus musculus

<400> SEQUENCE: 3

| | |
|---|---|
| tgtaaactag atctccatct tagattaggc tgtgtgaacc gaatttattt acatcgttag | 60 |
| aaaccaaata gaggcctctc ggctattgtt ctcagattgc tctcattggt catccctgcc | 120 |
| ctccctctac tgaccagaac cttgccccaa aacagcctgt aataaacatc aacgctggct | 180 |
| tagcttgggc tgctatctct ggcggagaga tctttaaagg atgtatctaa atgcaatgtt | 240 |
| tgagtagctt cagagagctc taatagaact gtaaatatcc ccggtttaat tagcagtcct | 300 |
| gcagttcggt aatggcccat agctctctga gccgagcctc ttgaggtttc tagacttcag | 360 |
| aggctgcctg caactatgct gtgtggacct atgaaatttt ccttctcctg tactctaaac | 420 |
| ccccagctag cctttcctag acacctactc gcaattattg caaatccata actgactact | 480 |
| atcctccgga tttctaaaat gatccagtgt ttcagcttag gtctcaactc agagatactt | 540 |
| tagggctcag attggcatcc tgagaattaa gtcccctggg aaaagaacaa taaggaagaa | 600 |
| aactctacct acattggagt tgatgtcatt tttttttttcc ctccaagctc aaggtgatcg | 660 |
| cttgctttgt ggctggttgg tgggggagga ggggctgtac gctagttatc agcatttctg | 720 |
| aaccagctct ctcaaccgcg acaggtcagc caatcccggc agtaagcttt tacttgacag | 780 |
| gtttgttctg ggctgacagc cattgactag gtgctcagat aagtcacttg gctgagtcta | 840 |
| cggtaggtgg ggcgcgctca ccagttcagg ggcagtgact ggaagtttgt tgcaacatcg | 900 |
| gtaagcctaa ccagccagca gcaacaggag atacccttt gccccgcgag tacagatcta | 960 |
| gaaagggttc acctcattaa gcgaaggaga tgcgtcaatc ccccccaccc ccgccccgcg | 1020 |
| cctcccccta gggcccggcc tcttctccca cggtttgggaa cgcgcggtgt gggcagatcc | 1080 |
| agaacaggag tctcgtgtcc cggccttctg gctagctcta tgggttacaa gcgaaaggga | 1140 |
| ggaacagctt ggggactctc cgcgtcagcg tgcacaaacc ggcggcggcc agcagagagg | 1200 |
| ggtggcgggg gcacgtgctt ggatgtggct gcttgtgtaa ccagctcccc aggcgctcgg | 1260 |
| ccccgacagc gctcctgcgg acggctcgtg gatgctattc tctgctccga tccggcaaga | 1320 |

```
gaggggtcca gcagaccaca cgggagaagg aggcggggc  gatcacctaa tagagcagag   1380
gggaccaagc tcctgccca  ggagcacaca gataggggaa tgggaatttg gaaagttccc   1440
caactaggac cacacgtgac ctcctcctga agtagttcc  gaccgcggct catgtatcct   1500
tccacctcgc ctttgagccc tcccaggcct gctcgcccg  cccactcgct ggctgcagct   1560
tccgaacgtc ccatactcca cacccgggct cagtaaccgg gtcctcgaac atgcaaggtc   1620
cgacagggtc agaacctggc catcgcgatc caattctgcc gggttttcat agcggccacg   1680
aagtggggat tggggtggg  ggcttagctc tttgaagact gagcttggct gtgatccggt   1740
agacccaccg ctgcggggag ctgcgggtct catcaccggg cggtggaggg gtgtgtgtga   1800
ggtgcactct attcacggag acccactttg tccaaccagg ggtgtccttt gggccctgga   1860
aactcagggg agatgtgaat gtacacgccc cgtatgcaca atcatcatgc ttggctggga   1920
gcgttcatct ttcgggcaaa tgaacccagc tgcctgggaa gcaagaggcg gggcagggaa   1980
ccggagcccg atgaggtgac ccacgcggga gacacaatag gggttgttct ttgtgcaaag   2040
actgacacct tgaggacacc gtgaggggga gaggtgtgtt atctaggtaa agactgtcgc   2100
cgacaaatcc tagcgaagca ctgcaatctg accacagcgc agggcaggga atgaaagccg   2160
ttccgaagaa acgcagggac agacgcagga aggataatcc tgcccctgag gctcccggag   2220
caccgaccaa ggcggtcagc tagtgcgatc cacctgtgag cggtcagcga ttgtgctcag   2280
cgcaccctca ctcggcccca gcctgttgta cctttgccgg gtctctctgc gctgaggcca   2340
aagccggcgt agctccggga gcgagccgcg gacacactgg gcatgctccg cggcgttccc   2400 cgccctgtc  ccttccgacg ccccgccccg cccgccccg  tccccggctc agcgcccgcc   2460
tcccgcccgc ctcccgcctc ccctccggct ttccgaggcg ccctgctctc ccggcggggc   2520
ggcggagggg gcgggctggc cggcgcacgg tgatgtggcg ggactctttg tgcactgcgg   2580
caggatacgc gcttgggcgt cgggacgcgg ctgcgctcag ctctctcctc tcggaagctg   2640
cagccatgat ggaagtttga gagttgagcc gctgtgaggc caggcccggc gcaggcgagg   2700
gagatgagag acggcggcgg ccacggccca gagcccctct cagcgcctgt gagcagccgc   2760
gggggcagcg ccctcgggga gccggccggg cggcggcggc ggcagcggcg gcgggcctcg   2820
cctcctcgtc gtctgttcta accgggcagc ttctgagcag cttcggagag agacggtgga   2880
agaagccgtg ggctcgagcg ggagccgcg  caggctcggc ggctgcacct cccgctcctg   2940 gagcggggg  gagaagcggc ggcggcggcc gcggctccgg ggaggggtc  ggagtcgcct   3000 gtcaccattg ccagggctgg gaacgccgga gagttgctct ctccccttct cctgcctcca   3060
acacggcggc ggcggcggcg gcacgtccag ggacccgggc cggtgttaag cctcccgtcc   3120
gccgccgccg cacccccct  ggcccgggct ccggaggccg ccggaggagg cagccgctgc   3180
gaggattatc cgtcttctcc ccattccgct gcctcggctg ccaggcctct ggctgctgag   3240
gagaagcagg cccagtctct gcaaccatcc agcagccgcc gcagcagcca ttacccggct   3300
gcggtccagg gccaagcggc agcagagcga ggggcatcag cgaccgccaa gtccagagcc   3360
atttccatcc tgcagaagaa gcctcgccac cagcagcttc tgccatctct ctcctccttt   3420
ttcttcagcc acaggctccc agacatgaca gccatcatca aagagatcgt tagcagaaac   3480
aaaaggagat atcaaggaga tggattcgac ttagacttga cctgtatcca tttctgcggc   3540
tgttcctctt tgcttttctg tcactctgat aacgtgggag tagacggatg cgaaaaattt   3600
ctgtagttgg ggtgactata acgtttaatt ctgggcgcat ttctagatcg tgcatattgt   3660
```

```
gtctcttcca gtgtattcaa cctagggagt gttcggctag acggaactca tgcctccttg    3720
caagtgtcaa ggcacggatt gttttcttgt cgagctctgt ggtctcttct taaaatctat    3780
tgtccggtaa tacagagtac tgtacactgg attagcgagc tcgtcaatcc agccttctaa    3840
atgaactaaa aaaaaaaaaa aaatagacg ctttgggttg tgcatatttc gattagatcg     3900
tgacttgggc cctagatcta gggtgtagat gagattaaaa tgaaagtccg tgctgcacgt    3960
aggcatgttg cctcagaatc ttgcagtgat tgttttagt ttcctgggtt gcattggaag     4020 attttctga aatgtgactt gtggactgat ttgcataact ttataagcat agtcatcgtc     4080
agcatggacg gtgcacattt gagggtagaa gtagttttgt gtgtttaaac cgacgtaatt    4140
acaaatttgg agcctgcatt tggaagtttt gtagtttaaa atcaatagtg ccagaatata    4200
tatcattgga gcttttaata gaactttgtt aaattagact ttctttcctg atgagatgtg    4260
ggataggata tgaaatttgc atttcagtgg tatgttccat tcatttgacc tcgccacact    4320
tgatagaatg gagatcgaat agttttgat cccagatgat gatgtctgtg agtccaggga    4380
tgcttgctgt gtgtggcaaa tgactgcaga ggttaaactc agttctcaca tgaaatttaa    4440
gtagtagcgt gaattcgctg ctcatatttt ttgtttcagg tgctctgact cgttggctta    4500
tcagtgggtt ttagcctgat ttgtgcagaa cgtcaagtat aatttagccc gctaatatcc    4560
agacaaactg gcaggaatgg atcactggct ccagattgta ggtatgctag ctctctgcat    4620
gcagtaattt actgagtcag cttgttgaat aagacagaaa cccaagaatt ttaacgttgt    4680
atagttctga ttgtctaaaa gttaggcctt tgtacttcaa agttcgtgg tttaaagcat     4740 ttatctttgc agtttcaggt atggtgctgg ttatgatcag gggtaggaaa gagagccctc    4800
ctcttttgca gagtgggaag tgttgacaga aattgagagc tttggggagg ccagtgtgca    4860
aggtgtgcga aaacacaagt tgcaggtctg aagtgactga gcctttaaat gattgggcct    4920
tttggtacaa cccaaaattt tgttatgtga cttgtagcat tgaacagtat ttagttaaaa    4980
ttatgtaatt ttataattgg tggtaaggta ttctttgtaa aaattatttt ttagttaata    5040
ttagtagaca ttttcttaag gtggaagggc agcagcaact tgtctataca tgtcctgcta    5100
atagatcact atggagaact ttgttttatta attaatttat tatttttttt gaagaaaatat   5160 tttcatttgg aagaggtttg atggattaca ttagtggcat ataaaatgca tagctaattt    5220
tgattgagtt ttttgttctg acatgaagat gaaactctca ctgaagagct ggcttcacac    5280
aggctaattt tcttcgagc taaaaataca gtttgaaagg aatctttaat ttccgagttt     5340
gcgttaattg agaagcttta ctcaggatga acttgaccaa aagataattg gtgagcattc    5400
tgagttgtca cttgcttcaa ggcagtttac tgttggtgtg aattaatgtt aataatctcg    5460
atctagaagg aattagtcag gtatctattt aattaaaaaa aaaaaaacat tcaaagaaaa    5520
gtctagaatg cctggtaggc agacttcttg tagagtccaa agtacacttc tgctttgcct    5580
tcctttcccc aaaggacttc aagattattt tgtaaatttt ttttttttgt ctgagcagtg    5640
acgtgattgc agttccttat ttgatttcat actgcatggg cttctgcacg tgcagtttat    5700
gtggctgaag aaatccaaag ctctcccttt agttatggta tgcgtagaaa gcagcatcaa    5760
atactgcatc aaatgactaa taacaaactc ttaatttcta gagctgtggt ttgatggagc    5820
caaatgttga tgtgagaacg agtcaggagg ggaaaaagtc agcgagcctt gctcttctga    5880
gaggtgtgcg cccccttagtt ctgagaagct agggagaggg cttgcttggt tcctcatcag    5940
ggttttctgt gtttggggca gggattaaaa tggtcattga agatttgtgc tggtcagtgt    6000
tggcaatgag gttggccaag ttaaattttca ttatgaaagt agtaagttga atattttcat   6060
```

```
ttgctgaagg cacaattgaa ttactgtagg aatgtgttgg ttggaaatta ttattttttt   6120
tttaatatat aaaactctga agtctttttt tttttaaaga tttatttatt tttatttata   6180
caagcacgct gtagctctct tcagatacaa aagaagaggg catcagaccc cattacagat   6240
ggttgtgagc caccatgtgg ttgctgggaa ttgaactcag gacctctgga agagcagtcg   6300
gtgtgctctt acccgctgag ccatctctcc agcccaggaa attttcttta ccgtctggaa   6360
agtaggctga atgtgagaca gcaagagtta atgatgttaa agcacagaga aggttcaggt   6420
ttctggtaca gcttttttgt ttggtatatt tacttttcag atactgacca caggaatatt   6480
agtaccttgc agagagaata gtgattattg atattagctc ttttgttaaa ggcaagtgat   6540
tgttgcaggt aattatggtt tttctttata agtgactcta caaacttcat cttgccttt   6600
tcatagtcat ttgtgtcttt cctgaaaaat acaactagta tagtaagttg caaatttcat   6660
ttttcctaaa acttaagagg agtaaagtgc atcaaaagga gtaattttca gttatgtgta   6720
attcaatata aggaaaagaa attttattac tgtcaatttt agaagtttac acagcaatag   6780
agatgtagac tgagattcct tataacgtat taaataaaga ttaaatgttt caagttaaat   6840
atgatgaata taatctggtt atttctagac atagatttag aaagtggaga ttcatggcct   6900
ttaaaaatct ttattttagt aacaggagaa aggcagatag tgtattttca ttttttttgtg  6960
tggaacatta tgtctaaattt atcataatta tataaaatat atacctaagt attatgaaat  7020
agcttacctc ctggaaatga attcagttct tattttttaaa tgttacaaca tgagttgttg  7080
gttttttttt tttttttttt tttttttttt ctgttcattt gtttatagag tgacagtatt   7140
tttttttttt ttttcccgag acagggtttc tctgtgtagc cctggctgtc ctggtactca   7200
ctctgtagac caggctggcc ttaactcaga aatccacctg cctctgcctc ccgagtgctg   7260
ggattaaaag cttgcgtcac caccgcccgg caagtgacag cattttaagc cacttctaaa   7320
atagtcactt taatgacttg attagaaaat tgttcatgta ggaaaataga agtttgaac    7380
attcactta gtaaatattc agttttcaat actttatgtc tcagtaagct ccaaatgtag    7440
gcagtgtttt tctattgata acttatgtaa attcagagtt gacagggata agtttagagt   7500
cctgagtatg taggtcaggt tttcatttct gtaggcctat tccatttaga agtattctgt   7560
tctatgaggc agtgttagtt attagtacag cttaaaaagt ttacttgctc gcattttttg   7620
tttttccatg ataaactact ggctcataaa acagaagttt ggctgcacag agctggtggc   7680
tcgcgttttg ttcccctttc ttctcccctgt agataaaaaa gttgattttc agaaccagcg   7740
ttggagagtt ggttttgtga tccactcttt tgaaaagtta caggacttgt tccaaagatc   7800
atgatttagg tatgacactt tgtgtggttt tatcagaagt gatttctgta aatattcagg   7860
gttttttttgt agttgatttg tatgtggtag ttttgaagtt catgcagttg ctgagctatt   7920
agtgatgttg aatacagatt aaatagcttt atgttagtat ttgctgattt ttttttttat   7980
aggtcttgct gctgttgctt aaaagtgtct aattgtggga tgatggttct caggtcctga   8040
agctattggc agagatgaaa ttaggatcct ggctttgatg tcttaccttc ccattctgta   8100
ttctctgcta tggtttcaga agggacgata tagcagtttc agcttctaaa ataatttata   8160
ctggaacaaa aagcctgttt cttggaggaa ggttactatc agagtaaaca actaattttg   8220
cctgggaagt tttaattaca tttagaatag tcaggtatac tcttctattg caacggacat   8280
ttgtggacat ctttggagta ctaagactta acacttgttt gtggtgttaa ctttggagag   8340
atgcaaactg cagttgcacc cactaatgac ctgtatgtgc gtggtgtgga aaagcttgca   8400
```

-continued

```
aatctgctgt tttgtgtaat tagtcaaaca gttataatca gaaagccaac gcttaatacg    8460
aacagtgact ttaacgtaaa tatttgaatt tttctatgtg taggcatgca tgtgagtatc    8520
aagttaacaa acttactagt ctggaaaatg gattttctcc ttaaagaaca gactactttg    8580
gaagccattt taaaccataa ttgagtcttt taaattacat tgaaatacgg ctggtcttat    8640
ctatactctg aagttataat tatttatctt agttttaggt agacagggtc cctgtcttgg    8700
ctctgtcaca gagctgggta actatgctat ttaatttctc ttagtcttac tttacctgaa    8760
ataaaggaag gataatgata cccaccacaa aagtttatct aataccagca aggcagagga    8820
aggaggctat tgctaattcc taggcagtag ccttcagtac tacatagtga atttgaggtc    8880
cactatagtt ctatactgtg agttccaagc cggctaaggc tccatagcga gaccatgtct    8940
gaacaagcaa caatcaaatc acatagttaa tcccctaca gggtttctct gtgtagctct    9000
ggctgtcctg ggactcactc tgtagaccag gctgacctcg aactcagaaa tccgcctgcc    9060
tctgcctccc gagtgctggg attaaaggcg tgtatcacca ctgtctggat gttttcaact    9120
tttaagggaa catgaaaact tccttagttt tcacataata actttaagaa ctatctgttg    9180
taagattaaa ttttcttagt attcaatata gatgaatata aatagcatga catttataat    9240
atgtgtgctt atatgatacg atacatagca tatatgatct atgatacagt tatggtatgc    9300
ttgtccttag gaggcagagc ctcaccatgt agccctggct tgtctggaac ttgtggccat    9360
gcttggtcag tatcacagtt cttttttcaca aagagtattc ctcaccacta agaagtagga    9420
cttcgaatat gtaactcagt tatataaact ctcaggaaag gtacattagc atttcctttc    9480
tgctcttcca gctcacatac atacagcaga caatacagtc tgcagtgagc tactatagga    9540
atttaaagtt actgttaaac cttgccctca gtttcacagt gagccaggat tttcagtata    9600
actacaactt tgaaatggga agaaagagct agagagattt ttttccttcc catactgcat    9660
ttttaaaaat tactcatttta tttggggttg gggatgggag gaatggaaca gggcatacgt    9720
ttggaggtta gagaacagct ttcgggagtt gattctctca ttcctctctt tgacactggg    9780
aatggcagtc aggttgttag ggtagcagga agtgccttt agccagctga gccatcctag    9840
aagctcacat gcttttttct tatctagggg agggaagaac ggagtaagct taaggctcac    9900
ctacctgcac gtgacaggga ctagtttttc cttcctgtgc ttgtggtttc ctgggaatgg    9960
agcgccttaa tttccagggc tgtttcttat ttattttgaa atgcagagtg gatgctgctg    10020
taattattca tgactgcgct cttgtaattt ttatttattt tttgctgagc tttccctgag    10080
tattttagct gttttttttt tttgtagcag attataaaat tgagttgcat atcttttatt    10140
ctgaacctat ctcactgtct gaacgagttt ctatctttct cttctgtctg tgtacctgta    10200
ctataagcac ataggtgtta tatcactaga ggaccagtga ctttcattgc atggtaacac    10260
tcatgtaggt tttcaggctg aagtagaata atttcctccc tccctccctc cctccctccc    10320 ttttcttcc ttcctagtga tgcagacctc atttgtatgt tgttcttga ccctaggagt    10380 aggatgcagt tactcaaggt gtatggaagg gtatgaattc tgctttgaaa cagcttatct    10440
tttaaggaga tatatttcta aaagtgaatt gtaaaaatca atatttgttt aacaacgcta    10500
gaagcaaatt tttgctttga aacaaaatgc agatttttc caataaattt tttctctttta    10560 atgagacttt aaaaaaaaaa aaggttggtt tattagtgta tatgagtaca ttgtagctgt    10620
ctacagacac accagaaggg ggcatccaat cccattacag atggttgtga gccaccgtat    10680
ggtttctggg aactgaactc aggacctctg gaagagcagt cagtgctctt aaccactgag    10740
ccatctctct agcctgagac ttgtttttg aatgttttat gtttctctca actaaataga    10800
```

```
attaaaattt ttcttttatg ttgagaatga agtttgggga gatattatta aagttgtcct   10860
taggactctg tattacatta tctcctatca aacaaacctt aatgtactat attctctgtg   10920
tatgtgtgtg tttatagttt ataggctagc aatcaacatt ggtgtctcct ctgttgctct   10980
gtgccttgtt tattgagaca gggtctctca ttgaacctgg agcttgccaa tttggcaaga   11040
ctgtcttctg tctgtgccct ccagtgctgg gatcacaggt gtacacacca tacatggttg   11100
tacacaccac acatagctgt acatactata catgggtgcg taccaccata catggttttg   11160
acattggtgc tagggctctg acctcagatc tttgtgcgtg catagtaaag tactttatcc   11220
actgagccat tccctcagct cccatgctat atactcattg agttaatagt atttacaggt   11280
gcattatatc aatagacata agtcctaaat accctaatgt aagaaatatg ttgatttgtt   11340
ttgtagacaa ggcccagtga attagaaagg cagcctgcta gaatgcaaag aacatagcct   11400
ggcattagcc aggccctgga attagattcc tgccctagtt cccatctttc taatgagggg   11460
taaagctgtg acttgtaggt gtttcttttt gttgatctga acttttggta atgtctagaa   11520
acatttggt gaacatggtc atacctgagg tgacagaagg cctacttgca cttagtgggt   11580
tgaggctact gggctcttag acatttgcag aacctgggat ctgtttaatg ttaggggaag   11640
tgtttgatat gtagatatag tacctttgcc aaggtcaact gttgctgggt ggtaaaaact   11700
gggcccacat aggttttctg actattgtgg ggcctttctc tctctctccc cccccccctc   11760
tcttttcttt cttcctttct tccttccttc cttccttcct ttcttccttc cttccttcct   11820
tccttccttc cttttcttct ttctttcttt ctttctttct ttctttcttt ctttcttttct   11880
ttctttcttt ctttctttct ttctttcttt ctttcttttct agacatggtt tctctgtaaa   11940
gacctggctg tcctggacct cactttgtag accaggctgg cctcgaactc agaaatccgc   12000
ctgcctctgc ctcctgagtg ctgggattaa aggcgtgtgc caccaccgcc cagcggggct   12060
tatgtttctt ctaacaactt tgtccactaa agatatctct aataagaaaa agatttattt   12120
gacaaggtct catgtctttt agcattttgt gggagtttga acctctgctg aaatgctgtc   12180
tttgtcgctg ttctgaagag tatgacaggg aatgcaaggt ggatgtgcag tcaggtgttt   12240
tgctccttga agctgaagca ggaggattat ttttatgttt gaggacagct tgggcaacct   12300
catactacac cttgagttct agggccaggt cagactgtct caaaggccag gttcgcgctc   12360
accccactc agtgtttgaa cagttttctt tgtaattgtt tagggagtta ctttgctgct   12420
agtgtcttta atgttactgt tgtttaactg cttctttagt cttagatttt tttttttttt   12480
tttactctaa accttttgttt cttcagatgg ggtgaagtta aatgtgctca tgtgaagaag   12540
gggcaggttt ctgacaaaga ataagaaaaa tcatgaaatt tttccagatg aagagaatgg   12600
gttggcctga ctgaagttcc cgggtgctgg tcacctgctt ttctgagcct tacattggtt   12660
gttagcctgg ttactggaaa ttaccgtgat gctcctgaat tgggcatgcg agtttgcatt   12720
agtccaaaga tgcacagaaa ctaaagcagt aaaaaggaca gagaatttct tggtttattt   12780
ttagggatca caagcataat tataagtgtt ctaggaatag attagttgct atgttggttt   12840
cttttttcctg tttaattttta caatttcatt tgctgctcac tttacaacag aataaaatgt   12900
ccaaggcctt aatttttaat ttcttaggaa acttaagtac tgatttagag ttttggttct   12960
tgaagttgag ggcagtgttt aggtatgtat actgataaat gttttgaaac cgacatgact   13020
tgtcatgata gcttcatatt caccaagaaa agcaaatagt atccattgct actaaatact   13080
atccattgct aaattgaata gattaacagt gattaagtct gaattaagag ctcatttgct   13140
```

```
tactaaagaa aattccttttt ataaagagat tactaagaga aaaattttgt tgtttgctca    13200 tttgttttttt catttcttca aaacttcaag ttgttttcta attcttggtg aactcaaaga    13260
ggtatctttt ttgaataatt tatatagtgc ttcataattg aaattatcaa aaatacatat    13320
ttacctataa attaagattt ctccattttt ttctcttact attttttttat atagtggact    13380 taaagtttca aatagggaca attttttatga ttgagatttt acacaaatca caatcaacaa    13440
gaacaaaaaa aacaattgaa atattagagc tttgaaatgc cttcatctga aattacttct    13500
aggccatcta ttgcacattt aatacttaat gtttatatta cttatgtgag atagcacaca    13560
cacatataat gttatatgtt acatataata tatattaaat atttgggaca actttccagt    13620
ttcctagacc atgctgccct cgaactcatt ataaacatcc cattttttcct gcttctcaag    13680 ggctatggtt ataggtttat attagaattc caggctccaa atactttga tatattaatt     13740 tcatttattt tggagtatttt tgctgatttg aaattgaaat ggaatagaaa taatttgaac    13800
aattttcata ctaaagtggg catagctttg ttgctgtacc tttgaatcca taattattgg    13860
cttgccatga tgttacagtt gcagtttgaa taatgtggtt tatatttgta tagttggctt    13920
gtatttgttg tactatcaat taatcaatgt gcactgataa ctagtactag cttttggtga    13980
aaaatctgca tttaacagtt tgtcagattt tattttttaag tcagatacta aaagagaatc    14040 ttttttttcat agattttttat tatttaaatg cattttatat atatcaaaca taataatact    14100
gagtatttta ggaatcaaat aatacataaa aatttgttca atttttatat tcatatctaa    14160
aagagaatct ttaaccatat cagctaacca ttaattctttt atcaataaat tatattaata    14220 tttttttgtat aaacaatttta aaacaaagtg atagaaacat cgttttttat tttataaaca    14280
aagttactac taggtgtgct ctgtggcctg tgaccttagc accctggagc tgtccccaag    14340
gaaaccagaa gtgcagttac tcttggccac attgtaaggt gaagcttagt ctagaccaaa    14400
agagacagaa ccaagacaga aaaacaaatt acctgcttat tattaagtac gattcttttcc    14460 caaataaagt gaaacttaag cttgaaattt tcatctaggc ataaggttgc tatcttgggt    14520
tctaataaaa attagtggtg gcaaaaatct tttgttactg ttttcttgtt gctgcctggg    14580
gactgaagac ccagtcttca gtagcttttgg tggtctggtt tgtagggcat ttgatgaaag    14640
aacagtattg gaaaactgtg aagcactttc tcctgcattg tgtccggatt gtggtcatga    14700
ttgcgtgagt ttgaaaatat gagaaggtcc ttagaaagat gtttgtttgt tattactgca    14760
aaggtcatag gttgtggttg tgccgtgtcc agatacccag gcctgccatc tgttcctcag    14820
atgtaggaaa aagttaaggt aatttagtgg tagtaagtgg ttttgacacc tttgtttttg    14880
gaatcatcta attataagtt ttaagaccta agattaagtt ttaggccttt gtaaaaatga    14940
aacttacaca gtatgctatc atttgtgcaa aaccactaag ggcctgcttc agagctgaag    15000
atggctgctc cgagcccaac tctttactga agtgtctgca tgcttcagca caggagtgtc    15060
acgtgtcacg tgtcatgctt tcacctgacg tactaaatta cacaaaatgt tggggttttt    15120
taaactaggt tttctaacac gttatgtaag aattgataat acagaactca gtgagggcac    15180
tgacttagta agcagttta aacatttctt ttaagtatttt tttcaagcc ctgtgctttt     15240 tttctctcct acaacttaat tcttaattttt catctgcgtt tgaaggagct tcctcaggta    15300
aaccttttct cttgcattat acttgcatga aaatgatgtt agctatgctg tatttaaaat    15360
ctttaaaatg cctctatatg gcttaatata atctgatgag ttttgtatta tagttggagt    15420
ttttgatgtg ccaagtggtt attgtaaaaa taatgtctga agtttaaata tttgaatttg    15480
tatttttttt taaagattta tttattgtat ttatatgagt acactgtcac tgtcttcaga    15540
```

-continued

```
cacaccagaa gaggacattg aatcccatta gagatggttg tgagccacca tgtggttgct    15600
gggatttgaa ctcaggacct ctggaacaac agtcagtgct cttaaccact gagccatgtc    15660
tccagcccga atttgtattt tcaaacccaa cttcgggcct ggggtctata gttttgagt     15720 gcaagcttct tgtcaggtta atgtctggga ggaagaaggt tttgtcagta aagtttctga    15780
acttttgact agaataactg actttctgtg atgaagacta aactacaggc catgactgca    15840
caggagtcag ggcgtacata gatgatcctc agattttggg cagcttttac ccaaacattg    15900
agtttagaaa ctgttctcca ttcggctcac ttcgtatttg gatagcatgg agtattaaag    15960
gagttctcat tattgtcatt tttattgctt ccatttaact ggtattttg tcttttgtgt     16020 attgagctct ctttctgtct cccccctctc tgttagggcc tcactgtgta ggtctagttg    16080
gcctgaacct cacaagactc ccactgcctt tgcctccttg ggttacagga gggtgccacc    16140
tcacttcagc caaacaaacc ttgtatgttt cagcacttta tttatcagtt gaaaatactg    16200
actttcttct tttttaaat tttagccttt tttctatgg ctttaaaata tattcttga      16260 acataaggat gataaattac aaaggtgctt tctcccacag agccagtaat tattttctta    16320
taaaaattgt acccctccaa tcaatttctt taaaaagtag tttatttaaa tgtgcaccaa    16380
agactcattt cttttttttc caaatatttt tgtatttat atgtaagatt gttctgtctg     16440
catgtatgcc tgcatcaagt ccagtggttg tgagccacca tctgggtgtt gggaattgaa    16500
ctcaggatct ctgggagagc agccagtgtt cttaactgct gagctatgtt cccagcccct    16560
aaagacttgt tcttactttc catctatcaa tacagttaaa atgttaatag aaaagtttca    16620
tattctaaag tgaattttaa ctagcatatt ttaaaataca atttcacagt tcagggaata    16680
attttataat tcaaagttga ttataatgat ttaaatgttt tcagtgggaa taggaatcct    16740
tttacaatat taaaacaagg caattataaa atcatcaata tgactctact ctagtaatga    16800
gtgacagtat atatgtcttc atgatttaaa atctacataa ttacttccgg ttcattttat    16860
ttttcttcag tccaaaacag tccatagggg caaatttatt tataccactt gcaatagaaa    16920
cgaagccatt tcatttgatt tctatgttag taatacaggg taaagaaaca ttttatttca    16980
tgtattacat caaagtcata tgtaaagtga actaattcag cccacagatt tggagttttt    17040
ctgttttaaa tagtctcaaa gtctgctttg aagggtaaaa ttttgactgt taaaagcaac    17100
taaaaatttt gcaattttgg ctaaattgaa ggagactggt ccatcggcag gcaggacata    17160
ctgcgtgagg accctgagtc tcttcattct cagtgctgaa cttgctaagg cattgcaggt    17220
gaatgttttg ggtttttttt tattttgca agatgcagct actactaagt taattggcac     17280
taaatatgac aggggctttg ttctcaagtt actggtccat ccttcaggca cataggaata    17340
tctctcctgt cgtaagttag agactttaat atcttttgaa tgattataaa gtagctaaaa    17400
cttagtgttt tgtttctaag cagcctgttg caggagtaac ttagaaatct aatatcaaat    17460
atgaagatta gagcattaga gagatatctc ttatagcttt atgttagtgt tgaatcaatt    17520
acagctttag tttttatagt cttgtgtgta ccattatgat ttttctgtag acagtttgga    17580
gtttgtgttt gccttagttc tcataaagtt gttaatatgc ctgatacatg ttgggcttct    17640
gcacttttgt gcatattttg tcattagtgg tcaatcttag atggcttttt tagtggcaag    17700
aaaaccaaag agatgccggg ctggtggcgc acgcctttga tcccagcatt tgggagctag    17760
aggcaggcga atttctgagg ccagcctggt ctacaaagtg agttctagga cagccagggc    17820
tacacagaga aaccctgtct cgaaaaacca aaaaaaaaaa aagaaaacc aaagagtgtt      17880
```

```
atgcataaaa gtgtgtatgt gtgtgtgaac caaagagaca gcgttgtgtg tggatgtgtg   17940
cgcacacttg aatgtagtgt aaatgcagta gagctttgaa acaggaaacc agtcttttca   18000
tattttccag agacctagga agaagctaat tgttctatat aaactcatta gaaattaaaa   18060
gttttagagg ctcacatatg taggcttttg agcagttgca ggtacattat ttcataatta   18120
acttctagga agaaaaactg ggtgggaaac tagtagggat gactagtaag caagccatcg   18180
gtaaatatgc ccaataaacc ttactttgga tttcggagtt gctgacttta aaaggaactt   18240
aataaactaa gtaaaccctta tttgaaattc agaatacttt tttcattgaa aaattgaaag   18300
ttttattgaa agttttttcat tgaatttatt catatccaga tataaataag attggaatca   18360
cttttaaaga gattctaaaa cttaaggatt cagtggaaaa aaatgtgctg gggataccca   18420
gggacttcca gatgtaaggc agagtgctct accattgagc tatgaaacca ttcctttctt   18480
tctttacttt ttttttttaaa gagatttatt tattttatgt atatcagtat accattgctc   18540
tcttcagaca caccagaaga ggtcatcaga tcacattaca gatggttgtg agccaccatg   18600
tggttgctgg gaattgaact caggacctct ggaagaacaa gcagccagcg ctcttaaccg   18660
ctgagccatc tctccagccc tctttcttta cttttgagtc aagttttcct tcactgaccc   18720
aggctagtct taaaccctgg aggcccagaa cttgtgatcc tccagtctca ccctaccaaa   18780
tagctaagca ttatatagcc ctgcaccacc atgccaggtt gattctgttt caaagggtgt   18840
tactggcact tgggtgtggt gcctgtaatc ccagtattta gggaagacag gaggaacaag   18900
aggagttaaa ctttcctgct ggcaagttgc agaccagttc aggctaagac acccctcttc   18960
ccacaaaaag aaagtttgtc actggaaatt aagttagtta atgtatatgc ttacattctc   19020
atgtatgttg ttattgcata gccattgtca gtgtttgata cggttttctt ttcacaaaga   19080
gttttttttt ttttttttggt ttttcgagac agggtttctc tgtgtctggc ctagtatttg   19140
tttttgtttg tttgtttttt tttttttta ctttatttat tatatgtaac tacactgtag   19200
ctgtcttcag acactccaga agagggagtc ggatctcttt acggatggtt gtgagccacc   19260
atgtagttgc tgggatttga actcggaact ttgaaccttt ggaagagcag ttgggtgctc   19320
ttacccactg agccatttca ccagcccta tttatttatt tatttattta tttatttat   19380 tattttttga gacagggttt ctctgtgtag ccctggctgt cctggaactc actcggtaga   19440
ccaggctggc ctcgaactca gaaatccgcc tgcctctgcc tcccaagtgc tgggattaaa   19500
ggcgtgcgcc aacacaccca gcttgccctt tctttcttaa gcattttctt tgtaatatgt   19560
tacatgcatg ttagggcttt cagtgtccct tgttgaaagc actccagtaa tggtaaatgt   19620
aggttgttct tgatgtctgc tgacttgaca ggccatgacg aggcttttcc ccttcaggct   19680
ttcccttgtt cttgactatg acccccattta tgcatatatg cctgagtaaa ttgaactact   19740
tgacaggcat ccctaaacct gtgtctgttt tatgtaaatc ctgtcctttc tgtgtgtctt   19800
tatgagttgc attgggctct tgttcctgga tagatttctg tctctttcct gcagttctct   19860
gcttggactg ttctagccac ttaagtatat cttttctaat ataaatctta tttttatgt   19920 gtatgagtgt tatgcctgca acatgtctc tttcccgtat gcgtgtctgg tcttcactttt   19980 gatatgggta cagggaacca aaccggatgc tctttctgca agagcagcaa gtatgtttaa   20040
ctgctgggtc atctctccaa acactcctgt gttttcttct gtcaccagaa ggcgtgtgtg   20100
agtgctaccc aacataatac tcacttggtg atgcttatac atacttccac ggatccctct   20160
gaaaacatct tcatttaaaa aatacagtag tactttagt gccatggtag gtctgtgtgc   20220
ctgtcttcct tgaggacggt aaccactgcc cggccctaca gactttttaa tttgtctcat   20280
```

```
ttattcttgc ataatattat ttagcctgtc cctctatatt attcctataa gttaacattt   20340
tttttctcaa aggctttgag agttggtgtt aaagattctt ggccattaca gatgatgctc   20400
tgcctttgta gtacctatgg ccaaagcctt ctcatgactt ggagatcaat tactgagtta   20460
tatgtagaag gcaaatgtat ccagaatatg taggcggagg tcttaagtgg ttgttttaaa   20520
ggaggtaact tggtatagtt gatgtgaaaa tcttgtaggt agttatgaga tggaacccca   20580
gaacaaatga gagctagaaa gatggataaa attcatggaa gtgtagattt ttagttaatc   20640
ggaaataaat tctcccagaa tatagagatg ggtttttatg ttaactggtt ttgaattgaa   20700
actaaggaca tgctaaggac taattacact gatgagaaga aagcatgtag gcttgagcct   20760
cagtcgcgta ttctgacatc acagctgtca gggatgaggt tatcactgcc cgccgagtca   20820
ctgtgggcag taggaactta tagaagtcta aggatagtga gtggctgact gtccaggcta   20880
tagctcaagg agcagacaag tacatttgac gacctttat aatcacagct agcgtgggaa   20940
aagctaatgt tttcaaatgc atgcatattt gtgtcattgt atattctagg tatttcctta   21000
acttaataat ttagatattt atccaaatat tattgctatg ggatttcctg cagaaagact   21060
tgaaggtgta tacaggaaca atattgatga tgtagtaagg taagcattct tgattttcta   21120
tttcttatat taataaatta ttttgatgtg ttttatttag aaaagatccc gaaaacacag   21180
accagtattt gcattttgat gtgttttggt aaaactctga agttttaac ctaaagcacc   21240 tgacagctct cactcggctg gatgcgtcac tggatgagaa ctggctagtt atatagtcgt   21300
gtttgtttat gtcatgaaga tttttttttt tgtattccat aatatgtctc ttaccaggtt   21360
attctctggc ttgtattaca gtacaaggtt ttgactttgt atttgggtta ggccttgctt   21420
aagtaggttt gtttagttat tcaccctgcg gtatgagtga ccgatgtgtt ttatgtagca   21480
cttatacctg tagcagtgtt tgatacaatg attttggaga gacttgctgg acattcattc   21540
aaaagagtaa atgaagagta tcataatttt acaaaatttc caagtgtgat tgttgcttag   21600
ttcagaaaag tgtttctcaa ggcccactta aaaaatttag tttcagaata aaaatgcaat   21660
tgtatgagta aatgaacatt aaatttttgt tgcaaactat catagttttt aacaattcat   21720
taatactgag tcttgctgta tttgctatgc tggttctgaa gtactttaat gaatttaaaa   21780
gttaaaattc tggattattt cctttttact cataagtgag catctttcct ggtgcttta   21840 actatgtgtg attatgcaga tttaaatagg tgggagagtg ctttgtaact tagagtgtca   21900
tgcagatgta ggatgctttt gtggtactgc atgacttat gtctttagat gagctagtag   21960
tcagtttcct aagtggctaa ttttactgt tttaaattgt gcttgtttgg ataatttatt   22020
ataatattgt ttatgttttg ttcaggttta aatttcacca tctataaaag tctaccaaaa   22080
ctaacaccaa accccttact gctttgtagt ttccattaaa ccttaggtta tcctgttaga   22140
ggtaactgtt taaaagcctt taacaatagg gaaatacatt tgccttctta taattaggta   22200
gaacacagtg gaaggatact tagcatggca ggcccacagg aacacagctc gataggaaca   22260
cagtgatgat gcagagaaaa tgaaatacgc cacagaaaaa aagtaagaga ggaaattttt   22320
tcattgaaag ttgcagagta tggttaagtg gcagtttggc cagataatta ttttctgctt   22380
tgatgcagaa ttgtttatgt ctttcatgtt atgcctcata agatacacta tttcacatca   22440
attttatatt cagccaagga ccaatttaac caaaccaaat tcagctgtat tgaaaagggg   22500
agcaagttct ttcttaagt ggaggggatc ttttctggcc atgtaatgtt cttttgacta   22560
atctggcatg ctaattttat attgattct cttaagtatg aattagtaag tgagggtgat   22620
```

```
tagattatct ttaaggttac aattccagtt tctagacctt taccoctggt tattagacct    22680 tatactacag taacttagcc aaaaatatgt tgtgttgaaa aattagtttg gtcctgagtc    22740
ttctggtttc atgattccta tacttttgct tgcaaattaa gagaattgca cattcatttt    22800
tataattagt aactaagacg gaattaatt ctatctagct ttatctatct agtttttta     22860 tttagcctta ggtgttctct ctcttttaaa gaaatctatc tgtattattt agcttgttct    22920
tttagcttct tactttaatg tttttataaa actgttctgt gtttggtttt tgttgtttgt    22980
ttgttaagat aaatgaccat taaggcctgg ataacttctg tttatcagtt ccccacccac    23040
ttttatagta aagtatgaat agtgactaga aaggaagata ggcctttcc tacaaactaa     23100 agtgactaaa aataactttt ttgtgatttg tttgtttgtt tgcttttttt ttttttttt     23160 ttgagatagg gtctgaatta agtaagtagc cttggctagc ctggaagtcc ttatgtagaa    23220
ctgtcttgtt ttgaactcat aggcatttgc ctctctgtct ccgcctcgga ggactgggat    23280
caaagccaac accattacat tagccctac aaataatgaa ttacaatgcc ttttaggatt     23340
gccttctcca aagaacactt gtgtctaata tctaaataac tgattacttc agtttgttca    23400
cactatattg gtgatgttag ttttaatcaa tagtgagtgc ttccttttgc tttaaagttg    23460
ataacatctc agtacaagta ttttgtttt catatcacca gatagcccag aagaagcagg     23520
tgatgtaaga gggggttcgt ttgcctcatt gtttgagaag gctttctggc tgtggagggt    23580
gaggagggag ggcagaggcc ctccatccct ccatccatgg cttcctgagt ttggggcaga    23640
gttcatggtg gaaggagtgg aggcagtaac tcctcatggc tgtgaaagga agcaggaacc    23700
agagaaacct gcagataatt tgccctgact gactgatttc tgtcagccag atttcacttc    23760
caaaggctcc acaaccgggc tgggaggagg atttcagatt gaaactataa catgtttgct    23820
ttcttattaa taaactttt ttttgcagtt aattttctt tgctttgtct agtagggtat     23880
ccaaaagata ttttaaacta tttttctttt atctaattcc atattttct tatatttccc     23940 ccaaacaaga aatatataaa acttaaatct ttgctattgt actatagcgt tacctggagt    24000
gaggtaaact taaattgcaa atattttcat gcttaaattg tcctatgcag aaaggtttgg    24060
aagatatagt gtgctatgat aagtaaaatt tcatagctga gatctacaaa atttgagaaa    24120
aatatttagc ttcttcattt gagatctggg attcatgtaa aaaatggaaa tggaggaaca    24180
ctgggcttgg aatttgcttt ctaattacag atgatttgct tttttaatc taaggagtga     24240 gctgacaggg caggcagggc aggagggact gcggaggctc ccacagtagt tgttgtcgtt    24300
cctcttaact gcttccttct ttttttttt cctcattttt tgcaatgaag agggggtgat     24360
gcaccaccag cacttggctt gatttgtgct tttccagtgt cctttaggct ggtgggaaag    24420
ctctgtggct ttaaatctaa gcagtcgtga acagactggg gcatagtgtg tctaaggagc    24480
ttgtcttgta atctcttctg cccaatgact caggaaaatg tagatgtaac agaggcaaac    24540 tacttttac acaaaatgtt tagtacagtg ccaccaggta gacctttccc cacctttatg     24600
ttttctcttg gtttcctttt ataatttgct aactctcatc ttcctagaca gtgtttcatg    24660
gagctcaatt tggaaaatgt tgaaaatgaa aaagttatgt gtacagaatt gttctaagtt    24720
tgatatgttt tgaggtggag gcatgctata tgacccaggc tgacttatgt atagtccatg    24780
ctggtttcta attcatgatt tttacactcc tgcctatggg tgtccatcaa gcccagtttg    24840
tctatagctt ttataaggaa atgattagag ctcagtcttg tgacataatg atttaacaaa    24900
aagctattac tgttttgtaa acccatgtat aacctgttac aggttcaaga gtcttattgt    24960
ttcttgactg ctggcatata tatttctttt ctgaagaaac tttgcaaatg ttcaattctt    25020
```

```
ttttttttttt ttttttttttt ttttggtttt tttgagacag ggtttctctg tgtagctttg    25080
tttgtactgg aactcactct gtagaccagg ccggccttga actcagaaat ccgcctgcct    25140
ctgcctccca agtgctggga ttaaaggcgt gcaccaactc tgcacagccc tattcattac    25200
ttaatggccc tctgaataat gttttcaagt cttattttta attgatagtc aataatgatg    25260
ctagaataac aaatagttct ttctcattga aaatcaagaa aaaaaatgt tgagcggtgg      25320 tggtgcacgc ctttaatccc agcacttggg aggcagaggc aggcggattt ctgagttcaa    25380
ggctggcctg gtctacagag tgagttccag gacagccagg gctacacaga aaaccctgt     25440 cttggaaaac aaaaaaaaaa aaaggaaat aattaataat aataataata aacaggaaag     25500
attacttctg ttttccatt ctaacatttt tttgcccctt tcctcatttt gccttcctct      25560
tttccatttt aaaaaaatta gtgagttaac ataatagtca ctgttttaaa ctgtaatttg    25620
agtgacattt aatattttca cagtatagcc agaggtaatg cagtcaccac cgataccaaa    25680
ttccagaacc tttttatcac tcctgaaagc tcctggctgc ccttcccttc tgctggctgt    25740 cttttcctgca catggggaga tttagtgtgt tggacaataa taatgttatg ggcacaaact    25800
agctttgcta tttaatagcg gatactgttt tctgtacatt tatttattta ctatttatat    25860
ctgttaacta ttgtataacg agcttgcata taccatctta ctaagtttgt agacggaatc    25920
taatccctat ttcacttta taagtgcctt aaaagaaatt agaatcttca gttgccacag       25980
cttagaagta gcaagaagct ggaagttgag tccgtgtctg tgagattcca agttgatttt    26040
tttttctttt ttgtttgtta ctgtatttaa ggcaaggtct cactgtgtag ctaaggccag    26100
tcttgaactc aaggtcctcc tggttccata ttctcagagt gctctgtgta taatcttatg    26160
gtgatctggc cagcaaaaat tcaatttta aaaagttttt taaccagggg agggatgcag     26220
tctggagttt gaactcagtc attactaggt acttcaccac tgggcattac ttaaagctgc    26280
ttcccttaat atcttttttc tgtacatcaa aggacaaaat ctagaaacac ttggacaaat    26340
cgagactata cttaaaaatc atgaagcctc gtgcaaaacc ctgtatttct agcttatttt    26400
taaaagctga aagagctgtc aaaactgaat tcaacattcc tgtgtgatgg atcaagtatg    26460
gttgtgtaat gctctctggc attaaattgt taccatttct ccattaagga ctgtttctta    26520
gtgaggtttc cattgctgga aatgtgcctg gcccaaggaa tggcactatt aggaggtgtg    26580
gtcttgttga gggatgtgtg tgtgtcattt tggggttagg ctttgagacc ctctcataac   26640
tgcctgagga cagtctgctc ctggtgtcct ttggatgaag atatagaatc ctggacacca    26700
ccatgcttct tgctgtgata actttcatta tattgaaagt tgttatattt taataatact    26760
gttaatgttt taccttgcct agtttattca acttcattga taagtgtgta tatggaaaat    26820
gtacatacag tttgtcgctg tccaaagttt caggcagcca tatggaaggc gtgtgtatag    26880
tgtaaggttt cagctgagga tacattacat tccttgttaa accttagtgc tgcagatgtt    26940
ctctcacttc cacttgaagg gctgtctata gcatttcttt taagttttcg taacttttgt    27000
ttctctggga atatttcaat ttatttctca ttttttgaag acagttttg ctggatattt    27060 tttatttcta ggaccttaaa tgttatattc ttacttcctg ttctgagggg gaaaaatctg    27120
ctgataccaa cgctcctttg tgacatgttc cttctctctg tatttgagac tgtgggtctt    27180
tctcaggaga gggtcttgca taatacaggc tagcctggag tccttgtata tatgcaagga    27240
tgtactaact gactttttgat cctcctgctt ccacttgact agtgctctga tttcaggagt    27300
gcaccaccat caaaggttta tgtagagatg gggacagatt tctcagagct ctgtttgtgt    27360
```

```
tatccaatga gatatgcccc cagcctgtct ttgtcttgtg atggtttgat tgcgatctgt   27420
cttagtaagt ctctgagttt ttgtgaattg tggttcattg agccagaagt tctttatatt   27480
cttttatcaa atttgagaag ttttgactgt acttctgtat ataattattt ttctggaact   27540
ttaaagatcc ctaaggtagt ccagttgctg ttgtctcaca ggttggttaa tctcttacg    27600 tttcttcagt aagttgcttt ctgtatttg atatttatcc tcctacccta gttcctgggt    27660
gtggaatgtg gtttactcca ggaaagaaga ttgactttct cactcttggt agccaatagc   27720
tccttagccg gggatgggac tttggtcatc acttttcttt gcttggcttg tgctttcaca   27780
ggtcttgtgt atgctgttag ggttgctgtg agttcatatg tgcatctggc ctgttgtgtc   27840
tagcaagcgc tgtctccttg aagtcaccta tcattcttgc tcttacagcc ttcctgccct   27900
cttccacata gatgcctgag ccttgaaagg aagggtatga tgcagaatac catttgctct   27960
gaacattttg aagtctttct ttgcaggttg tatgtactaa ttgccatcaa cagaagcttc   28020
tctgatgagg gttgagctgt gcactgtctg tggtttattt agcagtagtc attagcaatc   28080
attctattgc tgtgtccact tacccgagga atattggtag gttttcccta ggctccatgc   28140
ccatctagct acaggctttt ggcctcattt tgacaatgtt agatgtggct tccatcttat   28200
agaacagacc taaatctaat caaaaggtgg ttggttattc ctataaacat ttttattcca   28260
cttgactgta cttttcagcc atggctagga ttacaagtat gaactactgt attgttctat   28320
ttaaattttt attaagagtt ttttcatata tcttgatgat attctttccc attcttcaac   28380
tcctcccagg tcttttccca cctcccattc cgacaaatgt catgttcttt ttttctttcc   28440
ttctcaagaa gaaaaaaaag aaaatcaaca aaacccaata agacaaaaag tgacaaaaca   28500
aaacagaaaa gcacaaaaac catggagtcc attctatgtt ggccaactac tcctgtgcat   28560
gagcgctgat tggagcgtag ttgatatgtt ggagaaaact gatcttctgt ttctcagtag   28620
gaatcaactg caaatcgttt cttggttaga ggcagggctt tgtgtctgct tcagatttag   28680
tgctgagatt ttgtttggtt tgacttgagc agatcttgca catgctgaaa caatctgtga   28740
gtttgtgtga caccettgtt gtgtctggaa gatgctgttt gcttagactc atttactacc   28800
tctagctctt cccatctttc ttccctttcc tcggagtaga tccctgaacc ttgaggggag   28860
gggttcaata aatgcatccc atttagtact gagtgttcca aagcctctcc atttgtacgc   28920
tgtgttgatg tatatgctta atttcatgtg ggggttactg ctttagatca ttcagtttcc   28980
agataaaaaa cacaaacttt taaaaattat ttataagcct aatgagcac taaagctggg    29040 ctggtatcta ccttctaggc tattagtatc tacttcctta ttggtagccc tgagttataa   29100
cttgccatat ttcatctggg ccactcttaa ctccaattgg ccagccttca tgaccgagtt   29160
ttcatgaatc acttaacccc actgtggctt ctcctctctc tattgtttcc tgatcttctg   29220
cctcagaccc caagcctggg aacccaaacc ccacctaact ctcttcagcc tagctataag   29280
ctgtaggcat cttcattcac caatcaagga tagctttcag ggttatagag cattatttga   29340
tgtatgtgag gatcaccttg gcccagaggt aaccagggcc aatatttagc attacaatat   29400
ataacaacag accaaacctt aacggtttta aattaaggtg taaggtttat acagcaaagg   29460
ctggtaaatg tgaaattcac ttgtaggtct aaatctttta gtacagaatt cagcattgct   29520
atacatagca acagaccaaa cctcaacaca ctcttcagtt gtgggtctct gtgttaatca   29580
ccatctactg caaaaagaat tttctctgat gagtgacaca ctcatctata gggagagcag   29640
tatgttagga atatttctgt ttctttaata gaataatagt agtagtaggt tttcccctag   29700
gctcatgact tgtctagcct taaattctta gcctcactag cagtggcagg catgggttct   29760
```

```
attttaagga atgggtctta aattcagttt ttaaaaagtg gttgtttgtt cccataacat    29820
ttatgccaat attggatcaa tatatatgcc cgcgagcatg caggtctttg ttgtgggtca    29880
cagagtttgt agctgggtta tattgatgac tacttttatc ttccagtcgt gtgcaaaagt    29940
accttccagc accacgagtg ctagtcagta gtgctgaatc tctagttggc tgtcagctca    30000
atctctctgt gctcgatgac acaagtaagc agtatcttaa gcaacaggac taccatctgg    30060
ttgtggagga aaacagtagc cttggcagta gccatgatgt tgggattgca agtatgtgct    30120
atcgcacttt gttctttttt tcaagacagg gtttctctgt ataccccttg cttcctggaa    30180
ctcactctgt agaccagaaa tccacctgcc tctgcctccg aagtgctagg attaaaggcg    30240
tgtggcacca ctgcctggcc tgtgctttgt tctttatgtg ggttctggga ccctaaactt    30300
agactaaggt gccttcctag tcctggaatt ttcctttta aaattttttt atttgttttt    30360
gtatgttggg gtgtgtgtgt gctatgccat gccacacttt tagaggtcag aggacaactt    30420
ataattcttt ccttttactg catggttcag tttggtggca gttatctttt ttttatcttc    30480
tcagctaccc atcttgttaa taactcagaa gctgcacttt cctgcctcag ccttccgaat    30540
gctggcggac aagtgtgtac cactacacct agctctttgt ttctcttca ctttattgat    30600 acttctgttc atcatttttc ttgatcttac ccgtgtcttt ttttctttt tttgagacag    30660 ggtttctctg tgtagccctg gctgtcctgg aactcactct gtagatcagg ctggccttga    30720
actcagaaat ccgcctgctt ctgcctccca gtactggga ttaaaggcgt gcgccaccac    30780
gcctggcata cccctgtctt tcattagctt tctgagtatc attaagacca cacaaatctt    30840
tgcctagtaa atttgctttc tggtttttct gagagacagt tgttgactt tttaacttat    30900 tcgattttg agtatccaca catcttattt tggggtgtga gatgcacac ttgtgtatgc    30960 atgtatgttt ttgtcttggt cttgtaaatg tgtgtgtatg tgtgtgtgtg tgtgtgtgtg    31020
tgtgtgtgca tgtggtgtgt gtgtgtgtgt gtgtgtgcat gtgcgcttgt gtgtgtgtgt    31080
gcatgtgtgt gtgtgtgcat gtgtgtgtgt gtgtgtatgt gtgtgtgtgt gtgtgtgcat    31140
gtgtgtgtgt gtgtatgggg ggaggtagct aaaaacaatc tggatcttgt agggtcgaag    31200
atcctctctc ttttcttgat ggcccagctt tcccttgttt tctgtattgg gtatctacta    31260
tgctatacct atgcaaagat taccatgcta aactcatgca aacttaagat ctttggggct    31320
ggagcagtgg ccgagtgttt ggggacactg gctgttctca caactgcctg ccaatctagt    31380
ctgagggtac ccgatagcct cttctaaact cgggtggcag gcactacatg ctagtggcat    31440
gcaagtggtg cacagacata cattcaggca aaatactaaa tacacaaaat cataataaat    31500
taaagatctt ttaggcttgg gctttttttc taggtatagg gaatgacttc ctaaattttt    31560
tttgtatgtg taattaatct cagttgttat tatctttaaa tgttgggttc tttgaaagat    31620
ccaaaggaag gaaaagaag tgggcagggc gagtagattt aaaatcccctt gatgtcttca    31680 gttggtgggc gacagcttcc tccatctacg tatgcgtgtt caaaagcagc aattagtgac    31740
cagcacacag atttaaaata ttggaacgta cggcatttat tattaacttt ggcttttgaa    31800
agttgtttgt aagtctctat agaggtatat caatgactgt atgagaagtc cttgttgtat    31860
aagagctaaa atcagggctg tggagatggc tcccttagta aagttcttgc tattctgagt    31920
tcccattgtt ctttttttt ttttaataga agaaaaggtt tattttactc acagttccat    31980
ataacagttc attatcaaaa gtaatgagga caggaactga aacagggcag gaacctggag    32040
gcaggagcca atgcagagag catgaagggg cactcctgac tggcttgctc agcatgcttt    32100
```

```
cttttctttt ctcttctttt cttttctttt cttttctttt cttttctttt cttttctttt    32160
aatattttt attattacgt attttcctca attacattta gaatgctatc tcaaaaatcc      32220
cccatacct ccccccacca ccacttccct acccacccat tcccattttt ttggccctgg      32280
cgttccctg tactgggggca tataaagttt gcgtgtccaa tgggcctctc tttccagtga     32340
tggctgacta ggccatcttt tgatacatat gcagctagag tcaagagctc cagggtactg    32400
gttagttcat aatgttgcac ctacagggtt gcagatccct ttagctcctt ggatactttc    32460
tctggctcct ccattggggg ccctgtgctc catccagtag ctgactgtga gcatccactt    32520
ctgtgtttgc taggccccgg cctagtctca ctgagttccc attcttagaa ctcatacaaa    32580
agccagcttg ctcagcatgt ttctgcgacc tctgtgacag gaagcaggca gagaagacta   32640
tcctggggggc ttgctggcca gttagcttag ccaaaataac tagctccgtg ttcagtgagg  32700
gaaccgttct caaaaacaga ctagttgcaa agtcatagag aaatacctgt tgttcccatg    32760
acacacacac acacacacac acacacacac acacctaaaa ttgtttaagt taaccttcat   32820
tttctgtcag agctgactca ctgaaagtgt cagcgtttgc ctagattccc tgggaaaggt    32880
tccgcaagtg cagtcggtgg tcagggctgg cttctggggc tgcttctctg tcctcttgaa    32940
ctactttggt ttctttgttt ctgttttgtg gggtttttta agatttgttt ttgttgtttt   33000
gttgtggatt tttggtaata ctttctagca tttgaaatac atgtttatat aaaataaatt   33060
taaaattcac tattgtggct tatctagatt tatttcctaa gaaatctttc atgctcatac   33120
atcagcctca gtttatctca gtgagacaga cacacagaca cagcacagtt ggaaaggagg   33180
ctcaacaggg ataggagggt gagagtggtg aggcgatgtg agacagacac acagacacac   33240
cacagttgga aaggaggctc aacagggata ggagggtgag agtggtgagg gcgatgtgag   33300
acagacacac agacacacca cagttggaaa ggaggctcaa cagggatagg agggtgagag   33360
tggtgagggc gatgtgcagt cagttccttc aaggaagatg cagttctagg aggtgtctta   33420
ggtcgtgcag ggttagggag cattgcctct cactgctgtc taatatttta gcctctacta   33480
tctaaataca tctctgtagg caagtttgcc catttctctt tggaatgtgc tgtttcactt   33540
gtctttcctc acttgtcttt ctatgtgtca gactgagaga acagtggggg aagtgcggaa   33600
tgtgtcccta agtaatcagt tctctttgag acagttatcc ccccaccct tcaaatgatg    33660
gaatgatgta ctgtacccat taaagggctg ctttcttctg ttagacttgc tgttgctcac   33720
atgctagcta agaaatcaga atgttcaact gttaagggggc acacagatag gatttcccta  33780
agcctaaggt aaacacacgg taggaaagac tcttgaaaga attatgagtt tttagttgca   33840
aatgacataa aatgtcttta ccagaaagga ataatgctct ggaggaagtt cccattgtgg   33900
aaagcagaag tttaggaaac gtggtgtagg ggctacagtc tgcttagaca ccaatgcatg   33960
gtcctacatc ctggttgctg tctgtgaatt cccaggtctt ccagtgagat ctttgaagaa   34020
tctactgttc tcttgtacct tgctgcccac tctgtaggag tgagtgtctc acaacaaggg   34080
aaagagaaaa gaaataccetg cctctgatct cagtgtttgc taactggttg acataagggt  34140
ggcacaattt ccttatgaaa tttttatact tcatccccct ttcagaaatt tgtagctgtg   34200
tttacatata agaagccgtg gtctttgttt gtttgtttgg gtgttcttgg actttctagc   34260
ttccaaagct tcggacagtt aacttctgtg gggcattgtg tgcatacgtg gtgtttactt   34320
tgtgttgact ttctttttcaa ctgagttttc ttttaaattg tttaaactgc tttgattcct  34380
tttgtagaca cagcttttata atgctttata agtcctttct ttatgccttt ataatatagc  34440
ctttataaat cccttctgtg cccttagatt cagataaatg ttgactaaag aaattgatgg   34500
```

```
gttatatttt gctcagaata actgattgct aactctgctt tattgttgta tataattact    34560
atattttcta ttgctagctc ttaaataatc aagaagcagc tttgcttaaa ttatcaagta    34620
gaaaagattt aacttatgag gaattgttaa tatatctcct actactgact cggcattttt    34680
cttttggaca gagaatagag aagtgaaagg tttagggctc cctgccttt tcctgtttcc    34740 agcattatac accagtcaag cgtatggaat tctagtttct ttttgttctg ttgctccact    34800
ccaaccttta gttgatactg tttttgtgtt ccttcttata caccactttg tgctgttctg    34860
atttcatctc tgagcactcc ttctgccatt gtgatgaccg tgttttaaaa tggagctttg    34920
tgagctctct gcagctaagt gttttttcct gaataatttg ttcattacaa aagagaattc    34980
tagagaatcc taccaagtcc atagcattgt tactgtgatt gctgttttga gatggtgtcc    35040
aactctaatc ccagctgact tcaaactcag ttctatagac ctggctgtgt ttacatgtgt    35100
gcggtggtaa catgcatggc acatgtcact tagtgggctt gacctttctt tctctctctt    35160
tctttctttc tttctttctt tctttctttc tttctttctt tctttctttc tttctttctt    35220
tctttctttc tttgaatcat caaagtatga cttcatgttt tgtcttttaa aaaattacat    35280
ttccctctgt gtttaaacaa atgagcctag tttatagttc cccatggatt acagttaaat    35340
cctctctgta gtcttctttt agattgggtt gtagattcct aggctgctgc tgaggcgaag    35400
catttgcaat gctttacagt ccagtatggt atctcactat gccagcattt ccttccttgt    35460
ctgatgtcag ctctagaatt acatgaacac tttccctctg tttcctgaca tttccagagt    35520
tgtagtttcc ttctaaaaat tatttataaa agagaactaa ccaaccattt caagatttt    35580 tttttttaaag aaaaaacctca gaagttaaaa gaaccagatt cctaatattt tgctctattt    35640
ttcttgtaat tttataatgt attccgagga tgtgcccact ttggtaacct gactgtgaca    35700
caaatgtatt gtgtcatact gcttggtttt ctttctttaa ttgaaaataa aaatagata    35760 tttttcata caatattctg attatggttt ctcctatccc aactcctcct agtttccctc    35820
ccttctccca tacagattta caccctttct gtctctcatt agaaaacagg tgtctaaaaa    35880
ctaatagagt gaaataaagt aagcaaacaa actggaatag gacaaaacaa acaaacaaga    35940
aaaacacaag acccacgtag gctcagagac acgtgtttgc acacatagaa ctcttataaa    36000
atcacaactg gaaaccgtac tatgtgtcca ggagatctat gttctcggtt ttaatttaca    36060
cgcacacaca cacacacaca cacacacacc ctgctctgta aatctcacag tgattgagca    36120
catttggtgc tcatcagttt ctcgtactcc tgggtcttcc tgaccgacct aactctgacc    36180
taattgcctt ctgtgtgtgc agcctgaggt accccttgcg atccttgggg tcctcacttc    36240
ttttacaggt tgggctccct ggttcccaga accgattatg attttttcact ctcaacatct    36300 tttacaactg agatagtgta tgggaaacaa atgacttgtt gtagaacagt gcctttattg    36360
tattatatac tcacccacga tttatagtct gtcttgtata gcattctagg ctggaagtaa    36420
attttctgaa aaatcaaact ttgtataatt gttttagga agctagtgtt aatggcagtg    36480
cgtttgtcgt tttgtcttat gctgtctact ttccatgcca actttagggt ctggtgttct    36540
ctttggcact tagaaataac gtagatatat atggctccat ttgcggctcc cctagacccc    36600
ctttttaaag tcaattttat tagctatttta tgtcttcatc ttgggaactc atgttggacc    36660
tggagatgta aactgacaga atgttttgct gaggctctag gtttaattgc cagcactgca    36720
taaacccagg ttggtgatac agacctgtag tcccagcacc ccagaaatgg agggaggagg    36780
gtcaggaatt cagggccagc ccgggctaca tgaaactatt ttctcctttt gtctcattat    36840
```

```
taattcttca ccattatacc ttgctgagtc ttctgtttca ggcctgaagg ttaaacaaat    36900
ttacatacat aaagtactta aataatacct ggcatgtaat aggtgctttg gtacctgtga    36960
tcactgtgtg gtttcacagc tggttggaag gagtggcccc tgctctgact cttcatttac    37020
tagcttcaca ccttggacaa gcttcataat ctcttgaggt ttacttcctt ttcctgtaaa    37080
atgtaaattc catctctgcg atgttggtca gggacaagag aaagtataca tgtatacatg    37140
tgaaaaatgc ttacagaact acattgctat tgtacttttc agattgtggg ttttttttt    37200 tttccctgct aggaagatta catttttaagc ttttttttttt tttcatgga agtctgtgag    37260 ctgggtacac ttgaactgct aatatcgttt tgtcaagacg tgattgtaat ttattagact    37320
gaagacatag atatgaaaac agtttttgat aaagtcagct ctacttcaga atgtataaat    37380
ctgtgtaatg taataactat taatgaatga ggggatatgt atttgtgtta ttaatagtat    37440
gtgagataag ggtaaataaa tctgttttag tcctgtgcag cattaatgta atttgaaata    37500
ttagctcatt tttgttaatg gtgttttttt tgtttgtttt gttttaaggt ttttggattc    37560
aaagcataaa aaccattaca agatatacaa tctgtaagta tgcttttttt atttgtctct    37620
gttaaaataa ctaaataaaa gttatttctt tgttgaagat aaaaatatat ttagatattt    37680
ttatatttga ggaactggat tcctgaaaac agttgcagtc tgatagagag agttgttggg    37740
tctcgaagcg tggtgatgag gtgcagcagc ttggcacagc ctccggttac ttgatctgct    37800
tttacagact tggcacctcg cccatccttg agcccataat catgtgataa tttgaaatgt    37860
aatccacagc ggagctgctg ttagtattaa cgatggcttc taaggagaca gactccaggg    37920
tggatggaca gacttttgtt tcctctgtgc ttgttgatca atatactgaa acagctattt    37980
gaatattttc tgtgtataac ctagtaagtt atgcagcatt gtttagttat ctagtatagg    38040
atttgaggga ttgctcatta aaacttattg gcctatcttt aaaccttcac tttcttttga    38100
cttttggagt agtgacatga aaacaggaaa ggaagacaaa tcattaaaca ccctttgtct    38160
ttcaaaacca ttttttatttt ccccaaatac tgagcatttt taaaaattta aaagataaat    38220
taccatgttt ctattatgtc ctttaatttt ctatgtctat gatttatata acaggagaat    38280
gttatgcaat ggtagaatac caattagtaa ttaaccattt tctgtagact ttatcaaata    38340
taactacaag tgttttctgt tctgcttcga gtggctattt gaattgctac ccagaaggat    38400
ggagaatttt ctatgtcttg ttatagtgct agatgttact tttatttttt cagtctttaa    38460
tgatatttct gttttgataa gacttcaaag tattcatgtg caatagttac caatattatt    38520
tctcttcgct tttgctgact tcagatcaga aaggtgcagc catggtgaaa catgcagata    38580
gagtgctcat atggctagtt ccagccctct agtagcctat agcttgatgt gaaagtagga    38640
gggagcagga gagaagtgtg gacaaagtaa ctggccccac aggaggcctc tgtaaaagac    38700
cagatgtgtg ggctgtgatt aacttctgat accttctttc ttctatccct gcttgttata    38760
tacttgtaag actaagagga gtttctgttt tatttctttt aattttaaga ttatttcttt    38820
gcaaacataa atttaaagat cttgaaatat ttccatggct tttctactaa tgaaaatcaa    38880
taggagttat ctattagacc tgggaggatg agccaaggca agtcagaaga ttgatagtat    38940
aatggtattt gaaatatggc agataactca ttttgggcag gtggtggtgt atgctggctt    39000 aggtgggggtt gtgctaataa aaggtggata ggagaaccac aagactgttt ctgaacagct    39060
gcattcagaa ggtgactgaa aaaggacaag aactgttgaa agctggaatt gatgaaatga    39120
atcatttcag actcacactg tcaggtttgg ggatttagag aggtcccaat agggaagtag    39180
aaagacatta gaagacacat ttctgcctga gctgaaatct tatgcctgtt aacatatct    39240
```

```
aaagcacagg gaggaaattc ttttcattcc tgcctatagt gacttcctgc ccctagaatt   39300
tagggattag gtttatgctg tctcctttgt tgtatttcag tatagttaga ggtggcattg   39360
ggtggaccta ggaacttgat ttgagtttcc aagcatttga ttcccaattt aatgaaccat   39420
ctctttatta gttgagagca gcctttagtg catatgaact tattcccttg tcatttggaa   39480
ctgaggcttt cagaatggca aaggatctga agggtccttt tagcagtgcc ttcttatctt   39540
atagacaggg cattaggcct aggaagttaa atgaggtagc caaagacagg taggtgcata   39600
ataacagact acccactgtt tgcaccagaa tcccttttgt ttgctggtta gctcttcgtt   39660
ttatttactt caaaagtttt taaacatata caaaattgag tgttttaatt tgagtacccc   39720
ctctcccctg cctactgtgt atctgatttt aggcaagtga gactagccac aacagatgtt   39780
tttgttttat ttcttttgt cttaggatag gaattacagg tagtatgtat ttttttttc    39840 ttggaaatgt agatgtttga aggtcctaaa gtattttca ctggacatct gtatagttag    39900
tagtttgtga gacctttat agcagcagtg ttgcacatga atgaagaact atcagcctaa    39960
gctttctgat aatctagctt atctattatt attaatcagt tattttgaaa aagggcaaca   40020
ttaattaatc agttttatat gagtgttttt aaaatttctt tgttgctccc tgttcagaga   40080
atacaagatt ttaagttttt attatatttt agtgaatatt tgctgtactt ggcaaacatt   40140
taactgtgtt attttctgt taagatttcc tttgtaaaac actgtagagt gaagaagaga    40200
gctccctacc atgtagttct atggcaaggc ctagttgtct gcaagtttgc ctttctggtt   40260
tcactcctcc tcttaatttc tgttgccacc ttgggaaacc tcattttcct tgttttttt    40320 tttttttcatt tctcttttca tataagccaa tttaagataa ggacaaaaat atcgtttgag  40380
ttttaattac aaagaaaaat ttaaatccaa attgttattt gctatcttct attttagtat   40440
gtggagtgac ttactgctaa tatgccataa gaaatttaaa agaaactccg ctgtgaattt   40500
tggctatata ccagagattc taactaaggt ggaaggtttc ttcttgaccc tgtgacccct   40560
tctttctctt gagcactgtt tcacaggcag ccctagcatg tcctcccaaa gcccctccgc   40620
ttgcctataa ggagctgcat gctcccctcc cccccaagt caattgttag gtctgtcttc    40680
agtgacaaat actgctcatg tttgtgctgt aaaatttgtc actgctttt catttaagac    40740 ttgaatgttt ctgttatgtt gaatgaaact gtaatagaag ttgttggatt tagttgagca   40800
aggatactaa gcttgagttc ctgtctcacg gtgacttcat gttgttatta ggaaagcttt   40860
taagggcctt tctaaatctt agcttttcca tatatacata tgcctcacat atacaatggg   40920
gatgtaaact gttacatgat tgtgagggtg aaaacatgga tgtcagctgt aaggtgccca   40980
tatcctgtag acttcagttg ttactgtgtt cctttcacct taactgatga tacatgacaa   41040
ccagtttgta atggtgatct taagcagtgc ttattaaacc aaacttttca gagtgtttgt   41100
tccatctttc tctggggtgg gaccctccct tcccctcctc tccccttccc tgcatcacct   41160
ccgcaggcaa ttgggatccc tgaccctaga ccagaaagtg tggcaaactg aaaaatctga   41220
cttgtaggac actaacaacc ggcttcttag ggtatgtgcc tagcttcctc ttgtttcctg   41280
attgtatcct taattcttga ctgtcttcca ctgtgggctc ttcaccacac agcacctctc   41340
agaagagcag aacctggctt ccctgtgtgg agttctaaca cttggaggtg gagggagaag   41400
ggaattcaga gccagtcttg ggtatatgag atcctgactc aaggaaaacc aaagaggaag   41460
ggaggaaaga gaatatagaa tatgtgatct tttgtatatg tgtcagtttt cttcttccta   41520
tctcattttt aggtaagcag acatttagca gagtatttag caaggatgca tacgtcatct   41580
```

```
aataaattttt ctcttttcaa aaacagtaca tcaggtaata cactaaaaga aaaacacatg   41640
tgtgtgtccg tgtctgtgtg tgtgtgtgtg tgtgtgtgtg tgtgtgaata cagaagttaa   41700
ttcccctcag gtctgctcca ttgggctgta gtttatggat aatttgttca atctttgtgt   41760
gaactgggtt ttgaaataca gttgagttgt acaaattcca gatgcccagt gcaggcccac   41820
agctatttat ttggaagtct tggatcagtt ttattttggt acatagaaaa tttcagtttt   41880
caaaaaacta aaaaactaaa taaaacaaga aaatccatat cttttgtgtt actctagtat   41940
ccactgtggt agactagtcg gtactcagca ggtatgttgg ttgaacaacc tcagattggg   42000
tcctgttcga gttgagatta cctatttata actttggagt ttgagatttg ggctaaggaa   42060
taatggaact ttgttttaaa acactaactt ttattttcca gtaatttctt tttgtttgtt   42120
tgtttgtttt ttttgagaca gggtcttgta tcccaggctg gcctaggact cactagatag   42180
caaaggctaa tcttaaagat ataatctttc ccagtaactc ttctgaagtg ctaggattac   42240
agcctgtggt aacactccta gcttatttga ataatgctta agtgtctgat ttccttagta   42300
gttggagtca ccaggatgct tctgaccccca ctaatatgta ggatacccctt catagtatca   42360
ctgattagtg ttattattga aaagctaagt gtttgtctta atgtgtcagt attttactat   42420
cagtgggttt tagttatttt attgtgatct ggtattaaat tttgtactct gagagattat   42480
tggaaatgag atttgtatat aaagagtaaa aggtctggct tacaattttt agtaagcatt   42540
gtgttaataa ttaaattagt atcattcagt tgtcttttac atttcctttg ttcttttct   42600
ttattttttaa catgtatgtt ttaagtaatg gtttaagatt gtatgtgatc atctgtcagg   42660
taaagataat agtaagagta gctatttatt cataggtatt tgtgaaataa aaaatacatt   42720
ctaaagccat gtatagtctt tatccaagaa attacagggt cagtgcagtt gaatttacag   42780
tgttgcatgt tgatgtcaca aattctgtga acaaatatat gcacacaaat tgcatgcatg   42840
cgtttaactt ttattaaagc tttggtctcc ttaattataa gaatgataat agtacctact   42900
tcagaattct tgaagttaac ggaaatagtg actgtaaaaa cacttagcgc agtgttttta   42960
catgatagaa aaggtggtat gatagaaagg gtggataaat attgctaata ttgatactct   43020
tccttccagt gtgaaaggta actttatgcc acatttaaac tttcttgtag atgtgctgag   43080
agacattatg acaccgccaa atttaactgc agaggtatgt ataaacataa ccacagcata   43140
ctgtataact aaagaccaat agacttgtct tttactgcct ggtgataatt atcaagatta   43200
gtgagataaa aatcttaaga atggccttg acaattaaaa aaagtgtatt taatgttaga   43260
gttgttcttt aagacctatc tattgtcagg aaaactaaat cacagaatac ttggagaggt   43320
cccaagacta aactaggatt ggaggtgctt attgacggtg tgggacagct agcgctgctg   43380
gaaacaatca caagaagaga gcagaaccat tttaactttt ctacatcgaa gaatggcata   43440
aagttaggaa aagatgtagc attggtctgt ctgtctgtct gtctgcctgt ctgtcttctc   43500
agaatcatga agcactaagg agtaagtaag aacagtttct ggggaccgac agacctaggc   43560
tactgctcat taggaaacat gccatggttg aaggtcactt agctttaaat gtacatttta   43620
acagactctt gaatgttctt gtgtgccact ggggaaatga ggtcgggagc acagttagac   43680
agatggttaa gtaaaagctg gcctgcagcc tcttggtgaa tgtagtttgc cattgttttac  43740
cacagagctt tcctgtcatg gaaaggagta aatggatgga ttgttcttgt accatttttac  43800
gatggcttgc tttaggataa gtcagagttt ttacatatta gataatatgg cagataatca   43860
gaacagtaat atcaccagga tttttgtttt taatttttaag acaagggtct cagggtctca   43920
gtgtcccaga gtgaccctga actcaatgtt tagctgaggg tgactttgaa cttgtgatcc   43980
```

```
caattctcct gcttttactc ctcaagtatt aggattacag acttgcacca catcctcagt    44040
tgtgtgttta ctcaaggcag ggatgagccc agagctgagc atcctaagca agcactctgc    44100
gaactgagct acatcccaga gttcatacca ggatttaagg atctcaatag gatagaatca    44160
aaacagatac tagtaagata aaaaccagta gtgatagaac ggaagtcttg cttctagata    44220
atagcatctt gccttcaaaa acttaactct gactatagag aacaaagaca tcttagattc    44280
ttaattcatg tgaaaaaaat ctgaaactta atttgctata aactttactt cagttgtatg    44340
tttttctgtg agtgattaat ctcatgtata tggaaatata atgtttgtga gaccatttta    44400
aaaacaagtc actgggtaat tttattatgg gataggaaaa gtcagtcttt tccatagttg    44460
actctattag taattatact ttcttcggag catgtctggc aatgctgtag taatatctgc    44520
tattggtcct gatagaagtt actacttgac aagaggcctg ggtgacgtgc atttggattc    44580
agttgtactg ataggctatg acgtgttccc ttcatgcaca gattcatcct ccctggagtg    44640
aagagcacaa tgcttgtttc catgtctaat gaatgcattt aagaattaat aaaagacttt    44700 cttaaaatc taggtttaat tagtaataaa ttaaaatttc ctgaaagtta ggcttctttt    44760
aagaaccagt aagtttatat ataacatttt gaaagttaac ctatgttttt aaataaaaaa    44820
tttaaaattt tcttacactg ggattatctt tttgcaacag ttgcacagta tccttttgaa    44880
gaccataacc caccacagct agaacttatc aaacccttct gtgaagatct tgaccaatgg    44940
ctaagtgaag atgacaatca tgttgcagca attcactgta aagctggaaa gggacggact    45000
ggtgtaatga tttgtgcata tttattgcat cggggcaaat ttttaaaggc acaagaggcc    45060
ctagattttt atggggaagt aaggaccaga gacaaaaagg taagctgttt acttttcct     45120 tcctccctct ttgtggacca agaatttatt gggaaacagg ttttctccct cttgctttat    45180
tgaggtataa ccaacaaagt cttaatctac ttacagtgtg atgctttgag aactgttata    45240
ttgtggttgt atccacttag tgtatccctc atccctggta tccccaccct cttccttagc    45300
tgtactgaga acatccaaga cctacctgga gtaggtgcta ggcacacagt atggatttg     45360 atgacaactt gaatgccatt acctagtaaa gcaaggtatt taatttgatg gtaaataaaa    45420
cattttctga tgggggtatt cactagtata gttaactaat caaagattca ttggttattc    45480
agaaaactaa agactgttga attagtggca tgttttgtct atggtacaat tgaaaacaaa    45540
agcaaattct tggactgctt tttcagagga ctcgtttagt tagtgtaaca ccaagattct    45600
ttgcatgttt ttcttttctcc aagcacagca cctatagtac ttcagatgaa ttgaaagctc    45660
agggtagcag tgaaagtgcc ccaacataag gtcataaact cacttaacct ttgagttggt    45720
ttgcagtctt ttttgtagac attgtaagtg acaacatcag tttgcaatgc caagggttgg    45780
acatggctgc tctggggagt aagacatttg aaacttgatt ctagtattaa atttggactt    45840
gtgccccacc ccgcttctc ttctgcctcc tctcccttct gtctttctcc tcctctactc      45900
cattcttccc ccttctcctt tttttgagcc ctgattttat ctggatcaac tttgggccat    45960
gcccatcaca ctaaggtctg tggctgcagc ggtcctgggc cctgtacttc tctttcacct    46020 gcttttttaaa aaccctgtcg ttataactct tttgagtttg tacaagaata tcaagactgt    46080
ttgttcattg gtgggagttc acaaaattac atctttaatg cagtaaaaaa gtcatgtgtt    46140
agaaaatcag atttaagcta gagactcctc aactctgact cccgatgaag tgttcagatg    46200
ttctgttatt cgatgtatgt ggtatataca taaccataaa ttgttgttgg tagcttccat    46260
ttgccttcag acaaaatata aaggaacttc taacaaatta tgtctcattt ctcccatta     46320
```

```
aaaaatcagt accccttacc tgagaacagt aggtatctaa atgggttgat tctgttcaat    46380
agtgaaattt atgataaaca agttttaaaa acaagttgaa agcttgccat tgtttgactc    46440
ttacatcatc cttgctctca gtgttatttt tattcttgtt tagtgaaaat aaattatgaa    46500
aactcttatt tcacctatga gagaaatatg gaacataata tgtttttgac caattaaagt    46560
aggctgtgtc agataaaatc tctaagacta gatacgatca tctattagtt tctttgcctt    46620
caagatcatt atctctgtgg ggcaggaaaa gattatggac cattttaatt ttcaggttaa    46680
agcattaaac tgcttgacag cacagcgttg tctggcttct agatatcagt ggacctgtgt    46740
gcagtgaaga gctttctagg tccttctgtc tgttgacaaa gcctcttgag attctcttgc    46800
ttgaaggtct tggctctctc ttgtgaattt gggtctttca cagcagtagg ttttttcatga   46860 caaatcatca gcagggaac ttttcacaac tgtagaagag agtctcctag gattaatgtg    46920
atcttgctac ccagtgcagc agtgagggcc agggcagaga tatcatccac ttttaccagt    46980
gcagggaaac cagaggagct gcagggaaag ctgctagagt gtggaggact cttagggcca    47040
gcgatgtgct cagccatttt tatttaactt ttttacatta agactttca gttctttgag    47100 actgtaataa attatatcat gagtatgtat gtatgtgtag tacaacctgt ggatatgttt    47160
ttagggctta ccatttggat aacaaattgg catgctctct tagcatttct tagttaccag    47220
tagatctttg tctagggttg aggcttggtc agctttctcc cattctggca tgtcttttgt    47280
tctccttgct cagctcatgt ttggtagtca tgttgatgag actttatggg tgtagcttct    47340
gacattgcca gtagacaatc tcacagcaaa ctcccagatc ctctacctct tacagtctct    47400
aagccttcgt ctacaatggt ccctgagctg taggtgcagt tattgtgttg tagatggctc    47460
agttggaact gagttccaca actctgtgtt ttgaactgtt gtggttttct gcaatgtttt    47520
ccttatgcta caaagagaaa tttccttgat gagggataag cactatgctt atctattggt    47580
ataaatttag agcatagtta tggactatat atattattta gtaaattagt ggttgtaggt    47640
tctctgtcaa gaagcatgac ttccctagcc caaggtagtt ggctaggttt ccaataccag    47700
gcagtttctc tgtctttaag gggatttaaa attttatt gtttatctgt ccatccatct     47760
gtccatctgt ctgaaatcta tctatccgtc cacccattta ggtgaggcct gagagacaga    47820
gtcaaggaaa tgtcaccatc tttaaaaaaa aaaattaaga aggacccttt ctttaaaaga    47880
ccttaaatta tttgctgatt atttattcat ttgttttat tgccatgcat aattttgatg     47940
gaaactttga actgattaca ctaagagctt aattactagt aagtggtact cctgatactt    48000
ctatggcctg tcttgtattt tgagagagca atgtttgctt tggagaaatg gatgagaata    48060
tttgaagtcc tgcgactctc tcagccattt cctgccagga atctcagcta cttgacattt    48120
ttttctgttt ctgtttgttt gtttattgtt gttttgatgt tttcattttt ctctctttct    48180
ctcattcccc ttttgtaatg gtaaggattg agcctagggc cttgtacatg gacacatatt    48240
ctaccagtaa gctatatccc tcagcccttg tttgactcat tcatcatgtt aaactacatg    48300 acctttgtt ttgctttgtt tctgtttgtt tgctagttca gacaaggatt tcacttgag     48360 acaaataatg gttgtgaaat ggtttaggct tctctaagct ctgctgtcaa tctccattct    48420
ttttccttca cttcttcaga attgccgcg tgtgtataga gtgataagat gctggggtgg     48480
tctgtttcct tatgttcaag ggtaagagca agacttgggc acttgaactt tcctgtaaat    48540
ttctctgttt ccaggccagg gtaaatgcag gaatccaggt tagacgcagg agtcaagtta    48600
ggtgcaggag acccatgtca gaaactgagg tcttgacaca ctagtcatta cagcctggtg    48660
gcaacagttc tgtttccctc tagaagggag gggagggtgt ttgtggaagt gacaagaagt    48720
```

```
cttgggaaat gttacaaggt aggggggtatt tgtgagtgaa atgtgaagcc tctagtgtca   48780
tttggtaaaa tgtaataata atacttgtgt cctccataga acttttcttg gcactctcca   48840
tctcttgacc atttcttcca tgtgaaaatg atagactaat ggacatagaa gatgcagggc   48900
tgtgcacatt gttagagctg tagctggtgc atttgatgtt tagccattgc attatactaa   48960
gactccttaa gtaatttagc atcttacagc cacatcagta ggatctactg tacctgttgc   49020
atagttaata tacctagaca agtgttttgg ataagtttat acacggacct aaagcagaat   49080
ccttatgtgt atcctacctt tattctttcg attatttaaa aaacaagaaa gaacttatga   49140
acagatactg ttgaccaagc tgtgttttac taatggttgc ttttgcattt taagctacaa   49200
tagtattaga aacctacatc cagataaaag ctttcagata tccctactcc aggaatgctt   49260
ctttacagat gacatcaagg cccagaaaag tgaactgtag tgatcagaat tcgtgacggg   49320
gtcaatcagt tcatgacagc atttacagta aaaacaagtc ccttggtgtg ttgttaaatt   49380
tctttgtata ttatcaagct tacagattct gaactgcaaa aggttccata tttattgctg   49440
atggttttga aaggcttctc agttttatgc ttttctttac aaatcgtagt gtttaataac   49500
cctccaggtt aaaatcttgg agtgtttaac ctccagtcta agtttaaaat ctccagagag   49560
agattgctag ttttgtaact ataatgctgt gcatttcctt aaaattttta caatttaatt   49620
ttctcaaagc ttttaaatgt aaagaaaaat aaaatcatgg catttatagg aagagaatgg   49680
aactagaagt cattacttta agtaaaacaa atctgatcag aaaaacgtgt tttctctcat   49740
gggaagaacc tagcttggag gtatgcatac cctttggggg agggagatct gaagggaaga   49800
tggtgaaagg aagagtggaa cctgctccac acagaaatgc agaagaggaa ctgtttaggg   49860
agggaggtga ctcagaagga agtacaacgg tacctctatg aggaaatgtc atagtgaaat   49920
gcgctagtaa caaagaaaaa taataaaaca aaccttaaaa ggcaccgggc cttgggctgg   49980
tagagtggct gtggaatgat ggatgtgttt tagcttgctg agtataggaa agctgcttta   50040
gtacagctga ggaagtcttc ctagaagaat cttagagaat tgatgactca gtgtggcagt   50100
gtagacacac agtggacttg cagacttgta gactagctag gagtccctgt ggctacgttc   50160
gtgctgcttg ttgtgtttgc tgtttctgga tttatacttt gtgattgtaa atgtgaactt   50220
ctggagatta atacttaaat ctgctttgta gttaatcata ttagaattgt ctgtattatt   50280
ttgtttatat ttgtaatttt aactatggag ggaccataag aagctgaaga atttgtgtt   50340 ctggtacaga atcctcatct tctttctttt atgttaaagg aggaggcaat tggcctgttg   50400
tgaaaaaatt gtagactttg cctaaaatgt gtgtttttt ttttttggct tttacttata   50460
gtactttctt tctcagagtc ctgtagttag gtcttgatat gatgcaggtt ggatttgcaa   50520
gctgaccata aaatgtagca ttgtgttctt aatgctggaa caatacttca ggttttgaat   50580
attgcaatga agttcaacag ttgctacttc ctataaagaa aaaatatctc aagggcgaag   50640
taactgctca agggaacaaa gacccatacc cttattcagt caaagaagtg tgttgccac    50700 tttactggga attatttact tgtatagttg atattttcct ttgtgaaaag gtggcaaatt   50760
atccaaatcc aaagtcactg agggtgaatc ccgactgact gcacatgcgc gcgcgcgcac   50820
acacacacac acacacacac acacacacac accccgcgcc agcccctcct gctgtaaatt   50880
accttctggg gttggtttcc acgtgtgcct tgctgtttgc aaatgcactt agggttcagt   50940
gctgcaatac atggtttgcg ggatgtaaac tatgaggaga gtgtaagaaa gacctttca   51000 gaatggcaat gagcgcaggt tttggagtaa cttttccaaac ttgagggaag acactgccac   51060
```

```
taaccatacg tagtgtctgt tctccctggc ctccagcagt ggcaaggaaa gtaaccttaa    51120
tgcttagttc tcttattaaa cttaggggag ggattgaaac gtttcagttt gccttttctt    51180
tgcttacaag ttggttatta ggtaggtgtg tgtgttttga ctacgtgagt gtgtgtgaga    51240
gagaatgtgt gtgtgtgatt agttactac ctcagtttgt caactttact aaaataacaa     51300
tgccaagctt aattttaaga gatttcatta ttttctgtga gaagtgaact tttataacct    51360
actatcaagg ttatccccct acccctgttt tacttattaa atcccctcat cataaaattt    51420
tcttgcttag tccttatttt taaatcaaac aagttgtggt tgctgttgct aaaacaaaaa    51480
actcagtata attttcttgt aatgtcaatt atcatgtgtt ctcttctgat gcatactgtt    51540
tgggctatta tctactatct agcagtccac tgattcataa agctgtgcag ttttaggctt    51600
tgaaagattt aagcagttac ttaatacaaa cccatttgca aagaccacac tgccctgatt    51660
catagtcttt ctttgtcata ctcaacacct ggcttcctaa ttttgttcct tggattctct    51720
ctgctgtact aagctctact taattttttc cttttctttt tgattcctaa aatagaaacc    51780
aacaccaaaa aaaaaaaaaa aaagagagag agagagagag aaaaattgct gttttgaatg    51840
tgtgagtttt tcagttttag gtaagagaaa cccaagtagg agaaggagac agagaagaca    51900
caagggagat gtttattgac taatagaacc taaaaggtca ggtctggatc taaatgctca    51960
ataagtgtca ggaacctctc ctttctacac tcttcccttt tctttcttgg ctatgtttat    52020
tcagaaagga tctttgcaag taataccaag ctatggtccc gtagctttag gcttacactc    52080
ttgactaact gcagtggtaa aagaacaccc atttgactag aggttcctag aataggttct    52140
gatttccctg gctaaagggt gtgtctttt tattttttta tttttttgta agatttgttt     52200
atgtatatga gtatactgtc actgtcttca acacaccag aagagggcat cagaccccat      52260
tacagatggt tataagacac catgtggttg ctgggaattg agctcttaac cactgagcca    52320
tttctccagc ccacatctac ctctttttg aaacaaatac ttttgctagt gagtggaatc      52380
ctcttacaaa ttcatatatc tgaattgaag aataggccca acaccccaaa ccacaaaact    52440
gtcattatag cttctaaaga aaatccaggt gaggaaagag tgttggccag aaatgatctg    52500
tgtcactttt gtcacagaga ttctgtaagt taccatagaa ctcgaagcat tatgtattcc    52560
aaacttcaga ggttcttcat aaaggggaaa aactgaatta agagaagtta tggcttcatt    52620
cagatcgcat agcattcctg ttttcaggtc acctgagtca gattcattta ggtcctgtac    52680
tgcatttgag caagataaac atgtatagtc ctacttgttt cttattaaag tagaggcagc    52740
agggctggcc tcagtgtgcg tgggacccag cagttggcag gtagagttag gaggatcaag    52800
agtcaaagcc accatcagat cctgcagtgt gtttgaggcc agctctcccc tgggggaaa     52860 ttgaggttgt aatggttggc tgtggtgtca cagaggccta taatctccac tgttggagcc    52920
tgaagcaata gaatacctat tttgagacca ttctggggta cataatgaga ccctgtctta    52980
aaacataaga tatgtgataa tatatacctt gtaattttat gggaataata gaaatatgtt    53040
ttgaatatta gaaaatatct acaataacta ctattgtcat agtattagta accacattct    53100
tttgtttatt gaattactgc cttgtttatt gtggtcattc agaatgtagg ttttcctct    53160 tcaagcaaat actttttagg ttgaaacttt tatttatgag tttagacttg gaaaatattt    53220
tccagtttat taagaaagtt tgctcaaata gaaaattact tctttaagga ctctaagttg    53280
tgaatttacc ttctagaaga tcatctagaa tctgaatgca tagaggatga acatacatta    53340
tatatacata tatatataca cacacacact gtgttgttcc gtgctaatcc cgtatagtag    53400
tcttatgaca gtagtataga tctcaaagat gtatgtcctc catataagtc tgtttttcaa    53460
```

```
agagccagcc aggcatggtg gaacacacct taaatcccga gcacttggga agtatgagtt    53520
tcaagacaca aagaaactct tatcttgaaa accaaaaaga gaaaagtaa ttagcatcaa     53580
gtagccaagg cttataaaag aagaattaat gaaaaataca ctaggaaaat gtaaaattcc    53640
aaggcaggct tttcttatcg gaatagcatt ataataaaaa ccataaaact gatcaaagat    53700
gtcattttac actcacacag gagacacttc atacggacac tgagctgtta cgaacgtctg    53760
tgccaaaagg agtcaacttt gttaagcaaa tgctagagaa ggaaaataaa aagctagact    53820
cggaggaggc gcaaagtaaa tatgtgcaca ctgaagacag tgatagagtc ggcacctgag    53880
tgctttgcag tgcccacttg cttaggttaa taactcacca gattaactac aaatcccaca    53940
agcttggaaa gtagagccct gttacctgtc ttgacagttg agtggaacta tagtttgaag    54000
tttaattcag gtcattatgg aaatttaaag ccatttcctt caataatttt tgagccattt    54060
gaagaaagat acattgatta ttcaccagta gaaatgaaa caaaaatata aaggagtgaa     54120
ctgaggaaat gctgaactat ttgggctagc aaatcgaaca ttgactacaa gaaagagaac    54180
tggtgttttt tttaatagtg tttagggtta aatctgggtt tttgtaactg tctcaaagat    54240
gaataatgta gcacatgttt gtgtttagct aggcagttaa gtcctagggg tgtacgatgc    54300
tctggcctcg ccttgctgcc taggccttag tatggtgcaa gcttccctct gtatcaccac    54360
tgcctgtgag ctctgtgagc tctattcaca caactgctgt tgatctgaga attgtttact    54420
tacatatcaa cccagctttt ttcaaaagga tgagcatata aatgcttgtg ataataggtg    54480
tccttcccat cacttgagaa tctgtttatt gctgtacaca agtgtgaaat gtgtaccaaa    54540
agctagagag caggagaaat gccatctgaa cattatcagc tactatattt ttttgtttat    54600
tttaacttct tttatataac tgaatttgct ggtttatcct catgtaaatt ctattaagga    54660
ggtttgtatt attgtattaa ttttttttaaa gaagcaaatt ggaagtttat attttctcag    54720
aattcaaata taagctttga ctatttagta tgtgattttt cactctagcc aaagtcttaa    54780
attgccaatc atgatttcaa gtggtttata tccattttg tttgtttgtt tttgtttttg     54840
agacggggtc tctctttgta gccctgttgg cttggaatgc acagagatcc accagcttct    54900
ttcttcctcc tgaattctgg aattaaagtt gtatactgcc acttatccat tttgatacac    54960
atatggagca gagaaacaga gaaagacaga gagaggggaa gagggtgggg tcagagttca    55020
tatacctgta tttgctagac atcgtattcc ttctatactt cttagcttgt atgctgtctt    55080
cttccccagc agaagggtgt ctgtgtctag agtccttatc acagtagaag ttgagaggcc    55140
atcagtaaac taaagagcat tgtaatacct tttttcttatt aacataaaat acctattttc   55200
tgcaattctg tttgttgaga ctgggcctca cataggtcaa gctggcctta aacttacgat    55260
tttggttgta cccaagtacc gagattacaa gagggtactg ccatgccaaa actgctgttt    55320
actttaaact gttagattaa atgcttatta tttgccttat attgactttt ttactgttat    55380
attgtgaata gaaaaatatt aactcattag tgaatgaatt gttacacata tggtatgtat    55440
gtctttgtgt gtgtgtgtct atatgtatat atgtatgtgt ctgtatgttc cttggatgtc    55500
catcctctgg tgccatctat cttgttcaga cagggtctct aattggtctg gaattcacca    55560
agtaggctag gccagcctgt gaatcccaag aatctgcctg tctctgctcc cccatgccga    55620
agttttaggc atatatatgg ttacgtggta ccttaaaaaa tgtatatagg catgggctag    55680
gttggctgaa gtgatagctg gtttaaagca ctgttgttct tgcagaggac ccaggttaac    55740
tcccagtacc cacacaatgg cttacaaaca tctgtaactc cagtttcatg gcatgccttc    55800
```

```
tggtttctgt gggcaccagg tatacatatg gcaaaacact cacaaaatat ttcaagaact   55860
aagaaaaaaa catatgcatg ggttttgggt catacatgcg attgattgat tgattgactg   55920
gtttccggct ggcctggaac tatataaacc ctgggctggt tcggaacagt cctctgcttc   55980
atccccttta gtggtaggat tacaggtgtg ggacaccatt cctggttagg gtcccctttt   56040
aaatgtcata tgaattatgt cttttaaata tttgtaatat tttctaagcc attttatgct   56100
tccctaatgt ctgcaaggag tggatatagc acaaggatac cgatacccct tactgcctct   56160
gttaacaagt tgtattgaat atgtttatca ttcagctgca tactctctct tttcctttt   56220 tttttggact ctaaggtcag aatctcattt ttcctgcaca gaggcaacac gtttctctag   56280
tgtactgatt ctgatatgat tttgcttaga aagtatgtaa acaggtttgt gaagacttgc   56340
ctagtaaacc catctttgag aggagacttg ggtatgtgta gctgcagtac agagaccatt   56400
gactgtctgt ttgaatacac agtggccttt gcttattggg ttcatagatc agagcattat   56460
ttaatatttg aataaatgag gtatttaata actacatttt aagaatattc ttttgttatt   56520
gctcttattt attctaatac tgagttagat ttgattgtta gccacttaaa ggagaaactt   56580
tgggataacc cagttatagc aattttgtat aataacttta atgaaacttt cctttgaat   56640 ttgacttctc ttttctttt gtctccctcc tccctctgcc ccctgggcct atcagggagt   56700
cacaattccc agtcagaggc gctatgtata ttattatagc tacctgctaa aaaatcacct   56760
ggattacaga cccgtggcac tgctgtttca caagatgatg tttgaaacta ttccaatgtt   56820
cagtggcgga acttgcagta agtgctctaa attcttagct gtctgtgtgt cggaaaactt   56880
tttaaaacca tatctaaatg tatatgtaaa tgtttagaaa tacatttacc aggttaaaag   56940
gagtatattt ctgaagttgg aattaattag ttcagttgtt caactcactg ggttaagaaa   57000
gctaacccaa tgaattttgg tgttctttt ttgtttgttt gtttttatgt ttttcgagac   57060
agggtttctc tgtatcgccc tggctgtcct ggaactcact ttgtagacca ggctgtccct   57120
gaactcagaa atctgcctgc ctctgcctcc caagtgctgg gattaaaggt gtgagccacc   57180
acacctggca attttggtgt tcttcaagtc aattatattt atgggagaaa tattctatgt   57240
tataaccacc agatgcagtc tctgttctga caaaataacc gagagactct tgacagatca   57300
gtgtgagaat ctgagagaca ctcttgacag atcagtgtga aatggcctc tggctacaac   57360 caggtcctca tcagagggaa acatgttcac tgtcagagac agaaagagag gagcccttca   57420
aatatagaga ataaagggt gtgtgaattg ggatgtgtgg agaaaaccta agtgtagctt   57480
tgaagtcaag ctctcagcct gtggcttgga cttgtcatct cctcactgag tttgcttgtt   57540
agtaaaataa agaaatcttg gtaagtatga cgtcatgaca tcagtgtgtg cttgtagtaa   57600
tttctcttac cttagtgaca cctgggagtg gtcagtcatg ttttacactt aagatatttt   57660
atttgtattt tcaatataac gtcatagtat cagatgtcac ttattagaat cccttgatat   57720
tattttatgg atgtttgcag tttgtcagtg attttagttt ttcgcctcca tgaaatactt   57780
cattaaatta acttgttctt tctaaaataa ttttatgta gagaatcagt ttcttcgtca   57840
gataggtgtg attgcccatg agtatggcaa ctttgttaag ggcccctaat ttatttatat   57900
agcttgttgg aaagttctaa ggaacttcca tactgattaa gtatattagt ataattttaa   57960
aagtgtgagt acaaggcaca atggactatt gaaagcaatt gacctaggaa cttcactagg   58020
ttcattgaga aggaaagggg ataggaactc atgttcttcc tatagtttag gcatcaatat   58080
agagctgtaa aggcggtatg gaggcaatac ggaaaagctc tgctcaggaa tctcactagg   58140
tactgacttt ttgtcagctc tactttgctt attgattaaa ctgctgttgg gcttttagtc   58200
```

```
ggacaacatt atgtttgcat ctctacgctt aaaaaatatt gactactaaa ttctttttaa    58260
tctttaaaaa tttctagtta cttatttatg tgctgggatt taacactata tgttgaagtt    58320
atattaaaat aaagctcatg agattcatat gtataaatta taactgccat gttcacaaaa    58380
ggttttggaa acaatttcat gaagaaagtc ggtcactgga gaacacatgc agtttggatt    58440
ggcattgagt gtgaaggaaa tattacaggc agtagaaata aggtgaccga aacacagcag    58500
aagaactgga cgagaaatag aagatgtgat tggctgtcac aggatcttga atgggatgta    58560
atagacttgg actattggtg tcacgataat tctaggaact tcagctgtgt tttaaggaca    58620
ggcccatgtt gtatagacag ttgtgatgta ggaggggtag tacagccagc tctgtgactt    58680
ggcagatgtt gctagagcga tggaatgtac tttgtttgga ttttctttag ttgttcatac    58740
ccagagtgca tttgagattt ggagatataa atattatcac tttgctttta agttatttta    58800
aatctgatga gatcaaggta cttgtgagga tctgcagtgg ggctgcagct ctgtcttggt    58860
ggtgtagtgt ttttctcaag ctagagtgca ggattgcctt cagtctccag cccgaggagg    58920
aggaggcatg agtgaaacag acagaactag tgataaaagg tttagtgtct tctgcagagg    58980
gaccaggaag tgtttgccaa gcgtttgtct tattaccttt cttttttctac gtgaagagaa    59040 gttgctgtat aataaaaatg atcagtttgc ttttgtgtca ggatgcactc tcatccttgt    59100
ttttgtcaag tccagatcct gtcatttctt cagaacatag ttaattaaca tagcatatat    59160
ttcagatgtg catctcagaa gtcaagagga ctgtactaat attagaatat tgatgttaga    59220
acttccatcc ctcctgctgg gcgtggtggc acacaccttt aatcccagca cttgggagac    59280
agaggcaggc ggatttctga gttcgaggcc agtctggtct acaaagtgag ttccaggaca    59340
gccagagcta tacagagaaa tcctgtctcg aaagaccacc aaaaacaaaa acaaaaaaga    59400
aacaaacaca caaacaaaaa aaacaatttc caactcaatg ggaaactcat ggtctatagg    59460
aggtcgtttt gtctcagtgg tcttagaaaa agctgctgtt ttttcattac tgtacactac    59520
agctggggac attgtcaagg aaagatgcca tgacaaggca attcttataa aagagttaat    59580
tgggacttgc ttacactttc agaggatttg tccattatca acctatcagg aagcatggtg    59640
gcacacaggc agatacgctg agagttctac atccagaggc tggcagcctc tacctcctga    59700
gtgccagcac ttttaaaagc acgggctacc atcacccagc tatacatgtt ttttattttt    59760
ttaaacatat tatttttatt aattccttga gaatttcaga taagcattca gtgtatcttg    59820
atgtaactca tttcctactt ctcccaacag ccttgtctag ttccaggaca gccagggcta    59880
actaaacaaa gaaactctgt cttaaaatgc caaaccaaac aaacaaaaac ttgtgaactg    59940
gaggtcaaaa gaaagatgat cagtattgta tatttctata ttataaaggc ttaggtttac    60000
atcgtttatt aaaatattct tgtaaagttg cctctatgca gttcacaaaa gtcccaggaa    60060
attgttaaag ttattttatg cttaaagtag tttgtgatgt gtcttttgca tgttaatgta    60120
aagctttaat tgttaaatatg ctgctagagt ctagtcttag aacttactgt ttgtgaagta    60180
gcaattgatt atcatatctg taatagaact ttacttaagg attcagattg aagaagtcct    60240
tacatgggtt ggttatgttt ttacatattt tatttctact gatttgtttt agataagcag    60300
tcaatatgaa gagttatcat tttgtgtata tttctgttta ttttatcatt aaagtagttt    60360
ttgataagtt gaagacattt cttgtgaaat gatcctatat gtatttaacc acacagatcc    60420
tcagtttgtg gtctgccagc taaaggtgaa gatatattcc tccaattcag gacccacgcg    60480
gcgggaggac aagttcatgt actttgagtt ccctcagcca ttgcctgtgt gtggtgatat    60540
```

```
caaagtagag ttcttccaca aacagaacaa gatgctcaaa aaggtttgca attcagttct   60600
attgtgtaga aatagccatt cctcaatgag taaccacaga ccttttgctt aaagcctttg   60660
gttaggaaat tattctgtaa ggagagacta tttctctgcc atctaccaaa ctgattactc   60720
ttttgttaga ttggcagact cttcatttct gtggcattga tgagacatgt aagcagactc   60780
acctgccccg acccttagtt tgttggcttt tttggtttgt tctatgttct tatgttgcac   60840
aagccatgtt ttacccattt gggtttatgt ttcttgagag tagactattt tatattttgt   60900
ttccccaggt tactgagtat ttagtcagta ctgagtattt agtcagtact gagtatttag   60960
tcagtattac ttagttgaaa gaagtggttg tgaagaagta atagtaatta aaaaaaaaa    61020 aaaaaacata ccaaaaaaca aagggtgga aacagctaag catatcctct gtccagggtt    61080
gctgggcctt gagatacact tgggaggagg agagagctca ggtgcagtgt ccttggtgtg   61140
aacatttatc cttggtggct ttagtaccct tagttgaatg tgaacattaa aatgagtctt   61200
aaggtgtaga agtttagct ggatcagaag aagataccag ttttgtgcag aatcaattcc    61260
cgtgaagcac atagagcagt acatagtccg gaaggggggtt ttataaaaag cagtaaaagg  61320
agagcttact tactataaaa ccttgcaatg tcagatcaat ttatcaggag ataatttc    61380 ttttttctag gatctacata gctaagaag aaaaaaatc acaaagttaa ccaaattaat    61440 gttttatca tggacctctc atgaaacaaa aaagctaaat ataaatatct ttgagttact   61500 ggttttttg tttatttttct gagaccacaa taaatgtgag caaacatttc aaaaattagg   61560
tatttggaag gctttagttt ttttccctct tacttcattt gtttgtttgt ttgtttgttt    61620
gtttgagaga catggtctct ctgtctagct ctagctgtct cgaacttgtt ttgtagacaa    61680
ggctagtctc aaactcagag atcgattgcc tctgcatcct aaatgctggg attaaaggcc    61740
tgtgccatcc ctgcccgcta tctcttacat cttgtaagac tctgattcac ataagagtgt    61800
gtgtgtgctc acacttgtgt gtgtgcgtgc gctcacacat gcatatgttt ttctttcctt    61860
gtttgtttga agacagattc ttactctgta gctcaagctg gtctggaact cactaagtag   61920
ctcaggttgg cttcatataa aacagtcttt ttgcttttaaa ttcccaagac aggagccgcc   61980
tctcttggct ttatattgct tgtaaaaaga gataattacc tcactgtctc cttgtagtttt   62040 tagagatgtg ctgtttctta ctccagatct ctgaagattg gatatttata atatatttgt    62100 atatttaga ttacttttcca taaatttcca tttatcatag gttttcctta ctaattatat    62160
gcctgttctg atttaaataa aaacagtttt agaaaatcag tgcacatcag tgagctacat    62220
ttgcaagttt aaataatatt accgtgtttt cttctaagta aaatatgatt gccaactgaa    62280
caactttgtt aaaataattg agatcaataa ggtttgaaaa gggctggaaa cacgactcag    62340
cagttaggag ggagcgctgg atgttctgga ggacacaggc ttggtcctca gcacccatct    62400
gttgtcttac agttgtctgt aataccagac ctgggggga atctgagtcc tacctcgggc    62460
ctccatggac actggacaga tacaggggcc agaaatgtag ttgccatagg gatcaactta    62520
ctagggcttc tgttgaagta gcaacacctg atctttgttt atatttacat atgcataaac    62580
tcagaatatt tttaaaatcc agtattagaa taagaagtag ttttcttagg attttaagat    62640
aaaagtaaga taccagattt tacatgatta tatttttttat ttgaaatttt agaaaagata   62700
acttagtgaa taagaatatt ccacaaggtg tttgccttca cttaagaata tcaaataata   62760
tatggtttat atgttgacta tttgtggtac atttttaaat aagtgaaata catcttccat    62820
ttcttttctg tttaggacaa aatgtttcac ttttgggtaa atacgttctt cataccagga    62880
ccagaggaaa cctcagaaaa agtggaaaat ggaagtcttt gtgatcagga aatcgatagc    62940
```

-continued

```
atttgcagta tagagcgtgc agataatgac aaggagtatc ttgtactcac cctaacaaaa    63000
aacgatcttg acaaagcaaa caaagacaag gccaaccgat acttctctcc aaattttaag    63060
gtcagttaaa accatttggg ggtgggaggg tgtgttttat tctgattgtg aagctaagag    63120
ctagacattg ttctagtatt gttcaatatg taacattccc gagtggttgc gtagcctttc    63180
cttttctgtt tattactcca cttgctctcc ttatttcttc tcctccccccc tccccatctt    63240 gagtctttcc tctttccttt ttccttttta aattcttttt tcattccatt gtatttgttt    63300
cattcacatg taacaaactc aaccatagat tattatatta ttattataac ataataatac    63360
tcctaatatt taaaatagaa aatgaccttc acacatgtta agtgaacata gacctaatat    63420
tcagtgcctt tggatctcaa gtatgtttta agtttccttt agaatcttca acttttcatt    63480 ttttccttt ctctaaattt acatttctat caaccacctg cttcctgatt tttattttag    63540
ataggatctt ggtatatagg ctcaggctgg ccttgaactg gcatgtctct gcctcagcct    63600
cacctggcaa ccatttgctt ttaaaatgta tttctctcta gttttactgt tttaatattt    63660
ttctggcaat gtgcctcaat gcttgtctaa catgagaaat gccttgagtt gaacaccaag    63720
tcctacaaaa caaccagtaa aaaaataaag cataaaatag ttcgtgtaga taaaagctgt    63780
tttcattgtc actgtaaggt aagtcctatg aagcatgcag ctggcaaaga aagtctggtc    63840
aagtggatgg tctgtaaaga gggttgtctg cgtgaaatgg gtgcatttaa ttatgcaaat    63900
tgtatgcgac ctacagaaca gttatgtggg ggaaggagga agagtagaaa tgagaatctg    63960
aggcatgaat gagcttggta tattcagtgg ctgaagtcat ttccactgag tcacaggaac    64020
ccagtcttga tgtagcagtg tggagtgctg aacacagaga aggtataatc tgagcttttt    64080
aaccttccag ttcacttcct aaattgagac tggctcagaa actagggaga ggagaggccg    64140
tggggctgta gtggcaagga gcagtggtaa attactaact ttgaagggg attttttaaag    64200 caaatgttgg ttataagaaa aacttataat gacttgcata atgggaaaag agcaaagata    64260
tgatttaaac ctggtctctg ccaattgttc actagagatt gtcctttagc atgtggccta    64320
gacttcaggg ttttttgtttc ttacctttta aaatggaaat aacctaagaa ctgcagccat    64380
gcatgtaaag gctactgatc aatcctcaca gcacagagtg ctctgttagc ttgcaccatt    64440
ctctcgtcag atgactgttg tagagctagt tgaccttatt aatcagtatt gtgtagtgtc    64500
actaatgtaa acatagagtt gtctcagaga ttgcaagaga aatgttttg aaacataagc    64560 acttgtaaat tgaattttgt gatttagtga gttcattgcc ttcagtttgc acttttatag    64620
aattatacag tgcttatggc tgatgtattt taaaaatagc tttcaactca tcattgtgtc    64680
ttttgagagc acagtagtca atcttcaggt catctgaaaa gcagtgccct tcagaattca    64740
ttttgttata gtactttcaa gtaaatctgc aaaacagaat gtctttgcta atacagaact    64800
cattctaatt gttcattttc atcttaaact ttctttctct aggtgaaact atactttaca    64860
aaaacagtag aggagccatc aaatccagag gctagcagtt caacttctgt gactccagat    64920
gttagtgaca atgaacctga tcattataga tattctgaca ccactgactc tgatccagag    64980
aatgaacctt ttgatgaaga tcagcattca caaattacaa aagtctgatt ttttttttct    65040
tatcaagagg gataaaatac catgaaaaaa aaaaaacttg aataaactga aatggaccct    65100 ttttttttt ttttttttttt aaatggcaat aggacattgt gtcagattgc agttatagga    65160
acaattctct tctcctgacc aatccttgtt taccctatac atccacaggg ttttgacact    65220
tgttgtccag ttaaaaaaag gttgtgtagc tgtgtcatgt atataccttt ttgtgtcaaa    65280
```

```
aggacattta aaattcaatt aggataaata aaagatggca ctttcccatt ttattccagt    65340
tttataaaaa gtggagacag gctgatgtgt atacgcagga gtttttcctt tattttctgt    65400
caccagctga agtggctgaa gagctctgat tcccgggttc acgtcctacc cctttgcact    65460
tgtggcaaca gataagtttg cagttggcta aggaagtttc tgcagggttt tgttagattc    65520
taatgcatgc acttgggttg ggaatggagg gaatgctcag aaaggaatgt ttctacctgg    65580
gctctggacc atacaccatc tccagctcct tagatgcacc tttctttagc atgctccact    65640
tactaatctg gacatccgag agattggctg ctgtcctgct gtttgtttgt gcattttaaa    65700
gagcatattg gtgctagaca aggcagctag agtgagtata tttgtagtgg ggtacaggaa    65760
tgaaccatct acagcatctt aagaatccac aaaggaaggg atataaaaaa agtggtcata    65820
gatagataaa agacacagca gcaatgactt aaccatacaa atgtggaggc tttcaacaaa    65880
ggatgggctg gaaacagaaa atttgacaat gatttattca gtatgctttc tcagttgtaa    65940
tgactgctcc atctcctatg taatcaaggc cagtgctaag agtcagatgc tattagtccc    66000
tacatcagtc aacaccttac ctttatttt  attaattttc aatcatatac ctactgtgga    66060
tgcttcatgt gctggctgcc agtttgtttt tctccttaaa tattttataa ttcttcacag    66120
gaaatttcaa cttgagattc aacagtaagc aggttttgtt tttttttttt cctagagatt    66180
gatgatgcgc gtcctcagtc cagtggctgt cagacgttca gccccttttga ccttacacat    66240 tctattacaa tgagttttgc agttttgcac attttttta  aatgtcatta actgttaggg    66300
aattttactt gaatactgaa tacatataat gtgtatatta aaaagtcat  tgtttgtgtt    66360 aaaaagaaa  ttagagttgc agtaaattta cagcactgca cgaataataa ggcattgaag    66420
tttttcagta gaaattgtcc tacagatgct ttatcgactt gctattggaa gaatagatct    66480
tcttaaatgt gcagtgttga gtcacttcgt tatagtggta gagttgggat tagggcttca    66540
attttacttc ttaaatatca ttctatgttt gatatgccca gactgcatac aatttaaagc    66600
aagagtacaa ctactatcgt aatggtaatg tgaagatgct attacaaagg atctcctccc    66660 aaccctcgg  gaatttggtg tctttcaaat tatatcttga ccttgacatt tgaatatcca    66720
gccattatta gatttcttaa tggtgtgaag tcccatttc  aataacttat tggtgctgaa    66780
attgttcact agctgtggtc tgacctagtt aatttacaag tacagattgc ataggaccca    66840
ctagagaagc atttatagtt tgatggtaag tagattaggc agaacgccat ctaaaatatt    66900
cttagaaaat aatgttgatg tattttccat acctcatcag tttcactcaa ccaataaagt    66960
ttttaaaatt gtaacaaagc tcttaggatt tacacattta tatttaaaca ttgatacatg    67020
aatattgact gactgttgat aaagtcagag acaactttc  ctgagatctc accatggaaa    67080
tctgtacacc cccttgtctt tcctaaaagc tgaaagtggc tgactaaaat gcaaagcagc    67140
tgttgatgtt ttgaagatag tgataaacac tgttctttgt tagttttggg cacagcatgc    67200
taaactataa cttgtattgt tccaatatgt aacacagagg gccaggtcat gaataatgac    67260
attacaatgg gctgttgcac tgttaatatt tttcctttgg aatgtgaagg tctgaatgag    67320
ggttttgatt ttgaatgttt cagtgttttt gagaagcctt gcttacattt tatggtgtag    67380
tcattggaaa tggaaaaatg gcattatata tatattatat atatataaat atatatatta    67440
tacatactct ccttactta  tttcagttac catccccata gaatttgaca agaattgcta    67500
tgactgaaag ggttttgagt cctaattcaa acttcttta  tgacagtatt cacgattagc    67560
ctgaagtgca ttctgtaggt gatctctccc gtgtttctgg aatgctttct tagactcttg    67620
gatgtgcagc agcttatgtg tctgaaatga cttgaaggca tcacctttaa gaaggcttac    67680
```

```
agttgggccc cgtacatccc aagtcctctg taattcctct tggacatttt tgccataatt  67740
gtaaagggt  agttgaatta aatagcgtca ccattctttg ctgtggcaca ggttataaac  67800
ttaagtggag tttaccggca gcatcaaatg tttcagcttt aaaaataaaa gtaggttaca  67860
agttacatgt ttagttttag aaaatttgtg caatatgttc ataacgatgg ctgtggttgc  67920
cacaaagtgc ctcgtttacc tttaaatact gttaatgtgt cgtgcatgca gacggaaggg  67980
gtggatctgt gcactaaacg gggggctttt actctagtat tcggcagagt tgccttctac  68040
ctgccagctc aaaagttcga tctgttttca tatagaatat atatactaaa accatccagt  68100
ctgtaaaaca gccttacccc gattcagcct cttcagatac tcttgtgctg tgcagcagtg  68160
gctctgtgtg taaatgctat gcactgagga tacacaaata tgacgtgtac aggataatgc  68220
ctcataccaa tcagatgtcc atttgttact gtgtttgtta acaacccttt atctcttagt  68280
gttataaact ccacttaaaa ctgattaaag tctcattctt gtcattgtgt gggtgtttta  68340
ttaaatgaga gtatttataa ttcaaattgc ttaaatccat taaaatgttc agtaatgggc  68400
agccacatat gattacaaag ttcctgtgca ttttctatt  tttcccctc  cttgctatcc  68460
ttccaagcaa agcatctttc tgtcatcttg gtagacacat acctgtctac tcatggttaa  68520
gaagagcact ttaagcctta gtcatcactt aataagttat tccaggcaca gtaaaaagtt  68580
caaggttctt ggaaaacggt gcttatttct cttcttataa gccagatgtc tgaagatagc  68640
cctaacccca agaacgggct tgatgtctca ggtctgttct gtggctttct gttttttta   68700
acactgcagt tggccatcag cacatgggag gtttcatcgg gacttgtcca gagtagtagg  68760
ctcaaatata ctatctcctt tctaatattc ttaaaggcta aggagtcctt tcaatataac  68820
agtaagataa cttgtgatgt tttagaagta agcagaccat taatgtcaat gtggagtctt  68880
aatgttacat gaagttgata gtttctctgt gacccattta aaaatacaaa ccgagtagca  68940
tgcaattatg taaagaaata tgaagattat atgtagtcac acatttcttt tagaattctt  69000
agtttggtga aaacttgaat ataaaggtat tttgattat  atgacatttt gatgatattt  69060
gaaaaaagg  aatttcctga cattttgctt ttagatcatg tcccccattg tgctgtaatt  69120
taagccaact tggttcagtg aatgccatca ccatttccat tgagaattta aaactcacca  69180
gtgtttaaca tgcaggcttc tgagggctcc cggagaatca gaccttaagc ccagttgatt  69240
tacttctaac gtgaaacttc gagttcctgt atactttgct agataatttg tggtacatct  69300
aaagcttagt cttaagtggc ttgtgtgtgg atttttattca acattcttgt tgctagggta  69360
gagagaaatg ttgctgagta gaaacaagag tacccagttc aatgtggtac agagagcagt  69420
ccctaaaatc tgtacacagt gtaatggacc actttaggag tcaagaggct gattttttcct  69480
atgaaattac attgcaacag gaagccttct agtatagttc cttttactgt tagaatatgt  69540
ttttatgcat acgctatagc tgctttccca tcttccaaca acaggtatca ggatgtaagc  69600
aagctttaaa cagtgtgaag atggcaggat agtgtcatcg gtaacagtcc tctgactcta  69660
aatgtagttg ctctgtaaca ctttgtgaat ataacatcac aattctcatg tccttggggg  69720
gggggggcat acccagtatt agtatgtttt agtgactaag caatcatttt tctgtttact  69780
catgtacatt ttctctttaa aactaaaacc tgtactgtgt atgtctccaa agcctttag   69840
cttagttttt aggaaatgaa cactgaatgg atcacttttt agtgtagcag gtatgggata  69900
tgtgcattat agagagacct tgtcagctct ctgggcctat ttgaatgttt attgttggtg  69960
tgaggatggt aggggaatca gtaaatacaa gttacgttgg tttagcagag caagctcagt  70020
```

```
gtgggtattt ctctttgaag cgtggtgcgt gacgcactgt gagtagagaa tttggtcacc    70080
ctttgagtcc tcttgcattt tgcaaacttg ctcagcaaat gcgtacctac cttgccccct    70140
aggtaaaagc aggaactact actgatttat ctgtcactca gctgtcttta tatgtgtgct    70200
tctgtgactt gtatcacaca agaatcttaa agatttcaca aattgttacc ttttagctct    70260
gaatgttgag tattctggtg ggctaacaac aagacaaact cttgacagtc atttgagaat    70320
tttcatgaaa catttagctg aaaacatttt ataatttatg aaaaaaatgt gttaccttaa    70380
acttttacat atgtgggaga cattaactgc catatttgag catactgaat tttaaattta    70440
aaataaagct gcatattttt aaatgaaatg tttaacaagg attcatattt tttgtttttt    70500
aagattaaaa ataatttatg tcttctcatg tggaacctca tctgtcacaa tggttagatt    70560
atacagaatg gagcaaggct tgtagtggtt tagcttacag taaaattctt aatgtttaga    70620
tgtgtttact tactggctgt tatgtatact tttgagattt tccacctgtt ctgtgtagtt    70680
ttctaaatga tactcctact taaaaacagc attttagtat ctattttctg tctccattaa    70740
atggtcctca ttttctattg agtttggaag tgtgcacatt gtgtgtgtgt gtgtgtgtgt    70800
gtgtgtgcac acgtgtgcgc gcccgtgcgt gtgtctattt gtggagtttg tatgggagaa    70860 ttagtttttga aagtgctaga atagagatga aatttggttc aagtaaaaatt ttcccactgg    70920 gatttttacag tttattgtaa taaaatgtta attttggatg accttgaata ttaatgaatt    70980
tgttagcctc ttgatgtgtg cattaatgag atatatcaaa gttgtatatt aaaccaaagt    71040
tggagttgtg gaagtgtttt tatgaagttc cgtttggcta ccaatggaca taagactaga    71100
aataccttcc tgtggagaat attttttcctt taaacaatta aaaaggttca ttattttttga    71160 tgatttgctt cttagctttt tattcatccg agaatcaatc cctgctatgt gtaacaggta    71220
tttggactat attacttagt gaaagaggaa catcctgatc ttactgttga aaagtttata    71280
cttcaccaga gtaaactacg taaaagctgt ggggtgtgct aggaagtatg agacctcatg    71340
gctcccttgc atgtccatcc tcagagttta gattctgttt actagagcat tactagagtg    71400
aaatagccat gaaagtgcag agaaacttcc aagtaaaggc agtgagagat ccctgtaccc    71460
tcctgtcttt ttccttccct agtgcagtgt cctgaagtgt gtcctagtgt gtgtcatggc    71520
tctgccagcc caggtcttga ggtaacaccct gcagtggagc tcctgagggt cttcctctac    71580 ccccttttcaa cacaagcaag aaacaataat attttgggtt gctattctaa ccaatatgct    71640
ttgaaaaact tagctttctt gagcagcaaa gggaattaat aataaaaccc aacatattta    71700
gattagtttg tccaattaac aggatgcaag atgtccaaat gttttttttt ttgatgagta    71760
gttattgcgg tacgtcaggc attgtgaacg ctcggcatgc acttgggtga acagcagttt    71820
cctgtctgtg aagtttgcat tctagcaaga aaaatagagc aaagataaat gtgtcagctc    71880
acctcaagca gagtgacttc agtgttggat aggttatttg agagtggctt cagcaggtgt    71940 gggggtttc agtagactgg tgcaatttgt acccagaaac ttccacaaaa ctttactcag    72000
acttggagtt tgaaaatgtt tagtatatct aaggagaatt tatagtaacc tcatcttaag    72060
tagccatgac cattctgttg tctaaattgg tttggtaaag cctgtttaaa caattggttc    72120
ctctttattc tcagagttaa cttttttagtg ttctctgtgt atgtttcaaa aacactaagt    72180
cattttccag aagttaaagg ctctattttg accttaaata gttttgtaat gttgaagagt    72240
catgccattt atgatttgtt gttggacagt gagttataaa tgttgagtta ctcaggatat    72300
gggtgtgatt tatgacctgg tgctctatgt attagttcct aacccataac caaacatcct    72360
gaaaaatacc attatctaag tatcagaagc agcatttcca cacaaagata aaaatcccca    72420
```

```
cctctcctgc ttcatctcaa agattgaagt caaagtgttt aataatctgc tacaatggac   72480
acttgaaaca ttttattcat tacatcatta acattttagt agtggcaggg tccactcctc   72540
agatcaggcc caggactaag gggtgaggtc ttttatttat ttgtttattt ctgtgtatac   72600
acgttcacat gtgtgggagc atgtatggca cgtgtatgta tatgtgggtg gagtcagagc   72660
ttaatgttag ttgccttcct ccatggctat tgaggaagcc atctcttcct aaaatcttcc   72720
taaatctctt cctaaacttg gtgcttggtg attcatctgc aattacagtt ggatgtacag   72780
cccagcatgt agtgttggga tcataacact agtcctcata gttgcaaagc aagtactttg   72840
ctcagtgagc catctcccca gtccctaggg aggaaatctt gaagaaaat gttgactttt    72900 tttttttaat tcttgatttt aaaataggtt taaagaatt tgatagtcat ctatagatag    72960
accatgaatc tgagcaagga gaggtatata ggaagatttg gaagggagga aggcaagggg   73020
agaaattatg taattaaatt acattatcgg gctggtgaga tggctcagag gttaagagca   73080
ccgactgctc ttcggaaggt cctgagttca aatcccagca accacatggt ggctcacaac   73140
catccgtaat gagatatgat gccctcttct ggtgtgtctg aagacagcta cagtacttac   73200
atataacaat aaataaatta aaaaattaca ttgtctcaaa aaataagaaa ataactaaaa   73260
attttaattt tacttaatgt tttcctgtga atattattga taagaaacct ttttgtgtgg   73320 ctgccttttaa cagaggagcc acaagctata ttcttgttac ttattacgtt tgtgtgtttt   73380
tgtatatgca aatgtttgcc atgatactcc atgtaggtta agaggacaac ttgtcaggag   73440
tcttttttct ccttccacta tgtaggtccc agaagttaaa cttaggttgt caggcttggt   73500
gctcatctcc tgagccttct catctgccca taccaggtat tctttagcaa gtacttcagt   73560
aagtacagcc attgtaagtc acaagagcaa ttagacttct tcatggtaga ataattagc    73620 tgatggaaag attatatttt aggattataa atgttcttgg gggggtttg tttttgtttg    73680 ggagttttg gtttgttttg agacagggta cttaggctgg cattatactc acgatatagt    73740
tctggctgac ctgcagcaca tgatcctttg gcttcagtct cccaggtaag aatactggaa   73800
ttacagatgt gttgccaaca cctctggtta ttagtgatgt gtgtgtgtgt gtgtgtgtgt   73860
gtgtatacac acacagtgaa tgttttactc ttttggtaaa aatggaggtc tgaggtaaaa   73920
gtttcctatg tcagctgtcc atagggaaga cttaaaagac tttgcttcaa aagattgagg   73980
gctggtgaga tggctcagca                                               74000

<210> SEQ ID NO 4
<211> LENGTH: 9001
<212> TYPE: DNA
<213> ORGANISM: Mus musculus

<400> SEQUENCE: 4
ggcagatttc taagtttgag gccagcctgg tctacagagt gagttccagg acagtcaggg    60
ctacacagag aaaccctgtc tcgaaaaaaa aaaaaaaatc cctttctctg ctataaggga   120
tggctcagtg gttaagagca ctgactgctc tgccagaggt cctgagttca agtcccagca   180
accatctgta atgggaaata atgcactctt ctagtgtgtg tctgaagaca gctgtagtgt   240
actcatataa ataaaaaata aatcctaaaa aaaaaagaa ttcccttcct cttattgata    300 cccttttctttg tctctaggga ccccccatat atctttctag acatttctga gaactcatgt   360
aaatacatgc tgagcccccct cttttgtagtt tgtaaccttt gctcattcca taccatttta   420 acaaatatttt tccttgaaac actatttctc acccattgca tggaggtatc acataggact   480
```

```
ttatcaggca tcctgttctc cagtgtgtgg cttagagcca gtggaatgca cggcgtgtcc     540
gagaaccact tcacacaggg aagagaatac agatttttac tcagcaagta acaccagctg     600
ggaatggtgg ggcagacaag caatcctagt tactagggat gctgaggcag gaggatctta     660
aattcaagtt tagtccctat ctcaaaaatt aaaaagaac ccctctaacc ccagcaactg      720
agaggcagag gccagggaga tctctgtgag ttcaaggtca gcctgtctgt tctacacaat     780
gagttccatg agagccaaag gtacacagtg tgatatttt aaaaaggtat gtgtgtcttt      840
tttttttca aattttatt attttcttca tttacattc aaatgctatc tggggagtcc        900
cctataccac gcccccctgc tcccctcccc acccactccc acttcttggc cctggcattc     960
cactgtactg aggcatataa atttgcaaga ccaagggcct ctcctcccag tgattgtcga    1020
gttggccatc ttctgctaca tatgcagcta gaaacgcgag ctccggaggt actgggtagt    1080
tcatattgtt gttccaccta tagggttgta gaccccttca gctccttggg tactttctct    1140
agctcctcca ttaggggccc tgtgttccat ccaatagatg actgtgaaca tccacttctg    1200
tatttgccag gcactggcaa agccttacac gagacagcta tatcagggtc ctttcagcaa    1260
aatcttgctg gcatacgcaa tagtgtctgc atttggtggc tgattatggc acggatctcc    1320
aggtggggca gtctctggat ggtccatcct ttgtctcag ctccaaactg tgtctctgta     1380
actccgtcca tgggtatttt gttcgttatt ttaaggagga atgaagtatc cacacgttgg    1440
tcttccttcc tcttgatttt cttgtgtttt gcgtgtgtgt gtgtgtgtgt gtgtgtgtgt    1500
gtgtgtctta actggcagag cacttgtctg tcatgcaggg ggcggggtgg ggggtgggga    1560
ctgtctaatc tccagctcta gtaacaaaaa taaagaagt aaaaaataag taagaaacgg     1620
gggtgtgtct agagatagaa catgggcttt acacatttta gacatcatga gaaaataaag    1680
ctggaaatga cactgggcat ccatcttggc gcatctcaac tttcacactg caaccgaggc    1740
gcgctgtgca aagtcagtga caatccgcat ttccagacac agtgggttca gaccttccag    1800
gcgcgcacgc gggcctcgtg ttctcggttt ccgcggcgac tcggccgacg tcacagttag    1860
aagacaatag cgactttccc cgctcaggct cctcgggaac tttctcagtc cgcacgctcc    1920
aggagccgga gctaccctcc gccccgcccc cagcgtgccc cgcggccagg gagctccacg    1980
aagggcgggc ggaggccgcg ggtagcgatt ggttccgtgc caaggtgggc gtggtcagac    2040
tcaggcctat aaaagctccg tggcgccagg gcctcgtttt tttgcgcggt cctttcctgc    2100
ggcgccttcc gtccgtcggc ttctcgtctt gctctctctg gtccctccgg aggaggccgc    2160
cgcgcgtctc ccggggaagc atggcgatga aagcggtgtg cgtgctgaag ggcgacggtc    2220
cggtgcaggg aaccatccac ttcgagcaga aggcaaggcc cggggcgcgg ggcgcaggcc    2280
gcggtgacgc ggcgcacctg tgcgggagca cgccacgccc ccgccacggc ctgagcccgc    2340
taagtgctga gtcaccgtgg cctggggcag gggctgggcg ccgggaagcg aggcccgggg    2400
cgccgcgggg ccttccgggc gggcggggc ctccccgcgc ccggagcgg ctgggcctgc      2460
ccgggagagc cggcttggca tccgttatcc ttctggggct gctgcttttc cggtgtccgt    2520
gtcccacagg ctcagagccc cgtggccacc ggctgcgatt gttgtaagaa tatttgaacc    2580
cggtggtgcc agaccggact aaggccgcag gacgcgtttg cggcactta aagcaaagtc     2640
ctgggctgtt ctgtactagg tcagggtcgt gtcgcaaggc ggaaagaaag agatggcctt    2700
ggacagccgt cccttgcttt gcactccaga gagagacccg gctgtgggtt ttttctacca    2760
cagcgagttt ctgagcacat tttggaaaag tacatagaga tattttcgaa aatactgtga    2820
ccctgcaaaa acacatgcgt cacagggaag atgtgtgtgg taaggttgtg tccagagcct    2880
```

```
tagggaggtt accgttgttg tattcacctt aatcccgaga gaatatttga taaatgagcg   2940
ttatgtgctc tctgaagtgg tggacatacg tgtgagaagg cagacaccat agtgaatccc   3000
aagtgtttgg tttacgacga gaactgataa cggcaattta gagttttttcg taactagcct   3060 cgtttccagc agtttcttgg cattgaaatg cgttttgttg ttttcctgtg gaagtttttt   3120 gttttgtct ttttctcctc cccacgtaat tcactgtgag aaagacgaag ttcggctggg    3180
tcttacccct gtgtgtgggt ttctgtcatc ttccaccatg ccatgccaga gcagctcgca   3240 ctattttgt gacgctgcaa actacacatc gctggtgccc tttgtaccca atgaaacgat    3300
agttaagcat tccagattgg cagttgtaat caaagctggt tgatttaacc tgttgccaac   3360
ttttcagaat cagatttttc tacccaaagt tcatattccc ttattctgtt gcaaagttg    3420 gacatttaaa aaaaaaaaaa cctaaaaaat gattgtcctt gcttgttggt cggttgctct   3480 tacatttct ccctattgct acactttctg gagcagtact aatttgaatt ttgggtgttc    3540
ttttcttttt tgttaagtgg caaattttct agatttggat agctaatgag attttttttt   3600
taaggtagct ctggttagac ccaaatggat ctccacaggc agtaggacaa aggcattttc   3660
tgaccactaa ataaaaatag gggaactgat aaaatcactg aatgtggaga acagggttct   3720
cggcagccag tgttctgtaa gagtcaagtc tgacagtgca gtagccatct cttccccagg   3780
cctggcattc agtagcccct gtttgttcca cctggtgctt tctaaatgct gttcagtcca   3840
ggtgcctgca cacatggcat ctggcagcaa gtgttaggag aagtgtgaca gggagagaga   3900
ggcctagagc tgagcgtctc cagagccacc ctgtaggaag tgggtctact tggatctgaa   3960
cataggtttg attttcactg ttgtgtgttt tgacttgagc ttttttactgt gcttggttag   4020 ggtgtaaccc agcaacagcc ctggtgcagg agtatttaca ctcaaacttg atgtcttcat   4080
ttttgtattt ttttaaatca aggcaagcgg tgaaccagtt gtgttgtcag gacaaattac   4140
aggattaact gaaggccagc atgggttcca cgtccatcag tatggggaca atacacaagg   4200
taggtcctag gctggctagt gaccagtgat ggaaaggaac tgagtcagga cccaattact   4260
aaccatttaa aactatctcg tttgttttct ttttctttta gataaagtta aaatgaccac   4320
ttaggtcaac cttggaaagt agccacaaaa gtattttatt tagtatcaag tattgcttgc   4380
ttccttaagt gtgggaaggt aaagaaggtg attttcttc attgtaatta taattaagca    4440
gcaccttgct tattctgggt gtttattggg tgcttatttg ggtgtttgga gctgggcgtt   4500
gaggatggat gcattaggca gagtgtctaa ggacaaccat gccttagcat gagaggcata   4560
gcgggacaga agtgacaaaa actgaagatt caatataaat gcttaagtaa gatttatttt   4620
ctctatttgg gattagaatc aagtcagtaa aaagtagtgg cttaaattgc agttagtgaa   4680
cttttaccat attggagtaa tgatctgaat ttgcttaccg tcatttaaga gcctcatcca   4740
tgttgcgaga gccttttcct ttcctctcct tctcccctgc cttcttccct tctccacata   4800
gcccacggtg gcctggaatt tagtcttgtg tgtgctgtgt taaaggcatg taccatcaac   4860
ctgtgtgcta tgtgccataa tttgttctac agttacttag gattgggttt gacccatttg   4920
ataattacta aagttacccc gagttgcctc tggcctggta gctttgattt gttaagctcc   4980
ttccagaatc ctgcccagtt cctatttct tggtctgagt aaacactgga agtcctgcat    5040
ataaaaggac ttgctgcatt gttgagctgt gccttgtgac tggcatccct tagcccacat   5100
gagtagtgtg gtacacctcc tggagttgag gacaccagcc ctggcccttg ggaacaagcc   5160
atctaacagt ctgcctgccc caagtaaaag ctagacaggt gagctgtttg gtggcacatg   5220
```

```
gtctagaaag ataagtattt ttatcatgaa gtatgctccc ttcttaaaag ccaaggtctt    5280
taaatgtggg actttaactt tagaagtgcc attaaagatc acatctgttc cagttacaag    5340
gaaggaacaa gagccaggca tgctgtcctg acactgccat ggccctaagg ctaaggtggg    5400
agggtcatag gtcgcagata tcctgagctg tagtagtgag acactgtctc aaaactcaaa    5460
agcaaacaaa aagaaaaatg tgacagtcta ggaaaaaaag gtagcctgag aatgtaaggc    5520
tatacagtgc agctacttac accagggcgc tgctgcctgt ttttatcgcc ccagcacata    5580
ccaggtcagt gtttgctatg ttggaggttg taagaatgcc tgtgttgtta catataggg     5640 tttacttcat aatctgactg ctggtttctg gtaaataggc tgtaccagtg caggacctca    5700
ttttaatcct cactctaaga aacatggtgg cccggcggat gaagagaggt gagcagcacg    5760
ctctgtatgc atggtggagg agaggggtct gtggaggacc ccagtaagac agaactgcat    5820
ggcctcctgc ctctgctttt gtgtttgttt ccattcaccc aactcactcc cacaacccca    5880
cgtgctagaa tagcttctgt tgggtgaagg agctgacaaa tgtggactct taaagtgatt    5940
tggttttgta gcatttattg aagatgaact aatacaagtg ccaaaaggaa ccaatacaga    6000
aaatatcatg gataacagta ctgtcagtca ctggcaaagt aaatcattgt ataataggac    6060
gctaatgcag ataatgaaaa ctagttgaga ttccatttgt atgtgaaacc ttaggaaagt    6120
cctaaataaa gaagggctag cctgttttta gaatgggggc ctgggagcaa cctttgcta    6180 actcaggagc tggcatactt tactaaagcc ccagattatg actcttctca gagcactacc    6240
tttaaacttg aagaactgtc tgtcaaggta tcctgtagct acctgttttg aactttgtgt    6300
ttccagacct ttgccggtct ggaaaagcca tcatagttga taatgtatgt gtacttttc     6360 atccactcat acgtatttga cttagtcaga ttttaactta gttattgaac tctagtgatg    6420
tgaaatagac atcattgttc atccacctga tgctgttta atgttaggca tgttggagac     6480
ctgggcaatg tgactgctgg aaaggacggt gtggccaatg tgtccattga agatcgtgtg    6540
atctcactct caggagagca ttccatcatt ggccgtacaa tggtggtaag ttttcatat     6600 aaggatatat acataggatt tcttctaaca tagttatgta ccttcccatg actttatggt    6660
ggttaaacta gtttctaaag agtcacataa attgttaaga gttcagggta ggaaaaagt     6720 tctttattg gctgtgatag taaagaatta atttgcctag gtcagttaag aacactgttg     6780
tgctgaaatg cagtagaaag cagttacatt tgatgagact ggatctgagt tgaggataca    6840
atagtcttta gtctaaaaca gccggatttt cttgccatga ttgcccccc ccttgcaaca     6900 tttcgttgag tctaaaatct gcgatggatg gcagtattca agtctgtagg ttatcgcttg    6960
gttaccatat gggagccgtc ttcccaagtt accctcggga gatgcatctg ggtcatgcag    7020
aacaccaagt agtaaaggct cttgcccacc tcgggcagct aacttttcag taggcacttc    7080
cttccttgca gttgacccct tatccttaga atgctcttca gccctattgg tgaagcagaa    7140
cagtcattca taagtgttgt aaaataaagc tttagagtct tgttgctaag tagagatact    7200
tagaattgcc tcttatgtgt aggcctatag ttctttcaac atgagatttt gatagagaaa    7260
tttgtaagaa tgactactgt gtagttgggg aggagctaag atcagcatgt acctggtagt    7320
tacttgggtc ttagtatttc atctagaaat agccactagc aaggaaaaac ttagtggtct    7380
gctcttaact gctagtattt aagtctgtag tattgctggg aagaagtact agttacttga    7440
tcattcaaac ctaaatgttc ttcttttcaa aggtccatga gaaacaagat gacttgggca    7500
aaggtggaaa tgaagaaagt acaaagactg gaaatgctgg gagccgcttg gcctgtggag    7560
tgattgggat tgcgcagtaa acattccctg tgtggtctga gtctcagact catctgctac    7620
```

```
cctcaaaccca ttaaactgta atctgaagag ttgtaactgt gtgactcctt tgactgggct    7680
aaggacagca atgacagctg atggagactg tgtacaactc actgaattca aatctgtttc    7740
tgtgcctttc catattttgc cagactacac aggtgataag ctgaaattct catttgagcc    7800
tgttagtaaa tatgtgtggc acttattttg agcctattaa tgtgtacaaa aaaaaatttt    7860
aagttagctc tatacattga gcatcaataa cagactcaat gatgctaact catagtattt    7920
cattttgaaa gtgttttatg tgataccatc aaaatggtgg gtggtagccc aaacaaaatt    7980
tgagcagaaa attttctgcc cctttatcaga gaaattattg aaagctctca agattcagag    8040
tacttaacct tatattttaa aattgtatta ggattagatg tcatgattta agaaaaagcc    8100
ctttagtaaa cttgtatcaa actcatagaa ggcaaacatg gagcctcagc tagctctact    8160
agccaagtga agttggtacc acccatcttt aaggttggca ctcagggaaa acacaatagc    8220
tcggggaatg acaccaagtt tgactggagg ttctggctaa atcgactttt atagccccag    8280
gtaatgaaat tgagtgcctt aatacccaag aaagagtgcc tttgaaagga atattaaca    8340
ggcttgtgac tatctgaaat agttcaattg aagtattttc aacaaattgg gtgtaaacca    8400
tagttctcac tgatatactg aagtcactga agaagagaca actaaattgg aaaagcacat    8460
aatttggtgt ttccaacctt aaaatttta agtttagatt tccaatctaa gattgctcat    8520
aatgcttttt caagtagtta tgttgaagtt ccaggtaaat cctatgtaac tgatttcctt    8580
aatgtagttt tgatgtgggg gatgactcaa tgcggattaa cttggtaatc acaaaccatt    8640
tagtggctca cgtctcagta ttttttagttg gaaagacaag ctgcaagtct gtccttggaa    8700
tctgacattg gatcatcgtc ggatgcatgt tttatgatac tctaataagg acttaaaagc    8760
ctaagtaggg tcaccagaaa gctgaagcct ggcaaagcta cagacacatt tcttccatca    8820
ttaggaagag ctcagatcta aatgtcaaat gggaacatac aaaaaggaac ttctaggtac    8880
gataaagcta agtttgacaa gttttttgtt taacctagca ccttgtagtt ttaaaaatca    8940
tttttagggt gtgtgcacta agaggaaaac aagttcatat tcttccacct tttattgtcc    9000
c                                                                    9001
```

<210> SEQ ID NO 5
<211> LENGTH: 66001
<212> TYPE: DNA
<213> ORGANISM: Mus musculus

<400> SEQUENCE: 5

```
ggccttggcc tcactgagga aggaagtcac cccatgcctc agggtttttt tttttttttt      60
tttttttttt tttttttttt ttggctgtaa cacgaagcat ttagaattaa aggcttaaag     120
gctctggctg tggtctgaga acgagctaac tgggcactgg gcagagcagg gaaagacaga     180
gtccctacca ccctgctggt atcctgagtg gggttcatgg ccaaagaacg cataactgag     240
ctcaactgag ctggtggtgt ctctgggtga taaggaagag tcagcagaga gcatagccgc     300
caggcagtct gataagcccc tcgaacacat tcctggatgg agtcaggggc ccagcgcgtg     360
tctgggccct ggagttttga gtggaggggta tgcttaaggc ctcgagggac acagaattct     420
gtacgaaggg tgtgcaaagg tcccgggaga catggaattc cgaggggaca gtgtgcaaag     480
gccacgaggg acacagaatg gagggtgtgc aaaagcccaa agggatatgg aattccgagt     540
gggggaagtg caaagggccc cgagggacac ggaattttga gtggagggcg ttcatggccc     600
agaggctggc ccgggctgac tgcaactgat tttaatgcag gggagcggga ggcattcgca     660
```

-continued

```
ggagtccgga agaaagaaga ggtcgcaggg gcggggggtag tggatgcaga cggtgccagg    720
gtcttctgcc ctctgtagag ggcacatcgg ttcccaccta gaccagcaac caccaggaaa    780
gcccagcagc tcggagggc ggcgcccaaa ggaagccacg cccacgcctc accatcagag    840
caccgcccac tccccgcctc ttcccacccc tcgccggaat cccgcgccga actcgggggc    900
gggctgcccg ggccatggcg cataaagcct ctggccacct gcagggctac tgctgctccg    960
gccaccgcca ggcacacacc ttgctgctga gggagtctcg gcttctgtca tctctgtggc   1020
ctccgtcacc tctgtctccg tctccttcag gtcctgagcc ccgagagccc cttccgcgca   1080
cgcggacatg ggcggcagct ccagggcgcg ctgggtggcc ttgggggttgg gcgccctggg   1140
gctgctgttt gctgcgctcg gcgttgtcat gatcctcatg gtgccctccc tcatcaagca   1200
gcaggtgctc aaggtgagtg aagtgtcttg gggagatggg ggttggggat cgggacgcag   1260
ggtgggacgg tggagctacc tcctcaccac cagggaggcc caggctcacc ccagaggctt   1320
ggtctgagtc accagcgtcc caggagccta aacctcactg aagcagaagt atggcctggt   1380
tgtccctgag tttcgactgt agctgtcgcg acctccagcc cttctgaacg cgccggccgg   1440
tgactgtacc tagtaacctc agagctgcgc gaaaccctg tacatctgtg aggctcccac   1500
gggctccagt tctttgggtg ctctgcctgt ttcctcccgc ccagatgccc cagagatgcc   1560
ctggctcgcc cccacactgc ctgccagtct cgagagttaa gctgctttct gcccccacg   1620
ctctggcaga ggtagacacg actcaggtct gccgaggata ggcagcccag cctctcccct   1680
gatctcagcc ttaggccctg ttttgcccct tcaaccgggc accgatatta ggcgggtggt   1740
gccggtccag ccacagactc tgccctggga tccggtgtcc ttctatttga gccgggagct   1800
cattaagtcc tggagattac cgagtaattg tgttttctga gacgcagggt tactgcggaa   1860
ggggaaacgg gggctggctc tcagggaaca tccagttaga actggatctg ggatccagaa   1920
ggggctgttg tcacagggtt tgactgacat cttttcctctt agcgggtttg tttactggga   1980
gtttaagaat ggcttcgtgt cccatgtccc atcgcccgct gaaaggaggg aatgaatgag   2040
ggatactccc tcttgggctg gccgctacct gccaggtcct ggcgggtctt caggatggag   2100
ccacaggtgg ctttcctgga gttgtggtgg gtatttccga gttctcttgg ccacactgtc   2160
atttctcttg cttagaattt tcaacccttg tacatgaagg tcccaggagt tgccctgtct   2220
tgggtagagg gaagatcctt cttgttggag catcagaatt gctctgggcc tttctgttag   2280
gtttggcaaa gtagtggtga cagccttgtc tcagtggcag cctgtggttt cagtaagaac   2340
ccagccctgt gcactccgca cgtggactgg gttttcctgct cagccagcct gtagtgggta   2400
gagtgagcag atatcccctg ttcttcgatt tgggggtgag ggggaatctg agctggttcc   2460
ttctcaaact cctttcggga atgttttctt ttgggggttg gcacagagac taaggatggg   2520
gggggttggt gtgtgtgggc gtgcacgtta gcgttgggac tgcgcaggcc tgctccatca   2580
gtcagggtcc catctgcccg tgcttgagaa agaccacgac tggcagaatt gccccatagc   2640
tggtagcttg gggcttcacg tttgagcgag cggcttccac aatcttactt gtgaaaatcc   2700
caaaggcgat tggttggggg ctgagtggcg tgaaggaagg aagagcctaa gacacgccta   2760
gcccaaaaca gcctcttctt agaggccctg gctggaagcc gacctcttga gggaggaaaa   2820
aaaagttcac ttcaggggat ggtgggagga tggcagcgag gggagcaggg agggaccctg   2880
gagttgactt tggattcttg cgttctgtgc tacttgaatg gaagccttgt ctttgtgtgt   2940
gtgtgtgtgt gtgtgtgtgt gtgtgtgttt ctttctttcc ttttttttttt tttttgtaa   3000
gttaaagaag ttgatttata aaagtcagga atactaggtt gtttaagaaa acaagttcag   3060
```

```
gacttggggt gtagctcagt ggtagagaac ttaccttgca ttcaacaggc cttgggttcc    3120
aacacacaca cacacaccttt gcattcaacg gccttgggtt ccaacacaca cacacacaca   3180
gagagagaga gagagagaga gagagagaga gagagagaga gatttcactc ttattttctt    3240
ctgatgatat cattttttga cataaattgt gtgtgtgtgt gtgtgtgtgt gtgtaggtca    3300
cctgatttct tcccttacag atagggtctc ttgatgagct agacagccat ccccctgtct    3360
ctggggttac aggtgcaatc ctatcgatgc acaatattgt atatgtcact gggagtttga    3420
actcaggtcc tcatgtttgc ctagcgtgga catcttttac aaaacccgag ttggatagta    3480
tgtggttttc ttcttttctt cctcctttct ttccttcctt tcttcttctt ttttctcctt    3540
tctcttgatt cgtggtctca ctagatagcc caggaactca gtgcatagtc caggctggcc    3600
tcaaactcag agatccacct acctttgcct cttgagtgtt aggattaaag gtctgtctac    3660
catgcctggc ttaaatagta tggttttttct gttcagtgtt agtattcaaa ggggtgtgtg    3720
tatgcctgtg tgtgtatgtg tgtatacacg cacacgtgta cacacacata catgcacgta    3780
tactcatgca cctgtatgga cgtgcttgcc acgcggtgag accagaggtt gaagtgcagt    3840
gtcttccaca gtgtctctcc accttatttt tttgagacag gctctctcat taaatatgag    3900
gtgtgccttc tctgctagcc actgaacaac aggtccctgg aatctgcctg tctccgcctg    3960
tcctggtact ggggttccag acatgtatca gacgtgctca gctatttttt tttctgcgtg    4020
tccctggcca tcctagaact ccctctgtag gctctccctg cctcctgagt gctgagacta    4080
aaggtatagg ccaccacccc tggctctgtg ttgagctttt gtttgggttt tgagaatcag    4140
aactcagatc ctccagcgag cactttaccc actgggcgat cttcccagcc cctttcaaag    4200
gttttgacag gccgaacatg ccaagtctgt tactgccttt tccccccttta ctgtgctggg    4260 attcctttgt ttacagttcc tctgttgact ggccatgtct ttgtctcaga ctccagagaa    4320
cacatagcgt cctgtgtgag tccaggaaca cttgcacggt ctgagcctta gctgtggacc    4380
cacaggtgcg ctctgttttgg aatttggaat tctctactat tgctcccgct gtcaagctgt    4440
gggaccatcc acttcgatgg caatgaagtg tcatttctaa accccatcac cctcttttggc    4500 tacctgtggt tttgatttca catcttcagc gccacaaggt tgggcaggag gaacgtgatc    4560
cccgtgtagg tgacagttt cagagctcag gggctcaggc ctactgtacc atgtgctagc    4620
tggagccggt tcatcactca agagagccaa gttttttcccc cagcagtgag acaggggtca    4680
gatctggttt gctgtccctg agggattagc aagttgcaaa ggagattaca agcggccttt    4740
ggaaatgccc tgtgagcttg cctgcttctg gactcaatct aaccacggca gcgttgtgaa    4800
acaggcagag gctgcgaatt cttcctctct acagataagg gatctggccc atagcaaagg    4860
tcggcagctg gttattaaac atggcctgtg gtgggctggg agggacttca agcggccatg    4920
ctcggtttac cttccatagg gaagtaggaa gcaagcaaga gccctctctt tctgtacagt    4980
gagctgctgg gcagtccaag aaaagaatta agaagggcca ggtttcagga agacatgcat    5040
gatagaaaaa aggctctgtt actattaaag tccctcttcc ccagcctctt acccggcatc    5100
ccagctactt ggagtctgag gcaggaggaa tgaatattca aagccggagg aagttcagag    5160
cctgcctggg ttgcacagga agctcagggg agcttagtga gacccctgtc tttatatcaa    5220
atgtaagcaa ggtgcattag tgcatatttt taaatcccag cgctcagaag gcagaggcag    5280
gcagatctct gagtcaagtc aagtgcctgg atagccaggg ctatagagag agatcctgtc    5340
tcataaagaa acaaacacac aaataaataa cacataaata agtaagtaaa taaataaata    5400
```

```
ggtaagtgga aaactgaaga tagagctcac tgattgatag actgcttccc agtatgtgca   5460
catccctggg ttcaatcccc agcactgcaa aacataaaga gaaacacaca cacacacaca   5520
cacacacaca cacacacaca cacacaccaa aatccctcag ccagtcggtg gtcgcagcgg   5580
cggctcatac ctttaatccc agcactcggg aggcagagac agagtgatct ctgtgtcagc   5640
cagggttaca cagagaaacc ctgtctcaag acaaaacaag tcaaccaacc aaccaaaccc   5700
aaaatgacaa gaatgacatc aaaaccctaa cagtattcta tattttcaac agactcgtgt   5760
tagtgccaaa atggtttaga aaaaggtgcg gaagggtgcg tgccagacac acaaggtaga   5820
taatgctggc tgcacgactc tctgtacatt tttgttttat tttatgtgta ggggtgtttt   5880
tcctgcatgt acctctgtgc atgcagtgcc cttgtagacc agacaggaca tcagatcctc   5940
tggaacttgg acttacagat ggttgtgagc caccatgagg gtgctaggaa tttcacgaac   6000
ccaggtcctg tatcagagcg gccagcctgg ctcttaacca ccgagcaatc tccaaaccat   6060
catgattctt tttgtaaaat attatgtgta tgtatttgtt ggtgtgtgag tggagggggtg   6120 gtgctgcaac atgcctatgc aggtcatggg acaactttga ggagtgattt ctctcctgct   6180
cctaagtggg gtcctaggga ttgaactcag gtcgtcaggc tgccgagccg tctcactgag   6240
cccaatggtt actatcttgt ttgtagttct ttagggcaag gtttcgttgt attactcagg   6300
ctttatttga aatcctcctg cctcagcttc ttgttcatca ctgttcatca tggaagggag   6360
tcagggcagg aactagaaca agggagggac ctggaggcag gagctggtgc agagaccatg   6420
gagggatgct gctacgaact ttctctttat gacttgctca gcttgctttc ttacagaacc   6480
gaggaccacc agctctgggg agaccccctcc cacaataggc cacgcccttc ccatcaatc    6540 actaattaag aaaatgttct acaggcttgc ccattgccca gtctttttt tttttttaa    6600 gatttactta tttattaat gtatatgagt acaccgtagc tgtcttcaga cacaccagaa   6660
gagggcgtca gatctcatta cagatggtta tgagccacca tgtggttgct gggaattgaa   6720
ctcacgacct ctggaagaac agtcagtgct cctaaccact gagccatctc tccagccccc   6780
cccccccccc ccccccagtct tatggaggaa tttgtcttaa ttgaggttac ctcctctcaa   6840
atgacaatag actgtgtcaa gttgacgcaa agctagccgg cacaggcagc gtggttgaca   6900
caggtccttg tcagttaagg aaacagctga aaatggtaag aagtaccccg tgactttctt   6960
ggagtgtgtg taagtgtcac acggagggaa acccaccagc cctggaaccc ctgtgtgtct   7020
cacctagaac ccagcctggc acgcggcttg cccgtccaca gggccaccgc cttcagcaca   7080
gagcctcata atctttccca agtctgggtc tgcatcagct ccactgtcct gacgtggcat   7140
ttcctgttgc actgtgcgtg atctgttcat ctgctgatgc ctccctcctc tgtcccatgt   7200
gtcccctagg tgcaaagcgg aagcctcagg ctgccctcac ctgctccgtt gttctttctg   7260
ctacctcata cctgcttcac cattacccttt tatgaccccct ctaccccat ggccttactg   7320 cctgcttgga cccgtgtggt agtctatcct gctcttctag tgagggatgg tgcccaccct   7380
gctcagactc tctaacattc ccgtctttt ctgagtgaac cccaaattcc tctcagcagc   7440
ttgaaggctc ccaatttgtt tctctttccc accctcaatt cagcacccca ccccacacc    7500 actatgctcc tggtttgagc ccattagacc tagtccctct tcagaggccc tggcgtgtcc   7560
ctttggtggc acatgccttt aattcccagc acttggaagg cagagaggta ggtggatctc   7620
tgagttcaag gccagcctgg tctatagagt gggttttatg acagccaggg ctacacagag   7680
aaaccctgtc tcaaaacgcc ctatccccct aaaaaaatga tttatttatt attttcagtg   7740
ttttgtctgt attcacgtgt gtggtgcttg aggagggtca aaagaggtgt caggattccc   7800
```

```
tggaactgtg acctgtcatg tgggtgctgg gaaccgaact cagattctct atgggtgcag    7860
ccagtgcttg taaacctcgg agccatccct ccagcccacc atccttattc tgtcacaggc    7920
ttggatgtgg ctcgctcttt ttcctgattg agaagttggt cagccaggtg aagggctagg    7980
gagctgactg gatgctggcc aatagctggc tctctacccc tccttgcctc aattctaatc    8040
tgatcccttc tcccacagct aggagttggg ctagcctggg atatctactc tgttcctgag    8100
ttgttttgtg acctctggca gagcccattg gcttgacact tggaaggtgt ccctgatggc    8160
agatagctcc ttgtagatag atactgtgtt acgatgctcc tcagagcctt ttattaagta    8220
tctaaacgac tacagttgct ctctgcttca tctaggagga gggacacaaa gagagattaa    8280
gtaaaacttg tcccctggtg tcccatgtct ccccacccca accctctacc tccgcattcc    8340
agatttaggt gacagaacca agatgtagcc tctgctaaaa gattgtaacc cttgaacagc    8400
tggccttgac tggccgttcc ttctttttct cccttctctt ccatcgatgt gcatggctag    8460
cgggtgtatt ccaggttttt ctcccacaag agaaggctgc agattcagca cccccttggta   8520
cctcctcagg aggactctta agtgggaagg tctgcctttt cccagtttgt accaccctgt    8580
gaccttggga tcaaggtctg cctgggccat cgtgggctgc tccccaagtg gagactgggg    8640
ccccagatgt caggatgggt gtccctgcaa gttccctgtt ctctgggccc tgggtaagaa    8700
tgcttgggtg tgctgggatt tcttctgttt tcttcctctt tcctgatgcc tggtttccgg    8760
ttcccatggc ttccggtccc cctggcatgt gtggaactat tttagttccc ttcagggtgc    8820
agctgtggct atagactacc tattttagt cccaagcatt tatttctgtt cctttctggc     8880
tcctcgtaca tccacaagtc ctcatagctt cagtgtgtgt gtctgttggt atacacacct    8940
tttggtgcgg gtccacgtaa tagtgtcccc caggtatagt agcacacaga cagagcttgg    9000
tgtatgtatg gtccagtgct gacatccatg gatgtgagtg tttctgtgta ccgcacgagc    9060
tacaacctat ccacatggag aaaagccagg aaggggatgc aggcacatgg gtcattgtct    9120
gggcccatgt agacacatgc acatatgttg atgcctgttc catttgctgg gggtgggcag    9180
tggacatggc tgcatggcag aatgatggcc ttcgaggtgc aagccactgg gctccgacct    9240
tagcactgca gcagacagaa ggggtcacgg gcactgcatg gtcactgtgt gcagtagtta    9300
ggtgctggta ttttgaagcc agactctcct gttgcattcc tggaaggaag ttaccctggg    9360
acccttcctg gaaggatgga ttctttgcta tcttcccaca gtgactcatc ccctcattcg    9420
ctccaattcc tggagttcgg ctaccaggaa tcctgttctc tggccttgga tcccagcagc    9480
cgactctggg gccagtcctg gagagagcca cttggttctc tgcagagctt atcctaggtg    9540
catcttggtt cctaggaggc ttggcccagg ctgccagctc tgtggccttc tgtggctttt    9600
agggtacaga ggagtattca aatgtccttc cttggccagc aaaagagagg ccctgggcta    9660
ccgtgagctt ctccccaggt tgccactgga tgtttgacat ttcactctta aggaccatga    9720
gttcagctga gaggccttct gaatgagaga gggggggggg agagagagag agagagagag    9780
agagagagag agagagagag agagaagaaa acatggatgc tcttgggtat agtggaggag    9840
aaggtttatt gtagataaaa gggagaacgg gagaacatag ctagaggcag agaccgctgg    9900
aagagtccag agtggacatg accttgaacc ctgagctaga tgaggggagg gggagggaaa    9960
aggagaggag agaggggagc caggtgcaac tgccaagaag gagggagggc aatcaaaatg   10020
gttggattat cctgggggaga gtagcccagc cctctgggct atagagttca gggtaggggg   10080
cagggtatgc cagcctgaag gggttctgaa actggtaggg actgagggat gctgggagaa   10140
```

```
cgtggcagcc aggtctgctt tgatatgtta actagccacc taaaccattt gtgcagggtt  10200
tgaaactcaa taccttcagt gccagatcct gtgccatcaa tttagtttga ggaggattta  10260
gcctggcagg ggtgggtggg ggtgtaggtg gggctctgcc caaaatagaa acaggttagg  10320
aggctaaagc aggggggattg ctagttctag gccagcctgg gctaccctcc ccccaaaata  10380
aataaaaaaa attccataaa aatgaaaaac cagaaaacaa aaacacttga tccttttacc  10440
tctctcctct ctcctcactc tctccctcac tggtgacctt ggcctccact ggcctagggc  10500
agggtcaggc caggctgagc tacaaagaga aacaacaaca acaaaaaaac ccaggtctgg  10560
ctcagcctgg ctctgagtcc cagtggctga ggaggttcca tggctgccga gggaagattt  10620 ccaccctct cctcagatcc cgggctttct ggcctctccc cagctcccat ctcctctgct  10680
ttgtgatctt cagctgccta gggagggaa ggaataggag tgacctgacc cttgcttgct  10740
tcctggcttt tcaatgaagt tccttccacc ctctctggaa gcttctagaa aagggtcttg  10800
gctgggccct ctctggctgt gggttgtctc catggttctc gtggggcagg ggttctcttt  10860 cccccctttgc ctcagccaga ctctggtgga atatgcccag gcccaattca cagctcaggg  10920
ccttaacttc ccccccaacc ccccaccc caccccctgc tcagcccaa actgtcccct  10980 cctgggcctt gacctcaaag gagtctggtg tgccaggtgg ctcaacttt tcctgacctt  11040 cccccttcaac tccaggcctg tcccccttca ccttcctggt tagcttggcc tgtggtcttc  11100
tagcttgtgg cggcagcaag ccacgacctt ggcagcggcc ttccctcgcc ctctctgctt  11160
cccacacgtg agccctgggg aagtgagcgt ctcccacctt tttgtccgtt tcccgaggct  11220
gacttctgtc attttcttat ctggatcctt aaattccttt cctctgtctc ttgtgttcct  11280
cccagctccc agtacagcag ccagaaacag accctaggtc cttcccatgt gtcaagaggc  11340
cagtaccttg ccctctgata ccttctcggc ttgcacaccc caccccttga ttcctctcgt  11400
gcgtgggcta ggtctatagt ctaatgtctg acatttccaa gtgggactcc gctgaggtca  11460
attcagaccc aatatgccac actagttaca tgtacattgg gctttttttcc ttctgccacg  11520 ttgtccccat ggggagtccc caggctcagg agggcaagga cctctgtggt gtttgttctt  11580
tgtccccagc gttggaactg atgccagaca ctgggcttg ggttcccaaa tgtttaccca  11640
aagtggacag ggtcgaatca cagggtgttc tggtaccctg gcactaggaa gtcctgtgcc  11700
aggctagacc atgggtgccg tgtgctact gtcctgccat gggtgatccg gctgatccgg  11760
cacttccccc tgtcacagac agagtgctct ttcgaagaca cagtgcttta gtttaaagct  11820
gtttcaggat ccagctaggt gagatgatgt ggatttgatc cccagagccc acgtcaaaca  11880
agctggtaat tccatccctg gggaggcaga gacaggagac tccatggggc tcccgggatt  11940
cattcctgca acgcaactgg ggagctccag gcttagaaaa gaatcgatct taaaaaaaaa  12000
gatagatagt gctggaggga gcacacctga ggttggattg gcctctggcc tctacatata  12060
tacatacaca cacacacaca cacacacaca cacacagaga gagagggga gagagagaga  12120 cccacaccca cagaggcaga cagacagaca aacacacaca cccagagaga cagacagaca  12180
cacacaaaga gccaaacaca tacacccaca gagacacaca catagagaca tacatgcaca  12240
cagaggcata gagaaagata gacacacaca cacacacaca gagacggagg agagacatat  12300
agagacacac acacacacac acacacacac acagacacac atacaaagac agacagacag  12360
acagacagac acacgcacac actcactcac tcttgccccg atccatcagt cctttcttca  12420
caggctccaa cctgtctggc cagtcagcgg ttctgttcta agcccacaag tctctctcct  12480
cctccattct cacacgcgcc ggaagttcct tctgcccaga tacttttccc cttggctctt  12540
```

```
tcactcagtt cctctcctgt gtttcaaaat aaatgacacg tatttgtatt ttggggtgct    12600
tgggagggac acagagaggc actcatacta gacaagtgtt ctcacaccag tacacccaaa    12660
gcctgtgtgg ggatgttttt gaagacactt cctggtccca gcttccctga cctcccttga   12720
cctttggaag tttccttgcg cccatctcta gtgaactcat tcctttggtt gatgtcctac    12780
caggatgggg atctggtgtg ttttgtacat agctttactc ctgcagtggt ggcctggctg    12840
gggtgggacc ctagcagcca tcgctgaggt cacaagcctt gctgactgcc tctgctccat    12900
tggggggggg ggggctgtgc ctctgttttg cttttttgtt tttgtttttt tgttttgtt    12960 tttgttttg ttttgtttt tttttttttt ttttttttgg tttttcgaga cagggtttct      13020
ctgtgtagcc ctggctgtcc tggaactcac tttgtagacc aggttggcct tgaactcaga   13080
aatctgcctg cctctgcctc ccgagtgctg ggattaaagg cgtgcgccac cactgcccag    13140
caagggctgt gcctctgtct caggggggct gcctcctgat gccactacct aagcctcaga    13200
ccatgagcct ctgtcccctg gatgccattt cttgaagcca cctgggtgag ttggtgttca    13260
tatgtcccag accacaccca ctggcccgag tctctggcag gtgaccctag atccagggtc    13320
tgagtctctg catgttttct cttgactcca gcaactcctc actggtgtct gtgccagggc    13380
tgctggcttc ccccagtaac ctcttcctgt cccaccacaa aggcagtgga ccagaaggaa    13440
gagacccagt tctcagccat gtcatcggga tggctgtggg cggtggataa ataaatcaca    13500
cctgtcttag ccaagggcgg gagagaccag gaggtggggt gcaggtttgc aatgcacggc    13560
cttcgggagt gaacgggagt cttcagcagc cttggtttga cgtggtccgt gtacagtcct    13620
ccgcagggga caagtttagg tttatgaata aagcgaagtc acttcctccc cggagttcca    13680
gataacctgc cccagtgcgg gatgcagtgc gggatgcagt gcgggatgca gtgcggggtg    13740
cagtggacag ctgctttctc ctgccagtga tctatataga aggacctggg aggtgtggct    13800
cacaggtgcg aagaacaaaa ataaactggg tgccattaca cacctgtaat cctggcattc    13860
cagaggcgaa aacaagagaa ccaggtgtta agtcatcctg actacagagg gaattggagg    13920
ccagccctgg ctaaagaggc tgtctaaagg gttcagtgag taatgcttgc caccaagcct    13980
gttgattggc gttcgatcct gggacccaca cagtggaaga aaagaacagg ctctttcaag    14040
ttgtcctctg accgctgtgg gtgtacctca ggcacattca cactcctcac acatacactc    14100
aaataacaaa tgcaaaaaac aataacaaat gcaaagcaat gacgttaagg gctgggaaa    14160 gggggcgggg cttggggctg tccattgcct ctgattggct taggtcacat gctcatgttt    14220
gagccaatca gtgtgtgtca agaaagcttt cctttggaaag aggcgctctc tctgaggact    14280
caggagggga tggagcgatg ttctatgggt tggcaggagg caagggagac aggtagccag    14340
agtaaggaca gaaccttgg cccctagtta gcaccggatc accccaggtt ccgctcgctg    14400
cctcttatgt acgtacatgg gtgctttttt tgacgctggc tccaggcttt tttgattggg    14460
gaggcagcgc gccagggtaa attttataaa tcttaggttg ttgggtcttc aagtacttac    14520
ttgggtttct ctcttttat tttatttcat tcttatcctc attgttattt tggtttttg     14580 aaacagggtt tctctatgta gtcctggctg gcctggaact tactttgtag accaggctgt    14640
cctcgaactc atagagatcc atctgcctct acctccctcc tgagtgctag gattagagta    14700
tttcaccacg cccagatttt gctacgggct acggctgctt ctgcttctcc ttcctattta    14760
ttattattat tattattatt attattatta ttatttttg aggcaggggc tcacactgta    14820
gcccaggctg gcctcacact tttggcaatc cttctgcctc tgcttcccaa atcctgggag    14880
```

```
taaagacatg tgccgtagtg cctggcccat cttttgttt gttaaaatca catgtttgtt  14940
tatttgtgtg tattgtggag ggtaggggtg ccatatgtgt actacacatg tgtagagggc  15000
agaggacaac ttgcaagagt cagttttctt cttctaccat tatgcatggg gttgaactca  15060
ggcaggcttg gctgctgggg ctttattggc taagtcatct ctcctgccct catgcttttg  15120
tttttgtttt tattttgttt cttgagactg ggtttctctg tgtagccctg actgtcttag  15180
aactcaatca gtagaccagg ctggcctcga actcacagag atctgtctgc ctctgcctcc  15240
caagtgctgg aattaaatgt gtgtgccatc accgcccagc ttagcgcctg tgttttattt  15300
ttctctttaa ggacccagat ctcagaggga gctgtgatct gttcaaggcc atagttggta  15360
gccagtgtta gctggtcgtg ggccaggtta actgccaggc tggccgggga agtggggtgc  15420
tgggctaggg aaagataaga gatctcggta agtgagggct agtcatgttg ttttctggtg  15480
acttcgggca gtctcccagc tccctcccac ctacctcttc tttgctctca tctgactgta  15540
ggagtgggag gaggtgtttt gataaagtag gagagatgtc aggacccggt ataccaaagt  15600
tcaagctcta tgcgccttct ctgaggctct gagtgcgccg taggatgcaa acagcgagaa  15660
ccagcccaag cctccgcgcc cttcactaca ctcggcatca ggctcagatg cagaggaggt  15720
aatctgctct ggacgtgttc tgcaatatag ctcaggagtc ggctcacgcc ccagacagag  15780
cagctgttgg ctcttaccca agactctgag gtacgccatg tccttctgga gcagtatggg  15840
gactgaagct gagcttctgc tagtgtctct ttgtaagccg agctgggctc tctggctacc  15900
cacatgtttg ccgtctgcct ggaggagagg tgggaggtga gtgtgttcct ggagggtcac  15960
tgccaaggtt gtaaacccat tggaaagtct ctgggcttga gccttgcggg ggatggctct  16020
gccaattccc tgctgggtaa cctcgggcaa gtgccttaat tcctctgtgc cttttcaccg  16080
tgttcttaat agtgtcctgt gtctgaggag atcatacctg ttaaacacct agaataacaa  16140
gctgctgagt atcgctcagt atgctgatgc acacatcctc ggggacctgt catcaatgct  16200
tgcaactgac ttctcttcta catcctgctc tgagatgtca cagggcatgc tcatggcaca  16260
cccagctttc ccaccagcct taagagtggc tggggatgtc tcaagactga ttctgcagtt  16320
gcccaagtac cttgctggct agccatgtcc cagtaaactc agccaccggc tgttctccct  16380
ccccacgtct aggtttttct tttaaaaatt attgttttgg aaaaatcgct gacacaatgg  16440
gacagtgggt cacattggca ctcacccaaa cctcttggcc ctgcagagaa tgtgcgtaga  16500
cctctgttag agtcaaggtc acttatcctc ctgcccacag cctgcagcta caggctggcc  16560
cctgtgtgtg aggcctctgc ctccagtctt gtccttttc cattcaaatc tgtcttactt  16620
attttctgcc agggtaggaa ctgaacctgg ggtctcctgc ttgatgtgcc atatccccag  16680
tcctttctcc ttaaaaacct ttttacactt acttatttaa agatttttt tttaaattat  16740 gtgtctttgt gtgggtatgt gcacatgagt gcaggtgcct gtggaggcca catgaaggcg  16800
ccagatcccc tggagcaaga gttctagtga gccacctgac tatagggtac tggaaatgga  16860
acttagggtc tctgcaatag cactccatgc ttttaactgc taagcggtct ctctggccct  16920
tatttttgtt tgtttgtttg tttgtttgta tagcgattag aggacatccc tagtttgtca  16980
gttccctttt ctgtcatgtt gacagcaagc acctttactt gctgagccat tttgaaagcc  17040
caactctttc ctaatattat tattaaagtt agtctcacta agtgtcccag gctagccttg  17100
gatgttcagt cctcctgctt tagcctgggg tggcaggctt gcccacagag tccatatttg  17160
gttgtagctg ttaagtttag aggtttgtcc tgtgtggatc tccttcctcc tatcagtggt  17220
acaaccaggc ctctcttgcc acctgttctg caagccttgt ttcccaggag ctgatggcca  17280
```

```
ccttctaggc agggcgccct ggttgtggtt gctatgtgct cttcccacag accctgcaca    17340
taaactgcct agggttatcc tggctgagca ggcagtgcga gcagcggggc ttagagtttc    17400
ttgcaccagc ttctgcttga gtttcctggc tttcccagcc ccacctccat gttcggagag    17460
gtgttgatcc ctctgacgac caggctgagg ccagctcagg gctcccaccc acccttgcag    17520
ctgtaggagt cctggcatgt cagagctggc cttctggagt tggaggccca ggaaggtggg    17580
acctgggggc tcatcctgct ctgctcccta ccgccacccc aacccccatc ctgacctctg    17640
agccctgcag aaattctaag ccctggccct ggtcccctca tctggcctct tagcccagga    17700
ggctcccctg ggctgagagc ccatcttagc cagtgctcca ttgtagctgg ggtcctgacc    17760
tgcgctggcc tcgggatctc cttctcctgt ctgttcccag ccctcactgt gcctcttgcg    17820
cttcctttct tattattgtg aaatagtaca aagttctaac aaaggtcata atacacatcc    17880
gtcaggttaa atcagcccca ggtgaaaaga tggagcctca tggtcccgag gccctgctgg    17940
agggagccac cacccttggg tgctccttgc cttttgtaga accatcccta tatatccgac    18000
ttggtctggt tttgaacttc ctttagtgtc tacaaactct gactttattg ctgtggcatt    18060
ttgctttcgt tgctttgttt gtttgtttgt ttggagacca agcctgctct gtagctcaga    18120
ctaacctggt atcagtcttt ctgtctcagt ctctggcatg caaggcccac agatgcgcac    18180
cgccaagcct gaccacattt gcatcctggc tgtggcccgt tttttcaag ttcatctatg     18240
taatagcgta tacctgtgcc tcctaactct ctgtgactgg acaatgtttt gtgtgtgtgt    18300
gcggttttta atggtataga tgtcacattg tgtttatctg tctttagccg gtggcagcag    18360
gtagctagtg gctcttgtgg gtgtggggag cgtggtgctg tggggtgtgg acacatgctc    18420
acttgtcatg tcctctctct ctccttccct gtctcctcct gtcagtgtct ccctctgtgg    18480
ctcatcctct ctctggcttc gatcttgagt acgttcttcc atctgcttca gtcccatcca    18540
tccacatcac tgtgggtgag agcttacgtt ccgaggcctt gggctggggt ccaggtgttg    18600
gctcagcctt ctcccagcta tgtgacctag tgccattggc tcacctctct gccttaggtg    18660
acttgcttta ccaggccatc atcgtgaaag gccatcagct gtgtgactta agcaacatcc    18720
gcttcctttc tggctcttct ggaggctgca tgcccttggc tgccatggct gctcctgctg    18780
tctagcttgc agccactgcc tgcctttccc tgtctccctg ctgctatcct cagtatctct    18840
ctcctagctc ttcttgctgt agactccggt cacaccgcat cagggaccat cctgactaat    18900
ttattgcctc cttttttttt tttaacctac tgtggcccca tcatgggctc tgaatccagt    18960
acattccaat acagtttgag gcatgggggt ggggtagaca ggtgggagtg gttcggcacc    19020
tggaacgctt caggcaatga cgctatgtgg acaccttgaa atcagagtct ctgtgattag    19080
tggctgggac ccttgaaaga ctgggtcttg tgggaatgaa gaggtgccct ggagtagcca    19140
tgcagtaagc agttgctagg gatggggtgg ggtcacacag ctgcctttga gtcatccgtg    19200
cttctataag tgaccccagt atcattgctg caccccatct gatgggccag aatctcctct    19260
taggtcaggt gtcactttgg ggtgaataga aagagtctca aggaaaaatc acacaagaac    19320
aggggggttg ctgggcagtg gtggtggcgc acgcctttaa tcccagcact gggaggcag    19380
aggcaggtgg atttcagagt tcgaggccag cctggtctac agagtgagtt ccaggacagg    19440
cagggctata cagagaaacc ctgtctcaaa aaaccacccc cccaaaaaa aacccaaaaa     19500
aaaaccccag ggggttttat gtttattttg tttatgtatt tacttgtgtg tgtacgtgca    19560
catgtatgtt tgtgtgtgtg tgcatgagtt tttgcgtatg cacgagtgtg tgtgtgtgtg    19620
```

-continued

```
tgtgtgtgtg catacagacc tacagaccca aagatgacat caggtgtctt cttttcctgt    19680
cattttctgt gggaataaag gtagattcta gtattctggt tacagtgtcc agggaggtgg    19740
tggcatatcc cagcactggc caatcactta gccaggtgtt accatcttat ctgggttgcc    19800
cgtgtgcata tctggctcct ggctccttgc tgttgcctgg tctccctgtt taatgtctgt    19860
gagagcttgt ctgttaccat ggtgacagat gccctggttt ttccaactct atcaaccata    19920
tacagcatac gcaacacact tcctgggacc tgccacattg ggtggcttca gattggtccc    19980
tgggatgttt gagtaggcag ctggctgcct actgttagca ggctggttac acaagtgtcc    20040
attcaccctc tcagagttct gtgtgaccag ccttcttgaa gaagacgacc tgtgggtgtt    20100
tcagtttgca tttctgaggt gtgtgtgtgt gtgtgtgtgt gtgtgagcat acatctatga    20160
gtgtgtgtat atgtgtaggt gggtgcattt ctgtgtactt gtggatacca gagtctaggt    20220
tgggtgttct cccccatgat tctcaagttt gcatgtttgt ttattctgag gcaagctctt    20280
attgtgtagt gtaggctgac caggaactca ctgtgtagat caggctagcc tcggaactca    20340
ctatgtagat caggctagcc tcgaacttac agagatgcac ctgccttttc ctcctaagtg    20400
ctgggattaa tggcatgcac caccacactt gatcgtaaat tatgtgtgtg tatataaatt    20460
atatatttat ataaatctac aaaatgtata ctatatttat gttatatata tttatatata    20520
taagtaaatg tatatttggt ggtgccggag tttgagccca gagcttcgta ggtgctagtt    20580
aagctctctg ccactctcct acctcccatg ccagtttatt tatttatta tttatttat    20640 tatttattat ttatagattt atctttagat ttatttattt tatgtaagta cactgtagct    20700
gtcttcagac actccagaag agggcgtcag atctcattac ggatgggtgt gagccatgtg    20760
gttgctggga tttgaactca ggaccttcag aagggcagtc agtgctctta cctgctgagc    20820
cacctctcca gccctgccag tttatttttg actcagggtc tctcactgaa tctggagctt    20880
gctgattgtc tagactgtct gaccatcaag cttcaggaac cctcctttct ccactgatcc    20940
caatgcccag agtgctgtag ttatagacct gtatgtctgg gtttgatgac ccacttggct    21000
ttttcatggg tgctggggcg agggtccgca ctcgggtcct cagcttgaac ggctggtact    21060
tgtgtctaga gccgtctgtg cagcctgctg agcctcgctg gcttgtgagt aaggctctga    21120
gaacttgaag gactttaaca ggctaacctg aggtttgggc ttcacttctt cagagcattt    21180
gtgttgcgct gagcatgtgg ctcactttgt agctgcttgc ctggcacaca cgaggccccg    21240
ggggcagccc ccaggacccc atgaacttta tatgatggtc cctatctgtc atctcagatt    21300
ctgcttggct actctaggga gtaggaagcc aatctgggct agagagacac tggcccccaa    21360
aaaggaatct gtgatgaagg tcatggggct caggagtgtc tgcatcttgc ctgggatgac    21420
agtttgatag aggccagcag aaacgtcccg ccaagggcta gaggccaagg acgagtctgt    21480
cccatcacca gagctgaaat cagggtgtgt ttctttcagt ggtggtgccc cagcctccta    21540
gagaggcctg tgttagtcac ctaggtctaa acttgtgtcc ttaagccgtg gaacttcat    21600 ggctaggctg ggcgcttcta gtgtcttgag ggctcttggc tctctccatt cctggaggtg    21660
ttcaccgttc ctcagttgac ggcatcaatg ctcctgtttc tgtctctatc tctgtctcaa    21720
cgtggcctcc tttgtatttt ccatttcctc ttcaaaactg agttattagt attatttatg    21780
tgtatgtgca tatgcctgca tgagtttatg tgcatagcat gcgtgcttgg tccccatgaa    21840
ggccggagga catcagagcc cctggacctg gagttacaga tagtgtgagc caccacgtag    21900
ctgctgggaa ccgaacaccg atgcctgcat ccatcgagcc atctttccag ctcccctgct    21960
cttctttgag acccaaccta agtccaaaca ctttgacatt cattcctatt ttgagttaag    22020
```

```
agtctcaccg tgcagcccag gcaggcttta aattcacaat cctcctgcct cagcttccca   22080
agtgctgaag tgacaggcct gtgccactgc gctgatctga tattttaac ttgacatctg    22140 gccagaccct atttccgatt aaggtcacac agggcacagt caagtatctt aggatcacca   22200
cctacataga tgcatggcag agtaccttt gcccagacag cccctactgt gaaaataaac    22260
tacaggacaa aaatcaccag tctgtcctga tagccggctc tcagcacttg aaggtaggaa   22320
gcaagaggat cagaagttca aggtcatctc tgctaatagt gagtttgaag ccagtccaga   22380
ggggaatgac cctctgggaa gacaaaggtg acatgacact cgcgtccccc agcgtcccaa   22440
gcacagaggt aactttggtt catggctctt tgttccttgc tgcaaaaaac atgtttgtgt   22500
ttagaagagc ccctccctgc cctccctggc ctccctctcc tggcccccgg taccgtgcg    22560 cacttcctgc actttgcagt ctcggattgg gcactcagat ggctctgggt ctcccccttc   22620
tttccagagc gctggaggga tcagccgtgt ttcccatcag ccaaggccgc ggggaatggc   22680
tgtgcattca atagcatgtc tctgggaaat tgggcctatt ccagcaccat cttcccgtgt   22740
cttccggagc tttctcagga gatatatttg tttctacaga cgccactaat tactcctggc   22800
tgggtgcctg gaaatcacat ctgtggatta aggtgccacc agatctgagc ttcctctagg   22860
gccccaggag tcctgacata tcccccattc agcatacttg ctcgcttgct tgcttgagct   22920
cagtttgatt tctccactca tacagcccag gaccccttgc ctagggaatg gggccgccaa   22980
tggtggacta ggtcttctca ggtcagataa gctaatcatt tagacaatcc ccacaggcca   23040
atccaaatgt aggcaggccg tccttcactg agaccctctt cccagggaa tctacgttgt     23100 gtcaggttgc cagagctaac cgctgcaagg ttataatttt aaaggacaag acacatcatt   23160
gggcgtgctt agctcaaagt tgtggcttaa gtacgtaaaa gagtaaaggt taatcaacac   23220
agaatttggt ccccgaagtc acttgccgtg tttagtcacc ctcagagctt cacagtaaga   23280
acttttctca aagaaaaaaa aaaaagaac agccgggcag tggtgtcgca tgtctttaat    23340
cccagcactt gagaggctca tatttctgag ttcaaggcca gcctggtcta ccctccaggt   23400
accatgctgt gtgaggtcca ggcaagctca ccagatccag atccgctccc atctactgag   23460
gtccactcaa ggcattttct gcaagtggag gctcacaggc actgaggtag aggtaccgt     23520 gtgaggccag atgagtgaac cttgactcaa atccccatgt ccaggaactt gctgtgcatc   23580
aagatggcag gatttatgtg gcagcccctg gcagagctgt cccttaagg atcttgatct    23640 ttagaccatc tcctctctgg atggtcatct ctggtgtgtg gctgagggca agaacttgat   23700
tccttgcgcc tttggtttcc tgcttgtcag tggggctggg gctgagagag ataaatgggt   23760
atcattgggg aatcagagag gtgttgccgg gatcggatcc agctgctggc tggcatgggt   23820
agcaaggtgg ccaattcaaa tcgacagtga agagggccag agacgggct catcacgggg    23880 aagggttctt gctgctaagc ctagtaaccg gaattggatc tctggaaccc acatggtgga   23940
aggacagaca gactcctata agttatctat cctctggctt ccacacgtgt gctgtggtgc   24000
atctgtgcct gtgcacataa taaataaata cacaaataag taaatgtgat ttaaaaaaat   24060
aattgaaagg gtctaagaag tgtcctgtgt tttctgtaat tctccactaa gtttatggcc   24120
gatggccgta tggagtagaa tggaggaggc gggcccaggt ctagcttccg actcagtcag   24180
ggtctcatct cccaaggact cagtttcccg gtctgcagag tggttggtgt taattcctgt   24240
atccagttgt caggacttag gggtcagccc acctacctat aaggctgttg tctggggtgg   24300
gagtcattga tgatgatgaa ggtgtccccg gggacctctc acacaagggg acgagtcaaa   24360
```

```
gaaaggtgag gagaagaggc cagccaggga aatggccatg gctgtgggcg ggaggctgca    24420
gtggactgag cagcctggcc ttcgaggtct ccccacagct gaccttccca gtctgggctt    24480
tcatggtgtg tggtccagga gcagataagt ggaccgagct atcagcagtc agggtcaccg    24540
agtcctcatg tggaagtgga ggcggggag aaggggaagg gagatataga atgggctttg     24600
tttcaaggta gaggccaatg gagagccatt gtggaagaac cctatatgta tagcctggcc    24660
tcagagagtc ccattgcccc ctacccagac ccacagcggg gtctagctga gctctggctg    24720
aaaaaaaaaa ccaaaacccc ccaaacaaca ataacaacac aaaacctgtg ggattggaag    24780
gtgcctgtct cctagcagct gggataccca caaactccag ctctaagtgt cgatttaaga    24840
cacttggtgc cttaagtcac ctccaggtgt ctttcagtcc caccaaaacc ttggggatta    24900
ttgatctggc agatgggaca gacacagagg agcagggtag agaggaggag gagtctgagg    24960
ctcttctggg gaagcaggtg ttccctcttc ctgttgagct gactgccccg ttgcatgctg    25020
ggcccctccc aggccctgga gttgcatggt gggcagagaa acagggtctt gatggactgt    25080
ctgcaggact tgacacctgc acaagagggg cagtgtgact ggcctgtggt gagtgtggct    25140
aacaaggcca ctggtgaggg aggggcctct ggtgctgagg agaagcaggc ccctctgagg    25200
gccaggcaag gagcatttcc acctgacaga aaacgaaatg agtatccgaa gtagtttaca    25260
ggtggtgaga gccctggagc agatagatgc tcaggacacc tgtcactggg ctgcaggttg    25320
ctgaaggtca aaggtcgtgc aaacccacaa ggacagcctc tgttgaactt agtaggtcgt    25380
aggtgatgtt gctggtactg taaaagggtg cagctgccat gagaagctgg tgtcaggtca    25440
ctgtcccgtg cagccgtcct cctggggagt ctggacacca cacaacagct gaaggtagaa    25500
gggtcccaat acttagtgat gctggatggg cagataggaa aagcagatga aatacagaga    25560
ggtgagctgg agagggtttc agaggtcagg agctcacatg gctcttccaa aggaccagag    25620
ttcagttccc tgcacccaca tcaggcgagt cacagctact tgtaatatca gctccaggag    25680
atctgacacc cttctgggag cctctttagg gactgtgctc atgtgcacag agcaacacac    25740
acattaataa aattaagatt aaatcttcag aaatgaaaag agggctctcc aagagggaat    25800
agtatgcagc cgtataaagg aagagagaga ttccatttat ttatttattt atttatttat    25860
ctatctatct atctggagac agggtttcat tatatagtcc ccaggtaaat agttcaaact    25920
cgtggtcctc ctgcctcagc tttaaagtcc tgcgatagct gctgcagagg agagaattct    25980
cccacacact ggaacatgga tgaatgctga agttagattc tgagagacgg caggatggtt    26040
gcagcgtgat ttcgtttact ggggccccta gagtacctat tgatgaggtt ggagaaatgg    26100
gacactaagg aggtagtggg aggggaaagg ggccagggag agtgttaagt ggagacaggg    26160
tctcagaagg acatggaagg gcgtggccat tggtggggac agttgcccaa gccatgggtg    26220
tacttaacac catcagaatg gatgctataa aatggcactg cctttaatcc tagcagtgga    26280
agcagaggca ggcagatctc tgagttcaag accagcttgg tctacagatg gcgttccaag    26340
acagctgagg ctacagagaa accatgtctg gggttggggg cttgggggga gagtgacaaa    26400
acaaaaccca agtctggaga ctttagcatg ataaaaatga ataaatcatt atggctgatg    26460
tcccctgaag ggacatgggt cacagccctc cttactctgg tttgtaaaag ggggacccag    26520
tggccatagt gactatgttc cagcctgatg agtgtcttag aaaaaaccca gttccctgga    26580
aatatggccc tgagctgata gctgatgctg gctgccactg cccttcctct gaggtttggc    26640
agggctctgg gattgttctt gaaccccagc cagtctacag ctggaggctc tgtgatatgt    26700
cttccttgaa gtgtctggga gttggtatct tcctagggac agccttgtgc cccaggctat    26760
```

```
tgcatgcagt gccactggaa ggagccctaa ggggaccagg caacagcctg gggattaggc    26820
tgtagagacc tgaggatggg gcccctggcc aaccccaacg gccttgtgtg gcactggctc    26880
aatggagaac tcacacgttt ctaatgtctg tagctgctac tgaaagcatt ctctagaagt    26940
ctcccaaaga cttctcactc agtctaaagt cagggctacc ttccctgtat ggttgggctc    27000
tacccaacag gtgaaccaca tgtgtttcta gaggggtagg aggcagagag gccttgggtg    27060
ggcaacaagg taatctgctt ctgtgtcaat ttcttatctg gcatgtggct gtcgagaagc    27120
agagaccgga ggatcatggg catgagctat acactgaggt ccaggctagc ctgggtgaca    27180
taacctgtca gaaaaactac aagaaaagat tcgcattcac catctggctt ggaccttggt    27240
taagtgataa ccattgtcat tagcctgaca cttaggcgcc aggatcaaga aacaagaact    27300
cccagaatcc tttggggcac cagaaagcct ttcattttga gataggctct ggctgtgtct    27360
ctggctctcg tggaagtcac acagcaatcc ctttgcctta gcctaagtgc agagattgta    27420
gacgtgagtt atactagcct cctctgcatg gattggcttg acctaaactg agctgggctc    27480
tccatcgact tgcttctgcg atttcagagt ggcagcctga cctagctctg cagtggcttg    27540
gtgcagctca gcctgaggct ggtgagatgc ttacaagtca tagctggttg ctgcttggtg    27600
ctggtggtca tgttatgagc aaactggtcc ctggtcagtg ggctccggat tagggctgtg    27660
atggaggcct ctaggaatct cgctaagtct ctcactggtt gttttcatct ctctgagcga    27720
tgtgtaggat tgagtgacag atggcagata attgggagtg ggtgacaggc ttcagtattc    27780
tactttaatg gctgttaccc ggtgatgccg gcataggcgt ctgatgctct gagtacttcc    27840
tctcatgtcc ctgagtcatg cagacttagg aggcctcttc tccactcaca accgtttccc    27900
tgagggcaga atccagttcg gttaactttg cttcgtagta ctaaatacca gtttggggcc    27960
tcgacagtgc gggggagtgg ggcgggttag aatgaaaaaa aaaggagcaa acaggttcat    28020
taacagctaa atgaatgaat gactgatgaa aggatgaatg aatgaagtgt tctcagcctg    28080
tgctgttctg ggtcagggct gagtgggaat gtcaaagggt gtggccacta tgtgagccat    28140
ggagttgggg ttagagggaa ggctgcctgt gggctgcacc agtgttgggg tgcaacccctt   28200 gttgggcagc acctagtttt ccaaagggag tcagaaacga ggcttttgag actaaccttg    28260
gttatgtctg acagggtttg ggggtggggt gggcacatag acactcttgc tttttgtttg    28320
tttccttttc ttttctgggg agtgtgtggt gtcaacttga cagggtctag aatcaccttg    28380
gagacaaatc tctggatgtg tctgtgatgg agccatccta actgctggag cagagaaaaa    28440
ggagaaagat cctagcagtc attcacccct ccctgcttcc tgactgtgga cacagcctgg    28500
caagctgccc ctggcttctt cctctattgc cttccacca agatggactg cggctttgat    28560
cagtgagcca gattagcctt ccttaagctg cttctgtcct acgtatgtat gtatgtatgt    28620
atgtatgcat gtatgtatgt atgtagcaag ccaggggcct gtgcacatac cacacaagtg    28680
ctccgatgtt agcatttggc ccttgagact tgagcgttgg agtttctatc gagtctggga    28740
aaattactgc acaccagaag cctgttaaac agtaacaggc cccagagcga gagccaacct    28800
cacacgcctc ccgtaagctt ctcccactga cagctgtctg tgggccagac acggttgata    28860
tgcgcacctg ctccctggtc agcatggtag gggttctcct ctgagggact ttattggggt    28920
agcccttggg agcagaagga atatggtccg gggattgaca tacacatagg tgcccacgtg    28980
tttgcgtcca gtccagtcca accagggagc ttcctaagaa ccctggagtg gctctcactc    29040
cacttgtctc cagggaaact cactaggtcc tgatgttgcc ctagaggatg ctgggacctt    29100
```

```
ctgatggagc caccttagcc ctctttcctg gggctctgac ttttatagct ggacaggctc   29160
tctgctttgt caagctgggg tcaaagtgag gtcacaaggc ttataccttg aggacaccct   29220
tctacttctg tccctaagat gtatctgcct gctctggtgt gtcaccggag cagaaaccag   29280
tttccccata gcccgaggga ctcaccggcc acacccttg acgtctaggg atcatttgag    29340
gatgagatta tgcatctccc agccactcaa tcggacgtcg gcttcaccct tgtgtattaa   29400
gctactgtag caaaacccttt gaaaacattt atggataacc agcgggcagg tgctggcgtt   29460
tccccaggat gtacagtgaa caggtactta gctctagcag gcaaaccatg gcgccgacac   29520
agttccaccg acatcgtgca tgcattctgg ttgccccaga gccttgccaa cacttgtgat   29580
tatcaatccg tctccttttg gctgtgctgg tatacgtcat agagattctt gtgaatttgg   29640
gggatatgtc cagagttggg gagggcttta tgatgtcaca ggccaccagt ctttatgctc   29700
tgtcatcctt tgggtatggt tttcagtctc aaagctttcc catgatccaa ggtagctctg   29760
tagctctctc catcaggacc gaatttctgg gtggggtgg cgggtgtttc actgaaacca    29820
ccggaacttt tagtgtggtg ggagggggctg ctgttacaaa gattggtcct gtccatttc   29880 ttttttcttt ttttaagatt tatttattta ttacatgtaa gtatactcag acacctacag   29940
tatgcatagg gcatcagatc tcattacgga tggttgtgag ccaccttgtg gttgctggga   30000
tttgaactca ggacctttgg aagagcagtc agtgctctta actgctgagc catctctcca   30060
gcccttgtcc atttttcttcc ctgctgtggt ttaggcctag cacacagcct cttgtgcact   30120
gggtgctcag cagaggcctc gtggatgcca ggaactgaac ccaggtcctt tgtaagagca   30180
gccagtgctc ctaaccactg agccatctct ccagccattc ctggtgtgtt cctggtgtgt   30240
ggtgtcttca tgccctaggc tggattgtcc tttggggccc atccttcctg tatacatagt   30300
aactctacag ggctagtaca ttgcgactgg ctggctggct cagagctgac aggatatgtg   30360
tctcaaccca gatccagggc tggtgaaccc agtggcaatg accagaactg tttcctctcc   30420
ctcctcctcc tccctctcct cctcctcctc ctcctccttc tcttcttctt cctcttctct   30480
ccttcctctt cttcctcctc ttgtttggag atagggtttc tttctgcatc cctagctgcc   30540
ctggtagacc accaggttag ccttgaacac agagatccac ctgcttctgc ctcctaagag   30600
ttggattaaa ggtgtgagcc gacctctgtc agcctggctc aaaaacctgg ttttttttg    30660 aacctgaaat gtgtttgctg tgattcttgg gggaggaggg actggatttt gcaatttccc   30720
aggtcagatt aatgattgct ttgcgagggc tgcagcacct gagctgagcc acactgagca   30780
gggcctggag aggctaggta cagtgtcctg gagatcctgt gcagtcctgt gtggggatag   30840
aggctggggg agcttccatc tctgtgatct tcatgaacca gaggcctctg agcctgatgc   30900
ctgtgcacct gggatatatg gtcagagagt taaagaggtg tagtgaccag aagtgtcctg   30960
ttacccacac agagggtctg ttgggtccct agcacctcat gtggcggcct tgatcagctc   31020
cagctgcctt tttgtttgtt ttctttttga atggagcctc tgatgtccaa gtgtgttcgg   31080
ttcctgcaga ctgacctata tcctggccat cagagaaccc gctaaccccc ggattatggt   31140
gctcactccc agtttggctt gcccagaccc cacctcagac tcaaagcctt tgtttctctg   31200
atgcccagcc accctaccca atccctctct ggaaggcaga tggcttattc tgtgcttatt   31260
ctgtacccag gtcactgctg ccaagcacat gcctagtatg tactggggtc gtgggggagc   31320
aggggtccaa gcaaatgatc agaatgctca cagacctttg tggtgtggag catggagatt   31380
gctccagttt tcctgtctct cgggcacttg gtgtgcattt tggacatccc caaggcttgc   31440
agaatggagt cgaggtagcg tatggctccc cacggaagga ggaaacctca gtgcattagt   31500
```

```
ctgtcggtat tgctgtaatg aaagacacag gcttggtgtt agcatcacat ctgatggggc   31560
cacttcatgt tgttgcgaac tgcttggagc agctatgagc cgagagatta cagtggggaa   31620
gccagaaggc aaagaaagtc tgcaccatcc ccaccaccaa tccccagccc tttcccagtg   31680
gggctaagcc tcctgagggt cccctcccaa ggcttcatgt cagagaccaa gtctccaact   31740
gccaccgaaa gcacgagaat aaagtgtttg cagagcagac atttttaagg taatgatctg   31800
gtgggccaat gagtgtcctt tagagaagac agaaaagaat gtgcagtgga gaggagggga   31860
cagagaagca ggggtgggag ccaagaggct gtacgaggct gagaggctca ccgctggagc   31920
tcagggatgc tttggtgaca gctggcccag gaagtgggag ctgtggtcat ttatttaga    31980 aatataaatg tgtgtgtgtg tgtgtgtgtg tgtatctgtg cacatgtgca tactcggtga   32040
ctttggaggc cagaggatga tgtcatatcc catggaacta gagttacaga tgattgtgag   32100
ccaccaagtg ggtcctggga tttgaacctg ggtcctctgg aagaacccag ccaatgctct   32160
aaccaatgaa ccacctcact tgttgttcaa aaggcagggt ctctcactag gatgtgagtc   32220
tcgccatttt taggctagcc tggctggcca gcaagccctg gcattatcc cgctgtctcc    32280 acctctccag agctgggatc acaagcatac accaccatgc ctggctttgt atggggccca   32340
aactcggctc cttccactta tgaagcaagc actttatggc tgagccatct ccctagaatt   32400
ccaaactctg ttctcaagaa cacactatgt caaaggtgcc cacaggatgc tgggggtttg   32460
tttcctacaa tgatggatta tggcgctcca gaattggctt gggctccttc ctccaagtcc   32520
tctgaggtcc ttccaggtgc ctggcactgc tcagagttca cggatccagc atgagcatca   32580
ttggtggggt ttatggcctg cagagagac gtgagcacaa tacacaggat gagtcattaa    32640
cgtaatcggg aagaaggcag ggagagcctc ggaataaaca agagtttaag agggagccca   32700
gggctcgggg tgggctctgt gggggttcct gagcacagac acaggatccc aggaggcttc   32760
ctctgcaaac atggaaggca gaagaagcga cgaccagtgc aagggcctgg tgggtgagag   32820
tgtgtgaaca ggcaaggcag agcaagcatg ccaggctggt ctaaaggact aatgggggta   32880
tcagtaagac acagccctag agatgccact gagccagatg ggcaaaggct tataggtcag   32940
tgttagcatg gtaaaattta caataaataa ataaacaaac aatccatttg gtttgggat    33000 ggccatacat atgccagggt gcatgtagaa gacacagaac aatgtcttgg agtcttctgt   33060
tctgttgtgt gggtcctggg gatccagctc tggtccttag gcttggtgat taagctcctt   33120
tattttgcag gccacaatct gaaagatgct gggccctggg cttcagatag gggaaggcca   33180
ctccccacag gcattccatt ccccactctg gtggctgtac atgaggtacc tcgtggttca   33240
gcctcccgca acaccccaac cacctgcttg cagagggaac cgcccatcac cccatggttt   33300
tcagtgagat tctgcctagt cctctgtgcc aaaaaagcca agcagaatct ttggggaggc   33360
tgcctttcct gctctcctga gagttctctg ggtggcgaag ggagacaatc tgtctgagat   33420
gaggaccttc gggcgctctc caccgctctg ttggcctctc aaaccttgag aatccctccg   33480
gggcagagtt ttcaaactgg gatgttatct ttctgatatc ggttgtgaca tccctgggg    33540 gtgtgggcaa ctgatgttta aaacatggcg ggagtgtgct ggtgatgatg gggtgataaa   33600
gaaatggctc agaggttatg aggagtatgt ctcatctcac acacacacac acacacacac   33660
acacacacac acacatacac acacacacac acgcgcacgc acatttgagt gtgggtgct    33720 aggaactgaa ttcagtctcc tggaacagcc tcaagtgctt ttaaccacta agccagctcc   33780 ccaccccac cccaccccg caaattaaaa acaagcaaat atataaaagt ctaaaacaca    33840
```

-continued

```
gtgtgagcca ggtgtaatga tacccccaggc tccctataat ctggacattg aagaggcgga    33900
ggcagaaaga tcaggagttt cagagtcatc ctcagctaca tatcaaatca gaaatcctgg    33960
agttggggtg gaaatcattt tgtactggag aggttgccct gggtggcagg cagcatttgg    34020
gagctggtat tcggggtgtt gtcccaggta gaggctccgc agagccatag gcactgcac     34080
agatatgatc tatgttagaa gtgcacacaa gtacccgctg gctgcccggg ctgtgtacct    34140
cacccatgcc ctcacttatt tagcttcagc ttcctattgc agtgttctgg ggaagtatag    34200
tctacttgac tttacagctg acctttaaa aatgatgggt gcatttcagt ttcggtattc     34260
aatggagggc gcagcaagat ggctcagtgg gtgaaggcac ttgctgccaa gcctaatggc    34320
ctgagttcga tccctggggc ccatatggtg aaggaggga gaactgtcct ctgacctcca     34380
cacatgcacc ctggcgtaag caaacccaca cataccca tatacacaaa taagtaactg      34440
cagagattaa aagaatataa aaacctttat tgagacacgc cagccttgtt tattctggaa    34500
tttctcacag taggactcac aacgccctgt gcatatttcc ttctgtattc tctccccag    34560
tagtatactg agtccttccc cttcccctcc cttttttcttt ttgagatggt cttacgtagc   34620
ccaggctagc cctgaattca ctatgtagct gaggatggcc tgggactcct gctcctcctg    34680
cctgtgcttc tggagggctg gggtggcaga ggtgggcact gtgcccactt tgttcagggc    34740
tggggatgga tctaatttaa tccaccaggt cacacacaca cgagtggagc catgagcacc    34800
cgtgggactt gtctcgtgtt ggcagaggca ggttggtaat ctcccagcag ctccacagat    34860
gtttcctaga gtctcggttt ataaacactc ctgtcatggg tggacacgga ccccgcacg    34920
cttgctcggc aggccagcct ttgctggaac accctcctgg dacctttttcc tggcaaagcc   34980
tgttttgtct ttgttttgtc ctcttgctgt tgtgaagcgg gtgattgcca tgcagcaagg   35040
ctggcctcag aaagccagtc aaccctctgc cttagctgcc tgagcgctaa agtgactggc   35100
gtgtgctcca acagcgtgca ccccgagagc cagctcttaa ttttttttttt tttttagttt   35160
tccaccatgt gttgatttgg ttgtggtggt agggattgaa cccagggcct tgcacgggct   35220
gggtaagctc ttttccactg agctgcatct atgtcttctc ttcttttaaa tgtaaaatcg   35280
tttattcagt ctttgagaac cacaacattc atacaacgta tttcaatgat acacgcttgc    35340
tactcctccc agatccccct acaggccact cctgatttta tatccatttt ggttttggtt   35400
ttggttttgt tcaccccttc gagacaggat ctcactagta agtgctggct ggtcttaaac   35460
tcacatagat ccttgtgcct ctgcctccca agcgttggaa gtaaagtcac gtgccaccac    35520
agccagtact ttcttcttgt ctttttcttt tccccccttat ttacccactc aatccaattg  35580
ctgtggccca tatacatatt gtaggggcag ttttacactg tgtggcagta agcaaaatag    35640
tagttctggg gtcatggggg aacagcaccc ccagagcctg tctcagccat ttgattctca    35700
gccagattta tagtatcggg catgttttc gtcctatgga aaggcctta aatccagtca     35760
gagagtattg gctaaaccca taatatccgt gccactaatg cgtccgtggg cagatcttac    35820
caggctgata agctgcaggg tagtttgcag gagtcacagc tgcctaaggg tgccagggtc   35880
ttgaaatgcc tctctgtttt tgccagatgt tcaggctgtg ggtgaccaac ggaaggtgcg    35940
gcaggacatc tcttaggtgg actcagcagg ggattttcct ttcagtgggt cccgaggagg   36000
acaggccaga cccagccatg gctttcatga ctccggcctt gcagtactca aggacaaacc    36060
ccaggcccag agagccaagc taggcctgag agagtgtggc ccagtgtccg cctgcctcgg   36120
agtctactct gacgtggggc tgggcttgac ctgccagttc tggcttgcca cctcccctgg    36180
agcctctgcc tgttgtttct ggctgtttgg ggacagtggg gtggttgtct ttgtcctggc   36240
```

```
aggtcgagtt caaagtcaaa gctgtttggc ttttggacac tgctatctct gatgagctgg    36300
gggtggtgac tcttagctct gtggcattag cagaggtccc aggtcaggga atggtccacc    36360
tcttcctcct agccttggag aaaatcagta gttctgtttt gagacagagt gtctcattca    36420
ctgtgtatcc caggctgacc tcaaagttac catctaactc cttcagtgtc caagtgcta     36480 ggatgacagc cctgcatgac tggacccagg gctgcctgca cactaggcaa tcactaagcc    36540
ccgcccccgg tcctgcttac tgtcttctgt ccctcactgc tggtgactca agaatcatcc    36600
tcttccctct ccctgctcct cagtacatca cacagcactg gctctgcccc cgctccaccc    36660 cccccaccc ccaccccccc acccggtgca taaagccctt gtcttcccga tttggtaaaa     36720
gcttcacggg actggagaca gccagcctgt ctacttccca ctcctgtctg ctactgcggg    36780
aacctcatct gtcaaaaatg aatgaatgag tgaccaaatg aatgaatgaa gaaagaacaa    36840 aagaatgcg ggagtaaatg tgaaatgatc agtgaataat gaatgaatga acgaacgaac    36900
ggctttctgg atgagttatt gactgaaaga atggagagac agccacctgt gcagagctcc    36960
agccctagga gcacctccct cgatgagcac tacctagcca gtgttctgtt ttgctgtgaa    37020
gagagaccac aacgaagaca actctgtatt ataaagcatt taactggggg cttgtttaca    37080
gtttcagagg cttagtccgt tatcctcatg gcagggagca tggtgcaagt taggtggagt    37140
tagtgttgga gcaagttagt gttggagcag tagctgagat cacaggcaga gagggagaga    37200
gagagacagg gagggaggga gaccaatgga ccctgtgctt ggagtgagct tttgtaacct    37260
caaaccctgc ccctagcgac acacctcctt caacaaggcc acacctcctc cgacaaagac    37320
acgcctcttc ctccgacaag gccacacctc ctccaacgac acacccccta atccctgccc    37380
atagcgacac gcctcctccg acaacgacac acctcctaat ccttccaagc cgttctccaa    37440
ctaaaggcta agctgcaaat atctgagcct gtggggcctt tctcattcag accacccag     37500 acacccttcc agatgagcct tggagggtcc atggcgcagg ccaagtctca ggcagctgtt    37560
gcagagccgt aaagtgggga agcccctcct cacactcctc cctgtgtctc cccacagaat    37620
gtccgcatag acccgagcag cctgtccttc gggatgtgga aggagatccc cgtcccttc    37680 tacttgtctg tctacttctt cgaagtggtc aacccaaacg aggtcctcaa cggccagaag    37740
ccagtagtcc gggagcgtgg acccctatgtc tacaggtgag gccaggcagg gtggggtggg    37800
actgtgtgtg ggtgtgtggg tgtggagggg ggtgttctgc catgctgagt tttggagatt    37860
gattgctcca gagacagaag tcggacagac accgcctctc cacagactgt cagccacaca    37920
gagaagccgg aggccacagt ggctgacagt ctgtggagag cggtgtctg tccgaggcga     37980 gtgcatactc gcatgcgtgt cctggggtga gggctaatgt gagtgtaaat gtgttgtcat    38040
ggggggcggg cacagaggac ccaacagcgc acaaaatggg caaaatggct gctgttgagt    38100
cagaaaagtc aaacaaacat gcagaagtga agccagttac gcagcatcta agaagtgagc    38160
ggtgctgggt agtggtggca cacaccttga atcccagcac ttgggaggca gaggcaggtg    38220
gaattctgag ttgaaaactg gatccaggag cggctgcctg gtcctccacc ttggacagag    38280
agttttaact tccataatgc ctatttagc cccatctgtg agacagaggt aatggtaccc     38340
actgtgggta ggttcaagga taagatgaga tagttagttg gagccactta agctctgtct    38400
gccatgccat aaaactctcag taaacgctgc ctgtgtggat atctgctcca tgctggttgt   38460
caagtgaaag ggagacgtgg gggtggggg cagcagttgg agttgttttc cagagaggct     38520
caaagagcct tatggctcac cagggaaagc agagaagagc tgattggtgg tggcagtgtc    38580
```

```
ttgccctgga cagacagcga ggatataaac aagaggtggc aagcttgatt tggtggcctt    38640
ggtgctgttg ggtatcagtg taccatcacc ccagggcatg ctgggagatg atgggtgctt    38700
tcatgtgacc tcacagagcc acagctgact caatgccttt ttacagggag ttcagacaaa    38760
aggtcaacat caccttcaat gacaacgaca ccgtgtcctt cgtggagaac cgcagcctcc    38820
atttccagcc tgacaagtcg catggctcag agagtgacta cattgtactg cctaacatct    38880
tggtcctggt gagactgtgg ccctgtgtca accccatgcc aaccctgctt cctcccagct    38940
tagccttcag gagtcagaga gcaagggcca cctcagcccc actgtctcca tggtgaccat    39000
cccctccttc tcattgcctt acctcccatc tgagactccg ggacctccac tgtggtccct    39060
ggggaagcat gaaggtcaga gccactgggg gccagagggc aggtgggagt ccggaagagc    39120
aggcatttat tgagcacact gtgtggggtc gctgagtctg tcctttggtg tatgcgggga    39180
tctactcaac cctgctgttc aggggaggaa gcaaaagcca ggcagaggca gggaatttac    39240
acagggccca gaaggaccct ccccaaggac aaaatcccag ataccaattg ggccagtgtt    39300
accaaggcag gatcggatcc tgtggtcaga catcacggcc ctcgctggaa gtttgaggac    39360
agggtacacg gtggttggta gtgggggggac agtcaaggca tgatgtcacg aggtaagcat    39420
taccattccc agtgacacta acttgagaga ttggaactgt gagctttgtg tgattttcat    39480
gcttttagaa agattcttct gatctccccc cacccccacc ctcaaccata ggaaactgtt    39540
gaaaacacca gctttcctgc agttgatgcg ggccgatgct gactggattg gtcctttagc    39600
caccttgcct cgagtccatt ttcagaggtg tcccccgggt ccgatggggc tggagggaca    39660 cttttgttt ttattaattt attatattac tactatcatt atcattattt tgagataggg    39720
tgttactggg cagccatagc tgccctgtat ctcattatgt agaccaggcc agccttgaac    39780
tcacagagat ctgccagcct ctgcctcaag tgctgggtgt gagccaccac atttgtcata    39840
ttaattccag ttttttaaaaa ttatttattt tatgtatatg agtacactgt agctggcttc    39900
agacacacca gaagaggtca tcggatccca ttacagatgt ttgtgaacca ctttgtggtt    39960
gctgggaatt gaactgagga agtagtactt taaccactga gccatctctc cagcccttaa    40020
ttccattttt gatattgaaa aagcaacagc attctgtgct gggccagcag gatggctcag    40080
taggtaaaag gtgcctgtca ctaagtcgga tggcctggct ttaatctcca ggacccacat    40140
gactgcctca cattgtcctt tgacctctat acgtgcacta tagcaccccct caataaaatat    40200 aataaaagcc ctgtgttgaa ggagacctgt aagtgttggt gggtaggcat catgcgcttg    40260
cttgatggaa agaacctgga gacaccagcc atgcgttgcc caggaggtgg aaggtggctt    40320
ttggttgaat ggcctttggg aaaaaacaag agcccagatg ctccatacgg aggaagaaca    40380
aacaagaaaa ctataaactc aactgaactt ggggcagtta gaccctgggg gggcttcggg    40440
ggagtagata ttctgggctc ccagtgttga ggtggggcag ggacatgaga agtgaggtgg    40500
aatccctgtg aggagactgc ggcaggagaa tgctgatttc caagccagcc cagattaatc    40560
attgagacct tgctgtaaac atgttcaaaa ggaggccacg gggagtcggg gaggctttct    40620
ccatatgctg tgtttctagg ctcatgttac tgatagaata gggttcacgt cctagctata    40680
aaccgggtat ccaaggggct ggcgagatgg ctcagcgggt aagagcacta ctgactgctc    40740
ttccagagat cctgagttca aatcccagca accacatggt gactcacaac cacctgtaat    40800
gagatctgac accctcttct ggtgtgtctg aagacagcca cagtgtactt atttataata    40860
ataaatgaat ttgggaacaa gaagaggccc taaaaattca attcccaaca acatgaaggc    40920
tcacaaccat ctgtacaact acagtgtagt catatacatt aaaataaata aataaatctt    40980
```

```
taaaaatcaa aaacaaaaca aaacaaggta ttcatatctt tgctggcccc cttctgtgtt    41040
aggttttctc ttaaccttgg ctccagcctc atccgttcgc ttggtgaggg atggcatggg    41100
agcctccttc tctgtgcccc ggctctgcgg agtgtctctg gtggttcact ggttccattt    41160
aggcctcagg tgtggctcta cagacacagt ggctcaggaa ggcttccgga ggtcaggcct    41220
gagcttcgtg tatgcctctg agtccttgta gagttcactc aatctgaacc catcatcggg    41280
tgttctcgag agtacaggtt accctggcaa caaggaccag agaaaggtcc atcctgaggg    41340
cctgagctct ttgcctgaag cctggttgaa agtgggggat ggtgtcctac catgtccttt    41400
accctaatcc catgtccttg gctttccagg ggggctcgat attgatggag agcaagcctg    41460
tgagcctgaa gctgatgatg accttggcgc tggtcaccat gggccagcgt gcttttatga    41520
accgcacagt tggtgagatc ctgtggggct atgacgatcc cttcgtgcat tttctcaaca    41580
cgtacctccc agacatgctt cccataaagg gcaaatttgg cctgtttgtt ggggtaagtg    41640
tcttctgtcc cttcagagag tcaggttatc tctcaaggac cctaactcaa accagcttaa    41700
acaaaaattg ggaaattatc agctcatata acaggagatg ccaggattac attcaggtgc    41760
ggcttgatcc agttcgagtg gggggatatg ctgggggttt aacttagaag atttgaggca    41820
cagcttgcgg ggaggaggag gaggactgga tcttcgaagc acacctctca aatgtcccca    41880
tcagtgtgac ttagaggcac ccactatttc tcacagttga cctttggtaa cctgagctaa    41940
ggtttggtct ctgacccctg accccaactc tctggttcag ctcagctttc tctgtgggga    42000
tctactgacg gggtgtgctt gcagtaacgt tacccacacc ctccaggacc tgttattact    42060
gagttcacgt gagatttact acccagtggt tagagcactg gctgttcttc aagaggaccc    42120
aggttcgatt cccagcaccc acatgacggc tcacacccca tctgtagctc cagttccagg    42180
ggatctgaca ccctcttctg gctcactcag gcactgcagt gcaggcaatg cacagaccta    42240
catgcaggca aaaagactca gacacataaa ataaaaatat gtccaatctt gtggagagga    42300
gacggggtaa ggcactgtgt ctcccagtga ccagatgggg accccatggg gtgaacacat    42360
aacgagggcg gcaggctgaa tacccagtct taaagctttt acagagttag aggccctggg    42420
taaagccctg tacctgtctg tacctgccct tcccagtacc ccatagagac tgccatccct    42480
ctcttcctga caattgaggt ggggcccttc tactgagctt ctagatcgtt cctgtcagaa    42540
atttgtatta aattctttct ttcttttat ctttgtttta ttatttttat tgagtcaggg    42600
tctctctatg cagtcctggc tgtcctggaa ttcactttgt agaccaggct ggcctcaaac    42660
agatgtctgc ctacctctct ctcctgagtg ttgggagtaa gggtgtgtgc cactaaaccc    42720
ccgctaaaat gccttttttac tttattagct gttggccctg attgagtaga cttgtcatct    42780
gtgtacatgg gagtatgagg caggagtatg caaattcaa aaccagcctg gacaaccctg    42840
tctgaaaatg tgcaataaaa aagaatgctg gatggagggt ggagctggag agatggctca    42900
gcagttaaga gcactgactg ctctaccaga ggtcctgagt tcaattccca gcaaccacat    42960
ggtagctcac aaccatctgt aatgagatct gatgccctct tctgatgtgt ctgaagagag    43020
ctacagtgta ctcacataaa attttttaaa gggtggggg aagctggggg tgtgactcag    43080
tggatgagta cttgcccaca tgtgtaaggc actgggttct gtcccatca tttatgcagc    43140 aacagtgagg ggacatacct atagctgaag aataggtggg cttgtgccta tgttgtgatc    43200
tatgcccagg gctaaaggtg ctgttccctg cctgtctgta gatgaacaac tcgaattctg    43260
gggtcttcac tgtcttcacg ggcgtccaga atttcagcag gatccatctg gtggacaaat    43320
```

```
ggaacggact cagcaaggtg agcaggaggg cagacagtcc ccatcgattg gtgtggggac   43380
tacaccagaa caagccttgg cagagggtgt ccgggtcacc cgaggacttc acggatccca   43440
caactgtccc tgcggtattt ctgtcgggaa ctcttttctg ttcctgagtt gtcatttcta   43500
aggctgacag gaagacattc ccataaagat aagacaatga ggtccagcac cttgcctagg   43560
cccacccgga aatcccccaa cactgcttat agaacccagc ttcctggcca tttacccacc   43620
accacgcctc tgtgtaccca gagaaatgtg ttttccttcc ttcttcgaat acacagaaat   43680
cctgtcatgt gctattttgc tgctggcttt tctccttagg ggcatcttta tggataatgt   43740 gttttttgttc tgttgtgttg tccagaggcc caggtactaa agatggaacg caggccatgt   43800
gaatctttga caaggacacc actgctgagc tagacttctg cccttcactg ggggaattct   43860
aggcaggggc tctaccactg agccacgccc ccagcccctc actgggggat tctaggcagg   43920
tgctctacca ctgagccaca cccttaaatt tttttattct gaaataaggt ctctgtgtat   43980
cccaggctag cttcaaaaat tcaatcctcc tgtctctgtt gccttgtaag tgtttaattc   44040
atagatgtgt gttaccacac ccagccaaca gctattctta gtgggtgctg ttcacattaa   44100
ccagctgctg ttttatatgc attggcattt tgtctgcatg tatgtctgtg tgagggcctt   44160
ggatcccctg gaactggaat tatagacagt tgtgagctgc catctgggtg ctaggcattg   44220
aacctgggtc ctctggaaaa acagccagtg ctcttaacca ctgagccatc tctccagccc   44280
ctaatcgtct cctttctact atgagaaggg ctgattgaaa gctcttacgg cagagtggga   44340
agtgcgttta gttttgctgt tgctgttgct gttttgtttt gttttgtttt ggaagcaggg   44400
tctcagtgta gtcctggcta gcctggaact cgatattgta caggtgactt aactgagtcc   44460
ccacaatact gtatgttctg tccccactgt ggggaacagg aagctgggct agaacctctg   44520
tgcacacagc ctgctcacgg gcttggatat gatgatgtct gtactagggc acacattggg   44580
tgtagatctt ggctgtccct caaggctata tctcatcctg tcctgcagat cgattattgg   44640
cattcagagc agtgtaacat gatcaatggg acttccgggc agatgtgggc acccttcatg   44700
acacccgaat cctcgctgga attcttcagc ccggaggcat gcaggtaagc cctgtgtagg   44760
gactccctgc ctcctaccag gaaactctgc ttctgagatg gttcagggtc cactcaggta   44820
gctccctgga agtgtgctca agtgtctggg ccttctgtgt actatgcctc aatggttttt   44880
cttgtcactg tgacaagata cctgacagag gtgacttgcg aggtgtctgg ggactcagtc   44940
atggtggcag tggtgaaggg tactggtagg aaagtgttaa agtcttgtag cttgggctcc   45000
accatcccca gggtcctaac tgtggcctag aagacatgg tgggtcttca gagacccatt   45060
tccaggtggt gccctagcct gtgcatccat tctggccaca ccagagatga ctctggcctg   45120
gggactcact gggctgatct ttgagccctc ttcctctcta gctcacacag gcagccatgc   45180
ttcatgccag gtgtgaacac agccacgacg gggtgagcaa agtctgtgtg ctctggtgga   45240 cttttcaaaag cagaacttcg ggtttggttt tgttttgttt ttacatttta tttattactg   45300
gttttttaat tttgtgtatc tgtgtgtgtg cacatgagtg caggtgcctg aggaggccag   45360
cagagggcgt cagatcacct ggagctcctg taagaggtgg ctgtgagctg ccctacgagg   45420
atgctgggac tcaaacgttt tgttttgttt tgttttgttt tttgagacag ggtttctctg   45480
tatagtcctg gctgtcctgg aactcacttt gtagaccagg ccggcctcga actcagaaat   45540
ccgcctgcct ctgcctccca agtgctggga ttaaaggtgt gctgcgccac cacgcccggc   45600
tgctgggact cgaacttaag tgttgctcta aactactgag ccacctctcc agcccattta   45660
tttgtgtgtg tgtgtgtgtg tgtgtgtgtg tgtgtgtgtg tgtgtgctga taatggaacc   45720
```

```
cagggcctca cacactctaa gtaagtggcc tgatactgag tcatgccgca gacactaaat   45780
aggatttcag cctggcagaa ttatatgaga gcagggtgca ggccaggtgt ctctttcctt   45840
cagtccttca tggggttatc tccagaaaca aaggcctctt cttacacaat cacaaggatc   45900
gaaatcagag aatttaacat cgccctaata agagcctcta agctggtgct gctgcataaa   45960
ataacaaaac aaactgtgct tataatttca gattaggggc catctttgtg ctggtggtg    46020 gggggagatc aaagcaggaa ctccaggcag ctaatcaatc cacttacagg aacagagtca   46080
cactgaatgc actcatgcct atagctcaga tggctgtctc cattcttata cagtccatga   46140
gccaaaccta gggaatagtg ccgcccacag tgggctggct cttcccacat caattagggg   46200
aatccagaca atttcacaca gtgagagtct cttcacagga gattctaact atgtcaaatt   46260
gacatttaaa aacttaccac cagactgtgt gaaaagattt tctgagaaga cttttgctt    46320 agtgttgggt cttagaaatc tgggtgtcgg tcaggtgtgg cagtgcttgc atttaatcct   46380
agcactcaag gcagaggcaa gggaatcctt gggagtctaa ggccagcctg gtctacatag   46440
ctatttccag ttctttacat agagagacta tagaactaca taaggaaggg cagagggag    46500 ggagggaggg ggagagagag agagagagag agagagagag agagagagag agagagagag   46560
agagagagag agagcgccaa tgtcttatcc tcttttttt ggttcatccc aattggtttc    46620
ctcttgtttt gctttgttgt tttgagttgg ggggggggg ctcactgtgt agcctggcaa    46680
aaaagtatcc tcctgcctca gcctgcacag tcctaggatt gaagccatga gccacagacc   46740
gagttctgcc ctggactctc tttgtttga ggattgagca gacatgtgtg tgtgttatgg    46800
tgttgaccat ggacagtgtg ggtcacccgg gccttgtttc ccatcagaag agtgtttgag   46860
gccagacagt gggagtgaat ggatgaagag gagtcagggt ggacaaggga gactgggaaa   46920
gccgaagtct gggctgaggg agaggtggga tccggaggtt caggggcagg aagggacatg   46980
actaaggccc tggcaggtac agtgagacag gaagtggaga gggaagctgt ggatggcatc   47040
tgtggatggc atcgcactgc agggtgactg cagggccatg gtggttgctc atccctccgc   47100
atgcacagaa aaccattgcc caaagccttg gtttccacag tcctcatcag ctctcaagcc   47160
cctatcaaga gaacatggca catcgttgta agtgtaaggg aactctgtaa acttcagatt   47220
atctcaagtg actgacacag ctactgcaga catgtgctgt gcatgtttta gcttgctttc   47280
tttctttctt tctttcttcc tttctttctt tctttctttt tttttgtgtg gttttctgag   47340
acagggtttc tctgtgtagc ccttgctgtc ctggaactca gtctgtagac ccaggctagc   47400
ctggaactca gaaatccgcc tgcctctgcc tccaagtgc tgggattaaa ggcgtgtgcc    47460
accactgccc ggctgctacc gtactgttat gaatcataat ggaaatgtct gcgttttcca   47520
gtgggctttt gtggcggtt acgacccaca ggttgagaac ctccggccta gggcatgctg    47580
gccaaactgt gctaaactgt gctgagttct ggttttaat ttgcctcatt gggaggatgg    47640
attagtgagt ggggagccaa gggagcaggc agaacattga gggaccgctg aagtttcctc   47700
agcaacaggt gactagtgtc attgctggtc cctgtggttt cttctgcagg ggtgcccag    47760 cctctgtgct caaggcacag ttctcaccct gcctcccctc tgcaggtcca tgaagctgac   47820
ctacaacgaa tcaagggtgt ttgaaggcat tcccacgtat cgcttcacgg ccccgatac    47880 tctgttgcc aacgggtccg tctacccacc caacgaaggc ttctgcccat gccgagagtc    47940
tggcattcag aatgtcagca cctgcaggtt tggtgagtgt cctctaagtg ttctccacct   48000
ctaggctgag gtgagagggt ggtaccggga ttttatctgc tgccagcttg ctgtcccatt   48060
```

```
aatctctggt ctctgcaccc atgatgatct cagtgctaca gatagggagc taaaggtaac    48120
tggaaaaaag ataacagcca ccctgataaa tgtcccaccg gcacgcgtta tccacaagcc    48180
gtgtcgctcc gaagtccgaa gggtcctgcc ccgaggttaa gattccatca gtgggcactg    48240
cttcttggcc aaggagagga gcctgccctc atcctttcct gcttccggag gcaccacatt    48300
ccttggcttg tggtcccttc cttctcaac ctagcatcca gcttgagact gggtagcgcg    48360
ttgtggccca agttagcttc aaacttgcgc atccttcctg cctctgcctt cagaggtatc    48420
gggatagaag gcatgtaccc agacaccaga tcccccaaa acactccgtt ctatgaccac    48480
ctcctcctcc tctatccagc ccatagcttt caggacccca gagactgact gggtagaggc    48540
cactgggata acctggtctg ttatcctggt ggctctaact tctttgccca ctaggacgag    48600
gctggaaaca ttccctgtgg ccattcacct gctgggagca aaagctagag tcctgccctt    48660
cactcaaact ggccacgctc ctattgtgtc aaactctcct ctttagccaa gttgggtgtg    48720
aatcttggta ctggctgtgg cccctggca catctgctct gtgttctaat cctgggccct    48780
accctgctgc tattgctcaa gtctgctccg tgcctcaccc ctcacctggc agtcaggccc    48840
aggctgctct aagcacctcc cacacagtct ttctccttcc cacccacctt cttcccgtgt    48900
cactcgggtg cccttgctct ctcgccagct cgtattgcac cagatgtcaa tcaaactcaa    48960
atgaaatgct tcctctgatc ctgatcagat cctcccagac actctccctg atcttccgtc    49020
ccctctggct ctccagccgc tctctggtac actctctctt atgccttcct gttgcctgct    49080
catggctgtc gatgttattt actgaaccct cccctgcttg tctcctcctt ggactgcaaa    49140
ccctgtggcc atgtcccagt aggatattgg gagtcaaact tctaaggccc ctacacagac    49200
gtgggatcca gggcttgcct gcggacagga agtttcactc acaactgcac ctccgccttc    49260
ccctccttgt accagcaaaa atcccagggc ttggttgaac tggtccagct ctgacctagt    49320
cattaggctg tgttaattgg ccaggctggg tcccacacac cgcagggca gcaacaggcc    49380 cacatcacac agaactctgc tgtcaggaac agaatttcag ctgtgaaaga gaatctaagt    49440
gtagttgtgt ctgtagcttg ttcttttgtt ttgttttgtt ttgttttccg gagacagtgg    49500
gtttaagtat gcgtgtgcgt gtcgcacacg cgtggaggga ggtataaaca ggtgcatcga    49560
tggatggaga ccggaagtga gtgtcttcct tcatcactct ttgtttgttt gtttgtttgt    49620
ttattgatgc agatttttca atcactaatc ctggatcttg ggaggtccag ggatccacct    49680
gtctctgcct cccagttaca gatgtggcgc tgctgggaac ccgaattcgg gtcctcacac    49740
ttgcacagga ggctcttaac tgactaaact gttttcccag cccctaaagc ttgcccttg    49800 taaatcgggt gagaacaaga aaggggaaga ggaacaggga ttcgagtgat agggaacacg    49860
gccatgtgac caacaacccc acaaagaggc aactcttacc acacccaaca tctcccttc    49920 ctgctcctcc tgcccactgg cctgactttt ggtctctcgg ctctctgcct ggcattactg    49980
tttacataga tggagtcaca actgttcttt ctccctcgat ccctgatgcc tcccatgatg    50040
gctctcatga ttatatggta aatctgcaag atagcgggtg atagcctaga ttgttgggtg    50100
gtgttccatg gtggggctaa ctctgcttgc cttactcctt cctggctcac ggagctttct    50160
tttggcattt caccactaca aggatgcttc tagaacattc tcgcacctgc tgtaggagga    50220
gtgcacctga gttcgaattt ctgtggcatt ttatcttaag ataaagaata cacataggtt    50280 tcccttttctg ggtcacgaga ctttcttgga ctcaggactc ccgtgtttc ctgtccttgt    50340 cttgggagca ccttggatct tccctgaagt ggtccttaat caccacgcgg gtaatcctga    50400
gcagttaagt ctggatacac gggccataaa gctataaatt aattatactt attgcccggg    50460
```

```
tgcgtctctc tgagggtgtt tggaaatcaa agaaaagat  gagccacacc tattgttaga   50520
aagccacggg catgccacct gcagcaggtc tgtgctggca gccttgacat cctgttggaa   50580
tctgtgcttc caggtctggt taggtggggg cttcatctcc cggggatcca tggcatccct   50640
ctgaaagaaa tggggttctc tctgatcttt gctggtgtct cctttcacag tatggttgga   50700
aggatgggta gggttttcca agtagaaggc agcatatctc agcgtgactt tagaagggtc   50760
cacagaggtg acgttaggcc tcagggattg atcaggtctc ttttctgttc tgttgtatcc   50820
ttggtgttgt gtttccatga gggcttgaag gccaccctga ggatccttcg cctgtctttc   50880
tgacaggacc aggtgtgtct ctggagcctc gaaggtgcta gggttcacct ggactctcag   50940
tgatccgggt tctctgctgc atccctgccc acgtgcacct cctggctagg ccatttctct   51000
gccaaggctg tcacaggtgc agcactcttg tgtctgacac ctgcacttga agatgcccat   51060
agcagccggt tcaggggttg ggagcaagag gtaggggttg ggggcttcaa gcagtggatg   51120
tcctggagac cagactcgga tggaactcag agatccacct gcctctggct cccaattaaa   51180
gaggtatgct agcctgtctg gctttggatt ttaaagaaat gttttctttt ttttaaaagg   51240
tttattattt attttattta tgagtacacc atagctgtct tcagacatgc cagaagaagg   51300
catcggatcc ccattacaga tggttgtgag ccaccatgtg attgctggga attgaactca   51360
ggacctatgg aagagcagtc agtgctctta accactgagc catctctcca gccctgtttg   51420
ttgtgttttt gagacagagt ttcttttttgt agtcttagct gtcctggaac tcactatgta   51480
ggccaggctg gcctcaaact cagagatctc cttgcctctt cctcctaggt gctgggattc   51540
aaggtgtgca ccaccagacc cagctaaaac acaatgcccc ccctgtggat ctgttgccct   51600
gggagcctct tgtggcctcc ccaggggagac tcagaactcg gaactcccca ggcccttgtc   51660
ctgagatctc tgggttgagc cactttggct ggttggtggt aaagtcccac ctcagggccc   51720
tgggtgggaa tatctcattg gtgctgtccc ttccattcct gtgatgtcag agacccactc   51780
acgtgtaccc ctgagctaca atgtctccaa aagcagtctg tgtgcctggc ttgacattca   51840
gactccgctt ccactcctaa attcatatgg tgttaatttt cctttccact ttcatctccc   51900
atgattccct gctgcacctc cagacctgga ggggtggggg tgggggttg  aaaatcacgt   51960 ccaagctctc acctcttgct acactcccac ccggaatgcc tttcccttgc cgggtagcag   52020
ctgctctctc ccttcctcca cccacccacc cacccacccc caacactgta atcggccact   52080
ctggctccat ccaccctcc  caggtcctgt gtgtgctcag cttggtcccc agtgttagca   52140
tccctgcatc cctggcaccg aggcaggcca acgtgacgct cccgtcttct aacgcctctc   52200
ttcccctcct ccaggtgcgc ctctgtttct ctcccacccc cacttttaca acgccgaccc   52260
tgtgttgtca gaagctgttc ttggtctgaa ccctaaccca aaggagcatt ccttgttcct   52320
agacatccat ccggtaagct ccgtgtcctg ctagtggctg gggcccattc ccagagattg   52380
ccactggccg ctgggcaccc gccccgctcc ccccaattcc ccaggacaga gcgggttcca   52440
actgaggcag gggagttcag ttccttccac agcggctgct cctagaactt caagtcatca   52500
aagtcttact ttaccccaat tccagagttc agtgatatca ttacctttttt tattggggcc   52560 tataaaaaga tataagatag taaattaatt aagacctatc agccgggacg tctccttcac   52620
cagagacaga taccccttgac agtgtcaaga cactaaagac atcatcgtgg gccagtgtct   52680
cacagagaaa tcagggggag gaatttgtcc tctgttaact tctctctgcc tctggtcact   52740
gtaagatgtg tccagtccag ggttcctgcc ctacgtgacg ccctgaaggc attccgtgaa   52800
```

```
gaactctttt ttgttttact gggtggggat ggaagcctgg gttttgaaca cacaaggccc   52860
caggctctga tgccgagctg tgcctgcagc tggccttgaa cttgcaaatc ctcctgcctc   52920
ggcttccagt gtttcttcac acctggctca tagctgaggg ttatcgcaga ggaagggtgg   52980
gcacatgggg cacagtcgtc tgaagtcttt cccaggttgt gcctagctcc ccagcaagga   53040
acttgacata gaggtgtttt atatcaggaa agcccctcag aataggggg cctagttgtc   53100 gactggggac ctgtcctgtg agcctctctc cctgggcag atccatgctt catcccagag   53160
gacgaaggtg tttggtatta ttaactgtct atgcaaatgg cacagtgagg ccaacacact   53220
agcttagaga atggggcacc ctcacctcac ccccagaac ttaggttcca agaccaacac    53280
tgggcaccta ccctggacga cttctaggga gggttgccgg gcccacccat ggtatgcgtg   53340
gttatcacat ccatgcctct gtccaaaagt cataccaggt ttctggaggc ctttgccctg   53400
ggggcaggag ggatctgggc gtcctgggca aaacgtgtcc tggccttcta ctgtgggtga   53460
ttacaatctg agaggtggcc tccggcctcc catcaatctt tcaagagtct catgatctgg   53520
gcagggctaa aggcatcaaa cggtggtctc ttttcaccaa cctttccat tctagaactt    53580 tcttcctgat ttaaataata cctgtgaatt ctcctagtga ttttttggtt gttgttgttt   53640
ttaattttat gtatgtgagt acactgtcac tctcttcaga cacaccagaa gaggacattg   53700
gatccaattc cagatggttg taagccacca tgtggtggct gggaattgaa ctcagcacct   53760
ctggaagagc cgtcagtgct cttaaccgct gagccatctc tccagcgaga tttttttta    53820 aaagcatcac attttaaaaa gagagctgca agcaggcagc tctctgtggc tacctctgtt   53880
agggagcgcc aggatgctac atagtgggaa actggctcga ttaaacctac tcaccctgga   53940
ccaggccctt cctttggttc cctgggctat taggaaatgt aaacaggaga aaaaagacat   54000
ccttactgcg catgccccac acttgggagg cactgtctta ggcagcttcg tgagggctgg   54060
gaggatagct tagtaggtag ggtgctcccc tgccctgcac agagccctgg cttccatccc   54120
agcaccatgt aaagttaggc ataagccagt cctcagaagg tagagacagg aagatttgga   54180
gttcaaggtc atccttggct acatagcaaa ttggagtcca acctggacca catgaaatct   54240
gtccccaaac gaacatgcag atgtggggg cggggggtgt catccctctg caacaagtg     54300 tctagagagg ggatcttgcg atagctgatc cctttgggag caggtatttc ctgagggaga   54360
gcccagtggg tgtgtgggaa atttctagaa gggtggatgc cccagcaggt attatctggt   54420
ttaagttgga taagaaaccc cagggctgga gcaggctgga gcaggctgga gcaggctgga   54480
gcaggctggg aggctcccca caggatctta catctcctca ctgtatttat gctctaggtc   54540
actgggatcc ccatgaactg ttctgtgaag atgcagctga gcctctacat caaatctgtc   54600
aagggcatcg ggtgagtgga gttgggacgg gagcttctga aagcttcagg ggccaggagg   54660
tttcatgcat tggtgatgca aggcacagga cagggcgagg cccaagcgtt gggatccaac   54720
cacctctttt cctgggattg catcattgct ctggatggag actcagaccc aggctgcatc   54780
ctgacactac ctccatcctc cacgcccaag ggctcttctg ccattagtcg cattggtaat   54840
cttgtctccc ccacagtagg atggatttgc ctgcttgtat gtctgtgcac catgtaagtg   54900
caagagccgc cgaggccgga agagggcata gggacctgga gttagacgga gttgtgagcc   54960
actgaatgga tgctgagact tgaacctggg tcctgccagt gttctcaacc acaattccct   55020
gggtttactt tatgtttagc tttgtgtaac gtacagagtg agactgagag tcctcctgcc   55080
cccattccct gcttgcccgg cagaaacatg gtggtaggaa tccagccttg gggctggaga   55140
gatgtcttag cagttaagag cactgacggc tcttccagag gtcctgagtt caattcccag   55200
```

```
caaccacatg gtggctcaca accatctcta atgggatctg atgccctctt ctggagtgtc   55260
tgaaaacact aaagtgtact tatgcaaata aaataaataa ttctttgaac gaaaggaccc   55320
acatgctggt cactcctcag catcgcagat cacatgcctg ggaaccactg aggaagaggt   55380
ggactctggg cttcatggtg aaaactaagt ccgggaattg ctggactcag ctaggcttct   55440
gtacacacac acaccctggg actcctgcat gccagaaaac actctttcac tgaattacat   55500
cccagccctc ttcactttt aggtctcact agattaccca ggctgccctt aatctctctg   55560
tagcccatca tggccttgaa catgcgccac ttgatctgac tcatctgggc tcttgaaacc   55620
ggaggccaaa gtgggctggc cacgggcttg agttcctgag gtcagcagcc aaacattgat   55680
ttgctccact gcctcaaata ctctttagaa atctttatag atttatggag aggtgtcaga   55740
gacgcaagca aatctttgtt ctctgtcccc ggtgcattca gtactgtccg ctcctggcag   55800
tatctgtcac ggtaaggaac caaagtctag tgcagcgtta ttgccacaac tgcagcttct   55860
cagcacgaga tgccgcccgc tcacgcctca cgcccggctc ccgtggctgt gatgggttgt   55920
tttgttttgt ttttttcttt taatctttgt ttcttgttgg tgttgtgagt tttgggattt   55980
tgttttggtt tttggagggg aaggtggttc atacagaggc caaaagagga tgccatgtgt   56040
cctcttttat ccctcttccc tttcttccct cgcggcagga attctcaccg aagccccagc   56100
tagcttctac ctgtctcagc cctggggtca caggttcaaa gccacacaca gcttttagcc   56160
tgggttcagg ggtctcacct cgggttcatt tgcttgagca gcaaatgctt tccccactga   56220
accatcccca gcacagtgat agtttctcct ctagcttttg gggtgttaaa gtacttgctg   56280
gacctgggtg tgtgtggtgc gatcaggttc ccctgtagat agtaacaggg gcagccaccc   56340
aggctttggt gggaggagac tcattattat tttattatta ttggtattat tattattatt   56400
attattatta ctactactac tactactact actactacta tttggctttt tgagacaggg   56460
tttctctgtg ttaataacct tggctgtcct ggaactcact tgtagacca ggttgacctc   56520 aaactcacag agatccacct atctctgcct tcccaagagc tgggattaaa ggcattgtgc   56580
caccacatac acagatatta ttatttattt ttaaagttgt atttatgtat tttatgaatg   56640
agtggtctgt ctgaatgtac acctgtgagc cagaggaggg catcagatgc catgatagat   56700
ggttgtgagc caccatgtgg tggctaggaa ttgaactcag gaccttttaa ccgttgagtt   56760
atctctctag ccccatttt agttgtgttt agtgtgtgtg tgtgtgtgtg tgtgtgtgtg   56820
tgtgtgtgtg tgtgtgtata ggtgcatgcc acaatgaaca tgtgaaggtt gggacaactt   56880
tagggagcct gttccacctt ctgggtcccg gggatggaac tcaggtcttc aggcttagca   56940
gcaagcactg tcacccactc agctgagcct tgccacgccc cttaattaat ttttttgcatc   57000 agggtttcct gtagcccagg ctagcctcaa acttggctaa ggatagtcaa ctgtacgtag   57060
cgttacaggc tccccttat ctttctgtct cattttcttg tgaagtggtt tcgactgagc   57120
gaaggccttt cacatggtaa ccagtagctc tcccactgac accccaagcc caaacatag   57180 ctccattgcg agggtcacat caccccctggt cactcacttt gtgtcccatg tttccaggca   57240 aacaggaag atcgagccag tagttctgcc gttgctgtgg ttcgaacagg tgagtctatg   57300
aaggtagaag ggagtctggg gtctctgtat gttagctgag gcttttagtt cgctttgatg   57360
ctaatgttat gttaacttcc ggtacctaaa tttagctatt tgtatgttta gcctgcccat   57420
atgtatgtat gtatggttat catgtgagtg cccggtaccc gcagaagccc agagagcatc   57480
aggtctccta gaactggaat tacagatggt tgtgagccgt caagtctgaa acgtgggctc   57540
```

```
tcttgaagag cagccagcgc tcttaaccac agagccattt ccaggttttg ttaatggccc    57600
ctgagagggg ggagtggaga tggaattccg caccaggcca ccctgcaggc atcctgatct    57660
cgtcgccctt caggtcctaa gactagattc taaccagcga aagagatgac tgttaggcga    57720
ggaggcttgg ggccagatcc acctcccatt agccagtgcc tcatttcatg ggcgtgccaa    57780
cagcaagggc gtctgggaaa tgtagttctc tttggacttc tagccaaagc gcccgaggct    57840
ctctgttctg atttgggcg gggcacggca cagtgggatg ggtgccttgg agacgcagcg    57900
tgcagcccga cctttcttct gcagagcgga gcaatgggtg gcaagcccct gagcacgttc    57960
tacacgcagc tggtgctgat gccccaggtt cttcactacg cgcagtatgt gctgctgggg    58020
cttggaggcc tcctgttgct ggtgcccatc atctgccaac tgcgcagcca ggtaagtagg    58080
aggggcggcc acgcctcgga ctcggctcgg gtttcagccg acctctgttt cctgcagcta    58140
gctcttgttc tacctcctct ctcgcaccct gcagtaactt ttctctacaa gtcctggaag    58200
gcccaggacc ctcccaggtc ggggctaggc tgaggctagg tacccagtca tttggccaac    58260
aagtgggtgc cacttggtgc ccgctctgga aagtgcctgc cgaaggtaga ggtgggggt    58320
cagggctggg ctggttagag aagcaaagga aagccaggtt aaaccaaaca gagaagatag    58380
tttttcccaa ggaaaatgct ctgggctgga gttgggtgtg agatggaagt gggaggagcc    58440
acgtgtggaa ccatgaactt agattttcta agtccagaga aaaagtgaa agaaattagt    58500
tataaatttt gctgacccca atatatcag catatgaggc tgaagtttta catcagccat    58560
agagcacttg tttagccagt gtgaggcctt gtattcaggc ctcagcgctg acaggaaaaa    58620
aaaataatca aaaataatga aaatatttaa aaagaagaa gaaagaaaa gaaggtctgg    58680
agagatagct cagtgattat gagcacttac tgcttgcagg gacccaggtt cgattcccag    58740
cacctacctg gtgttctgca accaactgta acccttgttc tgtaacccta gttctgtaac    58800
cctagttcca ggtgatctca aggcacacac acagtgcata tacttgcatg gagaacactc    58860
atacacataa actaatacag gtgcctataa tcccagcact caggaaggaa ggaggccagg    58920
ggagaaggat ccggttcaaa atcatccctg gttacatgta gggtttgatc aaggccagcc    58980
taggatacgt gacatcttgt ctccgaaaat caattaaact tcaaaaaaag aatagtgtgg    59040
gcgactggag agatggctca gcagttaaga gcactggctg ctcttccaga ggtcctgagt    59100
tcaagtctca gcaaccacat ggtggctcac aaccatctgt aatgggatcc gatgcctgca    59160
gagcaacagt gtacttgtat acataacata aataaataaa tcttaaaaga caagaatagg    59220
gctggtgaga tggctcagtg ggtaagagca cccgactgct cttccaaagg tcaggagttc    59280
aaatcccagc aaccacatgg tggctcacaa ctatccgtaa cgagatctga ctccctcttc    59340
tggagtgtct gaggacagtt acagtgtact tacaataaat aaataataa ataaataaat    59400
aaataaataa atctttaaaa aaaaacttta aaagaaaaa gacaagaata gtgtggttca    59460
gacagggta ggggtcactt ccataaagaa aggatgactg aggaatgtaa catcagggca    59520
tgcagcccct gaaagcagga agcaaagggg tcatgactag aaccttcgtt cccttctggc    59580
ctcaggagta ccggctcgtg catgagatct tggggttacg acattggtca agtcccctgg    59640
ggtgcttgct gatagctgta gttgtgaagc agggaatttg aggacaggac tgtgatcagc    59700
tgtgattcaa gagggctgct gtctgcaaac aggggagcca ctggccacct ttgaacactc    59760
gtacaagagc cactcacagg gtcccacctg agatgtcctg gggccacagg ctgggctttc    59820
tgtgcgtgct tggtgtgtgt gttggggggg tcttcccacc tgctctcctg cagtcagcca    59880
gctggctgcc tttcttcttt aaggcttgct tgcttgcttg cttgcttgct tgcttgcttg    59940
```

```
cttgcttgct ttgggaagaa cggatccctg tggagtcccc agcacccggc ttccctttcc    60000
aaacacaggc cccaagtctc ttgtcatcac caaggggtgt ctggttgcct ctggctctcc    60060
atgttgactg tagctatgag gatctggagg acatcacggt ctgggcttcc gggctggtgt    60120
tcctccctgc tgctgcccag tgagaactga gccaggcttt ttcagtcaac cattggagga    60180
gagacccccaa aatagaaggc aggcgtctcg ctggggtctg ggggcaaggt tgtttgtcct    60240
gcgggtttca tcagagagag gccaaagaag ccttgtcctg acaaagctag gcctcacctg    60300
tgtgttcctg tccttgagca tctgggggcg gggggttaa ctgcttgctg gtaaagaaca    60360
tactcagtca tacgccattc ataaatcaag agtatgttaa tgtttccctc agattgacaa    60420
ataccatgga cttggagaag aggttaagag agagattgta cccagtaggc tccaggccct    60480
aggttcaaat ccagcccccac cagaccagac cagagaaatt caaacactca gcaggccagt    60540
cccgctgtgg ccacctccgc cactctcttc ctgtcggtga ctttctgctt gccggacttc    60600
cggggcgctt cgcccacagt gcagggtgga acaagactct gcaatcttgt tctcttctgt    60660
ccctttgctt ctggggggac ccagcgtcac cccagtgaca cggcatgcca tataaactag    60720
cttggttgtc ttccaggaga aatgcttttt gttttggagt ggtagtaaaa agggctccca    60780
ggataaggag gccattcagg cctactctga gtccctgatg tcaccagctg ccaagggcac    60840
ggtgctgcaa gaagccaagc tataggtgcg taccaggtaa ccccccctct tcaccccacc    60900
tactcatagc cagtagacct accgtctcta cctatagcat cttcctggat gttattcaca    60960
tggagagcag ttaccctcct gcctctcacc ctcctgcgag atgggaatct tgcctcggtt    61020
tcttggaccc tttcagtcat tgactctcat ttacaaagtc ctgttagaag atgacagtta    61080
gggctggtga gatggctcag tgggtaagag caccgactg ctcttccaaa ggtccggagt    61140
tcaaatccca gcaaccacat ggtggctcac aaccatccgt aacgagatct gacgctctct    61200
tctggagtgt ctgaagacag ctacagagta cttacatata ataaataaat aaataaatct    61260
ttaaaaaaaa aaaagaaga tgacagttag gccagttgct tctcagtgtc ctatccctg    61320
caggttgcta aatacaggtc cctgggcatc ccggaaagcc aagagactct cctagcccaa    61380
aaggtttgaa acttttttt tttttggac ttcaagggca tgtaaaagga cacactgact    61440
ccagttcaga atagagagac tgaaaatgaa gacgtttaaa catcagttaa gcaccagcta    61500
catactcagt cagggcctga ggatagaatt tcatggtcaa gtacacaggg tgtgcgacag    61560
actgctcaat acagtctgaa tttagatgga gtcgtgtgtc cgccctgtgc tttgctgcga    61620
tgggtggtcc agtggtgag ccaccgagtc aggtatagct ggcgtcctgg tttacttagt    61680
agccatctcg caaggatcca ggaccgtact tctccaagat ctccaggtcc tgtagggatc    61740
aaggctcagg agagaggctg agccctacag ggtgtgtccc tgcctgggaa gggactggaa    61800
gagctgtggt ccctgcaatt tggggttagc agaggtgagt gagtgtctca atagaagctg    61860
ctattttagc ttgtgagcca acttgggtgt gagcactttc ttggagggag ctgggggtgg    61920
ggggtggagg cgggggcttgg ggggggcgggg aggggaggcc acagctcagc tcctggaggc    61980
cagctgacta tttgctgcaa tgtcatttgc ttgagaagca aataaggcag aactctggtg    62040
actgtgtgat tgtcctggtg agtgccacct ccctggagga ggaagaagct ctgcagctca    62100
gtgggtcccc atatgtccct ggagctgaga aagggtcctg ccaggaagag gtggggagat    62160
ggttagtgtc tgccagtcat ggtgatgttt gggtattgcc agagtgcgag gggacaaatg    62220
taggctccga gcagaggctc cgcagtccct ttagcccaga tggagcccat aggtacacag    62280
```

```
ccatagccct gtccagaccc taatagaatg aacaagattg ggcttacctc tttactttcc   62340
cagcttggtc taatcctcgt ttggcttcaa gattccctg ggtgccccct agtcctggcc   62400
atgtgctagg gagggcagtg tcctctgagg atcagctaca gcacatgggt ccttgcatag   62460
ggacctcacc ctcccccccc cgaccccca gtgcctggct aagtgaaatt cggtggggcc   62520
ccacactctg ccatgcacct gggtgtgggg gtggtcccta gaggctgctg ctgattgcta   62580
tagaatggaa acagacgtgc cgctagacca aagggtatta ttatatgaat aacgtccctc   62640
tgggtggatg ggcatttctg taaggcaagg gggttggggg ttggcaggca gggttggctg   62700
tccggccagc tgctgtgaac acagtagcct ttaagaaaat gacctgatcc tctgcttctt   62760
tttggtctgt ctctcattct gaattctcct ctgtcagaca cagtacaggg aggagccagg   62820
acagaggagg ggaaatctgc ccacccgccc tggctgccca gagccttgtg gctttgtgtg   62880
tgttttcatg ggagagacca agctacagag ttaactcttg ctttattctc tggcaacaag   62940
ggcgttctgg gccactcacg ctggcttcga acttgtggac atcctcctgc ctctgtctcc   63000
cgagtgcgga gattccaagc atgcaccact actgtgcctt gtgtcccctt ccccatttta   63060
cttctgtttt ggttttggtt ttgtgttttg ttgttttcgt ttttgggtt ttggttttgg   63120
gttttgaga cagggtttct ctgtgtagcc ctggctgtcc tggaactcac tctatagacc   63180
aggctggcct cgaactcaga aatctgcctg cctctgcctc ccaagtgctg ggattaaagg   63240
cgtgcgccac cactgtccgg cctttactt ctgttttttt gtctgtccat ttgtctgtct   63300
gtctgtgtgt ggtgaagcca gggccttttg cttagtgtag tccacctctg agcttcaccc   63360
cagcacttcc tgttttactt ctgagtgaga ctatctggaa tgctgggtg ctgtgtcggg   63420
ggtggaggag tgggatgggg ggtgctcgtt ggctttgatc caaagagaag acgcctccct   63480
gcagtttcct tccctgccac tagggggatc ggtatggggg ttgcagggca ggggtgccca   63540
gtgttcttaa acccggcctt ccattcattt tcctaagttg ggaagtcttt tcaagtcaga   63600
gtctcccaac ttaccaagcc atccttcct gttctgcacc cttgcccaa catcctactg   63660
tccctaaggc ccgaggccac cattacagca gtctggtgag agtgtgtctc tcttacctct   63720
atgaacaaga gccagtttta atagctgttc ctggcccgtc aggtgacagc attttaaaca   63780
tgtgggcaga catttaagcc attcctagtt tctttgtgcg gcggtgttat ctacccactc   63840
cggactctgc cccttcact gtaacaggcc agtctccctg gcctcagttt tcccatctct   63900
aaagggagag gttggaacca agagacctac atgactgagg agtcccgtg tctatagagt   63960
ggcatctctg ggttcatggc agacagggct ggatgtgtca ggaagtggtt tctgtgctgg   64020
tgggatgtgc ggtgggacta ggggaggtag gcagggcagg gctaggtgac aggcttgtga   64080
ctcagcttcc ttttttctcc acagggtcct gaagacacta taagcccccc aaacctgata   64140
gcttggtcag accagccacc cagtccctac accccgcttc ttgaggactc tctcagcgga   64200
cagcccacca gtgccatggc ctgagccccc agatgtcaca cctgtccgca cgcacggcac   64260
atggatgccc acgcatgtgc aaaaacaact cagggaccag ggacagacct gctgccaagt   64320
gagcctgatg ggccacaggt gtgctcttct aaatggcctg tgagccaggc tgtgggaact   64380
ctagctgctg tcagcccctc ctgtaggagc tggccctgcc caggctcctg acttccctca   64440
ggaagtcttt ctgtctttct ccatcagtct gaaagcctta gttcccacag aggacggatc   64500
tgtcactcct agggctggg catatgtcgg cctcttgtgc caaggccagg caagcagctc   64560
caggtcctga ccagtttgca cacacactct ggagctgtat ctggcgcttt ttctatcgtc   64620
tctgctatgt cactgaatta accactgtac gtggcagagg tggcaggccc ctcagggtcc   64680
```

```
ttattttttca ggcatggggt caaagctaga ggtatgggcc gtctacaccc ccccgccccc    64740
cggcatctag tgtacctcac cagagggtat tcggaggccc agcatcctgc aaccgacccc    64800
tttttttctac tggaagagaa attttatcat cttttgaaag gaagtcatga ctgaagcaat    64860
aaaccttttc actgattcaa caacactggc ttctgtgact gttttctggg cagggctggg    64920
tctccagaat ccaggccaca tcagtaggtg ttcccatgac tgccagcgag tctcctggtg    64980
tgaggccagc accggccact agccatgttt ccacctcaag gctaatgtgg tatgtggctt    65040
ggatgcacca ggacaggcta gctctgtcct ttctctgtcc cgtggaacct tctgggcctt    65100
ccagcagtct gtgtccaaga tcagaacatc cttgtgaccc caagtgacaa gcctgcagcg    65160
tctgggggag ggctggaagg gagggtctaa cttttgtccc aagttcaagc aggggttcta    65220
cctggcatct ctgagagtaa aaccatgttt tgcccttaag ggacccacta ggaactgggc    65280
aatagatttt cactgtgaac attaaaaact acatagccgg gctggagagg tggctcagtg    65340
gttaagagca ccgactgctc ttccaaaggt cctgagttca attcccagca accacgcgat    65400
gactaacaac catctaatgg gatctgatgc cctcttctgg tgtgtttctg aagacagcta    65460
cagtgtactc atataaaatg aataaataat taaaaaaaaa actacataga cactcactcg    65520
gtggttgtaa tggtcttcac ccttcccttt cttagaaaag aatttgaatt attgtgtgtg    65580
ggtccatgcc atggcataag tcagagggtg agctctaaga gttggttctt ttctcaccat    65640
gtgggtcccg ggcatcgaac tcaggtcccc aagtttggca gcaagctcct ctagctgcgg    65700
agccatctcg ctggccttgc acttccttaa tgagcactgt tctctacctg ccctggaagc    65760
attgaaagtt tcctacctca tactataaac tgcattataa tcgtgagaca taaacttcta    65820
tataaggcaa acattttag tcttgtaaga cggggtctag ctttgtaggc caagctgggc    65880
tggacctcat catccgcttg ccttctgctc ctaatgctgg ggtgacaggc acaccctcac    65940
catagccaga tttctttttt tccaagacag gatttctctg tgtatcctta gctgtcttgg    66000
a                                                                    66001

<210> SEQ ID NO 6
<211> LENGTH: 70000
<212> TYPE: DNA
<213> ORGANISM: Mus musculus

<400> SEQUENCE: 6
agtgtcctca gaggccagaa gagggtatac ggtccctcat aactcaagtt acagaggatt      60
gagagccacc aagtggaggt gaaacagagt ccaggagctg gatcctcagc aagagcagcc     120
tctgcccata actgttgagc ctcgtcttca gcccttttcat ttttccaccc aagaaaaatg     180
aaaaatgaaa ggcctagggc agccacacag taaacctcag cagaagaccg gagttcagtt     240
cccagaatct atacagagcc gctcacaacc acctctaact ccagctcctg agacctagtg     300
ccctcttcta acctgagggc acccacacat ccgtgaacac agataaaaag ctttaaaatc     360
tttaagaata aataaataaa tagatagata ttttaaaaac aaaactccta atgacagagc     420
ttcttgcctc acctgtttcc tctaccccca gaggctctgt cacctaccta ggcatcaact     480
gggcacagcc cagacttatc tgaggacata acatgagggg aattgcctca ttcaattggc     540
ctgtggcaca tctgtgggag tagctcaatt ggtagggtac tcaacatcct ggccattgtc     600
tccagcacca cacagacctg gcacaatgga gcacatctgc agtcccagta tgggcaggta     660
gtggcaggtg atcaggagtt caaggtcact cttggctacg tcacgagtac cagaccaaca     720
```

-continued

```
tgcactactt ctcaaagaat ggtagggtgg aggggcagga gcactcactg gacactcttg    780
ccgaggaccc aagttcaagt attcctagca tccagatggt agttcacaag catttgtgca    840
tggagcctta tctgtgtatg ttcgtgagtg tgtgtgtgta ccatttcctg ctgagccatg    900
tctctggccc tgacttcatt tcctagggta ggaaactgag gcttacacgg gaccaggagg    960
ggctcacact gacacaccta gccctggtct tgtggcttcg attgtttctt ctctgggata   1020
gtaaacactg ccaactttcc tttcactggg tgctcgggaa ggcaaggcag aagaaaacag   1080
tggagtggcc cccaaagtgg gacaggcagg gtacatttca caggacattt tcactctctg   1140
gtgggaacag cgggacacag aagaagcctc atggactcca gtttcttttt cccacactcg   1200
ttggcagcct tgggtttgtt atccttgcga caatgccact gtcctcatga aacctggtga   1260
cgttggctga gcaaatacta cctccgatat tgactcaaaa cgtgtacagg ggctcaaagt   1320
tcaagttcag tggggcctga ggcttggagg aggagtggaa aacactgcct cctgtgatta   1380
caacattctt tagtatgaag tagagttccc tcaaaactag gtctcatagc caagtcccca   1440
aacgtcttaa gcactttgga tagatatcta ttgagtcctg ccaaccggaa aggaggctag   1500
agagaatgac catggagcag ccatcctctt ggcaaaacag tgggggctgt gaaaattccc   1560
tgtcacatat attaggtggg atagttaggg ttgggatgtt gtttggcctt ctacacataa   1620
gaccttggct tccagctcta gtactgaaaa aaaaaccaaa ccaaaacaaa acaaaacaaa   1680
caaacaaaca aacaaaaaaa cgagggctgt ggtagctccg tggcagagca cctgactagc   1740
atgcatgcaa ccctacgatt aatcagctta tcttattctt tccattgtcc tcaaacttga   1800
tatgtggcca aggacaattt gaacttcttg ctgggatcac aagtgtgcat cattataccc   1860
tctttatgtg gtgtggggga tgggatctag gacttcatgc ctgctagaca agcgctgtaa   1920
tactgagcca catccccagt tgtggtttgt ttttttagatt aaaaataatg tgtatgggaa   1980
tgtatgaaca tataaatgca ggtgcccatg atggccagaa gggggagcaa gatccccagg   2040
agctggagtt ataggtgttt gtgaacattg agacttggat gccgggaacc aaactgtggt   2100
cttgggcaag agtagtattc gtacttagtt actgagcaat ttcctccaac tctgtttttg   2160
ttttgttttg ttttgtttttg ttttggtttg gtttggtttg gtttggtttg gtttggtttg   2220
gtttggtttg gtttttgaga caggctcacg ctgtaaccca ggctggtctc caactcatat   2280
atgatcctcc tgcctcagtc tcccaagtaa tgaaattaca gatgtgagcc accacacagg   2340
gcaaacgtat ccatcgtgag cagctggcac agtctatggg attgaaactg agaagaatg   2400
tgaaaaataa acaggcgagc ttgagaaagg ttattctagc cttggtgcca gttcctggta   2460
tattttcagc gctcagggag tttaggttaa tgccccaagc ttccccatcc ccaccccgag   2520
gggcgagggg gaggttaagc tctttattaa tagccactcc gggagctaca gtccttggga   2580
aagggctat ggtgagggta gaggaaggaa aatgaggtcc ccacaggata aaaccaggtg   2640
caggcggctc tggctcatta tggtgcctcc ccaaggcacg aggtgtctga gagttccttc   2700
tgatgttgtc tccgcccctg ctcctgtccc tcctggccgg cagggagggc ctgctgtcaa   2760
ggccgctgag cctcctggac agacagggca cagggccaat ccagagggac gcaaagcagg   2820
acgccaagaa aagaggaagt gtccttgggg agggaccgg ttaggactgg ggttctaggg   2880
agagaaggaa gggcatttaa ggtgagtcca acagtccagg acttaaaagg agccttaagt   2940
aggggggcagc aagaggtgac actagagcca tcgaggccga tgaggccggg ggacagcag   3000
aaagtgtttc cagatagcac ctctgcagtg ccagccacat gtcacactgg tctctgcttc   3060
cacgctcagg aacaggtgct cagataagga tgcttaagaa gatggaaggc gtttgggtgt   3120
```

```
gtcagaacaa tgaaggcaag tgaaagaccc cgattctcta tgagtccctt cacataaact    3180
aaaaatctca aagttacacc caacaatcgc ctgtccttt aaataataga ggtgtagggg     3240
gagatgagat acagcaacag ttaactacag ttggggcgg gatcaagggg aactttcatt     3300
ttctctatgg aacccttcca cggcaaggca gagaaagatg gaggcaaaca gggctcttcc    3360
atgaccaggc gtgcttgacc tcagagctgc gactcttcct tcttcagcgc atttatggag    3420
agcttgctac acgcagggcc tggagctgca gcctgggagg gcgccccatc tggcgggtag    3480
agtgctttgc catgtctggc ccgacttctc tacaccctgt tcacaactca ccctgcaacc    3540
ttcgttcccc gtgtgctgcc agcgatcccc ctccagaagc cactctgtcc gaggttccaa    3600
tcactcccct attgacacct attcgttctc agcgttcaaa gagtacttcg attccgttgc    3660
ttttgggcgc agagacttga atccaggacc ttacacaggc aaggaatgca cggcattgtg    3720
agctacccac acaccctaat tgttccgcag atgagggttc ccccgccccc tgacgatttt    3780
atcccaggga gactatgagt gtgttggcct ctggcgccaa cctgccccg gatgtcaaac     3840 atctgttctc aaacttggaa cctgagctta cttcttcatt ctctgatgtt agacaagccg    3900
ttcttcccaa caccacccca agcgtcccac tcccctttt taaaaaaaaa aataatcaac     3960
caaacaacca aacaaaccaa aagtctggag caaaatcagc ataactcccg cagggttgca    4020
gagaagttta cgggcggatt agtgtaaacc gcgagtgtaa gccaagtatg gtgcaaagag    4080
ctgttttgga catggcttta atgagttggt ccctttgta tatgaagaaa ctgaggctct     4140
cagggtaagg aatgttgtcc taggtctgcc gttggcaagc tcgggactta gcctcagttt    4200
ccttactgac ctcctccccg cagccccgcc ccgtccaggc ccgccccgt cctgcccgcg     4260 ctgcagccca gctgggctca gccaatcacc cgcggcgcgc gtcggtgagc ctggcctcgc    4320
ccgccccggc ccggactccg ctcgctcatt ccgccgccgc cgtctgcaga ctcggtaaga    4380
caccgcgagg gcagcgctgc ggcaccgccc tgggctgggc gcgcgggtgt cattcttaag    4440
agtgtggagg gagacccaga ctgtgcccgt agggtacgcg tgagccgcgc attggagaag    4500
cagagggcac tccctccccc gcgcagtgac ggatctgggg gatcccggga cgggaggaaa    4560
gatgcttggt ccccagactg ggcaaaatgc ctccactcgg gacgcgtggg acctcggctc    4620
gtggtgtccc gccccacggt ggattcactc accgcgtggg tttggggtct tcattgctct    4680
gtgaaagatg cttatgatta ggcgtgactc cttggtccct gaccagtagg agtgtcaact    4740 cccttctga cccctgctca ctccccactc cgcgggtggc ttggggccag tgtggacgcc     4800
gagcgttctc caggctcttt ccacccgcta ctctgcaggt ggattggttc tcggggtccg    4860
tgagggtcgg gctcggcagt aggaaggatg ctcgcacagg ggacttggca ggtggccggt    4920
gccctctctt cgtgcgggtc cctgcagtat agccttcggg acacacccct ggcgcagaga    4980
cttaagtgtt ttgcaccct caccgcggtt ttgcccgggg ttcaagggca ggtgggtgtc     5040
agagactgcc caaggtcgcg ccgggaccag agcccgggag ggtgggggcg tcacgtgacc    5100
tggcctgagc gaacttggcc tgggacagcc ggacagcacg gtctgggcaa ccaggctgtg    5160
cggtaacagc gggtacccctt cgttttct catcttattg tgaatcgggt ctggttttcg     5220
ttgatgtcac agaacacaga tgaacgctca agttttaag gagttaaaaa gttcctagtg     5280
tgaaccaggc tacatacaat caagctcagt actctcagct ctgggccgac tctcgttccg    5340
tgcatttaaa tagttgtcca aaaacagatt ttagtcggaa actgctaact ttggaagttc    5400
gcaaataaaa tgaaagtgag tttagaagcc tttcggaacg cgtatttagt tacagcattt    5460
```

```
tgttgcacag gcgtctggtt tctggtcatt cctgatattc aagcgtgttt atcactgtca    5520
aaaccacaag ccaaatgact aaaacacagc tttggccttt tatttgtgcc agcaagcata    5580
catcaccacc accccttcc tagtcggtcg actcaggact cagtgaggac ctaaagcaga     5640
ggactgtggt gtggggagga cagtgcttgc tccggggcag tgcagagtag taggtaggtc    5700
tgggcagcgt ccgcattcag agtcctgggc tagactggtt ttgctgcagc acccggagct    5760
cttttgtcat gtaaattatt gcttttctta actaaagcct cgctagactt aaccttacac    5820
ttgaattttc tcttttatct atttatttac ttttaaaaaa tgagatagga tctcatgtaa    5880
cacaggctgc cctccagcct gctctgtacc caaggttggt tttgaacccc cgatctcctt    5940
cctgcaccca cccataagtg cggtgattat aggcgagcac caccacgccc ggctttgaac    6000
tccttaaccg tctttggaat caagctccgg ttaggttttg tatcaaaagt ggccgaagcg    6060
gcttcctgca caagacaaaa ccttttcgagt ttgagctaga aagccacctg actgcagatg   6120 agggggtggaa cgcctccctt ccgccgccgc tgccgcttggc cctgacccag tggtcacgaa   6180
accggcaggc ctgattctct cgggagtttg gggcgctggc cggggtttag ccaaccctga    6240
ttcctcttgc ccattttgcc cattcataaa agcgctgcaa ttttactttt attttcccct    6300
tgggtttcgc agcgaaaccc ttcgaggcac ggtgccggct ggctgttttg ttgtatgcga    6360
cagctgtcct cggacaaagc ggatcggtga ctccgggatg gcagcggcga cgcgtcgctc    6420
cggaaggcct gcgtgggctc ggccggtgga acaggatccg agcgcccgg acgcgccagc    6480 acggggggcgg ggcacccgta accttttccc tacttttctc agccgtcacg tgacccggct    6540
gggtagggga aggggcgggg cgggaagccg ctgttgttag tgcccttccc ttccccagcg    6600
ccttgaactt gcagtctgga tctgcaggcg gctagagcca cgcgactttc ctgtactttg    6660
accgtttgaa ggttttttt tttttttggt tagaaaatat gtttagtcac tcttcagtca     6720
ctcttcatag atatttaccg gtaggcccga gtcttaaagc tggtggaagt ctgcatttga    6780
actagtttag aataaaatgg tagtccaagg tggataattt taaagtgtgt ttagcagact    6840
ggacagtccc ctgaaggagg gagagtcgct cgaatctggg agttaaggga cagcctggga    6900
ataggcaaag atccatcctc agctcgggaa agaagaaaaa gggaggtggg gttttaagcc    6960
ggtggcggtg gcgcgcctag taggcttaaa aaggattact gcacacttga attaatgcca    7020
atttaagctc ttagtgcaag aattttttgtt gtttggaaaa taagcctgct gccaagcctg    7080
actaccctaa ctcgaagggt gaaaatgatc ccgacttctg cacaccgtgc tatagtgtgc    7140
actcaaccgc caccataaat aaataagata catggttttg ttttaagtaa aaagcaatac    7200
aagcatattg tgcaaaatta gaaaggcaaa aatggggtgc gatgcagtca cctacttact    7260
cagtagttac tgcaaaggcc accactgtga gcagttcatt caggactgtg atggtgtgta    7320
cctgtaccat ctagctcttc ggaggtggac agaggagagc cggacttaag gccagctacc    7380
accatccgtg agttggagtc ctgtgtggga tacacaagaa cttgtctcta aaccaaacct    7440
agactgcaaa gtttgtttat tttttttaatc tcttacctaa cacaaggagt gagttctcct    7500
tgttgatttc aaatatctgt tgccttttgt actcttcacc ttgaaccccg tgcaaatatt    7560
gaggcggaca ttgggtcccc acaggccctg ggctaaggcc agctttgctc tgttgaggta    7620
acgtggcagc ctggttctga gaagtgccca ccctttgccc ttttttgtgcg agttgttctg    7680 accttcagga atgttttttcg gaagttaata gcagcaggca cactgccgt ttcgcgcccc    7740 gacacctggg taactgccac tttagaaggt tgggaaatag gatggctact gaccttgcct    7800
ctgaggagtg ttgcacaccg accatttagg tagaaatgta agagaagctt ggtgtggtac    7860
```

```
aaaacactta taatcctagg gtttggggga tggtgctgag gcaggattcc gtgactccat    7920
agtgagacct tgactcaaaa aacaaaatta accaaaccaa acccagcaaa gaccggatta    7980
ggctgggttg tccatgccta taatcccagt ccttagtagg tggagacaaa attagtagtt    8040
caagatcagc atcagtgatg tacctggttt agggctagca tggactacat aagacctgtc    8100
tcaaaaacaa gacaaaatac tgtatgcact ggtattaatg cactggtgat atatattgga    8160
gttatgcact ggtgctgtgc actggtgtga atgcactggt gctgtgcact ggtgctgtgc    8220
actggtgtga atgcactggt gctgtgcact ggtgtgaatg cactggtgcg aatgcactgg    8280
tgctgtgcac tggagttgtg cactggtgtg aatgcactgg tgctgtgcac tggtgctgtg    8340
cactggtgtg aatgcactgg tgctgtgcac tggagttgtg cactggtgtg aatgcactgg    8400
tgctgtgcac tggtgctgtg cactggtgta aatgcactgg tgctgtgcac tggtgtgaat    8460
gcactggtgt gaatgcactg gtgctgtgca ctggtgctgt gcactggtgt aaatgtactg    8520
gtgctgtgca ctggtgctgt gcactggtgt aaatgcactg gtgctgtgca ctggtgctgt    8580
gcactggtgt gaatgcactg gtgctgtgca ctggtgtgaa tgcactggtg tgaatgcact    8640
ggtgctgtgc actggtgctg tgcactggtg tgaatgcact ggtgtgaatg cactggtgct    8700
gtgcactggt gtgaatgcac tggtgctgtg cactggtgct gtgcactggt gtgaatgcac    8760
tggtgctgtg cactggtgtg aatgcactgg tgtgaatgca ctggtgctgt gcactggtgc    8820
tgtgcactgg tgtgaatgca ctggtgtgaa tgcactggtg ctgtgcactg gtgtgaatgc    8880
actggtgctg tgcactggag ttgtgcactg gctgtggcac ttaggaaaac aaaggtcatc    8940
tatactcttt ctgtctcctc ctcctccatg tgtggtccaa ggagctgagt ctcacttctg    9000
tttcttaagt cccactagaa tttgtcttcc tcagtctccc tgaccctatg caggcctgca    9060
aatcattgct gaaggaagga caggtttggg gcgcccttc tccgctggac tgaaccagcc    9120
tactgatatt aaggggdtga gggccttttg gaagtttcac tggctacacc cctagaaatt    9180
aatgcccgag agggagggct tagaggaagt ggttgggccc ctagctcagt gtgcttccat    9240
ggtacgtggc tctgggatga cttgcctgac atctctgtcc ccatccaggc cacatgctct    9300
ctgcagtgac cacgtccaca cccacctctc ttcttttagg gtttccttgg ctttgggtaa    9360
agccatgaaa agagaattca acaagcctcg ttatcatggc ctgaagggat attcgtatgt    9420
ctacaggaca gggacactga gtaactcccc acaaccctat cccccttgta gtcctggcta    9480
gcctgaaact cactatgtag accaggatga ctttgaactt gtgatcctct tgctccactt    9540
cagataaaaa cttggcccctt tatgaaactg gctggtttat taacatactc acccctagct    9600
tccagcagct gctcctggaa atgctacaag gaaggtccag ccccggagcc cattgcgtcc    9660
tgcgggcctg tgaaggtatt ctgaaaagat atgaatgagc tgcccatgtt agtcagttag    9720
aagataggct gaggtaccat atgctcgccc tgaagcattg agctgggtgg gccttggggg    9780
atagagccag gacagacacc cactttcttg aaggacaggt gttgactgct caggctcctg    9840
gtgggataac agagtgtggc cttgtattaa agaacacgtt ctgtgtttgc acactctagt    9900
atccttcgat tgatgggagc tgaggcagtc tgttctgccc tgtgctgata aagcatagga    9960
gagaggctga tgtttgtcag tgagctgcag atctggaagt gaacccagat ctgtgttgta   10020
gccactctct cacctgctgt catagagcag ggctcttagt ggcagccatc acctctatat   10080
atgcagactt agactgatat cgaagtgcgg gcatgtctgg gtgttcattt ccttctctgt   10140
caaatggcag ctctgatacc tgctctcctg tgtcccttga gtcccaggag actccattaa   10200
```

```
ggagtgagac ctcagtctta gcattcaggt gacaaagata ggctgatctc taggtttgag   10260
gctggctttg tcttcccgca gtatgaccta tgcaaaatcg tgaactttat ataaaaaaag   10320
gatttatttt attcatcttt tttgttttttt gttttttgtt ctttgttttg ttttaggatc   10380
gctatgtata tagcctttac tagcctggaa cttgctacat agaccaggct agtcttgaac   10440
tcacagatat ctacctgtct ctcgctccag agtgctggga ttaaagtgta ccaccacaca   10500
cagtgctttt tacattttta acttttttat ttacgagtat gctatgcatc tccgtgtgcg   10560 caccctccgat ggctgggggc atcagctccc caggggctgg agacaggcag ttataagctg   10620
cagaggcact aggagctgtg ctcactcctc tgaagagcct caggcactct tagcctccct   10680
ctagcctggt ccctgatgcc tgaaaacacc acacatccca tggaaagtga atttagaagg   10740
ttgactttgg atcttctcct ggggctaatg aggtgaagtg ccatcttcca tgtgagtctg   10800
ggtgacttca gcatgaccca caactgtgag gaggaccaga agcccttcac aggacattat   10860
gttgttaagg tgtgaaggtg tgacagacaa gcagtagatt gaatggactc cgtgcttttt   10920 ccttttttt ttcccactgc atggagactg gctatgagga ttattgacga acttgtgcaa   10980
gcagcagaca ttcttaagcc ctaagccatg tctccagccc cacctaacag cattttctac   11040
ctggaggtgg cctgtggcat gtgacccctg ccccacacat caaaacattt gtagatacag   11100
gttctagacg ccagtgtcag gactgcaccc gggcgggttt tctggtggtc agatctcagg   11160
ttgctgaggt gacaaacata gacaggatgt ttagaacagt ccctgaggat ttgggaacgt   11220
gtatagggac agtggtatga ggagaagttc agtttctttg agctaacaga ttcatgccac   11280
ttcctggcag tcaagagttc aggctggcat cctgttctgg caagattgga cccatgtgct   11340
gtttcagaat ggatggggta gactgttagc cttgttaaag tgtatttcac gtcttattac   11400
aaatttttac atgttttgtt gttgttgttg ttgttgtttt ggtattgtga ggcagaggtg   11460
tgtgtgtgtg tgtgacctgt ggggaggtca gaggacagtt tgtgggactt ggttctcttc   11520
ctctcctgtg cgggtctctt gaagattgaa ctcagttgac ttggcagcaa gagccttctc   11580
ctgctgaatc atgttgctgg tcctctttgt tactttgttt tgcagttttt gagacagagt   11640
cttagatatg cttggtgagc ttgaactcac tatgtagttg aggacaatct gatcctcctg   11700
cctccccctc ttgagtactg ggattacagg tctgtgccac caagcctgct ttagtggtgt   11760
tagagatgca gggtcattcg gacttacccc atgctagaca agcactctgt caactaagcc   11820
atgtccccag tcgtggctac ttcccttaga agtgtgtcct ctgctggctt ccccatgtgt   11880
cacatttctc tgattgccat ttcttaatga tgtgctgcag tcgcctaaat tggatttgc   11940 tttactttga acttttctttt actaagtagc tctagctggc ttagaactgg agatgtagac   12000
caggctggcc ccaaatgtac agcagtccct ctgcctgctc ggattacggg caagctccac   12060
cacacccggc ttttatttca ttattattgt tatcatttta aatggaggca gggtctctgt   12120
agcctcagct ggctttatgg ccacagagcc tttgcattcc tgattctgtt gtcttcagct   12180
cccaagtgct ggagctggaa cgattcggca tcctgtctag catgggtttt tacagtgtgt   12240
ggtaggcggg acttctcttg ttatttggg ggaatgtaga ctgaattgaa aatagattaa   12300
aaaaaaaaaa gaaaatagat ggaaatctta cttttaccat ccaaaaacta accctgctta   12360
gcttctttta aaaatcagac catttaaaat ggtatggcca gggctggaga gatggctcag   12420
cggttaagag ccgactgctc ttccaaaggt cctgagttca attcctagca accacatggt   12480
ggctcacaac cacctgtaat gggatccaat gccctcttct ggtgtgtctg aagacagcaa   12540
actatgtact cacatatgta aaataaataa ataaatcttt tttaaaaaat taataataaa   12600
```

```
atagaatgat atggccatag accagaatttt gttttctaac ctgatctgaa ctattgtgtt    12660
cagccaaaca gcacaaatgg cttatggtga tatgccatga tgtgggaaag tcacctaggg    12720
ctaaattaca taatgcaaat gaagactgtt caggcatgaa ttccaaattt aacctttcag    12780
ggtgagttcc tgtgacctct ccacctatac agtaagttaa caacaacaaa ttgaaatctg    12840
gtagccaatg tgacagtttc caaggtggag tctttcaagc agggtctagt gtcttggtct    12900
ggattcgttc ttagattgga ttaattctca taggtacagt gccttgggcc tgcttttctct   12960 cctccacact cttccactct tgcccacgct ccaacccctc cagtgccttc tcccatccca    13020
ggacatagca taaggctctc accgagaagg agtgatcctg aactctccag tctctggagc    13080
tatgagaccc ataactctct ttataaagta cccaccttg gcaactctgt tacagcaact     13140
gtaaatctac taagacattc cttcaccttc ctcatacccc aagccagccc acagaaggca   13200
caaggtgcaa aggtctcatt tctatttggg tatagcagtt gtactcagat ttttaagtct    13260 ctttttatt tttgatgtgt gcgcatttca catgtgtatg tagcccagag gccacaggca    13320
gtgtcatctg cagttactct tcggctttct tttttttttc tttgaaagga aggttacccc    13380
taccaagtct ttcttgttta ttttagattt gaagtgattt acagaactta gatataaggc    13440
tttgaaacct ttctttcatc ctagagaagc tcacatgtat ttgtctttt aaaaatattt    13500 ttattaggta ttttcctcat ttacatttcc aatgctatcc caaaagtccc ccataccctc    13560
ccccccccac tcccctcccc acccactccc ccttttggc cctggcattc ccctgtactg    13620
tggcatataa agtttgcaag tccaatgggc ctctctttcc agtgatggct gactaggcca    13680
tcttttgata catatgcagc tagagacatg agctctgggg tactggttag ttcataatgt    13740
tgttccacct atagggttgc agatcacttt agctccttgg gtactttgtc tagctcctcc    13800 attggggtc ctgtgatcca tccaatagta tttttttttc tttgaaacag gagtgtgtgt    13860
gtgtgtgtgt gtgtgtgtgt gtgtgtaatg gccttggcta acgtggactt atttattgac    13920
caggctggcc tcgaactcac agagctccac ctgcctctgg ctcttgagtg gtatgctcga    13980
ccatgcccag cctctctaag ttacagccat ttctgtttag cggagcagag cgctcccaga    14040
agttagatcc cagcagcagc atctgtccag gggcaaggcc cagggttcat cagcctggtg    14100
ctgttccttg tgagggatgc ctgccatgtt cctggatgtc ctgcctagaa ttctgttaag    14160
gtgccacttc ctgtgggtaa ccctttctct caggatttcc agaggttgtt tactgctagt    14220
caagatggac agctggtgag ggattagagc tgcaggcaga gcctgtgtct gcctggcaat    14280
gaatgatgtg attctggtgg gcacctaggt cacactgata agagtcatta gccttggtcc    14340
gagtttgtag taatcaagtt ttcctgttgg ctaccatcta tcattttggc tacagcagtg    14400
acgtaagctg tgtgtgttg caactgcagg aatcttttgc tagcctttgc tgtcacagct    14460
gctactgcac tttggaaggt aaggacatgc ccactggagc tgagcctgga cctgattcct    14520
gctttacagt tggctagcta tgaccttacg caagcgtttg acatctgagt cttgttttcc    14580
tcgtcagtga atggggacaa ccggggattc attaattaga gttgtagtta gaatttaaca    14640
agctgatgga tgagaaacaa attaataata ataataaaac cggcaggtgg cccatgccct    14700
taattccact tggtaagcag aaggtggaat ctgtgagtct caggccaggc agggcctccc    14760
tcatagaccc tgtcagaaga agaagagaaa aggcttggga tgaggatacg gttcggtgag    14820
ttatgtgctt gccgtgcaag catgaggagc tgagtacgga tcccagggcc cacataagaa    14880
gccgggagca gtggtgcata tctgtaatgc taaccctggg attagagaca gagaccggag    14940
```

```
gaaccctggg gctcgctggt tagccagcct ccccacatcg gcggtctctg ggctccgagg   15000
gagacccttt ctcaaacaat aaggtaaaga gtgatggaca ccgatttgga cacaggcatt   15060
catgcacaaa atagggaggg cattgtttgg tttgtgccaa gcagttatta ggcaaacccc   15120
acaccttctt ggccatgaaa acaagcctgc taaccatcca tgctagtata cggtgagtca   15180
cctgcttgcc tgttgtcttg tctaccgacc tatctggctc cccatctgtg ggctgcaggg   15240
ctgtgttgca atactccctg ggcccagaa tccatttgca taattcagtt actcagaagc   15300
ctgtcatccc tgggtaggtc ttattgtttg atttatatgg tggacacggt tttctcattg   15360
cagtttctct ggcatgtgcc agtttctggc ggtgtgctgg gcctctcctg aacttcgccc   15420
tcctttccta gctgactgcc tctcaactct gcagccctgg ggagctacag aagagcaga   15480 gaggctgaga gggcctggtc gtggggtggc agcttggtgg catggccatc gttagggctc   15540
atgggctgac ctcagaggtg aaatggtttt gatgcaggcg gcttgactgt ggagaaagca   15600
agcccagtag ataagtccat cagccaagct cagaggactg gcgcttgaca ccaagccatg   15660
ttattaaaat gaagacagtc tcaagtcagc aagaagcctc agcagataaa gtgcttgctg   15720
cgcaagcttt gtgacctgag acaactccct gatcccacat acatgtagaa gataagagac   15780
tccacagagc tgtccactgc ctctgcacat gctcagtagc gtgtgtcccc accccacccc   15840
accccctcca tgcacaaaca ctagaacaat actaaagaca aattaaaaaa atgaagacag   15900
ttgtggcaga ggtaattgtg ctgcagcctg cagggttctc atgatttgat caagagcatt   15960
aagctttggg gtctttgaaa agctttcagc ttattggggg ggggtgatt agacacggct   16020 tggaaagggg gaatcctttg ccagagagca gaggtgagtg cttgagtgcc atcttgtgca   16080
tctctgtgct ttgggaatgt gaagtcagta gctgtccaaa accgggtcct gaggggcta   16140 actgtgatga aggtaagaac aggtatgacc cagtaggggc taaggaaatg gaacagacag   16200
tgaagtgctt gccttgcaag cgtggggacc caagaaaggt caggtgtggc agtgcacagt   16260 tgcaaccca gctcaggaga ggtgaattca ggagaacctc tggggctcac caccagccaa   16320
accagcctcg ctgaattagc cagggagaga agcttggccc ttcaggaaca cacccagga   16380 ttgatctcag gtacacacac acacacacac acacacacac acacacacac accaagagca   16440
tagtgcaggc agagatacaa catagcaagc aggtgccagt taagcaccag acctaatatg   16500
tgtccttagt ttttggtgga ggtctcttgt tctgcattgc agtgaggggc ttaggagact   16560
aaagtagccc tctttgggag ttcctccttg gcaagtgagg ttcgaggctg gtatgtaggc   16620
agggttgggc ctggaagcat ggggacacct gcgacaagga agttggcagg taggatttgg   16680
gagtgagcag tcacccacca cactaacact gccacttggg gcagagcaag agcacaggtc   16740
tccacgggag catctttgtg ttctctctga caccagaaac caagcctagt catacaccta   16800
acggaggttt taactctagg ctttgtgggt gtattcctgt ccgtgtctaa ctctaggcct   16860
tgtgggtgca tccctggcca tgtcctcctg ggacctgggc tagggtagag gtttctgtca   16920
cagaaaccac ctgcagtttt gccctgagcc attgtgagga cacagggcaa gacactgtgt   16980
tgtgttagga acaatcccag aggggccttt cctgtgtacc tggccagact tgcttctggg   17040
ttgaagctgt ccgtgtgttt accctacagg gtgtgtccca tgtaacccett ttcctctggt   17100 tttgatttct aatccaaagg ctaaagctag gtgtggtggt tatatatact gtaatcccaa   17160
tatgagggca gccacaaggt caaggccagt ctggtgtaga cactgagttg tccttgctga   17220
gcagcttggg agggacagtg agtggcagag ggcaggtcaa agcccttctc tctgtgccca   17280
tgtgtctcca tcatgcttct gtccagtgtg tgctcttgtg gccctctttg aacttgggtc   17340
```

```
ccaggtgcat gccctacagg tatagtccct gtggtcctgg tgctgtgatg gctcagcccc   17400
tgggggaata tacaaagcag agcttcatgg ggcacttggg acatcttgtg agcagtaata   17460
gaggtcgggg agttgggggg gggcactgaa aagccgagtc tatacccagg caaagaaggg   17520
tgcaggttga ggaggtgctg gtgggctaac acacctcctt cctctgtggg ttctgtgcct   17580
gggtgagtga agcagaggca gggagattat tttgggtaac tgatggttcc tgtgtgcccc   17640
actgaggcag gccaagtagg ggagaggtca ggtcgagagg gtgcagcttg agagatgggc   17700
tgatgtccag tctctgtagt ttgggtcttg aaggtgggt  ttgtaacatc tgatcacatg   17760
cacaggttgt agaggtctgg ttagggacag gggccctggc tagctcctag ggtaaagaga   17820
gccaaagaag ctcctattag tgcagacaga gatcggggct ggaggtctag cagacaatgt   17880
ggtgggcctg gctgtgtaa  tcgaggactg gttgtgggaa ggcagtgctt tagtgccccc   17940
tgcatggagc caccatggag gtctgccggg ccctccctgc aacagccttt ggaagggagg   18000
aagcagctgc ccaatgtcag tggtctgtat ccaggcacag ctggcttgcc agacagaatg   18060
gctgggacag ttggccccga gggccttcct tccaggacgt caggttccca gcttggtaga   18120
cacaagaatg cagccttgtg cccaggctgg gcagggtgtg atggcaggaa gggagagtgg   18180
gaagggagag tgggagtcag agcagtcagg gctcttactc tccggcctca ggtgccagct   18240
ggggaatgga ttggctttct attggcaagg gcacaccaaa gaagaatggg ggatacggca   18300
agatttgtgg accacatgca catacatgct tgcatgtaca aatgtgtaca ctcacacagg   18360
tagcccatgg ctgctcagaa gcccagggtt ccagggaaga ggtgtctgaa atgtctgcgt   18420
gtgtgtatca tgtgcattgc agtggccttg gagcctagaa gaagacattg ggccctctgg   18480
agttggagtt caggcagcta ttgagcctca tagtgttggt gctgggaact gaacttgggt   18540
cctctgcatg aacagagtgt gttttttaact acctagccac ctctccagcc cgaggtgttc   18600
ttatttattt attttttactt tttattgatt  ctttgtgagt ttcacactgt gcaccccagt   18660
cccactcatc ttcctgtccc ctcaggtcag cccttgtaac cccaaaataa cacacacaca   18720
atagaaaaaa catctcatca cataagctgt agtgtgttag tgtgtcccac agtatatccg   18780
tctgtccaca catattccct tgcaacaagg agtcattgga agtgtctggc ttctgtgaca   18840
ccatcaatac tgggtcctca ctgggtctcc tccaggttat gctgttgtta ccctgtgtcg   18900
tggaggttct gcacctttgg atcagtagta ccagcttttc catgcatccc agcgattgac   18960
agatgataca gattttgggg tgggccaatt cagtgccctg ggtctgggcc tgggcagtag   19020
ctgagctgat ggtcagcaca ctggctcttc ctcaccagca ccactagggc aagttctcca   19080
gcattgtttc agctaagcca tccaatgcca ccatcagcag gaggcagagc tatgccctca   19140
ggctggttca cccacaccca tgccttcaga gccagctcca ctgtgctgcc cagtcaaggt   19200
gcagggccca cttttcccag ggctgcaacc agtaaggggg cagggccagt tctcccgctc   19260
tcacactctt ggagctggct ccccttgcc  tttgccatca gagccagctc cactgagttg   19320
cccaggcaag gtgcagggcc cactcttccg agtgctatag ccagtgaggg tgcagagcta   19380
ggtctcccac tctcatccct agggaccaac taactaccct aactgctgag atggtaaggg   19440
aaggagggaa ggcatcaccc ccgcatcctt gccatctccc agcagacaag tggcagagcc   19500
tgcctccccc ccttgctctt gtcctcaggg ttggagcacc cacacactct tgaccagggc   19560
cagcccttct gtgttgtcca ggtgaggggc aggaccagct catctgctct cacagccctg   19620
tggtcagctc tcccaactgc cacaggtggc aagagaggag ggaagtgcat cacggccaaa   19680
```

-continued

```
accacatcac ctcctggcaa cgtggggcca gctctccccc acccccaccc ccatccccac    19740
cccactccac tcttaccctc aggggaccag ctcacctgtg ctcccaccac cagggccagc    19800
tctgctgtgc tgtccagggg aggggcaggg cctgctctcc cgagggctgc agctggtgag    19860
ggacggggct agctctcgtg agtccactgc cagagtcaac tctccccact ctcacaccat    19920
gagggccagc tctccagagt gctgtagcca atgaggggca gggccagttc tgcacagccc    19980
ttggtcagcc ttatggtccc ctatggctgt cccaactagg aacttgccca tgtcctctag    20040
tggtaatatg agtcaaggat agaaacaccg gcccctgcca ctgggtagcc attgactcag    20100
acttggccct taacagcagc aagctgggac ctgtaacaag ctcaggtggc agggctggcc    20160
actcacaaca ggcgactcct ctccaccctc gagtctccag tcccatctct tcataatact    20220
caagctgctg cgcttctccc tctcttccct ctgaccaccc attcctgcga attgtggtgg    20280
ctcctgctgc aggctggtca tgcagttggt ggccctggg tgacatcctc agtctgtaca    20340
acagagcagc agcctgtgct gtgtgccaga gggcagtcct gtgggtggca ttgtggtctg    20400
caggccttgt cttccttctc gttacactgc gtggtgacag cgggggctct gtgtgtctgt    20460
ggcctgcctg tgccacgggg cagctctggc caccaagcca ggcatcaaac taggatgaac    20520
aaatgactgc cctaaccta taaggttaga ctgctataag acagcaagg tgtctcttcg    20580 cctttggctg ggggttgggg ggtgctgtat tattaattga agaggaccag attgccatag    20640
gtctgtgtca ccaacaggcc attgctggag caggtacaca ggtgaagttc tgtactgacc    20700
tgtatgtgtt gtgttttata actgagcatt tgaggaagtg ttcagttaag gccaagttca    20760
tggaggcttt gggggaactc ttgcaagctc cttggatttg tgggcatttt gcttcctcca    20820
tgggactgtg tatccccag taccttctcc ccacacatcc agccggctct gccaggtgca    20880
ccaggcctcc aatcccacgc ttgagggtga actcgctttt ggtgctttgc agagagctac    20940
tcattctacc acagtggctt caaatggtag gtgaggggga ccgagggtgt ctgacccgca    21000
gcctgtgggg cacatgcagc taaggctatg aaaacagccc agcacatgct ccatagcatt    21060
gagtagaggt tagaagacag cttttcagggg ttggttcgct tatcccaccc accgtatat    21120 tctgggaatt gactgtgagt gggcaggact tggcagcatg cacctgtccc cggtagcaat    21180
cttgctggcc caggatgttt ttccttttttt cttttcgta acttgattga ttgttgtaga    21240
taagtaatgt tctgttgaaa gtcaaaacgt gagacaccct gcctacggtt actttccctc    21300
gagggcctct gggatgctgg ctctgagtca gggatgaaga gagccttccc cacacgggcc    21360
tgggatcagg tttactaagc agaactgtgg tgactgggtt gggactctct gggactactg    21420
tttctggggt cacagagcct cccacaggga catctgtgcc cacctgaaaa ggagggagct    21480
gcaggtggca gtttctgcca ggtgtggggt gtggtctcca gggcaggaag agaatggcag    21540
gaccagcgtg catcccgacc agcaggtgtc attgggtctg gtcaaagtgg agagtggcgt    21600
atgtacacac atgaactcaa tccagatcag gccacaaaag cccaactggg caaaacagtg    21660 attttttggcg gggagaggta tttacgggaa tatagggggag ggattcctta ctggagcaga    21720
aattactcaa agacagctgc cttcccaagg cacaccccag catgggtgac agcccacaaa    21780
gctgggaact tagagcacac tgcacacact gatggcccct cacacattgg agagagttct    21840
ttccaggagc ctcggttagt ctaaacctct atcagttagc ttggctggtt tctgcttctt    21900
ttaggcagct ggtctctaga ggcttctttg aagcttgtct tgtctttgtc ttagtagcag    21960
ctctgttgtt gggctagtct cagagggacc caccgctttt attgctttct ctgtcagtga    22020
gtgcctagtg gatctggtca gtttcaggga cttcctggag gtgtttaccc ttgttaagga    22080
```

-continued

```
gcctgcctgc atgatggggt gttttggagg aaatggatac acaagaagtg ggcatgggat    22140
gggagttggg agcttgggtt gctgcagctg ccttcccctc cctcctgact ccacttgcag    22200
gagtctgctg tgctgtacgt gggtggagca agtgcttact tcacagcaag catgggcacc    22260
cagttctgct tagcatccat gagagctctg gcttactgaa cagacagctg tgtgggtaca    22320
ttcagagctg tggggagacg atagacttga acagaggaag agctcagagg atggggcttc    22380
ctgtggtcac tgcccacctt tccgggctct cactgaagct ttgcccactc ttcctcaccc    22440
aagccctagg tgccatggaa tccatgctgg gattcgtgtg ggtcagaggt cagccgtgat    22500
tgtcattcct tgcacagtct gccttgtttt tttgaggcag ggttgaagca ggctggctgg    22560
tgagcccaag ggatcctcct gtgtctgcct cccagtgttg ggattacatt gtgcctggct    22620
ttttttgtag attgagctca gatcttcatt ccgctcagca agggacgcgc ctaacagtct    22680
gagctgtctg cagatgcttt ggtatctgtc ctaccgcacc aggggatccc tgaaaaatta    22740
cttagttctg gagggtgata tttgttctga atgaagcctt ggtgggaaca gtggtggggt    22800
ggcctgctag agccactcct tccacactga tggccgcaac tgtgtgacca gagatggatt    22860
tgatgcttaa gtgtaagtgt taagaagaca acatttgtgt tttgtgagag gacatttcct    22920
tttttccctt tctttcttca cagttttttc tttgtgaatg tgcagtatat tcatgtgtat    22980
gcgtgccttc atgtgtgtgc atgtggaggt cagaggtcaa ttgtcttagc agtggtcagt    23040
tttctttcca cttaaaaatt ttagtttagc actggggagg cagaggcagg aggatttctg    23100
agctcgaggc cagcctggtc tacagagtga gctccaggac agccagggct atacagagaa    23160
accctgtctc aaaaaacaaa aacaaacaa acaaacaaaa ttttagtttta ctattactgt    23220
gtacatgatg tgtgtgagag agagtgggga tgcatgcacc ataatgtatg gagggcagag    23280
gacagctctg gaagtcagtc ctttcctttc aaatttttttt cctttttaatt aaaagaaatt    23340
tgggggggggg gtgtgcacgc gcatgtgtgc acatgagtgt aagtgtcctc agagagcagg    23400
attaggaccc aactcgggct gttttcttca ggtgcttcac aactgaacca cctccctgtt    23460
ctgttttttg tttctttgtt tgtttatttt ttaaagacag tttcttactt ctgtaggttt    23520
cacagcaaac ctcctgcctc aaccactcag agtctgggat tgcagatgtg aactaccatg    23580
cccagctgag acagggttgg tttttttttt cccctaagtg atatgtttag cagggcgtgg    23640
tggtgcccac actttaatcc cagtactggg gagaaagagg cagaggggtc gctggaagtc    23700
caagaccatt ctggtttaca gagtaagttc caggataact agggctacat ataaagaccc    23760
tgactcaaac taccaagaca aaacaaaaaa gataagttta tgcatcaatt tttaaaattt    23820
attttttatt gattgattga ttggttttttc aagacagggt ttctctgtat agccctggct    23880
gtcctggaac tcactttgta gatcaggctg acctcgaact cagaaatcca cctgcctctg    23940
cctcttggtg ctgggattaa aggcgtgtgc caccatgccc ggcaaaattt atttattttt    24000
ctgtgtttgg atagtttgtc tgtatgcaca gctatgcacc atgtgagtgg agtgtctggt    24060
ggccagggag accagaggaa ggcatcacat cccctgggac aggggtcaca gatggttgtg    24120
agctaccata tgggtgctgg gaatctgacc caggtcactt agaagagcaa ccagtggctg    24180
ctgagccatc taggaagaga agctcaattt aaatttctct ttatttattt gtgtatgtaa    24240
cgcgcacgtg tgtgtgtgtg tgtgtgtgtg tgtatgtgtg tatgtgtgtg tgccacataa    24300
gtgcagtgcc catagaggcc agaagaaggc atcaaatatc ctggaactat aattacaggt    24360
ggttgtgagc tgcttgataa gggttctggg aactgaactc agatcttcgg gaagagcagt    24420
```

```
aagctctctt aatgactgag tctctgagac tatatttta aataacaacc tcaatgaggt    24480
gtgcctaagc tagttttata tgaacttgac acagggtata gtcagtcatc tgagagggag    24540
gaggaaacct cagttgagaa aatgcctcta taagaccagg ctataaggga ttttcttaat    24600
tagtaattga tgggggaggg cccagcccca gcctattgtg ggtggtacca tccctgggct    24660
gtaagaaagc agactgagta agccatgcag agcaagccag taaacaacat gcactgtggc    24720
ctctgcatca gctcctgcct ctaggtttgg agtgagttcc tatcccaact tcctttgatg    24780
atgtactgtg atacagacgc ttgtgccaaa taaaccttt cctccccagc ttgttttgtt     24840
catgtgtttc attgaagcag ccgaatccta agacggtgga gaattcacag aaggaattca    24900
cccatctaaa gtgtgttttg gtgatctttg atttattcac agcaacgtgc cactgtgtag    24960
cattgtaacc agttagggaa cattttatc aaccctccca aatactcctt cttagcctca     25020
tccagcctcc cctggtgtgt ccctggctgc tctggtcttt ccttctctgt aggtttgttc    25080
tgttctggac acgtcatgta aatggagtga gacattggct tccttggctt cctgccatgc    25140
tggtttggtt tgtcttggtt ttgtgagaca gggtctcctg tagctcaggc taacttctag    25200
ctaaggatga tttgaacatc tgatcctccc acctcctctc tcaagtgctc tgacctcagg    25260
agagtgccac catgctgtgt tcatgtgtcg ctgggatgga accctgcacc atgtatgtgt    25320
aaggtgaacc ctctgctgtg tccccagacc ctggtgccat gctatcatct gtgtcactgc    25380
gtgtgttggt gctgctgtcc ttcttaggat agagtcatgt tcctggtgtg tggctgcatc    25440
agtttaccca cgctcttcct ctgtggaagg ggctggctgt actttcctct cctgctgtaa    25500
ttttgtctgt catgagcatt gtgaacgtgt gtgtgtgtgt gtgtgtgtgt gtgtgtgtag    25560
gttttcctga gaacttgttg gggttagctt agccaaggag aggttgctgg gttccatggg    25620
ttttagtttt gatttgttgt tgttgttgtt gttgagatga tggtcattta gtgtagccca    25680
ggctagcctg gaattagctt tatgcttagc ctttcaggaa aggacaggct gtcttccaga    25740
atgacctgaa cctgtcacat ttctttgaca gtggcgtagg taggggacag ggtgggggtgg    25800 gggagagctc ctgatctctc tcctccctct gacagcacct gtcactcatt gtttgcattc    25860
tagccattcc tgtgggtagt atgtgctgtg atttgattgt acttctggaa gcagtcagag    25920
aatttgaatt agtctgtgaa gccaacatgg aggctgtggc cgcctcatta gatctgtagg    25980
cctgagtttc tcaggctcat gttttctggc accagtgcct gcttaatgac ttgaagcagg    26040
gaggctgtga gggcagagtg cattgttcat gcatgcccac ggagcagcag gagtgcctgc    26100 tatcggggggc cttttattaag gccttttatta agtttaggca ggtctttta gtctgttgga     26160 ggcagggttt tatgtagacc aggctggtct tgaattcact gtgtagccaa agataacctt    26220
gaagagcctc ttgcttctac atcgataatg ttaggtttat aggcttgtgc cgtcacacct    26280
ggtaggttcg ggtggttctg aacattagac tcaggtcatg tgacagggct atttcaccct    26340
ggaaaggaca ccataaatat tcccaggccc catgattgtc ctgagaccag gtttggtttc    26400
cgggcaaaca tgggggttcat gactttggat agaattaatt gcaacactgt gtttaatcca    26460
ctgctgttaa caaccccctt gtgagctggg gagatgactc agtgggtaaa gtgcaggctg    26520
ggcttgaggg cctgagtttg agcctcagta tccatggaaa gtgctgagaa cagaagcgca    26580
ggtcagtttc cagtgctggg gttggtggtg ggagcaggag gttcctcggg ttcacggatc    26640
actcagccag tcagcgtgct ccaggtcctg tgagagacct tgcctccaaa cagtaaggtt    26700
ataagccaca gaagaatgca tctcgtgttg aactcaggcc tgcaggtatg cacacccacg    26760
aacgcatgtg cactcacata cacatacaga aaagtttgca tcgaaatagt tccccggtgt    26820
```

```
ttcaaaagtt cattaatgta tttattgagt tcgtttgttt ttgttcttgc tacaagatct  26880
gtctgtagtc cagcctggaa ttcactgttg agcccacagg ctggctttga acttgaaaca  26940
atactcctgc ctctgcctta taactagtgg gattacagag tatgagccat tgtgcctggc  27000
tcacccttga ggttgtataa aagattggcc aggtggccag ccacagagct ctgttgccaa  27060
gattgatgcc aaatgtagac attcaccatg ctaggcctt  gttgccctct tcctgcctgt  27120
cacaggatgt agatacacag gaacttccct tgggctctaa attatcttca gtaccaggct  27180
gtctccacct caacctttct gaggtcagaa cagcactcaa aggccagttt ccaggtgtgc  27240
cacccacagg cattgtcctc ttcctcccac atccacctgt ccctagccgc cccacctagg  27300
tgtcctagat gacactgtgc catttccaac acagcaggcc cacaggtgca ttgtctgatg  27360
tctgctcctg ccaccccagg aatggctccg cagagcacaa tagttcaagg ctggagggtc  27420
cctttgatca gcttgtccag ctcacaggtc tcagacctgt tcattagggt ggcatcttca  27480
tcttcactag caccacactg ggccagggct gtctgctctc cttttcagag tggcctgctg  27540
agctgtgtgg tgtcctgcct ggccctcttt ctctaactac tatgtaggca ttgcttgctc  27600
tttgcctctc agctctgcca caggagggca gaagggtcgt ttctgcgagg gtctagttcc  27660
tcacctcttg agttcacggg acgcagacag caagtatttg ttgaatggac aagtgattga  27720
cagttgatac catctcattc tgcagcttaa gctggtagat cactcaagct ggcctcaaac  27780
ttgtggcaat catcctcctg aggtgcatgt caccacacac agctagcttt ggttgatatc  27840
tttgagttgt attgatgtgt gtgtgtgtgt gtgtgtgtgt gtgtgtgtgt gtgtgtgtat  27900
tatttattta cttatttatt tataatttct tttgcagtgc tggggttaaa acccaggcct  27960
cacatacatt agcaaatgat ccaaccactg agctacatcc ccaattctgc ttgttgatat  28020
catgtagccc aggctggcct ctaactttcg atataaccaa ggataacact gaactcctga  28080
ttttcttgcc tccatctcct gagtgctgga attacaggca tgtactacca cacacaataa  28140
taagcatcac accgagggct cgtgcaagct aaacaggcat tcttctatct gagctacagc  28200
ctagaacccct gactgctgat tttctaaaaa ggcacatatt taaagttttt tttaaaatct  28260
gagtgttttg cctacatgca tataaatatg cagcatatat aagtcgtacc taggaaagac  28320
agaagacagt gtgtgatcct atggaactga agatacagat ggttgtgagc caccatttaa  28380
atgctgggaa ctaaagacag gtcctctgta agaccagtaa gtacttttaa aagctaaacc  28440
atctctctag tcctgatacc tattggtttt gacaggtttc tcagactatc tgggcctcag  28500
taggaaagtt actatctgat gagaacatac ccataaattt gattttatta ttgttctgca  28560
tagttttttac cttgtatctt ttatatattt gtgtgtatac aaatacatat atgtatacac  28620
atttatatg tatatagtat atacaaagtg tgtgtatata tagatacaca cacacataca  28680
cacactttgg acacacactt tgtaacaaac agctttggaa aacagaggga ttgcacactt  28740
tcagaagagg ggataccctca ggcagtgctg gggagtgagg gaagccagga aggggtgata  28800
cgtctgctgt actgagtgtg gaggggttg gaagctgttg attctgaaga caacaggagt  28860
aaatgaagaa gagagggaaa gaatgcattg tagatccctc ttgttctatt ttttacctgt  28920
attagtgtac actgtgtgta tgtgcatgtg agtgtagtac ccacagaggc cagaagaggg  28980
catcagatct catggagctg gaggtataga tggcagtgag ctagctgctt gtcttgggtt  29040
ctgggaattg aactcaggtc ctctgcaaga gcaggaaaca ttgttcccag ccaagccatc  29100
tcttcagctc cagatcctct tattttgggg ggttggggat ctaacctggg cttcacacat  29160
```

```
gacaggtatt gagatagcac ctgtagattt ctaagattta ctgtattgag ttgggcaaag    29220
tacagaagag gccttgtttt gtgcagggat gacgaaggcc ccatacatgg gtgcttaaga    29280
ccagtttgac tttaggactg gcctcagagg atcaggacca gagggtgtct gtgcagtttg    29340
tagggtgcta gtggagtctt tttcattttt cttgttgggt tttgttttgt tttgtttttt    29400 aagttttgt tggttttttt gagtcagggt ttttctatgt agtcctggct gtcttggaac     29460
ttccactgta aaccaggctg gcctcaaact cagaaatctg ccttcttctg cctcctaagt    29520
gctgggatta aaggcataca tcaccacaac cagtgttaaa agcattttta tttattacgt    29580
gggggtgggg cagggcatgc acaccacagt gttgttgtga aggtcaaagg acaactttgt    29640
ggagtcggtc ctctccttcc acctttcctg gattctggga tggagctcac atttgtcagt    29700
ctttggagga ctgagcttgt ccagccgagc tatctcacca ccccacttgg agtctttata    29760
gcaccatcca aagctggagg tgcagtggtc ctgtctgaag gccagggttc agggccactg    29820
ggggcgtgtt tgtggctact ccaggtgtct tcacaaaaac tgaaggggat gagctgcaag    29880
aagctgccat ctctgcagtt caggtcaatg catggccacc aatgtccttt gcatgctgg     29940 ctgagaatgc cagtggaggt gtggctctgt gggataggta gagagggttg gtgagcccac    30000
accatcaccc cgggtctcta aatggagcag gcctgttggg agctacacag tgaggtgtgt    30060
ggtgtgaggg gcaaaactgt atctattgag catgagtctg ttgggccaca gggttcactt    30120
cgagagtgtc ttctcctgct gcttcctggt gccaggcttc tcaaagccat ctcttgcccc    30180
tcctccaggt caccactcaa gatggcagag gctcaccaag ctgtggcctt ccagttcaca    30240
gtcacccctg atggcatcga tctccgcctg agccatgaag ccctcaaaca gatctgcctg    30300
tcagggctgc actcctggaa gaagaagttc atccgattca aggttagttg gttgatcgtc    30360
tctgcagcac ttgcttgcat gcacctccct gggtcccgct gaagaaggaa tgtgtcttag    30420
gtgggtctct gacagagcag tggtctcagt gctggctaag gcttgtggag gacacagata    30480
tataaaatgg cctcatcgct tcatagctcc ttcttattgt tgggttttgg gcttttgtt    30540 tgtttgcttc tgtttttaa gacacagtct ctctgcatcc ctcactctcc tggaactcac    30600
tcagtagacc agactggcct tgaactcaca gagatccgct tgtttctgcc tcccaagtgc    30660
tgggataaca agcctatgct accatgccct ggaaggcaac tggagctcat cagattaatg    30720
taaaacaggc caagcacctg atgccagagc agggggccca cttatgggga gtcagtgtcc    30780
aaataggaac acaggcctgc cctctgcccc tcagctggat tccttgcacc ttactgaaga    30840
ggattatttt caaactttaa tgaatttgtg tcttatttgc ttaaagaaaa gttctccagg    30900 t agctcaggct agcctgaaat tctccatgta gctgaggatg gccttgtata tctggttctt    30960
ctgcctctgt cctccctggt gctgaaccac agacatgtct gttgggtttt attaggtttc    31020
ttagggtttg gttggcatca gggatgccag gggtttgctc aggctaggca gtcatacatg    31080
ttacatgtgt cacaaaaacg aaaggttctc agaggtcagt gtgatgtgac ctgtcatccc    31140
agcactttag aggctgaggc aggactgtct agcttggact acaatgagac cctatcttaa    31200
aaattgcttt taattatgta gatctctgtg tgtctgtgta tgggtaggtg cctgcagagg    31260
ccagaggcat gtgatcccct gaatctggca ttataggtgg tcaccagcta cctgacatgg    31320
gtgttaggaa ttcaactcgg gtctctacaa gagcaagtgc tcttaactac tgagccttct    31380
ctagccccaa gaatgtgtgt cttagttagg tttttactgc tgtgaacaga caccatgacc    31440
aaggcaagtc ttataaaaac aaaaacaaaa aacatttaat tggggctggc ttacaggttc    31500
agaagttcag tccattatca tcaagatggg aacatgacag catccaggca ggcatggcgc    31560
```

-continued

```
aggcagagtt gagagttcta cgtcttcatc caaaggctgc tagtggaaga ctgactttca    31620
ggcaactagg atgagagtct taagcccaca cccacagtga cacacctatt ccaaccaggc    31680
cacacctcca gatgttgcca ctccctggtc cgaaaatata caaaccatca caatgtgttt    31740
ttagttgaaa ggttttctt cttggttttg tttgcctgtg tttacaggag tgggggagga    31800
gagagagtgt gtgagagtga gtgtgtgtga gcacacgagt gtgtttatgc atggaggccc    31860
aacctttaca gcagatgtct tcttctctag cttcatttat tgagatgagt ctctcacaga    31920
acctgagatc actgattctg gctagtctag agtctggcta gtctagagtc tggctagtct    31980
agttagccag cttgcctctg gagcactggg gttacataca ggtgaaagcc attcctgcct    32040
ggcttttaca ttgattctag agatccaaat gccaggcctt ccccagctt gtgtgctaag    32100 tgctttaccc actgagccat gtcccagcct agttttactt ttttgagacg gtgtctgacc    32160
ctagccaggc tcctctgtaa ctaaaggcag ttctcctttc ttagcctctc aagtgcttgg    32220
aggatgtgtg agcccccaca ccgtgcttgg acagttgttg ttattgttgt taatatcaat    32280
attattgagt taggatctca ctgtgtactc atggctgacc cggatctcac ggtggagacc    32340
agactgccct caaactcaca gagctccatc tgcctctgct tcccaagtgc tgaggtgaaa    32400
tgtgtgtatc cattaagaat ttattatgca gggctggaga gatggcttag cggttaagag    32460
cactgactgc tcttctgaag gtcctgagtt caaatcccag caaccacatg gtggctcaca    32520
accatctata atgagatctg actccctctt ctggagtgtc agaagacaac tgcagtgttc    32580
ttacatataa taaataaatc tctttttaa aagaatttat tatgctgggt gtggtggcac    32640
acttctctaa tcgcagcatt caaaaaacaa aaccaaaaaa aacaacaaaa tagaattaac    32700 ttttgtaag actcaaacat ccaacaaagc agaaaaaaca gctctccctc cccattaccc    32760
tcctcctggt tcccagagct ggcggagtct gggcagtgtt gagtcacgca agccttctct    32820
ccccaaacct cagttctta gaccagtttt ttaatcgggt gggcaagatt gcagcccagc    32880
tgatgacctg agtttgaccc aaagttccac aaaataggag gagagatctg acctctgacc    32940
tccacctttg cgccttatgg tccttgcatg cacctacgta caataaataa atgtaacaac    33000
aaaaaattaa tgtaaacttt attttgctgg gttattttgc agcaatggta tgggggctcc    33060
tgtaaacaca tcttgactca ggaacagggc aagggtagtt tgggagctgg ggttcctgac    33120
tggcagatag tggcagtgta ggaatgggac ctcacagtgc ccaggctgcc agtcaccata    33180
tggagacctg tatggtaagt caggcctggc tgttttacca acctggagtc cctttcttgg    33240
agaatcttcc aagatgcatt tgggctcaga agtcagggga gagaatagac tgtgtaaaga    33300
aaggtaaggc agttgtgact ccaggcagag acacagctac tgggctttgg tctttggtgg    33360
cctgcatata tggcaccttc tccctgctgc ctgatgtccc aactgcctgt tgccacaggg    33420
ctgctgacag gtagtgatgg tgacctcggg gaggatgcag ctcacagctc acatgtcttt    33480
ccagaatggc atcatcactg gtgtgttccc cgcgagtccc tccagctggc ttatcgtggt    33540
ggtgggtgtg atatcatcca tgcataccaa agtggacccc tccctgggca tgattgcaaa    33600
gatcaatcgg accctagaca ccacgtgagt aacccactc cacctctgc atcttgaaga    33660 agatggtggt acctctgttg actgtcctcg ctctgaaatg tctgagtaca actatgctat    33720
cgctgttttt ccgcatgctc tttgccctcc tgacctgcta ttgaaagtct gcagacactg    33780
ccacccttct tctgaagact aggctaagag tggcagaggc acgggacct gccttccagg    33840 tgtctgtctc ctgaggtcaa gatggagaca gtgatgacct cagagggcat ctctgcccca    33900
```

```
gaagatggct ccaagtgtgg ctgttgccct ggagttggtc catccagtga tctggtcctc    33960
tgaacttact gccggtcatt gcttagggac aactcagccc ttggcccctt cacagtggct    34020
tagatgcctg cagggaagtg cgttactcct tggctttgag ttttagttta ttctgggaac    34080 ttaaaaagt agatgtcatc ctgtctaggg acaaatcctg ccatcttct ggttttttctt     34140 tttctttttct tttcttttct tttcttttct tttcttttct cttctcttct cttctgttct   34200 cttttctttct ttcttccttt cttctttct ttctttcttt cttctttct cccttccttt     34260 cttccttcct tccttccttc cttccttttt tttttttga cacagggtct caccgtatag     34320
ctccagctgt tctggcctag aactcaggga tcttatctct gtctgtctct gtctgtctgt    34380
ctgtctctct ctctctctct ctctctctct ctctctctct ctctctctct cctggttgtt    34440
cagctgtaga tactgtatgc taggaaggat tgcacaagca aacagatgag agagtggccc    34500
cagggaacac tcacagctgg aggagttggt ttctgctgac tcagagcaac tagcagattt    34560
aacccagcag tgtggcatgt ttaagacagc ttgaataggt gctcgggaat cctggaggtc    34620
agtctttaat gggtctgcat gccctgcctt ctgattgaga cacccaggag tgactgagaa    34680
gccagccagc tcctcagcct ccagccctcc tggcagcatt ggtcattcct ttgtaagcaa    34740
ctgtaggaaa caagataaaa atgcctgtcc aggcatcctg ccaagggtcc tgtctgcctg    34800
gggcctggaa catcgagctg gggctaggtt ctcagaagca gctggcagag ctggtcacta    34860
aagactggac ctgtgctgtc ctgagaggtg aggaaagtcc tgtgaacgct caccctgctt    34920
ccctgagtgt tgagctggct gccaggccca aggcagctgt gaggccaaca gccaagcttt    34980
gctcttacat gggctgtgtg tctcaaagcc ggattgcaca cagccacgcc agctactaaa    35040
accttgctta atctcagtct ttatacgatt tgtttctttg tcccttagac tctattttcg    35100
taaactgggt catgtctggc tcaaatttag aaaggtcagg tgaaggctca gagacttgca    35160
gcctgagggg ctgttctgga agcatctttc cagtgtgggt ggagtgcctg tgtctcctag    35220
gctgctttgg ttttgtttgc tgagatctga aaggaaggcc atagaggtta tcagcacagc    35280
tgaaagtgaa attactttttt tgtccttatt ggattttttt ttttttttt ggttttttga    35340 gacagggtct ctgtgtagcc ctggctgtcc tggaacttgc tatgttgcta tgttgaccaa    35400
ccttgtctca tgaactcata gagatctact tgcctctaca tgtgacacca tgcccagctt    35460
ggattttttc tttaaatttt attctgtgtg tatgtgtact atacgtgtgc ctggtgcctt    35520
cagaggtcag aagagggcat cagatcccct gagaccagag tttcagatga gtgtgagcca    35580
ctgtgtatct gttcccatca gctgcaggag gaagcatctt ccaatgacag ttgtgctagg    35640
cacccatcct gttcttctgg gaggcgaggc ctccagagca taggtctctc acatgatgtt    35700
aatgttttcc aatatcagag ctctgaaggt tagatatgct actactttga tcatttggga    35760
cctcttatgt tatgttttgc ttttagattt atttattttt atgtattatg tgttagtcac    35820
atattatgca tatatgtttt taagaattgt ctatttattt tagtacacta tagctgtcct    35880
cagacacacc tgaagagagc atcagattcc tttacagatg gttgtgagcc accatgtggt    35940
tgctgggaat tgaactcagg acctctggaa gagcagtcag tgctcttaac ctctgagcca    36000
tctctccagc ctcatattat gcatatatta tgtatgtatg tgtgtatgtg tgtatgtatg    36060
tatgtatgtg cctgcaggcc agaagagggc accagatctc attatagatc agccaccatt    36120
tggttgctgg gaattgaact taagataact ggaagagcag ccagtgtgct taacctctga    36180
gccagactcg atctctttta tttgttcctt gacaattgca tacacgtcaa caggatacct    36240
tgatttaacc catcccaact ctccactcaa accttttttaa aaacccgctg agttccctta    36300
```

```
gcgcccctg ctggaggatc cctggtcggc cagctggctt ggtccacttc tcagtgagtc    36360
ttgtctgcag cagccatgtt gtgttcacat ctggctgcac cctttccacc ccttcttcca    36420
tgatgtcccc tgagccatga aggggaaggg ctagttttta ttttgtcac tattttcct    36480 tttctaaaac aactgaaata acccctcaaa tagcagcact ttgttttgag ttttctttca    36540
tagtcggtga ctttgatttt taactattta aaaatctttt aagttttta aaagatttat    36600 ttatttttat ttatgtgggg attttttggc tttgttttgt tctgttttg tgtttgagac    36660 aaggtcttat gtagaccatg ctagtcttga actcacagag gtctacctgc ctctgcctcc    36720
agcttgctgg atatttgag tttcttataa ataaagacag catttaaggt tatatctgag    36780
gactggggat ataactcagg ggttgagccc ctgcctagaa agcatgaagc ccatagttca    36840
cccctgggca cagcaaaacc cagcaaatgc tagcaaagta tgtttgagag actggcaaag    36900
cattataatc tgaagaaaac gggccaggat cccttgagc agcagttggc aggtcccacc    36960
cactgggagc agttgccatc gtgagcagct ctctgcccca caggagcctc tccaccattc    37020
ctccagagac tggaaaaact gtgtgttgtt caagactgct caggtcgctg gccggcctct    37080
tgattcttcc ttgggcctcc agagacaggc cactctgctg cacccagcca aggctggccc    37140 atttgagag gaatagagac tgccagggcg cttggagaac tggggtccct caggcttctt    37200
ctgcagcctg ctcactcctg tcgctgggag ggtgcttggt cagcccgctt tctggtagct    37260
gccattacca ccttccatgc tgacgtctta gctccttgtc tgctccatcc tcacagtggc    37320
cgcatgtcaa gccagacgaa gaacatcgtg agtggcgtcc tctttggcac agggctctgg    37380
gtggcgatca tcatgactat gcgctactcg ctgaaggtgc tgctctccta ccatggctgg    37440
atgtttgcag agcacggcaa aatgagccgc agcaccagaa tctggatggt aaccacccgt    37500
cacccaccag gggacccgct ccgagtcaga gcaggaccct tgcctcctta gacctttcct    37560
cctctgttcc ttggtgtgta acctgtcccc agcctctggc tatgggagag ctatggctca    37620
tgacacttgc atggatggag ccagggctgc ttttgctaat ggtttctggg agttctgcca    37680
tctctctgtt cacctctgtg tgacctgtgg ttcaggctgg atattgagca taagtaccac    37740
ccaggaggtc tttgtagcct taggggccac tttgcaggca gacaccagac ggttttctga    37800
gttggtcaga tcacatgatt taccctaatc cgtcagtgtt ctctatttct tcgtgacctt    37860
aaggccaagg caccatgttt aagagagaga gagggttata ccatatacat gtgtgtttgt    37920
taaattataa ctggttgtga aggcttttgt tgttgtttag ttttggtttt tgagatgggg    37980
gctcatgtca ccctggctgg ccatttcctg actgtagcca atgatgacct tgagtttctg    38040
gttctcctgc accaccatgc ctgatgttta tgagatgcca gtgaccaaac ccagagcttc    38100
atgcctggct tacccagatg agccgtctgc ccagggaagg acatccaaag ccccaacgag    38160 ctgctttat aagcttagct ctctggagta gggggaggag gatgacggat cactcctggg    38220
acctccctct ttggcactca gaccccagcc tttccttccc acacacacca ttgtatggct    38280
gtcacatatc ccccacccac ccacccacat attgtcaccc ctcttggctt ctgatttta    38340 taaagaaaag gtcatttct gcacccaagg tttgtaaagg atttcagtga atctggttct    38400
ggtaacattg cctttcaaat gcttgttact ggagctcctc ctttgtgcat gggaggagta    38460
ggtcagcttg gccttgactt gcgggccagt gtgccccat gcccgcactt gtgaacgtct    38520
tcaaggtccc tttgctgccc accacgcact cctggcctcc atctttcaca aaccagcttc    38580
caccttatat attagttttt taatgtctag agtagcaaaa cttaaccaac aggcttaaca    38640
```

```
cagtgtcctc taggatggcc ctgtggctgc tgttgagctg agtcccagca cttcctgagc    38700
atcgcaaatg agaatcaccg actacacctt gaacccttag agatgcccta gctcctgcca    38760
gcaggaggca gctgccttcc atagctggcc tgcaaaatct tcctacaggc tgtgggggga    38820
gctcactctc taggctgctt gacctgatgg gcagggacac actgctgccc ctggggtgg     38880 cttgagggtc aggcacctca gctgatccta ctccctatgt gcagagcggg caccagcctc    38940
aaatcaagga ccttccagga ggaggcagac agccctcctg cagaatcggg aaggacagta    39000
ggcagccaca ccagaagact tctcttttca gctgagctct cggtgggacc ggagcctgat    39060
ggtgtagacc agggatggct ctgtcataaa acactcagag agtcaaacgc agttgaaccc    39120
tggctttggt tctttaacac agcctcatct ttgaaaacgt aacttgtatc tccaggctat    39180
ggtcaaggtc ttctcgggtc gaaagcccat gttgtacagc ttccagacgt ctctgccgcg    39240
cctgcctgtc ccagctgtca aagataccgt gagcagggta ggtattatcc acactcctgc    39300
tgagatgcca gtgtccttgg gatccatgtt tctgcctaat tgtgactgta aattaaagtt    39360
cttaatcttt gttattgctc tgcagtctct cctgtagggt tattataaga atgttcccct    39420
gtctcccacc ccacagagtc cttgcactgg ctagacaagt gttctaccag tgagctacat    39480
ccacagccct tgatatata tatatatatt ggatacaggt ctttctagtt agcacacact    39540
ggccttgaat cttttttgt ttgcttgttt ggttggggct tttgtttgt tttgttttc       39600 tcgacagggt ttctccatgt agccttgact gtcctggact gactttgtac actgggctgt    39660
cctagaactc ccagagatcc tcctgcctct gcctcctaag cactggtatt aaaggcatgc    39720
gcaaccactt ctggtgaaca ttttaagatc tactcacctt ttgctttata tgtgggagtg    39780
tttgactttg tgtatgtatg tacaccatat gctcgcagtg cctgaggagg ccagaagagg    39840
gtgttggatt ccctgggact gggggttacag atgactgtga gcctccaagt gaatgttagc    39900
gacagagcct gggtcctctg caagagtagc cagtgttctt ccctaccatc catccctcag    39960
ccccatgacc ttgaactcct gatctcttgc tgtagcctcc tgatggtaga cgagtttcac    40020
tatccatggc ttgatactgt tttctctaga gcattattgc atctgcagtg tttaaagtgc    40080
tgtgtcccac ctattggggc atgatcactt ttttgtttgt ttgtttggtt ggttggtttt    40140
gttttgtttt tttgagacag ggtttctctg tattagccct ggctgtcctg gaactcactt    40200
tgtagaccag gctggcctca aactcagaaa tctgcctgcc tctgcttcc gagtgctggg     40260 attaaaggcg tgcaccacca ccacccggct gcatgattgc ttttttaatgg tgttactgag   40320 atgcagttta ggactgtata gtgtccttga ttaatgtgca gagttcagtg atttgagttt    40380
gtatccatta ttttaaactg gaaaatacat acaaagacca catttattat ttttttttaag  40440 gctgggcatg gtggcactag ccacctttta atcttttaat cttagcaccc aaaaggcaaa    40500
ggaaggcaga tctcttgtga gttcagacca gccagggcta cacagtgaaa cactttccaa    40560
aaaaaagaaa aaacagaag gaagaaaatg gttaaggaga tggctcagtc ggtaaaacgt     40620
ttgcctggca aacatgagag cctgcattct gcatttgatt tgtcagcacc catacatgat    40680
agcgacagat ttgcagcata cactggtaat cccagtactg gggagtggag gcaggggat     40740 gcctgtggct cactgcccag taagcctagc ctgactggtg aacttcaggc ggcttccagg    40800
gaggtggata gcctgtgtca ggctgactcc tgagtgccac cacacatggg ttcatctttt   40860
cgctctggct ctcgggcacg tgtgcacata cacagaattg ttttaactgt ttccaagtgt    40920
acgcccagca gtgcaactct ctgtgcttta gggtgtcaag gagttgtgac caccctggat    40980
tgtcaggctt ttttatagcc ttgggcagaa gccacaaaac tccctgccac aggcctgcca    41040
```

```
gcttctgttc cactttctgt ttctagttct gcctcgagag ggagtatggt aggaatggga   41100
ttatgtaatc tgtgactttt gtgaggggtt cccctacta gcgtttattt ttctttgagt   41160
caggatctta accgaagcta gcctcagact tgtaatcctc ctgtctcagc ttcccaggca   41220
ggatgatttc aagcttcatc actgactttt gtttttgtt tttgtttt tttttttg      41280 tttttgcttt tgttttgtt tttcaagacg ggtttctctg tatagccctg gcttcatccc   41340
tttcttaaca aagctatgct tcttcccctt ttgtggctga taacgctcct cgctcgtcgt   41400
gtgggtagac cagttatctg tccatctgat ggtgtgaatg tgggttgtgt tgtaagcagg   41460
gaagctggga atatctatgc atgtttttta tctgggtact tgaccgcctc tggttgatag   41520
cagagtccat cacatcacag agtaagtagc agaggctggc tctgtcatga tcctgatctg   41580
ctgtaaaatg gcagcaccct agttctttcc agcttccaat gctggagggc acccatattg   41640
ttatgacttc tgccctcttc tcagaactgt aaatcaaaaa caccttggct tcaggtgttg   41700
gttcctggct tagggattta gtccttattg cccttggcaa gttcctttcc atctctcatc   41760
tcccagattg gggcacaaac gagactccca gccttggctt gggggtggtg cagccaccta   41820
cctgccccac tcttcttctt aaaacaggat ctcacattgc ccagactggt tttgaacttc   41880
ctagactccc tatatagctg agaacgacct agaacctcag gttcttcagt atctgccacc   41940
tgagtgctgg gtcacaggct ggcctattac actcagtttt atgcagtgct ggggatagaa   42000
tccagggcct tgtgtgtgct aggcaagtga tctgccagct tagccatgga gagtccaacc   42060 tttgtttat cagtttggag ttagccgac agttgcagct ggctctgacc cttcattgtg   42120
caaagctggc cctatgtagc ctctgttgcc ctggaatttt ccatgtagac caggctggac   42180
ttgaaccctc attggttcct gctacttcac ttcctaaatg ctgggattat aggtattgtc   42240
caccacaccc tgctcaaact ttgtttcctg accaatcagg cttggcggca gttctgcttc   42300
ctggaactca ctcagtatag gtgggagctt tcagaatcct cagaaagagc cacacttagc   42360
caagcgtggt ggcacatgct gtcaccccaa cacttgggag ataaaggtag gaggaggatc   42420
aggagttcaa gaccagcctc agttatattg tgagtttgag tccaaaaaag ggggctggag   42480
agatggctca gcagttactc ttccagaggt cctgaattca atttccagca accacatggt   42540
ggctcacaac catctgtaat gggatctgat gccctctttt ggcatgcaag tgtgcatgaa   42600
ggtagagcac tcatatgcat aaatctttag gaaaaagaa gattgcgtgt gagatgttcc   42660
tgtatgtttt accccaagc ctgttcaagg tgtgtgtctg ccagtctgtg tgagctgagg   42720
atctagaccc taaacatggc ctgtgtcatg actgccttgt tgagcacctg cctggcctca   42780
ctgggctgtc agggttccca cccatctcac cacaccaacc caggtcatca ctgaagcaat   42840
ggctaggtgt cttggtacct ccatcaggaa gccgtgacct taattatcat ccacctgcag   42900
ccctgctcag ccctgcaggg gactgtcttg tccggtctat ctgcctatgt aaaagcagag   42960
aggacagact gacttaggga agcttttcta acctttcta caccgtctta cttttctgag   43020
gcatttgaag tgatgcacgg cttggagaag ggtgtttaac tctgcccgtg ttttctctct   43080
ccagtacctg gagtctgtga ggccactgat gaaggaggga gacttccaac gcatgacagc   43140 actgcccag gattttgctg tcaaccttgg acccaaattg cagtggtatt tgaagctaaa   43200
atcctggtgg gccacaaatt atgtaagtaa ttctgcatgt agtgctgtga aagttcttac   43260
ttgggtacca gggctcacag agttctagct gtggctgagg gcagccatac tttcccctga   43320
gagctgtgct cagagatgct agcatctctt ccctcctgca agctccttag cagcctttgc   43380
```

-continued

```
accctgctca gggcagggag ctgctttgga ccctctagtc ccgacctggc ataccacagg   43440
ctgttctctc ctgtggtggc ccagccaccc cacctcccct tgtggcatct tctccatcca   43500
agagtatcac ttctgagtgc tctggtcaga gttcagatgc tgttgacagt ggcagctgtc   43560
tgctgggagc cagctaagcg tctgtgtgtg gtgttggggg tggggtagc aagtgggcac    43620 actgcaggat atgaagccaa gaggggggaat tcaggtgtca tgaataactt gatggaaggg  43680
aagggattga aaataaccta tgggagccag acacatgcct ataggcaaga taggtacatg   43740
cctatagtcc cagcactcag aaggcagagg caggagaact gtgggctcaa actaaccagg   43800
gtcacacagg gataccagac cctatctcaa gaaaaactct taaatttaaa aaattattta   43860
cttattcatg tatatatttg cctaggtgag tttatatgta ttacacaaat gcagatgaca   43920
tggaaactag agggcattgt atctcctaac agttgcaggt gattgtgtgc tgcccaacac   43980
aggtgctggg agccaaacta gggtcctctg taagagcagc acacactgag ccagctctgt   44040
agtccatcaa aaagaagtct caagagctgg gaatgaagct cagttggagt ctctgcctct   44100
ggtgcacaat gccctgggtt cagtctccag caccacacct gttctgtccc acacgcatgt   44160
atcccgaggg cttgagagat agaggcagaa agatcaaagt tcaaggttgt ctgtgcttct   44220
atagagttta aggtgagcct gaactgcttg agaccctgct ttaaaaataa aaccaggagc   44280
tggagagaag gctcagcagt taagagcatt tgccattctt gctgaagacc tgggtttggt   44340
tcccagcact cacaaggtgg ctcacaacta tctataactc cagggccagg ggatccaaca   44400
tccttttctg acttctatag gtgccatgca cacacatggt gcacatactt tatatgtaga   44460
caaaacacac acatgaaaga catcttagtg cacacctta gtcccagcac tgggaaggca    44520
gagagaggca ggtgggtctc tgagttcaaa gccagggcta cacagagaaa ccctgacccc   44580
tggcccctca aaaagaaaa attattttaa aaacacaaat aataagtaga caaaaatcaa    44640
cagagaaagt agacaaaaag aaacaagaga agagccagca gatggtgcca gacccaggca   44700
ctgtgcccag cagggcagga ggccacagca cctgggtcat caggactggg tctaatccta   44760
agcagctggc ccgctgtgca tttagactct cgtgcaagcc ttttctcagg tgtgcgctcc   44820
agcacgatgc tcaaatcatc acaggttgta gatcagcagc ccctgggtgg ctagggcagc   44880
ttgctgggta acattgccat ggtcactctg gagaatcgag acagcacatg ctggcctcag   44940
gcttagttct gtggctgaga tgtaccaggc atcaggaaga tcgatctttg gggagatctg   45000
ggttattttt ttttttcctgc agtgctgggg atgggactgg gacccaaggc ctggtgaata   45060
tcagacaagc attcggcaca gcactttggc agttaagggt ttttggaaat atggcccca    45120 ggctagcctt aaagttgcta catagcagtc ttgaacttgc tataaccttg aattcctgat   45180
cctcctgccc atgtgtgcac tgctatatag ttctatgcct agttttatac attccaacag   45240
ttgagctaaa acccagcccg actcttttta tttatttatt taaacgcaat atgaaactat   45300
gctctatagt ctagccaggt ctcccttaa gaccagtgtg tctctcaatt ccttatggcc    45360
tgtctgcttg agacaacttt gttttggagc ctgtcataca ctggaatttt ccagaaagat   45420
ttgcatacat ctgggcatga ctgctcagcg tgctgacttg tcgtgtttgt accataggtg   45480
agtgactggt gggaggaata catctacctg cggggccgag ggccgatcat ggttaacagc   45540
aactactacg ccatggtgag ttggtcttcc attcccactg cagccaagat gggtttgtcc   45600
tgctgggtgg cctgggaaag ctcctcttgc tcctgcttct tttgtccaag tcttcatgtt   45660
gctgtgaaga gcccacctgg ggcccatgtg ttagaccccc ctgtgtctta acgggcccct   45720
gccctccacc caacagtgca aatacatttt cattgcaaac aacacttgct atgtaagtgc   45780
```

```
aggctgacct tgaacctgtg gtagaacaac aggaagctgg cgttgtaata gagcaataac   45840
aaaattaggg cttgtggtgt ctcatgcctg ccaggcaagc actggggagg tgagacagg    45900 gggattagtt cagggtcatc cttggctaca taggtagttc aaggccctcc tagattgtat   45960
gagatactct ttcaaaaaag taagtctgag ccaggcgtgg gggcgcacgc ctttaatccc   46020
agcactcggg aggcagaggc aggcagattt ctgagtttga ggccagcctg gtctacagag   46080
tgagttccag gacagccagg gctacacaga aaaccctgt ctcgaaaaac caaaaaaaaa    46140
aaaaaagtaa gtctggcgct agaaggatgg tttagcagtt taagagccct tactgctctt   46200
ccagaggacc tgagttcggt ttccagtaca caccctcaagt ggttcagaac catctgtaac  46260
tccagttgca ggaaatctga tgccctcttc tggccactct gggtacctgc acacacatat   46320
acacttaacc ccacacaatc acacacatac acatagagag aaaaaacata tccaatttgc   46380
cagaaaaaca aatggaccta aaacagtaac aaaagtgtcc aaagttgtaa agtcaggcat   46440
agtgacacat agctttaatc ctagcactca gggacctggg gtaggagaat tgcctgaaag   46500
ctacataacc tgctcccaac aacaacaaaa gccaaaagcc cacctaaaac aaatacaaaa   46560
ggcggctgta acttagcaca gctgtcaggg agcaccccc ccacacacac acacaccttg    46620
tatacagacc gccgtgtcac cccatgagcc ctcttttctg tctcatcctc acaggagatg   46680
ctctacatca ccccaaccca tattcaggca gcgagagctg gcaacaccat ccacgccata   46740
ctgctgtatc gtcgcacggt agaccgtgag gaactcaaac ctgtatgtca acttgccttt   46800
aaaaatatct cttgggaggc tagagaggcg gctcgattaa taaagtgctt gctttgagaa   46860
gagtgttcag acttggccca gaggtgccca gctagatgca gcagtgcacg gttgtaatcc   46920
cggcactggg gagccagagt cagacaacgc tggggcttcc cagtcagtga ggcccaggtg   46980
cagcgagggg cttgtcgagg cctgggtgtt caatcccggg aatccacatg gtgggctgag   47040
agaaccagct cctgcaagct gtcctctgac ccccacatgt actgatacac gggtaaactc   47100
ctcaggagaa cggtttcttc ataacatcag gtggcttaag tgtttatctg gaaggaactt   47160
cagtagcctg gccctgctcg gcaagtcccc caggtgctac cctagggatg ctgagtgatg   47220
tggtcagact gggcagtgtg cacaggaaac aaaccgcatt ttaatcagtt cattgcaaag   47280
ctttcctctg ggattttgcc tgttggttta aaacacattt ttactacaga ttcgtcttct   47340
gggatctaca attcccctct gctctgctca gtgggagcga ctcttcaata cttcccgcat   47400
ccctggggag gagacaggtg ggtagtgctt actgggtct ccgctgggag ccagcatttg    47460
ccattttgct gctcggaacc aggaatagtt ggggaacgtt gggaacagaa tggtctacag   47520
ggtctgtccc aagagcgtct gactctgatt gttcctcctc ttggaatcgc tttgtctttt   47580
gtcattgggg gtggtttggg aatgggatct cacatgttcc aggctggcct aaaataatat   47640
gcagctaagg atgaccccttt tgcctcccag tggattctag acatgtgtca tcatgcccag   47700
agtatatatg ttgctcaaat tgaaactctt ggcttcatat atattagaca acccaactga   47760
accgaagttc agctctggcc tgaatttcct ttgtccacta ggcctgtaca acaggcccgt   47820
ttccagattt tagtgtttct tctgttgaga gtttctttcg ttgggcattt tcctcagacc   47880
tgctggaata ttttcacatg actccttggg caccttgttc tggcccatgc agggtttgct   47940
gtaagatacc cttgagaacc aatgtgcctg agaggctcga tggaggccca gctgctgctg   48000
ctggcagcct ggcctgggct gggctcatct catctgcttc taacctagga catccttgga   48060
aaaggatgga gggagggaga cggatgccag atggtgccat gcaggcctgc tggggtcaag   48120
```

```
tgtacagcat tggtcactttt taaacttggt gacaaataac gtgagcaaaa ccacttaggg    48180
aggaaagatt tattctacct cctggagcca gagcctggag cctattgttg ctgggctatg    48240
gaagggcaaa gcatcatggg tacaggacat gtgagggagc agagcattta cctctaacag    48300
gaaggacaca gctcaagaaa agggactaga gtcaaaggtc cccttcaggc tgacaggtga    48360
ctcagcgcct gaatgagcct gtctgtaaac cgggtgcttg tacttgatgc caggctctct    48420
tgtggtaaaa ggagacaaca gactcccagg agctgtcctc tgccatctac acatgtatgg    48480
ggcatgcttg tcctcacaca tatttgagct cacacaagat aaataaataa attccattta    48540
tttattttat ccttgaggga gctggttttc ttcttgtcca ggccaggcag caagtgtctt    48600
tgccacctga gccatttcac tggctccagc atggtcttca atagtagtga tcacaaatat    48660
taactaaaat ctgggtaaca ctgggtatgg tggcatatgc ctttaatcct agcattcagg    48720
aggctgaaac aggtagattt cagtgagtgt gagcccagtc tggtctatac tatgtctaca    48780
tagtgagtta caggccagct aaagcttctt aatgaaccct tgccacaaag acaagttatc    48840
atttatgaaa atgtagtatg ctcggtgagg tcgtacagcg catgctagct gtcagaggcc    48900
tctcctgctc tgtggtgggc tctgattgtt tgcgtcttct gagacaggat ctcctgaaac    48960
cctggctctt ctgaattccc tagctagacc aagttaactc acagagatcc acctgcctct    49020
gcctcctcag tgctgggatt aaaggtgtgt gccaccacaa ccggccttt gctatcaatt    49080 ctctttaaga ttttcactg tgtttgtgtg taggaaggac acagccacac tatagcagtc    49140
atgtgcaggt cagatgacag tgccgtgagg ctgcagatca aacgagggcc attggcttac    49200
acggcaaggg ttacccacaa gtcatctccc aggtcctctt ccccccctt gagacagggt    49260 cttatgtagc ccagactagc ctctaatttg ttatgtagaa gctggctttg agctcctgat    49320
ccttccaagt ggtacaccat tgtgcctggc taaaacattc cttttttttt aagatttatt    49380 tttgctttt attttatgt atgtgttgcc tctttatgtg tatatgcact gagcatatga    49440
agtgcccaca gaagccagaa gagggcacca gatccccgga gctggagatc cgggaggctg    49500
taaaccacct gatgtgggta ctgggacctg aactctgcct gtgacttatg ggagagatct    49560
cattcaatac tacgtgtgcc aaccttgttt catagatagg aaactgactt aggttatagg    49620
ggctggttaa gccaaaggga gtgactcagt atggagtcaa gggccacaca gcagtattcc    49680
cagaactcag gaggtggagg cagaagaatc gggagttcaa ggtcacccctt ggctacatag    49740 acagtttaag accagcctgg gatacatgag atcctcacga agcaaaccgg tcaggtcaga    49800
tgagcccaag gctttctgac ttcttgtcac tccttcgtct cctcaccacc tcagacacca    49860
tccaacacgt caaggacagc aggcacattg tcgtgtacca cagaggccgt tacttcaagg    49920
tctggctcta ccatgacggg aggctgctga ggccccgtga gctggagcag cagatgcagc    49980
agatcctgga tgacacctca gagccgcagc ccggggaagc caagcttgcc gccctcactg    50040
ccgcagacag gtgcgtgtgt gcgtgcgtgc gtgcatggcc tcgcacaccc ttccggtgt    50100 gtttgagggc ctcagtccaa tgccttaatc ctggggtcct ccgttcctcc acctcctata    50160
agcttggatc aaagtcctgt atcacggcat tcagttaact tccttcgttt cttttttctga    50220 ggtaagtgct ccaccactga gcagccaggg agactctgtg tgtgtgtgtg tgtgtgtgta    50280
atgtagtgta tgtgcatgtg tgtcaatgct gggtgtcttc atctgttcct ctccatctta    50340
tattatgcag acaaggtcac tcccaaagcc tggagctcac tgactggctt gtctggcaga    50400
ccagtgagtt ctagggataa tcttgtctct gccttctcag tactaggata ataggtcagg    50460
gccccagatc ctcatgctta tgcagagagt actttaccca cactccccaa cacacaccaa    50520
```

```
aggagcatgc gtatctttaa gaccagcatt gtggggttgg actgtgggaa agagaaactg  50580
ccctgtgccc tgtgccctgt gccctgtgcc ctgtgccctg ctttgaacag ggtaagaaac  50640
aggtagagtg agttggtggg gagaggattt tgctctctgg ggccaaaagt atacagcact  50700
tcacaaaaga ccatctttca cagaaccctg agctgctcta agctctaact ctttaataaa  50760
gagttgctcc aggcactcag gagataacaa ggctgtgtgt tgtttggagc ctgggactga  50820
gaaggaaaac cagaaagcga ggaaggccat agtctatgct tcatctcctg ccttgagggc  50880
tggggtgcac tgggggcctg cggcatttgt gggtgttgat accaaaagtt gttgagagag  50940
gtgggtagtg gatgggaggc agcacagaag gcctgaggct gagaactgtg ggagggaccc  51000
aggatccata ggaggaagct acttcagggt agctctgaag agagaccaag gtgagcatca  51060
tggtgggcac atggaggtca ttgtgggagt gtcatgtgac cagtcctggt ctggggtcag  51120 ggccagatg tgtcgttcc ttccctgccc caaagtagtt gtggcatgat ctctgtgcct  51180
caggtttcct catctgacaa atgggtctgt ggtgctgaag acatcagtgg actgattgat  51240
gcctgagaga ggctcaggtc agagcctggc tccagggcca ggtccttcgg catttgttat  51300
aacttctgct ggggatgtct ggggcagaga agggtgcttc tccctggctg ctgcagagac  51360
aggttggatt tcattctgag cagtgtgtgt gtgtgtgtgt gtgtgtgtgt gtgtgtgaat  51420
atgttgttcc tcgggtacta gctgtcgaca ctgatgttgg agacagggtc cctcactagc  51480
ctggagcata tccatttagg tgacctgtct ggctaacaag ccctggggat cctgattttg  51540
tctctcagac ctgagattag gagcacatac caccacacct ggctcctcta catgggctgt  51600
gggggtgaaa ttcaggttct cgggctgaca agcaagcact attgcctact gagccatctc  51660
cccaccctgg acaactgatt ttagatgcgt ttactccttg ccacagagtg ccctgggcga  51720
agtgtcggca gacctatttt gcacgaggaa aaaataagca atctctggat gcggtagaaa  51780
aggcagcatt cttcgtgacg ttggacgaat cggaacaggg atatagagag gaggaccctg  51840
aggcatctat tgacagctat gccaaatctc tgctgcatgg tagatgtttc gacaggtaac  51900
tcccattttt aatctctgag gttgatgggg ggttgtggga gatgtttctg ggggtacctg  51960
tgagcagcct ccccaaatct gacccctgct atggggttgt actaggaagg aataagcatc  52020
caaccagaaa gctctgcttt cttccctcca cacaaactca gacacagttg taggcccggt  52080
agttttgagg tcccctcctt tgcttaccca ccacccttct taactgtggg ttacctggct  52140
cccagcagaa ctgtgggagg ggcccaggat acatggagga agcacatagg acagtcctgg  52200
gaaccatcac tggccttgtg cagttgctgt gaccctgccc tcctggatcc cctttctgta  52260
ggtgtaaagt gaggaggtac ctcccaggcc tggctggaga gggcatggcc ccagactcct  52320
tgttacagta gtctacacgc ctctggaccc agggctcaca cacatgctat attgtatctc  52380
tgatacaaga agctatgaat ggctctgtgt tctctgtgcc cccttgagtc accttcctag  52440
gatgtagaag cctggagaat tgtcagggtg gagagaagca acgtctctg cagaaagaag  52500 cacccatgta gcttttgggt tcccatgtcg atataaccct ggaagcccat gatcatgttg  52560
tctccctgta ggtggtttga caagtccatc acctttgttg tcttcaaaaa cagcaagata  52620
ggcataaacg cagagcattc ctgggcggac gcgcccatcg tgggcatct gtgggaggtg  52680 agccacacca ttgttacctg tctgaatgtg gaaggtgctt tgggaaagaa acccaacgca  52740
ggcccacttg aactctgcag tatttgtcta attctgtatt ggttacattt ctctctccct  52800
gatgaaatac cttggagagg gaggagtgag tgtgtgtgag agtgagtatg agtgtgtgtg  52860
```

```
tgtgggggggg gtgctaggga tggaacccag ggcctgcctc atacttgctg ggcagctgct   52920
ccacaccaag gctgtataac cttagccttt attttggaga caaggtctca ctagatagaa   52980
acatgctaga cttgaactca ctgtgttgcc cagactggcc tcagacctgg aatcctcctg   53040
cctcagcgtg ttgagtatca gagattacag gtatgtgcca ccgggcctgg gttagcatct   53100
tggcttataa aatggcagtg tcctggagcc agagagatgc tagtagggta gagtctgacg   53160
atctgagttc aaccccctggc acccatgtga cagtagaagg gcagcacccc atgtgcaccc   53220
tcacttcaca caccccatgt gcaccctcac ctcacacacc ccatgtgcac cctcacctca   53280
cacaccccat gtgcatcctc acctcacaca ccccatgtgc accctcacct cacacacccc   53340
atatgcaccc tcacacaccc catgtgcacc ctcacacacc tcatgtgcac cctcacctca   53400
cacaccccat gtgcaccctc acacacctca tgtgcaccct cacacacccc atgtgcaccc   53460
tcacctcaca caccccatgt gcaccctcac ctcacacacc ccatgtgcat cctcacctca   53520
cacaccccat gtgcaccctc acacacccca tgtgcaccct cacacacctc atgtgcaccc   53580
tcacacaccc catgtgcatc ctcacctcac acaccccatg tgcaccctca cctcacacac   53640
cccatgtgca ccctcacaca cctcatgtgc accctcacac accccatgtg caccctcacc   53700
tcacacaccc catatgcacc ctcacacatc ccctatgcac cctcacacac ctcatgtgca   53760
ccctcacctc acacacccca tttgcaccct cacacatccc ctatgcaccc tcacacacct   53820
catatgcacc ctcacctcac acaccccatg tgcaccctca tacatcctaa tagttaaatc   53880
aaaaaaaatt aaggcaatgt atcttactga aaatatttca gttactaaaa tgaccaggtt   53940
acttaaagac caccaaatct ctgtccccct ttctcctaac ccagctttca aaaacacaga   54000
gttgggtgtg gtgacacatg tcaccctagt acaggagcct gaggcaggag gatcaggaac   54060
ttgaggccag cttggactat aaaacgaagt catttcaaaa cagagagagg caaagcaaaa   54120
gaaagggtca gacccagact gcagatctgg tgcctttgtg gacttctcag tcaaatagct   54180
gtattgcagg aatctgaaat ttattaaata ttgacgtaac tctcaacgaa gttttaaatt   54240
tttgtaagat tttggacttc aggctaggga tgctctctct cttcctctcc cttcctctct   54300
cttccagggt ctcaccattt agcccaagcc aaatggcact gctcttgcct cagcctcggg   54360
agtgctgctg gtttcgggtt gcccggccac ccccagctaa gactttgcat cttagttttt   54420
ccttgcagtc ctgtgccagc gatttctttt cctgtggtgc agagtcaact gcagggtgca   54480
gattgtgtct gcttgtttgt gcgcatgctc tggcctccct ccctccctcg atcactcacc   54540
ctctcatccc ttgggtgctc ggacctctgc ttggggtctt ggcagagtcc cagctgctcg   54600
gcttcagcca gggaagagtt cctacacgag acagcctggg aaaggaagaa gcaggcagtc   54660
tggatctaag acaccagcgt gctccgctga gacaccaatt ccaatggcga agtgcaaggg   54720
ctcgtgtccc tgcgaggcag cccctgaact gatgccagca gcagcctcag tccagatgca   54780
gatacctcac ctccattagc tcccagaccc tgcggctcac acacagatct ctgggaagct   54840
ctgcaaagcc caacagtata ggcccatgag aatatcccag ggactttca gataacacat   54900 gcacagctgc cgttgggtaa tgagggtctc tgaggcccag gcaacttgca gcatacacag   54960
caccgttctc aagggcagac atagagggca catagtggca catgcctata attccagcac   55020
tccagaggct gagatgggag aattactgaa aagcctgagg acaatcaggg ctacataata   55080
aaaaacaaaa ccaaacaaaa ggttgaaaag agatgaagaa gaaatttcag caagatatcc   55140
acaaggtctg gctgatgtta aggtttcttg tgtgtcaca tgtatgtgct catgagtgca   55200
gtacatgcag caaccaaagg ggggcgatag atcccttgga gctggggtta aaggtagttg   55260
```

```
tgagctggga cccaaacccc aaacttctgc tagagcagca ggcacttttta acagctgagt    55320 tggctctcca gccctcgggc taatatttta aagtaactga tcaagataag gctaaggagg    55380
ccaagatcaa gataaggcta aggccaaggc cacaagtaga atcagtattt agtttcctgt    55440
ctgcctggtg gaatgaggag gactcttgaa tggagcctag gttcccagga tagtgctggg    55500
cacccagctc tcatcttgga gggacagtgc cccagtaaca atgggctgat tctgagatgt    55560
gaaaccaggt ggggacaact tcgtagtagc atcctgtgtg ctgtgggtcc agcatcctga    55620
gaactgagga tcctcccatc agccctgatt caaggtttct ccgcttacct tctcttgaca    55680
gattcatctc ctagagcagc tctggctcgg ggagacgcct atgcttctct cttattacaa    55740
agggcgcaga aggctgtggc aggtgggctc cagagatgca gaggttcaga gccacggtgt    55800
taccctccct ggtttctaga aaccacccat cagttagctt tctggggcct tcctgctctt    55860
tgccctctgg tgtgtgtgtg tgtgtgtgtg tgtgtgtgtg tgtgtgagag agagagagag    55920
agagagagag agagagagtg tgacagagac tggagaaggt gcttggtgtg tggagattcc    55980
gcccttactc ccaggattgg tcccaggagt gtggagtgtc tgtcctgagc gcagtaggaa    56040
ggaaacactg ctcactcgtg gcttctactc catctctgct tctttgtctc agtatgtcat    56100
ggccaccgac gtcttccagc tgggctactc agaggatgga cactgtaaag gagacaagaa    56160
ccccaacatc cccaaaccca ccaggctaca gtgggacatt ccaggagaag taagtctggt    56220
gtcccagaga ccatcactca cctgggtggc aatcttgttc ctgagctctg gtgataggca    56280
agctctctac caaacagaaa gctgtttgcc cagagttggg gaaggggcct gggatgctga    56340
gagaaatggg acttccgttc tcagttgaga tttcagctga aaagtagctg ggcttctgta    56400
aattccctgt aaacagggat aaaaacttaa atcctagtca ggcaatggtg gtacactccc    56460
gtaatcccag cactcaggag gcagtagcag gcagatcttt tgagttcca ggccagcctg    56520 gtctacaaag ctagttccag gacaataagg actacataga aaacctagt cttagagatt    56580 ttggggctgt gtaaagatgg cctgtttctg tcatcccaac ccctgtggct gaggccagag    56640
aattctgtga ccgtgtctca acaaccaaca acagattctg agattcagtc cactcaagta    56700
ggagccctga gaagagatgt tagggttgga accataactc cagcctgtct gatccaagtg    56760
tgagtttctg gggcctgaga agtacttttt cgtgtggtaa agtccagcac tctgaggacc    56820
caggacagtg tgtgatccat agaggaacaa tacctctgtg gaggcctgac cttggggccg    56880
ggctgactgg accaccaggg ctcactggct ctcttcaaca cacctgtaat agagccatgc    56940
tgggttcatg gcagaatttt gagaaagatg caggtatttc ctggaaaccc acggtctgcc    57000
ccctcagcat cctcactagt ggtctgtcag gcctcctggc acatcccagg tttacacagc    57060
gtcgcctgga tgggattggg tgtgtagtgt cacgtgacta gtgcccagag tcagatggca    57120
gtgacattgc tataaacacc atggcctccg cctctcatcc agctccttcc tggcccctgg    57180
ccaccgtgga tccctgtgtt tgtccttttaa aaaacaatat tatttgtgct tctagaattg    57240
aacacatgta aacaatgtgt cttgattata tccatggctt cctcctccag ccagctcccc    57300
taaggcccta gactagagac tgaagtgcag acttccagac tgttccgccc tgcttccttc    57360
tcctcctgct gtgcttcccc actaagcaga gctgccttct tcctctgcag tgccaggagg    57420
tcatagagac atccctaagc agtgccagtt ttttggcaaa tgatgtggac ctgcattcct    57480
tcccatttga caccttggc aaaggcttga tcaagaagtg ccggacgagt cccgatgcct    57540
tcatccagct ggcactgcag ctcgcacatt acaaggtaag aagggcactc actgtgggca    57600
```

```
ctctggagct gtttccctag tgggcagagg ctataaagcc cagcatggag ggcagctgac    57660
accaaacacc agccctgggg ctacctgcgg taccaaggtg tgaaatgcta gactgcgag     57720 cagatcaccc ttggttttgt gacatccctc tcaggctcct atcacagatg agagcttggg    57780
acataagcaa atgaacagtg taacctggac tggagagatg gcctggcggt tcagaccacg    57840
tgctacctct gcagaggacc ccattcggct cttggcacct tcacatagcg gctcacagcc    57900
acctgtaact gcagttccat gggatctggt gccactcttc tgccttctgt gaactacaca    57960
tagttacaca tatgcacaaa ggcaagcaca cacataaaat gttaaaatat aaatcttgta    58020
aaacaacccc ataataagct ctgactctta cagtattgtt aagaaatact taggacaaat    58080
tgcttaatgt gtctgacttt tgacaggcct ttccttaaag cagaagttat gagctcctca    58140
ttgctctagg ctgagtcaga tttctgtatc cacccaggac tgtgtgccaa ttctatcgtt    58200
tccctgagca gtgctaaagg gtggcagaag caatctgtac ctgtgtgagg atgtggaagg    58260
aactttagtt cttggtagag gtcagcctac tccagacaga agcattcagt tgctggcaat    58320
gcagaagtca ttgtggcacc agatctagaa gtgcacagtg ggagggtgga catcccaggg    58380
gctcagcttc aggtgccacc agctgtgtcc accaccttg cctccccagg agctcttcct     58440
gccccacccc taccctgttt ctcttcttgt tctctctggc acaactccca aggcctctgt    58500
aatcacttct aaccccagct tcctcgactc tctccctagc cacgcccct gaccactccc     58560 ctgctgcctt ttccccagcc ctagccacac tctcctccag ccaggagcct ctcatctctt    58620
cctgaagctc atcgccagct tctactctgc ttccagaaag gcagccttac ctgcagacac    58680 cttttgcttca agctaaggag tgctggctgc agtagccttc cacctgtgat acctcccatc    58740
ctgccttcca caggtggccc ttctgtccca tccagacaat aggcttttcc catctgcatc    58800
tgctcgctcc tcctggctac tgtcttgtcc atggccatag tgactgaact cctcctcatt    58860
ccctagtcct gccctcttgc ctgtccctcc cctgtgtctc tcagacctca gaccttgctg    58920
tgtgccttgt cctttctcct aaaaattcac atcagctgga gggctttctg gaggacattg    58980
tggccttagt catgtcttgg accagaaacc atgcaaagac aaactccagg aggctggaga    59040
gacggctcag cagttaagag caccgtctgc acttccaggg gatttgagtt caatttctag    59100
cactcacatg gcagctcaca gtcatctgta actccagtcc tcagggatcc agtgccctct    59160
tctggcctct ggacaccagg tttatccttg ttggtcagat gtatgtgccg gcaacacaca    59220
cacacacaca cacacacaca cacacagtgg gggaagcaga ctgccacctc ctctcagatc    59280
cattccaggt cccttctccc ttagacttag atggccactc ccacctgtta gcctgttagc    59340
cctaagctag ttttccttcc ttcccaggac atgggcaagt tctgcctcac gtatgaggct    59400
tccatgactc ggctcttccg agaggggagg acagagactg tacgctcctg cactacggag    59460
tcctgcaact ttgtgctggc catgatggac cccacaacaa cggtaagacc atggtggcag    59520
aacatggcat ggtgcatggt ttctggacga cactagaaca gtggttctca acttgtgggt    59580
cgtgacccca ttggggtcac atatcagata tcctacacat cagatactta cactgtaatt    59640
cataaagtag caaaattaca gttatgaagt agcaatgaaa taattgtatt cattatgagg    59700
aaccatgtta cacaacatga ggaactgtgt taaagggaga cagcaagagg aaggttgaaa    59760
gtcactgccc tggaagctga ccatgaagct ccatagcccc tccagctcca cccttcctcc    59820
ctcaacccct cctcccctg ctcctccacc cttaccctac ttctgcatcc cctccccag     59880 ctccttatgc ataggaacag aaagcattta agaggacata cagaagagag tattgctcgc    59940
tgagctttgg gaatgagatt atatgtatcg agacccttca catgcgactg gacatggcac    60000
```

```
agacacagga aaccggacac ccatccctgg ggtcagagcc tgtctgacca atctaccaga   60060
tactacagag tactacagta tgttctgcct cttaggagcc ctgcagtggc cttgggaaaa   60120
tgaactcaga tgaatccaat gcattgctgg tcccagctgg cacatggcca cattcagagc   60180
tatgcctagg ttccccaagc cctgagacag gcgtttacca ccaacagaca acagactgca   60240
ttttttcttt tttttttttt ttactctaga gagaggaaaa aaaaaaaagc aagcggctac   60300
ttctgtcact agaacttcca ggaggctcct atgaggctgg gtctgtcata ggaaggccag   60360
tgccttgaca tacctccatg tagaggccac gtgtctcagg tggtgttgta atgtccagaa   60420
gattccaaag cagcctatat gtctgtgttt gttatgtgtg aacacatgtg tatgtatgta   60480
cttgtgttat gttgtacatg tgtatacaca tgtgtagtga ggccggaaat gtgcgctgtt   60540
gtcttcatcc attacgctcc accctgtact ttgagccagg gtctctcccc gaatgtagag   60600
ctgctactta ggctagactg gctgctcagc aagcctcccc cttgggtcat aaggaagccc   60660
tcacatttta gcagagtagc caaggagggt tagcgttcat ccctgtgaca aaataaactt   60720
ggggtcagag ctgggataga gctccaggtt tggcaagaac tcttaacagc ttgagtggtc   60780
cacatttggc tctctgtgta catagcacac acaccgtcac agggtgcctc tccatcaacc   60840
tacctactgc ccagcagccc ttctgaggca agaatctgga aagggatcgt gggctggtgg   60900
ggctctgtca agtatattgg tcacagcacc ctgccttta cagaccactg aagagaaagt   60960
ggcccgacgc acaacctgaa ccatgcaaag catgtccttc tcctgttgac ccttaggcag   61020
agcagaggtt caagctgttc aagatagctt gtgaaaagca ccagcacctg taccgcctcg   61080
ccatgacggg cgctggcatc gaccgccacc tcttctgcct ctatgtggtg tccaagtatc   61140
tggcagtcga ctcacctttc ctgaaggagg taagtgcttg gactgtgtgt gtccagcctg   61200
gcttttctgt gttgagacag gatcttactc tgtagcctag gctagcctta aatagcaatc   61260
ctcctgcttc agcctcctga atgctgggac tacaggcatg catcagcata ctggcttta   61320 acagtggctg catagaatga gctagaaaag cccttgagaa cctagaggtg ggtttgtaga   61380
ggctacctta gccccacgg gctgtcctct gccttccctg tgagaggcag tttggtcaag   61440
gggaggggct cagatacttt aaccttagtg tggccctgag gggcttggag aaatagtctc   61500
tgaccacgca gttttccctt gcctccctct taggggatcc tcagacaaaa aggaggtatt   61560
ctgcattgct ctctgcattg ctctctgcat tgctctctgc attgctctct gcattgctct   61620
ctgcattgct ctctgcattg ctctctgcat tgctctctgc attgctctct gcattgctct   61680
ctgcattgct ctctgctgct gtataaagca ctctgaccac ttgccccttg gaagtcaggg   61740
caggaactta agcaggaaca gagtcagaag ctgtggagga aggcttcttg ccggcctgtg   61800
cacgggctca catttggtta actttcttta caaatataat tttacatgtg tgctttgcct   61860
tcatgtgtag gtgtatgttt ggtgtgtgtg cagtgcctag agggatgtct aggaactaga   61920
gttacaggtc cactatgtgg gtgctagcaa tcaaagctgg gtgctcttag ccactgagcc   61980
ctctctctag tcctctccag ctagatggac acctgtccag ggacagaacc cacctaccct   62040
gagctggacc ttcctgcagc aagacaattt cccacagaca tgtctgtctt aatgagtgtt   62100
ttgggcagaa agtgttattt cagcttacat gtccatatca tagtccatta ctgaaggaag   62160
tcaggataga aacccaagca gaggtggacc tgtgaggtgg acctggcgc ataggccatg   62220 gaggggtgct gcttgctggc ttgctgcccc tggttcactc agcctttcct atagaactca   62280
gcatcaccag cccagggatg atcccatcca gaatgggctg ggcctcccta aattgatgga   62340
```

```
taattgagaa aatgccttac atctggatct cactgaggca gttcctcaac tgaagttcct   62400
tcctctatga tgactctagc ttgtgtcaac ctgacacata aaacaagcca ggacagtgtc   62460
cacaaatcag tgtgatggca gatagtcact cagttgagaa tgtcttgtgg ttcctcccag   62520
gtgattgtca gcagtgtcag gttgacagtc ggtgctcact aggagaagcg agtagggaag   62580
tcatgtggac attttttgct ttgtcgcagg tactgtctga gccatggagg ttgtccacga   62640
gccagactcc tcagcagcag gtggaactgt ttgactttga gaaatacccct gactatgtgt   62700 cctgtggcgg gggctttggg ccggtaagtg cagccaggcc cacccactaa cttcaagccc   62760
atcccattgt ccccaggctg gcctcaaact cactcactgt aaagtccagg ctggccatca   62820
ccatcctcct gcctcagcct cttcagtgcc cagacttaca ttgagaacag gaagtcgccg   62880
tccacgttat ctcatttcct agtgataaaa ctgccctttc tctctctgca ggttgctgat   62940
gacggctatg gtgtttccta cattattgtg ggagagaatt tcatccactt ccatatttct   63000
tccaagttct ctagccctga gacagtgagt atattgggca ctacttttttc tagacatgag   63060 gtaaatttct ttttggaggg agcacatctt taaccaaaac attcatttca ggtgtcatcc   63120 ttttttttagc ttagtttcac atcgatgaat ttcacccatt tgaaagacat atatttattt   63180
catttacctg cctttgatgg tagcagtggt cttaagtctc aatgtgtctg tgtttctgtc   63240
attctttcta ctctaaacaa ctccgtgagc aggttctggc cttccgtagg gagtaagtct   63300
ctgagggagc ctcttgggaa cctctaatgg tggccctccg cagtatcagc ctagccagtg   63360
ctacaaaatc ttccaggctg cccactccca cccacagacc ccgagtcctc aggaagctag   63420
gcatgagtta cacacctcta atcctagcat tatttaggaa gctgaggcag gaactgagag   63480
ttcagggata gcctggggtg tagtacagag tgacagggag gcctcagatc tgacccatcc   63540
atgcatatat caagccacct atggctgtcc cccactgagt gctcagggtg cttttattgc   63600
tcctccacta attccctcag agcttggaga gtgggaagac aggaggttgg cctaacccag   63660
ggacagatga taatgggcaa ttccaaaagt gagacttgct gcgtgccaga gcttttcctt   63720
ctctgtgtct ctgtctctgt ctctctctgt ctctctctct ctctctctcc ctctctctct   63780
ctctctctct ctctctctct ctctctctgt gtgtgtgtgt gtgtgtgtgt gtgtgtgtgt   63840
gtgtgcttgc acaagcactt tatccactga gccatctccc caactcctct catttggttc   63900
tttttttttt ttttccatttt tttattaggt atttagctca tttggttctt ttttttccat   63960 ttttttattag gtatttagct catttacatt tccaatgcta taccaaaagt cccccatacc   64020
cacccacccc cactcccccta cccacccact cccccttttt ggcccctggcg ttcccctgta   64080 ctggggcata taagtttgc gtgtcctatg ggcctctctt tccagtgatg gccgactagg   64140
ccatcttttg atacatatgc agctagagtc aagagctccg gggtactggt tagttcataa   64200
tgttgttcca cctatagggt tgcagatccc tttagctcct tggctacttt ctctagctcc   64260
tccattggga gccctatgat ccatccatta gctgactgtg agcatccact tctgtgtttg   64320
ctaggccccg gcatagtctc acaagagaca gctacatctg gatcctttcg ataatatctt   64380
gctagtgtat gcaatggtgt cagcgtttgg atgctgatta tggggtggat ccctggatat   64440
gggtctctac atggtccatc ctttcatctc agctccaaac tttgtctctg taactccttc   64500
cctgggtgtt ttgttcccaa ttctaaggag gggcatagtg tccacacttc agtcttcatt   64560
cttcttgagt ttcatgtgtt tagcaaattg tatcttatat cttgggtatt ctcatttggt   64620
tcttgaagac agagtcttgc tatatagccc aggctgggtt tgaacttgct gcagttgatg   64680
ctcctgcctc agttttcagg cgctgggatt tatttgcccg gctgctgatg tgctgttcgg   64740
```

```
cttctttctt ttaggactca caccgctttg ggaagcactt gagacaagcc atgatggaca    64800
ttatcacctt gtttggcctc accgccaatt ccaaaaagta actgtcggag ccgcacggaa    64860
ggaaaatgga ctctagtgat acaaaccaaa tgaataggtg ttgctcctga ccataggaca    64920
ggcagaaaat tgttcttata aaactcagtt ttccttccag aaggtttacc gtcggtctcc    64980
ctagaacaac cgtaggctcc accgtttgac ttgtgaccct actacatcca gagatgcctt    65040
ggctccagga atattgggca cagtccccg aagtcttttg aatcggctcc taatggataa     65100
agggatttaa atgctggtga atccctggat tttgggggtt gtatcaatat gtgttggagg    65160
tgacagactt cctcagtggt gaccctgtgg atacttggga cttgacttca cccaggcagt    65220
gagagcatca ccttgtggaa agagaaagtg gcttcagagc cagtggaggt aacagctcta    65280
gctaacacac ctgtaacaca ctaatggaat ggttaggcct ggggattaag gttctgctat     65340
gaatgacagc caccatcgct ttgggagtcc acatttgact ccacatttcc tggaagcagg    65400
ataccacctc ctcagtgcca ccttcgaaac ccagtgcctt aacgatggga gcccattggc    65460
aagtggggcc atagagaagg cttagcatgt gaagcctttg ggtggatatg tgagggtgct    65520
gcttcccctc acaagttcct gcatagagat gtccctaagt aagcacttcc cccaccctag    65580
aagatgaggt ccctggtgga gggagcgatg cagaatctca ttggccacca gttccattaa    65640
gcaacaaaat aacagatgtg tccacagagg gaagtgaggg gcttggtagt caaaggctac    65700
caagttggac accagctgga gagtgtggca gccattggca aggagagtga gaccctggtc    65760
actgagtcag gcatactgac acaggcagcc aaagccttgt catggcagcc aggagataga    65820
gatcctggca gatacaccaa cgggctcatc ttctaatccc acccagtcag attccaacca    65880
gagcaaattc gatagaaggc taggtcattt tggtgacaga ctcgggggtc tcaagtaatg    65940
ggtgctttgt acccaaatac catccctctg tgagagtgcc tttcttgaca acatccaata    66000
gactgtaaag caactccgtt tggtattcca tgtaaacata gcataatgga gtggcctccc    66060
ctacctgtta ccatcctgtc ctgacaagtt tagctcttcg tgttttaaat catgtattta    66120
ttttccagtg cccctttggc cttgcttgat tcctactcgt gtgctagctg taacagaagt    66180
gagggtgggg tggccagaag tacagagagg tgctggctga acagctcatg cgtgttttat    66240
aagtatccat gaatacaaaa aaagaatca cacctacaag ggccaaagtt ttttttcctac     66300 taaaacaag aaaacaaaag gcaacataaa tatatagcag agacaactgt aagtcaaagc      66360
cgcctgaccg cgctcttagg actacttgct aacctctgtt actcggagta ttcctgctag    66420
tacccaagtg tgacattcct ctctcaggtc tccagtgtcc ttccttgctg ctcctgagca    66480
gttaccaatg caattttta ctccttccaa ggcagaagag tgggctttca ctgtaagtgt      66540
tcaaaggagg aggtaagact actatgtatt taatgtggaa caaaacatag tcttaccgca    66600
gccaaggttc gaatttggtt ttctaatctg tccattgcat gtaaatacca tatgctgttt    66660
ggatataaat cttagaaatg catgtgtgaa cgaatatagc tgaccattaa taaaacatta    66720
atcccgccta ctacatcatc tgtccctgtc tcccttgtca tactaatcag ggttatacta    66780
tcaggtactg gctgtgagcc tgcagtgtgc agggcaccac tgtcatgtac ttgaccaagg    66840
agcagcacac agtggagcta tcctccattc ctgtgtgggt gcctggcacc acagaggtgc    66900
tatagtgcat gttcagtgaa tgataacact tccttttag aaacatgtaa tgtgtgtgcc     66960
tgtgtggcat atgcacattg gcatacggct gcaggtacat gaagaggcca gaggagttgt    67020
ccggcattct tcacccccctt tctttgagac agggtctgta tctaaacctg gagcttatat    67080
```

```
tttttttggca atgccagtgg ccagcaagcc ccaggagtgc tgactcggtc ccacttcagt   67140
gatgggtttt aggcatgtgt acaagcacac ctaccatgtt aagggatgaa ctctggtatc   67200
tgaactctgg tcctcatgtc atctgtgtct taactgctga gccatctctc cagaccagca   67260
ctgagtttct tcatcaggct cttccaagca tctgctctag gcacgagaa taaagaacta   67320 gctccctgcc tctagttctg gatgttagct ccagttccaa gacagccaac tgaaggaagg   67380
atcctaagta ttgcaactcg agtgaggtct gggcacgatg tcatggacct cgaatcccag   67440
tactaggaag gtgaaggtag aagatcatg actatgaggc caacctaggc tacatagaga   67500
gttccagact aacctgatct atatagtgaa accctgtctc atagaatgaa caacatgaa   67560 actggacata gcaattaaga acacttgttg ctcttccaga ggacctgggg tcaatgccca   67620
gcactcatgg taacttgcaa ccacctgtaa ctccagttca gagcatctga caccctcttc   67680
tgacctccaa cacaggcatg cacatggtgc acatacagac agacaaaaca tccattcaca   67740
taaaattttt tttttttttt ggttttcga gacagggttt ctctgtatag tcctggctgt   67800
cctggaactc actctgtaga ccaagctggc ctctaattca gaaatctgcc tgcttctgcc   67860
tcccgagtgc tgggattaaa ggggtgcgcc accaccacct ggcaaaaata aatctttaaa   67920
aaatgtaaaa ataaacaaga gccccaagag ccagatgtag aagtggaag ctggcacaag   67980 gaagtgccca gctgggcatg ggttagaact gtgaccaaca agaataacaa gacagaggca   68040
gctttagcca acctactggg acagcagcag tcatggaggt gccaggcttc attctgacca   68100
gcttggtgac ataccagtgt ctgtgtttat ctggtggata ggtgtctgag actccttacc   68160
attctttctt ggcaattttt gattgaatgc actaggattc tcaggctagc ccttaatgca   68220
gtgtgcttat tacagctgtg aacatgtgt gcacagaccc aggagagcat agggagatac   68280
gagccattgt gacagtctgg tgcacgacaa gatgtcagcc tcaccttcca tttaaacagt   68340
tggtgagaga cttcatagt atgtaactga gtcggggctc gcctcatttt aactggaaga   68400
agccgccaga gcactgtata gaatccttct caacgatatg ggaatgcaag gtgcaaagga   68460
attcttgctg ccgactgtgg gatgtggatt agcttacaga gtgcttgcct ggcatgcaag   68520
aagccctggg tttaattccc atactaaata agctgatgat agtggtgcat acctattatc   68580
ctagcactca gtaggcagag gcaggaaaat gagaagttca agattgcctt tgattacata   68640
gtaaattcaa ggaagtctgg gccacatgag accttaccttt aaaagatat aagtaaaaca   68700 tgagttggaa gccaacctgg actaaatagt gatcaccagg tcaactagag tcacgcaaca   68760
agaccctgtc tcaaacagac taacaagaaa ctaaaatggc tgatgaggta gcttagtggg   68820
taaaggtgtg tgctgccaag tctgacaacc tgagtttgat cccagaagcc gcacagggaa   68880
ggagagacaa ctctcgactc tggaacgttt tcctttcctt cagattaatg ccatggtgtg   68940
tccacaaatg tatatgcaaa tacgcattaa gtgtaaataa acaaaaccct gaaagcaaaa   69000
cctgatggca caggatttta attgcaacta ctgagactga gacaaggtaa cacgttcaag   69060
ggcagagttc ccagcatgta ggaggcccta gattcaatct ccagtactgc ctgagcaata   69120
atagataaat gtactggaag tgactcacag gttaatagca cttttttttcg ctgaggaccc   69180 aaactcactt cccagcacct attaactcag tttcgtaatg cccccccccc ccccaggttg   69240
gaccgttagg gaaggggggcg gggccatctc tgcctggaca gggcgggcct taacaggggt   69300
gggtggggcc tcccacctag cactgcttca aatttcctgg agtattagtc atgttttttaa   69360 ccccaatttt tgggaggcag aggcaggtgg agctctgtga gttccaggcc agcttggtct   69420
acgtaaagag ttctaagcca gccaagtcta cctactaaga ttctgactta aaaacaaaaa   69480
```

```
cagatgaaaa ggaggggtga aaatgatgta aatacagtac tcaccaatga aattttcaaa    69540
gtttaaaaaa agagagaaag aaccaccacc tgggagcctc agtttccccc actaggtgca    69600
ggagaggttg gctgataccc agtccctcca gcctccatcc aagcataccg aaaggctgcc    69660
ttgtgggcca accacagccc aggtccatc catcatgctc aggccccgcc caccaagagc     69720
caaagcccaa cctccatggc aaggccccgc ccaccataga cacccaccta ccacaaccca    69780
ggctcctgtc atcttggcag aggccccacc caccgcagcc caggctccgc cccgttcagt    69840
cagagacggg ccccgcccct ttccctaacg gtcaacggtc gtccagcctc tcagaagcaa    69900
ggcgagctgg acggccgcgt cgtgtcgctg ttctcgggtc ccagtggcca tggaggacgc    69960
gctgctcggc gccatgactg gccccgaaga cgagctgggc                          70000
```

<210> SEQ ID NO 7

<400> SEQUENCE: 7

000

<210> SEQ ID NO 8

<400> SEQUENCE: 8

000

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
ccagagccaa cgtcaagcat                                                20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
cagccgtgca acaatctgaa                                                20

<210> SEQ ID NO 11
<211> LENGTH: 29
<212> TYPE: DNA
<213> ORGANISM: Artificial sequence
<220> FEATURE:
<223> OTHER INFORMATION: Probe

<400> SEQUENCE: 11
tgaaaatcct caacactcca aactgtgcc                                      29

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
gccctcagaa agctctggaa                                                  20

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
tagggtcgag gctctgcttg t                                                21

<210> SEQ ID NO 14
<211> LENGTH: 30
<212> TYPE: DNA
<213> ORGANISM: Artificial sequence
<220> FEATURE:
<223> OTHER INFORMATION: Probe

<400> SEQUENCE: 14
ccatcggtgc aaacctacag aagcagtatg                                       30

<210> SEQ ID NO 15
<211> LENGTH: 23
<212> TYPE: DNA
<213> ORGANISM: Artificial sequence
<220> FEATURE:
<223> OTHER INFORMATION: Primer

<400> SEQUENCE: 15
tgatggtgtt gaggaagctt ttt                                              23

<210> SEQ ID NO 16
<211> LENGTH: 21
<212> TYPE: DNA
<213> ORGANISM: Artificial sequence
<220> FEATURE:
<223> OTHER INFORMATION: Primer

<400> SEQUENCE: 16
tccctcaagt ctcctgttcc a                                                21

<210> SEQ ID NO 17
<211> LENGTH: 26
<212> TYPE: DNA
<213> ORGANISM: Artificial sequence
<220> FEATURE:
<223> OTHER INFORMATION: Probe

<400> SEQUENCE: 17
acaacagatc gcgtgatgac cgtctc                                           26

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
gcatgttctc acatta                                                      16

<210> SEQ ID NO 19
<211> LENGTH: 16
<212> TYPE: DNA
<213> ORGANISM: Artificial sequence

```
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 19
gcaugttctc acatta                                                         16

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (7)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 20
gcatgtuctc acatta                                                         16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (7)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
```

```
<221> NAME/KEY: misc_feature
<222> LOCATION: (16)..(16)
<223> OTHER INFORMATION: bases at these positions are RNA

<400> SEQUENCE: 21
gcatgtuctc acatta                                                        16

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
gtctgtgcat ctctcc                                                        16

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(3)
<223> OTHER INFORMATION: bases at these positions are RNA
<220> FEATURE:
<221> NAME/KEY: misc_feature
<222> LOCATION: (5)..(9)
<223> OTHER INFORMATION: bases at these positions are RNA
<220> FEATURE:
<221> NAME/KEY: misc_feature
<222> LOCATION: (11)..(11)
<223> OTHER INFORMATION: bases at these positions are RNA
<220> FEATURE:
<221> NAME/KEY: misc_feature
<222> LOCATION: (13)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 23
gtctgugcat ctctcc                                                        16

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
atcatggctg cagctt                                                        16

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
```

-continued

```
<220> FEATURE:
<221> NAME/KEY: misc_feature
<222> LOCATION: (3)..(8)
<223> OTHER INFORMATION: bases at these positions are RNA
<220> FEATURE:
<221> NAME/KEY: misc_feature
<222> LOCATION: (10)..(14)
<223> OTHER INFORMATION: bases at these positions are RNA

<400> SEQUENCE: 25
atcauggctg cagctt                                                        16

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
tgaggtcctg cactgg                                                        16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(8)
<223> OTHER INFORMATION: bases at these postitions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these postitions are RNA

<400> SEQUENCE: 27
tgaggucctg cactgg                                                        16

<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
ttcagtcatg acttcc                                                        16

<210> SEQ ID NO 29
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(8)
<223> OTHER INFORMATION: bases at these positions are RNA
<220> FEATURE:
<221> NAME/KEY: misc_feature
<222> LOCATION: (10)..(12)
<223> OTHER INFORMATION: bases at these positions are RNA
<220> FEATURE:
<221> NAME/KEY: misc_feature
<222> LOCATION: (15)..(16)
```

<223> OTHER INFORMATION: bases at these positions are RNA

<400> SEQUENCE: 29
ttcagucatg acttcc                                                        16

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
<223> OTHER INFORMATION: n is a, c, g, or t

<400> SEQUENCE: 30
gcatnttctc acatta                                                        16

<210> SEQ ID NO 31
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 31
gcatattctc acatta                                                        16

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
gcatgatctc acatta                                                        16

<210> SEQ ID NO 33
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<223> OTHER INFORMATION: p

<400> SEQUENCE: 33
gcatuttctc acatta                                                        16

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(6)
<223> OTHER INFORMATION: p

<400> SEQUENCE: 34
gcatgutctc acatta                                                          16

<210> SEQ ID NO 35
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4)..(4)
<223> OTHER INFORMATION: p

<400> SEQUENCE: 35
gcaugttctc acatta                                                          16

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<223> OTHER INFORMATION: p

<400> SEQUENCE: 36
gcatuttctc acatta                                                          16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(6)
<223> OTHER INFORMATION: p

<400> SEQUENCE: 37
gcatgutctc acatta                                                          16

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: p

<400> SEQUENCE: 38
gcatgtuctc acatta                                                          16

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:

```
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (8)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 39
gcatgttcuc acatta                                                    16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<220> FEATURE:
<221> NAME/KEY: misc_feature
<222> LOCATION: (5)..(5)
<223> OTHER INFORMATION: n is a, c, g, or t

<400> SEQUENCE: 40
gtctntgcat ctctcc                                                    16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
gaggatggca agcaca                                                    16

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 42
cacctgcggg aagctc                                                    16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
tgtgccccag cccatt                                                    16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 44
cttccacagt atatct                                                    16

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
tactggtagt gttgct                                                    16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
ttgacacaaa gggagt                                                    16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
gaatctcctt ttccag                                                    16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
tttacacgct tccgcc                                                    16

<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
agactctcgg ttccga                                                    16

<210> SEQ ID NO 50

<400> SEQUENCE: 50

000

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide
```

<400> SEQUENCE: 51
cttttctatc agtctc                                               16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
cttcttgatg tctttc                                               16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
aagtgtcact aaaacc                                               16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
ggactgaaat agcaga                                               16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 55
aggctggccc ccactg                                               16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
ggtttttgat tcttcc                                               16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
gcatgccgcc ccgtcc                                               16

<210> SEQ ID NO 58
<211> LENGTH: 16

```
<212> TYPE: DNA
<213> ORGANISM: Artificial sequence
<220> FEATURE:
<223> OTHER INFORMATION: Synthetic oligonucleotide

<400> SEQUENCE: 58
tcttcataca atagca                                                    16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
cgttcaaatt ccgtct                                                    16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
tccggctgcg gctcag                                                    16

<210> SEQ ID NO 61
<211> LENGTH: 18
<212> TYPE: DNA
<213> ORGANISM: Artificial sequence
<220> FEATURE:
<223> OTHER INFORMATION: Primer

<400> SEQUENCE: 61
agaggagacc gagcgaat                                                  18

<210> SEQ ID NO 62
<211> LENGTH: 23
<212> TYPE: DNA
<213> ORGANISM: Artificial sequence
<220> FEATURE:
<223> OTHER INFORMATION: Primer

<400> SEQUENCE: 62
catggtttgt gttgatgtac gac                                            23

<210> SEQ ID NO 63
<211> LENGTH: 24
<212> TYPE: DNA
<213> ORGANISM: Artificial sequence
<220> FEATURE:
<223> OTHER INFORMATION: Probe

<400> SEQUENCE: 63
cctacatcag ggagcgagaa ggga                                           24

<210> SEQ ID NO 64
<211> LENGTH: 21
<212> TYPE: DNA
<213> ORGANISM: Artificial sequence
<220> FEATURE:
<223> OTHER INFORMATION: Primer

<400> SEQUENCE: 64
```

-continued

```
gtcaagacta caacacacag c                                              21

<210> SEQ ID NO 65
<211> LENGTH: 23
<212> TYPE: DNA
<213> ORGANISM: Artificial sequence
<220> FEATURE:
<223> OTHER INFORMATION: Primer

<400> SEQUENCE: 65
aaaactataa ggagggtga agg                                             23

<210> SEQ ID NO 66
<211> LENGTH: 33
<212> TYPE: DNA
<213> ORGANISM: Artificial sequence
<220> FEATURE:
<223> OTHER INFORMATION: Probe

<400> SEQUENCE: 66
ctgaaggact tttaaatgta gcctgctcac taa                                 33

<210> SEQ ID NO 67
<211> LENGTH: 20
<212> TYPE: DNA
<213> ORGANISM: Artificial sequence
<220> FEATURE:
<223> OTHER INFORMATION: Primer

<400> SEQUENCE: 67
tgcagggagc cactctgagt                                                20

<210> SEQ ID NO 68
<211> LENGTH: 24
<212> TYPE: DNA
<213> ORGANISM: Artificial sequence
<220> FEATURE:
<223> OTHER INFORMATION: Primer

<400> SEQUENCE: 68
agaaccccca ctgacttatc tgaa                                           24

<210> SEQ ID NO 69
<211> LENGTH: 26
<212> TYPE: DNA
<213> ORGANISM: Artificial sequence
<220> FEATURE:
<223> OTHER INFORMATION: Probe

<400> SEQUENCE: 69
cacagagcct aagatgtgca cgcctg                                         26

<210> SEQ ID NO 70
<211> LENGTH: 20
<212> TYPE: DNA
<213> ORGANISM: Artificial sequence
<220> FEATURE:
<223> OTHER INFORMATION: Primer

<400> SEQUENCE: 70
ccggagctag aagcgatcaa                                                20

<210> SEQ ID NO 71
<211> LENGTH: 24
<212> TYPE: DNA
<213> ORGANISM: Artificial sequence
```

```
<220> FEATURE:
<223> OTHER INFORMATION: Primer

<400> SEQUENCE: 71
cctttagctt ctcagcctct tcct                                            24

<210> SEQ ID NO 72
<211> LENGTH: 17
<212> TYPE: DNA
<213> ORGANISM: Artificial sequence
<220> FEATURE:
<223> OTHER INFORMATION: Probe

<400> SEQUENCE: 72
ctcgagtcag ggagatg                                                    17

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
aatgtgcctg ctgtccttga                                                 20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are RNA
<220> FEATURE:
<221> NAME/KEY: misc_feature
<222> LOCATION: (4)..(8)
<223> OTHER INFORMATION: bases at these positions are RNA
<220> FEATURE:
<221> NAME/KEY: misc_feature
<222> LOCATION: (10)..(11)
<223> OTHER INFORMATION: bases at these positions are RNA
<220> FEATURE:
<221> NAME/KEY: misc_feature
<222> LOCATION: (13)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA
<220> FEATURE:
<221> NAME/KEY: misc_feature
<222> LOCATION: (19)..(20)
<223> OTHER INFORMATION: bases at these positions are RNA

<400> SEQUENCE: 74
aatgugcctg ctgtccttga                                                 20

<210> SEQ ID NO 75
<211> LENGTH: 21
<212> TYPE: DNA
<213> ORGANISM: Artificial sequence
<220> FEATURE:
<223> OTHER INFORMATION: Primer

<400> SEQUENCE: 75
agatcaatcg gaccctagac a                                               21
```

```
<210> SEQ ID NO 76
<211> LENGTH: 18
<212> TYPE: DNA
<213> ORGANISM: Artificial sequence
<220> FEATURE:
<223> OTHER INFORMATION: Primer

<400> SEQUENCE: 76
cagcaccttc agcgagta                                                  18

<210> SEQ ID NO 77
<211> LENGTH: 24
<212> TYPE: DNA
<213> ORGANISM: Artificial sequence
<220> FEATURE:
<223> OTHER INFORMATION: Probe

<400> SEQUENCE: 77
aagaggacgc cactcacgat gttc                                           24

<210> SEQ ID NO 78
<211> LENGTH: 20
<212> TYPE: DNA
<213> ORGANISM: Artificial sequence
<220> FEATURE:
<223> OTHER INFORMATION: Primer

<400> SEQUENCE: 78
acatgacagg cgcgatctct                                                20

<210> SEQ ID NO 79
<211> LENGTH: 25
<212> TYPE: DNA
<213> ORGANISM: Artificial sequence
<220> FEATURE:
<223> OTHER INFORMATION: Primer

<400> SEQUENCE: 79
tctaggttca cgtacacatc tttgc                                          25

<210> SEQ ID NO 80
<211> LENGTH: 26
<212> TYPE: DNA
<213> ORGANISM: Artificial sequence
<220> FEATURE:
<223> OTHER INFORMATION: Probe

<400> SEQUENCE: 80
ttccttcaag caatgccctc agcaat                                         26

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
gttattgtgg ttggcg                                                    16

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide
```

```
<400> SEQUENCE: 82
attctgtgtg cactgc                                                    16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
tcttgtctga cattct                                                    16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
ttttgtgtct tctgta                                                    16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
ctgtttgagt tttctc                                                    16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
caaagtgata ccagtt                                                    16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
aatcttccag ggccac                                                    16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
tcatttctat ggaata                                                    16

<210> SEQ ID NO 89
```

```
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
gtcagtatcc cagtgt                                                        16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
ggttacagtg gaagag                                                        16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
tctgggtgtt cttacg                                                        16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
tttccttgag tagtag                                                        16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
tctccttgct gtattt                                                        16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
ttgccaatat caccat                                                        16

<210> SEQ ID NO 95
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 95
```

```
caactgaacc acccgt                                                      16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
gcacaatatc attaac                                                      16

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
gactctctga tgatac                                                      16

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
ctataccatc tctcat                                                      16

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
catcatctat accatc                                                      16

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
acacatttag catgac                                                      16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 101
attatatggc aactca                                                      16

<210> SEQ ID NO 102
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 102
gactaatatg cagttt                                                      16

<210> SEQ ID NO 103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
gtcaaattca agggtt                                                      16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
cataaagcat ggtgga                                                      16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 105
tagtctctgt cagtta                                                      16

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
gtacctatag tctctg                                                      16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
tcatgtacct atagtc                                                      16

<210> SEQ ID NO 108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
tcttaatttc atgtac                                                      16
```

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109
accctcaagt ctcctg                                                         16

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
cagatatagg actgga                                                         16

<210> SEQ ID NO 111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 111
gacgcgcctg aaggtt                                                         16

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
ggacacattg gccaca                                                         16

<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
ggccaccacg ctgtca                                                         16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
tgccaccgta gacacg                                                         16

<210> SEQ ID NO 115
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 115
gctagcctct ggattt                                                   16

<210> SEQ ID NO 116
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 116
gauaauguga gaacaugccu                                               20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
aggcatgttc tcacattatc                                               20

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
ggctactacg ccgtca                                                   16

<210> SEQ ID NO 119
<211> LENGTH: 19
<212> TYPE: DNA
<213> ORGANISM: Artificial sequence
<220> FEATURE:
<223> OTHER INFORMATION: Primer

<400> SEQUENCE: 119 tttttttgcgc ggtcctttc                                               19

<210> SEQ ID NO 120
<211> LENGTH: 22
<212> TYPE: DNA
<213> ORGANISM: Artificial sequence
<220> FEATURE:
<223> OTHER INFORMATION: Primer

<400> SEQUENCE: 120
gagggaccag agagagcaag ac                                            22

<210> SEQ ID NO 121
<211> LENGTH: 19
<212> TYPE: DNA
<213> ORGANISM: Artificial sequence
<220> FEATURE:
<223> OTHER INFORMATION: Probe

<400> SEQUENCE: 121
cgccttccgt ccgtcggct                                                19

```
<210> SEQ ID NO 122
<211> LENGTH: 21
<212> TYPE: DNA
<213> ORGANISM: Artificial Sequence
<220> FEATURE:
<223> OTHER INFORMATION: Primer

<400> SEQUENCE: 122
tggagactct cagggtcgaa a                                              21

<210> SEQ ID NO 123
<211> LENGTH: 22
<212> TYPE: DNA
<213> ORGANISM: Artificial Sequence
<220> FEATURE:
<223> OTHER INFORMATION: Primer

<400> SEQUENCE: 123
ggcgtttgga gtggtagaaa tc                                             22

<210> SEQ ID NO 124
<211> LENGTH: 20
<212> TYPE: DNA
<213> ORGANISM: Artificial Sequence
<220> FEATURE:
<223> OTHER INFORMATION: Probe

<400> SEQUENCE: 124
cggcggcaga ccagcatgac                                                20

<210> SEQ ID NO 125
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 125
gcatgttctc acattat                                                   17

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 126
caccugcggg aagctc                                                    16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(6)
<223> OTHER INFORMATION: bases at these positions are RNA
<220> FEATURE:
```

```
<221> NAME/KEY: misc_feature
<222> LOCATION: (8)..(10)
<223> OTHER INFORMATION: bases at these positions are RNA
<220> FEATURE:
<221> NAME/KEY: misc_feature
<222> LOCATION: (13)..(16)
<223> OTHER INFORMATION: bases at these positions are RNA

<400> SEQUENCE: 127
agacuctcgg ttccga                                                          16

<210> SEQ ID NO 128
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (5)..(6)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:
<221> NAME/KEY: misc_feature
<222> LOCATION: (10)..(12)
<223> OTHER INFORMATION: bases at these positions are RNA
<220> FEATURE:
<221> NAME/KEY: misc_feature
<222> LOCATION: (14)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 128
ctttuctatc agtctc                                                          16

<210> SEQ ID NO 129
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(5)
<223> OTHER INFORMATION: bases at these positions are RNA
<220> FEATURE:
<221> NAME/KEY: misc_feature
<222> LOCATION: (7)..(8)
<223> OTHER INFORMATION: bases at these positions are RNA
<220> FEATURE:
<221> NAME/KEY: misc_feature
<222> LOCATION: (10)..(10)
<223> OTHER INFORMATION: bases at these positions are RNA
<220> FEATURE:
<221> NAME/KEY: misc_feature
<222> LOCATION: (12)..(12)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA
```

<400> SEQUENCE: 129
cttcutgatg tctttc                                                    16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: bases at these positions are RNA
<220> FEATURE:
<221> NAME/KEY: misc_feature
<222> LOCATION: (11)..(16)
<223> OTHER INFORMATION: bases at these positions are RNA

<400> SEQUENCE: 130
ggacugaaat agcaga                                                    16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonuclotide
<220> FEATURE:
<221> NAME/KEY: misc_feature
<222> LOCATION: (1)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 131
aggcuggccc ccactg                                                    16

<210> SEQ ID NO 132
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (8)..(9)
<223> OTHER INFORMATION: bases at these positions are RNA
<220> FEATURE:
<221> NAME/KEY: misc_feature
<222> LOCATION: (12)..(12)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 132
ggttuttgat tcttcc                                                    16

<210> SEQ ID NO 133

```
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(5)
<223> OTHER INFORMATION: bases at these positions are RNA
<220> FEATURE:
<221> NAME/KEY: misc_feature
<222> LOCATION: (7)..(7)
<223> OTHER INFORMATION: bases at these positions are RNA
<220> FEATURE:
<221> NAME/KEY: misc_feature
<222> LOCATION: (9)..(10)
<223> OTHER INFORMATION: bases at these positions are RNA
<220> FEATURE:
<221> NAME/KEY: misc_feature
<222> LOCATION: (13)..(16)
<223> OTHER INFORMATION: bases at these positions are RNA

<400> SEQUENCE: 133
gttautgtgg ttggcg                                                    16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(6)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 134
attcugtgtg cactgc                                                    16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(3)
<223> OTHER INFORMATION: bases at these positions are RNA
<220> FEATURE:
<221> NAME/KEY: misc_feature
```

```
<222> LOCATION: (5)..(5)
<223> OTHER INFORMATION: bases at these positions are RNA
<220> FEATURE:
<221> NAME/KEY: misc_feature
<222> LOCATION: (7)..(9)
<223> OTHER INFORMATION: bases at these positions are RNA
<220> FEATURE:
<221> NAME/KEY: misc_feature
<222> LOCATION: (14)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 135
ctgtutgagt tttctc                                                   16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are RNA
<220> FEATURE:
<221> NAME/KEY: misc_feature
<222> LOCATION: (4)..(5)
<223> OTHER INFORMATION: bases at these positions are RNA
<220> FEATURE:
<221> NAME/KEY: misc_feature
<222> LOCATION: (7)..(16)
<223> OTHER INFORMATION: bases at these positions are RNA

<400> SEQUENCE: 136
aatcutccag ggccac                                                   16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (7)..(7)
<223> OTHER INFORMATION: bases at these positions are RNA
<220> FEATURE:
<221> NAME/KEY: misc_feature
<222> LOCATION: (9)..(9)
<223> OTHER INFORMATION: bases at these positions are RNA
<220> FEATURE:
<221> NAME/KEY: misc_feature
<222> LOCATION: (11)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 137
tcatutctat ggaata                                                   16
```

```
<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: bases at these positions are RNA

<400> SEQUENCE: 138
caacugaacc acccgt                                                       16

<210> SEQ ID NO 139
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(6)
<223> OTHER INFORMATION: bases at these positions are RNA
<220> FEATURE:
<221> NAME/KEY: misc_feature
<222> LOCATION: (8)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 139
attauatggc aactca                                                       16

<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: bases at these positions are RNA
<220> FEATURE:
<221> NAME/KEY: misc_feature
<222> LOCATION: (11)..(11)
<223> OTHER INFORMATION: bases at these positions are RNA
<220> FEATURE:
<221> NAME/KEY: misc_feature
<222> LOCATION: (13)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 140
acccucaagt ctcctg                                                       16

<210> SEQ ID NO 141
<211> LENGTH: 17
<212> TYPE: DNA
<213> ORGANISM: Artificial sequence
<220> FEATURE:
<223> OTHER INFORMATION: Synthetic oligonucleotide
```

```
<400> SEQUENCE: 141
ggcatgttct cacatta                                                  17

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
ggactgaaat tgcaga                                                   16

<210> SEQ ID NO 143
<211> LENGTH: 16
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(5)
<223> OTHER INFORMATION: bases at these positions are RNA
<220> FEATURE:
<221> NAME/KEY: misc_feature
<222> LOCATION: (7)..(9)
<223> OTHER INFORMATION: bases at these positions are RNA
<220> FEATURE:
<221> NAME/KEY: misc_feature
<222> LOCATION: (11)..(11)
<223> OTHER INFORMATION: bases at these positions are RNA
<220> FEATURE:
<221> NAME/KEY: misc_feature
<222> LOCATION: (13)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 143
gtcugtgcat ctctcc                                                   16

<210> SEQ ID NO 144
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 144
acatcttcag atcatt                                                   16

<210> SEQ ID NO 145
<211> LENGTH: 16
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (2)..(5)
<223> OTHER INFORMATION: bases at these positions are RNA
<220> FEATURE:
<221> NAME/KEY: misc_feature
<222> LOCATION: (7)..(7)
```

<223> OTHER INFORMATION: bases at these positions are RNA
<220> FEATURE:
<221> NAME/KEY: misc_feature
<222> LOCATION: (9)..(9)
<223> OTHER INFORMATION: bases at these positions are RNA
<220> FEATURE:
<221> NAME/KEY: misc_feature
<222> LOCATION: (11)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 145
taguctctgt cagtta                                               16

<210> SEQ ID NO 146
<211> LENGTH: 17
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:
<221> NAME/KEY: misc_feature
<222> LOCATION: (5)..(6)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 146
gcatgutctc acattat                                              17

<210> SEQ ID NO 147
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 147
acaaggacac caagat                                               16

<210> SEQ ID NO 148
<211> LENGTH: 25
<212> TYPE: DNA
<213> ORGANISM: Artificial sequence
<220> FEATURE:
<223> OTHER INFORMATION: Primer

<400> SEQUENCE: 148
gggattacag agatcgtgac tgatt                                     25

<210> SEQ ID NO 149
<211> LENGTH: 20
<212> TYPE: DNA
<213> ORGANISM: Artificial sequence

```
<220> FEATURE:
<223> OTHER INFORMATION: Primer

<400> SEQUENCE: 149
tgcagctgga agaaccaaaa                                               20

<210> SEQ ID NO 150
<211> LENGTH: 30
<212> TYPE: DNA
<213> ORGANISM: Artificial sequence
<220> FEATURE:
<223> OTHER INFORMATION: Probe

<400> SEQUENCE: 150
cagagtaaaa tacccattcc agctcctggg                                    30

<210> SEQ ID NO 151
<211> LENGTH: 21
<212> TYPE: DNA
<213> ORGANISM: Artificial sequence
<220> FEATURE:
<223> OTHER INFORMATION: Primer

<400> SEQUENCE: 151
gattcgtcag ctttgccaag t                                             21

<210> SEQ ID NO 152
<211> LENGTH: 22
<212> TYPE: DNA
<213> ORGANISM: Artificial sequence
<220> FEATURE:
<223> OTHER INFORMATION: Primer

<400> SEQUENCE: 152
cgtctgttca gttgtcaatg ca                                            22

<210> SEQ ID NO 153
<211> LENGTH: 29
<212> TYPE: DNA
<213> ORGANISM: Artificial sequence
<220> FEATURE:
<223> OTHER INFORMATION: Probe

<400> SEQUENCE: 153
tctgggcctc aaggataaca acatcgttt                                     29

<210> SEQ ID NO 154
<211> LENGTH: 16
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(4)
<223> OTHER INFORMATION: bases at these positions are RNA
<220> FEATURE:
<221> NAME/KEY: misc_feature
<222> LOCATION: (6)..(7)
<223> OTHER INFORMATION: bases at these positions are RNA
<220> FEATURE:
<221> NAME/KEY: misc_feature
<222> LOCATION: (7)..(10)
<223> OTHER INFORMATION: bases at these positions are RNA
<220> FEATURE:
```

```
<221> NAME/KEY: misc_feature
<222> LOCATION: (13)..(16)
<223> OTHER INFORMATION: bases at these positions are RNA

<400> SEQUENCE: 154
gttatugtgg ttggcg                                                 16
```

MODIFIED COMPOUNDS AND USES THEREOF

SEQUENCE LISTING

The present application is being filed along with a Sequence Listing in electronic format. The Sequence Listing is provided as a file entitled CORE0148USASEQ_ST25.txt created Aug. 4, 2020, which is 368 kb in size. The information in the electronic format of the sequence listing is incorporated herein by reference in its entirety.

FIELD

The present disclosure provides oligomeric compounds comprising a modified oligonucleotide having a central region comprising one or more modifications. In certain embodiments, the present disclosure provides oligomeric compounds having an improved therapeutic index or an increased maximum tolerated dose.

BACKGROUND

The principle behind antisense technology is that an antisense compound hybridizes to a target nucleic acid and modulates the amount, activity, and/or function of the target nucleic acid. For example, in certain instances, antisense compounds result in altered transcription or translation of a target. Such modulation of expression can be achieved by, for example, target RNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced silencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Regardless of the specific mechanism, sequence-specificity makes antisense compounds attractive as tools for target validation and gene functionalization, as well as therapeutics to selectively modulate the expression of genes involved in the pathogenesis of disease.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics, or affinity for a target nucleic acid.

SUMMARY

The present disclosure provides oligomeric compounds and methods of using oligomeric compounds that comprise a modified oligonucleotide consisting of 14-23 linked nucleosides, wherein the modified oligonucleotide comprises a gapmer consisting of a 5'-region, a central region, and a 3'-region wherein:
the 5'-region consists of 2-5 linked modified nucleosides, wherein each nucleoside of the 5'-region comprises a 2'-modified furanosyl sugar moiety;
the 3'-region consists of 1-5 linked modified nucleosides, wherein each nucleoside of the 3'-region comprises a 2'-modified furanosyl sugar moiety;
the central region consists of 7-10 linked nucleosides, where each nucleoside of the central region comprises a sugar moiety selected from an unmodified 2'-β-D-deoxyribosyl sugar moiety and a modified sugar moiety; wherein
the 3'- and 5'-most nucleosides of the central region each comprise a sugar moiety independently selected from a 2'-deoxyfuranosyl sugar moiety or a sugar surrogate; and wherein
the central region comprises:
at least one altered nucleotide, comprising a modified internucleoside linkage other than phosphorothioate and/or a modified nucleobase other than 5-methylcytosine and/or a modified sugar moiety; and
at least 6 nucleosides each comprising an unmodified 2'-β-D-deoxyribosyl sugar moiety.

In certain embodiments, oligomeric compounds are provided comprising a single conjugate group linked to the 5'-end. In certain embodiments, oligomeric compounds are provided comprising a single conjugate group linked to the 3'-end.

In certain embodiments, the oligomeric compounds provided herein have an increased maximum tolerated dose when administered to an animal compared to an otherwise identical oligomeric compound except that the otherwise identical oligomeric compound lacks the altered nucleotide in the central region.

In certain embodiments, the oligomeric compounds provided herein have an increased therapeutic index compared to an otherwise identical oligomeric compound except that the otherwise identical oligomeric compound lacks the altered nucleotide in the central region.

In certain embodiments, methods of inhibiting target RNA are provided comprising contacting one or more cells, a tissue or an animal with an oligomeric compound as provided herein wherein said oligomeric compound is complementary to a target RNA.

In certain embodiments, the cells are in a human. In certain embodiments, the target RNA is human RNA. In certain embodiments, the target is human mRNA. In certain embodiments, the target RNA is cleaved, thereby inhibiting its function.

In certain embodiments, in vitro methods of inhibiting gene expression are provided comprising contacting one or more cells or a tissue with an oligomeric compound as provided herein.

In certain embodiments, oligomeric compounds are provided for use in an in vivo method of inhibiting gene expression wherein the method comprises contacting one or more cells, a tissue or an animal with an oligomeric compound as provided herein.

In certain embodiments, oligomeric compounds are provided for use in medical therapy.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH(H) sugar moiety and a thymine base could be described as a DNA having a modified sugar (2'-OH in place of one 2'-H of DNA) or as an RNA having a modified base (thymine (methylated uracil) in place of an uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

As used herein, "2'-deoxyfuranosyl sugar moiety" or "2'-deoxyfuranosyl sugar" means a furanosyl sugar moiety having two hydrogens at the 2'-position. 2'-deoxyfuranosyl sugar moieties may be unmodified or modified and may be substituted at positions other than the 2'-position or unsubstituted. A β-D-2'-deoxyribosyl sugar moiety or 2'-O-D-deoxyribosyl sugar moiety in the context of an oligonucleotide is an unsubstituted, unmodified 2'-deoxyfuranosyl and is found in naturally occurring deoxyribonucleic acids (DNA).

As used herein, "2'-modified" in reference to a furanosyl sugar moiety or nucleoside comprising a furanosyl sugar moiety means the furanosyl sugar moiety comprises a substituent other than H or OH at the 2'-position of the furanosyl sugar moiety. 2'-modified furanosyl sugar moieties include non-bicyclic and bicyclic sugar moieties and may comprise, but are not required to comprise, additional substituents at other positions of the furanosyl sugar moiety.

As used herein, "2'-ribo-F" indicates a 2'-fluororibose.

As used herein, "2'-substituted" in reference to a furanosyl sugar moiety or nucleoside comprising a furanosyl sugar moiety means the furanosyl sugar moiety or nucleoside comprising the furanosyl sugar moiety comprises a substituent other than H or OH at the 2'-position and is a non-bicyclic furanosyl sugar moiety. 2'-substituted furanosyl sugar moieties do not comprise additional substituents at other positions of the furanosyl sugar moiety other than a nucleobase and/or internucleoside linkage(s) when in the context of an oligonucleotide.

As used herein, "4'-modified" in reference to a furanosyl sugar moiety or nucleoside comprising a furanosyl sugar moiety means the furanosyl sugar moiety comprises a substituent other than H at the 4'-position of the furanosyl sugar moiety. 4'-modified furanosyl sugar moieties include non-bicyclic and bicyclic sugar moieties and may but are not required to comprise additional substituents at other positions of the furanosyl sugar moiety.

As used herein, "4'-substituted" in reference to a furanosyl sugar moiety or nucleoside comprising a furanosyl sugar moiety means the furanosyl sugar moiety or nucleoside comprising the furanosyl sugar moiety comprises a substituent other than H at the 4'-position and is a non-bicyclic furanosyl sugar moiety. 4'-substituted furanosyl sugar moieties do not comprise additional substituents at other positions of the furanosyl sugar moiety other than a nucleobase and/or internucleoside linkage(s) when in the context of an oligonucleotide.

As used herein, "5'-modified" in reference to a furanosyl sugar moiety or nucleoside comprising a furanosyl sugar moiety means the furanosyl sugar moiety comprises a substituent other than H at the 5'-position of the furanosyl sugar moiety. 5'-modified furanosyl sugar moieties may but are not required to comprise additional substituents at other positions of the furanosyl sugar moiety.

As used herein, "5'-substituted" in reference to a furanosyl sugar moiety or nucleoside comprising a furanosyl sugar moiety means the furanosyl sugar moiety or nucleoside comprising the furanosyl sugar moiety comprises a substituent other than H at the 5'-position and is a non-bicyclic furanosyl sugar moiety. 5'-substituted furanosyl sugar moieties do not comprise additional substituents at other positions of the furanosyl sugar moiety other than a nucleobase and/or internucleoside linkage(s) when in the context of an oligonucleotide.

As used herein, "administration" or "administering" refers to routes of introducing a compound or composition provided herein to a subject to perform its intended function. Examples of routes of administration that can be used include, but are not limited to, administration by inhalation, subcutaneous injection, intrathecal injection, and oral administration.

As used herein, "administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel, sequentially, separate, or simultaneous administration.

As used herein, "ALT" means alanine aminotransferase. As used herein, "AST" means aspartate transaminase. In certain embodiments, plasma levels of ALT and AST in a subject are measured in units per liter. As used herein, "units per liter" in the context of plasma ALT or plasma AST levels means international units per liter, the standard units for measurement of plasma ALT or plasma AST levels used by those of ordinary skill in the medical arts.

As used herein, "animal" refers to a human or non-human animal, including, but not limited to, mice, rats, rabbits, dogs, cats, pigs, and non-human primates, including, but not limited to, monkeys and chimpanzees.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means a compound comprising an antisense oligonucleotide and optionally one or more additional features, such as a conjugate group or terminal group.

As used herein, "antisense oligonucleotide" means an oligonucleotide having a nucleobase sequence that is at least partially complementary to a target nucleic acid.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety, and the bicyclic sugar moiety is a modified furanosyl sugar moiety. In certain embodiments, the bicyclic sugar moiety does not comprise a furanosyl moiety.

As used herein, a "central nervous system target" is a target RNA that is expressed in the central nervous system.

As used herein, "cEt" or "constrained ethyl" means a bicyclic sugar moiety, wherein the first ring of the bicyclic sugar moiety is a ribosyl sugar moiety, the second ring of the bicyclic sugar is formed via a bridge connecting the 4'-carbon and the 2'-carbon, the bridge has the formula 4'-CH(CH$_3$)—O-2', and the methyl group of the bridge is in the S configuration. A cEt bicyclic sugar moiety is in the β-D configuration.

As used herein, a "cEt nucleoside" or "cEt nucleotide" is a nucleoside or nucleotide comprising a cEt.

As used herein, "complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases are nucleobase pairs that are capable of forming hydrogen bonds with one another. Complementary nucleobase pairs include adenine (A) and thymine (T), adenine (A) and uracil (U), cytosine (C) and guanine (G), 5-methyl cytosine ($^m$C) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

As used herein, "conjugate group" means a group of atoms that is directly or indirectly attached to an oligonucleotide. Conjugate groups may comprise a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" or "adjacent" in the context of an oligonucleotide refers to nucleosides, nucleobases, sugar moieties, or internucleoside linkages that are immediately adjacent to each other independent of the other moieties of the oligonucleotide. For example, "contiguous nucleobases" means nucleobases that are immediately adjacent to each other in a sequence. Moieties that are "directly linked" are immediately adjacent to each other and not separated by any other type of moiety.

As used herein, "cytotoxic" or "cytotoxicity" in the context of an effect of an oligomeric compound or a parent oligomeric compound on cultured cells means an at least 2-fold increase in caspase activation following administration of 10 μM or less of the oligomeric compound or parent oligomeric compound to the cultured cells relative to cells cultured under the same conditions but that are not administered the oligomeric compound or parent oligomeric compound. In certain embodiments, cytotoxicity is measured using a standard in vitro cytotoxicity assay.

As used herein, "double-stranded antisense compound" means an antisense compound comprising two oligomeric compounds that are complementary to each other and form a duplex, and wherein one of the two said oligomeric compounds comprises an antisense oligonucleotide.

As used herein, "effective amount" means the amount of compound sufficient to effectuate a desired physiological outcome in a subject in need of the compound. The effective amount may vary among subjects depending on the health and physical condition of the subject to be treated, the taxonomic group of the subjects to be treated, the formulation of the composition, assessment of the subject's medical condition, and other relevant factors.

As used herein, "efficacy" means the ability to produce a desired effect.

As used herein, "expression" includes all the functions by which a gene's coded information is converted into structures present and operating in a cell. Such structures include, but are not limited to, the products of transcription and translation. As used herein, "modulation of expression" means any change in amount or activity of a product of transcription or translation of a gene. Such a change may be an increase or a reduction of any amount relative to the expression level prior to the modulation.

As used herein, "gapmer" means an oligonucleotide having a central region comprising a plurality of nucleosides that support RNase H cleavage positioned between a 5'-region and a 3'-region. Herein, the nucleosides of the 5'-region and 3'-region each comprise a 2'-modified furanosyl sugar moiety, and the 3'- and 5'-most nucleosides of the central region each comprise a sugar moiety independently selected from a 2'-deoxyfuranosyl sugar moiety or a sugar surrogate. The positions of the central region refer to the order of the nucleosides of the central region and are counted starting from the 5'-end of the central region. Thus, the 5'-most nucleoside of the central region is at position 1 of the central region. The "central region" may be referred to as a "gap", and the "5'-region" and "3'-region" may be referred to as "wings".

replaced with a sulfur atom. Modified internucleoside linkages may or may not contain a phosphorus atom. A "neutral internucleoside linkage" is a modified internucleoside linkage that does not have a negatively charged phosphate in a buffered aqueous solution at pH=7.0.

As used herein, "abasic nucleoside" means a sugar moiety in an oligonucleotide or oligomeric compound that is not directly connected to a nucleobase. In certain embodiments, an abasic nucleoside is adjacent to one or two nucleosides in an oligonucleotide.

As used herein, "LICA-1" is a conjugate group that is represented by the formula:

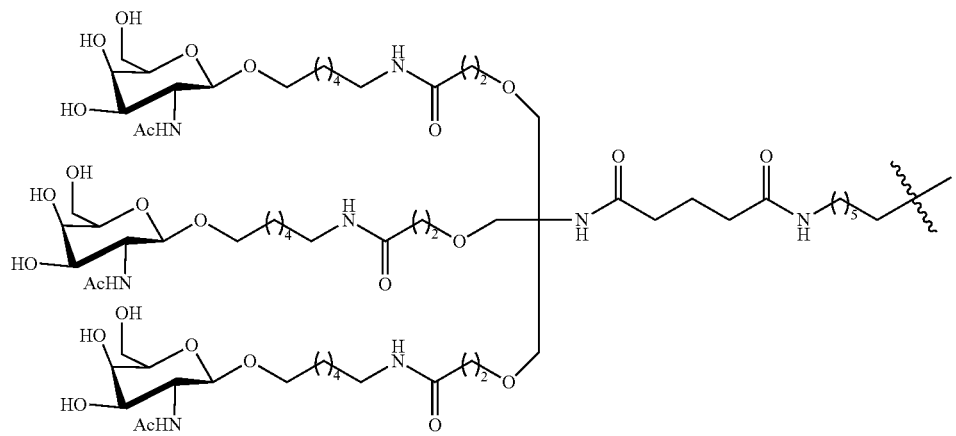

As used herein, "hepatotoxic" in the context of a mouse means a plasma ALT level that is above 300 units per liter. Hepatotoxicity of an oligomeric compound or parent oligomeric compound that is administered to a mouse is determined by measuring the plasma ALT level of the mouse 24 hours to 2 weeks following at least one dose of 1-150 mg/kg of the compound.

As used herein, "hepatotoxic" in the context of a human means a plasma ALT level that is above 150 units per liter. Hepatotoxicity of an oligomeric compound or parent oligomeric compound that is administered to a human is determined by measuring the plasma ALT level of the human 24 hours to 2 weeks following at least one dose of 10-300 mg of the compound.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "inhibiting the expression or activity" refers to a reduction or blockade of the expression or activity relative to the expression or activity in an untreated or control sample and does not necessarily indicate a total elimination of expression or activity.

As used herein, the terms "internucleoside linkage" means a group or bond that forms a covalent linkage between adjacent nucleosides in an oligonucleotide. As used herein "modified internucleoside linkage" means any internucleoside linkage other than a naturally occurring, phosphodiester internucleoside linkage. "Phosphorothioate linkage" means a modified internucleoside linkage in which one of the non-bridging oxygen atoms of a phosphodiester is As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic sugar" or "non-bicyclic sugar moiety" means a sugar moiety that comprises fewer than 2 rings. Substituents of modified, non-bicyclic sugar moieties do not form a bridge between two atoms of the sugar moiety to form a second ring.

As used herein, "linked nucleosides" are nucleosides that are connected in a continuous sequence (i.e. no additional nucleosides are present between those that are linked).

As used herein, "liver target" is a target RNA expressed in the liver wherein modulation of the expression of the target RNA in the liver is desired for therapeutic benefit. In certain embodiments, a liver target is expressed in tissues other than the liver as well as in the liver. As used herein, modulation of the expression of a target RNA that is "not a liver target" is desired in a tissue that is not the liver for therapeutic benefit. In certain embodiments, a target RNA that is not a liver target is expressed in the liver and is modulated by an oligomeric compound in therapy.

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "modulating" refers to changing or adjusting a feature in a cell, tissue, organ or organism.

As used herein, "MOE" means methoxyethyl. "2'-MOE" or "2'-O-methoxyethyl" means a 2'-OCH$_2$CH$_2$OCH$_3$ group at the 2'-position of a furanosyl ring. In certain embodiments, the 2'-OCH$_2$CH$_2$OCH$_3$ group is in place of the 2'-OH group of a ribosyl ring or in place of a 2'-H in a 2'-deoxyribosyl ring.

As used herein, "MOP" or "methoxypropyl internucleoside linkage" means the alkyl phosphonate internucleoside bond shown below:

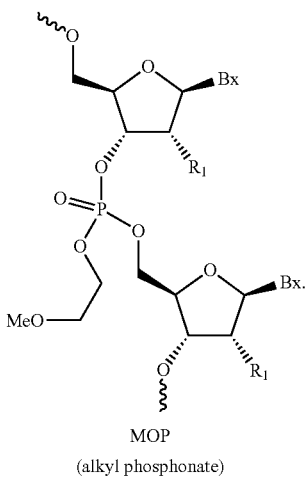

MOP
(alkyl phosphonate)

As used herein, "motif" means the pattern of unmodified and/or modified sugar moieties, nucleobases, and/or internucleoside linkages, in an oligonucleotide.

As used herein, "naturally occurring" means found in nature.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a modified nucleobase is a group of atoms capable of pairing with at least one unmodified nucleobase. A universal base is a nucleobase that can pair with any one of the five unmodified nucleobases. 5-methylcytosine (NC) is one example of a modified nucleobase.

As used herein, "nucleobase sequence" means the order of contiguous nucleobases in a nucleic acid or oligonucleotide independent of any sugar moiety or internucleoside linkage modification.

As used herein, "nucleoside" means a moiety comprising a nucleobase and a sugar moiety. The nucleobase and sugar moiety are each, independently, unmodified or modified. As used herein, "modified nucleoside" means a nucleoside comprising a modified nucleobase and/or a modified sugar moiety.

As used herein, "oligomeric compound" means a compound consisting of an oligonucleotide and optionally one or more additional features, such as a conjugate group or terminal group.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "parent oligomeric compound" in the context of an oligomeric compound comprising at least one modification in the central region other than phosphorothioate or 5-methylcytosine means an oligomeric compound that is identical to the oligomeric compound comprising the at least one modification in the central region except that the parent oligomeric compound does not comprise at least one modified internucleoside linkage other than phosphorothioate and/or at least one modified nucleoside comprising a modified nucleobase other than 5-methylcytosine and/or a modified sugar moiety. A parent oligomeric compound and its counterpart oligomeric compound comprising at least one modification in the central region have identical nucleobase sequences or differ in nucleobase sequence only due to inclusion of a modified nucleobase other than 5-methylcytosine in the oligomeric compound comprising at least one modification in the central region.

As used herein, "pharmaceutically acceptable carrier or diluent" means any substance suitable for use in administering to an animal. Certain such carriers enable pharmaceutical compositions to be formulated as, for example, liquids, powders, or suspensions that can be aerosolized or otherwise dispersed for inhalation by a subject. In certain embodiments, a pharmaceutically acceptable carrier or diluent is sterile water; sterile saline; or sterile buffer solution.

As used herein "pharmaceutically acceptable salts" means physiologically and pharmaceutically acceptable salts of compounds, such as oligomeric compounds, i.e., salts that retain the desired biological activity of the compound and do not impart undesired toxicological effects thereto.

As used herein "pharmaceutical composition" means a mixture of substances suitable for administering to a subject. For example, a pharmaceutical composition may comprise an antisense compound and an aqueous solution.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, the term "single-stranded" in reference to an antisense compound means such a compound consisting of one oligomeric compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex, in which case the compound would no longer be single-stranded.

As used herein, "standard cell assay" means any of the assays described in Examples 1-9, and reasonable variations thereof.

As used herein, "standard in vitro activity assay" means a procedure, as described in Example 1 herein, wherein expression is measured by RT-PCR in cultured cells expressing the target RNA following administration of an oligomeric compound to the cultured cells.

As used herein, "standard in vitro cytotoxicity assay" means a procedure, as described in Example 8 herein, wherein activation of caspases 3 and 7 is measured in cultured 3T3-L1 cells following administration of an oligomeric compound to the cells.

As used herein, "standard in vivo experiment" means the procedure described in Example 10 and reasonable variations thereof.

As used herein, "stereorandom" in the context of a compound or moiety comprising a chiral center means the chiral center has a random stereochemical configuration. For example, in a population of molecules of identical formula comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration.

As used herein, "subject" means a human or non-human animal selected for treatment or therapy.

As used herein, "sugar moiety" means an unmodified sugar moiety or a modified sugar moiety. As used herein, "unmodified sugar moiety" means a β-D-ribosyl moiety, as found in naturally occurring RNA, or a β-D-2'-deoxyribosyl sugar moiety as found in naturally occurring DNA. As used herein, "modified sugar moiety" or "modified sugar" means a sugar surrogate or a furanosyl sugar moiety other than a β-D-ribosyl or a β-D-2'-deoxyribosyl. Modified furanosyl sugar moieties may be modified or substituted at a certain position(s) of the sugar moiety, or unsubstituted, and they may or may not have a stereoconfiguration other than β-D-ribosyl. Modified furanosyl sugar moieties include bicyclic sugars and non-bicyclic sugars. As used herein, "sugar surrogate" means a modified sugar moiety that does not comprise a furanosyl or tetrahydrofuranyl ring (is not a "furanosyl sugar moiety") and that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "susceptible" in the context of a disease, disorder, condition, or symptom such as degeneration, damage, or elevated apoptosis means that a subject has a higher risk than the average risk for the general population for the disease, disorder, condition, or symptom.

As used herein, "target nucleic acid," "target RNA," "target RNA transcript" and "nucleic acid target" mean a nucleic acid that an oligomeric compound, such as an antisense compound, is designed to affect. In certain embodiments, an oligomeric compound comprises an oligonucleotide having a nucleobase sequence that is complementary to more than one RNA, only one of which is the target RNA of the oligomeric compound. In certain embodiments, the target RNA is an RNA present in the species to which an oligomeric compound is administered. As used herein, a "liver target" is a target RNA that is expressed in the liver, and modulation of expression of the target RNA in the liver provides a therapeutic effect. As used herein a "central nervous system target" is a target RNA that is expressed in the central nervous system, and modulation of expression of the target RNA in the central nervous system provides a therapeutic effect.

The present disclosure provides certain individual cellular, tissue, or organ targets. For example, a "macrophage target" or a "liver target." For each such individual target, modulation of the expression of the target RNA in the individual cellular, tissue, or organ target is desired for therapeutic benefit. In certain embodiments, modulation of the target RNA in an individual cellular, tissue, or organ target provides a therapeutic effect. In certain embodiments, a cellular, tissue, or organ target is expressed in tissues other than in a particular type of cell, tissue, or organ as well as being expressed in a particular type of cell, tissue, or organ. For example, certain target RNAs may be expressed in both a macrophage and a hepatocyte.

As used herein, "therapeutically effective amount" means an amount of a compound, pharmaceutical agent, or composition that provides a therapeutic benefit to a subject.

As used herein, "treat" refers to administering a compound or pharmaceutical composition to an animal in order to effect an alteration or improvement of a disease, disorder, or condition in the animal.

As used herein, "maximum tolerated dose" means the highest dose of a compound that does not cause unacceptable side effects. In certain embodiments, the maximum tolerated dose is the highest dose of a modified oligonucleotide that does not cause an ALT elevation of three times the upper limit of normal as measured by a standard assay, e.g. the assay of Example 12 or Example 1. In certain embodiments, the maximum tolerated dose is the highest dose of a modified oligonucleotide that does not cause caspase elevation of greater than 30,000 RLU as measured by a standard assay, e.g. the assay of Example 13, Example 8, or Example 4.

As used herein, "DNA isomer" means a nucleoside that comprises a modified sugar moiety that is a stereoisomer of β-D-2'-deoxyribosyl. As used herein, a "DNA isomer" does not include β-D-2'-deoxyribosyl nucleosides. Seven such isomers of 2'-β-D-deoxyribosyl exist: 2H3-D-deoxyxylosyl β-DANA), 2'-α-D-deoxyribosyl (α-D-DNA), 2'-α-L-deoxyribosyl (α-L-DNA), 2'-β-L-deoxyribosyl (β-L-DNA), 2'-α-D-deoxyxylosyl (α-L-XNA), 1,2'-α-L-deoxyxylosyl (α-LANA), 2H3-L-deoxyxylosyl β-LANA). In certain embodiments, a DNA isomer is 2'-α-D-deoxyribosyl, 2'-α-L-deoxyribosyl, 2H3-L-deoxyribosyl, or 2'-β-D-deoxyxylosyl sugar moiety. As used herein, "DNA isomer" does not include any nonfuranosyl sugar moieties.

As used herein, "DNA nucleoside" means a nucleoside comprising a 2'-H(H) β-D-2'-deoxyribosyl sugar moiety, as found in naturally-occurring DNA. A "DNA nucleoside" may comprise a modified nucleobase or a uracil nucleobase. A DNA nucleoside may be linked to adjacent nucleosides through unmodified phosphodiester internucleoside linkages or through modified internucleoside linkages.

As used herein, a "2'-modified DNA isomer" means a nucleoside that comprises a modified sugar moiety that is selected from 2'-β-D-deoxyxylosyl β-DANA), 2'-α-D-deoxyribosyl (α-D-DNA), 2'-α-L-deoxyribosyl (α-L-DNA), 2H3-L-deoxyribosyl (β-L-DNA), 2'-α-D-deoxyxylosyl (α-LANA), 1, 2'-α-L-deoxyxylosyl (α-LANA), 2H3-L-deoxyxylosyl β-LANA), and that further comprises a 2'-substituent. In certain embodiments, the 2'-substituent is fluoro, alkoxy, or $C_1$-$C_{10}$ alkyl.

As used herein, "DNA mimic" means a nucleoside other than a DNA nucleoside wherein the nucleobase is directly linked to a carbon atom of a ring bound to a second carbon atom within the ring, wherein the second carbon atom comprises a bond to at least one hydrogen atom, wherein the nucleobase and at least one hydrogen atom are trans to one another relative to the bond between the two carbon atoms. In certain embodiments, a DNA mimic comprises a structure represented by the formula:

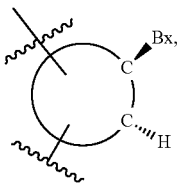

wherein Bx is a heterocylic base moiety, the ring contains 5-7 members, and the ring is attached at two positions to a hydroxyl, a phosphate, an internucleoside linking group, or a conjugate linker.

As used herein, a "standard RNase H cleavage assay" is an assay wherein a heteroduplex of the modified oligonucleotide and a complementary strand of unmodified RNA are incubated with each other to form a heteroduplex, and are then incubated with RNase H1 for specified time points before being analyzed on a polyacrylamide gel.

As used herein, a modified nucleoside "supports RNase H cleavage" when incorporated into an oligonucleotide if RNase H cleavage of the complementary RNA is observed within two nucleobases of the modified nucleoside in a standard RNase H cleavage assay.

As used herein, "therapeutic index" means a comparison of the amount of a compound that causes a therapeutic effect to the amount that causes toxicity. Compounds having a high therapeutic index have strong efficacy and low toxicity. In certain embodiments, increasing the therapeutic index of a compound increases the amount of the compound that can be safely administered. In certain embodiments, therapeutic index is the ratio of the amount of modulation of a target nucleic acid by a modified oligonucleotide compared to ALT elevation, wherein the ALT elevation is measured by a standard assay, e.g. the assay of Example 12 or Example 1. In certain embodiments, therapeutic index is the ratio of the amount of modulation of a target nucleic acid by a modified oligonucleotide compared to caspase elevation, wherein the caspase elevation is measured by a standard assay, e.g. the assay of Example 13, Example 8, or Example 4.

As used herein, an "altered nucleotide" is a nucleotide that comprises one or more modifications relative to a nucleotide comprising a 2'-β-D-deoxyribosyl sugar moiety, a nucleobase selected from adenine (A), thymine (T), cytosine (C), 5-methyl cytosine ($^m$C), uracil (U), or guanine (G), and a 5' to 3' internucleoside linkage selected from phosphodiester or stereorandom phosphorothioate. In certain embodiments, the altered nucleotide is an altered nucleoside attached to a phosphorothioate or phosphodiester internucleoside linkage. In certain embodiments, the altered nucleotide comprises a 2'-modified sugar moiety, or is a "2'-altered nucleotide". In certain embodiments, the altered nucleotide comprises a modified internucleoside linking group, and is a "linkage-altered nucleotide". Herein, a linkage-altered nucleotide comprises an internucleoside linking group other than phosphodiester or phosphorothioate attached to the 3' carbon of the sugar moiety, or the equivalent position for a sugar surrogate. The nucleotide on the 5'-end of an internucleoside linking group other than phosphodiester or phosphorothioate is not an "altered nucleotide", as used herein.

Certain embodiments are described in the numbered embodiments below:

1. An oligomeric compound comprising a modified oligonucleotide consisting of 14-23 linked nucleosides, wherein the modified oligonucleotide comprises a gapmer consisting of a 5'-region, a central region, and a 3'-region wherein:
   the 5'-region consists of 2-5 linked modified nucleosides, wherein each nucleoside of the 5'-region comprises a 2'-modified furanosyl sugar moiety;
   the 3'-region consists of 1-5 linked modified nucleosides, wherein each nucleoside of the 3'-region comprises a 2'-modified furanosyl sugar moiety;
   the central region consists of 7-10 linked nucleosides, where each nucleoside of the central region comprises a sugar moiety selected from an unmodified 2'-β-D-deoxyribosyl sugar moiety and a modified sugar moiety; wherein
   the 3'- and 5'-most nucleosides of the central region each comprise a sugar moiety independently selected from a 2'-deoxyfuranosyl sugar moiety or a sugar surrogate; and wherein the central region comprises:
   at least one modified internucleoside linkage other than phosphorothioate and/or at least one modified nucleoside comprising a modified nucleobase other than 5-methylcytosine and/or a modified sugar moiety; and
   at least 6 nucleosides each comprising an unmodified 2'-β-D-deoxyribosyl sugar moiety.

2. The oligomeric compound of embodiment 1, wherein the 5'-region consists of 2-4 linked nucleosides.

3. The oligomeric compound of embodiment 1, wherein the 5'-region consists of 2 linked nucleosides.

4. The oligomeric compound of embodiment 1, wherein the 5'-region consists of 3 linked nucleosides.

5. The oligomeric compound of embodiment 1, wherein the 5'-region consists of 4 linked nucleosides.

6. The oligomeric compound of embodiment 1, wherein the 5'-region consists of 5 linked nucleosides.

7. The oligomeric compound of any of embodiments 1-6, wherein each nucleoside of the 5'-region comprises a 2'-modified ribosyl sugar moiety.

8. The oligomeric compound of any of embodiments 1-7, wherein at least one nucleoside of the 5'-region comprises a bicyclic furanosyl sugar moiety.

9. The oligomeric compound of any of embodiments 1-8, wherein each nucleoside of the 5'-region comprises a bicyclic furanosyl sugar moiety.

10. The oligomeric compound of any of embodiments 1-8, wherein at least one nucleoside of the 5'-region comprises a non-bicyclic sugar moiety.

11. The oligomeric compound of embodiment 10, wherein the non-bicyclic sugar moiety of the at least one nucleoside of the 5'-region is a 2'-substituted ribosyl sugar moiety.

12. The oligomeric compound of any of embodiments 1-7 or 10-11, wherein each nucleoside of the 5'-region comprises a non-bicyclic sugar moiety.

13. The oligomeric compound of embodiment 12, wherein each nucleoside of the 5'-region comprises a 2'-substituted ribosyl sugar moiety.

14. The oligomeric compound of any of embodiments 1-7, wherein each nucleoside of the 5'-region comprises a 2'-modified furanosyl sugar moiety independently selected from a bicyclic sugar moiety and a non-bicyclic sugar moiety, 2'-substituted ribosyl sugar moiety.

15. The oligomeric compound of any of embodiments 8-11 or 14, wherein each bicyclic sugar moiety of the 5'-region is selected from among cEt, LNA, and ENA.

16. The oligomeric compound of any of embodiments 10-14, wherein each nonbicyclic sugar moiety of the 5'-region has a 2'-substituent selected from among 2'-MOE, 2'-OMe, and 2'-NMA.

17. The oligomeric compound of any of embodiments 1-16, wherein none of the nucleosides of the 5'-region comprise a sugar moiety having a 2'-F substituent.

18. The oligomeric compound of any of embodiments 1-17, wherein each nucleobase of the 5'-region is independently selected from among thymine, uracil, guanine, cytosine, 5-methylcytosine, and adenine.

19. The oligomeric compound of any of embodiments 1-18, wherein each internucleoside linkage of the 5'-region is selected from among phosphodiester and phosophorothioate internucleoside linkages.

20. The oligomeric compound of any of embodiments 1-19, wherein the 3'-region consists of 2-4 linked nucleosides.

21. The oligomeric compound of any of embodiments 1-19, wherein the 3'-region consists of 1 nucleoside.

22. The oligomeric compound of any of embodiments 1-19, wherein the 3'-region consists of 2 linked nucleosides.

23. The oligomeric compound of any of embodiments 1-19, wherein the 3'-region consists of 3 linked nucleosides.

24. The oligomeric compound of any of embodiments 1-19, wherein the 3'-region consists of 4 linked nucleosides.

25. The oligomeric compound of any of embodiments 1-19, wherein the 3'-region consists of 5 linked nucleosides.

26. The oligomeric compound of any of embodiments 1-25, wherein each nucleoside of the 3'-region comprises a 2'-modified ribosyl sugar moiety.

27. The oligomeric compound of any of embodiments 1-26, wherein at least one nucleoside of the 3'-region comprises a bicyclic furanosyl sugar moiety.

28. The oligomeric compound of any of embodiments 1-27, wherein each nucleoside of the 3'-region comprises a bicyclic furanosyl sugar moiety.

29. The oligomeric compound of any of embodiments 1-27, wherein at least one nucleoside of the 3'-region comprises a non-bicyclic sugar moiety.

30. The oligomeric compound of embodiment 29, wherein the non-bicyclic sugar moiety of the at least one nucleoside of the 3'-region is a 2'-substituted ribosyl sugar moiety.

31. The oligomeric compound of any of embodiments 1-26 or 29-30, wherein each nucleoside of the 3'-region comprises a non-bicyclic sugar moiety.

32. The oligomeric compound of embodiment 31, wherein each nucleoside of the 3'-region comprises a 2'-substituted ribosyl sugar moiety.

33. The oligomeric compound of any of embodiments 1-26, wherein each nucleoside of the 3'-region comprises a 2'-modified furanosyl sugar moiety independently selected from a bicyclic sugar moiety and a non-bicyclic sugar moiety, 2'-substituted ribosyl sugar moiety.

34. The oligomeric compound of any of embodiments 27-30 or 33, wherein each bicyclic sugar moiety of the 3'-region is selected from among cEt, LNA, and ENA.

35. The oligomeric compound of any of embodiments 29-33, wherein each nonbicyclic sugar moiety of the 3'-region has a 2'-substituent selected from among 2'-MOE, 2'-OMe, and 2'-NMA.

36. The oligomeric compound of any of embodiments 1-35, wherein none of the nucleosides of the 3'-region comprise a sugar moiety having a 2'-F substituent.

37. The oligomeric compound of any of embodiments 1-36, wherein each nucleobase of the 3'-region is independently selected from among thymine, uracil, guanine, cytosine, 5-methylcytosine, and adenine.

38. The oligomeric compound of any of embodiments 1-37, wherein each internucleoside linkage of the 3'-region is selected from among phosphodiester and phosophorothioate internucleoside linkages.

39. The oligomeric compound of any of embodiments 1-38, wherein the central region consists of 7 linked nucleosides.

40. The oligomeric compound of any of embodiments 1-38, wherein the central region consists of 8 linked nucleosides.

41. The oligomeric compound of any of embodiments 1-38, wherein the central region consists of 9 linked nucleosides.

42. The oligomeric compound of any of embodiments 1-38, wherein the central region consists of 10 linked nucleosides.

43. The oligomeric compound of any of embodiments 1-42, wherein each of the two internucleoside linkages connecting the central region to the 5'-region and 3'-region are independently selected from among phosphosdiester and phosphorothioate internucleoside linkages.

44. The oligomeric compound of any of embodiments 1-43, wherein the modified oligonucleotide consists of the gapmer.

45. The oligomeric compound of any of embodiments 1-43, comprising a conjugate group.

46. The oligomeric compound of any of embodiments 1-43 or 45, wherein the modified oligonucleotide comprises 1-3 linker nucleosides.

47. The oligomeric compound of embodiment 46, wherein the linker nucleosides are linked to the 5'-end or the 3'-end of the gapmer.

48. The oligomeric compound of any of embodiments 45-47, wherein the conjugate group comprises GalNAc.

49. The oligomeric compound of any of embodiments 45-47, comprising LICA-1.

50. The oligomeric compound of any of embodiments 1-49, wherein the central region comprises one, and no more than one, modified sugar moiety.

51. The oligomeric compound of embodiment 50, wherein the each internucleoside linkage within the central region is selected from among phosphodiester and phosophorothioate internucleoside linkages.

52. The oligomeric compound of any of embodiments 50-51, wherein each nucleobase of the central region is independently selected from among thymine, uracil, guanine, cytosine, 5-methylcytosine, and adenine.

53. The oligomeric compound of any of embodiments 1-50 or 52, wherein the central region comprises one, and no more than one, modified internucleoside linkage other than phosphorothioate.

54. The oligomeric compound of embodiment 53, wherein the modified internucleoside linkage other than phosphorothioate contains phosphorus.

55. The oligomeric compound of any of embodiments 53-54, wherein the modified internucleoside linkage other than phosphorothioate is a neutral internucleoside linkage.

56. The oligomeric compound of any of embodiments 1-50 or 52, wherein the central region comprises two, and no more than two, modified internucleoside linkages other than phosphorothioate.

57. The oligomeric compound of embodiment 56, wherein the two modified internucleoside linkages other than phosphorothioate each contain phosphorus.

58. The oligomeric compound of any of embodiments 56-57, wherein at least one of the modified internucleoside linkages other than phosphorothioate is a neutral internucleoside linkage.

59. The oligomeric compound of any of embodiments 56-57, wherein the two modified internucleoside linkages other than phosphorothioate are neutral internucleoside linkages.

60. The oligomeric compound of any of embodiments 1-51 or 53-59, wherein the central region comprises one, and no more than one, modified nucleobase other than 5-methylcytosine.

61. The oligomeric compound of any of embodiments 1-60, wherein each of the unmodified sugar moieties of the central region are 2'-β-D-deoxyribosyl sugar moieties.

62. The oligomeric compound of any of embodiments 50-61, wherein the one modified sugar moiety of the central region is at one of positions 2-9 of the central region.

63. The oligomeric compound of any of embodiments 50-61, wherein the one modified sugar moiety of the central region is at one of positions 1-6 of the central region.

64. The oligomeric compound of any of embodiments 50-61, wherein the one modified sugar moiety of the central region is at one of positions 1~4 of the central region.

65. The oligomeric compound of any of embodiments 50-61, wherein the one modified sugar moiety of the central region is at one of positions 2-4 of the central region.

66. The oligomeric compound of any of embodiments 50-61, wherein the one modified sugar moiety of the central region is at one of positions 3-4 of the central region.

67. The oligomeric compound of any of embodiments 50-66, wherein the one modified sugar moiety of the central region is a sugar surrogate, a bicyclic furanosyl sugar moiety, a non-bicyclic 2'-modified furanosyl sugar moiety, a non-bicyclic 4'-modified furanosyl sugar moiety, a non-bicyclic 5'-modified furanosyl sugar moiety, or a modified 2'-deoxyfuranosyl sugar moiety.

68. The oligomeric compound of embodiment 67, wherein the one modified sugar moiety of the central region is a bicyclic ribosyl sugar moiety, a non-bicyclic 2'-modified ribosyl sugar moiety, a non-bicyclic 4'-modified 2'-deoxyribosyl sugar moiety, a non-bicyclic 5'-modified 2'-deoxyribosyl sugar moiety, or a modified 2'-deoxyfuranosyl sugar moiety.

69. The oligomeric compound of embodiment 68, wherein the one modified sugar moiety of the central region is a bicyclic ribosyl sugar moiety, a non-bicyclic 2'-substituted ribosyl sugar moiety, a non-bicyclic 4'-substituted 2'-deoxyribosyl sugar moiety, a non-bicyclic 5'-substituted 2'-deoxyribosyl sugar moiety, or a modified, unsubstituted 2'-deoxyfuranosyl sugar moiety.

70. The oligomeric compound of any of embodiments 67-69, wherein the one modified sugar moiety of the central region is a 2'-substituted ribosyl sugar moiety.

71. The oligomeric compound of embodiment 70, wherein the 2'-substituted ribosyl sugar moiety is a 2'-F, 2'-MOE, or 2'-O-methyl substituted sugar moiety.

72. The oligomeric compound of any of embodiments 67-69, wherein the one modified sugar moiety of the central region is a 4'-alkyl substituted 2'-deoxyribosyl sugar moiety.

73. The oligomeric compound of embodiment 72, wherein the 4'-alkyl substituted ribosyl sugar moiety is a 4'-methyl substituted 2'-deoxyribosyl sugar moiety.

74. The oligomeric compound of any of embodiments 67-69, wherein the one modified sugar moiety of the central region is a 5'-alkyl substituted 2'-deoxyribosyl sugar moiety.

75. The oligomeric compound of embodiment 74, wherein the 5'-alkyl substituted ribosyl sugar moiety is a 5'-methyl, 5'-ethyl, or 5'-allyl substituted 2'-deoxyribosyl sugar moiety.

76. The oligomeric compound of any of embodiments 67-69, wherein the one modified sugar moiety of the central region is a modified, unsubstituted 2'-deoxyfuranosyl sugar moiety.

77. The oligomeric compound of embodiment 76, wherein the modified, unsubstituted 2'-deoxyfuranosyl sugar moiety is an unsubstituted α-D-2'-deoxyribosyl, α-L-2'-deoxyribosyl, β-L-2'-deoxyribosyl, or β-D-2'-deoxyxylosyl sugar moiety.

78. The oligomeric compound of any of embodiments 67-69, wherein the one modified sugar moiety of the central region is a bicyclic ribosyl sugar moiety.

79. The oligomeric compound of embodiment 78, wherein the bicyclic ribosyl sugar moiety is cEt, LNA, or ENA.

80. The oligomeric compound of any of embodiments 67-69, wherein the one modified sugar moiety of the central region is a morpholino, cEt, 2'-F, 2'-MOE, 4'-Methyl, 5'-Methyl, 5'-allyl, 5'-ethyl, β-L-2'-deoxyribosyl, α-D-2'-deoxyribosyl, β-D-2'-deoxyxylosyl, or α-L-2'-deoxyribosyl sugar moiety.

81. The oligomeric compound of embodiment 62, wherein the one modified sugar moiety of the central region is a 2'-O-Methyl substituted ribosyl, unsubstituted α-D-2'-deoxyribosyl, unsubstituted α-L-2'-deoxyribosyl, or unsubstituted β-L-2'-deoxyribosyl sugar moiety.

82. The oligomeric compound of embodiment 81, wherein the one modified sugar moiety of the central region is a 2'-O-Methyl substituted ribosyl or unsubstituted β-L-2'-deoxyribosyl sugar moiety.

83. The oligomeric compound of embodiment 63, wherein the one modified sugar moiety of the central region is a morpholino, 2'-O-Methyl substituted ribosyl, unsubstituted α-D-2'-deoxyribosyl, or unsubstituted β-L-2'-deoxyribosyl sugar moiety sugar moiety.

84. The oligomeric compound of embodiment 64, wherein the one modified sugar moiety of the central region is a morpholino, unsubstituted α-D-2'-deoxyribosyl, or unsubstituted β-L-2'-deoxyribosyl sugar moiety sugar moiety.

85. The oligomeric compound of embodiment 65, wherein the one modified sugar moiety of the central region is a 2'-F substituted ribosyl, 2'-MOE substituted ribosyl, 2'-O-Methyl substituted ribosyl, 5'-(S)-Methyl substituted 2'-deoxyribosyl, 5'-allyl substituted 2'-deoxyribosyl, unsubstituted α-D-2'-deoxyribosyl, or cEt bicyclic sugar moiety.

86. The oligomeric compound of embodiment 85, wherein the one modified sugar moiety of the central region is a 2'-MOE substituted ribosyl, 2'-O-Methyl substituted ribosyl, or 5'-allyl substituted 2'-deoxyribosyl sugar moiety.

87. The oligomeric compound of embodiment 85 or 86, wherein the 5'-allyl substituted ribosyl sugar moiety is stereorandom at the 5'-position of the modified sugar moiety.

88. The oligomeric compound of embodiment 66, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(S)-Methyl substituted 2'-deoxyribosyl, 5'-(R)-Methyl substituted 2'-deoxyribosyl, 5'-stereorandom Methyl substituted 2'-deoxyribosyl, 5'-(S)-Ethyl substituted 2'-deoxyribosyl, 5'-(R)-Ethyl substituted 2'-deoxyribosyl, 5'-stereorandom Ethyl 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted α-D-2'-deoxyribosyl, unsubstituted α-L-2'-deoxyribosyl, unsubstituted β-L-2'-deoxyribosyl, cEt, or morpholino sugar moiety.

89. The oligomeric compound of embodiment 88, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, cEt, or morpholino sugar moiety.

90. The oligomeric compound of any of embodiments 50-61 or 67-69, wherein the one modified sugar moiety of the central region is at position 1 of the central region.

91. The oligomeric compound of embodiment 90, wherein the one modified sugar moiety of the central region is a morpholino, unsubstituted β-L-2'-deoxyribosyl, or unsubstituted α-D-2'-deoxyribosyl sugar moiety.

92. The oligomeric compound of embodiment 90, wherein the one modified sugar moiety of the central region is a morpholino or unsubstituted α-D-2'-deoxyribosyl sugar moiety.

93. The oligomeric compound of any of embodiments 50-61 or 67-69, wherein the one modified sugar moiety of the central region is at position 2 of the central region.

94. The oligomeric compound of embodiment 93, wherein the one modified sugar moiety of the central region is a 2'-F substituted ribosyl, 2'-MOE substituted ribosyl, 2'-O-Methyl substituted ribosyl, 5'-(S)-Methyl substituted 2'-deoxyribosyl, 5'-Allyl substituted 2'-deoxyribosyl, unsubstituted α-D-2'-deoxyribosyl, or cEt sugar moiety.

95. The oligomeric compound of embodiment 93, wherein the one modified sugar moiety of the central region is a 2'-MOE substituted ribosyl, 2'-O-Methyl substituted ribosyl, 5'-(S)-Methyl substituted 2'-deoxyribosyl, 5'-Allyl substituted 2'-deoxyribosyl, or unsubstituted α-D-2'-deoxyribosyl sugar moiety.

96. The oligomeric compound of embodiment 94 or 95, wherein the 5'-allyl substituted 2'-deoxyribosyl sugar moiety is stereorandom at the 5'-position of the modified sugar moiety.

97. The oligomeric compound of any of embodiments 50-61 or 67-69, wherein the one modified sugar moiety of the central region is at position 3 of the central region.

98. The oligomeric compound of embodiment 97, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, unsubstituted β-D-2'-deoxyxylosyl, unsubstituted α-L-2'-deoxyribosyl, unsubstituted α-D-2'-deoxyribosyl, cEt, or morpholino sugar moiety.

99. The oligomeric compound of embodiment 97, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, unsubstituted β-D-2'-deoxyxylosyl, cEt, or morpholino sugar moiety.

100. The oligomeric compound of any of embodiments 50-61 or 67-69, wherein the one modified sugar moiety of the central region is at position 4 of the central region.

101. The oligomeric compound of embodiment 100, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, unsubstituted α-L-2'-deoxyribosyl, unsubstituted α-D-2'-deoxyribosyl, cEt, or morpholino sugar moiety.

102. The oligomeric compound of embodiment 100, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted L-2'-deoxyribosyl, unsubstituted α-L-2'-deoxyribosyl, unsubstituted α-D-2'-deoxyribosyl, cEt, or morpholino sugar moiety.

103. The oligomeric compound of any of embodiments 50-61 or 67-69, wherein the one modified sugar moiety of the central region is at position 5 of the central region.

104. The oligomeric compound of embodiment 103, wherein the one modified sugar moiety of the central region is a 2'-O-Methyl substituted ribosyl or unsubstituted β-L-2'-deoxyribosyl sugar moiety.

105. The oligomeric compound of embodiment 103, wherein the one modified sugar moiety of the central region is an unsubstituted β-L-2'-deoxyribosyl sugar moiety.

106. The oligomeric compound of any of embodiments 50-61 or 67-69, wherein the one modified sugar moiety of the central region is at position 6 of the central region.

107. The oligomeric compound of embodiment 106, wherein the one modified sugar moiety of the central region is a 2'-O-Methyl substituted ribosyl, unsubstituted β-L-2'-deoxyribosyl, unsubstituted α-D-2'-deoxyribosyl, or morpholino sugar moiety.

108. The oligomeric compound of any of embodiments 50-61 or 67-69, wherein the one modified sugar moiety of the central region is at position 7 of the central region.

109. The oligomeric compound of embodiment 108, wherein the one modified sugar moiety of the central region is a 2'-O-Methyl substituted ribosyl, unsubstituted β-L-2'-deoxyribosyl, or unsubstituted α-D-2'-deoxyribosyl sugar moiety.

110. The oligomeric compound of any of embodiments 50-61 or 67-69, wherein the one modified sugar moiety of the central region is at position 8 of the central region.

111. The oligomeric compound of embodiment 110, wherein the one modified sugar moiety of the central region is a 2'-O-Methyl substituted ribosyl, unsubstituted β-L-2'-deoxyribosyl, or unsubstituted α-D-2'-deoxyribosyl sugar moiety.

112. The oligomeric compound of any of embodiments 50-61 or 67-69, wherein the one modified sugar moiety of the central region is at position 9 of the central region.

113. The oligomeric compound of embodiment 112, wherein the one modified sugar moiety of the central region is a 2'-O-Methyl substituted ribosyl or unsubstituted β-L-2'-deoxyribosyl sugar moiety.

114. The oligomeric compound of any of embodiments 50-61 or 67-69, wherein the one modified sugar moiety of the central region is at position 10 of the central region.

115. The oligomeric compound of any of embodiments 50-61 or 67-69, wherein the one modified sugar moiety of the central region is a morpholino modified sugar moiety at position 1 of the central region.

116. The oligomeric compound of any of embodiments 50-61 or 67-69, wherein the one modified sugar moiety of the central region is a modified, unsubstituted 2'-deoxyfuranosyl sugar moiety at position 1 of the central region.

117. The oligomeric compound of embodiment 116, wherein the one modified sugar moiety of the central region is an unsubstituted β-L-2'-deoxyribosyl sugar moiety at position 1 of the central region.

118. The oligomeric compound of embodiment 116, wherein the one modified sugar moiety of the central region is an unsubstituted α-D-2'-deoxyribosyl sugar moiety 119. The oligomeric compound of any of embodiments 50-61 or 67-69, wherein the one modified sugar moiety of the central region is a 2'-substituted ribosyl sugar moiety at position 2 of the central region.

120. The oligomeric compound of embodiment 119, wherein the 2'-substituted ribosyl sugar moiety at position 2 of the central region is a 2'-F ribosyl sugar moiety.

121. The oligomeric compound of embodiment 119, wherein the 2'-substituted ribosyl sugar moiety at position 2 of the central region is a 2'-MOE ribosyl sugar moiety.

122. The oligomeric compound of embodiment 119, wherein the 2'-substituted ribosyl sugar moiety at position 2 of the central region is a 2'-O-methyl ribosyl sugar moiety.

123. The oligomeric compound of any of embodiments 50-61 or 67-69, wherein the one modified sugar moiety of the central region is a 5'-alkyl substituted 2'-deoxyribosyl sugar moiety at position 2 of the central region.

124. The oligomeric compound of embodiment 123, wherein the 5'-alkyl substituted 2'-deoxyribosyl sugar moiety at position 2 of the central region is a 5'-(S)Me 2'-deoxyribosyl sugar moiety.

125. The oligomeric compound of embodiment 123, wherein the 5'-alkyl substituted 2'-deoxyribosyl sugar moiety at position 2 of the central region is a 5'-allyl 2'-deoxyribosyl sugar moiety.

126. The oligomeric compound of embodiment 125, wherein the 5'-allyl 2'-deoxyribosyl sugar moiety is stereorandom at the 5'-position of the 5'-allyl 2'-deoxyribosyl sugar moiety.

127. The oligomeric compound of any of embodiments 50-61 or 67-69, wherein the one modified sugar moiety of the central region is a modified, unsubstituted 2'-deoxyfuranosyl sugar moiety at position 2 of the central region.

128. The oligomeric compound of embodiment 127, wherein the modified, unsubstituted 2'-deoxyfuranosyl sugar moiety at position 2 of the central region is a α-D-2'-deoxyribosyl modified sugar moiety.

129. The oligomeric compound of any of embodiments 50-61 or 67-69, wherein the one modified sugar moiety of the central region is a cEt or LNA sugar moiety at position 2 of the central region.

130. The oligomeric compound of any of embodiments 50-61 or 67-69, wherein the one modified sugar moiety of the central region is a 2'-substituted ribosyl sugar moiety at position 3 of the central region.

131. The oligomeric compound of embodiment 130, wherein the 2'-substituted ribosyl sugar moiety at position 3 of the central region is a 2'-F ribosyl sugar moiety.

132. The oligomeric compound of embodiment 130, wherein the 2'-substituted ribosyl sugar moiety at position 3 of the central region is a 2'-MOE ribosyl sugar moiety.

133. The oligomeric compound of embodiment 130, wherein the 2'-substituted ribosyl sugar moiety at position 3 of the central region is a 2'-O-methyl ribosyl sugar moiety.

134. The oligomeric compound of any of embodiments 50-61 or 67-69, wherein the one modified sugar moiety of the central region is a 4'-alkyl substituted 2'-deoxyribosyl sugar moiety at position 3 of the central region.

135. The oligomeric compound of embodiment 134, wherein the 4'-substituted 2'-deoxyribosyl sugar moiety at position 3 of the central region is a 4'-methyl 2'-deoxyribosyl sugar moiety.

136. The oligomeric compound of any of embodiments 50-61 or 67-69, wherein the one modified sugar moiety of the central region is a 5'-alkyl substituted 2'-deoxyribosyl sugar moiety at position 3 of the central region.

137. The oligomeric compound of embodiment 136, wherein the 5'-alkyl substituted 2'-deoxyribosyl sugar moiety at position 3 of the central region is a 5'-(R)-methyl 2'-deoxyribosyl sugar moiety.

138. The oligomeric compound of embodiment 136, wherein the 5'-alkyl substituted 2'-deoxyribosyl sugar moiety at position 3 of the central region is a 5'-(S)-methyl 2'-deoxyribosyl sugar moiety.

139. The oligomeric compound of embodiment 136, wherein the 5'-alkyl substituted 2'-deoxyribosyl sugar moiety at position 3 of the central region is a 5'-stereorandom methyl 2'-deoxyribosyl sugar moiety.

140. The oligomeric compound of embodiment 136, wherein the 5'-alkyl substituted 2'-deoxyribosyl sugar moiety at position 3 of the central region is a 5'-(R)-ethyl 2'-deoxyribosyl sugar moiety.

141. The oligomeric compound of embodiment 136, wherein the 5'-alkyl substituted 2'-deoxyribosyl sugar moiety at position 3 of the central region is a 5'-(S)-ethyl 2'-deoxyribosyl sugar moiety.

142. The oligomeric compound of embodiment 136, wherein the 5'-alkyl substituted 2'-deoxyribosyl sugar moiety at position 3 of the central region is a 5'-stereorandom ethyl 2'-deoxyribosyl sugar moiety.

143. The oligomeric compound of embodiment 136, wherein the 5'-alkyl substituted 2'-deoxyribosyl sugar moiety at position 3 of the central region is a 5'-(R)-allyl 2'-deoxyribosyl sugar moiety.

144. The oligomeric compound of embodiment 136, wherein the 5'-alkyl substituted 2'-deoxyribosyl sugar moiety at position 3 of the central region is a 5'-(S)-allyl 2'-deoxyribosyl sugar moiety.

145. The oligomeric compound of embodiment 136, wherein the 5'-alkyl substituted 2'-deoxyribosyl sugar moiety at position 3 of the central region is a 5'-stereorandom allyl 2'-deoxyribosyl sugar moiety.

146. The oligomeric compound of any of embodiments 50-61 or 67-69, wherein the one modified sugar moiety of the central region is a modified, unsubstituted 2'-deoxyfuranosyl sugar moiety at position 3 of the central region.

147. The oligomeric compound of embodiment 146, wherein the modified, unsubstituted 2'-deoxyfuranosyl sugar moiety at position 3 of the central region is an α-D-2'-deoxyribosyl modified sugar moiety.

148. The oligomeric compound of embodiment 146, wherein the modified, unsubstituted 2'-deoxyfuranosyl sugar moiety at position 3 of the central region is an α-L-2'-deoxyribosyl modified sugar moiety.

149. The oligomeric compound of embodiment 146, wherein the modified, unsubstituted 2'-deoxyfuranosyl sugar moiety at position 3 of the central region is an β-L-2'-deoxyribosyl modified sugar moiety.

150. The oligomeric compound of embodiment 146, wherein the modified, unsubstituted 2'-deoxyfuranosyl sugar moiety at position 3 of the central region is an β-D-2'-deoxyxylosyl modified sugar moiety.

151. The oligomeric compound of any of embodiments 50-61 or 67-69, wherein the one modified sugar moiety of the central region is a bicyclic ribosyl sugar moiety at position 3 of the central region.

152. The oligomeric compound of embodiment 151, wherein the bicyclic ribosyl sugar moiety at position 3 of the central region is a cEt or LNA sugar moiety.

153. The oligomeric compound of embodiment 151, wherein the bicyclic ribosyl sugar moiety at position 3 of the central region is a cEt sugar moiety.

154. The oligomeric compound of embodiment 151, wherein the bicyclic ribosyl sugar moiety at position 3 of the central region is a LNA sugar moiety.

155. The oligomeric compound of any of embodiments 50-61 or 67-69, wherein the one modified sugar moiety of the central region is a morpholino sugar moiety at position 3 of the central region.

156. The oligomeric compound of any of embodiments 50-61 or 67-69, wherein the one modified sugar moiety of the central region is a 2'-substituted ribosyl sugar moiety at position 4 of the central region.

157. The oligomeric compound of embodiment 156, wherein the 2'-substituted ribosyl sugar moiety at position 4 of the central region is a 2'-F ribosyl sugar moiety.

158. The oligomeric compound of embodiment 156, wherein the 2'-substituted ribosyl sugar moiety at position 4 of the central region is a 2'-MOE ribosyl sugar moiety.

159. The oligomeric compound of embodiment 156, wherein the 2'-substituted ribosyl sugar moiety at position 4 of the central region is a 2'-O-methyl ribosyl sugar moiety.

160. The oligomeric compound of any of embodiments 50-61 or 67-69, wherein the one modified sugar moiety of the central region is a 4'-alkyl substituted 2'-deoxyribosyl sugar moiety at position 4 of the central region.

161. The oligomeric compound of embodiment 160, wherein the 4'-substituted 2'-deoxyribosyl sugar moiety at position 4 of the central region is a 4'-methyl 2'-deoxyribosyl sugar moiety.

162. The oligomeric compound of any of embodiments 50-61 or 67-69, wherein the one modified sugar moiety of the central region is a 5'-alkyl substituted 2'-deoxyribosyl sugar moiety at position 4 of the central region.

163. The oligomeric compound of embodiment 162, wherein the 5'-alkyl substituted 2'-deoxyribosyl sugar moiety at position 4 of the central region is a 5'-(R)-methyl 2'-deoxyribosyl sugar moiety.

164. The oligomeric compound of embodiment 162, wherein the 5'-alkyl substituted 2'-deoxyribosyl sugar moiety at position 4 of the central region is a 5'-(S)-methyl 2'-deoxyribosyl sugar moiety.

165. The oligomeric compound of embodiment 162, wherein the 5'-alkyl substituted 2'-deoxyribosyl sugar moiety at position 4 of the central region is a 5'-stereorandom methyl 2'-deoxyribosyl sugar moiety.

166. The oligomeric compound of embodiment 162, wherein the 5'-alkyl substituted 2'-deoxyribosyl sugar moiety at position 4 of the central region is a 5'-(R)-ethyl 2'-deoxyribosyl sugar moiety.

167. The oligomeric compound of embodiment 162, wherein the 5'-alkyl substituted 2'-deoxyribosyl sugar moiety at position 4 of the central region is a 5'-(S)-ethyl 2'-deoxyribosyl sugar moiety.

168. The oligomeric compound of embodiment 162, wherein the 5'-alkyl substituted 2'-deoxyribosyl sugar moiety at position 4 of the central region is a 5'-stereorandom ethyl 2'-deoxyribosyl sugar moiety.

169. The oligomeric compound of embodiment 162, wherein the 5'-alkyl substituted 2'-deoxyribosyl sugar moiety at position 4 of the central region is a 5'-(R)-allyl 2'-deoxyribosyl sugar moiety.

170. The oligomeric compound of embodiment 162, wherein the 5'-alkyl substituted 2'-deoxyribosyl sugar moiety at position 4 of the central region is a 5'-(S)-allyl 2'-deoxyribosyl sugar moiety.

171. The oligomeric compound of embodiment 162, wherein the 5'-alkyl substituted 2'-deoxyribosyl sugar moiety at position 4 of the central region is a 5'-stereorandom allyl 2'-deoxyribosyl sugar moiety.

172. The oligomeric compound of any of embodiments 50-61 or 67-69, wherein the one modified sugar moiety of the central region is a modified, unsubstituted 2'-deoxyfuranosyl sugar moiety at position 4 of the central region.

173. The oligomeric compound of embodiment 172, wherein the modified, unsubstituted 2'-deoxyfuranosyl sugar moiety at position 4 of the central region is an α-D-2'-deoxyribosyl modified sugar moiety.

174. The oligomeric compound of embodiment 172, wherein the modified, unsubstituted 2'-deoxyfuranosyl sugar moiety at position 4 of the central region is an α-L-2'-deoxyribosyl modified sugar moiety.

175. The oligomeric compound of embodiment 172, wherein the modified, unsubstituted 2'-deoxyfuranosyl sugar moiety at position 4 of the central region is an β-L-2'-deoxyribosyl modified sugar moiety.

176. The oligomeric compound of any of embodiments 50-61 or 67-69, wherein the one modified sugar moiety of the central region is a bicyclic ribosyl sugar moiety at position 4 of the central region.

177. The oligomeric compound of embodiment 176, wherein the bicyclic ribosyl sugar moiety at position 4 of the central region is a cEt or LNA sugar moiety.

178. The oligomeric compound of embodiment 176, wherein the bicyclic ribosyl sugar moiety at position 4 of the central region is a cEt sugar moiety.

179. The oligomeric compound of embodiment 176, wherein the bicyclic ribosyl sugar moiety at position 4 of the central region is a LNA sugar moiety.

180. The oligomeric compound of any of embodiments 50-61 or 67-69, wherein the one modified sugar moiety of the central region is a morpholino sugar moiety at position 4 of the central region.

181. The oligomeric compound of any of embodiments 50-61 or 67-69, wherein the one modified sugar moiety of the central region is a 2'-O-methyl substituted ribosyl sugar moiety at position 5 of the central region.

182. The oligomeric compound of any of embodiments 50-61 or 67-69, wherein the one modified sugar moiety of the central region is a modified, unsubstituted 2'-deoxyfuranosyl sugar moiety at position 5 of the central region.

183. The oligomeric compound of embodiment 182, wherein the modified, unsubstituted 2'-deoxyfuranosyl sugar moiety at position 5 of the central region is a β-L-2'-deoxyribosyl sugar moiety.

184. The oligomeric compound of any of embodiments 50-61 or 67-69, wherein the one modified sugar moiety of the central region is a morpholino sugar moiety at position 6 of the central region.

185. The oligomeric compound of any of embodiments 50-61 or 67-69, wherein the one modified sugar moiety of the central region is a 2'-O-methyl substituted ribosyl sugar moiety at position 6 of the central region.

186. The oligomeric compound of any of embodiments 50-61 or 67-69, wherein the one modified sugar moiety of the central region is a modified, unsubstituted 2'-deoxyfuranosyl sugar moiety at position 6 of the central region.

187. The oligomeric compound of embodiment 186, wherein the modified, unsubstituted 2'-deoxyfuranosyl sugar moiety at position 6 of the central region is a β-L-2'-deoxyribosyl sugar moiety.

188. The oligomeric compound of embodiment 186, wherein the modified, unsubstituted 2'-deoxyfuranosyl sugar moiety at position 6 of the central region is an α-D-2'-deoxyribosyl sugar moiety.

189. The oligomeric compound of any of embodiments 50-61 or 67-69, wherein the one modified sugar moiety of the central region is a 2'-O-methyl substituted ribosyl sugar moiety at position 7 of the central region.

190. The oligomeric compound of any of embodiments 50-61 or 67-69, wherein the one modified sugar moiety of the central region is a modified, unsubstituted 2'-deoxyfuranosyl sugar moiety at position 7 of the central region.

191. The oligomeric compound of embodiment 190, wherein the modified, unsubstituted 2'-deoxyfuranosyl sugar moiety at position 7 of the central region is a β-L-2'-deoxyribosyl sugar moiety.

192. The oligomeric compound of embodiment 190, wherein the modified, unsubstituted 2'-deoxyfuranosyl sugar moiety at position 7 of the central region is an α-D-2'-deoxyribosyl sugar moiety.

193. The oligomeric compound of any of embodiments 50-61 or 67-69, wherein the one modified sugar moiety of the central region is a 2'-O-methyl substituted ribosyl sugar moiety at position 8 of the central region.

194. The oligomeric compound of any of embodiments 50-61 or 67-69, wherein the one modified sugar moiety of the central region is a modified, unsubstituted 2'-deoxyfuranosyl sugar moiety at position 8 of the central region.

195. The oligomeric compound of embodiment 194, wherein the modified, unsubstituted 2'-deoxyfuranosyl sugar moiety at position 8 of the central region is a β-L-2'-deoxyribosyl sugar moiety.

196. The oligomeric compound of embodiment 194, wherein the modified, unsubstituted 2'-deoxyfuranosyl sugar moiety at position 8 of the central region is an α-D-2'-deoxyribosyl sugar moiety.

197. The oligomeric compound of any of embodiments 50-61 or 67-69, wherein the one modified sugar moiety of the central region is a 2'-O-methyl substituted ribosyl sugar moiety at position 9 of the central region.

198. The oligomeric compound of any of embodiments 50-61 or 67-69, wherein the one modified sugar moiety of the central region is a modified, unsubstituted 2'-deoxyfuranosyl sugar moiety at position 9 of the central region.

199. The oligomeric compound of embodiment 198, wherein the modified, unsubstituted 2'-deoxyfuranosyl sugar moiety at position 9 of the central region is a β-L-2'-deoxyribosyl sugar moiety.

200. The oligomeric compound of any of embodiments 50-61 or 67-69, wherein the one modified sugar moiety of the central region is a 2'-O-methyl substituted ribosyl sugar moiety at position 2, 3, 4, 5, 6, 7, 8, or 9 of the central region.

201. The oligomeric compound of any of embodiments 50-61 or 67-69, wherein the one modified sugar moiety of the central region is a 2'-O-methyl substituted ribosyl sugar moiety at position 2, 3, 4, 8, or 9 of the central region.

202. The oligomeric compound of any of embodiments 50-61 or 67-69, wherein the one modified sugar moiety of the central region is a 2'-F substituted ribosyl sugar moiety at position 2, 3, or 4 of the central region.

203. The oligomeric compound of any of embodiments 50-61 or 67-69, wherein the one modified sugar moiety of the central region is a 2'-F substituted ribosyl sugar moiety at position 3 or 4 of the central region.

204. The oligomeric compound of any of embodiments 50-61 or 67-69, wherein the one modified sugar moiety of the central region is a 2'-MOE substituted ribosyl sugar moiety at position 2, 3, or 4 of the central region.

205. The oligomeric compound of any of embodiments 50-61 or 67-69, wherein the one modified sugar moiety of the central region is a 4'-methyl substituted 2'-deoxyribosyl sugar moiety at position 3 or 4 of the central region.

206. The oligomeric compound of any of embodiments 50-61 or 67-69, wherein the one modified sugar moiety of the central region is a 5'-(R)-methyl substituted 2'-deoxyribosyl sugar moiety at position 3 or 4 of the central region.

207. The oligomeric compound of any of embodiments 50-61 or 67-69, wherein the one modified sugar moiety of the central region is a 5'-(S)-methyl substituted 2'-deoxyribosyl sugar moiety at position 2, 3, or 4 of the central region.

208. The oligomeric compound of any of embodiments 50-61 or 67-69, wherein the one modified sugar moiety of the central region is a 5'-(R)-ethyl substituted 2'-deoxyribosyl sugar moiety at position 3 or 4 of the central region.

209. The oligomeric compound of any of embodiments 50-61 or 67-69, wherein the one modified sugar moiety of the central region is a 5'-(S)-ethyl substituted 2'-deoxyribosyl sugar moiety at position 3 or 4 of the central region.

210. The oligomeric compound of any of embodiments 50-61 or 67-69, wherein the one modified sugar moiety of the central region is a 5'-(R)-allyl substituted 2'-deoxyribosyl sugar moiety at position 3 or 4 of the central region.

211. The oligomeric compound of any of embodiments 50-61 or 67-69, wherein the one modified sugar moiety of the central region is a 5'-(S)-allyl substituted 2'-deoxyribosyl sugar moiety at position 3 or 4 of the central region.

212. The oligomeric compound of any of embodiments 50-61 or 67-69, wherein the one modified sugar moiety of the central region is a 5'-stereorandom allyl substituted 2'-deoxyribosyl sugar moiety at position 2, 3, or 4 of the central region.

213. The oligomeric compound of any of embodiments 50-61 or 67-69, wherein the one modified sugar moiety of the central region is a cEt ribosyl sugar moiety at position 2, 3, or 4 of the central region.

214. The oligomeric compound of any of embodiments 50-61 or 67-69, wherein the one modified sugar moiety of the central region is a cEt ribosyl sugar moiety at position 3 or 4 of the central region.

215. The oligomeric compound of any of embodiments 50-61 or 67-69, wherein the one modified sugar moiety of the central region is a LNA ribosyl sugar moiety at position 2, 3, or 4 of the central region.

216. The oligomeric compound of any of embodiments 50-61 or 67-69, wherein the one modified sugar moiety of the central region is a LNA ribosyl sugar moiety at position 3 or 4 of the central region.

217. The oligomeric compound of any of embodiments 50-61 or 67-69, wherein the one modified sugar moiety of the central region is a morpholino sugar moiety at position 1, 3, 4, or 6 of the central region.

218. The oligomeric compound of any of embodiments 50-61 or 67-69, wherein the one modified sugar moiety of the central region is a morpholino sugar moiety at position 1, 3, or 4 of the central region.

219. The oligomeric compound of any of embodiments 50-61 or 67-69, wherein the one modified sugar moiety of the central region is a modified, unsubstituted 2'-deoxyfuranosyl sugar moiety.

220. The oligomeric compound of any of embodiments 50-61 or 67-69, wherein the one modified sugar moiety of the central region is a modified, unsubstituted 2'-deoxyfuranosyl sugar moiety at position 1, 2, 3, 4, 5, 6, 7, 8, or 9 of the central region.

221. The oligomeric compound of any of embodiments 50-61 or 67-69, wherein the one modified sugar moiety of the central region is a modified, unsubstituted 2'-deoxyfuranosyl sugar moiety at position 1, 2, 3, 4, 5, or 9 of the central region.

222. The oligomeric compound of any of embodiments 50-61 or 67-69, wherein the one modified sugar moiety of the central region is an unsubstituted α-D-2'-deoxyribosyl sugar moiety.

223. The oligomeric compound of any of embodiments 50-61 or 67-69, wherein the one modified sugar moiety of the central region is an unsubstituted α-D-2'-deoxyribosyl sugar moiety at position 1, 2, 3, 4, 6, or 8 of the central region.

224. The oligomeric compound of any of embodiments 50-61 or 67-69, wherein the one modified sugar moiety of the central region is an unsubstituted α-D-2'-deoxyribosyl sugar moiety at position 1, 2, or 4 of the central region.

225. The oligomeric compound of any of embodiments 50-61 or 67-69, wherein the one modified sugar moiety of the central region is an unsubstituted α-L-2'-deoxyribosyl sugar moiety.

226. The oligomeric compound of any of embodiments 50-61 or 67-69, wherein the one modified sugar moiety of the central region is an unsubstituted α-L-2'-deoxyribosyl sugar moiety at position 3, 4, or 7 of the central region.

227. The oligomeric compound of any of embodiments 50-61 or 67-69, wherein the one modified sugar moiety of the central region is an unsubstituted β-L-2'-deoxyribosyl sugar moiety.

228. The oligomeric compound of any of embodiments 50-61 or 67-69, wherein the one modified sugar moiety of the central region is an unsubstituted β-L-2'-deoxyribosyl sugar moiety at position 1, 3, 4, 5, 6, 7, 8, or 9 of the central region.

229. The oligomeric compound of any of embodiments 50-61 or 67-69, wherein the one modified sugar moiety of the central region is an unsubstituted β-L-2'-deoxyribosyl sugar moiety at position 3, 4, 5, or 9 of the central region.

230. The oligomeric compound of any of embodiments 50-61 or 67-69, wherein the one modified sugar moiety of the central region is an unsubstituted β-D-2'-deoxyxylosyl sugar moiety.

231. The oligomeric compound of any of embodiments 53-55 or 60-230, wherein the one modified internucleoside linkage of the central region other than phosphorothioate is a phosphonate or phosphotriester internucleoside linkage.

232. The oligomeric compound of embodiment 231, wherein the one modified internucleoside linkage of the central region other than phosphorothioate is an alkyl phosphonate or alkoxy phosphonate internucleoside linkage.

233. The oligomeric compound of embodiment 232, wherein the one modified internucleoside linkage of the central region other than phosphorothioate is a methoxypropyl internucleoside linkage.

234. The oligomeric compound of embodiment 232, wherein the one modified internucleoside linkage of the central region other than phosphorothioate is a methyl phosphonate internucleoside linkage.

235. The oligomeric compound of embodiment 232, wherein the one modified internucleoside linkage of the central region other than phosphorothioate is an isopropyl phosphonate internucleoside linkage.

236. The oligomeric compound of embodiment 232, wherein the one modified internucleoside linkage of the central region other than phosphorothioate is an isobutyl phosphonate internucleoside linkage.

237. The oligomeric compound of embodiment 231, wherein the one modified internucleoside linkage of the central region other than phosphorothioate is a phosphonoacetate internucleoside linkage.

238. The oligomeric compound of embodiment 231, wherein the one modified internucleoside linkage of the central region other than phosphorothioate is an isopropyl phosphotriester internucleoside linkage.

239. The oligomeric compound of embodiment 231, wherein the one modified internucleoside linkage of the central region other than phosphorothioate is a tetrahydropyran phosphotriester internucleoside linkage.

240. The oligomeric compound of any of embodiments 53, 55, or 60-230, wherein the one modified internucleoside linkage of the central region other than phosphorothioate is a formacetal internucleoside linkage.

241. The oligomeric compound of any of embodiments 53, 55, or 60-230, wherein the one modified internucleoside linkage of the central region other than phosphorothioate is an acetamide internucleoside linkage.

242. The oligomeric compound of any of embodiments 53, 55, or 60-230, wherein the one modified internucleoside linkage of the central region other than phosphorothioate is a thioacetamide internucleoside linkage.

243. The oligomeric compound of any of embodiments 231-242, wherein the one modified internucleoside linkage of the central region other than phosphorothioate is between the nucleosides at positions 1 and 2 of the central region.

244. The oligomeric compound of any of embodiments 231-242, wherein the one modified internucleoside linkage of the central region other than phosphorothioate is between the nucleosides at positions 2 and 3 of the central region.

245. The oligomeric compound of any of embodiments 231-242, wherein the one modified internucleoside linkage of the central region other than phosphorothioate is between the nucleosides at positions 3 and 4 of the central region.

246. The oligomeric compound of any of embodiments 231-242, wherein the one modified internucleoside linkage of the central region other than phosphorothioate is between the nucleosides at positions 4 and 5 of the central region.

247. The oligomeric compound of any of embodiments 231-246, wherein the one modified internucleoside linkage of the central region other than phosphorothioate is directly linked to a nucleoside comprising a modified sugar moiety.

248. The oligomeric compound of any of embodiments 56-230, wherein the two neutral internucleoside linkages of the central region are independently selected from a phosphonate internucleoside linkage, phosphotriester internucleoside linkage, and a neutral internucleoside linkage that does not contain phosphorus.

249. The oligomeric compound of embodiment 248, wherein at least one of the modified internucleoside linkages of the central region other than phosphorothioate is an alkyl phosphonate or alkoxy phosphonate internucleoside linkage.

250. The oligomeric compound of embodiment 248, wherein at least one of the modified internucleoside linkages of the central region other than phosphorothioate is a methoxypropyl internucleoside linkage.

251. The oligomeric compound of embodiment 248, wherein at least one of the modified internucleoside linkages of the central region other than phosphorothioate is a methyl phosphonate internucleoside linkage.

252. The oligomeric compound of embodiment 248, wherein at least one of the modified internucleoside linkages of the central region other than phosphorothioate is an isopropyl phosphonate internucleoside linkage.

253. The oligomeric compound of embodiment 248, wherein at least one of the modified internucleoside linkages of the central region other than phosphorothioate is an isobutyl phosphonate internucleoside linkage.

254. The oligomeric compound of embodiment 248, wherein at least one of the modified internucleoside linkages of the central region other than phosphorothioate is a phosphonoacetate internucleoside linkage.

255. The oligomeric compound of embodiment 248, wherein at least one of the modified internucleoside linkages of the central region other than phosphorothioate is an isopropyl phosphotriester internucleoside linkage.

256. The oligomeric compound of embodiment 248, wherein at least one of the modified internucleoside linkages of the central region other than phosphorothioate is a tetrahydropyran phosphotriester internucleoside linkage.

257. The oligomeric compound of embodiment 248, wherein at least one of the modified internucleoside linkages of the central region other than phosphorothioate is a formacetal internucleoside linkage.

258. The oligomeric compound of embodiment 248, wherein at least one of the modified internucleoside linkages of the central region other than phosphorothioate is an acetamide internucleoside linkage.

259. The oligomeric compound of embodiment 248, wherein at least one of the modified internucleoside linkages of the central region other than phosphorothioate is a thioacetamide internucleoside linkage.

260. The oligomeric compound of any of embodiments 248-259, wherein the two modified internucleoside linkages other than phosphorothioate of the central region are adjacent to each other.

261. The oligomeric compound of any of claims 248-260, wherein the two modified internucleoside linkages other than phosphorothioate of the central region are the same as one another.

262. The oligomeric compound of any of embodiments 248-261, wherein one of the modified internucleoside linkages of the central region other than phosphorothioate is between the nucleosides at positions 1 and 2 of the central region.

263. The oligomeric compound of any of embodiments 248-261, wherein one of the modified internucleoside linkages of the central region other than phosphorothioate is between the nucleosides at positions 2 and 3 of the central region.

264. The oligomeric compound of any of embodiments 248-261, wherein one of the modified internucleoside linkages of the central region other than phosphorothioate is between the nucleosides at positions 3 and 4 of the central region.

265. The oligomeric compound of any of embodiments 248-261, wherein one of the modified internucleoside linkages of the central region other than phosphorothioate is between the nucleosides at positions 4 and 5 of the central region.

266. The oligomeric compound of any of embodiments 248-261, wherein one of the modified internucleoside linkages of the central region other than phosphorothioate is directly linked to a nucleoside comprising a modified sugar moiety.

267. The oligomeric compound of any of embodiments 60-266, wherein the one modified nucleobase other than 5-methylcytosine of the central region is 2-thiothymine, 6-methyladenine, inosine, or pseudouracil.

268. The oligomeric compound of embodiment 267, wherein the one modified nucleobase other than 5-methylcytosine is at position 1, 2, 3, or 4 of the central region.

269. The oligomeric compound of embodiment 267, wherein the one modified nucleobase other than 5-methylcytosine is at position 2, 3, or 4 of the central region.

270. The oligomeric compound of embodiment 267, wherein the one modified nucleobase other than 5-methylcytosine is at position 1 of the central region.

271. The oligomeric compound of embodiment 267, wherein the one modified nucleobase other than 5-methylcytosine is at position 2 of the central region.

272. The oligomeric compound of embodiment 267, wherein the one modified nucleobase other than 5-methylcytosine is at position 3 of the central region.

273. The oligomeric compound of embodiment 267, wherein the one modified nucleobase other than 5-methylcytosine is at position 4 of the central region.

274. The oligomeric compound of any of embodiments 267 or 270, wherein the one modified nucleobase other than 5-methylcytosine is 2-thiothymine.

275. The oligomeric compound of any of embodiments 267 or 271, wherein the one modified nucleobase other than 5-methylcytosine is 6-methyladenine.

276. The oligomeric compound of any of embodiments 267 or 271, wherein the one modified nucleobase other than 5-methylcytosine is inosine.

277. The oligomeric compound of any of embodiments 267-273, wherein the one modified nucleobase other than 5-methylcytosine is pseudouracil.

278. The oligomeric compound of embodiment 277, wherein the nucleoside comprising the pseudouracil nucleobase comprises an unmodified ribosyl sugar moiety.

279. The oligomeric compound of any of embodiments 1-52, 60-230, or 267-278, wherein each internucleoside linkage of the central region is independently selected from among a phosphodiester or a phosphorothioate internucleoside linkage.

280. The oligomeric compound of embodiment 279, wherein each internucleoside of the central region is a phosphorothioate internucleoside linkage.

281. The oligomeric compound of any of embodiments 1-279, wherein the central region does not comprise any phosphodiester internucleoside linkages.

282. The oligomeric compound of any of embodiments 1-281, wherein each phosphorothioate internucleoside linkage of the oligomeric compound is stereorandom.

283. The oligomeric compound of any of embodiments 1-281, wherein at least one phosphorothioate internucleoside linkage of the oligomeric compound is in the Rp configuration.

284. The oligomeric compound of any of embodiments 1-281, wherein at least one phosphorothioate internucleoside linkage of the oligomeric compound is in the Sp configuration.

285. The oligomeric compound of any of embodiments 1-284, wherein the nucleobase sequence of the modified oligonucleotide is complementary to a target RNA.

286. The oligomeric compound of embodiment 285, wherein the nucleobase sequence of the modified oligonucleotide is at least 75% complementary to the target RNA.

287. The oligomeric compound of embodiment 285, wherein the nucleobase sequence of the modified oligonucleotide is at least 80% complementary to the target RNA.

288. The oligomeric compound of embodiment 285, wherein the nucleobase sequence of the modified oligonucleotide is at least 85% complementary to the target RNA.

289. The oligomeric compound of embodiment 285, wherein the nucleobase sequence of the modified oligonucleotide is at least 90% complementary to the target RNA.

290. The oligomeric compound of embodiment 285, wherein the nucleobase sequence of the modified oligonucleotide is at least 95% complementary to the target RNA.

291. The oligomeric compound of embodiment 285, wherein the nucleobase sequence of the modified oligonucleotide is 100% complementary to the target RNA.

292. The oligomeric compound of any of embodiments 285-291, wherein the target RNA is a target mRNA or a target pre-mRNA.

293. The oligomeric compound of embodiment 292, wherein the target mRNA or target pre-mRNA is not a mouse, rat, monkey, or human PTEN RNA.

294. The oligomeric compound of embodiment 292 or 293, wherein the target mRNA or target pre-mRNA is not a mouse, rat, monkey, or human SRB-1 RNA.

295. The oligomeric compound of any of embodiments 292-294, wherein the target mRNA or target pre-mRNA is not a mouse, rat, monkey, or human MYD88 RNA.

296. The oligomeric compound of any of embodiments 292-295, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.

297. The oligomeric compound of any of embodiments 285-296, wherein the target RNA is a human RNA.

298. The oligomeric compound of any of embodiments 285-297, wherein the target RNA is expressed in the liver.

299. The oligomeric compound of any of embodiments 285-298, wherein the target RNA is a liver target.

300. The oligomeric compound of any of embodiments 285-297, wherein the target RNA is not expressed in the liver.

301. The oligomeric compound of any of embodiments 285-298 or 300, wherein the target RNA is not a liver target.

302. The oligomeric compound of any of embodiments 285-299, wherein modulation of the expression of the target RNA in the liver is associated with treating a disorder or condition.

303. The oligomeric compound of embodiment 302, wherein the disorder or condition is a liver disorder or condition.

304. The oligomeric compound of any of embodiments 285-303, wherein the target RNA is expressed in the central nervous system.

305. The oligomeric compound of any of embodiments 285-303, wherein the target RNA is not expressed in the central nervous system.

306. The oligomeric compound of any of embodiments 285-298, 300, 301, or 304, wherein the target RNA is a central nervous system target.

307. The oligomeric compound of any of embodiments 285-305, wherein the target RNA is not a central nervous system target.

308. The oligomeric compound of any of embodiments 285-298, 300-301, 304, or 306, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.

309. The oligomeric compound of any of embodiments 285-297, 300-301, 304, or 306, wherein the target RNA is a HTT RNA.

310. The oligomeric compound of embodiment 308, wherein the target RNA is a MeCP2 RNA.

311. The oligomeric compound of embodiment 308, wherein the target RNA is a DUX4 RNA.

312. The oligomeric compound of embodiment 308, wherein the target RNA is a HDAC2 RNA.

313. The oligomeric compound of embodiment 308, wherein the target RNA is a Ataxin 1 RNA.

314. The oligomeric compound of embodiment 308, wherein the target RNA is a Ataxin 2 RNA.

315. The oligomeric compound of embodiment 308, wherein the target RNA is a Ataxin 3 RNA.

316. The oligomeric compound of embodiment 308, wherein the target RNA is a Ataxin 6 RNA.

317. The oligomeric compound of embodiment 308, wherein the target RNA is a Ataxin 7 RNA.

318. The oligomeric compound of embodiment 308, wherein the target RNA is a C9ORF72 RNA.

319. The oligomeric compound of embodiment 285-297, 300-301, 304, or 306, wherein the target RNA is an alpha-synuclein RNA.

320. The oligomeric compound of embodiment 308, wherein the target RNA is an UBE3A RNA.

321. The oligomeric compound of embodiment 285-297, 300-301, 304, or 306, wherein the target RNA is a SOD1 RNA.

322. The oligomeric compound of embodiment 308, wherein the target RNA is a Prion RNA.

323. The oligomeric compound of embodiment 308, wherein the target RNA is a PMP22 RNA.

324. The oligomeric compound of embodiment 308, wherein the target RNA is a Tau RNA.

325. The oligomeric compound of embodiment 308, wherein the target RNA is a LRRK2 RNA.

326. The oligomeric compound of embodiment 308, wherein the target RNA is an APP RNA.

327. The oligomeric compound of embodiment 308, wherein the target RNA is a LINGO2 RNA.

328. The oligomeric compound of embodiment 308, wherein the target RNA is a GYS1 RNA.

329. The oligomeric compound of embodiment 308, wherein the target RNA is a KCNT1 RNA.

330. The oligomeric compound of embodiment 308, wherein the target RNA is a IRF8 RNA.

331. The oligomeric compound of embodiment 308, wherein the target RNA is a Progranulin RNA.

332. The oligomeric compound of embodiment 308, wherein the target RNA is a GFAP RNA.

333. The oligomeric compound of any of embodiments 304, 306, or 308-332, wherein modulation of the expression of the target RNA in the central nervous system is associated with treating a disorder or condition.

334. The oligomeric compound of embodiment 333, wherein the disorder or condition is a neurological disorder or condition.

335. The oligomeric compound of embodiment 333 or 334, wherein the disorder or condition alters the function of sensory or motor neurons.

336. The oligomeric compound of any of embodiments 333-335, wherein the disorder or condition alters the function of sensory neurons.

337. The oligomeric compound of any of embodiments 333-336, wherein the disorder or condition alters the function of motor neurons.

338. The oligomeric compound of any of embodiments 333-337, wherein the disorder or condition alters the function of glial cells.

339. The oligomeric compound of embodiment 338, wherein the disorder or condition alters the function of astrocytes.

340. The oligomeric compound of embodiment 338, wherein the disorder or condition alters the function of oligodendrocytes.

341. The oligomeric compound of embodiment 338, wherein the disorder or condition alters the function of microglia.

342. The oligomeric compound of embodiment 338, wherein the disorder or condition alters the function of ependymal cells.

343. The oligomeric compound of any of embodiments 333-342, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.

344. The oligomeric compound of embodiment 343, wherein the disorder or condition is Alzheimer's Disease.

345. The oligomeric compound of embodiment 343, wherein the disorder or condition is Amyotrophic Lateral Sclerosis.

346. The oligomeric compound of embodiment 343, wherein the disorder or condition is Parkinson's Disease.

347. The oligomeric compound of embodiment 343, wherein the disorder or condition is a Spinocerebellar ataxia.

348. The oligomeric compound of embodiment 343, wherein the disorder or condition is Angelman Syndrome.

349. The oligomeric compound of embodiment 343, wherein the disorder or condition is Alexander's Disease.

350. The oligomeric compound of embodiment 343, wherein the disorder or condition is Lafora Disease.

351. The oligomeric compound of embodiment 343, wherein the disorder or condition is Charcot-Marie Tooth Disease.

352. The oligomeric compound of embodiment 343, wherein the disorder or condition is Prion Disease.

353. The oligomeric compound of embodiment 343, wherein the disorder or condition is a dementia.

354. The oligomeric compound of embodiment 343, wherein the disorder or condition is neurodegeneration.

355. The oligomeric compound of embodiment 343, wherein the disorder or condition is MeCP2 Duplication Syndrome.

356. The oligomeric compound of embodiment 343, wherein the disorder or condition is encephalopathy.

357. The oligomeric compound of embodiment 343, wherein the disorder or condition is neuroinflammation.

358. The oligomeric compound of embodiment 343, wherein the disorder or condition is multiple sclerosis.

359. The oligomeric compound of any of embodiments 1-358, wherein the parent oligomeric compound of the oligomeric compound of any of embodiments 1-358 is cytotoxic in vitro.

360. The oligomeric compound of embodiment 359, wherein the parent oligomeric compound is cytotoxic in a standard in vitro cytotoxicity assay.

361. The oligomeric compound of any of embodiments 1-360, wherein administration to a mouse of the parent oligomeric compound of the oligomeric compound of any of embodiments 1-360 is hepatotoxic to the mouse.

362. The oligomeric compound of embodiment 361, wherein the administration of the parent oligomeric compound to the mouse is systemic administration.

363. The oligomeric compound of embodiment 362, wherein the systemic administration is subcutaneous administration.

364. The oligomeric compound of any of embodiments 361-363, wherein the mouse is a CD-1 mouse.

365. The oligomeric compound of any of embodiments 361-363, wherein the mouse is a C57BL/6 mouse.

366. The oligomeric compound of any of embodiments 361-363, wherein the mouse is a BALB/c mouse.

367. The oligomeric compound of any of embodiments 361-366, wherein the plasma ALT level in the mouse is higher than 500 units per liter following the administration of the parent oligomeric compound.

368. The oligomeric compound of any of embodiments 361-366, wherein the plasma AST level in the mouse is higher than 500 units per liter following the administration of the parent oligomeric compound.

369. The oligomeric compound of any of embodiments 361-366, wherein the plasma ALT level in the mouse is higher than 1000 units per liter following the administration of the parent oligomeric compound.

370. The oligomeric compound of any of embodiments 361-366, wherein the plasma AST level in the mouse is higher than 1000 units per liter following the administration of the parent oligomeric compound.

371. The oligomeric compound of any of embodiments 361-370, wherein the hepatotoxicity is measured 24-48 hours following the administration of the parent oligomeric compound.

372. The oligomeric compound of any of embodiments 361-370, wherein the hepatotoxicity is measured 72 hours following the administration of the parent oligomeric compound.

373. The oligomeric compound of any of embodiments 361-370, wherein the hepatotoxicity is measured 3 days following the administration of the parent oligomeric compound.

374. The oligomeric compound of any of embodiments 361-370, wherein the hepatotoxicity is measured 5 days following the administration of the parent oligomeric compound.

375. The oligomeric compound of any of embodiments 361-370, wherein the hepatotoxicity is measured 7 days following the administration of the parent oligomeric compound.

376. The oligomeric compound of any of embodiments 361-370, wherein the hepatotoxicity is measured 10 days following the administration of the parent oligomeric compound.

377. The oligomeric compound of any of embodiments 361-370, wherein the hepatotoxicity is measured 14 days following the administration of the parent oligomeric compound.

378. The oligomeric compound of any of embodiments 361-377, wherein 1-10 mg/kg of the parent oligomeric compound is administered to the mouse.

379. The oligomeric compound of any of embodiments 361-377, wherein 10-25 mg/kg of the parent oligomeric compound is administered to the mouse.

380. The oligomeric compound of any of embodiments 361-377, wherein 25-50 mg/kg of the parent oligomeric compound is administered to the mouse.

381. The oligomeric compound of any of embodiments 361-377, wherein 50-100 mg/kg of the parent oligomeric compound is administered to the mouse.

382. The oligomeric compound of any of embodiments 361-377, wherein 100-150 mg/kg of the parent oligomeric compound is administered to the mouse.

383. The oligomeric compound of any of embodiments 361-363, 366-370, 372, or 382, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.

384. The oligomeric compound of any of embodiments 1-383, wherein administration of 50 mg/kg of the oligomeric compound of any of embodiments 1-383 to a mouse is not hepatotoxic to the mouse.

385. The oligomeric compound of embodiment 384, wherein plasma ALT level in the mouse is lower than 100 units per liter following the administration of the oligomeric compound of embodiment 384.

386. The oligomeric compound of embodiment 384 or 385, wherein plasma ALT level in the mouse is at least 10-fold lower than plasma ALT level in a mouse administered the parent oligomeric compound of the oligomeric compound of embodiment 384 or 385, wherein the administrations and plasma ALT measurements of both the oligomeric compound of embodiment 384 or 385 and the parent oligomeric compound are completed in the same way.

387. The oligomeric compound of embodiment 386, wherein the plasma ALT level in the mouse is at least 100-fold lower than the plasma ALT level in the mouse administered the parent oligomeric compound.

388. The oligomeric compound of embodiment 386, wherein the plasma ALT level in the mouse is at least 500-fold lower than the plasma ALT level in the mouse administered the parent oligomeric compound.

389. The oligomeric compound of any of embodiments 359-388, wherein the therapeutic index in a mouse of the oligomeric compound of any of embodiments 359-388 is increased relative to the therapeutic index of the parent oligomeric compound.

390. The oligomeric compound of embodiment 389, wherein the therapeutic index in a mouse of the oligomeric compound of embodiment 365 is at least two-fold greater than the therapeutic index of the parent oligomeric compound.

391. The oligomeric compound of any of embodiments 1-390, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse;

and wherein the otherwise identical oligomeric compound has a central region consisting of phosphorothioate internucleoside linkages, unmodified 2'β-D-deoxyribosyl sugar moieties, and nucleobases selected from thymine, uracil, adenine, guanine, cytosine, and 5-methylcytosine.

392. The oligomeric compound of embodiment 391, wherein the at least one modified internucleoside linkage other than phosphorothioate and/or at least one modified nucleoside comprising a modified nucleobase other than 5-methylcytosine and/or a modified sugar moiety in the central region is a 2'-O-methyl modified sugar moiety.

393. The oligomeric compound of embodiment 392, wherein the 2'-O-methyl modified sugar moiety is at position 2 of the central region.

394. The oligomeric compound of embodiment 392 or 393, wherein the otherwise identical oligomeric compound lacks a 2'-O-methyl modified sugar moiety, and wherein the otherwise identical oligomeric compound comprises an unmodified 2'β-D-deoxyribosyl sugar moiety in place of the 2'-O-methyl modified sugar moiety.

395. The oligomeric compound of any of embodiments 391-394, wherein the nucleobase sequence of the otherwise identical oligomeric compound is 100% complementary to the target RNA.

396. The oligomeric compound of any of embodiments 391-395, wherein the otherwise identical oligomeric compound is a parent oligomeric compound of the oligomeric compound of any of embodiments 391-395.

397. The oligomeric compound of any of embodiments 285-396, wherein the oligomeric compound inhibits the target RNA with an $IC_{50}$ lower than 100 nM in a standard in vitro activity assay.

398. The oligomeric compound of any of embodiments 285-397, wherein the parent oligomeric compound of the oligomeric compound of any of embodiments 285-397 inhibits the target RNA with an $IC_{50}$ lower than 100 nM in a standard in vitro activity assay.

399. The oligomeric compound of any of embodiments 285-398, wherein the difference between the $IC_{50}$ of the parent oligomeric compound measured in a standard in vitro activity assay and the $IC_{50}$ of the oligomeric compound of any of embodiments 285-398 measured in a standard in vitro activity assay is less than 4-fold.

400. The oligomeric compound of any of embodiments 285-398, wherein the difference between the $IC_{50}$ of the parent oligomeric compound measured in a standard in vitro activity assay and the $IC_{50}$ of the oligomeric compound of any of embodiments 285-398 measured in a standard in vitro activity assay is less than 3-fold.

401. The oligomeric compound of any of embodiments 285-398, wherein the difference between the $IC_{50}$ of the parent oligomeric compound measured in a standard in vitro activity assay and the $IC_{50}$ of the oligomeric compound of any of embodiments 285-398 measured in a standard in vitro activity assay is less than 2-fold.

402. The oligomeric compound of any of embodiments 359-390 or 396-401, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

403. The oligomeric compound of any of embodiments 359-390 or 396-402, wherein the nucleobase sequence of the parent oligomeric compound is 100% complementary to the target RNA.

404. The oligomeric compound of any of embodiments 1-403, wherein administration of 10-50 mg of the oligomeric compound to a human is not hepatotoxic to the human.

405. The oligomeric compound of any of embodiments 1-403, wherein administration of 50-100 mg of the oligomeric compound to a human is not hepatotoxic to the human.

406. The oligomeric compound of any of embodiments 1-403, wherein administration of 100-300 mg of the oligomeric compound to a human is not hepatotoxic to the human.

407. The oligomeric compound of any of embodiments 404-406, wherein the administration is systemic administration.

408. A composition comprising the oligomeric compound of any of embodiments 1-407 and a second oligomeric compound, wherein the second oligomeric compound is complementary to the oligomeric compound of any of embodiments 1-407.

409. The composition of embodiment 408, wherein the second oligomeric compound comprises at least 14 contiguous linked nucleosides that are at least 90% complementary to the oligomeric compound of any of embodiments 1-407.

410. The composition of embodiment 408, wherein the second oligomeric compound comprises at least 14 contiguous linked nucleosides that are 100% complementary to the oligomeric compound of any of embodiments 1-407.

411. A pharmaceutical composition comprising the oligomeric compound of any of embodiments 1-407 or the composition of any of embodiments 408-410, comprising a pharmaceutically acceptable carrier or diluent.

412. A method comprising administering the oligomeric compound or composition of any of embodiments 1-411 to a human subject.

413. A method of treating a disease or disorder comprising administering the oligomeric compound or composition of any of embodiments 1-411 to a human subject.

414. A method of modulating the amount or activity of a target RNA in a human subject comprising administering the oligomeric compound or composition of any of embodiments 1-411 to the human subject; and thereby modulating the amount or activity of the target RNA in the human subject.

415. A method of treating a disease or disorder in a human subject comprising administering the oligomeric compound or composition of any of embodiments 1-411 to the human subject having the disease or disorder; and thereby treating the disease or disorder in the human subject.

416. The method of embodiment 413 or 415, wherein the disease or disorder is a liver disease, and wherein the oligomeric compound modulates the amount or activity of a liver target RNA.

417. The method of embodiment 413 or 415, wherein the disease or disorder is a central nervous system disease, and wherein the oligomeric compound modulates the amount or activity of a central nervous system target RNA.

418. The method of any of embodiments 413 or 415-417, wherein the disease or disorder is a cancer, a neurodegenerative disease, a cardiovascular disease, an immunological disease, a hereditary disease, a repeat expansion disease, a muscle-wasting disease, or a metabolic disease.

419. The method of any of embodiments 412-418, wherein the plasma ALT level of the human subject after the administration is not more than three times higher than it was prior to the administration.

420. The method of any of embodiments 412-418, wherein the plasma ALT level of the human subject after the administration is not more than 150 units per liter.

421. The method of any of embodiments 412-416 or 418-420, wherein the human subject is susceptible to liver damage.

422. The method of any of embodiments 412-416 or 418-420, wherein the human subject is susceptible to liver degeneration.

423. The method of any of embodiments 412-416 or 418-420, wherein the human subject is susceptible to elevated apoptosis in the liver.

424. The method of any of embodiments 412-416 or 418-423, wherein the human subject has a liver disease.

425. The method of any of embodiments 412-424, comprising administering the parent oligomeric compound of the oligomeric compound of any of embodiments 1-407 to a mouse.

426. The method of any of embodiments 412-424, comprising contacting a cell with the parent oligomeric compound of the oligomeric compound of any of embodiments 1-407.

427. The method of embodiment 425 or 426, wherein each sugar moiety of the central region of the parent oligomeric compound is an unmodified 2'β-D-deoxyribosyl sugar moiety, and wherein each internucleoside linkage of the central region of the parent oligomeric compound is a phosphorothioate internucleoside linkage.

428. A method of designing an oligomeric compound comprising starting with a parent oligomeric compound and changing the design of that compound in order to arrive at an oligomeric compound of any one of embodiments 1-407.

429. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 1-407.

430. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 1-407.

431. The method of embodiment 428, wherein the method designs an oligomeric compound with improved therapeutic index relative to the parent oligomeric compound.

432. The method of embodiment 428 or 431, wherein the method designs an oligomeric compound with lower hepatotoxicity relative to the parent oligomeric compound.

433. The method of embodiment 429, wherein the second oligomeric compound has an improved therapeutic index relative to the parent oligomeric compound.

434. The method of embodiment 429 or 433, wherein the second oligomeric compound has reduced hepatotoxicity in a mouse relative to the parent oligomeric compound.

435. The method of embodiment 430, wherein the oligomeric compound according to any one of embodiments 1-407 has reduced hepatotoxicity relative to the parent oligomeric compound.

436. A method comprising administering an oligomeric compound of any of embodiments 1-407 to a mouse and separately administering the parent oligomeric compound of the oligomeric compound of any of embodiments 1-407 to a second mouse, wherein the therapeutic index of the oligomeric compound of any of embodiments 1-407 is improved relative to the therapeutic index of the parent oligomeric compound.

437. The method of any of embodiments 412-436, wherein the level of p21 RNA is measured in the mouse, the cell, and/or the human subject.

438. A method comprising administering an oligomeric compound to a subject and measuring the level of p21 RNA in the subject.

439. A method comprising administering an oligomeric compound of any of embodiments 1-407 to a subject and measuring the level of p21 RNA in the subject.

440. The method of embodiment 438 or 439, wherein the subject is a mouse.

441. The method of embodiment 438 or 439, wherein the subject is a human.

442. The method of any of embodiments 437-441, wherein the p21 RNA level is measured within 24 hours of the administration.

443. The method of any of embodiments 437-441, wherein the p21 RNA level is measured 24-48 hours following the administration.

444. An oligomeric compound or composition of any one of embodiments 1-411, for use in medical therapy.

445. A method comprising contacting a cell with an oligomeric compound and detecting the cellular localization of p54nrb protein in the cell.

446. The method of embodiment 445, comprising determining the relative amount of p54nrb protein in the nucleolus relative to other cells contacted with different oligomeric compounds.

447. The method of embodiment 445 or 446, comprising determining the relative amount of p54nrb in the nucleolus relative to the amount of p54nrb in the rest of the cell.

448. The method of any of embodiments 445-447, wherein the cell is in a plate containing at least 96 wells.

449. The method of any of embodiments 445-448, wherein the detection of the cellular localization of p54nrb comprises contacting the cell with a p54nrb antibody.

450. A method of screening for a tolerable oligomeric compound comprising any of the methods of embodiments 445-449.

451. The method of any of embodiments 445-450, wherein the oligomeric compound is the oligomeric compound of any of embodiments 1-407.

452. An oligomeric compound comprising a modified oligonucleotide consisting of 12-23 linked nucleosides, wherein the modified oligonucleotide comprises a 5'-region, a central region, and a 3'-region wherein:
the 5'-region consists of 1-5 linked modified nucleosides;
the 3'-region consists of 1-5 linked modified nucleosides;
and the central region consists of 7-11 linked nucleosides and has the formula:

$(N_{d1})(N_x)(N_y)(N_z)(N_d)_q$ wherein one of $N_x$, $N_y$, and $N_z$ is a safety enhancing nucleoside;
the other two of $N_x$, $N_y$, and $N_z$ are independently selected from an unmodified 2'β-D-deoxyribosyl, a DNA isomer, and a DNA mimic;
$N_{d1}$ and each $N_d$ is independently selected from an unmodified 2'-β-D-deoxyribosyl, a DNA isomer, and a DNA mimic; and wherein q is 2-7.

453. The oligomeric compound of embodiment 1, wherein the safety enhancing nucleoside is $N_x$ or $N_y$.

454. The oligomeric compound of embodiment 1, wherein the safety enhancing nucleoside is $N_x$.

455. The oligomeric compound of embodiment 1, wherein the safety enhancing nucleoside is $N_y$.

456. The oligomeric compound of embodiment 1, wherein the safety enhancing nucleoside is $N_z$.

457. The oligomeric compound of any of embodiments 452-456, wherein the safety enhancing nucleoside has a sugar moiety selected from among a sugar surrogate, a bicyclic furanosyl sugar moiety, a non-bicyclic 2'-modified furanosyl sugar moiety, a non-bicyclic 4'-modified furanosyl sugar moiety, or a non-bicyclic 5'-modified furanosyl sugar moiety.

458. The oligomeric compound of any of embodiments 452-457, wherein the safety-enhancing nucleoside has a sugar moiety selected from among a morpholino, a 2'-O-methyl-2'β-D-deoxyribosy sugar moiety, a cEt bicyclic sugar moiety, a LNA sugar moiety, an ENA sugar moiety, a 5'-methyl substituted 2'-deoxyribosyl sugar moiety, 5'-ethyl substituted 2'-deoxyribosyl sugar moiety, a 5'-allyl substituted 2'-deoxyribosyl sugar moiety and a 2'β-L-deoxyxylosyl sugar moiety.

459. The oligomeric compound of any of embodiments 452-458, wherein the safety-enhancing nucleoside has a sugar moiety selected from among a 2'-O-methyl-modified sugar moiety and a 5'-modified sugar moiety.

460. The oligomeric compound of embodiment 459, wherein the safety-enhancing nucleoside has a 2'-O-methyl substituted ribosyl sugar moiety.

461. The oligomeric compound of any of embodiments 452-457, wherein the safety-enhancing nucleoside is a sugar surrogate.

462. The oligomeric compound of embodiment 461, wherein the sugar surrogate is selected from among a morpholino, a modified morpholino, and F-HNA.

463. The oligomeric compound of any of embodiments 452-462, wherein $N_{d1}$ is an unmodified 2'-β-D-deoxyribosyl sugar moiety.

464. The oligomeric compound of any of embodiments 452-462, wherein $N_{d1}$ is a DNA isomer.

465. The oligomeric compound of any of embodiments 452-462, wherein $N_{d1}$ is a DNA mimic.

466. The oligomeric compound of any of embodiments 452-465, wherein no more than 3 of the central region nucleosides comprise a sugar moiety other than 2'β-D-deoxyribosyl.

467. The oligomeric compound of any of embodiments 452-466, wherein each DNA isomer has a sugar moiety independently selected from among 2'β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl.

468. The oligomeric compound of any of embodiments 452-467, wherein each DNA mimic has a sugar moiety is independently selected from among 5'-methyl-2'-β-D-deoxyribosyl and 5'-ethyl-2'-β-D-deoxyribosyl.

469. The oligomeric compound of any of embodiments 452-463, wherein each nucleoside of the central region other than the safety-enhancing nucleoside has a 2'β-D-deoxyribosyl sugar moiety.

470. The oligomeric compound of any of 452-469, wherein at least one internucleoside linkage is a phosphorothioate linkage.

471. The oligomeric compound of any of embodiments 452-470, wherein at least 4 internucleoside linkages are phosphorothioate linkages.

472. The oligomeric compound of any of embodiments 452-471, wherein at least one internucleoside linkage is a neutral internucleoside linkage.

473. The oligomeric compound of any of embodiments 452-472, wherein at least one neutral internucleoside linkage is a phosphonate internucleoside linkage.

474. The oligomeric compound of any of embodiments 452-474, wherein at least one neutral internucleoside linkage is a methoxypropyl internucleoside linkage.

475. The oligomeric compound of any of embodiments 452-475, wherein at least one internucleoside linkage of the central region selected from among: the internucleoside Nd1 to Nx, Nx to Ny, Ny to Nz, or Nz to the adjacent Nd is a neutral internucleoside linkage.

476. The oligomeric compound of embodiment 475, wherein the modified oligonucleotide comprises one neutral linkage and the other internucleoside linkages are each independently selected from phosphodiester and phosphorothioate.

477. The oligomeric compound of any of embodiments 542-454 or embodiments 457-476, wherein the safety enhancing nucleoside is $N_x$ and is a 2'O-methyl-substituted nucleoside.

478. The oligomeric compound of any of embodiments 2-453, 455, or embodiments 457-476, wherein the safety enhancing nucleoside is $N_y$ and is a 2'O-methyl-substituted nucleoside.

479. The oligomeric compound of any of embodiments 452-453, 455, or embodiments 457-476, wherein the safety enhancing nucleoside is $N_y$ and has a 5'-substituted 2'-deoxyribosyl sugar moiety.

480. The oligomeric compound of any of embodiments 452 or embodiments 457-476, wherein the safety enhancing nucleoside is $N_z$ and has a 5'-substituted 2'-deoxyribosyl sugar moiety.

481. The oligomeric compound of embodiments 479 or 480, wherein the 5'-substituted ribosyl sugar moiety is a 5'-methyl, 5'-ethyl, or 5'-allyl substituted 2'-deoxyribosyl sugar moiety.

482. The oligomeric compound of embodiments 477-481, wherein at least one nucleoside of the 5'-region comprises a bicyclic furanosyl sugar moiety.

483. The oligomeric compound of any of embodiments 477-482, wherein each nucleoside of the 5'-region comprises a bicyclic furanosyl sugar moiety.

484. The oligomeric compound of any of embodiments 482 or 483, wherein each bicyclic sugar moiety of the 5'-region is selected from among cEt, LNA, and ENA.

485. The oligomeric compound of any of embodiments 452-482 or 484, wherein at least one nucleoside of the 5'-region comprises a non-bicyclic sugar moiety.

486. The oligomeric compound of embodiment 485, wherein the non-bicyclic sugar moiety of the at least one nucleoside of the 5'-region is a 2'-substituted ribosyl sugar moiety.

487. The oligomeric compound of any of embodiments 485-487, wherein each non-bicyclic sugar moiety of the 5'-region has a 2'-substituent selected from among 2'-MOE, 2'-OMe, and 2'-NMA.

488. The oligomeric compound of any of embodiments 477-480, wherein the 5'-region comprises a 2'-MOE modified nucleoside and an LNA modified nucleoside.

489. The oligomeric compound of any of embodiments 477-480, wherein the 5'-region comprises a 2'-MOE modified nucleoside and a cEt modified nucleoside.

490. The oligomeric compound of embodiments 477-489, wherein at least one nucleoside of the 3'-region comprises a bicyclic furanosyl sugar moiety.

491. The oligomeric compound of any of embodiments 477-490, wherein each nucleoside of the 3'-region comprises a bicyclic furanosyl sugar moiety.

492. The oligomeric compound of any of embodiments 490 or 491, wherein each bicyclic sugar moiety of the 3'-region is selected from among cEt, LNA, and ENA.

493. The oligomeric compound of any of embodiments 490 or 492, wherein at least one nucleoside of the 3'-region comprises a non-bicyclic sugar moiety.

494. The oligomeric compound of embodiment 493, wherein the non-bicyclic sugar moiety of the at least one nucleoside of the 3'-region is a 2'-substituted ribosyl sugar moiety.

495. The oligomeric compound of any of embodiments 490 or 492-494, wherein each non-bicyclic sugar moiety of the 3'-region has a 2'-substituent selected from among 2'-MOE, 2'-OMe, and 2'-NMA.

496. The oligomeric compound of any of embodiments 477-490 or 492-495, wherein the 3'-region comprises a 2'-MOE modified nucleoside and an LNA modified nucleoside.

497. The oligomeric compound of any of embodiments 477-490 or 492-495, wherein the 3'-region comprises a 2'-MOE modified nucleoside and a cEt modified nucleoside.

498. The oligomeric compound of any of embodiments 477-480, wherein each nucleoside of the 5'-region comprises a bicyclic furanosyl sugar moiety and each nucleoside of the 3'-region comprises a non-bicyclic sugar moiety.

499. The oligomeric compound of any of embodiments 477-480, wherein each nucleoside of the 5'-region comprises an LNA sugar moiety and each nucleoside of the 3'-region comprises a 2'MOE sugar moiety.

500. The oligomeric compound of any of embodiments 477-480, wherein each nucleoside of the 5'-region comprises cEt sugar moiety and each nucleoside of the 3'-region comprises a 2'MOE sugar moiety.

501. The oligomeric compound of any of embodiments 452-500, wherein the modified oligonucleotide has a nucleobase sequence complementary to a target RNA; wherein the target RNA is a mRNA or pre-mRNA.

502. The oligomeric compound of embodiment 501, wherein the target RNA encodes a protein that is expressed in the liver.

503. The oligomeric compound of embodiment 502, wherein the target RNA encodes a protein that is expressed in the CNS.

504. The oligomeric compound of any of embodiments 452-503, wherein the oligomeric compound is not toxic.

505. The oligomeric compound of any of embodiment 452-504, wherein a comparator compound is toxic; wherein the comparator compound is identical to the oligomeric compound except that each nucleoside of the central region of the comparator compound is a nucleoside comprising 2'-β-D-deoxyribosyl sugar moiety.

506. The oligomeric compound of embodiment 505, wherein administering a dose of the oligomeric compound to an animal results in a circulating ALT level that is at least 3-fold lower than the ALT level that results from administering the same dose of the comparator compound to an animal for at least one matched dose.

507. The oligomeric compound of embodiment 505 or 506, wherein the lowest dose of the oligomeric compound that raises circulating ALT to over 300 units per liter is at least three-fold higher than the lowest dose of the comparator compound that raises circulating ALT to over 300 units per liter.

508. The oligomeric compound of any of embodiments 502-507, wherein the oligomeric compound is capable of reducing the target RNA in a cell.

509. The oligomeric compound of embodiment 508, wherein the oligomeric compound has RNA-reducing activity comparable to a comparator compound, wherein the comparator compound is identical to the oligomeric compound except that each nucleoside of the central region of the comparator compound is a nucleoside comprising 2'-β-D-deoxyribosyl sugar moiety.

510. The oligomeric compound of embodiment 509 having RNA-reducing activity that is no more than 2-fold worse than the RNA-reducing activity of the comparator compound.

511. An oligomeric compound comprising a modified oligonucleotide consisting of 12-23 linked nucleosides, wherein the modified oligonucleotide comprises a 5'-region, a central region, and a 3'-region wherein:
the 5'-region consists of 1-5 linked nucleosides; wherein at least one 5'-region nucleoside is modified;
the 3'-region consists of 1-5 linked nucleosides; wherein at least one 3'-region nucleoside is modified; and
the central region consists of 7-11 linked nucleosides, and has the formula:

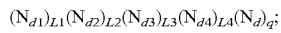

$(N_{d1})_{L1}(N_{d2})_{L2}(N_{d3})_{L3}(N_{d4})_{L4}(N_d)_q$;

wherein $N_{d1}$, $N_{d2}$, $N_{d3}$, $N_{d4}$, and each $N_d$ are independently selected from among a nucleoside comprising an unmodified 2'-β-D-deoxyribosyl sugar moiety, a DNA isomer sugar moiety, or a DNA mimic sugar moiety;
wherein each L1, L2, L3, and L4 is an internucleoside linkage; and wherein
at least one of L1, L2, L3, and L4 is a neutral internucleoside linkage.

512. The oligomeric compound of embodiment 511, wherein L1 is a neutral internucleoside linkage.

513. The oligomeric compound of embodiment 511, wherein L2 is a neutral internucleoside linkage.

514. The oligomeric compound of embodiment 511, wherein L3 is a neutral internucleoside linkage.

515. The oligomeric compound of any of embodiments 511-514, wherein the neutral linkage is a phosphonate internucleoside linkage.

516. The oligomeric compound of any of embodiments 511-515, wherein the neutral linkage is a methoxypropyl internucleoside linkage.

517. The oligomeric compound of any of embodiments 511-516, wherein each remaining internucleoside linkage is a phosphodiester or phosphorothioate internucleoside linkage.

518. A method comprising administering the oligomeric compound or composition of any of embodiments 452-517 to a human subject.

519. A method of treating a disease or disorder comprising administering the oligomeric compound or composition of any of embodiments 452-517 to a human subject.

520. A method of modulating the amount or activity of a target RNA in a human subject comprising administering the oligomeric compound or composition of any of embodiments 452-517 to the human subject; and thereby modulating the amount or activity of the target RNA in the human subject.

521. A method of treating a disease or disorder in a human subject comprising administering the oligomeric compound or composition of any of embodiments 452-517 to the human subject having the disease or disorder; and thereby treating the disease or disorder in the human subject.

522. The method of embodiment 520 or 521, wherein the disease or disorder is a liver disease, and wherein the oligomeric compound modulates the amount or activity of a liver target RNA.

523. The method of embodiment 520 or 521, wherein the disease or disorder is a central nervous system disease, and wherein the oligomeric compound modulates the amount or activity of a central nervous system target RNA.

524. The method of any of embodiments 519-523, wherein the disease or disorder is a cancer, a neurodegenerative disease, a cardiovascular disease, an immunological disease, a hereditary disease, a repeat expansion disease, a muscle-wasting disease, or a metabolic disease.

525. The method of any of embodiments 518-524, wherein the plasma ALT level of the human subject after the administration is not more than three times higher than it was prior to the administration.

526. The method of any of embodiments 518-525, wherein the plasma ALT level of the human subject after the administration is not more than 150 units per liter.

527. The method of any of embodiments 518-526, wherein the human subject is susceptible to liver damage.

528. The method of any of embodiments 518-527, wherein the human subject is susceptible to liver degeneration.

529. The method of any of embodiments 518-528, wherein the human subject is susceptible to elevated apoptosis in the liver.

530. The method of any of embodiments 518-529, wherein the human subject has a liver disease.

531. The method of any of embodiments 518-530, comprising administering the parent oligomeric compound of the oligomeric compound of any of embodiments 452-517 to a mouse.

532. The method of any of embodiments 518-531, comprising contacting a cell with the parent oligomeric compound of the oligomeric compound of any of embodiments 452-517.

533. The method of embodiment 518-532, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

534. A method of designing an oligomeric compound comprising starting with a parent oligomeric compound and changing the design of that compound in order to arrive at an oligomeric compound of any one of embodiments 452-517.

535. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 452-517.

536. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 452-517.

537. The method of embodiment 536, wherein the method designs an oligomeric compound with improved therapeutic index relative to the parent oligomeric compound.

538. The method of embodiment 534-537, wherein the method designs an oligomeric compound with lower hepatotoxicity relative to the parent oligomeric compound.

539. The method of embodiment 535-538, wherein the second oligomeric compound has an improved therapeutic index relative to the parent oligomeric compound.

540. The method of embodiment 535-539, wherein the second oligomeric compound has reduced hepatotoxicity in a mouse relative to the parent oligomeric compound.

541. The method of embodiment 540, wherein the oligomeric compound according to any one of embodiments 452-517 has reduced hepatotoxicity relative to the parent oligomeric compound.

542. A method comprising administering an oligomeric compound of any of embodiments 452-517 to a mouse and separately administering the parent oligomeric compound of the oligomeric compound of any of embodiments 452-517 to a second mouse, wherein the therapeutic index of the oligomeric compound of any of embodiments 452-517 is improved relative to the therapeutic index of the parent oligomeric compound.

543. The method of any of embodiments 518-542, wherein the level of p21 RNA is measured in the mouse, the cell, and/or the human subject.

544. A method comprising administering an oligomeric compound of any of embodiments 452-517 to a subject and measuring the level of p21 RNA in the subject.

545. The method of embodiment 543 or 544, wherein the subject is a mouse.

546. The method of embodiment 543 or 544, wherein the subject is a human.

547. The method of any of embodiments 543-546, wherein the p21 RNA level is measured within 24 hours of the administration.

548. The method of any of embodiments 437-441, wherein the p21 RNA level is measured 24-48 hours following the administration.

549. An oligomeric compound or composition of any one of embodiments 452-517, for use in medical therapy.

550. The method of any of embodiments 445-449, wherein the oligomeric compound is the oligomeric compound of any of embodiments 452-517.

551. An oligomeric compound comprising a modified oligonucleotide consisting of 12-21 linked nucleosides, wherein the modified oligonucleotide has the formula A-B-C, wherein A is a 5'-region, B is a central region, and C is a 3'-region; wherein:
  the 5'-region consists of 1-5 linked nucleosides, wherein at least one nucleoside of the 5'-region is a modified nucleoside comprising a modified sugar;
  the 3'-region consists of 1-5 linked nucleosides wherein at least one nucleoside of the 3'-region is a modified nucleoside comprising a modified sugar; and
  the central region consists of 7-11 linked nucleosides, wherein the 5'-most portion of the central region has the following formula:

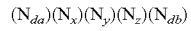

wherein one of $N_x$, $N_y$, and $N_z$ is a safety-enhancing nucleoside;
the other two of $N_x$, $N_y$, and $N_z$ are independently selected from a DNA nucleoside, a DNA isomer, a modified DNA isomer, and a DNA mimic; and
$N_{da}$ and $N_{db}$ are each independently selected from a DNA nucleoside, a DNA isomer, a modified DNA isomer, and a DNA mimic.

552. The oligomeric compound of embodiment 551, wherein the 5'-region consists of one nucleoside.

553. The oligomeric compound of embodiment 551, wherein the 5'-region consists of 2-5 linked nucleosides.

554. The oligomeric compound of embodiment 551, wherein the 5'-region consists of 2-4 linked nucleosides.

555. The oligomeric compound of embodiment 551, wherein the 5'-region consists of 2 linked nucleosides.

556. The oligomeric compound of embodiment 551, wherein the 5'-region consists of 3 linked nucleosides.

557. The oligomeric compound of embodiment 551, wherein the 5'-region consists of 4 linked nucleosides.

558. The oligomeric compound of embodiment 551, wherein the 5'-region consists of 5 linked nucleosides.

559. The oligomeric compound of any of embodiments 551-558, wherein each nucleoside of the 5'-region is a modified nucleoside.

560. The oligomeric compound of any of embodiments 551-559, wherein each nucleoside of the 5'-region is a modified nucleoside comprising a modified sugar.

561. The oligomeric compound of any of embodiments 551-560, wherein each modified nucleoside of the 5'-region has the same modification.

562. The oligomeric compound of and of embodiments 551-560, wherein at least two nucleosides of the 5'-region are modified nucleosides having different modifications.

563. The oligomeric compound of any of embodiments 551-562, wherein each nucleoside of the 5'-region comprises a 2'-modified ribosyl sugar moiety.

564. The oligomeric compound of any of embodiments 551-563, wherein at least one nucleoside of the 5'-region comprises a bicyclic furanosyl sugar moiety.

565. The oligomeric compound of any of embodiments 551-564, wherein each nucleoside of the 5'-region comprises a bicyclic furanosyl sugar moiety.

566. The oligomeric compound of any of embodiments 551-565, wherein at least one nucleoside of the 5'-region comprises a non-bicyclic sugar moiety.

567. The oligomeric compound of embodiment 566, wherein the non-bicyclic sugar moiety of the at least one nucleoside of the 5'-region is a 2'-substituted ribosyl sugar moiety.

568. The oligomeric compound of any of embodiments 551-567, wherein each nucleoside of the 5'-region comprises a non-bicyclic sugar moiety.

569. The oligomeric compound of embodiment 568, wherein each nucleoside of the 5'-region comprises a 2'-substituted furanosyl sugar moiety.

570. The oligomeric compound of any of embodiments 551-569, wherein each nucleoside of the 5'-region comprises a 2'-modified furanosyl sugar moiety independently selected from a bicyclic sugar moiety and a non-bicyclic 2'-substituted ribosyl sugar moiety.

571. The oligomeric compound of any of embodiments 551-570, wherein each nucleoside of the 5'-region comprises a bicyclic sugar moiety.

572. The oligomeric compound of any of embodiments 551-571, wherein each nucleoside of the 5'-region comprises a non-bicyclic 2'-substituted ribosyl sugar moiety.

573. The oligomeric compound of any of embodiments 551-572, wherein each bicyclic sugar moiety of the 5'-region is selected from among cEt, LNA, and ENA.

574. The oligomeric compound of any of embodiments 551-573, wherein each bicyclic sugar moiety of the 5'-region is a cEt sugar moiety.

575. The oligomeric compound of any of embodiments 551-574, wherein each bicyclic sugar moiety of the 5'-region is an LNA sugar moiety.

576. The oligomeric compound of any of embodiments 551-575, wherein each non-bicyclic sugar moiety of the 5'-region has a 2'-substituent selected from among 2'-MOE, 2'-OMe, and 2'-NMA.

577. The oligomeric compound of any of embodiments 551-576, wherein none of the nucleosides of the 5'-region comprise a sugar moiety having a 2'-F substituent.

578. The oligomeric compound of any of embodiments 551-577, wherein none of the nucleosides of the 5'-region comprise a sugar moiety having a 2'-MOE substituent.

579. The oligomeric compound of any of embodiments 551-578, wherein none of the nucleosides of the 5'-region comprise a sugar moiety having a 2'-OMe substituent.

580. The oligomeric compound of any of embodiments 551-579, wherein none of the nucleosides of the 5'-region comprise a cEt sugar moiety.

581. The oligomeric compound of any of embodiments 551-580, wherein none of the nucleosides of the 5'-region comprise a LNA sugar moiety.

582. The oligomeric compound of any of embodiments 551-581, wherein each nucleobase of the 5'-region is independently selected from among thymine, uracil, guanine, cytosine, 5-methylcytosine, and adenine.

583. The oligomeric compound of any of embodiments 551-582, wherein each internucleoside linkage of the 5'-region is selected from among phosphodiester and phosphorothioate internucleoside linkages.

584. The oligomeric compound of any of embodiments 551-583, wherein the 3'-region consists of one nucleoside.

585. The oligomeric compound of any of embodiments 551-583, wherein the 3'-region consists of 2-5 linked nucleosides.

586. The oligomeric compound of any of embodiments 551-583, wherein the 3'-region consists of 2-4 linked nucleosides.

587. The oligomeric compound of any of embodiments 551-583, wherein the 3'-region consists of 2 linked nucleosides.

588. The oligomeric compound of any of embodiments 551-583, wherein the 3'-region consists of 3 linked nucleosides.

589. The oligomeric compound of any of embodiments 551-583, wherein the 3'-region consists of 4 linked nucleosides.

590. The oligomeric compound of any of embodiments 551-583, wherein the 3'-region consists of 5 linked nucleosides.

591. The oligomeric compound of any of embodiments 551-590, wherein each nucleoside of the 3'-region is a modified nucleoside.

592. The oligomeric compound of any of embodiments 551-591, wherein each nucleoside of the 3'-region is a modified nucleoside comprising a modified sugar moiety.

593. The oligomeric compound of any of embodiments 551-592, wherein each modified nucleoside of the 3'-region has the same modification.

594. The oligomeric compound of and of embodiments 551-592, wherein at least two nucleosides of the 3'-region are modified nucleosides having different modifications.

595. The oligomeric compound of any of embodiments 551-594, wherein each nucleoside of the 3'-region comprises a 2'-modified ribosyl sugar moiety.

596. The oligomeric compound of any of embodiments 551-595, wherein at least one nucleoside of the 3'-region comprises a bicyclic furanosyl sugar moiety.

597. The oligomeric compound of any of embodiments 551-596, wherein each nucleoside of the 3'-region comprises a bicyclic furanosyl sugar moiety.

598. The oligomeric compound of any of embodiments 551-597, wherein at least one nucleoside of the 3'-region comprises a non-bicyclic sugar moiety.

599. The oligomeric compound of embodiment 598, wherein the non-bicyclic sugar moiety of the at least one nucleoside of the 3'-region is a 2'-substituted ribosyl sugar moiety.

600. The oligomeric compound of any of embodiments 551-599, wherein each nucleoside of the 3'-region comprises a non-bicyclic sugar moiety.

601. The oligomeric compound of embodiment 600, wherein each nucleoside of the 3'-region comprises a 2'-substituted furanosyl sugar moiety.

602. The oligomeric compound of any of embodiments 551-601, wherein each nucleoside of the 3'-region comprises a 2'-modified furanosyl sugar moiety independently selected from a bicyclic sugar moiety and a non-bicyclic 2'-substituted ribosyl sugar moiety.

603. The oligomeric compound of any of embodiments 551-602, wherein each nucleoside of the 3'-region comprises a bicyclic sugar moiety.

604. The oligomeric compound of any of embodiments 551-602, wherein each nucleoside of the 3'-region comprises a non-bicyclic 2'-substituted ribosyl sugar moiety.

605. The oligomeric compound of any of embodiments 551-603, wherein each bicyclic sugar moiety of the 3'-region is selected from among cEt, LNA, and ENA.

606. The oligomeric compound of any of embodiments 551-605, wherein each bicyclic sugar moiety of the 3'-region is a cEt sugar moiety.

607. The oligomeric compound of any of embodiments 551-606, wherein each bicyclic sugar moiety of the 3'-region is an LNA sugar moiety.

608. The oligomeric compound of any of embodiments 551-607, wherein each non-bicyclic sugar moiety of the 3'-region has a 2'-substituent selected from among 2'-MOE, 2'-OMe, and 2'-NMA.

609. The oligomeric compound of any of embodiments 551-608, wherein none of the nucleosides of the 3'-region comprise a sugar moiety having a 2'-F substituent.

610. The oligomeric compound of any of embodiments 551-609, wherein none of the nucleosides of the 3'-region comprise a sugar moiety having a 2'-MOE substituent.

611. The oligomeric compound of any of embodiments 551-610, wherein none of the nucleosides of the 3'-region comprise a sugar moiety having a 2'-OMe substituent.

612. The oligomeric compound of any of embodiments 551-611, wherein none of the nucleosides of the 3'-region comprise a cEt sugar moiety.

613. The oligomeric compound of any of embodiments 551-612, wherein none of the nucleosides of the 3'-region comprise a LNA sugar moiety.

614. The oligomeric compound of any of embodiments 551-613, wherein each nucleobase of the 3'-region is independently selected from among thymine, uracil, guanine, cytosine, 5-methylcytosine, and adenine.

615. The oligomeric compound of any of embodiments 551-614, wherein each internucleoside linkage of the 3'-region is selected from among phosphodiester and phosphorothioate internucleoside linkages.

616. The oligomeric compound of any of embodiments 551-615, wherein the modified nucleosides of the 5'-region have the same modifications as the modifications of the modified nucleosides of the 3'-region.

617. The oligomeric compound of any of embodiments 551-615, wherein at least one modified nucleoside of the 5'-region and one modified nucleoside of the 3'-region comprise modifications that differ from one another.

618. The oligomeric compound of any of embodiments 551-617, wherein the 5'-region and the 3'-region together include at least one non-bicyclic 2'-substituted modified nucleoside and at least one bicyclic nucleoside.

619. The oligomeric compound of any of embodiment 618, where the bicyclic nucleoside is a cEt nucleoside.

620. The oligomeric compound of embodiment 618, where the bicyclic nucleoside is an LNA nucleoside.

621. The oligomeric compound of any of embodiments 618-620, wherein the non-bicyclic 2'-modified nucleoside is a 2'-MOE nucleoside.

622. The oligomeric compound of any of embodiments 618-620, wherein the non-bicyclic 2'-modified nucleoside is a 2'-OMe nucleoside.

623. The oligomeric compound of any of embodiments 618-622, wherein at least one nucleoside of the 5'-region or the 3'-region is an unmodified DNA nucleoside.

624. The oligomeric compound of any of embodiments 551-623, wherein the central region has the formula:

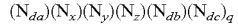

$(N_{da})(N_x)(N_y)(N_z)(N_{db})(N_{dc})_q$ wherein each $N_{dc}$ is independently selected from an unmodified DNA nucleoside, a DNA isomer, a 2'-modified DNA isomer, and a DNA mimic; and q is 2-6.

625. The oligomeric compound of any of embodiments 551-624, wherein the central region consists of 7 linked nucleosides.

626. The oligomeric compound of any of embodiments 551-624, wherein the central region consists of 8 linked nucleosides.

627. The oligomeric compound of any of embodiments 551-624, wherein the central region consists of 9 linked nucleosides.

628. The oligomeric compound of any of embodiments 551-624, wherein the central region consists of 10 linked nucleosides.

629. The oligomeric compound of any of embodiments 551-624, wherein the central region consists of 11 linked nucleosides.

630. The oligomeric compound of any of embodiments 551-629, wherein Nx is the safety-enhancing nucleoside.

631. The oligomeric compound of any of embodiments 551-629, wherein Ny is the safety-enhancing nucleoside.

632. The oligomeric compound of any of embodiments 551-629, wherein Nz is the safety-enhancing nucleoside.

633. The oligomeric compound of any of embodiments 551-632, wherein the safety enhancing nucleoside is a DNA isomer or a modified DNA isomer, or a modified nucleoside comprising either a sugar surrogate, a bicyclic furanosyl sugar moiety, or a non-bicyclic modified furanosyl sugar moiety.

634. The oligomeric compound of any of embodiments 551-33, wherein the safety enhancing nucleoside is a DNA isomer or a modified DNA isomer, or comprises either a sugar surrogate, a bicyclic furanosyl sugar moiety, a non-bicyclic, 2'-modified furanosyl sugar moiety, a non-bicyclic 3'-modified furanosyl sugar moiety, a non-bicyclic, 4'-modified furanosyl sugar moiety, or a non-bicyclic 5'-modified furanosyl sugar moiety.

635. The oligomeric compound of any of embodiments 551-634, wherein the safety enhancing nucleoside comprises a sugar surrogate selected from a morpholino, a modified morpholino, a modified cyclohexenyl, or a modified tetrahydropyran.

636. The oligomeric compound of any of embodiments 551-634, wherein the safety enhancing nucleoside comprises a sugar surrogate selected from a morpholino, a modified morpholino, CeNA, F-CeNA, HNA, OMe-HNA or F-HNA.

637. The oligomeric compound of any of embodiments 551-634, wherein the safety enhancing nucleoside is a DNA isomer comprising a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

638. The oligomeric compound of any of embodiments 551-634, wherein the safety enhancing nucleoside is a DNA isomer comprising a sugar moiety selected from among 2'-β-D-deoxyxylosyl, 2'-α-L-deoxyribosyl, and 2'-O-L-deoxyribosyl.

639. The oligomeric compound of any of embodiments 551-634, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

640. The oligomeric compound of any of embodiments 551-634, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

641. The oligomeric compound of any of embodiments 551-634, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

642. The oligomeric compound of any of embodiments 551-634, wherein the safety enhancing nucleoside is a modified DNA isomer comprising a sugar moiety selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

643. The oligomeric compound of any of embodiments 551-634, wherein the safety enhancing nucleoside is a modified nucleoside comprising a bicyclic furanosyl sugar moiety 644. The oligomeric compound of any of embodiments 551-634, wherein the safety enhancing nucleoside is selected from among cEt, LNA, α-L-LNA, and ENA.

645. The oligomeric compound of any of embodiments 551-634, wherein the safety enhancing nucleoside comprises a 2'-substituted furanosyl sugar moiety.

646. The oligomeric compound of embodiment 645, wherein the 2'-substituted furanosyl sugar moiety of the safety enhancing nucleoside has a 2' substituent selected from: halo, allyl, amino, azido, SH, CN, OCN, $CF_3$, $OCF_3$, O—$C_1$-$C_{10}$ alkoxy, O-C1-C10 substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$$SCH_3$, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl.

647. The oligomeric compound of embodiment 645, wherein the 2'-substituted furanosyl sugar moiety of the safety enhancing nucleoside has a 2' substituent selected from: halo, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl.

648. The oligomeric compound of embodiment 645, wherein the 2'-substituted furanosyl sugar moiety of the safety enhancing nucleoside has a 2' substituent selected from: fluoro, OMe, MOE, NMA.

649. The oligomeric compound of any of embodiments 551-648, wherein the safety enhancing nucleoside comprises a 2'-substituted furanosyl sugar moiety comprising a 2'-OMe or 2'-MOE.

650. The oligomeric compound of any of embodiments 551-649, wherein the safety enhancing nucleoside comprises a 2'-substituted furanosyl sugar moiety comprising a 2'-OMe.

651. The oligomeric compound of any of embodiments 551-650, wherein the safety enhancing nucleoside comprises a 2'-OMe modified 2'-β-D-deoxyribosyl sugar moiety.

652. The oligomeric compound of any of embodiments 551-634, wherein the safety enhancing nucleoside comprises a 3'-modified furanosyl sugar moiety having a 3' substituent selected from: halo, allyl, amino, azido, SH, CN, $CF_3$, $OCF_3$, $C_1$-$C_{10}$ alkyl, $C_1$-$C_{10}$ substituted alkyl, S-alkyl, N($R_m$)-alkyl, N($R_m$)-alkenyl, N($R_m$)-alkynyl, O-alkylenyl-O-alkyl, alkynyl, alkaryl, or aralkyl.

653. The oligomeric compound of any of embodiments 551-634 or embodiment 652, wherein the safety enhancing nucleoside comprises a 3'-modified furanosyl sugar moiety having a 3' substituent selected from: $C_1$-$C_{10}$ alkyl, or $C_1$-$C_{10}$ substituted alkyl.

654. The oligomeric compound of any of embodiments 551-634 or 652-653, wherein the safety enhancing nucleoside comprises a 3'-methyl furanosyl sugar moiety.

655. The oligomeric compound of any of embodiments 551-634, wherein the safety enhancing nucleoside comprises a 4'-modified furanosyl sugar moiety having a 4' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$$SCH_3$, O($CH_2$)$_2$ON($R_m$)($R_n$) or $OCH_2$C(=O)—N($R_m$)($R_n$), where each $R_m$ and Rn is, independently, H, an amino protecting group, or substituted or unsubstituted $C_1$-$C_{10}$ alkyl.

656. The oligomeric compound of any of embodiments 551-634 or 655, wherein the safety enhancing nucleoside comprises a 4'-modified furanosyl sugar moiety having a 4'-methyl.

657. The oligomeric compound of any of embodiments 551-634, wherein the safety enhancing nucleoside has the structure shown below, wherein R represents an optional 2' substituent group and Bx is a heterocyclic base moiety:

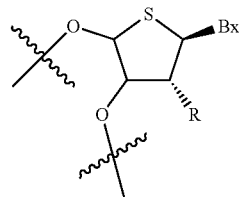

658. The oligomeric compound of embodiment 657, wherein in R is selected from among H, OH, OMe, F, or MOE.

659. The oligomeric compound of any of embodiments 551-634, wherein the safety enhancing nucleoside comprises a 5'-modified furanosyl sugar moiety having a 5' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$$SCH_3$, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl.

660. The oligomeric compound of any of embodiments 551-634 or 659, wherein the safety enhancing nucleoside comprises a 5'-modified furanosyl sugar moiety with a 5' substituent selected from: 5'-methyl, 5'-ethyl or a 5'-allyl.

661. The oligomeric compound of any of embodiments 551-634 or 659-660, wherein the safety enhancing nucleoside comprises a 5'-modified furanosyl sugar moiety with a 5' substituent selected from: 5'-(R)-methyl- or 5'-(R)-ethyl.

662. The oligomeric compound of any of embodiments 551-634 or 659-661, wherein the safety enhancing nucleoside comprises a 5'-(R)-methyl-2'-β-D-deoxyribosyl sugar moiety.

663. The oligomeric compound of any of embodiments 551-634 or 659-662, wherein the safety enhancing nucleoside comprises a 5'-(R)-ethyl-2'-β-D-deoxyribosyl sugar moiety.

664. The oligomeric compound of any of embodiments 551-663, wherein the safety enhancing nucleoside does not comprise a 2'-F modified sugar moiety.

665. The oligomeric compound of any of embodiments 551-664, wherein the safety enhancing nucleoside does not comprise a cEt modified sugar moiety.

666. The oligomeric compound of any of embodiments 551-665, wherein the safety enhancing nucleoside does not comprise a 2'-MOE modified sugar moiety.

667. The oligomeric compound of any of embodiments 551-666, wherein the safety enhancing nucleoside comprises a hypoxanthine nucleobase.

668. The oligomeric compound of any of embodiments 551-667, wherein the safety enhancing nucleoside comprises a nucleobase selected from among A, T, G, C, $^m$C, and U.

669. The oligomeric compound of any of embodiments 551-668, wherein the safety enhancing nucleoside is a modified nucleoside other than cEt, MOE, LNA, or FANA.

670. The oligomeric compound of any of embodiments 551-669, wherein each Nd is independently selected from among a DNA nucleoside, a DNA isomer, a modified DNA isomer, and a DNA mimic.

671. The oligomeric compound of embodiment 670, wherein each DNA isomer comprises a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

672. The oligomeric compound of embodiment 671, wherein each DNA isomer comprises a sugar moiety selected from among 2'-β-D-deoxyxylosyl, 2'-α-L-deoxyribosyl, and 2'-β-L-deoxyribosyl.

673. The oligomeric compound of embodiment 670, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

674. The oligomeric compound of embodiment 673, wherein each modified DNA isomer comprises a 2'-modified sugar moiety, wherein the sugar moiety has the conformation 2'β-D-deoxyxylosyl, 2'-α-L-deoxyribosyl, 2'β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

675. The oligomeric compound of embodiment 674, wherein each modified DNA isomer comprises a 2'-modified sugar moiety, wherein the sugar moiety has the conformation 2'β-D-deoxyxylosyl, 2'-α-L-deoxyribosyl, 2'β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

676. The oligomeric compound of embodiment 675, wherein each modified DNA isomer comprises a 2'-modified sugar moiety, wherein the sugar moiety is selected from among 2'β-D-deoxyxylosyl, 2'-α-L-deoxyribosyl, and 2'-β-L-deoxyribosyl and the 2' position is further substituted with a hydroxyl, fluoro, or OMe substituent.

677. The oligomeric compound of embodiment 670, wherein each DNA mimic comprises a structure represented by one of the formulas below:

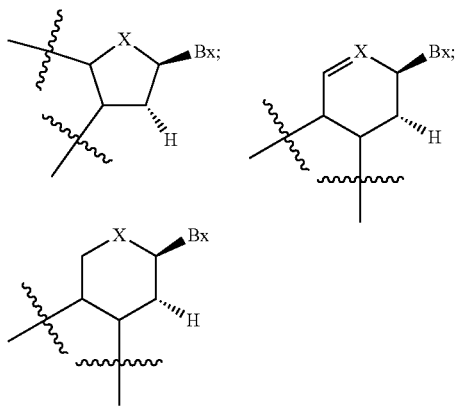

wherein X is O or S and Bx represents a heterocylic base moiety.

678. The oligomeric compound of embodiment 670, wherein each DNA mimic comprises a structure represented by one of the formulas below:

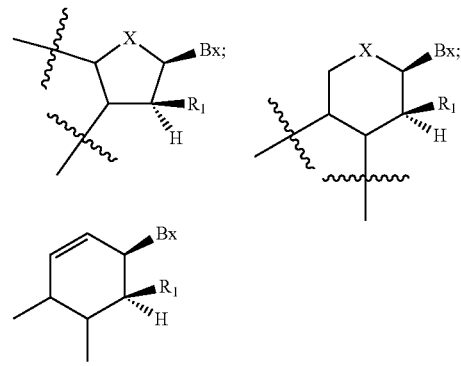

wherein X is O or S, Bx represents a heterocyclic base moiety, and R1 is selected from among H, OH, halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$SCH$_3$, O($CH_2$)$_2$ON($R_m$)($R_n$) or OCH$_2$C(=O)—N($R_m$)($R_n$), where each $R_m$ and $R_n$ is, independently, H, an amino protecting group, or substituted or unsubstituted $C_1$-$C_{10}$ alkyl.

679. The oligomeric compound of embodiment 678, wherein R1 is H, OH, OMe, or F.

680. The oligomeric compound of embodiment 678, wherein R1 is not F.

681. The oligomeric compound of embodiment 670, wherein each DNA mimic comprises a structure represented by the formula below:

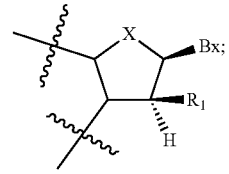

wherein X is O, Bx represents a heterocyclic base moiety, and R1 is H.

682. The oligomeric compound of embodiment 670, wherein DNA mimic has a sugar moiety selected from among: 5'-methyl-2'-β-D-deoxyribosyl, 5'-ethyl-2'-β-D-deoxyribosyl, and 5'-allyl-2'-β-D-deoxyribosyl.

683. The oligomeric compound of embodiment 670, wherein DNA mimic comprises a 2'-fluoro-β-D-arabinofuranosyl sugar moiety 684. The oligomeric compound of embodiment 670, wherein the DNA mimic does not comprise a 2'-fluoro-β-D-arabinofuranosyl sugar moiety.

685. The oligomeric compound of any of embodiments 551-684, wherein each Nd is a DNA nucleoside.

686. The oligomeric compound of any of embodiments 551-685, wherein the central region comprises no more than four nucleosides selected from among DNA isomers, modified DNA isomers, and DNA mimics.

687. The oligomeric compound of any of embodiments 551-685, wherein the central region comprises no more than three nucleosides selected from among DNA isomers, modified DNA isomers, and DNA mimics.

688. The oligomeric compound of any of embodiments 551-685, wherein the central region comprises no more than two nucleosides selected from among DNA isomers, modified DNA isomers, and DNA mimics.

689. The oligomeric compound of any of embodiments 551-685, wherein the central region comprises no more than one nucleoside selected from among DNA isomers, modified DNA isomers, and DNA mimics.

690. The oligomeric compound of any of embodiments 551-689, wherein the central region contains exactly one safety enhancing nucleoside and the remainder of nucleosides in the central region are DNA nucleosides.

691. The oligomeric compound of any of embodiments 551-690, wherein at least one internucleoside linkage of the central region selected from among: the internucleoside Nda to Nx, Nx to Ny, Ny to Nz, or Nz to the adjacent Ndb is a neutral internucleoside linkage.

692. The oligomeric compound of embodiments 691, wherein the neutral linkage is a phosphonate internucleoside linkage.

693. The oligomeric compound of embodiments 691, wherein the neutral linkage is a methoxypropyl internucleoside linkage.

694. The oligomeric compound of embodiments 691, wherein each remaining internucleoside linkage is a phosphodiester or phosphorothioate internucleoside linkage.

695. A chirally enriched population of modified oligonucleotides of any of embodiments 551-690, wherein the central region has at least one particular phorphorothioate internucleoside linkage having a particular stereochemical configuration.

696. The chirally enriched population of embodiment 695, wherein the central region has at least one phorphorothioate internucleoside linkage having the (Sp) configuration.

697. The chirally enriched population of embodiment 695, wherein central region has at least one phorphorothioate internucleoside linkage having the (Rp) configuration.

698. The chirally enriched population of embodiment 695, wherein the central region has a particular, independently selected stereochemical configuration at each phosphorothioate internucleoside linkage.

699. The chirally enriched population of embodiment 698, wherein the each phosphorothioate internucleoside linkage of the central region has the (Sp) configuration.

700. The chirally enriched population of embodiment 698, wherein the central region has one phosphorothioate internucleoside linkage having the (Rp) configuration and wherein each remaining central region phosphorothioate internucleoside linkage has the (Sp) configuration.

701. The chirally enriched population of embodiment 695, wherein the central region has an (Rp) phosphorothioate internucleoside linkage adjacent to an (Sp) phosphorothioate internucleoside linkage.

702. The chirally enriched population of embodiment 695, wherein the central region has an (Rp) phosphorothioate internucleoside linkage adjacent to a second (Rp) phosphorothioate internucleoside linkage.

703. The chirally enriched population of embodiment 695, wherein the central region has an (Rp) phosphorothioate internucleoside linkage adjacent to a second (Rp) phosphorothioate internucleoside linkage, and wherein each remaining central region phosphorothioate internucleoside linkage has the (Sp) configuration.

704. The chirally enriched population of any of embodiments 696, 697, 701, or 702 wherein each phosphorothioate internucleoside linkage that does not have the (Rp) or (Sp) configuration is stereorandom.

705. The oligomeric compound of any of embodiments 551-704 comprising a conjugate group.

706. The oligomeric compound of embodiment 705, wherein the conjugate group comprises a linking group attaching the remainder of the conjugate group to the modified oligonucleotide, wherein the linking group comprises 1-5 nucleosides.

707. The oligomeric compound of any of embodiments 1-705, wherein the oligomeric compound does not comprise additional nucleosides beyond those of the modified oligonucleotide.

708. The oligomeric compound of any of embodiments 551-707, wherein the nucleobase sequence of the modified oligonucleotide is complementary to a target RNA.

709. The oligomeric compound of embodiment 708, wherein the nucleobase sequence of the modified oligonucleotide is at least 85% complementary to the target RNA.

710. The oligomeric compound of embodiment 708, wherein the nucleobase sequence of the modified oligonucleotide is at least 90% complementary to the target RNA.

711. The oligomeric compound of embodiment 708, wherein the nucleobase sequence of the modified oligonucleotide is at least 95% complementary to the target RNA.

712. The oligomeric compound of embodiment 711, wherein the nucleobase sequence of the modified oligonucleotide is 100% complementary to the target RNA.

713. The oligomeric compound of any of embodiments 708-712, wherein the target RNA is a target mRNA or a target pre-mRNA.

714. The oligomeric compound of embodiment 713, wherein the target mRNA or target pre-mRNA is not a mouse, rat, monkey, or human PTEN RNA.

715. The oligomeric compound of embodiment 713 or 714, wherein the target mRNA or target pre-mRNA is not a mouse, rat, monkey, or human SRB-1 RNA.

716. The oligomeric compound of any of embodiments 713-715, wherein the target mRNA or target pre-mRNA is not a mouse, rat, monkey, or human MYD88 RNA.

717. The oligomeric compound of any of embodiments 713-716, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.

718. The oligomeric compound of any of embodiments 708-717, wherein the target RNA is a human RNA.

719. The oligomeric compound of any of embodiments 708-718, wherein the target RNA is expressed in the liver.

720. The oligomeric compound of any of embodiments 708-719, wherein the target RNA is a liver target.

721. The oligomeric compound of any of embodiments 708-718, wherein the target RNA is not expressed in the liver.

722. The oligomeric compound of any of embodiments 708-718 or 721, wherein the target RNA is not a liver target.

723. The oligomeric compound of any of embodiments 708-722, wherein modulation of the expression of the target RNA in the liver is associated with treating a disorder or condition.

724. The oligomeric compound of embodiment 723, wherein the disorder or condition is a liver disorder or condition.

725. The oligomeric compound of any of embodiments 708-724, wherein the target RNA is expressed in the central nervous system.

726. The oligomeric compound of any of embodiments 708-724, wherein the target RNA is not expressed in the central nervous system.

727. The oligomeric compound of any of embodiments 708-725, wherein the target RNA is a central nervous system target.

728. The oligomeric compound of any of embodiments 708-726, wherein the target RNA is not a central nervous system target.

729. The oligomeric compound of any of embodiments 708-727, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.

730. The oligomeric compound of any of embodiments 708-729, wherein the target RNA is a HTT RNA.

731. The oligomeric compound of embodiment 729, wherein the target RNA is a MeCP2 RNA.

732. The oligomeric compound of embodiment 729, wherein the target RNA is a DUX4 RNA.

733. The oligomeric compound of embodiment 729, wherein the target RNA is a HDAC2 RNA.

734. The oligomeric compound of embodiment 729, wherein the target RNA is a Ataxin 1 RNA.

735. The oligomeric compound of embodiment 729, wherein the target RNA is a Ataxin 2 RNA.

736. The oligomeric compound of embodiment 729, wherein the target RNA is a Ataxin 3 RNA.

737. The oligomeric compound of embodiment 729, wherein the target RNA is a Ataxin 6 RNA.

738. The oligomeric compound of embodiment 729, wherein the target RNA is a Ataxin 7 RNA.

739. The oligomeric compound of embodiment 729, wherein the target RNA is a C9ORF72 RNA.

740. The oligomeric compound of embodiment 708-727, wherein the target RNA is an alpha-synuclein RNA.

741. The oligomeric compound of embodiment 729, wherein the target RNA is an UBE3A RNA.

742. The oligomeric compound of any of embodiments 708-727, wherein the target RNA is a SOD1 RNA.

743. The oligomeric compound of any of embodiments 708-727, wherein the target RNA is a Prion RNA.

744. The oligomeric compound of any of embodiments 708-727, wherein the target RNA is a PMP22 RNA.

745. The oligomeric compound of any of embodiments 708-727, wherein the target RNA is a Tau RNA.

746. The oligomeric compound of any of embodiments 708-727, wherein the target RNA is a LRRK2 RNA.

747. The oligomeric compound of any of embodiments 708-727, wherein the target RNA is an APP RNA.

748. The oligomeric compound of any of embodiments 708-727, wherein the target RNA is a LINGO2 RNA.

749. The oligomeric compound of any of embodiments 708-727, wherein the target RNA is a GYS1 RNA.

750. The oligomeric compound of any of embodiments 708-727, wherein the target RNA is a KCNT1 RNA.

751. The oligomeric compound of any of embodiments 708-727, wherein the target RNA is a IRF8 RNA.

752. The oligomeric compound of any of embodiments 708-727, wherein the target RNA is a Progranulin RNA.

753. The oligomeric compound of any of embodiments 708-727, wherein the target RNA is a GFAP RNA.

754. The oligomeric compound of any of embodiments 725-753, wherein modulation of the expression of the target RNA in the central nervous system is associated with treating a disorder or condition.

755. The oligomeric compound of embodiment 754, wherein the disorder or condition is a neurological disorder or condition.

756. The oligomeric compound of embodiment 754-755, wherein the disorder or condition alters the function of sensory or motor neurons.

757. The oligomeric compound of any of embodiments 754-756, wherein the disorder or condition alters the function of sensory neurons.

758. The oligomeric compound of any of embodiments 754-757, wherein the disorder or condition alters the function of motor neurons.

759. The oligomeric compound of any of embodiments 754-758, wherein the disorder or condition alters the function of glial cells.

760. The oligomeric compound of any of embodiments 754-759, wherein the disorder or condition alters the function of astrocytes.

761. The oligomeric compound of any of embodiments 754-760, wherein the disorder or condition alters the function of oligodendrocytes.

762. The oligomeric compound of any of embodiments 754-761, wherein the disorder or condition alters the function of microglia.

763. The oligomeric compound of any of embodiments 754-762, wherein the disorder or condition alters the function of ependymal cells.

764. The oligomeric compound of any of embodiments 754-763, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.

765. The oligomeric compound of embodiment 764, wherein the disorder or condition is Alzheimer's Disease.

766. The oligomeric compound of embodiment 764, wherein the disorder or condition is Amyotrophic Lateral Sclerosis.

767. The oligomeric compound of embodiment 764, wherein the disorder or condition is Parkinson's Disease.

768. The oligomeric compound of embodiment 764, wherein the disorder or condition is a Spinocerebellar ataxia.

769. The oligomeric compound of embodiment 764, wherein the disorder or condition is Angelman Syndrome.

770. The oligomeric compound of embodiment 764, wherein the disorder or condition is Alexander's Disease.

771. The oligomeric compound of embodiment 764, wherein the disorder or condition is Lafora Disease.

772. The oligomeric compound of embodiment 764, wherein the disorder or condition is Charcot-Marie Tooth Disease.

773. The oligomeric compound of embodiment 764, wherein the disorder or condition is Prion Disease.

774. The oligomeric compound of embodiment 764, wherein the disorder or condition is a dementia.

775. The oligomeric compound of embodiment 764, wherein the disorder or condition is neurodegeneration.

776. The oligomeric compound of embodiment 764, wherein the disorder or condition is MeCP2 Duplication Syndrome.

777. The oligomeric compound of embodiment 764, wherein the disorder or condition is encephalopathy.

778. The oligomeric compound of embodiment 764, wherein the disorder or condition is neuroinflammation.

779. The oligomeric compound of embodiment 764, wherein the disorder or condition is multiple sclerosis.

780. The oligomeric compound of any of embodiments 551-779, wherein the parent oligomeric compound of the oligomeric compound of any of embodiments 551-779 is cytotoxic in vitro.

781. The oligomeric compound of embodiment 780, wherein the parent oligomeric compound is cytotoxic in a standard in vitro cytotoxicity assay.

782. The oligomeric compound of any of embodiments 551-781 wherein administration to a mouse of the parent oligomeric compound of the oligomeric compound of any of embodiments 551-781 is hepatotoxic to the mouse.

783. The oligomeric compound of embodiment 782, wherein the administration of the parent oligomeric compound to the mouse is systemic administration.

784. The oligomeric compound of embodiment 783, wherein the systemic administration is subcutaneous administration.

785. The oligomeric compound of any of embodiments 782-784, wherein the mouse is a CD-1 mouse.

786. The oligomeric compound of any of embodiments 782-784, wherein the mouse is a $C_{57}BL/6$ mouse.

787. The oligomeric compound of any of embodiments 782-784, wherein the mouse is a BALB/c mouse.

788. The oligomeric compound of any of embodiments 782-784, wherein the plasma ALT level in the mouse is higher than 500 units per liter following the administration of the parent oligomeric compound.

789. The oligomeric compound of any of embodiments 782-788, wherein the plasma AST level in the mouse is higher than 500 units per liter following the administration of the parent oligomeric compound.

790. The oligomeric compound of any of embodiments 782-789, wherein the plasma ALT level in the mouse is higher than 1000 units per liter following the administration of the parent oligomeric compound.

791. The oligomeric compound of any of embodiments 782-790, wherein the plasma AST level in the mouse is higher than 1000 units per liter following the administration of the parent oligomeric compound.

792. The oligomeric compound of any of embodiments 782-791, wherein the hepatotoxicity is measured 24-48 hours following the administration of the parent oligomeric compound.

793. The oligomeric compound of any of embodiments 782-791, wherein the hepatotoxicity is measured 72 hours following the administration of the parent oligomeric compound.

794. The oligomeric compound of any of embodiments 782-791, wherein the hepatotoxicity is measured 3 days following the administration of the parent oligomeric compound.

795. The oligomeric compound of any of embodiments 782-791, wherein the hepatotoxicity is measured 5 days following the administration of the parent oligomeric compound.

796. The oligomeric compound of any of embodiments 782-791, wherein the hepatotoxicity is measured 7 days following the administration of the parent oligomeric compound.

797. The oligomeric compound of any of embodiments 782-791, wherein the hepatotoxicity is measured 10 days following the administration of the parent oligomeric compound.

798. The oligomeric compound of any of embodiments 782-791, wherein the hepatotoxicity is measured 14 days following the administration of the parent oligomeric compound.

799. The oligomeric compound of any of embodiments 782-791, wherein 1-10 mg/kg of the parent oligomeric compound is administered to the mouse.

800. The oligomeric compound of any of embodiments 782-791, wherein 10-25 mg/kg of the parent oligomeric compound is administered to the mouse.

801. The oligomeric compound of any of embodiments 782-791, wherein 25-50 mg/kg of the parent oligomeric compound is administered to the mouse.

802. The oligomeric compound of any of embodiments 782-791, wherein 50-100 mg/kg of the parent oligomeric compound is administered to the mouse.

803. The oligomeric compound of any of embodiments 782-791, wherein 100-150 mg/kg of the parent oligomeric compound is administered to the mouse.

804. The oligomeric compound of any of embodiments 782-791, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.

805. The oligomeric compound of any of embodiments 551-804, wherein administration of 50 mg/kg of the oligomeric compound of any of embodiments 551-804 to a mouse is not hepatotoxic to the mouse.

806. The oligomeric compound of embodiment 805, wherein plasma ALT level in the mouse is lower than 100 units per liter following the administration of the oligomeric compound of embodiment 805.

807. The oligomeric compound of embodiment 805 or 806, wherein plasma ALT level in the mouse is at least 10-fold lower than plasma ALT level in a mouse administered the parent oligomeric compound of the oligomeric compound of embodiment 384 or 385, wherein the administrations and plasma ALT measurements of both the oligomeric compound of embodiment 384 or 385 and the parent oligomeric compound are completed in the same way.

808. The oligomeric compound of embodiment 807, wherein the plasma ALT level in the mouse is at least 100-fold lower than the plasma ALT level in the mouse administered the parent oligomeric compound.

809. The oligomeric compound of embodiment 807, wherein the plasma ALT level in the mouse is at least 500-fold lower than the plasma ALT level in the mouse administered the parent oligomeric compound.

810. The oligomeric compound of any of embodiments 782-809, wherein the therapeutic index in a mouse of the oligomeric compound of any of embodiments 782-809 is increased relative to the therapeutic index of the parent oligomeric compound.

811. The oligomeric compound of embodiment 810, wherein the therapeutic index in a mouse of the oligomeric compound of embodiment 365 is at least two-fold greater than the therapeutic index of the parent oligomeric compound.

812. The oligomeric compound of any of embodiments 551-811, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse; and wherein the otherwise identical oligomeric compound has a central region consisting of phosphorothioate internucleoside linkages, unmodified 2'β-D-deoxyribosyl sugar moieties, and nucleobases selected from thymine, uracil, adenine, guanine, cytosine, and 5-methylcytosine.

813. The oligomeric compound of embodiment 812, wherein the at least one modified internucleoside linkage other than phosphorothioate and/or at least one modified nucleoside comprising a modified nucleobase other than 5-methylcytosine and/or a modified sugar moiety in the central region is a 2'-O-methyl modified sugar moiety.

814. The oligomeric compound of embodiment 813, wherein the 2'-O-methyl modified sugar moiety is at position 2 of the central region.

815. The oligomeric compound of embodiment 812-814, wherein the otherwise identical oligomeric compound lacks a 2'-O-methyl modified sugar moiety, and wherein the otherwise identical oligomeric compound comprises an unmodified 2'β-D-deoxyribosyl sugar moiety in place of the 2'-O-methyl modified sugar moiety.

816. The oligomeric compound of any of embodiments 812-815, wherein the nucleobase sequence of the otherwise identical oligomeric compound is 100% complementary to the target RNA.

817. The oligomeric compound of any of embodiments 812-816, wherein the otherwise identical oligomeric compound is a parent oligomeric compound of the oligomeric compound of any of embodiments 812-816.

818. The oligomeric compound of any of embodiments 708-817, wherein the oligomeric compound inhibits the target RNA with an $IC_{50}$ lower than 100 nM in a standard in vitro activity assay.

819. The oligomeric compound of any of embodiments 708-818, wherein the parent oligomeric compound of the oligomeric compound of any of embodiments 708-818 inhibits the target RNA with an $IC_{50}$ lower than 100 nM in a standard in vitro activity assay.

820. The oligomeric compound of any of embodiments 708-819, wherein the difference between the $IC_{50}$ of the parent oligomeric compound measured in a standard in vitro activity assay and the $IC_{50}$ of the oligomeric compound of any of embodiments 708-819 measured in a standard in vitro activity assay is less than 4-fold.

821. The oligomeric compound of any of embodiments 708-820, wherein the difference between the $IC_{50}$ of the parent oligomeric compound measured in a standard in vitro activity assay and the $IC_{50}$ of the oligomeric compound of any of embodiments 708-820 measured in a standard in vitro activity assay is less than 3-fold.

822. The oligomeric compound of any of embodiments 708-821, wherein the difference between the $IC_{50}$ of the parent oligomeric compound measured in a standard in vitro activity assay and the $IC_{50}$ of the oligomeric compound of any of embodiments 708-821 measured in a standard in vitro activity assay is less than 2-fold.

823. The oligomeric compound of any of embodiments 708-822, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

824. The oligomeric compound of any of embodiments 708-823, wherein the nucleobase sequence of the parent oligomeric compound is 100% complementary to the target RNA.

825. The oligomeric compound of any of embodiments 551-824, wherein administration of 10-50 mg of the oligomeric compound to a human is not hepatotoxic to the human.

826. The oligomeric compound of any of embodiments 551-824, wherein administration of 50-100 mg of the oligomeric compound to a human is not hepatotoxic to the human.

827. The oligomeric compound of any of embodiments 551-824, wherein administration of 100-300 mg of the oligomeric compound to a human is not hepatotoxic to the human.

828. The oligomeric compound of any of embodiments 825-827, wherein the administration is systemic administration.

829. A composition comprising the oligomeric compound of any of embodiments 551-828 and a second oligomeric compound, wherein the second oligomeric compound is complementary to the oligomeric compound of any of embodiments 551-828.

830. The composition of embodiment 829, wherein the second oligomeric compound comprises at least 14 contiguous linked nucleosides that are at least 90% complementary to the oligomeric compound of any of embodiments 551-828.

831. The composition of embodiment 830, wherein the second oligomeric compound comprises at least 14 contiguous linked nucleosides that are 100% complementary to the oligomeric compound of any of embodiments 551-828.

832. A pharmaceutical composition comprising the oligomeric compound of any of embodiments 551-828 or the composition of any of embodiments 829-831, comprising a pharmaceutically acceptable carrier or diluent.

833. A method comprising administering the oligomeric compound or composition of any of embodiments 551-832 to a human subject.

834. A method of treating a disease or disorder comprising administering the oligomeric compound or composition of any of embodiments 551-832 to a human subject.

835. A method of modulating the amount or activity of a target RNA in a human subject comprising administering the oligomeric compound or composition of any of embodiments 551-832 to the human subject; and thereby modulating the amount or activity of the target RNA in the human subject.

836. A method of treating a disease or disorder in a human subject comprising administering the oligomeric compound or composition of any of embodiments 551-832 to the human subject having the disease or disorder; and thereby treating the disease or disorder in the human subject.

837. The method of embodiment 835-836, wherein the disease or disorder is a liver disease, and wherein the oligomeric compound modulates the amount or activity of a liver target RNA.

838. The method of embodiment 835-837, wherein the disease or disorder is a central nervous system disease, and wherein the oligomeric compound modulates the amount or activity of a central nervous system target RNA.

839. The method of any of embodiments 834-838, wherein the disease or disorder is a cancer, a neurodegenerative disease, a cardiovascular disease, an immunological 840. The method of any of embodiments 834-839, wherein the plasma ALT level of the human subject after the administration is not more than three times higher than it was prior to the administration.

841. The method of any of embodiments 834-840, wherein the plasma ALT level of the human subject after the administration is not more than 150 units per liter.

842. The method of any of embodiments 834-841, wherein the human subject is susceptible to liver damage.

843. The method of any of embodiments 834-842, wherein the human subject is susceptible to liver degeneration.

844. The method of any of embodiments 834-843, wherein the human subject is susceptible to elevated apoptosis in the liver.

845. The method of any of embodiments 834-844, wherein the human subject has a liver disease.

846. The method of any of embodiments 834-841, comprising administering the parent oligomeric compound of the oligomeric compound of any of embodiments 551-832 to a mouse.

847. The method of any of embodiments 833-846, comprising contacting a cell with the parent oligomeric compound of the oligomeric compound of any of embodiments 551-832.

848. The method of embodiment 846-847, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

849. A method of designing an oligomeric compound comprising starting with a parent oligomeric compound and changing the design of that compound in order to arrive at an oligomeric compound of any one of embodiments 551-833.

850. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 551-833.

851. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 551-833.

852. The method of embodiment 851, wherein the method designs an oligomeric compound with improved therapeutic index relative to the parent oligomeric compound.

853. The method of embodiment 851-852, wherein the method designs an oligomeric compound with lower hepatotoxicity relative to the parent oligomeric compound.

854. The method of embodiment 853, wherein the second oligomeric compound has an improved therapeutic index relative to the parent oligomeric compound.

855. The method of embodiment 851-852, wherein the second oligomeric compound has reduced hepatotoxicity in a mouse relative to the parent oligomeric compound.

856. The method of embodiment 855, wherein the oligomeric compound according to any one of embodiments 551-833 has reduced hepatotoxicity relative to the parent oligomeric compound.

857. A method comprising administering an oligomeric compound of any of embodiments 551-833 to a mouse and separately administering the parent oligomeric compound of the oligomeric compound of any of embodiments 551-833 to a second mouse, wherein the therapeutic index of the oligomeric compound of any of embodiments 551-833 is improved relative to the therapeutic index of the parent oligomeric compound.

858. The method of any of embodiments 833-857, wherein the level of p21 RNA is measured in the mouse, the cell, and/or the human subject.

859. A method comprising administering an oligomeric compound of any of embodiments 551-833 to a subject and measuring the level of p21 RNA in the subject.

860. The method of embodiment 858 or 859, wherein the subject is a mouse.

861. The method of embodiment 858 or 859, wherein the subject is a human.

862. The method of any of embodiments 858-861, wherein the p21 RNA level is measured within 24 hours of the administration.

863. The method of any of embodiments 858-862, wherein the p21 RNA level is measured 24-48 hours following the administration.

864. An oligomeric compound or composition of any one of embodiments 551-832, for use in medical therapy.

865. The oligomeric compound of any of embodiments 551-832, wherein the oligomeric compound is not toxic.

866. The oligomeric compound of any of embodiment 551-832, wherein a comparator compound is toxic;

wherein the comparator compound is identical to the oligomeric compound except that each nucleoside of the central region of the comparator compound is a nucleoside comprising 2'-β-D-deoxyribyl sugar moiety.

867. The oligomeric compound of embodiment 866, wherein administering a dose of the oligomeric compound to an animal results in a circulating ALT level that is at least 3-fold lower than the ALT level that results from administering the same dose of the comparator compound to an animal for at least one matched dose.

868. The oligomeric compound of embodiment 866 or 867, wherein the lowest dose of the oligomeric compound that raises circulating ALT to over 300 units per liter is at least three-fold higher than the lowest dose of the comparator compound that raises circulating ALT to over 300 units per liter.

869. The oligomeric compound of any of embodiments 865-868, wherein the oligomeric compound is capable of reducing the target RNA in a cell.

870. The oligomeric compound of embodiment 869, wherein the oligomeric compound has RNA-reducing activity comparable to a comparator compound, wherein the comparator compound is identical to the oligomeric compound except that each nucleoside of the central region of the comparator compound is a nucleoside comprising 2'-β-D-deoxyribosyl sugar moiety.

871. The oligomeric compound of embodiment 870 having RNA-reducing activity that is no more than 2-fold worse than the RNA-reducing activity of the comparator compound.

872. A method of modulating the amount or activity of a target RNA in a human subject comprising administering the oligomeric compound or composition of any of embodiments 551-832 to the human subject; and thereby modulating the amount or activity of the target RNA in the human subject.

873. A method of treating a disease or disorder in a human subject comprising administering the oligomeric compound or composition of any of embodiments 551-832 to the human subject having the disease or disorder; and thereby treating the disease or disorder in the human subject.

874. The method of embodiment 872-873, wherein the disease or disorder is a liver disease, and wherein the oligomeric compound modulates the amount or activity of a liver target RNA.

875. The method of embodiment 872-873, wherein the disease or disorder is a central nervous system disease, and wherein the oligomeric compound modulates the amount or activity of a central nervous system target RNA.

876. The method of any of embodiments 872-874, wherein the disease or disorder is a cancer, a neurodegenerative disease, a cardiovascular disease, an immunological disease, a hereditary disease, a repeat expansion disease, a muscle-wasting disease, or a metabolic disease.

877. The method of any of embodiments 872-876, wherein the plasma ALT level of the human subject after the administration is not more than three times higher than it was prior to the administration.

878. The method of any of embodiments 872-877, wherein the plasma ALT level of the human subject after the administration is not more than 150 units per liter.

879. A method of treating a disease or disorder in a human subject comprising administering the oligomeric compound or composition of any of embodiments 1-410, 452-518, 551-828, or 864-871 to the human subject having the disease or disorder; and thereby treating the disease or disorder in the human subject.

880. The method of embodiment 879, wherein the disease or disorder is not a CNS disease or disorder.

881. The method of embodiment 879, wherein the disease or disorder is a disease or disorder of the muscle.

882. The method of embodiment 879, wherein the disease or disorder is a disease or disorder of the lung.

883. The method of embodiment 879, wherein the disease or disorder is a disease or disorder of the kidney.

884. The method of embodiment 879, wherein the disease or disorder is a disease or disorder of the eye.

885. The method of embodiment 879, wherein the disease or disorder is a disease or disorder of the pancreas.

886. A method of screening a library of oligomeric compounds for activity against a target RNA, wherein the library of oligomeric compounds comprises a plurality of oligomeric compounds of any of embodiments 1-410, 452-218, 551-831, or 864-871.

887. An oligomeric compound comprising a modified oligonucleotide consisting of 12-21 linked nucleosides, wherein the modified oligonucleotide has the formula A-B-C, wherein A is a 5'-region, B is a central region, and C is a 3'-region; wherein:
the 5'-region consists of 1-5 linked nucleosides, wherein at least one nucleoside of the 5'-region is a modified nucleoside comprising a modified sugar;
the 3'-region consists of 1-5 linked nucleosides wherein at least one nucleoside of the 3'-region is a modified nucleoside comprising a modified sugar; and
the central region consists of 7-11 linked nucleosides, wherein
the 5'-most portion of the central region has the following formula:

$(N_{da})(N_x)(N_y)(N_z)(N_{db})$ wherein one of $N_x$, $N_y$, and $N_z$, is a safety-enhancing nucleoside;

the other two of $N_x$, $N_y$, and $N_z$ are independently selected from a DNA nucleoside, a DNA isomer, a modified DNA isomer, and a DNA mimic; and $N_{da}$ and $N_{db}$ are each independently selected from a DNA nucleoside, a DNA isomer, a modified DNA isomer, and a DNA mimic.

888. The oligomeric compound of embodiment 887, wherein the 5'-region consists of one nucleoside.

889. The oligomeric compound of embodiment 887, wherein the 5'-region consists of 2-5 linked nucleosides.

890. The oligomeric compound of embodiment 887, wherein the 5'-region consists of 2-4 linked nucleosides.

891. The oligomeric compound of embodiment 887, wherein the 5'-region consists of 2 linked nucleosides.

892. The oligomeric compound of embodiment 887, wherein the 5'-region consists of 3 linked nucleosides.

893. The oligomeric compound of embodiment 887, wherein the 5'-region consists of 4 linked nucleosides.

894. The oligomeric compound of embodiment 887, wherein the 5'-region consists of 5 linked nucleosides.

895. The oligomeric compound of any of embodiments 887-894, wherein each nucleoside of the 5'-region is a modified nucleoside.

896. The oligomeric compound of any of embodiments 887-895, wherein each nucleoside of the 5'-region is a modified nucleoside comprising a modified sugar.

897. The oligomeric compound of any of embodiments 887-896, wherein each modified nucleoside of the 5'-region has the same modification.

898. The oligomeric compound of any of embodiments 887-896, wherein at least two nucleosides of the 5'-region are modified nucleosides having different modifications.

899. The oligomeric compound of any of embodiments 887-898, wherein each nucleoside of the 5'-region comprises a 2'-modified ribosyl sugar moiety.

900. The oligomeric compound of any of embodiments 887-899, wherein at least one nucleoside of the 5'-region comprises a bicyclic furanosyl sugar moiety.

901. The oligomeric compound of any of embodiments 887-900, wherein each nucleoside of the 5'-region comprises a bicyclic furanosyl sugar moiety.

902. The oligomeric compound of any of embodiments 887-900, wherein at least one nucleoside of the 5'-region comprises a non-bicyclic sugar moiety.

903. The oligomeric compound of embodiment 902, wherein the non-bicyclic sugar moiety of the at least one nucleoside of the 5'-region is a 2'-substituted ribosyl sugar moiety.

904. The oligomeric compound of any of embodiments 887-889 or 902-903, wherein each nucleoside of the 5'-region comprises a non-bicyclic sugar moiety.

905. The oligomeric compound of embodiment 904, wherein each nucleoside of the 5'-region comprises a 2'-substituted furanosyl sugar moiety.

906. The oligomeric compound of any of embodiments 887-905, wherein each nucleoside of the 5'-region comprises a 2'-modified furanosyl sugar moiety independently selected from a bicyclic sugar moiety and a non-bicyclic 2'-substituted ribosyl sugar moiety.

907. The oligomeric compound of any of embodiments 887-901 or 906, wherein each nucleoside of the 5'-region comprises a bicyclic sugar moiety.

908. The oligomeric compound of any of embodiments 887-889 or 902-906, wherein each nucleoside of the 5'-region comprises a non-bicyclic 2'-substituted ribosyl sugar moiety.

909. The oligomeric compound of any of embodiments 887-903 or 906-907, wherein each bicyclic sugar moiety of the 5'-region is selected from among cEt, LNA, and ENA.

910. The oligomeric compound of any of embodiments 887-903 or 906-909, wherein each bicyclic sugar moiety of the 5'-region is a cEt sugar moiety.

911. The oligomeric compound of any of embodiments 887-903, or 906-907 or 909 wherein each bicyclic sugar moiety of the 5'-region is an LNA sugar moiety.

912. The oligomeric compound of any of embodiments 887-900, 902-906, or 908-911, wherein each non-bicyclic sugar moiety of the 5'-region has a 2'-substituent selected from among 2'-MOE, 2'-OMe, and 2'-NMA.

913. The oligomeric compound of any of embodiments 887-912, wherein none of the nucleosides of the 5'-region comprise a sugar moiety having a 2'-F substituent.

914. The oligomeric compound of any of embodiments 887-913, wherein none of the nucleosides of the 5'-region comprise a sugar moiety having a 2'-MOE substituent.

915. The oligomeric compound of any of embodiments 887-914, wherein none of the nucleosides of the 5'-region comprise a sugar moiety having a 2'-OMe substituent.

916. The oligomeric compound of any of embodiments 887-915, wherein none of the nucleosides of the 5'-region comprise a cEt sugar moiety.

917. The oligomeric compound of any of embodiments 887-916, wherein none of the nucleosides of the 5'-region comprise a LNA sugar moiety.

918. The oligomeric compound of any of embodiments 887-917, wherein each nucleobase of the 5'-region is independently selected from among thymine, uracil, guanine, cytosine, 5-methylcytosine, and adenine.

919. The oligomeric compound of any of embodiments 887-918, wherein each internucleoside linkage of the 5'-region is independently selected from among phosphodiester and phosphorothioate internucleoside linkages.

920. The oligomeric compound of any of embodiments 887-919, wherein the 3'-region consists of one nucleoside.

921. The oligomeric compound of any of embodiments 887-919, wherein the 3'-region consists of 2-5 linked nucleosides.

922. The oligomeric compound of any of embodiments 887-919, wherein the 3'-region consists of 2-4 linked nucleosides.

923. The oligomeric compound of any of embodiments 887-919, wherein the 3'-region consists of 2 linked nucleosides.

924. The oligomeric compound of any of embodiments 887-919, wherein the 3'-region consists of 3 linked nucleosides.

925. The oligomeric compound of any of embodiments 887-919, wherein the 3'-region consists of 4 linked nucleosides.

926. The oligomeric compound of any of embodiments 887-919, wherein the 3'-region consists of 5 linked nucleosides.

927. The oligomeric compound of any of embodiments 887-926, wherein each nucleoside of the 3'-region is a modified nucleoside.

928. The oligomeric compound of any of embodiments 887-927, wherein each nucleoside of the 3'-region is a modified nucleoside comprising a modified sugar moiety.

929. The oligomeric compound of any of embodiments 887-928, wherein each modified nucleoside of the 3'-region has the same modification.

930. The oligomeric compound of and of embodiments 887-928, wherein at least two nucleosides of the 3'-region are modified nucleosides having different modifications.

931. The oligomeric compound of any of embodiments 887-930, wherein each nucleoside of the 3'-region comprises a 2'-modified ribosyl sugar moiety.

932. The oligomeric compound of any of embodiments 887-931, wherein at least one nucleoside of the 3'-region comprises a bicyclic furanosyl sugar moiety.

933. The oligomeric compound of any of embodiments 887-932, wherein each nucleoside of the 3'-region comprises a bicyclic furanosyl sugar moiety.

934. The oligomeric compound of any of embodiments 887-933, wherein at least one nucleoside of the 3'-region comprises a non-bicyclic sugar moiety.

935. The oligomeric compound of embodiment 934, wherein the non-bicyclic sugar moiety of the at least one nucleoside of the 3'-region is a 2'-substituted ribosyl sugar moiety.

936. The oligomeric compound of any of embodiments 887-935, wherein each nucleoside of the 3'-region comprises a non-bicyclic sugar moiety.

937. The oligomeric compound of embodiment 936, wherein each nucleoside of the 3'-region comprises a 2'-substituted furanosyl sugar moiety.

938. The oligomeric compound of any of embodiments 887-937, wherein each nucleoside of the 3'-region comprises a 2'-modified furanosyl sugar moiety independently selected from a bicyclic sugar moiety and a non-bicyclic 2'-substituted ribosyl sugar moiety.

939. The oligomeric compound of any of embodiments 887-935, or 938 wherein each nucleoside of the 3'-region comprises a bicyclic sugar moiety.

940. The oligomeric compound of any of embodiments 887-932 or 934-938, wherein each nucleoside of the 3'-region comprises a non-bicyclic 2'-substituted ribosyl sugar moiety.

941. The oligomeric compound of any of embodiments 887-935 or 938-939, wherein each bicyclic sugar moiety of the 3'-region is selected from among cEt, LNA, and ENA.

942. The oligomeric compound of any of embodiments 887-935, 938-939, or 941, wherein each bicyclic sugar moiety of the 3'-region is a cEt sugar moiety.

943. The oligomeric compound of any of embodiments 887-935, 938-939, or 941, wherein each bicyclic sugar moiety of the 3'-region is an LNA sugar moiety.

944. The oligomeric compound of any of embodiments 887-932, 934-938 or 940, wherein each non-bicyclic sugar moiety of the 3'-region has a 2'-substituent selected from among 2'-MOE, 2'-OMe, and 2'-NMA.

945. The oligomeric compound of any of embodiments 887-944, wherein none of the nucleosides of the 3'-region comprise a sugar moiety having a 2'-F substituent.

946. The oligomeric compound of any of embodiments 887-945, wherein none of the nucleosides of the 3'-region comprise a sugar moiety having a 2'-MOE substituent.

947. The oligomeric compound of any of embodiments 887-946, wherein none of the nucleosides of the 3'-region comprise a sugar moiety having a 2'-OMe substituent.

948. The oligomeric compound of any of embodiments 887-947, wherein none of the nucleosides of the 3'-region comprise a cEt sugar moiety.

949. The oligomeric compound of any of embodiments 887-948, wherein none of the nucleosides of the 3'-region comprise a LNA sugar moiety.

950. The oligomeric compound of any of embodiments 887-949, wherein each nucleobase of the 3'-region is independently selected from among thymine, uracil, guanine, cytosine, 5-methylcytosine, and adenine.

951. The oligomeric compound of any of embodiments 887-950, wherein each internucleoside linkage of the 3'-region is independently selected from among phosphodiester and phosphorothioate internucleoside linkages.

952. The oligomeric compound of any of embodiments 887-951, wherein the modified nucleosides of the 5'-region have the same modifications as the modifications of the modified nucleosides of the 3'-region.

953. The oligomeric compound of any of embodiments 887-951, wherein at least one modified nucleoside of the 5'-region and one modified nucleoside of the 3'-region comprise modifications that differ from one another.

954. The oligomeric compound of any of embodiments 887-898, 900, 902-903, 906, 909-932, 934-935, 938, 941-953, wherein the 5'-region and the 3'-region together include at least one non-bicyclic 2'-substituted modified nucleoside and at least one bicyclic nucleoside.

955. The oligomeric compound of embodiment 954, where the bicyclic nucleoside is a cEt nucleoside.

956. The oligomeric compound of embodiment 954, where the bicyclic nucleoside is an LNA nucleoside.

957. The oligomeric compound of any of embodiments 954-956, wherein the non-bicyclic 2'-modified nucleoside is a 2'-MOE nucleoside.

958. The oligomeric compound of any of embodiments 954-956, wherein the non-bicyclic 2'-modified nucleoside is a 2'-OMe nucleoside.

959. The oligomeric compound of any of embodiments 954-958, wherein at least one nucleoside of the 5'-region or the 3'-region is an unmodified DNA nucleoside.

960. The oligomeric compound of any of embodiments 887-959, wherein the central region has the formula:

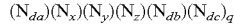

$(N_{da})(N_x)(N_y)(N_z)(N_{db})(N_{dc})_q$ wherein each $N_{dc}$ is independently selected from an unmodified DNA nucleoside, a DNA isomer, a modified DNA isomer, and a DNA mimic; and q is 2-6.

961. The oligomeric compound of any of embodiments 887-960, wherein the central region consists of 7 linked nucleosides.

962. The oligomeric compound of any of embodiments 887-960, wherein the central region consists of 8 linked nucleosides.

963. The oligomeric compound of any of embodiments 887-960, wherein the central region consists of 9 linked nucleosides.

964. The oligomeric compound of any of embodiments 887-960, wherein the central region consists of 10 linked nucleosides.

965. The oligomeric compound of any of embodiments 887-960, wherein the central region consists of 11 linked nucleosides.

966. The oligomeric compound of any of embodiments 887-965, wherein Nx is the safety-enhancing nucleoside.

967. The oligomeric compound of any of embodiments 887-965, wherein Ny is the safety-enhancing nucleoside.

968. The oligomeric compound of any of embodiments 887-965, wherein Nz is the safety-enhancing nucleoside.

969. The oligomeric compound of any of embodiments 887-968, wherein the safety enhancing nucleoside is a DNA isomer or a modified DNA isomer, or a modified nucleoside comprising either a sugar surrogate, a bicyclic furanosyl sugar moiety, or a non-bicyclic modified furanosyl sugar moiety.

970. The oligomeric compound of any of embodiments 887-969, wherein the safety enhancing nucleoside is a DNA isomer or a modified DNA isomer, or comprises either a sugar surrogate, a bicyclic furanosyl sugar moiety, a non-bicyclic, 2'-modified furanosyl sugar moiety, a non-bicyclic 3'-modified furanosyl sugar moiety, a non-bicyclic, 4'-modified furanosyl sugar moiety, or a non-bicyclic 5'-modified furanosyl sugar moiety.

971. The oligomeric compound of any of embodiments 887-970, wherein the safety enhancing nucleoside comprises a sugar surrogate selected from a morpholino, a modified morpholino, a modified cyclohexenyl, or a modified tetrahydropyran.

972. The oligomeric compound of any of embodiments 887-970, wherein the safety enhancing nucleoside comprises a sugar surrogate selected from a morpholino, a modified morpholino, CeNA, F-CeNA, HNA, OMe-HNA or F-HNA.

973. The oligomeric compound of any of embodiments 887-970, wherein the safety enhancing nucleoside is a DNA isomer comprising a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-O-L-deoxyxylosyl.

974. The oligomeric compound of any of embodiments 887-970 or 973, wherein the safety enhancing nucleoside is a DNA isomer comprising a sugar moiety selected from among 2'-β-D-deoxyxylosyl, 2'-α-L-deoxyribosyl, and 2'-β-L-deoxyribosyl.

975. The oligomeric compound of any of embodiments 887-970, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

976. The oligomeric compound of any of embodiments 887-970 or 975, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

977. The oligomeric compound of any of embodiments 887-970 or 975-976, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

978. The oligomeric compound of any of embodiments 887-970 or 975-977, wherein the safety enhancing nucleoside is a modified DNA isomer comprising a sugar moiety selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

979. The oligomeric compound of any of embodiments 887-970, wherein the safety enhancing nucleoside is a modified nucleoside comprising a bicyclic furanosyl sugar moiety.

980. The oligomeric compound of any of embodiments 887-970, wherein the safety enhancing nucleoside is selected from among cEt, LNA, α-L-LNA, and ENA.

981. The oligomeric compound of any of embodiments 887-970, wherein the safety enhancing nucleoside comprises a 2'-substituted furanosyl sugar moiety.

982. The oligomeric compound of embodiment 981, wherein the 2'-substituted furanosyl sugar moiety of the safety enhancing nucleoside has a 2' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—N($R_m$)($R_n$), where each $R_m$ and $R_n$ is, independently, H, an amino protecting group, or substituted or unsubstituted $C_1$-$C_{10}$ alkyl.

983. The oligomeric compound of embodiment 981, wherein the 2'-substituted furanosyl sugar moiety of the safety enhancing nucleoside has a 2' substituent selected from: halo, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, $O(CH_2)_2ON(R_m)(R_n)$ or $OCH_2C(=O)$—N($R_m$)($R_n$), where each $R_m$ and $R_n$ is, independently, H, an amino protecting group, or substituted or unsubstituted $C_1$-$C_{10}$ alkyl.

984. The oligomeric compound of embodiment 981, wherein the 2'-substituted furanosyl sugar moiety of the safety enhancing nucleoside has a 2' substituent selected from: fluoro, OMe, MOE, NMA.

985. The oligomeric compound of any of embodiments 887-978 or 981-984, wherein the safety enhancing nucleoside comprises a 2'-substituted furanosyl sugar moiety comprising a 2'-OMe or 2'-MOE.

986. The oligomeric compound of any of embodiments 887-978 or 981-986, wherein the safety enhancing nucleoside comprises a 2'-substituted furanosyl sugar moiety comprising a 2'-OMe.

987. The oligomeric compound of any of embodiments 887-978 or 981-986, wherein the safety enhancing nucleoside comprises a 2'-OMe modified 2'-β-D-deoxyribosyl sugar moiety.

988. The oligomeric compound of any of embodiments 887-970, wherein the safety enhancing nucleoside comprises a 3'-modified furanosyl sugar moiety having a 3' substituent selected from: halo, allyl, amino, azido, SH, CN, $CF_3$, $OCF_3$, $C_1$-$C_{10}$ alkyl, $C_1$-$C_{10}$ substituted alkyl, S-alkyl, N($R_m$)-alkyl, N($R_m$)-alkenyl, N($R_m$)-alkynyl, O-alkylenyl-O-alkyl, alkynyl, alkaryl, or aralkyl.

989. The oligomeric compound of any of embodiments 887-970 or embodiment 988, wherein the safety enhancing nucleoside comprises a 3'-modified furanosyl sugar moiety having a 3' substituent selected from: $C_1$-$C_{10}$ alkyl, or $C_1$-$C_{10}$ substituted alkyl.

990. The oligomeric compound of any of embodiments 887-970 or 988-989, wherein the safety enhancing nucleoside comprises a 3'-methyl furanosyl sugar moiety.

991. The oligomeric compound of any of embodiments 887-970, wherein the safety enhancing nucleoside comprises a 4'-modified furanosyl sugar moiety having a 4' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O- alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—N($R_m$)($R_n$), where each $R_m$ and $R_n$ is, independently, H, an amino protecting group, or substituted or unsubstituted $C_1$-$C_{10}$ alkyl.

992. The oligomeric compound of any of embodiments 887-970 or 991, wherein the safety enhancing nucleoside comprises a 4'-modified furanosyl sugar moiety having a 4'-methyl.

993. The oligomeric compound of any of embodiments 887-970, wherein the safety enhancing nucleoside has the structure shown below, wherein R represents an optional 2' substituent group and Bx is a heterocyclic base moiety:

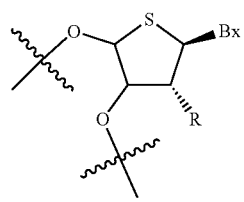

994. The oligomeric compound of embodiment 993, wherein in R is selected from among H, OH, OMe, F, or MOE.

995. The oligomeric compound of any of embodiments 887-970, wherein the safety enhancing nucleoside comprises a 5'-modified furanosyl sugar moiety having a 5' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O- alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—N($R_m$)($R_n$), where each $R_m$ and $R_n$ is, independently, H, an amino protecting group, or substituted or unsubstituted $C_1$-$C_{10}$ alkyl.

996. The oligomeric compound of any of embodiments 887-970 or 995, wherein the safety enhancing nucleoside comprises a 5'-modified furanosyl sugar moiety with a 5' substituent selected from: 5'-methyl, 5'-ethyl or a 5'-allyl.

997. The oligomeric compound of any of embodiments 887-970 or 995-996, wherein the safety enhancing nucleoside comprises a 5'-modified furanosyl sugar moiety with a 5' substituent selected from: 5'-(R)-methyl- or 5'-(R)-ethyl.

998. The oligomeric compound of any of embodiments 887-970 or 995-997, wherein the safety enhancing nucleoside comprises a 5'-(R)-methyl-2'-β-D-deoxyribosyl sugar moiety.

999. The oligomeric compound of any of embodiments 887-970 or 995-998, wherein the safety enhancing nucleoside comprises a 5'-(R)-ethyl-2'-β-D-deoxyribosyl sugar moiety.

1000. The oligomeric compound of any of embodiments 887-999, wherein the safety enhancing nucleoside does not comprise a 2'-F modified sugar moiety.

1001. The oligomeric compound of any of embodiments 887-1000, wherein the safety enhancing nucleoside does not comprise a cEt modified sugar moiety.

1002. The oligomeric compound of any of embodiments 887-1001, wherein the safety enhancing nucleoside does not comprise a 2'-MOE modified sugar moiety.

1003. The oligomeric compound of any of embodiments 887-1002, wherein the safety enhancing nucleoside comprises a hypoxanthine nucleobase.

1004. The oligomeric compound of any of embodiments 887-1003, wherein the safety enhancing nucleoside comprises a nucleobase selected from among thymine, uracil, guanine, cytosine, 5-methylcytosine, and adenine.

1005. The oligomeric compound of any of embodiments 887-1004, wherein the safety enhancing nucleoside is a modified nucleoside other than cEt, MOE, LNA, or FANA.

1006. The oligomeric compound of any of embodiments 887-1005, wherein each Nd is independently selected from among a DNA nucleoside, a DNA isomer, a 2'-modified DNA isomer, and a DNA mimic.

1007. The oligomeric compound of embodiment 1006, wherein each DNA isomer comprises a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

1008. The oligomeric compound of embodiment 1007, wherein each DNA isomer comprises a sugar moiety selected from among 2'-β-D-deoxyxylosyl, 2'-α-L-deoxyribosyl, and 2'-β-L-deoxyribosyl.

1009. The oligomeric compound of embodiment 1006, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

1010. The oligomeric compound of embodiment 1009, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

1011. The oligomeric compound of embodiment 1010, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

1012. The oligomeric compound of embodiment 1011, wherein each modified DNA isomer comprises a 2'-modified sugar moiety, wherein the sugar moiety is selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

1013. The oligomeric compound of embodiment 1006, wherein each DNA mimic comprises a structure represented by one of the formulas below:

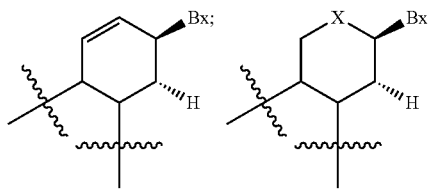

wherein X is O or S and Bx represents a heterocylic base moiety.

1014. The oligomeric compound of embodiment 1006, wherein each DNA mimic comprises a structure represented by one of the formulas below:

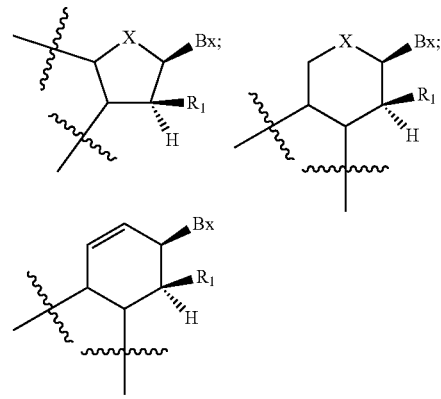

wherein X is O or S;
Bx represents a heterocyclic base moiety; and
$R_1$ is selected from among H, OH, halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—$N(R_m)(R_n)$, where each $R_m$ and $R_n$ is, independently, H, an amino protecting group, or substituted or unsubstituted $C_1$-$C_{10}$ alkyl;
wherein if the DNA mimic comprises the structure:

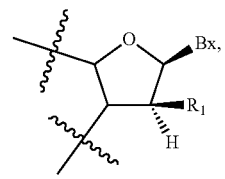

$R_1$ is other than H.

1015. The oligomeric compound of embodiment 1014, wherein $R_1$ is H, OH, OMe, or F.

1016. The oligomeric compound of embodiment 1014, wherein $R_1$ is not F.

1017. The oligomeric compound of embodiment 1006, wherein each DNA mimic comprises a structure represented by the formula below:

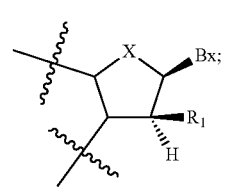

wherein X is S, Bx represents a heterocyclic base moiety, and $R_1$ is H.

1018. The oligomeric compound of embodiment 1006, wherein the DNA mimic has a sugar moiety selected from among: 5'-methyl-2'-β-D-deoxyribosyl, 5'-ethyl-2'-β-D-deoxyribosyl, and 5'-allyl-2'-β-D-deoxyribosyl.

1019. The oligomeric compound of embodiment 1006, wherein the DNA mimic comprises a 2'-fluoro-β-D-arabinofuranosyl sugar moiety.

1020. The oligomeric compound of embodiment 1006, wherein the DNA mimic does not comprise a 2'-fluoro-β-D-arabinofuranosyl sugar moiety.

1021. The oligomeric compound of any of embodiments 887-1020, wherein each $N_d$ is a DNA nucleoside.

1022. The oligomeric compound of any of embodiments 887-1021, wherein the central region comprises no more than four nucleosides selected from among DNA isomers, modified DNA isomers, and DNA mimics.

1023. The oligomeric compound of any of embodiments 887-1021, wherein the central region comprises no more than three nucleosides selected from among DNA isomers, modified DNA isomers, and DNA mimics.

1024. The oligomeric compound of any of embodiments 887-1021, wherein the central region comprises no more than two nucleosides selected from among DNA isomers, modified DNA isomers, and DNA mimics.

1025. The oligomeric compound of any of embodiments 887-1021, wherein the central region comprises no more than one nucleoside selected from among DNA isomers, modified DNA isomers, and DNA mimics.

1026. The oligomeric compound of any of embodiments 887-1025, wherein the central region contains exactly one safety enhancing nucleoside and the remainder of nucleosides in the central region are DNA nucleosides.

1027. The oligomeric compound of any of embodiments 887-1026, wherein at least one internucleoside linkage of the central region selected from among: the internucleoside Nda to Nx, Nx to Ny, Ny to Nz, or Nz to the adjacent Ndb is a neutral internucleoside linkage.

1028. The oligomeric compound of embodiments 1027, wherein the neutral linkage is a phosphonate internucleoside linkage.

1029. The oligomeric compound of embodiments 1027, wherein the neutral linkage is a methoxypropyl internucleoside linkage.

1030. The oligomeric compound of embodiments 1027, wherein each remaining internucleoside linkage is a phosphodiester or phosphorothioate internucleoside linkage.

1031. A chirally enriched population of modified oligonucleotides of any of embodiments 887-1026, wherein the central region has at least one particular phorphorothioate internucleoside linkage having a particular stereochemical configuration.

1032. The chirally enriched population of embodiment 1031, wherein the central region has at least one phorphorothioate internucleoside linkage having the (Sp) configuration.

1033. The chirally enriched population of embodiment 1031, wherein central region has at least one phorphorothioate internucleoside linkage having the (Rp) configuration.

1034. The chirally enriched population of embodiment 1031, wherein the central region has a particular, independently selected stereochemical configuration at each phosphorothioate internucleoside linkage.

1035. The chirally enriched population of embodiment 1034, wherein the each phosphorothioate internucleoside linkage of the central region has the (Sp) configuration.

1036. The chirally enriched population of embodiment 1034, wherein the central region has one phosphorothioate internucleoside linkage having the (Rp) configuration and wherein each remaining central region phosphorothioate internucleoside linkage has the (Sp) configuration.

1037. The chirally enriched population of embodiment 1031, wherein the central region has an (Rp) phosphorothioate internucleoside linkage adjacent to an (Sp) phosphorothioate internucleoside linkage.

1038. The chirally enriched population of embodiment 1031, wherein the central region has an (Rp) phosphorothioate internucleoside linkage adjacent to a second (Rp) phosphorothioate internucleoside linkage.

1039. The chirally enriched population of embodiment 1031, wherein the central region has an (Rp) phosphorothioate internucleoside linkage adjacent to a second (Rp) phosphorothioate internucleoside linkage, and wherein each remaining central region phosphorothioate internucleoside linkage has the (Sp) configuration.

1040. The chirally enriched population of any of embodiments 1032, 1033, 1037, or 1038 wherein each phosphorothioate internucleoside linkage that does not have the (Rp) or (Sp) configuration is stereorandom.

1041. The oligomeric compound of any of embodiments 887-1040 comprising a conjugate group.

1042. The oligomeric compound of embodiment 1041, wherein the conjugate group comprises a linking group attaching the remainder of the conjugate group to the modified oligonucleotide, wherein the linking group comprises 1-5 nucleosides.

1043. The oligomeric compound of any of embodiments 887-1041, wherein the oligomeric compound does not comprise additional nucleosides beyond those of the modified oligonucleotide.

1044. The oligomeric compound of any of embodiments 887-1043, wherein the nucleobase sequence of the modified oligonucleotide is complementary to a target RNA.

1045. The oligomeric compound of embodiment 1044, wherein the nucleobase sequence of the modified oligonucleotide is at least 85% complementary to the target RNA.

1046. The oligomeric compound of embodiment 1044, wherein the nucleobase sequence of the modified oligonucleotide is at least 90% complementary to the target RNA.

1047. The oligomeric compound of embodiment 1044, wherein the nucleobase sequence of the modified oligonucleotide is at least 95% complementary to the target RNA.

1048. The oligomeric compound of embodiment 1047, wherein the nucleobase sequence of the modified oligonucleotide is 100% complementary to the target RNA.

1049. The oligomeric compound of any of embodiments 1044-1048, wherein the target RNA is a target mRNA or a target pre-mRNA.

1050. The oligomeric compound of embodiment 1049, wherein the target mRNA or target pre-mRNA is not a mouse, rat, monkey, or human PTEN RNA.

1051. The oligomeric compound of embodiment 1049 or 1050, wherein the target mRNA or target pre-mRNA is not a mouse, rat, monkey, or human SRB-1 RNA.

1052. The oligomeric compound of any of embodiments 1049-1051, wherein the target mRNA or target pre-mRNA is not a mouse, rat, monkey, or human MYD88 RNA.

1053. The oligomeric compound of any of embodiments 1049-1052, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.

1054. The oligomeric compound of any of embodiments 1044-1053, wherein the target RNA is a human RNA.

1055. The oligomeric compound of any of embodiments 1044-1054, wherein the target RNA is expressed in the liver.

1056. The oligomeric compound of any of embodiments 1044-1055, wherein the target RNA is a liver target.

1057. The oligomeric compound of any of embodiments 1044-1054, wherein the target RNA is not expressed in the liver.

1058. The oligomeric compound of any of embodiments 1044-1054 or 1057, wherein the target RNA is not a liver target.

1059. The oligomeric compound of any of embodiments 1044-1056, wherein modulation of the expression of the target RNA in the liver is associated with treating a disorder or condition.

1060. The oligomeric compound of embodiment 1059, wherein the disorder or condition is a liver disorder or condition.

1061. The oligomeric compound of any of embodiments 1044-1060, wherein the target RNA is expressed in the central nervous system.

1062. The oligomeric compound of any of embodiments 1044-1060, wherein the target RNA is not expressed in the central nervous system.

1063. The oligomeric compound of any of embodiments 1044-1061, wherein the target RNA is a central nervous system target.

1064. The oligomeric compound of any of embodiments 1044-1062, wherein the target RNA is not a central nervous system target.

1065. The oligomeric compound of any of embodiments 1044-1064, wherein the target RNA is expressed in white fat cells.

1066. The oligomeric compound of any of embodiments 1044-1064, wherein the target RNA is expressed in brown fat cells.

1067. The oligomeric compound of any of embodiments 1044-1064, wherein the target RNA is expressed in adipocytes.

1068. The oligomeric compound of any of embodiments 1044-1064, wherein the target RNA is expressed in macrophages.

1069. The oligomeric compound of any of embodiments 1044-1064, wherein the target RNA is expressed in cancer cells.

1070. The oligomeric compound of any of embodiments 1044-1064, wherein the target RNA is expressed in tumor cells.

1071. The oligomeric compound of any of embodiments 1044-1064, wherein the target RNA is expressed in smooth muscle cells.

1072. The oligomeric compound of any of embodiments 1044-1064, wherein the target RNA is expressed in lymphocytes.

1073. The oligomeric compound of any of embodiments 1044-1064, wherein the target RNA is expressed in pulmonary cells.

1074. The oligomeric compound of any of embodiments 1044-1064, wherein the target RNA is expressed in heart muscle cells.

1075. The oligomeric compound of any of embodiments 1044-1064, wherein the target RNA is expressed in cardiomyocytes.

1076. The oligomeric compound of any of embodiments 1044-1064, wherein the target RNA is expressed in endothelial cells.

1077. The oligomeric compound of any of embodiments 1044-1064, wherein the target RNA is expressed in fibroblasts.

1078. The oligomeric compound of any of embodiments 1044-1064, wherein the target RNA is expressed in glial cells.

1079. The oligomeric compound of any of embodiments 1044-1064, wherein the target RNA is expressed in Schwann cells.

1080. The oligomeric compound of any of embodiments 1044-1064, wherein the target RNA is expressed in pancreatic cells.

1081. The oligomeric compound of any of embodiments 1044-1064, wherein the target RNA is expressed in kidney cells.

1082. The oligomeric compound of any of embodiments 1044-1064, wherein the target RNA is expressed in beta cells.

1083. The oligomeric compound of any of embodiments 1044-1064, wherein the target RNA is expressed in non-parenchymal cells.

1084. The oligomeric compound of any of embodiments 1044-1064, wherein the target RNA is expressed in hepatocytes.

1085. The oligomeric compound of any of embodiments 1044-1064, wherein the target RNA is expressed in oligodendrocytes.

1086. The oligomeric compound of any of embodiments 1044-1064, wherein the target RNA is expressed in astrocytes.

1087. The oligomeric compound of any of embodiments 1044-1064, wherein the target RNA is expressed in microglia.

1088. The oligomeric compound of any of embodiments 1044-1064, wherein the target RNA is expressed in ependymal cells.

1089. The oligomeric compound of any of embodiments 1044-1064, wherein the target RNA is expressed in sensory neurons.

1090. The oligomeric compound of any of embodiments 1044-1064, wherein the target RNA is expressed in motor neurons.

1091. The oligomeric compound of any of embodiments 1044-1064, wherein the target RNA is expressed in skeletal muscle.

1092. The oligomeric compound of any of embodiments 1044-1064, wherein the target RNA is expressed in cardiac muscle.

1093. The oligomeric compound of any of embodiments 1044-1064, wherein the target RNA is expressed in smooth muscle.

1094. The oligomeric compound of any of embodiments 1044-1064, wherein the target RNA is expressed in adipose tissue.

1095. The oligomeric compound of any of embodiments 1044-1064, wherein the target RNA is expressed in white adipose tissue.

1096. The oligomeric compound of any of embodiments 1044-1064, wherein the target RNA is expressed in the spleen.

1097. The oligomeric compound of any of embodiments 1044-1064, wherein the target RNA is expressed in the bone.

1098. The oligomeric compound of any of embodiments 1044-1064, wherein the target RNA is expressed in the bone marrow.

1099. The oligomeric compound of any of embodiments 1044-1064, wherein the target RNA is expressed in the intestine.

1100. The oligomeric compound of any of embodiments 1044-1064, wherein the target RNA is expressed in the adrenal glands.

1101. The oligomeric compound of any of embodiments 1044-1064, wherein the target RNA is expressed in the testes.

1102. The oligomeric compound of any of embodiments 1044-1064, wherein the target RNA is expressed in the ovaries.

1103. The oligomeric compound of any of embodiments 1044-1064, wherein the target RNA is expressed in the pancreas.

1104. The oligomeric compound of any of embodiments 1044-1064, wherein the target RNA is expressed in the pituitary gland.

1105. The oligomeric compound of any of embodiments 1044-1064, wherein the target RNA is expressed in the prostate gland.

1106. The oligomeric compound of any of embodiments 1044-1064, wherein the target RNA is expressed in the skin.

1107. The oligomeric compound of any of embodiments 1044-1064, wherein the target RNA is expressed in the epidermis.

1108. The oligomeric compound of any of embodiments 1044-1064, wherein the target RNA is expressed in the uterus.

1109. The oligomeric compound of any of embodiments 1044-1064, wherein the target RNA is expressed in the bladder.

1110. The oligomeric compound of any of embodiments 1044-1064, wherein the target RNA is expressed in the brain.

1111. The oligomeric compound of any of embodiments 1044-1064, wherein the target RNA is expressed in the glomerulus.

1112. The oligomeric compound of any of embodiments 1044-1064, wherein the target RNA is expressed in the distal tubular epithelium.

1113. The oligomeric compound of any of embodiments 1044-1064, wherein the target RNA is expressed in breast tissue.

1114. The oligomeric compound of any of embodiments 1044-1064, wherein the target RNA is expressed in the lung.

1115. The oligomeric compound of any of embodiments 1044-1064, wherein the target RNA is expressed in the heart.

1116. The oligomeric compound of any of embodiments 1044-1064, wherein the target RNA is expressed in the kidney.

1117. The oligomeric compound of any of embodiments 1044-1064, wherein the target RNA is expressed in the ganglion.

1118. The oligomeric compound of any of embodiments 1044-1064, wherein the target RNA is expressed in the frontal cortex.

1119. The oligomeric compound of any of embodiments 1044-1064, wherein the target RNA is expressed in the spinal cord.

1120. The oligomeric compound of any of embodiments 1044-1064, wherein the target RNA is expressed in the trigeminal ganglion.

1121. The oligomeric compound of any of embodiments 1044-1064, wherein the target RNA is expressed in the sciatic nerve.

1122. The oligomeric compound of any of embodiments 1044-1064, wherein the target RNA is expressed in the dorsal root ganglion.

1123. The oligomeric compound of any of embodiments 1044-1064, wherein the target RNA is expressed in the epidymal fat.

1124. The oligomeric compound of any of embodiments 1044-1064, wherein the target RNA is expressed in the diaphragm.

1125. The oligomeric compound of any of embodiments 1044-1064, wherein the target RNA is expressed in the colon.

1126. The oligomeric compound of any of embodiments 1044-1064, wherein the target RNA is a white fat cell target.

1127. The oligomeric compound of any of embodiments 1044-1064, wherein the target RNA is a brown fat cell target.

1128. The oligomeric compound of any of embodiments 1044-1064, wherein the target RNA is an adipocyte target.

1129. The oligomeric compound of any of embodiments 1044-1064, wherein the target RNA is a macrophage target.

1130. The oligomeric compound of any of embodiments 1044-1064, wherein the target RNA is a cancer cell target.

1131. The oligomeric compound of any of embodiments 1044-1064, wherein the target RNA is a tumor cell target.

1132. The oligomeric compound of any of embodiments 158-178, wherein the target RNA is a smooth muscle cell target.

1133. The oligomeric compound of any of embodiments 1044-1064, wherein the target RNA is a lymphocyte target.

1134. The oligomeric compound of any of embodiments 1044-1064, wherein the target RNA is a pulmonary cell target.

1135. The oligomeric compound of any of embodiments 1044-1064, wherein the target RNA is a heart muscle cell target.

1136. The oligomeric compound of any of embodiments 1044-1064, wherein the target RNA is a cardiomyocyte target.

1137. The oligomeric compound of any of embodiments 1044-1064, wherein the target RNA is a endothelial cell target.

1138. The oligomeric compound of any of embodiments 1044-1064, wherein the target RNA is a fibroblast target.

1139. The oligomeric compound of any of embodiments 1044-1064, wherein the target RNA is a glial cell target.

1140. The oligomeric compound of any of embodiments 1044-1064, wherein the target RNA is a Schwann cell target.

1141. The oligomeric compound of any of embodiments 1044-1064, wherein the target RNA is a pancreatic cell target.

1142. The oligomeric compound of any of embodiments 1044-1064, wherein the target RNA is a kidney cell target.

1143. The oligomeric compound of any of embodiments 1044-1064, wherein the target RNA is a beta cell target.

1144. The oligomeric compound of any of embodiments 1044-1064, wherein the target RNA is a non-parenchymal cell target.

1145. The oligomeric compound of any of embodiments 1044-1064, wherein the target RNA is a hepatocyte target.

1146. The oligomeric compound of any of embodiments 1044-1064, wherein the target RNA a oligodendrocyte target.

1147. The oligomeric compound of any of embodiments 1044-1064, wherein the target RNA is a astrocyte target.

1148. The oligomeric compound of any of embodiments 1044-1064, wherein the target RNA is a microglia target.

1149. The oligomeric compound of any of embodiments 1044-1064, wherein the target RNA is a ependymal cell target.

1150. The oligomeric compound of any of embodiments 1044-1064, wherein the target RNA is a sensory neuron target.

1151. The oligomeric compound of any of embodiments 1044-1064, wherein the target RNA is a motor neuron target.

1152. The oligomeric compound of any of embodiments 1044-1064, wherein the target RNA is a skeletal muscle target.

1153. The oligomeric compound of any of embodiments 1044-1064, wherein the target RNA is a cardiac muscle target.

1154. The oligomeric compound of any of embodiments 1044-1064, wherein the target RNA is a smooth muscle target.

1155. The oligomeric compound of any of embodiments 1044-1064, wherein the target RNA is a adipose tissue target.

1156. The oligomeric compound of any of embodiments 1044-1064, wherein the target RNA is a white adipose tissue target.

1157. The oligomeric compound of any of embodiments 1044-1064, wherein the target RNA is a spleen target.

1158. The oligomeric compound of any of embodiments 1044-1064, wherein the target RNA is a bone target.

1159. The oligomeric compound of any of embodiments 1044-1064, wherein the target RNA is a bone marrow target.

1160. The oligomeric compound of any of embodiments 1044-1064, wherein the target RNA is an intestinal target.

1161. The oligomeric compound of any of embodiments 1044-1064, wherein the target RNA is an adrenal gland target.

1162. The oligomeric compound of any of embodiments 1044-1064, wherein the target RNA is a testicular target.

1163. The oligomeric compound of any of embodiments 1044-1064, wherein the target RNA is an ovarian target.

1164. The oligomeric compound of any of embodiments 1044-1064, wherein the target RNA is a pancreatic target.

1165. The oligomeric compound of any of embodiments 1044-1064, wherein the target RNA is a pituitary gland target.

1166. The oligomeric compound of any of embodiments 1044-1064, wherein the target RNA is a prostate gland target.

1167. The oligomeric compound of any of embodiments 1044-1064, wherein the target RNA is a skin target.

1168. The oligomeric compound of any of embodiments 1044-1064, wherein the target RNA is an epidermal target.

1169. The oligomeric compound of any of embodiments 1044-1064, wherein the target RNA is a uterine target.

1170. The oligomeric compound of any of embodiments 1044-1064, wherein the target RNA is a bladder target.

1171. The oligomeric compound of any of embodiments 1044-1064, wherein the target RNA is a brain target.

1172. The oligomeric compound of any of embodiments 1044-1064, wherein the target RNA is a glomerulus target.

1173. The oligomeric compound of any of embodiments 1044-1064, wherein the target RNA is a distal tubular epithelium target.

1174. The oligomeric compound of any of embodiments 1044-1064, wherein the target RNA is a breast tissue target.

1175. The oligomeric compound of any of embodiments 1044-1064, wherein the target RNA is a lung target.

1176. The oligomeric compound of any of embodiments 1044-1064, wherein the target RNA is a heart target.

1177. The oligomeric compound of any of embodiments 1044-1064, wherein the target RNA is a kidney target.

1178. The oligomeric compound of any of embodiments 1044-1064, wherein the target RNA is a ganglion target.

1179. The oligomeric compound of any of embodiments 1044-1064, wherein the target RNA is a frontal cortex target.

1180. The oligomeric compound of any of embodiments 1044-1064, wherein the target RNA is a spinal cord target.

1181. The oligomeric compound of any of embodiments 1044-1064, wherein the target RNA is a trigeminal ganglion target.

1182. The oligomeric compound of any of embodiments 1044-1064, wherein the target RNA is a sciatic nerve target.

1183. The oligomeric compound of any of embodiments 1044-1064, wherein the target RNA is a dorsal root ganglion target.

1184. The oligomeric compound of any of embodiments 1044-1064, wherein the target RNA is a epidymal fat target.

1185. The oligomeric compound of any of embodiments 1044-1064, wherein the target RNA is a diaphragm target.

1186. The oligomeric compound of any of embodiments 1044-1064, wherein the target RNA is a colon target.

1187. The oligomeric compound of any of embodiments 1044-1186, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.

1188. The oligomeric compound of any of embodiments 1044-1186, wherein the target RNA is a HTT RNA.

1189. The oligomeric compound of embodiment 1187, wherein the target RNA is a MeCP2 RNA.

1190. The oligomeric compound of embodiment 1187, wherein the target RNA is a DUX4 RNA.

1191. The oligomeric compound of embodiment 1187, wherein the target RNA is a HDAC2 RNA.

1192. The oligomeric compound of embodiment 1187, wherein the target RNA is a Ataxin 1 RNA.

1193. The oligomeric compound of embodiment 1187, wherein the target RNA is a Ataxin 2 RNA.

1194. The oligomeric compound of embodiment 1187, wherein the target RNA is a Ataxin 3 RNA.

1195. The oligomeric compound of embodiment 1187, wherein the target RNA is a Ataxin 6 RNA.

1196. The oligomeric compound of embodiment 1187, wherein the target RNA is a Ataxin 7 RNA.

1197. The oligomeric compound of embodiment 1187, wherein the target RNA is a C9ORF72 RNA.

1198. The oligomeric compound of embodiment 1044-1186, wherein the target RNA is an alpha-synuclein RNA.

1199. The oligomeric compound of embodiment 1187, wherein the target RNA is an UBE3A RNA.

1200. The oligomeric compound of any of embodiments 1044-1186, wherein the target RNA is a SOD1 RNA.

1201. The oligomeric compound of embodiment 1187, wherein the target RNA is a Prion RNA.

1202. The oligomeric compound of embodiment 1187, wherein the target RNA is a PMP22 RNA.

1203. The oligomeric compound of any of embodiments 1044-1187, wherein the target RNA is a Tau RNA.

1204. The oligomeric compound of embodiment 1187, wherein the target RNA is a LRRK2 RNA.

1205. The oligomeric compound of embodiment 1187, wherein the target RNA is an APP RNA.

1206. The oligomeric compound of 1187, wherein the target RNA is a LINGO2 RNA.

1207. The oligomeric compound of any of embodiments 1187, wherein the target RNA is a GYS1 RNA.

1208. The oligomeric compound of any of embodiments 1187, wherein the target RNA is a KCNT1 RNA.

1209. The oligomeric compound of any of embodiments 1187, wherein the target RNA is a IRF8 RNA.

1210. The oligomeric compound of any of embodiments 1187, wherein the target RNA is a Progranulin RNA.

1211. The oligomeric compound of any of embodiments 1187, wherein the target RNA is a GFAP RNA.

1212. The oligomeric compound of any of embodiments 1044-1211, wherein modulation of the expression of the target RNA is associated with treating a disorder or condition.

1213. The oligomeric compound of any of embodiments 1212, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.

1214. The oligomeric compound of embodiment 1212, wherein the disorder or condition is Alzheimer's Disease.

1215. The oligomeric compound of embodiment 1212, wherein the disorder or condition is Amyotrophic Lateral Sclerosis.

1216. The oligomeric compound of embodiment 1212, wherein the disorder or condition is Parkinson's Disease.

1217. The oligomeric compound of embodiment 1212, wherein the disorder or condition is a Spinocerebellar ataxia.

1218. The oligomeric compound of embodiment 1212, wherein the disorder or condition is Angelman Syndrome.

1219. The oligomeric compound of embodiment 1212, wherein the disorder or condition is Alexander's Disease.

1220. The oligomeric compound of embodiment 1212, wherein the disorder or condition is Lafora Disease.

1221. The oligomeric compound of embodiment 1212, wherein the disorder or condition is Charcot-Marie Tooth Disease.

1222. The oligomeric compound of embodiment 1212, wherein the disorder or condition is Prion Disease.

1223. The oligomeric compound of embodiment 1212, wherein the disorder or condition is a dementia.

1224. The oligomeric compound of embodiment 1212, wherein the disorder or condition is neurodegeneration.

1225. The oligomeric compound of embodiment 1212, wherein the disorder or condition is MeCP2 Duplication Syndrome.

1226. The oligomeric compound of embodiment 1212, wherein the disorder or condition is encephalopathy.

1227. The oligomeric compound of embodiment 1212, wherein the disorder or condition is neuroinflammation.

1228. The oligomeric compound of embodiment 1212, wherein the disorder or condition is multiple sclerosis.

1229. The oligomeric compound of any of embodiments 887-1228, wherein the parent oligomeric compound of the oligomeric compound of any of embodiments 887-1228 is cytotoxic in vitro.

1230. The oligomeric compound of embodiment 1228, wherein the parent oligomeric compound is cytotoxic in a standard in vitro cytotoxicity assay.

1231. The oligomeric compound of any of embodiments 887-1229 wherein administration to a mouse of the parent oligomeric compound of the oligomeric compound of any of embodiments 887-1229 is hepatotoxic to the mouse.

1232. The oligomeric compound of embodiment 1230, wherein the administration of the parent oligomeric compound to the mouse is systemic administration.

1233. The oligomeric compound of embodiment 1230, wherein the systemic administration is subcutaneous administration.

1234. The oligomeric compound of any of embodiments 1230-1232, wherein the mouse is a CD-1 mouse.

1235. The oligomeric compound of any of embodiments 1230-1232, wherein the mouse is a $C_{57}BL/6$ mouse.

1236. The oligomeric compound of any of embodiments 1230-1232, wherein the mouse is a BALB/c mouse.

1237. The oligomeric compound of any of embodiments 1230-1236, wherein the plasma ALT level in the mouse is higher than 500 units per liter following the administration of the parent oligomeric compound.

1238. The oligomeric compound of any of embodiments 1230-1237, wherein the plasma AST level in the mouse is higher than 500 units per liter following the administration of the parent oligomeric compound.

1239. The oligomeric compound of any of embodiments 1230-1238, wherein the plasma ALT level in the mouse is higher than 1000 units per liter following the administration of the parent oligomeric compound.

1240. The oligomeric compound of any of embodiments 1230-1239, wherein the plasma AST level in the mouse is higher than 1000 units per liter following the administration of the parent oligomeric compound.

1241. The oligomeric compound of any of embodiments 1230-1240, wherein the hepatotoxicity is measured 24-48 hours following the administration of the parent oligomeric compound.

1242. The oligomeric compound of any of embodiments 1230-1241, wherein the hepatotoxicity is measured 72 hours following the administration of the parent oligomeric compound.

1243. The oligomeric compound of any of embodiments 1230-1241, wherein the hepatotoxicity is measured 3 days following the administration of the parent oligomeric compound.

1244. The oligomeric compound of any of embodiments 1230-1241, wherein the hepatotoxicity is measured 5 days following the administration of the parent oligomeric compound.

1245. The oligomeric compound of any of embodiments 1230-1241, wherein the hepatotoxicity is measured 7 days following the administration of the parent oligomeric compound.

1246. The oligomeric compound of any of embodiments 1230-1241, wherein the hepatotoxicity is measured 10 days following the administration of the parent oligomeric compound.

1247. The oligomeric compound of any of embodiments 1230-1241, wherein the hepatotoxicity is measured 14 days following the administration of the parent oligomeric compound.

1248. The oligomeric compound of any of embodiments 1230-1241, wherein 1-10 mg/kg of the parent oligomeric compound is administered to the mouse.

1249. The oligomeric compound of any of embodiments 1230-1241, wherein 10-25 mg/kg of the parent oligomeric compound is administered to the mouse.

1250. The oligomeric compound of any of embodiments 1230-1241, wherein 25-50 mg/kg of the parent oligomeric compound is administered to the mouse.

1251. The oligomeric compound of any of embodiments 1230-1241, wherein 50-100 mg/kg of the parent oligomeric compound is administered to the mouse.

1252. The oligomeric compound of any of embodiments 1230-1241, wherein 100-150 mg/kg of the parent oligomeric compound is administered to the mouse.

1253. The oligomeric compound of any of embodiments 1230-1241, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.

1254. The oligomeric compound of any of embodiments 887-1253, wherein administration of 50 mg/kg of the oligomeric compound of any of embodiments 887-1253 to a mouse is not hepatotoxic to the mouse.

1255. The oligomeric compound of embodiment 1254, wherein plasma ALT level in the mouse is lower than 100 units per liter following the administration of the oligomeric compound of embodiment 1254.

1256. The oligomeric compound of embodiment 1254 or 1255, wherein plasma ALT level in the mouse is at least 10-fold lower than plasma ALT level in a mouse administered the parent oligomeric compound of the oligomeric compound of embodiment 1254 or 1255, wherein the administrations and plasma ALT measurements of both the oligomeric compound of embodiment 1254 or 1255 and the parent oligomeric compound are completed in the same way.

1257. The oligomeric compound of embodiment 1256, wherein the plasma ALT level in the mouse is at least 100-fold lower than the plasma ALT level in the mouse administered the parent oligomeric compound.

1258. The oligomeric compound of embodiment 1256, wherein the plasma ALT level in the mouse is at least 500-fold lower than the plasma ALT level in the mouse administered the parent oligomeric compound.

1259. The oligomeric compound of any of embodiments 1230-1258, wherein the therapeutic index in a mouse of the oligomeric compound of any of embodiments 1230-1258 is increased relative to the therapeutic index of the parent oligomeric compound.

1260. The oligomeric compound of embodiment 1259, wherein the therapeutic index in a mouse of the oligomeric compound of embodiment 1259 is at least two-fold greater than the therapeutic index of the parent oligomeric compound.

1261. The oligomeric compound of any of embodiments 887-1229, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse; and wherein the otherwise identical oligomeric compound has a central region consisting of phosphorothioate internucleoside linkages, unmodified 2'β-D-deoxyribosyl sugar moieties, and nucleobases selected from thymine, uracil, adenine, guanine, cytosine, and 5-methylcytosine.

1262. The oligomeric compound of embodiment 1261, wherein the at least one modified internucleoside linkage other than phosphorothioate and/or at least one modified nucleoside comprising a modified nucleobase other than 5-methylcytosine and/or a modified sugar moiety in the central region is a 2'-O-methyl modified sugar moiety.

1263. The oligomeric compound of embodiment 1262, wherein the 2'-O-methyl modified sugar moiety is at position 2 of the central region.

1264. The oligomeric compound of embodiment 1261-1263, wherein the otherwise identical oligomeric compound lacks a 2'-O-methyl modified sugar moiety, and wherein the otherwise identical oligomeric compound comprises an unmodified 2'β-D-deoxyribosyl sugar moiety in place of the 2'-O-methyl modified sugar moiety.

1265. The oligomeric compound of any of embodiments 1261-1264, wherein the nucleobase sequence of the otherwise identical oligomeric compound is 100% complementary to the target RNA.

1266. The oligomeric compound of any of embodiments 1261-1265, wherein the otherwise identical oligomeric compound is a parent oligomeric compound of the oligomeric compound of any of embodiments 1202-1206.

1267. The oligomeric compound of any of embodiments 1044-1266, wherein the oligomeric compound inhibits the target RNA with an $IC_{50}$ lower than 100 nM in a standard in vitro activity assay.

1268. The oligomeric compound of any of embodiments 1044-1266, wherein the parent oligomeric compound of the oligomeric compound of any of embodiments 1044-1266 inhibits the target RNA with an $IC_{50}$ lower than 100 nM in a standard in vitro activity assay.

1269. The oligomeric compound of any of embodiments 1044-1268, wherein the difference between the $IC_{50}$ of the parent oligomeric compound measured in a standard in vitro activity assay and the $IC_{50}$ of the oligomeric compound of any of embodiments 1044-1268 measured in a standard in vitro activity assay is less than 4-fold.

1270. The oligomeric compound of any of embodiments 1044-1268, wherein the difference between the $IC_{50}$ of the parent oligomeric compound measured in a standard in vitro activity assay and the $IC_{50}$ of the oligomeric compound of any of embodiments 1044-1268 measured in a standard in vitro activity assay is less than 3-fold.

1271. The oligomeric compound of any of embodiments 1044-1268, wherein the difference between the $IC_{50}$ of the parent oligomeric compound measured in a standard in vitro activity assay and the $IC_{50}$ of the oligomeric compound of any of embodiments 1044-1268 measured in a standard in vitro activity assay is less than 2-fold.

1272. The oligomeric compound of any of embodiments 1044-1271, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

1273. The oligomeric compound of any of embodiments 1044-1272, wherein the nucleobase sequence of the parent oligomeric compound is 100% complementary to the target RNA.

1274. The oligomeric compound of any of embodiments 887-1273, wherein administration of 10-50 mg of the oligomeric compound to a human is not hepatotoxic to the human.

1275. The oligomeric compound of any of embodiments 887-1273, wherein administration of 50-100 mg of the oligomeric compound to a human is not hepatotoxic to the human.

1276. The oligomeric compound of any of embodiments 887-1273, wherein administration of 100-300 mg of the oligomeric compound to a human is not hepatotoxic to the human.

1277. The oligomeric compound of any of embodiments 1274-1276, wherein the administration is systemic administration.

1278. A composition comprising the oligomeric compound of any of embodiments 887-1277, and a second oligomeric compound, wherein the second oligomeric compound is complementary to the oligomeric compound of any of embodiments 887-1277.

1279. The composition of embodiment 1278, wherein the second oligomeric compound comprises at least 14 contiguous linked nucleosides that are at least 90% complementary to the oligomeric compound of any of embodiments 887-1277.

1280. The composition of embodiment 1278, wherein the second oligomeric compound comprises at least 14 contiguous linked nucleosides that are 100% complementary to the oligomeric compound of any of embodiments 887-1277.

1281. A pharmaceutical composition comprising the oligomeric compound of any of embodiments 887-1277 or the composition of any of embodiments 1278-1280, comprising a pharmaceutically acceptable carrier or diluent.

1282. A method comprising administering the oligomeric compound or composition of any of embodiments 887-1281 to a human subject.

1283. A method of treating a disease or disorder comprising administering the oligomeric compound or composition of any of embodiments 887-1281 to a human subject.

1284. A method of modulating the amount or activity of a target RNA in a human subject comprising administering the oligomeric compound or composition of any of embodiments 887-1281 to the human subject; and thereby modulating the amount or activity of the target RNA in the human subject.

1285. A method of treating a disease or disorder in a human subject comprising administering the oligomeric compound or composition of any of embodiments 887-1281 to the human subject having the disease or disorder; and thereby treating the disease or disorder in the human subject.

1286. The method of embodiment 1284 or 1285, wherein the disease or disorder is a liver disease, and wherein the oligomeric compound modulates the amount or activity of a liver target RNA.

1287. The method of embodiment 1284 or 1285, wherein the disease or disorder is a central nervous system disease, and wherein the oligomeric compound modulates the amount or activity of a central nervous system target RNA.

1288. The method of any of embodiments 1284-1287, wherein the disease or disorder is a cancer, a neurodegenerative disease, a cardiovascular disease, an immunological disease, a hereditary disease, a repeat expansion disease, a muscle-wasting disease, or a metabolic disease.

1289. The method of embodiment 1284 or 1285, wherein the oligomeric compound modulates the amount or activity of a white fat cell target.

1290. The method of embodiment 1284 or 1285, wherein the oligomeric compound modulates the amount or activity of a brown fat cell target.

1291. The method of embodiment 1284 or 1285, wherein the oligomeric compound modulates the amount or activity of an adipocyte target.

1292. The method of embodiment 1284 or 1285, wherein the oligomeric compound modulates the amount or activity of a macrophage target.

1293. The method of embodiment 1284 or 1285, wherein the oligomeric compound modulates the amount or activity of a cancer cell target.

1294. The method of embodiment 1284 or 1285, wherein the oligomeric compound modulates the amount or activity of a tumor cell target.

1295. The method of embodiment 1284 or 1285, wherein the oligomeric compound modulates the amount or activity of a smooth muscle cell target.

1296. The method of embodiment 1284 or 1285, wherein the oligomeric compound modulates the amount or activity of a lymphocyte target.

1297. The method of embodiment 1284 or 1285, wherein the oligomeric compound modulates the amount or activity of a pulmonary cell target.

1298. The method of embodiment 1284 or 1285, wherein the oligomeric compound modulates the amount or activity of a heart muscle cell target.

1299. The method of embodiment 1284 or 1285, wherein the oligomeric compound modulates the amount or activity of a cardiomyocyte target.

1300. The method of embodiment 1284 or 1285, wherein the oligomeric compound modulates the amount or activity of a endothelial cell target.

1301. The method of embodiment 1284 or 1285, wherein the oligomeric compound modulates the amount or activity of a fibroblast target.

1302. The method of embodiment 1284 or 1285, wherein the oligomeric compound modulates the amount or activity of a glial cell target.

1303. The method of embodiment 1284 or 1285, wherein the oligomeric compound modulates the amount or activity of a Schwann cell target.

1304. The method of embodiment 1284 or 1285, wherein the oligomeric compound modulates the amount or activity of a pancreatic cell target.

1305. The method of embodiment 1284 or 1285, wherein the oligomeric compound modulates the amount or activity of a kidney cell target.

1306. The method of embodiment 1284 or 1285, wherein the oligomeric compound modulates the amount or activity of a beta cell target.

1307. The method of embodiment 1284 or 1285, wherein the oligomeric compound modulates the amount or activity of a non-parenchymal cell target.

1308. The method of embodiment 1284 or 1285, wherein the oligomeric compound modulates the amount or activity of a hepatocyte target.

1309. The method of embodiment 1284 or 1285, wherein the oligomeric compound modulates the amount or activity of a oligodendrocyte target.

1310. The method of embodiment 1284 or 1285, wherein the oligomeric compound modulates the amount or activity of a astrocyte target.

1311. The method of embodiment 1284 or 1285, wherein the oligomeric compound modulates the amount or activity of a microglia target.

1312. The method of embodiment 1284 or 1285, wherein the oligomeric compound modulates the amount or activity of a ependymal cell target.

1313. The method of embodiment 1284 or 1285, wherein the oligomeric compound modulates the amount or activity of a sensory neuron target.

1314. The method of embodiment 1284 or 1285, wherein the oligomeric compound modulates the amount or activity of a motor neuron target.

1315. The method of embodiment 1284 or 1285, wherein the oligomeric compound modulates the amount or activity of a skeletal muscle target.

1316. The method of embodiment 1284 or 1285, wherein the oligomeric compound modulates the amount or activity of a cardiac muscle target.

1317. The method of embodiment 1284 or 1285, wherein the oligomeric compound modulates the amount or activity of a smooth muscle target.

1318. The method of embodiment 1284 or 1285, wherein the oligomeric compound modulates the amount or activity of a adipose tissue target.

1319. The method of embodiment 1284 or 1285, wherein the oligomeric compound modulates the amount or activity of a white adipose tissue target.

1320. The method of embodiment 1284 or 1285, wherein the oligomeric compound modulates the amount or activity of a spleen target.

1321. The method of embodiment 1284 or 1285, wherein the oligomeric compound modulates the amount or activity of a bone target.

1322. The method of embodiment 1284 or 1285, wherein the oligomeric compound modulates the amount or activity of a bone marrow target.

1323. The method of embodiment 1284 or 1285, wherein the oligomeric compound modulates the amount or activity of an intestinal target.

1324. The method of embodiment 1284 or 1285, wherein the oligomeric compound modulates the amount or activity of an adrenal gland target.

1325. The method of embodiment 1284 or 1285, wherein the oligomeric compound modulates the amount or activity of a testicular target.

1326. The method of embodiment 1284 or 1285, wherein the oligomeric compound modulates the amount or activity of an ovarian target.

1327. The method of embodiment 1284 or 1285, wherein the oligomeric compound modulates the amount or activity of a pancreatic target.

1328. The method of embodiment 1284 or 1285, wherein the oligomeric compound modulates the amount or activity of a pituitary gland target.

1329. The method of embodiment 1284 or 1285, wherein the oligomeric compound modulates the amount or activity of a prostate gland target.

1330. The method of embodiment 1284 or 1285, wherein the oligomeric compound modulates the amount or activity of a skin target.

1331. The method of embodiment 1284 or 1285, wherein the oligomeric compound modulates the amount or activity of an epidermal target.

1332. The method of embodiment 1284 or 1285, wherein the oligomeric compound modulates the amount or activity of a uterine target.

1333. The method of embodiment 1284 or 1285, wherein the oligomeric compound modulates the amount or activity of a bladder target.

1334. The method of embodiment 1284 or 1285, wherein the oligomeric compound modulates the amount or activity of a brain target.

1335. The method of embodiment 1284 or 1285, wherein the oligomeric compound modulates the amount or activity of a glomerulus target.

1336. The method of embodiment 1284 or 1285, wherein the oligomeric compound modulates the amount or activity of a distal tubular epithelium target.

1337. The method of embodiment 1284 or 1285, wherein the oligomeric compound modulates the amount or activity of a breast tissue target.

1338. The method of embodiment 1284 or 1285, wherein the oligomeric compound modulates the amount or activity of a lung target.

1339. The method of embodiment 1284 or 1285, wherein the oligomeric compound modulates the amount or activity of a heart target.

1340. The method of embodiment 1284 or 1285, wherein the oligomeric compound modulates the amount or activity of a kidney target.

1341. The method of embodiment 1284 or 1285, wherein the oligomeric compound modulates the amount or activity of a ganglion target.

1342. The method of embodiment 1284 or 1285, wherein the oligomeric compound modulates the amount or activity of a frontal cortex target.

1343. The method of embodiment 1284 or 1285, wherein the oligomeric compound modulates the amount or activity of a spinal cord target.

1344. The method of embodiment 1284 or 1285, wherein the oligomeric compound modulates the amount or activity of a trigeminal ganglion target.

1345. The method of embodiment 1284 or 1285, wherein the oligomeric compound modulates the amount or activity of a sciatic nerve target.

1346. The method of embodiment 1284 or 1285, wherein the oligomeric compound modulates the amount or activity of a dorsal root ganglion target.

1347. The method of embodiment 1284 or 1285, wherein the oligomeric compound modulates the amount or activity of a epidymal fat target.

1348. The method of embodiment 1284 or 1285, wherein the oligomeric compound modulates the amount or activity of a diaphragm target.

1349. The method of embodiment 1284 or 1285, wherein the oligomeric compound modulates the amount or activity of a colon target.

1350. The method of any of embodiments 1282-1349, wherein the plasma ALT level of the human subject after the administration is not more than three times higher than it was prior to the administration.

1351. The method of any of embodiments 1282-1350, wherein the plasma ALT level of the human subject after the administration is not more than 150 units per liter.

1352. The method of any of embodiments 1282-1351, wherein the human subject is susceptible to liver damage.

1353. The method of any of embodiments 1282-1352, wherein the human subject is susceptible to liver degeneration.

1354. The method of any of embodiments 1282-1353, wherein the human subject is susceptible to elevated apoptosis in the liver.

1355. The method of any of embodiments 1282-1354, wherein the human subject has a liver disease.

1356. The method of any of embodiments 1282-1355, wherein the human subject has kidney disease.

1357. The method of any of embodiments 1282-1356, wherein the human subject is susceptible to kidney damage.

1358. The method of any of embodiments 1282-1357, wherein the human subject has heart disease.

1359. The method of any of embodiments 1282-1358, wherein the human subject is susceptible to heart damage.

1360. The method of any of embodiments 1282-1359, wherein the human subject has pancreatitis.

1361. The method of any of embodiments 1282-1360, wherein the human subject is susceptible to pancreatic damage.

1362. The method of any of embodiments 1282-1361, wherein the human subject has a neurological disease.

1363. The method of any of embodiments 1282-1362, wherein the human subject is susceptible to neurological damage.

1364. The method of any of embodiments 1282-1363, comprising administering the parent oligomeric compound of the oligomeric compound of any of embodiments 887-1281 to a mouse.

1365. The method of any of embodiments 1282-1363, comprising contacting a cell with the parent oligomeric compound of the oligomeric compound of any of embodiments 887-1281.

1366. The method of embodiment 1364 or 1365, wherein each sugar moiety of the central region of the parent oligomeric compound is an unmodified 2'β-D-deoxyribosyl sugar moiety, and wherein each internucleoside linkage of the central region of the parent oligomeric compound is a phosphorothioate internucleoside linkage.

1367. A method of designing an oligomeric compound comprising starting with a parent oligomeric compound and changing the design of that compound in order to arrive at an oligomeric compound of any one of embodiments 887-1281.

1368. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 887-1281.

1369. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 887-1281. 1370. The method of embodiment 1368 or 1369, wherein the method designs an oligomeric compound with improved therapeutic index relative to the parent oligomeric compound.

1371. The method of embodiment 1368 or 1369, wherein the method designs an oligomeric compound with lower hepatotoxicity relative to the parent oligomeric compound.

1372. The method of embodiment 1368, wherein the second oligomeric compound has an improved therapeutic index relative to the parent oligomeric compound.

1373. The method of embodiment 1368 or 1369, wherein the second oligomeric compound has reduced hepatotoxicity in a mouse relative to the parent oligomeric compound.

1374. The method of embodiment 1368, wherein the oligomeric compound according to any one of embodiments 887-1281 has reduced hepatotoxicity relative to the parent oligomeric compound.

1375. A method comprising administering an oligomeric compound of any of embodiments 887-1281 to a mouse and separately administering the parent oligomeric compound of the oligomeric compound of any of embodiments 887-1281 to a second mouse, wherein the therapeutic index of the oligomeric compound of any of embodiments 887-1281 is improved relative to the therapeutic index of the parent oligomeric compound.

1376. The method of any of embodiments 1282-1375, wherein the level of p21 RNA is measured in the mouse, the cell, and/or the human subject.

1377. A method comprising administering an oligomeric compound of any of embodiments 887-1281 to a subject and measuring the level of p21 RNA in the subject.

1378. The method of embodiment 1377, wherein the subject is a mouse.

1379. The method of embodiment 1377, wherein the subject is a human.

1380. The method of any of embodiments 1377-1379, wherein the p21 RNA level is measured within 24 hours of the administration.

1381. The method of any of embodiments 1377-1380, wherein the p21 RNA level is measured 24-48 hours following the administration.

1382. An oligomeric compound or composition of any one of embodiments 887-1281, for use in medical therapy.

1383. The oligomeric compound of any of embodiments 887-1281, wherein the oligomeric compound is not toxic.

1384. The oligomeric compound of any of embodiment 887-1281, wherein a comparator compound is toxic; wherein the comparator compound is identical to the oligomeric compound except that each nucleoside of the central region of the comparator compound is a nucleoside comprising 2'-β-D-deoxyribosyl sugar moiety.

1385. The oligomeric compound of embodiment 1384, wherein administering a dose of the oligomeric compound to an animal results in a circulating ALT level that is at least 3-fold lower than the ALT level that results from administering the same dose of the comparator compound to an animal for at least one matched dose.

1386. The oligomeric compound of embodiment 1384 or 1385, wherein the lowest dose of the oligomeric compound that raises circulating ALT to over 300 units per liter is at least three-fold higher than the lowest dose of the comparator compound that raises circulating ALT to over 300 units per liter.

1387. The oligomeric compound of any of embodiments 1384-1386, wherein the oligomeric compound is capable of reducing the target RNA in a cell.

1388. The oligomeric compound of embodiment 1387, wherein the oligomeric compound has RNA-reducing activity comparable to a comparator compound, wherein the comparator compound is identical to the oligomeric compound except that each nucleoside of the central region of the comparator compound is a nucleoside comprising 2'β-D-deoxyribosyl sugar moiety.

1389. The oligomeric compound of embodiment 1388 having RNA-reducing activity that is no more than 2-fold worse than the RNA-reducing activity of the comparator compound.

1390. A method of modulating the amount or activity of a target RNA in a human subject comprising administering the oligomeric compound or composition of any of embodiments 887-1281 to the human subject; and thereby modulating the amount or activity of the target RNA in the human subject.

1391. A method of treating a disease or disorder in a human subject comprising administering the oligomeric compound or composition of any of embodiments 887-1281 to the human subject having the disease or disorder; and thereby treating the disease or disorder in the human subject.

1392. The method of embodiment 1390 or 1391, wherein the disease or disorder is a liver disease, and wherein the oligomeric compound modulates the amount or activity of a liver target RNA.

1393. The method of embodiment 1390 or 1391, wherein the disease or disorder is a central nervous system disease, and wherein the oligomeric compound modulates the amount or activity of a central nervous system target RNA.

1394. The method of any of embodiments 1390-1393, wherein the disease or disorder is a cancer, a neurodegenerative disease, a cardiovascular disease, an immunological disease, a hereditary disease, a repeat expansion disease, a muscle-wasting disease, or a metabolic disease.

1395. The method of any of embodiments 1390-1394, wherein the plasma ALT level of the human subject after the administration is not more than three times higher than it was prior to the administration.

1396. The method of any of embodiments 1390-1395, wherein the plasma ALT level of the human subject after the administration is not more than 150 units per liter.

1397. A method of treating a disease or disorder in a human subject comprising administering the oligomeric compound or composition of any of embodiments 887-1281 to the human subject having the disease or disorder; and thereby treating the disease or disorder in the human subject.

1398. The method of embodiment 1397, wherein the disease or disorder is not a CNS disease or disorder.

1399. The method of embodiment 1397, wherein the disease or disorder is a disease or disorder of the white fat cells.

1400. The method of embodiment 1397, wherein the disease or disorder is a disease or disorder of the brown fat cells.

1401. The method of embodiment 1397, wherein the disease or disorder is a disease or disorder of the adipocytes.

1402. The method of embodiment 1397, wherein the disease or disorder is a disease or disorder of the macrophages.

1403. The method of embodiment 1397, wherein the disease or disorder is a disease or disorder of the cancer cells.

1404. The method of embodiment 1397, wherein the disease or disorder is a disease or disorder of the tumor cells.

1405. The method of embodiment 1397, wherein the disease or disorder is a disease or disorder of the smooth muscle cells.

1406. The method of embodiment 1397, wherein the disease or disorder is a disease or disorder of the lymphocytes.

1407. The method of embodiment 1397, wherein the disease or disorder is a disease or disorder of the pulmonary cells.

1408. The method of embodiment 1397, wherein the disease or disorder is a disease or disorder of the heart muscle cells.

1409. The method of embodiment 1397, wherein the disease or disorder is a disease or disorder of the cardiomyocytes.

1410. The method of embodiment 1397, wherein the disease or disorder is a disease or disorder of the endothelial cells.

1411. The method of embodiment 1397, wherein the disease or disorder is a disease or disorder of the fibroblasts.

1412. The method of embodiment 1397, wherein the disease or disorder is a disease or disorder of the glial cells.

1413. The method of embodiment 1397, wherein the disease or disorder is a disease or disorder of the Schwann cells.

1414. The method of embodiment 1397, wherein the disease or disorder is a disease or disorder of the pancreatic cells.

1415. The method of embodiment 1397, wherein the disease or disorder is a disease or disorder of the kidney cells.

1416. The method of embodiment 1397, wherein the disease or disorder is a disease or disorder of the beta cells.

1417. The method of embodiment 1397, wherein the disease or disorder is a disease or disorder of the non-parenchymal cells.

1418. The method of embodiment 1397, wherein the disease or disorder is a disease or disorder of the hepatocytes.

1419. The method of embodiment 1397, wherein the disease or disorder is a disease or disorder of the oligodendrocytes.

1420. The method of embodiment 1397, wherein the disease or disorder is a disease or disorder of the astrocytes.

1421. The method of embodiment 1397, wherein the disease or disorder is a disease or disorder of the microglia.

1422. The method of embodiment 1397, wherein the disease or disorder is a disease or disorder of the ependymal cells.

1423. The method of embodiment 1397, wherein the disease or disorder is a disease or disorder of the sensory neurons.

1424. The method of embodiment 1397, wherein the disease or disorder is a disease or disorder of the motor neurons.

1425. The method of embodiment 1397, wherein the disease or disorder is a disease or disorder of the skeletal muscle.

1426. The method of embodiment 1397, wherein the disease or disorder is a disease or disorder of the cardiac muscle.

1427. The method of embodiment 1397, wherein the disease or disorder is a disease or disorder of the smooth muscle.

1428. The method of embodiment 1397, wherein the disease or disorder is a disease or disorder of the adipose tissue.

1429. The method of embodiment 1397, wherein the disease or disorder is a disease or disorder of the white adipose tissue.

1430. The method of embodiment 1397, wherein the disease or disorder is a disease or disorder of the spleen.

1431. The method of embodiment 1397, wherein the disease or disorder is a disease or disorder of the bone.

1432. The method of embodiment 1397, wherein the disease or disorder is a disease or disorder of the bone marrow.

1433. The method of embodiment 1397, wherein the disease or disorder is a disease or disorder of the intestine.

1434. The method of embodiment 1397, wherein the disease or disorder is a disease or disorder of the adrenal glands.

1435. The method of embodiment 1397, wherein the disease or disorder is a disease or disorder of the testes.

1436. The method of embodiment 1397, wherein the disease or disorder is a disease or disorder of the ovaries.

1437. The method of embodiment 1397, wherein the disease or disorder is a disease or disorder of the pancreas.

1438. The method of embodiment 1397, wherein the disease or disorder is a disease or disorder of the pituitary gland.

1439. The method of embodiment 1397, wherein the disease or disorder is a disease or disorder of the prostate gland.

1440. The method of embodiment 1397, wherein the disease or disorder is a disease or disorder of the skin.

1441. The method of embodiment 1397, wherein the disease or disorder is a disease or disorder of the epidermis.

1442. The method of embodiment 1397, wherein the disease or disorder is a disease or disorder of the uterus.

1443. The method of embodiment 1397, wherein the disease or disorder is a disease or disorder of the bladder.

1444. The method of embodiment 1397, wherein the disease or disorder is a disease or disorder of the brain.

1445. The method of embodiment 1397, wherein the disease or disorder is a disease or disorder of the glomerulus.

1446. The method of embodiment 1397, wherein the disease or disorder is a disease or disorder of the distal tubular epithelium.

1447. The method of embodiment 1397, wherein the disease or disorder is a disease or disorder of the breast tissue.

1448. The method of embodiment 1397, wherein the disease or disorder is a disease or disorder of the lung.

1449. The method of embodiment 1397, wherein the disease or disorder is a disease or disorder of the heart.

1450. The method of embodiment 1397, wherein the disease or disorder is a disease or disorder of the kidney.

1451. The method of embodiment 1397, wherein the disease or disorder is a disease or disorder of the ganglion.

1452. The method of embodiment 1397, wherein the disease or disorder is a disease or disorder of the frontal cortex.

1453. The method of embodiment 1397, wherein the disease or disorder is a disease or disorder of the spinal cord.

1454. The method of embodiment 1397, wherein the disease or disorder is a disease or disorder of the trigeminal ganglion.

1455. The method of embodiment 1397, wherein the disease or disorder is a disease or disorder of the sciatic nerve.

1456. The method of embodiment 1397, wherein the disease or disorder is a disease or disorder of the dorsal root ganglion.

1457. The method of embodiment 1397, wherein the disease or disorder is a disease or disorder of the epidymal fat.

1458. The method of embodiment 1397, wherein the disease or disorder is a disease or disorder of the diaphragm.

1459. The method of embodiment 1397, wherein the disease or disorder is a disease or disorder of the colon.

1460. A method of screening a library of oligomeric compounds for activity against a target RNA, wherein the library of oligomeric compounds comprises a plurality of oligomeric compounds of any of embodiments 887-1281.

1461. An oligomeric compound comprising a modified oligonucleotide consisting of 12-21 linked nucleosides, wherein the modified oligonucleotide has the formula A-B-C, wherein A is a 5'-region, B is a central region, and C is a 3'-region; wherein:
the 5'-region consists of 1-5 linked nucleosides, wherein at least one nucleoside of the 5'-region is a modified nucleoside comprising a modified sugar;
the 3'-region consists of 1-5 linked nucleosides wherein at least one nucleoside of the 3'-region is a modified nucleoside comprising a modified sugar; and
the central region consists of 7-11 linked nucleosides, wherein
the 5'-most portion of the central region has the following formula:

$(N_{da})(N_x)(N_y)(N_z)(N_{db})$ wherein one of $N_x$, $N_y$, and $N_z$, is a safety-enhancing nucleoside;
the other two of $N_x$, $N_y$, and $N_z$ are independently selected from an unmodified 2'β-D-deoxyribosyl sugar moiety, a DNA isomer, a modified DNA isomer, and a DNA mimic; and $N_{da}$ and $N_{db}$ are each independently selected from an unmodified 2'-β-D-deoxyribosyl sugar moiety, a DNA isomer, a modified DNA isomer, and a DNA mimic.

1462. The oligomeric compound of embodiment 1461, wherein the 5'-region consists of one nucleoside.

1463. The oligomeric compound of embodiment 1461, wherein the 5'-region consists of 2-5 linked nucleosides.

1464. The oligomeric compound of embodiment 1461, wherein the 5'-region consists of 2-4 linked nucleosides.

1465. The oligomeric compound of embodiment 1461, wherein the 5'-region consists of 2 linked nucleosides.

1466. The oligomeric compound of embodiment 1461, wherein the 5'-region consists of 3 linked nucleosides.

1467. The oligomeric compound of embodiment 1461, wherein the 5'-region consists of 4 linked nucleosides.

1468. The oligomeric compound of embodiment 1461, wherein the 5'-region consists of 5 linked nucleosides.

1469. The oligomeric compound of any of embodiments 1461-1468, wherein each nucleoside of the 5'-region is a modified nucleoside.

1470. The oligomeric compound of any of embodiments 1461-1469, wherein each nucleoside of the 5'-region is a modified nucleoside comprising a modified sugar.

1471. The oligomeric compound of any of embodiments 1461-1470, wherein each modified nucleoside of the 5'-region has the same modification.

1472. The oligomeric compound of and of embodiments 1461-1470, wherein at least two nucleosides of the 5'-region are modified nucleosides having different modifications.

1473. The oligomeric compound of any of embodiments 1461-1472, wherein each nucleoside of the 5'-region comprises a 2'-modified ribosyl sugar moiety.

1474. The oligomeric compound of any of embodiments 1461-1473, wherein at least one nucleoside of the 5'-region comprises a bicyclic furanosyl sugar moiety.

1475. The oligomeric compound of any of embodiments 1461-1474, wherein each nucleoside of the 5'-region comprises a bicyclic furanosyl sugar moiety.

1476. The oligomeric compound of any of embodiments 1461-1474, wherein at least one nucleoside of the 5'-region comprises a non-bicyclic sugar moiety.

1477. The oligomeric compound of embodiment 1476, wherein the non-bicyclic sugar moiety of the at least one nucleoside of the 5'-region is a 2'-substituted ribosyl sugar moiety.

1478. The oligomeric compound of any of embodiments 1461-1474 or 1476-1477, wherein each nucleoside of the 5'-region comprises a non-bicyclic sugar moiety.

1479. The oligomeric compound of embodiment 1478, wherein each nucleoside of the 5'-region comprises a 2'-substituted furanosyl sugar moiety.

1480. The oligomeric compound of any of embodiments 1461-1474 or 1476-1477, wherein each nucleoside of the 5'-region comprises a 2'-modified furanosyl sugar moiety independently selected from a bicyclic sugar moiety and a non-bicyclic 2'-substituted ribosyl sugar moiety.

1481. The oligomeric compound of any of embodiments 1461-1477 or 1480, wherein each nucleoside of the 5'-region comprises a bicyclic sugar moiety.

1482. The oligomeric compound of any of embodiments 1461-1474 or 1476-1480, wherein each nucleoside of the 5'-region comprises a non-bicyclic 2'-substituted ribosyl sugar moiety.

1483. The oligomeric compound of any of embodiments 1461-1477 or 1480-1481, wherein each bicyclic sugar moiety of the 5'-region is selected from among cEt, LNA, and ENA.

1484. The oligomeric compound of any of embodiments 1461-1477 or 1480-1481, wherein each bicyclic sugar moiety of the 5'-region is a cEt sugar moiety.

1485. The oligomeric compound of any of embodiments 1461-1477 or 1480-1481, wherein each bicyclic sugar moiety of the 5'-region is an LNA sugar moiety.

1486. The oligomeric compound of any of embodiments 1461-1474, 1476-1480, or 1482-1485, wherein each non-bicyclic sugar moiety of the 5'-region has a 2'-substituent selected from among 2'-MOE, 2'-OMe, and 2'-NMA.

1487. The oligomeric compound of any of embodiments 1461-1486, wherein none of the nucleosides of the 5'-region comprise a sugar moiety having a 2'-F substituent.

1488. The oligomeric compound of any of embodiments 1461-1487, wherein none of the nucleosides of the 5'-region comprise a sugar moiety having a 2'-MOE substituent.

1489. The oligomeric compound of any of embodiments 1461-1488, wherein none of the nucleosides of the 5'-region comprise a sugar moiety having a 2'-OMe substituent.

1490. The oligomeric compound of any of embodiments 1461-1489, wherein none of the nucleosides of the 5'-region comprise a cEt sugar moiety.

1491. The oligomeric compound of any of embodiments 1461-1490, wherein none of the nucleosides of the 5'-region comprise a LNA sugar moiety.

1492. The oligomeric compound of any of embodiments 1461-1491, wherein each nucleobase of the 5'-region is independently selected from among thymine, uracil, guanine, cytosine, 5-methylcytosine, and adenine.

1493. The oligomeric compound of any of embodiments 1461-1492, wherein each internucleoside linkage of the 5'-region is independently selected from among phosphodiester and phosphorothioate internucleoside linkages.

1494. The oligomeric compound of any of embodiments 1461-1493, wherein the 3'-region consists of one nucleoside.

1495. The oligomeric compound of any of embodiments 1461-1493, wherein the 3'-region consists of 2-5 linked nucleosides.

1496. The oligomeric compound of any of embodiments 1461-1493, wherein the 3'-region consists of 2-4 linked nucleosides.

1497. The oligomeric compound of any of embodiments 1461-1493, wherein the 3'-region consists of 2 linked nucleosides.

1498. The oligomeric compound of any of embodiments 1461-1493, wherein the 3'-region consists of 3 linked nucleosides.

1499. The oligomeric compound of any of embodiments 1461-1493, wherein the 3'-region consists of 4 linked nucleosides.

1500. The oligomeric compound of any of embodiments 1461-1493, wherein the 3'-region consists of 5 linked nucleosides.

1501. The oligomeric compound of any of embodiments 1461-1500, wherein each nucleoside of the 3'-region is a modified nucleoside.

1502. The oligomeric compound of any of embodiments 1461-1501, wherein each nucleoside of the 3'-region is a modified nucleoside comprising a modified sugar moiety.

1503. The oligomeric compound of any of embodiments 1461-1502, wherein each modified nucleoside of the 3'-region has the same modification.

1504. The oligomeric compound of and of embodiments 1461-1502, wherein at least two nucleosides of the 3'-region are modified nucleosides having different modifications.

1505. The oligomeric compound of any of embodiments 1461-1504, wherein each nucleoside of the 3'-region comprises a 2'-modified ribosyl sugar moiety.

1506. The oligomeric compound of any of embodiments 1461-1505, wherein at least one nucleoside of the 3'-region comprises a bicyclic furanosyl sugar moiety.

1507. The oligomeric compound of any of embodiments 1461-1506, wherein each nucleoside of the 3'-region comprises a bicyclic furanosyl sugar moiety.

1508. The oligomeric compound of any of embodiments 1461-1506, wherein at least one nucleoside of the 3'-region comprises a non-bicyclic sugar moiety.

1509. The oligomeric compound of embodiment 1508, wherein the non-bicyclic sugar moiety of the at least one nucleoside of the 3'-region is a 2'-substituted ribosyl sugar moiety.

1510. The oligomeric compound of any of embodiments 1461-1509, wherein each nucleoside of the 3'-region comprises a non-bicyclic sugar moiety.

1511. The oligomeric compound of embodiment 1510, wherein each nucleoside of the 3'-region comprises a 2'-substituted furanosyl sugar moiety.

1512. The oligomeric compound of any of embodiments 1461-1511, wherein each nucleoside of the 3'-region comprises a 2'-modified furanosyl sugar moiety independently selected from a bicyclic sugar moiety and a non-bicyclic 2'-substituted ribosyl sugar moiety.

1513. The oligomeric compound of any of embodiments 1461-1512, wherein each nucleoside of the 3'-region comprises a bicyclic sugar moiety.

1514. The oligomeric compound of any of embodiments 1461-1512, wherein each nucleoside of the 3'-region comprises a non-bicyclic 2'-substituted ribosyl sugar moiety.

1515. The oligomeric compound of any of embodiments 1461-1509 or 1512-1513, wherein each bicyclic sugar moiety of the 3'-region is selected from among cEt, LNA, and ENA.

1516. The oligomeric compound of any of embodiments 1461-1509, 1512-1513, or 1515, wherein each bicyclic sugar moiety of the 3'-region is a cEt sugar moiety.

1517. The oligomeric compound of any of embodiments 1461-1509, 1512-1513, or 1515, wherein each bicyclic sugar moiety of the 3'-region is an LNA sugar moiety.

1518. The oligomeric compound of any of embodiments 1461-1506, 1508-1512 or 1514, wherein each non-bicyclic sugar moiety of the 3'-region has a 2'-substituent selected from among 2'-MOE, 2'-OMe, and 2'-NMA.

1519. The oligomeric compound of any of embodiments 1461-1518, wherein none of the nucleosides of the 3'-region comprise a sugar moiety having a 2'-F substituent.

1520. The oligomeric compound of any of embodiments 1461-1519, wherein none of the nucleosides of the 3'-region comprise a sugar moiety having a 2'-MOE substituent.

1521. The oligomeric compound of any of embodiments 1461-1520, wherein none of the nucleosides of the 3'-region comprise a sugar moiety having a 2'-OMe substituent.

1522. The oligomeric compound of any of embodiments 1461-1521, wherein none of the nucleosides of the 3'-region comprise a cEt sugar moiety.

1523. The oligomeric compound of any of embodiments 1461-1522, wherein none of the nucleosides of the 3'-region comprise a LNA sugar moiety.

1524. The oligomeric compound of any of embodiments 1461-1523, wherein each nucleobase of the 3'-region is independently selected from among thymine, uracil, guanine, cytosine, 5-methylcytosine, and adenine.

1525. The oligomeric compound of any of embodiments 1461-1524, wherein each internucleoside linkage of the 3'-region is independently selected from among phosphodiester and phosphorothioate internucleoside linkages.

1526. The oligomeric compound of any of embodiments 1461-1525, wherein the modified nucleosides of the 5'-region have the same modifications as the modifications of the modified nucleosides of the 3'-region.

1527. The oligomeric compound of any of embodiments 1461-1525, wherein at least one modified nucleoside of the 5'-region and one modified nucleoside of the 3'-region comprise modifications that differ from one another.

1528. The oligomeric compound of any of embodiments 1461-1474, 1476-1477, 1480, 1483-1506, 1508-1509, 1512, 1515-1527, wherein the 5'-region and the 3'-region together include at least one non-bicyclic 2'-substituted modified nucleoside and at least one bicyclic nucleoside.

1529. The oligomeric compound of any of embodiment 1528, where the bicyclic nucleoside is a cEt nucleoside.

1530. The oligomeric compound of embodiment 1528, where the bicyclic nucleoside is an LNA nucleoside.

1531. The oligomeric compound of any of embodiments 1528-1530, wherein the non-bicyclic 2'-modified nucleoside is a 2'-MOE nucleoside.

1532. The oligomeric compound of any of embodiments 1528-1530, wherein the non-bicyclic 2'-modified nucleoside is a 2'-OMe nucleoside.

1533. The oligomeric compound of any of embodiments 1528-1532, wherein at least one nucleoside of the 5'-region or the 3'-region is an unmodified 2'β-D-deoxyribosyl sugar moiety.

1534. The oligomeric compound of any of embodiments 1461-1533, wherein the central region has the formula:

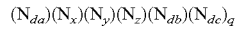

$(N_{da})(N_x)(N_y)(N_z)(N_{db})(N_{dc})_q$ wherein each $N_{dc}$ is independently selected from an unmodified 2'β-D-deoxyribosyl sugar moiety, a DNA isomer, a modified DNA isomer, and a DNA mimic; and q is 2-6.

1535. The oligomeric compound of any of embodiments 1461-1534, wherein the central region consists of 7 linked nucleosides.

1536. The oligomeric compound of any of embodiments 1461-1534, wherein the central region consists of 8 linked nucleosides.

1537. The oligomeric compound of any of embodiments 1461-1534, wherein the central region consists of 9 linked nucleosides.

1538. The oligomeric compound of any of embodiments 1461-1534, wherein the central region consists of 10 linked nucleosides.

1539. The oligomeric compound of any of embodiments 1461-1534, wherein the central region consists of 11 linked nucleosides.

1540. The oligomeric compound of any of embodiments 1461-1539, wherein Nx is the safety-enhancing nucleoside.

1541. The oligomeric compound of any of embodiments 1461-1539, wherein Ny is the safety-enhancing nucleoside.

1542. The oligomeric compound of any of embodiments 1461-1539, wherein Nz is the safety-enhancing nucleoside.

1543. The oligomeric compound of any of embodiments 1461-1542, wherein the safety enhancing nucleoside is a DNA isomer or a modified DNA isomer, or a modified nucleoside comprising either a sugar surrogate, a bicyclic furanosyl sugar moiety, or a non-bicyclic modified furanosyl sugar moiety.

1544. The oligomeric compound of any of embodiments 1461-1543, wherein the safety enhancing nucleoside is a DNA isomer or a modified DNA isomer, or comprises either a sugar surrogate, a bicyclic furanosyl sugar moiety, a non-bicyclic, 2'-modified furanosyl sugar moiety, a non-bicyclic 3'-modified furanosyl sugar moiety, a non-bicyclic, 4'-modified furanosyl sugar moiety, or a non-bicyclic 5'-modified furanosyl sugar moiety.

1545. The oligomeric compound of any of embodiments 1461-1544, wherein the safety enhancing nucleoside comprises a sugar surrogate selected from a morpholino, a modified morpholino, a modified cyclohexenyl, or a modified tetrahydropyran.

1546. The oligomeric compound of any of embodiments 1461-1544, wherein the safety enhancing nucleoside comprises a sugar surrogate selected from a morpholino, a modified morpholino, 2'-fluoroarabinose, 2'-fluororibose, CeNA, F-CeNA, HNA, OMe-HNA or F-HNA.

1547. The oligomeric compound of any of embodiments 1461-1544, wherein the safety enhancing nucleoside is a DNA isomer comprising a sugar moiety selected from among 2'-β-D-deoxyxylosyl, 2'-α-L-deoxyribosyl, 2'β-L-deoxyribosyl, 2'-α-D-deoxyxylosyl, 2'-α-D-deoxyribosyl, 2'-α-L-deoxyxylosyl, and 2'-O-L-deoxyxylosyl.

1548. The oligomeric compound of any of embodiments 1461-1544 or 1547, wherein the safety enhancing nucleoside is a DNA isomer comprising a sugar moiety selected from among 2'-β-D-deoxyxylosyl, 2'-α-L-deoxyribosyl, and 2'-β-L-deoxyribosyl.

1549. The oligomeric compound of any of embodiments 1461-1544, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

1550. The oligomeric compound of any of embodiments 1461-1544 or 1549, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

1551. The oligomeric compound of any of embodiments 1461-1544 or 1549-1550, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

1552. The oligomeric compound of any of embodiments 1461-1544 or 1549-1551, wherein the safety enhancing nucleoside is a modified DNA isomer comprising a sugar moiety selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

1553. The oligomeric compound of any of embodiments 1461-1544, wherein the safety enhancing nucleoside is a modified nucleoside comprising a bicyclic furanosyl sugar moiety.

1554. The oligomeric compound of any of embodiments 1461-1544, wherein the safety enhancing nucleoside is selected from among cEt, LNA, α-L-LNA, and ENA.

1555. The oligomeric compound of any of embodiments 1461-1544, wherein the safety enhancing nucleoside comprises a 2'-substituted furanosyl sugar moiety.

1556. The oligomeric compound of embodiment 1555, wherein the 2'-substituted furanosyl sugar moiety of the safety enhancing nucleoside has a 2' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$$SCH_3$, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl.

1557. The oligomeric compound of embodiment 1555, wherein the 2'-substituted furanosyl sugar moiety of the safety enhancing nucleoside has a 2' substituent selected from: halo, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl.

1558. The oligomeric compound of embodiment 1555, wherein the 2'-substituted furanosyl sugar moiety of the safety enhancing nucleoside has a 2' substituent selected from: fluoro, OMe, MOE, NMA.

1559. The oligomeric compound of any of embodiments 1461-1558, wherein the safety enhancing nucleoside comprises a 2'-substituted furanosyl sugar moiety comprising a 2'-OMe or 2'-MOE.

1560. The oligomeric compound of any of embodiments 1461-1559, wherein the safety enhancing nucleoside comprises a 2'-substituted furanosyl sugar moiety comprising a 2'-OMe.

1561. The oligomeric compound of any of embodiments 1461-1560, wherein the safety enhancing nucleoside comprises a 2'-OMe modified 2'-β-D-deoxyribosyl sugar moiety.

1562. The oligomeric compound of any of embodiments 1461-1544, wherein the safety enhancing nucleoside comprises a 3'-modified furanosyl sugar moiety having a 3' substituent selected from: halo, allyl, amino, azido, SH, CN, $CF_3$, $OCF_3$, $C_1$-$C_{10}$ alkyl, $C_1$-$C_{10}$ substituted alkyl, S-alkyl, N($R_m$)-alkyl, N($R_m$)-alkenyl, N($R_m$)-alkynyl, O-alkylenyl-O-alkyl, alkynyl, alkaryl, or aralkyl.

1563. The oligomeric compound of any of embodiments 1461-1544 or embodiment 1562, wherein the safety enhancing nucleoside comprises a 3'-modified furanosyl sugar moiety having a 3' substituent selected from: $C_1$-$C_{10}$ alkyl, or $C_1$-$C_{10}$ substituted alkyl.

1564. The oligomeric compound of any of embodiments 1461-1544 or 1562-1563, wherein the safety enhancing nucleoside comprises a 3'-methyl furanosyl sugar moiety.

1565. The oligomeric compound of any of embodiments 1461-1544, wherein the safety enhancing nucleoside comprises a 4'-modified furanosyl sugar moiety having a 4' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)- alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$$SCH_3$, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl.

1566. The oligomeric compound of any of embodiments 1461-1544 or 1565, wherein the safety enhancing nucleoside comprises a 4'-modified furanosyl sugar moiety having a 4'-methyl.

1567. The oligomeric compound of any of embodiments 1461-1544, wherein the safety enhancing nucleoside has the structure shown below, wherein R represents an optional 2' substituent group and Bx is a heterocyclic base moiety:

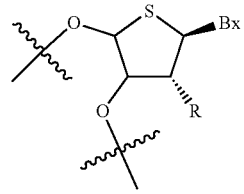

1568. The oligomeric compound of embodiment 1567, wherein in R is selected from among H, OH, OMe, F, or MOE.

1569. The oligomeric compound of any of embodiments 1461-1544, wherein the safety enhancing nucleoside comprises a 5'-modified furanosyl sugar moiety having a 5' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)- alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$$SCH_3$, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl.

1570. The oligomeric compound of any of embodiments 1461-1544 or 1569, wherein the safety enhancing nucleoside comprises a 5'-modified furanosyl sugar moiety with a 5' substituent selected from: 5'-methyl, 5'-ethyl or a 5'-allyl.

1571. The oligomeric compound of any of embodiments 1461-1544 or 1569-1570, wherein the safety enhancing nucleoside comprises a 5'-modified furanosyl sugar moiety with a 5' substituent selected from: 5'-(R)-methyl- or 5'-(R)-ethyl.

1572. The oligomeric compound of any of embodiments 1461-1544 or 1569-1571, wherein the safety enhancing nucleoside comprises a 5'-(R)-methyl-2'-β-D-deoxyribosyl sugar moiety.

1573. The oligomeric compound of any of embodiments 1461-154 or 1569-1572, wherein the safety enhancing nucleoside comprises a 5'-(R)-ethyl-2'-β-D-deoxyribosyl sugar moiety.

1574. The oligomeric compound of any of embodiments 1461-1573, wherein the safety enhancing nucleoside does not comprise a 2'-F modified sugar moiety.

1575. The oligomeric compound of any of embodiments 1461-1574, wherein the safety enhancing nucleoside does not comprise a cEt modified sugar moiety.

1576. The oligomeric compound of any of embodiments 1461-1575, wherein the safety enhancing nucleoside does not comprise a 2'-MOE modified sugar moiety.

1577. The oligomeric compound of any of embodiments 1461-1576, wherein the safety enhancing nucleoside comprises a hypoxanthine nucleobase.

1578. The oligomeric compound of any of embodiments 1461-1577, wherein the safety enhancing nucleoside comprises a nucleobase selected from among thymine, uracil, guanine, cytosine, 5-methylcytosine, and adenine.

1579. The oligomeric compound of any of embodiments 1461-1578, wherein the safety enhancing nucleoside is a modified nucleoside other than cEt, MOE, LNA, or FANA.

1580. The oligomeric compound of any of embodiments 1461-1579, wherein each Nd is independently selected from among an unmodified 2'-β-D-deoxyribosyl sugar moiety, a DNA isomer, a 2'-modified DNA isomer, and a DNA mimic.

1581. The oligomeric compound of embodiment 1580, wherein each DNA isomer comprises a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

1582. The oligomeric compound of embodiment 1581, wherein each DNA isomer comprises a sugar moiety selected from among 2'-β-D-deoxyxylosyl, 2'-α-L-deoxyribosyl, and 2'-β-L-deoxyribosyl.

1583. The oligomeric compound of embodiment 1580, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

1584. The oligomeric compound of embodiment 1583, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

1585. The oligomeric compound of embodiment 1584, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

1586. The oligomeric compound of embodiment 1585, wherein each modified DNA isomer comprises a 2'-modified sugar moiety, wherein the sugar moiety is selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

1587. The oligomeric compound of embodiment 1580, wherein each DNA mimic comprises a structure represented by one of the formulas below:

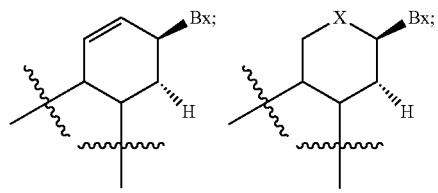

wherein X is O or S and Bx represents a heterocylic base moiety.

1588. The oligomeric compound of embodiment 1580, wherein each DNA mimic comprises a structure represented by one of the formulas below:

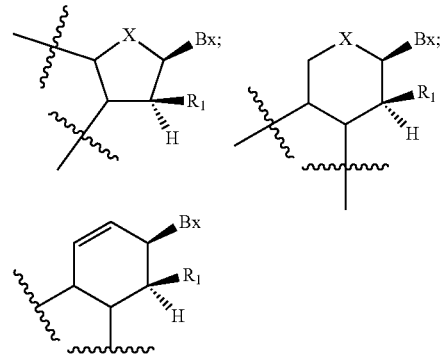

wherein X is O or S;
Bx represents a heterocyclic base moiety; and
$R_1$ is selected from among H, OH, halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$$SCH_3$, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl;
wherein if the DNA mimic comprises the structure:

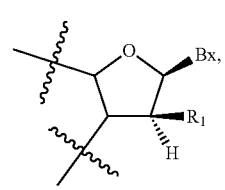

$R_1$ is other than H.

1589. The oligomeric compound of embodiment 1588, wherein $R_1$ is H, OH, OMe, or F.

1590. The oligomeric compound of embodiment 1588, wherein $R_1$ is not F.

1591. The oligomeric compound of embodiment 1580, wherein each DNA mimic comprises a structure represented by the formula below:

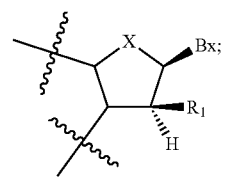

wherein X is S, Bx represents a heterocyclic base moiety, and $R_1$ is H.

1592. The oligomeric compound of embodiment 1580, wherein the DNA mimic has a sugar moiety selected from among: 5'-methyl-2'-β-D-deoxyribosyl, 5'-ethyl-2'-β-D-deoxyribosyl, and 5'-allyl-2'-β-D-deoxyribosyl.

1593. The oligomeric compound of embodiment 1580, wherein the DNA mimic comprises a 2'-fluoro-β-D-arabinofuranosyl sugar moiety.

1594. The oligomeric compound of embodiment 1580, wherein the DNA mimic does not comprise a 2'-fluoro-β-D-arabinofuranosyl sugar moiety.

1595. The oligomeric compound of any of embodiments 1461-1594, wherein each $N_d$ is an unmodified 2'-β-D-deoxyribosyl sugar moiety.

1596. The oligomeric compound of any of embodiments 1461-1595, wherein the central region comprises no more than four nucleosides selected from among DNA isomers, modified DNA isomers, and DNA mimics.

1597. The oligomeric compound of any of embodiments 1461-1595, wherein the central region comprises no more than three nucleosides selected from among DNA isomers, modified DNA isomers, and DNA mimics.

1598. The oligomeric compound of any of embodiments 1461-1595, wherein the central region comprises no more than two nucleosides selected from among DNA isomers, modified DNA isomers, and DNA mimics.

1599. The oligomeric compound of any of embodiments 1461-1595, wherein the central region comprises no more than one nucleoside selected from among DNA isomers, modified DNA isomers, and DNA mimics.

1600. The oligomeric compound of any of embodiments 1461-1599, wherein the central region contains exactly one safety enhancing nucleoside and the remainder of nucleosides in the central region are unmodified 2'-β-D-deoxyribosyl sugar moieties.

1601. The oligomeric compound of any of embodiments 1461-1600, wherein at least one internucleoside linkage of the central region selected from among: the internucleoside Nda to Nx, Nx to Ny, Ny to Nz, or Nz to the adjacent Ndb is a neutral internucleoside linkage.

1602. The oligomeric compound of embodiment 1601, wherein the neutral linkage is a phosphonate internucleoside linkage.

1603. The oligomeric compound of embodiment 1601, wherein the neutral linkage is a methoxypropyl internucleoside linkage.

1604. The oligomeric compound of embodiment 1601, wherein each remaining internucleoside linkage is a phosphodiester or phosphorothioate internucleoside linkage.

1605. The oligomeric compound of any of embodiments 1461-1600, wherein at least one internucleoside linkage of the central region is a 2'-5' internucleoside linkage.

1606. The oligomeric compound of any of embodiments 1461-1600, wherein exactly one internucleoside linkage of the central region is a 2'-5' internucleoside linkage.

1607. The oligomeric compound of any of embodiments 1461-1600, wherein at least one internucleoside linkage of the central region selected from among: the internucleoside Nda to Nx, Nx to Ny, Ny to Nz, or Nz to the adjacent Ndb is a 2'-5' internucleoside linkage.

1608. A chirally enriched population of modified oligonucleotides of any of embodiments 1461-1607, wherein the central region has at least one particular phorphorothioate internucleoside linkage having a particular stereochemical configuration.

1609. The chirally enriched population of embodiment 1608, wherein the central region has at least one phorphorothioate internucleoside linkage having the (Sp) configuration.

1610. The chirally enriched population of embodiment 1608, wherein central region has at least one phorphorothioate internucleoside linkage having the (Rp) configuration.

1611. The chirally enriched population of embodiment 1608, wherein the central region has a particular, independently selected stereochemical configuration at each phosphorothioate internucleoside linkage.

1612. The chirally enriched population of embodiment 1608, wherein the each phosphorothioate internucleoside linkage of the central region has the (Sp) configuration.

1613. The chirally enriched population of embodiment 1608, wherein the central region has one phosphorothioate internucleoside linkage having the (Rp) configuration and wherein each remaining central region phosphorothioate internucleoside linkage has the (Sp) configuration.

1614. The chirally enriched population of embodiment 1608, wherein the central region has an (Rp) phosphorothioate internucleoside linkage adjacent to an (Sp) phosphorothioate internucleoside linkage.

1615. The chirally enriched population of embodiment 1608, wherein the central region has an (Rp) phosphorothioate internucleoside linkage adjacent to a second (Rp) phosphorothioate internucleoside linkage.

1616. The chirally enriched population of embodiment 1608, wherein the central region has an (Rp) phosphorothioate internucleoside linkage adjacent to a second (Rp) phosphorothioate internucleoside linkage, and wherein each remaining central region phosphorothioate internucleoside linkage has the (Sp) configuration.

1617. The chirally enriched population of any of embodiments 1609, 1610, 1614, or 1615 wherein each phosphorothioate internucleoside linkage that does not have the (Rp) or (Sp) configuration is stereorandom.

1618. The oligomeric compound of any of embodiments 1461-1617 comprising a conjugate group.

1619. The oligomeric compound of embodiment 1618, wherein the conjugate group comprises a linking group attaching the remainder of the conjugate group to the modified oligonucleotide, wherein the linking group comprises 1-5 nucleosides.

1620. The oligomeric compound of any of embodiments 1461-1618, wherein the oligomeric compound does not comprise additional nucleosides beyond those of the modified oligonucleotide.

1621. The oligomeric compound of any of embodiments 1461-1620, wherein the nucleobase sequence of the modified oligonucleotide is complementary to a target RNA.

1622. The oligomeric compound of embodiment 1621, wherein the nucleobase sequence of the modified oligonucleotide is at least 85% complementary to the target RNA.

1623. The oligomeric compound of embodiment 1621, wherein the nucleobase sequence of the modified oligonucleotide is at least 90% complementary to the target RNA.

1624. The oligomeric compound of embodiment 1621, wherein the nucleobase sequence of the modified oligonucleotide is at least 95% complementary to the target RNA.

1625. The oligomeric compound of embodiment 1621, wherein the nucleobase sequence of the modified oligonucleotide is 100% complementary to the target RNA.

1626. The oligomeric compound of any of embodiments 1621-1625, wherein the target RNA is a target mRNA or a target pre-mRNA.

1627. The oligomeric compound of embodiment 1626, wherein the target mRNA or target pre-mRNA is not a mouse, rat, monkey, or human PTEN RNA.

1628. The oligomeric compound of embodiment 1626 or 1627, wherein the target mRNA or target pre-mRNA is not a mouse, rat, monkey, or human SRB-1 RNA.

1629. The oligomeric compound of any of embodiments 1626-1628, wherein the target mRNA or target pre-mRNA is not a mouse, rat, monkey, or human MYD88 RNA.

1630. The oligomeric compound of any of embodiments 1626-1629, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.

1631. The oligomeric compound of any of embodiments 1621-1630, wherein the target RNA is a human RNA.

1632. The oligomeric compound of any of embodiments 1621-1631, wherein the target RNA is expressed in the liver.

1633. The oligomeric compound of any of embodiments 1621-1632, wherein the target RNA is a liver target.

1634. The oligomeric compound of any of embodiments 1621-1631, wherein the target RNA is not expressed in the liver.

1635. The oligomeric compound of any of embodiments 1621-1631 or 1634, wherein the target RNA is not a liver target.

1636. The oligomeric compound of any of embodiments 1621-1635, wherein modulation of the expression of the target RNA in the liver is associated with treating a disorder or condition.

1637. The oligomeric compound of embodiment 1636, wherein the disorder or condition is a liver disorder or condition.

1638. The oligomeric compound of any of embodiments 1621-1637, wherein the target RNA is expressed in the central nervous system.

1639. The oligomeric compound of any of embodiments 1621-1637, wherein the target RNA is not expressed in the central nervous system.

1640. The oligomeric compound of any of embodiments 1621-1638, wherein the target RNA is a central nervous system target.

1641. The oligomeric compound of any of embodiments 1621-1639, wherein the target RNA is not a central nervous system target.

1642. The oligomeric compound of any of embodiments 1621-1641, wherein the target RNA is expressed in white fat cells.

1643. The oligomeric compound of any of embodiments 1621-1641, wherein the target RNA is expressed in brown fat cells.

1644. The oligomeric compound of any of embodiments 1621-1641, wherein the target RNA is expressed in adipocytes.

1645. The oligomeric compound of any of embodiments 1621-1641, wherein the target RNA is expressed in macrophages.

1646. The oligomeric compound of any of embodiments 1621-1641, wherein the target RNA is expressed in cancer cells.

1647. The oligomeric compound of any of embodiments 1621-1641, wherein the target RNA is expressed in tumor cells.

1648. The oligomeric compound of any of embodiments 1621-1641, wherein the target RNA is expressed in smooth muscle cells.

1649. The oligomeric compound of any of embodiments 1621-1641, wherein the target RNA is expressed in lymphocytes.

1650. The oligomeric compound of any of embodiments 1621-1641, wherein the target RNA is expressed in pulmonary cells.

1651. The oligomeric compound of any of embodiments 1621-1641, wherein the target RNA is expressed in heart muscle cells.

1652. The oligomeric compound of any of embodiments 1621-1641, wherein the target RNA is expressed in cardiomyocytes.

1653. The oligomeric compound of any of embodiments 1621-1641, wherein the target RNA is expressed in endothelial cells.

1654. The oligomeric compound of any of embodiments 1621-1641, wherein the target RNA is expressed in fibroblasts.

1655. The oligomeric compound of any of embodiments 1621-1641, wherein the target RNA is expressed in glial cells.

1656. The oligomeric compound of any of embodiments 1621-1641, wherein the target RNA is expressed in Schwann cells.

1657. The oligomeric compound of any of embodiments 1621-1641, wherein the target RNA is expressed in pancreatic cells.

1658. The oligomeric compound of any of embodiments 1621-1641, wherein the target RNA is expressed in kidney cells.

1659. The oligomeric compound of any of embodiments 1621-1641, wherein the target RNA is expressed in beta cells.

1660. The oligomeric compound of any of embodiments 1621-1641, wherein the target RNA is expressed in non-parenchymal cells.

1661. The oligomeric compound of any of embodiments 1621-1641, wherein the target RNA is expressed in hepatocytes.

1662. The oligomeric compound of any of embodiments 1621-1641, wherein the target RNA is expressed in oligodendrocytes.

1663. The oligomeric compound of any of embodiments 1621-1641, wherein the target RNA is expressed in astrocytes.

1664. The oligomeric compound of any of embodiments 1621-1641, wherein the target RNA is expressed in microglia.

1665. The oligomeric compound of any of embodiments 1621-1641, wherein the target RNA is expressed in ependymal cells.

1666. The oligomeric compound of any of embodiments 1621-1641, wherein the target RNA is expressed in sensory neurons.

1667. The oligomeric compound of any of embodiments 1621-1641, wherein the target RNA is expressed in motor neurons.

1668. The oligomeric compound of any of embodiments 1621-1641, wherein the target RNA is expressed in skeletal muscle.

1669. The oligomeric compound of any of embodiments 1621-1641, wherein the target RNA is expressed in cardiac muscle.

1670. The oligomeric compound of any of embodiments 1621-1641, wherein the target RNA is expressed in smooth muscle.

1671. The oligomeric compound of any of embodiments 1621-1641, wherein the target RNA is expressed in adipose tissue.

1672. The oligomeric compound of any of embodiments 1621-1641, wherein the target RNA is expressed in white adipose tissue.

1673. The oligomeric compound of any of embodiments 1621-1641, wherein the target RNA is expressed in the spleen.

1674. The oligomeric compound of any of embodiments 1621-1641, wherein the target RNA is expressed in the bone.

1675. The oligomeric compound of any of embodiments 1621-1641, wherein the target RNA is expressed in the bone marrow.

1676. The oligomeric compound of any of embodiments 1621-1641, wherein the target RNA is expressed in the intestine.

1677. The oligomeric compound of any of embodiments 1621-1641, wherein the target RNA is expressed in the adrenal glands.

1678. The oligomeric compound of any of embodiments 1621-1641, wherein the target RNA is expressed in the testes.

1679. The oligomeric compound of any of embodiments 1621-1641, wherein the target RNA is expressed in the ovaries.

1680. The oligomeric compound of any of embodiments 1621-1641, wherein the target RNA is expressed in the pancreas.

1681. The oligomeric compound of any of embodiments 1621-1641, wherein the target RNA is expressed in the pituitary gland.

1682. The oligomeric compound of any of embodiments 1621-1641, wherein the target RNA is expressed in the prostate gland.

1683. The oligomeric compound of any of embodiments 1621-1641, wherein the target RNA is expressed in the skin.

1684. The oligomeric compound of any of embodiments 1621-1641, wherein the target RNA is expressed in the epidermis.

1685. The oligomeric compound of any of embodiments 1621-1641, wherein the target RNA is expressed in the uterus.

1686. The oligomeric compound of any of embodiments 1621-1641, wherein the target RNA is expressed in the bladder.

1687. The oligomeric compound of any of embodiments 1621-1641, wherein the target RNA is expressed in the brain.

1688. The oligomeric compound of any of embodiments 1621-1641, wherein the target RNA is expressed in the glomerulus.

1689. The oligomeric compound of any of embodiments 1621-1641, wherein the target RNA is expressed in the distal tubular epithelium.

1690. The oligomeric compound of any of embodiments 1621-1641, wherein the target RNA is expressed in breast tissue.

1691. The oligomeric compound of any of embodiments 1621-1641, wherein the target RNA is expressed in the lung.

1692. The oligomeric compound of any of embodiments 1621-1641, wherein the target RNA is expressed in the heart.

1693. The oligomeric compound of any of embodiments 1621-1641, wherein the target RNA is expressed in the kidney.

1694. The oligomeric compound of any of embodiments 1621-1641, wherein the target RNA is expressed in the ganglion.

1695. The oligomeric compound of any of embodiments 1621-1641, wherein the target RNA is expressed in the frontal cortex.

1696. The oligomeric compound of any of embodiments 1621-1641, wherein the target RNA is expressed in the spinal cord.

1697. The oligomeric compound of any of embodiments 1621-1641, wherein the target RNA is expressed in the trigeminal ganglion.

1698. The oligomeric compound of any of embodiments 1621-1641, wherein the target RNA is expressed in the sciatic nerve.

1699. The oligomeric compound of any of embodiments 1621-1641, wherein the target RNA is expressed in the dorsal root ganglion.

1700. The oligomeric compound of any of embodiments 1621-1641, wherein the target RNA is expressed in the epidymal fat.

1701. The oligomeric compound of any of embodiments 1621-1641, wherein the target RNA is expressed in the diaphragm.

1702. The oligomeric compound of any of embodiments 1621-1641, wherein the target RNA is expressed in the colon.

1703. The oligomeric compound of any of embodiments 1621-1641, wherein the target RNA is a white fat cell target.

1704. The oligomeric compound of any of embodiments 1621-1641, wherein the target RNA is a brown fat cell target.

1705. The oligomeric compound of any of embodiments 1621-1641, wherein the target RNA is an adipocyte target.

1706. The oligomeric compound of any of embodiments 1621-1641, wherein the target RNA is a macrophage target.

1707. The oligomeric compound of any of embodiments 1621-1641, wherein the target RNA is a cancer cell target.

1708. The oligomeric compound of any of embodiments 1621-1641, wherein the target RNA is a tumor cell target.

1709. The oligomeric compound of any of embodiments 1621-1641, wherein the target RNA is a smooth muscle cell target.

1710. The oligomeric compound of any of embodiments 1621-1641, wherein the target RNA is a lymphocyte target.

1711. The oligomeric compound of any of embodiments 1621-1641, wherein the target RNA is a pulmonary cell target.

1712. The oligomeric compound of any of embodiments 1621-1641, wherein the target RNA is a heart muscle cell target.

1713. The oligomeric compound of any of embodiments 1621-1641, wherein the target RNA is a cardiomyocyte target.

1714. The oligomeric compound of any of embodiments 1621-1641, wherein the target RNA is a endothelial cell target.

1715. The oligomeric compound of any of embodiments 1621-1641, wherein the target RNA is a fibroblast target.

1716. The oligomeric compound of any of embodiments 1621-1641, wherein the target RNA is a glial cell target.

1717. The oligomeric compound of any of embodiments 1621-1641, wherein the target RNA is a Schwann cell target.

1718. The oligomeric compound of any of embodiments 1621-1641, wherein the target RNA is a pancreatic cell target.

1719. The oligomeric compound of any of embodiments 1621-1641, wherein the target RNA is a kidney cell target.

1720. The oligomeric compound of any of embodiments 1621-1641, wherein the target RNA is a beta cell target.

1721. The oligomeric compound of any of embodiments 1621-1641, wherein the target RNA is a non-parenchymal cell target.

1722. The oligomeric compound of any of embodiments 1621-1641, wherein the target RNA is a hepatocyte target.

1723. The oligomeric compound of any of embodiments 1621-1641, wherein the target RNA a oligodendrocyte target.

1724. The oligomeric compound of any of embodiments 1621-1641, wherein the target RNA is a astrocyte target.

1725. The oligomeric compound of any of embodiments 1621-1641, wherein the target RNA is a microglia target.

1726. The oligomeric compound of any of embodiments 1621-1641, wherein the target RNA is a ependymal cell target.

1727. The oligomeric compound of any of embodiments 1621-1641, wherein the target RNA is a sensory neuron target.

1728. The oligomeric compound of any of embodiments 1621-1641, wherein the target RNA is a motor neuron target.

1729. The oligomeric compound of any of embodiments 1621-1641, wherein the target RNA is a skeletal muscle target.

1730. The oligomeric compound of any of embodiments 1621-1641, wherein the target RNA is a cardiac muscle target.

1731. The oligomeric compound of any of embodiments 1621-1641, wherein the target RNA is a smooth muscle target.

1732. The oligomeric compound of any of embodiments 1621-1641, wherein the target RNA is a adipose tissue target.

1733. The oligomeric compound of any of embodiments 1621-1641, wherein the target RNA is a white adipose tissue target.

1734. The oligomeric compound of any of embodiments 1621-1641, wherein the target RNA is a spleen target.

1735. The oligomeric compound of any of embodiments 1621-1641, wherein the target RNA is a bone target.

1736. The oligomeric compound of any of embodiments 1621-1641, wherein the target RNA is a bone marrow target.

1737. The oligomeric compound of any of embodiments 1621-1641, wherein the target RNA is an intestinal target.

1738. The oligomeric compound of any of embodiments 1621-1641, wherein the target RNA is an adrenal gland target.

1739. The oligomeric compound of any of embodiments 1621-1641, wherein the target RNA is a testicular target.

1740. The oligomeric compound of any of embodiments 1621-1641, wherein the target RNA is an ovarian target.

1741. The oligomeric compound of any of embodiments 1621-1641, wherein the target RNA is a pancreatic target.

1742. The oligomeric compound of any of embodiments 1621-1641, wherein the target RNA is a pituitary gland target.

1743. The oligomeric compound of any of embodiments 1621-1641, wherein the target RNA is a prostate gland target.

1744. The oligomeric compound of any of embodiments 1621-1641, wherein the target RNA is a skin target.

1745. The oligomeric compound of any of embodiments 1621-1641, wherein the target RNA is an epidermal target.

1746. The oligomeric compound of any of embodiments 1621-1641, wherein the target RNA is a uterine target.

1747. The oligomeric compound of any of embodiments 1621-1641, wherein the target RNA is a bladder target.

1748. The oligomeric compound of any of embodiments 1621-1641, wherein the target RNA is a brain target.

1749. The oligomeric compound of any of embodiments 1621-1641, wherein the target RNA is a glomerulus target.

1750. The oligomeric compound of any of embodiments 1621-1641, wherein the target RNA is a distal tubular epithelium target.

1751. The oligomeric compound of any of embodiments 1621-1641, wherein the target RNA is a breast tissue target.

1752. The oligomeric compound of any of embodiments 1621-1641, wherein the target RNA is a lung target.

1753. The oligomeric compound of any of embodiments 1621-1641, wherein the target RNA is a heart target.

1754. The oligomeric compound of any of embodiments 1621-1641, wherein the target RNA is a kidney target.

1755. The oligomeric compound of any of embodiments 1621-1641, wherein the target RNA is a ganglion target.

1756. The oligomeric compound of any of embodiments 1621-1641, wherein the target RNA is a frontal cortex target.

1757. The oligomeric compound of any of embodiments 1621-1641, wherein the target RNA is a spinal cord target.

1758. The oligomeric compound of any of embodiments 1621-1641, wherein the target RNA is a trigeminal ganglion target.

1759. The oligomeric compound of any of embodiments 1621-1641, wherein the target RNA is a sciatic nerve target.

1760. The oligomeric compound of any of embodiments 1621-1641, wherein the target RNA is a dorsal root ganglion target.

1761. The oligomeric compound of any of embodiments 1621-1641, wherein the target RNA is a epidymal fat target.

1762. The oligomeric compound of any of embodiments 1621-1641, wherein the target RNA is a diaphragm target.

1763. The oligomeric compound of any of embodiments 1621-1641, wherein the target RNA is a colon target.

1764. The oligomeric compound of any of embodiments 1621-1763, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.

1765. The oligomeric compound of any of embodiments 1621-1763, wherein the target RNA is a HTT RNA.

1766. The oligomeric compound of embodiment 1764, wherein the target RNA is a MeCP2 RNA.

1767. The oligomeric compound of embodiment 1764, wherein the target RNA is a DUX4 RNA.

1768. The oligomeric compound of embodiment 1764, wherein the target RNA is a HDAC2 RNA.

1769. The oligomeric compound of embodiment 1764, wherein the target RNA is a Ataxin 1 RNA.

1770. The oligomeric compound of embodiment 1764, wherein the target RNA is a Ataxin 2 RNA.

1771. The oligomeric compound of embodiment 1764, wherein the target RNA is a Ataxin 3 RNA.

1772. The oligomeric compound of embodiment 1764, wherein the target RNA is a Ataxin 6 RNA.

1773. The oligomeric compound of embodiment 1764, wherein the target RNA is a Ataxin 7 RNA.

1774. The oligomeric compound of embodiment 1764, wherein the target RNA is a C9ORF72 RNA.

1775. The oligomeric compound of embodiment 1621-1763, wherein the target RNA is an alpha-synuclein RNA.

1776. The oligomeric compound of embodiment 1764, wherein the target RNA is an UBE3A RNA.

1777. The oligomeric compound of any of embodiments 1621-1763, wherein the target RNA is a SOD1 RNA.

1778. The oligomeric compound of embodiment 1764, wherein the target RNA is a Prion RNA.

1779. The oligomeric compound of embodiment 1764, wherein the target RNA is a PMP22 RNA.

1780. The oligomeric compound of any of embodiments 1621-1764, wherein the target RNA is a Tau RNA.

1781. The oligomeric compound of embodiment 1764, wherein the target RNA is a LRRK2 RNA.

1782. The oligomeric compound of embodiment 1764, wherein the target RNA is an APP RNA.

1783. The oligomeric compound of 1764, wherein the target RNA is a LINGO2 RNA.

1784. The oligomeric compound of any of embodiments 1764, wherein the target RNA is a GYS1 RNA.

1785. The oligomeric compound of any of embodiments 1764, wherein the target RNA is a KCNT1 RNA.

1786. The oligomeric compound of any of embodiments 1764, wherein the target RNA is a IRF8 RNA.

1787. The oligomeric compound of any of embodiments 1764, wherein the target RNA is a Progranulin RNA.

1788. The oligomeric compound of any of embodiments 1764, wherein the target RNA is a GFAP RNA.

1789. The oligomeric compound of any of embodiments 1621-1788, wherein modulation of the expression of the target RNA is associated with treating a disorder or condition.

1790. The oligomeric compound of embodiment 1789, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.

1791. The oligomeric compound of embodiment 1790, wherein the disorder or condition is Alzheimer's Disease.

1792. The oligomeric compound of embodiment 1790, wherein the disorder or condition is Amyotrophic Lateral Sclerosis.

1793. The oligomeric compound of embodiment 1790, wherein the disorder or condition is Parkinson's Disease.

1794. The oligomeric compound of embodiment 1790 wherein the disorder or condition is a Spinocerebellar ataxia.

1795. The oligomeric compound of embodiment 1790 wherein the disorder or condition is Angelman Syndrome.

1796. The oligomeric compound of embodiment 1790, wherein the disorder or condition is Alexander's Disease.

1797. The oligomeric compound of embodiment 1790, wherein the disorder or condition is Lafora Disease.

1798. The oligomeric compound of embodiment 1790, wherein the disorder or condition is Charcot-Marie Tooth Disease.

1799. The oligomeric compound of embodiment 1790, wherein the disorder or condition is Prion Disease.

1800. The oligomeric compound of embodiment 1790, wherein the disorder or condition is a dementia.

1801. The oligomeric compound of embodiment 1790, wherein the disorder or condition is neurodegeneration.

1802. The oligomeric compound of embodiment 1790, wherein the disorder or condition is MeCP2 Duplication Syndrome.

1803. The oligomeric compound of embodiment 1790, wherein the disorder or condition is encephalopathy.

1804. The oligomeric compound of embodiment 1790, wherein the disorder or condition is neuroinflammation.

1805. The oligomeric compound of embodiment 1790, wherein the disorder or condition is multiple sclerosis.

1806. The oligomeric compound of any of embodiments 1461-1805, wherein the parent oligomeric compound of the oligomeric compound of any of embodiments 1461-1805 is cytotoxic in vitro.

1807. The oligomeric compound of embodiment 1806, wherein the parent oligomeric compound is cytotoxic in a standard in vitro cytotoxicity assay.

1808. The oligomeric compound of any of embodiments 1461-1805 wherein administration to a mouse of the parent oligomeric compound of the oligomeric compound of any of embodiments 1461-1805 is hepatotoxic to the mouse.

1809. The oligomeric compound of embodiment 1808, wherein the administration of the parent oligomeric compound to the mouse is systemic administration.

1810. The oligomeric compound of embodiment 1809, wherein the systemic administration is subcutaneous administration.

1811. The oligomeric compound of any of embodiments 1808-1810, wherein the mouse is a CD-1 mouse.

1812. The oligomeric compound of any of embodiments 1808-1810, wherein the mouse is a $C_{57}BL/6$ mouse.

1813. The oligomeric compound of any of embodiments 1808-1810, wherein the mouse is a BALB/c mouse.

1814. The oligomeric compound of any of embodiments 1807-1813, wherein the plasma ALT level in the mouse is higher than 500 units per liter following the administration of the parent oligomeric compound.

1815. The oligomeric compound of any of embodiments 1807-1814, wherein the plasma AST level in the mouse is higher than 500 units per liter following the administration of the parent oligomeric compound.

1816. The oligomeric compound of any of embodiments 1807-1815, wherein the plasma ALT level in the mouse is higher than 1000 units per liter following the administration of the parent oligomeric compound.

1817. The oligomeric compound of any of embodiments 1807-1816, wherein the plasma AST level in the mouse is higher than 1000 units per liter following the administration of the parent oligomeric compound.

1818. The oligomeric compound of any of embodiments 1807-1817, wherein the hepatotoxicity is measured 24-48 hours following the administration of the parent oligomeric compound.

1819. The oligomeric compound of any of embodiments 1807-1817, wherein the hepatotoxicity is measured 72 hours following the administration of the parent oligomeric compound.

1820. The oligomeric compound of any of embodiments 1807-1817, wherein the hepatotoxicity is measured 3 days following the administration of the parent oligomeric compound.

1821. The oligomeric compound of any of embodiments 1807-1817, wherein the hepatotoxicity is measured 5 days following the administration of the parent oligomeric compound.

1822. The oligomeric compound of any of embodiments 1807-1817, wherein the hepatotoxicity is measured 7 days following the administration of the parent oligomeric compound.

1823. The oligomeric compound of any of embodiments 1807-1817, wherein the hepatotoxicity is measured 10 days following the administration of the parent oligomeric compound.

1824. The oligomeric compound of any of embodiments 1807-1817, wherein the hepatotoxicity is measured 14 days following the administration of the parent oligomeric compound.

1825. The oligomeric compound of any of embodiments 1807-1817, wherein 1-10 mg/kg of the parent oligomeric compound is administered to the mouse.

1826. The oligomeric compound of any of embodiments 1807-1817, wherein 10-25 mg/kg of the parent oligomeric compound is administered to the mouse.

1827. The oligomeric compound of any of embodiments 1807-1817, wherein 25-50 mg/kg of the parent oligomeric compound is administered to the mouse.

1828. The oligomeric compound of any of embodiments 1807-1817, wherein 50-100 mg/kg of the parent oligomeric compound is administered to the mouse.

1829. The oligomeric compound of any of embodiments 1807-1817, wherein 100-150 mg/kg of the parent oligomeric compound is administered to the mouse.

1830. The oligomeric compound of any of embodiments 1807-1817, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.

1831. The oligomeric compound of any of embodiments 1461-1830, wherein administration of 50 mg/kg of the oligomeric compound of any of embodiments 1461-1830 to a mouse is not hepatotoxic to the mouse.

1832. The oligomeric compound of embodiment 1831, wherein plasma ALT level in the mouse is lower than 100 units per liter following the administration of the oligomeric compound of embodiment 1831.

1833. The oligomeric compound of embodiment 1831 or 1832, wherein plasma ALT level in the mouse is at least 10-fold lower than plasma ALT level in a mouse administered the parent oligomeric compound of the oligomeric compound of embodiment 1831 or 1832, wherein the administrations and plasma ALT measurements of both the oligomeric compound of embodiment 1831 or 1832 and the parent oligomeric compound are completed in the same way.

1834. The oligomeric compound of embodiment 1833, wherein the plasma ALT level in the mouse is at least 100-fold lower than the plasma ALT level in the mouse administered the parent oligomeric compound.

1835. The oligomeric compound of embodiment 1833, wherein the plasma ALT level in the mouse is at least 500-fold lower than the plasma ALT level in the mouse administered the parent oligomeric compound.

1836. The oligomeric compound of any of embodiments 1807-1835, wherein the therapeutic index in a mouse of the oligomeric compound of any of embodiments 1807-1835 is increased relative to the therapeutic index of the parent oligomeric compound.

1837. The oligomeric compound of embodiment 1836, wherein the therapeutic index in a mouse of the oligomeric compound of embodiment 1836 is at least two-fold greater than the therapeutic index of the parent oligomeric compound.

1838. The oligomeric compound of any of embodiments 1461-1805, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse;
and wherein the otherwise identical oligomeric compound has a central region consisting of phosphorothioate internucleoside linkages, unmodified 2'β-D-deoxyribosyl sugar moieties, and nucleobases selected from thymine, uracil, adenine, guanine, cytosine, and 5-methylcytosine.

1839. The oligomeric compound of embodiment 1838, wherein the at least one modified internucleoside linkage other than phosphorothioate and/or at least one modified nucleoside comprising a modified nucleobase other than 5-methylcytosine and/or a modified sugar moiety in the central region is a 2'-O-methyl modified sugar moiety.

1840. The oligomeric compound of embodiment 1839, wherein the 2'-O-methyl modified sugar moiety is at position 2 of the central region.

1841. The oligomeric compound of embodiment 1838-1840, wherein the otherwise identical oligomeric compound lacks a 2'-O-methyl modified sugar moiety, and wherein the otherwise identical oligomeric compound comprises an unmodified 2'β-D-deoxyribosyl sugar moiety in place of the 2'-O-methyl modified sugar moiety.

1842. The oligomeric compound of any of embodiments 1838-1841, wherein the nucleobase sequence of the otherwise identical oligomeric compound is 100% complementary to the target RNA.

1843. The oligomeric compound of any of embodiments 1838-1842, wherein the otherwise identical oligomeric compound is a parent oligomeric compound of the oligomeric compound of any of embodiments 1838-1842.

1844. The oligomeric compound of any of embodiments 1621-1843, wherein the oligomeric compound inhibits the target RNA with an $IC_{50}$ lower than 100 nM in a standard in vitro activity assay.

1845. The oligomeric compound of any of embodiments 1621-1843, wherein the parent oligomeric compound of the oligomeric compound of any of embodiments 1621-1843 inhibits the target RNA with an $IC_{50}$ lower than 100 nM in a standard in vitro activity assay.

1846. The oligomeric compound of any of embodiments 1621-1845, wherein the difference between the $IC_{50}$ of the parent oligomeric compound measured in a standard in vitro activity assay and the $IC_{50}$ of the oligomeric compound of any of embodiments 1621-1845 measured in a standard in vitro activity assay is less than 4-fold.

1847. The oligomeric compound of any of embodiments 1621-1845, wherein the difference between the $IC_{50}$ of the parent oligomeric compound measured in a standard in vitro activity assay and the $IC_{50}$ of the oligomeric compound of any of embodiments 1621-1845 measured in a standard in vitro activity assay is less than 3-fold.

1848. The oligomeric compound of any of embodiments 1621-1845, wherein the difference between the $IC_{50}$ of the parent oligomeric compound measured in a standard in vitro activity assay and the $IC_{50}$ of the oligomeric compound of any of embodiments 1621-1845 measured in a standard in vitro activity assay is less than 2-fold.

1849. The oligomeric compound of any of embodiments 1621-1848, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

1850. The oligomeric compound of any of embodiments 1621-1849, wherein the nucleobase sequence of the parent oligomeric compound is 100% complementary to the target RNA.

1851. The oligomeric compound of any of embodiments 1461-1850, wherein administration of 10-50 mg of the oligomeric compound to a human is not hepatotoxic to the human.

1852. The oligomeric compound of any of embodiments 1461-1850, wherein administration of 50-100 mg of the oligomeric compound to a human is not hepatotoxic to the human.

1853. The oligomeric compound of any of embodiments 1461-1850, wherein administration of 100-300 mg of the oligomeric compound to a human is not hepatotoxic to the human.

1854. The oligomeric compound of any of embodiments 1851-1853, wherein the administration is systemic administration.

1855. A composition comprising the oligomeric compound of any of embodiments 1461-1854, and a second oligomeric compound, wherein the second oligomeric compound is complementary to the oligomeric compound of any of embodiments 1461-1854.

1856. The composition of embodiment 1855, wherein the second oligomeric compound comprises at least 14 contiguous linked nucleosides that are at least 90% complementary to the oligomeric compound of any of embodiments 1851-1853.

1857. The composition of embodiment 1855, wherein the second oligomeric compound comprises at least 14 contiguous linked nucleosides that are 100% complementary to the oligomeric compound of any of embodiments 1461-1854.

1858. A pharmaceutical composition comprising the oligomeric compound of any of embodiments 1461-1854 or the composition of any of embodiments 1855-1857, comprising a pharmaceutically acceptable carrier or diluent.

1859. A method comprising administering the oligomeric compound or composition of any of embodiments 1461-1858 to a human subject.

1860. A method of treating a disease or disorder comprising administering the oligomeric compound or composition of any of embodiments 1461-1858 to a human subject.

1861. A method of modulating the amount or activity of a target RNA in a human subject comprising administering the oligomeric compound or composition of any of embodiments 1461-1858 to the human subject; and thereby modulating the amount or activity of the target RNA in the human subject.

1862. A method of treating a disease or disorder in a human subject comprising administering the oligomeric compound or composition of any of embodiments 1461-1858 to the human subject having the disease or disorder; and thereby treating the disease or disorder in the human subject.

1863. The method of embodiment 1861 or 1862, wherein the disease or disorder is a liver disease, and wherein the oligomeric compound modulates the amount or activity of a liver target RNA.

1864. The method of embodiment 1861 or 1862, wherein the disease or disorder is a central nervous system disease, and wherein the oligomeric compound modulates the amount or activity of a central nervous system target RNA.

1865. The method of any of embodiments 1861-1864, wherein the disease or disorder is a cancer, a neurodegenerative disease, a cardiovascular disease, an immunological disease, a hereditary disease, a repeat expansion disease, a muscle-wasting disease, or a metabolic disease.

1866. The method of embodiment 1861 or 1862, wherein the oligomeric compound modulates the amount or activity of a white fat cell target.

1867. The method of embodiment 1861 or 1862, wherein the oligomeric compound modulates the amount or activity of a brown fat cell target.

1868. The method of embodiment 1861 or 1862, wherein the oligomeric compound modulates the amount or activity of an adipocyte target.

1869. The method of embodiment 1861 or 1862, wherein the oligomeric compound modulates the amount or activity of a macrophage target.

1870. The method of embodiment 1861 or 1862, wherein the oligomeric compound modulates the amount or activity of a cancer cell target.

1871. The method of embodiment 1861 or 1862, wherein the oligomeric compound modulates the amount or activity of a tumor cell target.

1872. The method of embodiment 1861 or 1862, wherein the oligomeric compound modulates the amount or activity of a smooth muscle cell target.

1873. The method of embodiment 1861 or 1862, wherein the oligomeric compound modulates the amount or activity of a lymphocyte target.

1874. The method of embodiment 1861 or 1862, wherein the oligomeric compound modulates the amount or activity of a pulmonary cell target.

1875. The method of embodiment 1861 or 1862, wherein the oligomeric compound modulates the amount or activity of a heart muscle cell target.

1876. The method of embodiment 1861 or 1862, wherein the oligomeric compound modulates the amount or activity of a cardiomyocyte target.

1877. The method of embodiment 1861 or 1862, wherein the oligomeric compound modulates the amount or activity of a endothelial cell target.

1878. The method of embodiment 1861 or 1862, wherein the oligomeric compound modulates the amount or activity of a fibroblast target.

1879. The method of embodiment 1861 or 1862, wherein the oligomeric compound modulates the amount or activity of a glial cell target.

1880. The method of embodiment 1861 or 1862, wherein the oligomeric compound modulates the amount or activity of a Schwann cell target.

1881. The method of embodiment 1861 or 1862, wherein the oligomeric compound modulates the amount or activity of a pancreatic cell target.

1882. The method of embodiment 1861 or 1862, wherein the oligomeric compound modulates the amount or activity of a kidney cell target.

1883. The method of embodiment 1861 or 1862, wherein the oligomeric compound modulates the amount or activity of a beta cell target.

1884. The method of embodiment 1861 or 1862, wherein the oligomeric compound modulates the amount or activity of a non-parenchymal cell target.

1885. The method of embodiment 1861 or 1862, wherein the oligomeric compound modulates the amount or activity of a hepatocyte target.

1886. The method of embodiment 1861 or 1862, wherein the oligomeric compound modulates the amount or activity of a oligodendrocyte target.

1887. The method of embodiment 1861 or 1862, wherein the oligomeric compound modulates the amount or activity of a astrocyte target.

1888. The method of embodiment 1861 or 1862, wherein the oligomeric compound modulates the amount or activity of a microglia target.

1889. The method of embodiment 1861 or 1862, wherein the oligomeric compound modulates the amount or activity of a ependymal cell target.

1890. The method of embodiment 1861 or 1862, wherein the oligomeric compound modulates the amount or activity of a sensory neuron target.

1891. The method of embodiment 1861 or 1862, wherein the oligomeric compound modulates the amount or activity of a motor neuron target.

1892. The method of embodiment 1861 or 1862, wherein the oligomeric compound modulates the amount or activity of a skeletal muscle target.

1893. The method of embodiment 1861 or 1862, wherein the oligomeric compound modulates the amount or activity of a cardiac muscle target.

1894. The method of embodiment 1861 or 1862, wherein the oligomeric compound modulates the amount or activity of a smooth muscle target.

1895. The method of embodiment 1861 or 1862, wherein the oligomeric compound modulates the amount or activity of a adipose tissue target.

1896. The method of embodiment 1861 or 1862, wherein the oligomeric compound modulates the amount or activity of a white adipose tissue target.

1897. The method of embodiment 1861 or 1862, wherein the oligomeric compound modulates the amount or activity of a spleen target.

1898. The method of embodiment 1861 or 1862, wherein the oligomeric compound modulates the amount or activity of a bone target.

1899. The method of embodiment 1861 or 1862, wherein the oligomeric compound modulates the amount or activity of a bone marrow target.

1900. The method of embodiment 1861 or 1862, wherein the oligomeric compound modulates the amount or activity of an intestinal target.

1901. The method of embodiment 1861 or 1862, wherein the oligomeric compound modulates the amount or activity of an adrenal gland target.

1902. The method of embodiment 1861 or 1862, wherein the oligomeric compound modulates the amount or activity of a testicular target.

1903. The method of embodiment 1861 or 1862, wherein the oligomeric compound modulates the amount or activity of an ovarian target.

1904. The method of embodiment 1861 or 1862, wherein the oligomeric compound modulates the amount or activity of a pancreatic target.

1905. The method of embodiment 1861 or 1862, wherein the oligomeric compound modulates the amount or activity of a pituitary gland target.

1906. The method of embodiment 1861 or 1862, wherein the oligomeric compound modulates the amount or activity of a prostate gland target.

1907. The method of embodiment 1861 or 1862, wherein the oligomeric compound modulates the amount or activity of a skin target.

1908. The method of embodiment 1861 or 1862, wherein the oligomeric compound modulates the amount or activity of an epidermal target.

1909. The method of embodiment 1861 or 1862, wherein the oligomeric compound modulates the amount or activity of a uterine target.

1910. The method of embodiment 1861 or 1862, wherein the oligomeric compound modulates the amount or activity of a bladder target.

1911. The method of embodiment 1861 or 1862, wherein the oligomeric compound modulates the amount or activity of a brain target.

1912. The method of embodiment 1861 or 1862, wherein the oligomeric compound modulates the amount or activity of a glomerulus target.

1913. The method of embodiment 1861 or 1862, wherein the oligomeric compound modulates the amount or activity of a distal tubular epithelium target.

1914. The method of embodiment 1861 or 1862, wherein the oligomeric compound modulates the amount or activity of a breast tissue target.

1915. The method of embodiment 1861 or 1862, wherein the oligomeric compound modulates the amount or activity of a lung target.

1916. The method of embodiment 1861 or 1862, wherein the oligomeric compound modulates the amount or activity of a heart target.

1917. The method of embodiment 1861 or 1862, wherein the oligomeric compound modulates the amount or activity of a kidney target.

1918. The method of embodiment 1861 or 1862, wherein the oligomeric compound modulates the amount or activity of a ganglion target.

1919. The method of embodiment 1861 or 1862, wherein the oligomeric compound modulates the amount or activity of a frontal cortex target.

1920. The method of embodiment 1861 or 1862, wherein the oligomeric compound modulates the amount or activity of a spinal cord target.

1921. The method of embodiment 1861 or 1862, wherein the oligomeric compound modulates the amount or activity of a trigeminal ganglion target.

1922. The method of embodiment 1861 or 1862, wherein the oligomeric compound modulates the amount or activity of a sciatic nerve target.

1923. The method of embodiment 1861 or 1862, wherein the oligomeric compound modulates the amount or activity of a dorsal root ganglion target.

1924. The method of embodiment 1861 or 1862, wherein the oligomeric compound modulates the amount or activity of a epidymal fat target.

1925. The method of embodiment 1861 or 1862, wherein the oligomeric compound modulates the amount or activity of a diaphragm target.

1926. The method of embodiment 1861 or 1862, wherein the oligomeric compound modulates the amount or activity of a colon target.

1927. The method of any of embodiments 1802-1926, wherein the plasma ALT level of the human subject after the administration is not more than three times higher than it was prior to the administration.

1928. The method of any of embodiments 1802-1926, wherein the plasma ALT level of the human subject after the administration is not more than 150 units per liter.

1929. The method of any of embodiments 1802-1928, wherein the human subject is susceptible to liver damage.

1930. The method of any of embodiments 1802-1928, wherein the human subject is susceptible to liver degeneration.

1931. The method of any of embodiments 1802-1930, wherein the human subject is susceptible to elevated apoptosis in the liver.

1932. The method of any of embodiments 1802-1931, wherein the human subject has a liver disease.

1933. The method of any of embodiments 1802-1932, wherein the human subject has kidney disease.

1934. The method of any of embodiments 1802-1933, wherein the human subject is susceptible to kidney damage.

1935. The method of any of embodiments 1802-1934, wherein the human subject has heart disease.

1936. The method of any of embodiments 1802-1935, wherein the human subject is susceptible to heart damage.

1937. The method of any of embodiments 1802-1936, wherein the human subject has pancreatitis.

1938. The method of any of embodiments 1802-1937, wherein the human subject is susceptible to pancreatic damage.

1939. The method of any of embodiments 1802-1938, wherein the human subject has a neurological disease.

1940. The method of any of embodiments 1802-1939, wherein the human subject is susceptible to neurological damage.

1941. The method of any of embodiments 1859-1940, comprising administering the parent oligomeric compound of the oligomeric compound of any of embodiments 1461-1858 to a mouse.

1942. The method of any of embodiments 1859-1940, comprising contacting a cell with the parent oligomeric compound of the oligomeric compound of any of embodiments 1461-1858.

1943. The method of embodiment 1941 or 1942, wherein each sugar moiety of the central region of the parent oligomeric compound is an unmodified 2'β-D-deoxyribosyl sugar moiety, and wherein each internucleoside linkage of the central region of the parent oligomeric compound is a phosphorothioate internucleoside linkage.

1944. A method of designing an oligomeric compound comprising starting with a parent oligomeric compound and changing the design of that compound in order to arrive at an oligomeric compound of any one of embodiments 1461-1858.

1945. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 1461-1858.

1946. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 1461-1858.

1947. The method of embodiment 1945 or 1946, wherein the method designs an oligomeric compound with improved therapeutic index relative to the parent oligomeric compound.

1948. The method of embodiment 1945 or 1946, wherein the method designs an oligomeric compound with lower hepatotoxicity relative to the parent oligomeric compound.

1949. The method of embodiment 1945, wherein the second oligomeric compound has an improved therapeutic index relative to the parent oligomeric compound.

1950. The method of embodiment 1945 or 1946, wherein the second oligomeric compound has reduced hepatotoxicity in a mouse relative to the parent oligomeric compound.

1951. The method of embodiment 1945, wherein the oligomeric compound according to any one of embodiments 1461-1858 has reduced hepatotoxicity relative to the parent oligomeric compound.

1952. A method comprising administering an oligomeric compound of any of embodiments 1461-1858 to a mouse and separately administering the parent oligomeric compound of the oligomeric compound of any of embodiments 1461-1858 to a second mouse, wherein the therapeutic index of the oligomeric compound of any of embodiments 1461-1858 is improved relative to the therapeutic index of the parent oligomeric compound.

1953. The method of any of embodiments 1859-1952, wherein the level of p21 RNA is measured in the mouse, the cell, and/or the human subject.

1954. A method comprising administering an oligomeric compound of any of embodiments 1461-1858 to a subject and measuring the level of p21 RNA in the subject.

1955. The method of embodiment 1954, wherein the subject is a mouse.

1956. The method of embodiment 1954, wherein the subject is a human.

1957. The method of any of embodiments 1954-1956, wherein the p21 RNA level is measured within 24 hours of the administration.

1958. The method of any of embodiments 1954-1956, wherein the p21 RNA level is measured 24-48 hours following the administration.

1959. An oligomeric compound or composition of any one of embodiments 1461-1858, for use in medical therapy.

1960. The oligomeric compound of any of embodiments 1461-1858, wherein the oligomeric compound is not toxic.

1961. The oligomeric compound of any of embodiment 1461-1858, wherein a comparator compound is toxic; wherein the comparator compound is identical to the oligomeric compound except that each nucleoside of the central region of the comparator compound is a nucleoside comprising 2'-β-D-deoxyribosyl sugar moiety.

1962. The oligomeric compound of embodiment 1961, wherein administering a dose of the oligomeric compound to an animal results in a circulating ALT level that is at least 3-fold lower than the ALT level that results from administering the same dose of the comparator compound to an animal for at least one matched dose.

1963. The oligomeric compound of embodiment 1961 or 1962, wherein the lowest dose of the oligomeric compound that raises circulating ALT to over 300 units per liter is at least three-fold higher than the lowest dose of the comparator compound that raises circulating ALT to over 300 units per liter.

1964. The oligomeric compound of any of embodiments 1961-1963, wherein the oligomeric compound is capable of reducing the target RNA in a cell.

1965. The oligomeric compound of embodiment 1964, wherein the oligomeric compound has RNA-reducing activity comparable to a comparator compound, wherein the comparator compound is identical to the oligomeric compound except that each nucleoside of the central region of the comparator compound is a nucleoside comprising 2'β-D-deoxyribosyl sugar moiety.

1966. The oligomeric compound of embodiment 1965 having RNA-reducing activity that is no more than 2-fold worse than the RNA-reducing activity of the comparator compound.

1967. A method of modulating the amount or activity of a target RNA in a human subject comprising administering the oligomeric compound or composition of any of embodiments 1461-1858 to the human subject; and thereby modulating the amount or activity of the target RNA in the human subject.

1968. A method of treating a disease or disorder in a human subject comprising administering the oligomeric compound or composition of any of embodiments 1461-1858 to the human subject having the disease or disorder; and thereby treating the disease or disorder in the human subject.

1969. The method of embodiment 1967 or 1968, wherein the disease or disorder is a liver disease, and wherein the oligomeric compound modulates the amount or activity of a liver target RNA.

1970. The method of embodiment 1967 or 1968, wherein the disease or disorder is a central nervous system disease, and wherein the oligomeric compound modulates the amount or activity of a central nervous system target RNA.

1971. The method of any of embodiments 1967-1970, wherein the disease or disorder is a cancer, a neurodegenerative disease, a cardiovascular disease, an immunological disease, a hereditary disease, a repeat expansion disease, a muscle-wasting disease, or a metabolic disease.

1972. The method of any of embodiments 1967-1971, wherein the plasma ALT level of the human subject after the administration is not more than three times higher than it was prior to the administration.

1973. The method of any of embodiments 1967-1972, wherein the plasma ALT level of the human subject after the administration is not more than 150 units per liter.

1974. A method of treating a disease or disorder in a human subject comprising administering the oligomeric compound or composition of any of embodiments 1461-1858 to the human subject having the disease or disorder; and thereby treating the disease or disorder in the human subject.

1975. The method of embodiment 1974, wherein the disease or disorder is not a CNS disease or disorder.

1976. The method of embodiment 1974, wherein the disease or disorder is a disease or disorder of the white fat cells.

1977. The method of embodiment 1974, wherein the disease or disorder is a disease or disorder of the brown fat cells.

1978. The method of embodiment 1974, wherein the disease or disorder is a disease or disorder of the adipocytes.

1979. The method of embodiment 1974, wherein the disease or disorder is a disease or disorder of the macrophages.

1980. The method of embodiment 1974, wherein the disease or disorder is a disease or disorder of the cancer cells.

1981. The method of embodiment 1974, wherein the disease or disorder is a disease or disorder of the tumor cells.

1982. The method of embodiment 1974, wherein the disease or disorder is a disease or disorder of the smooth muscle cells.

1983. The method of embodiment 1974, wherein the disease or disorder is a disease or disorder of the lymphocytes.

1984. The method of embodiment 1974, wherein the disease or disorder is a disease or disorder of the pulmonary cells.

1985. The method of embodiment 1974, wherein the disease or disorder is a disease or disorder of the heart muscle cells.

1986. The method of embodiment 1974, wherein the disease or disorder is a disease or disorder of the cardiomyocytes.

1987. The method of embodiment 1974, wherein the disease or disorder is a disease or disorder of the endothelial cells.

1988. The method of embodiment 1974, wherein the disease or disorder is a disease or disorder of the fibroblasts.

1989. The method of embodiment 1974, wherein the disease or disorder is a disease or disorder of the glial cells.

1990. The method of embodiment 1974, wherein the disease or disorder is a disease or disorder of the Schwann cells.

1991. The method of embodiment 1974, wherein the disease or disorder is a disease or disorder of the pancreatic cells.

1992. The method of embodiment 1974, wherein the disease or disorder is a disease or disorder of the kidney cells.

1993. The method of embodiment 1974, wherein the disease or disorder is a disease or disorder of the beta cells.

1994. The method of embodiment 1974, wherein the disease or disorder is a disease or disorder of the non-parenchymal cells.

1995. The method of embodiment 1974, wherein the disease or disorder is a disease or disorder of the hepatocytes.

1996. The method of embodiment 1974, wherein the disease or disorder is a disease or disorder of the oligodendrocytes.

1997. The method of embodiment 1974, wherein the disease or disorder is a disease or disorder of the astrocytes.

1998. The method of embodiment 1974, wherein the disease or disorder is a disease or disorder of the microglia.

1999. The method of embodiment 1974, wherein the disease or disorder is a disease or disorder of the ependymal cells.

2000. The method of embodiment 1974, wherein the disease or disorder is a disease or disorder of the sensory neurons.

2001. The method of embodiment 1974, wherein the disease or disorder is a disease or disorder of the motor neurons.

2002. The method of embodiment 1974, wherein the disease or disorder is a disease or disorder of the skeletal muscle.

2003. The method of embodiment 1974, wherein the disease or disorder is a disease or disorder of the cardiac muscle.

2004. The method of embodiment 1974, wherein the disease or disorder is a disease or disorder of the smooth muscle.

2005. The method of embodiment 1974, wherein the disease or disorder is a disease or disorder of the adipose tissue.

2006. The method of embodiment 1974, wherein the disease or disorder is a disease or disorder of the white adipose tissue.

2007. The method of embodiment 1974, wherein the disease or disorder is a disease or disorder of the spleen.

2008. The method of embodiment 1974, wherein the disease or disorder is a disease or disorder of the bone.

2009. The method of embodiment 1974, wherein the disease or disorder is a disease or disorder of the bone marrow.

2010. The method of embodiment 1974, wherein the disease or disorder is a disease or disorder of the intestine.

2011. The method of embodiment 1974, wherein the disease or disorder is a disease or disorder of the adrenal glands.

2012. The method of embodiment 1974, wherein the disease or disorder is a disease or disorder of the testes.

2013. The method of embodiment 1974, wherein the disease or disorder is a disease or disorder of the ovaries.

2014. The method of embodiment 1974, wherein the disease or disorder is a disease or disorder of the pancreas.

2015. The method of embodiment 1974, wherein the disease or disorder is a disease or disorder of the pituitary gland.

2016. The method of embodiment 1974, wherein the disease or disorder is a disease or disorder of the prostate gland.

2017. The method of embodiment 1974, wherein the disease or disorder is a disease or disorder of the skin.

2018. The method of embodiment 1974, wherein the disease or disorder is a disease or disorder of the epidermis.

2019. The method of embodiment 1974, wherein the disease or disorder is a disease or disorder of the uterus.

2020. The method of embodiment 1974, wherein the disease or disorder is a disease or disorder of the bladder.

2021. The method of embodiment 1974, wherein the disease or disorder is a disease or disorder of the brain.

2022. The method of embodiment 1974, wherein the disease or disorder is a disease or disorder of the glomerulus.

2023. The method of embodiment 1974, wherein the disease or disorder is a disease or disorder of the distal tubular epithelium.

2024. The method of embodiment 1974, wherein the disease or disorder is a disease or disorder of the breast tissue.

2025. The method of embodiment 1974, wherein the disease or disorder is a disease or disorder of the lung.

2026. The method of embodiment 1974, wherein the disease or disorder is a disease or disorder of the heart.

2027. The method of embodiment 1974, wherein the disease or disorder is a disease or disorder of the kidney.

2028. The method of embodiment 1974, wherein the disease or disorder is a disease or disorder of the ganglion.

2029. The method of embodiment 1974, wherein the disease or disorder is a disease or disorder of the frontal cortex.

2030. The method of embodiment 1974, wherein the disease or disorder is a disease or disorder of the spinal cord.

2031. The method of embodiment 1974, wherein the disease or disorder is a disease or disorder of the trigeminal ganglion.

2032. The method of embodiment 1974, wherein the disease or disorder is a disease or disorder of the sciatic nerve.

2033. The method of embodiment 1974, wherein the disease or disorder is a disease or disorder of the dorsal root ganglion.

2034. The method of embodiment 1974, wherein the disease or disorder is a disease or disorder of the epidymal fat.

2035. The method of embodiment 1974, wherein the disease or disorder is a disease or disorder of the diaphragm.

2036. The method of embodiment 1974, wherein the disease or disorder is a disease or disorder of the colon.

2037. A method of screening a library of oligomeric compounds for activity against a target RNA, wherein the library of oligomeric compounds comprises a plurality of oligomeric compounds of any of embodiments 1461-1858.

Certain Compounds

In certain embodiments, compounds described herein are oligomeric compounds comprising or consisting of oligonucleotides consisting of linked nucleosides. Oligonucleotides may be unmodified oligonucleotides or may be modified oligonucleotides. Modified oligonucleotides comprise at least one modification relative to an unmodified oligonucleotide (i.e., comprise at least one modified nucleoside (comprising a modified sugar moiety and/or a modified nucleobase) and/or at least one modified internucleoside linkage).

I. Modifications

A. Modified Nucleosides

Modified nucleosides comprise a modified sugar moiety, a modified nucleobase, or both a modified sugar moiety and a modified nucleobase.

1. Certain Modified Sugar Moieties

In certain embodiments, sugar moieties are non-bicyclic, modified furanosyl sugar moieties. In certain embodiments, modified sugar moieties are bicyclic or tricyclic furanosyl sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified furanosyl sugar moieties comprising one or more acyclic substituent, including but not limited to substituents at the 2', 3', 4', and/or 5' positions. In certain embodiments, the furanosyl sugar moiety is a ribosyl sugar moiety. In certain embodiments, the furanosyl sugar moiety is a β-D-ribofuranosyl sugar moiety. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("2'-OMe" or "2'-O-methyl"), and 2'-O(CH$_2$)$_2$OCH$_3$ ("2'-MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, C$_1$-C$_{10}$ alkyl, C$_1$-C$_{10}$ substituted alkyl, S-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 3'-substituent groups include 3'-methyl (see Frier, et al., The ups and downs of nucleic acid duplex stability: structure-stability studies on chemically-modified DNA:RNA duplexes. Nucleic Acids Res., 25, 4429-4443, 1997.) Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-allyl, 5'-ethyl, 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836. 2',4'-difluoro modified sugar moieties have been described in Martinez-Montero, et al., Rigid 2',4'-difluororibonucleosides: synthesis, conformational analysis, and incorporation into nascent RNA by HCV polymerase. *J. Org. Chem.*, 2014, 79:5627-5635. Modified sugar moieties comprising a 2'-modification (OMe or F) and a 4'-modification (OMe or F) have also been described in Malek-Adamian, et al., *J. Org. Chem*, 2018, 83: 9839-9849.

In certain embodiments, a 2'-substituted nucleoside or non-bicyclic 2'-modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)-N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted nucleoside or non-bicyclic 2'-modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)-N(H)CH_3$ ("NMA").

In certain embodiments, a 2'-substituted nucleoside or non-bicyclic 2'-modified nucleoside comprises a sugar moiety comprising a non-bridging 2'-substituent group selected from: F, $OCH_3$, and $OCH_2CH_2OCH_3$.

In certain embodiments, the 4' O of 2'-deoxyribose can be substituted with a S to generate 4'-thio DNA (see Takahashi, et al., *Nucleic Acids Research* 2009, 37: 1353-1362). This modification can be combined with other modifications detailed herein. In certain such embodiments, the sugar moiety is further modified at the 2' position. In certain embodiments the sugar moiety comprises a 2'-fluoro. A thymidine with this sugar moiety has been described in Watts, et al., *J. Org. Chem*. 2006, 71(3): 921-925 (4'-S-fluoro5-methylarauridine or FAMU).

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of sugar moieties comprising such 4' to 2' bridging sugar substituents include but are not limited to bicyclic sugars comprising: 4'-$CH_2$-2', 4'-$(CH_2)_2$-2', 4'-$(CH_2)_3$-2', ("LNA"), 4'-$(CH_2)_2$-O-2' ("ENA"), 4'-CH($CH_3$)—O-2' (referred to as "constrained ethyl" or "cEt" when in the S configuration), 4'-$CH_2$—O—$CH_2$-2', 4'-$CH_2$—N(R)-2', 4'-CH($CH_2OCH_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C($CH_3$)($CH_3$)—O-2' and analogs thereof (see, e.g., Seth et al., U.S. Pat. No. 8,278,283), 4'-$CH_2$—N($OCH_3$)-2' and analogs thereof (see, e.g., Prakash et al., U.S. Pat. No. 8,278,425), 4'-$CH_2$—O—N($CH_3$)-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., *J. Org. Chem*., 2009, 74, 118-134), 4'-$CH_2$—C(=$CH_2$)-2' and analogs thereof (see e.g., Seth et al., U.S. Pat. No. 8,278,426), 4'-C($R_aR_b$)—N(R)—O-2', 4'-C($R_aR_b$)—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672), 4'-C(=O)—N($CH_3$)-2', 4'-C(=O)—N(R)_2-2', 4'-C(=S)—N(R)_2-2' and analogs thereof (see, e.g., Obika et al., WO2011052436A1, Yusuke, WO2017018360A1).

In certain embodiments, such 4' to 2' bridges independently comprise from 1 to 4 linked groups independently selected from: $-[C(R_a)(R_b)]_n-$, $-[C(R_a)(R_b)]_n-O-$, $-C(R_a)=C(R_b)-$, $-C(R_a)=N-$, $-C(=NR_a)-$, $-C(=O)-$, $-C(=S)-$, $-O-$, $-Si(R_a)_2-$, $-S(=O)_x-$, and $-N(R_a)-$;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl ($S(=O)$-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem*., 2006, 71, 7731-7740, Singh et al., *Chem. Commun*., 1998, 4, 455-456; Koshkin et al., *Tetrahedron*, 1998, 54, 3607-3630; Kumar et al., *Bioorg. Med. Chem. Lett*., 1998, 8, 2219-2222; Singh et al., *J. Org. Chem*., 1998, 63, 10035-10039; Srivastava et al., *J. Am. Chem. Soc*., 2017, 129, 8362-8379; Elayadi et al., Christiansen, et al., *J. Am. Chem. Soc*. 1998, 120, 5458-5463; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

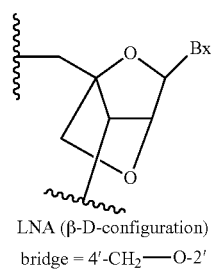

LNA (β-D-configuration)

bridge = 4'-$CH_2$—O-2'

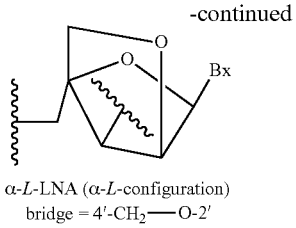

α-L-LNA (α-L-configuration)
bridge = 4'-CH₂—O-2'

α-L-methyleneoxy (4'-CH₂—O-2') or α-L-LNA bicyclic nucleosides have been incorporated into antisense oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

Nucleosides comprising modified furanosyl sugar moieties and modified furanosyl sugar moieties may be referred to by the position(s) of the substitution(s) on the sugar moiety of the nucleoside. The term "modified" following a position of the furanosyl ring, such as "2'-modified", indicates that the sugar moiety comprises the indicated modification at the 2' position and may comprise additional modifications and/or substituents. A 4'-2' bridged sugar moiety is 2'-modified and 4'-modified, or, alternatively, "2', 4'-modified". The term "substituted" following a position of the furanosyl ring, such as "2'-substituted" or "2'-4'-substituted", indicates that is the only position(s) having a substituent other than those found in unmodified sugar moieties in oligonucleotides. Accordingly, the following sugar moieties are represented by the following formulas.

In the context of a nucleoside and/or an oligonucleotide, a non-bicyclic, modified furanosyl sugar moiety is represented by formula I:

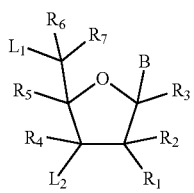

I wherein B is a nucleobase; and $L_1$ and $L_2$ are each, independently, an internucleoside linkage, a terminal group, a conjugate group, or a hydroxyl group. Among the R groups, at least one of $R_{3-7}$ is not H and/or at least one of $R_1$ and $R_2$ is not H or OH. In a 2'-modified furanosyl sugar moiety, at least one of $R_1$ and $R_2$ is not H or OH and each of $R_{3-7}$ is independently selected from H or a substituent other than H. In a 4'-modified furanosyl sugar moiety, $R_5$ is not H and each of $R_1$-4, 6, 7 are independently selected from H and a substituent other than H; and so on for each position of the furanosyl ring. The stereochemistry is not defined unless otherwise noted.

In the context of a nucleoside and/or an oligonucleotide, a non-bicyclic, modified, substituted fuarnosyl sugar moiety is represented by formula I, wherein B is a nucleobase; and $L_1$ and $L_2$ are each, independently, an internucleoside linkage, a terminal group, a conjugate group, or a hydroxyl group. Among the R groups, either one (and no more than one) of $R_{3-7}$ is a substituent other than H or one of $R_1$ or $R_2$ is a substituent other than H or OH. The stereochemistry is not defined unless otherwise noted. Examples of non-bicyclic, modified, substituted furanosyl sugar moieties include 2'-substituted ribosyl, 4'-substituted ribosyl, and 5'-substituted ribosyl sugar moieties, as well as substituted 2'-deoxyfuranosyl sugar moieties, such as 4'-substituted 2'-deoxyribosyl and 5'-substituted 2'-deoxyribosyl sugar moieties.

In the context of a nucleoside and/or an oligonucleotide, a 2'-substituted ribosyl sugar moiety is represented by formula II:

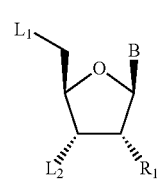

II wherein B is a nucleobase; and $L_1$ and $L_2$ are each, independently, an internucleoside linkage, a terminal group, a conjugate group, or a hydroxyl group. $R_1$ is a substituent other than H or OH. The stereochemistry is defined as shown.

In the context of a nucleoside and/or an oligonucleotide, a 4'-substituted ribosyl sugar moiety is represented by formula III:

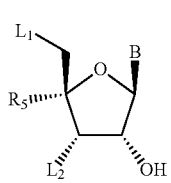

III wherein B is a nucleobase; and $L_1$ and $L_2$ are each, independently, an internucleoside linkage, a terminal group, a conjugate group, or a hydroxyl group. $R_5$ is a substituent other than H. The stereochemistry is defined as shown.

In the context of a nucleoside and/or an oligonucleotide, a 5'-substituted ribosyl sugar moiety is represented by formula IV:

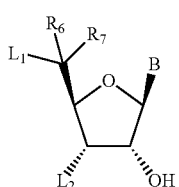

IV wherein B is a nucleobase; and $L_1$ and $L_2$ are each, independently, an internucleoside linkage, a terminal group, a conjugate group, or a hydroxyl group. $R_6$ or $R_7$ is a substituent other than H. The stereochemistry is defined as shown.

In the context of a nucleoside and/or an oligonucleotide, a 2'-deoxyfuranosyl sugar moiety is represented by formula V:

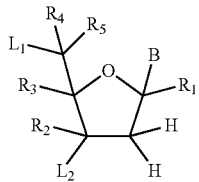

V wherein B is a nucleobase; and $L_1$ and $L_2$ are each, independently, an internucleoside linkage, a terminal group, a conjugate group, or a hydroxyl group. Each of $R_{1-5}$ are independently selected from H and a non-H substituent. If all of $R_{1-5}$ are each H, the sugar moiety is an unsubstituted 2'-deoxyfuranosyl sugar moiety. The stereochemistry is not defined unless otherwise noted.

In the context of a nucleoside and/or an oligonucleotide, a 4'-substituted 2'-deoxyribosyl sugar moiety is represented by formula VI:

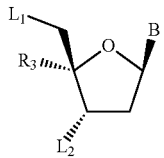

VI wherein B is a nucleobase; and $L_1$ and $L_2$ are each, independently, an internucleoside linkage, a terminal group, a conjugate group, or a hydroxyl group. $R_3$ is a substituent other than H. The stereochemistry is defined as shown.

In the context of a nucleoside and/or an oligonucleotide, a 5'-substituted 2'-deoxyribosyl sugar moiety is represented by formula VII:

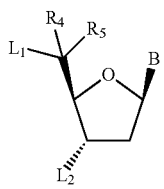

VII wherein B is a nucleobase; and $L_1$ and $L_2$ are each, independently, an internucleoside linkage, a terminal group, a conjugate group, or a hydroxyl group. $R_4$ or $R_5$ is a substituent other than H. The stereochemistry is defined as shown.

Unsubstituted 2'-deoxyfuranosyl sugar moieties may be unmodified (β-D-2'-deoxyribosyl) or modified. Examples of modified, unsubstituted 2'-deoxyfuranosyl sugar moieties include β-L-2'-deoxyribosyl, α-L-2'-deoxyribosyl, α-D-2'-deoxyribosyl, and β-D-xylosyl sugar moieties. For example, in the context of a nucleoside and/or an oligonucleotide, a β-L-2'-deoxyribosyl sugar moiety is represented by formula VIII:

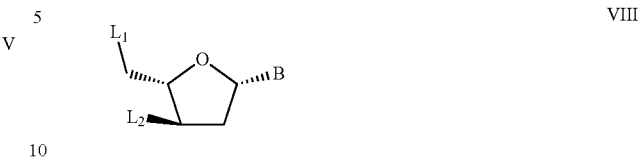

VIII wherein B is a nucleobase; and $L_1$ and $L_2$ are each, independently, an internucleoside linkage, a terminal group, a conjugate group, or a hydroxyl group. The stereochemistry is defined as shown. Synthesis of α-L-ribosyl nucleotides and β-D-xylosyl nucleotides has been described by Gaubert, et al., *Tetehedron* 2006, 62: 2278-2294. Additional isomers of DNA and RNA nucleosides are described by Vester, et. al., "Chemically modified oligonucleotides with efficient RNase H response," Bioorg. Med. Chem. Letters, 2008, 18: 2296-2300.

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), altritol nucleic acid ("ANA"), mannitol nucleic acid ("MNA") (see, e.g., Leumann, C J. *Bioorg. & Med. Chem.* 2002, 10, 841-854), fluoro HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), F-CeNA, and 3'-ara-HNA, having the formulas below, where $L_1$ and $L_2$ are each, independently, an internucleoside linkage linking the modified THP nucleoside to the remainder of an oligonucleotide or one of $L_1$ and $L_2$ is an internucleoside linkage linking the modified THP nucleoside to the remainder of an oligonucleotide and the other of $L_1$ and $L_2$ is H, a hydroxyl protecting group, a linked conjugate group, or a 5' or 3'-terminal group.

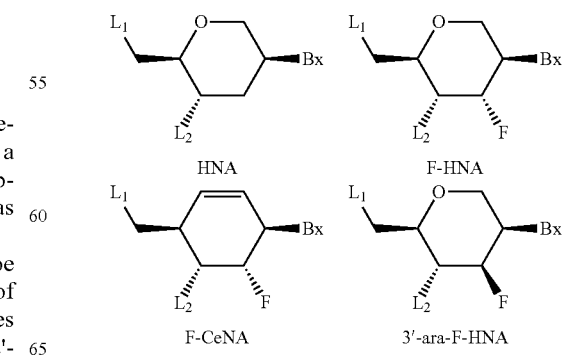

Additional sugar surrogates comprise THP compounds having the formula:

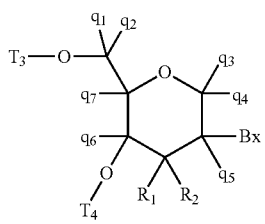

wherein, independently, for each of said modified THP nucleoside:
Bx is a nucleobase moiety;
$T_3$ and $T_4$ are each, independently, an internucleoside linkage linking the modified THP nucleoside to the remainder of an oligonucleotide or one of $T_3$ and $T_4$ is an internucleoside linkage linking the modified THP nucleoside to the remainder of an oligonucleotide and the other of $T_3$ and $T_4$ is H, a hydroxyl protecting group, a linked conjugate group, or a 5' or 3'-terminal group;
$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and
each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having no heteroatoms. For example, nucleosides comprising bicyclo [3.1.0]-hexane have been described (see, e.g., Marquez, et al., J. Med. Chem. 1996, 39:3739-3749).

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate comprising the following structure:

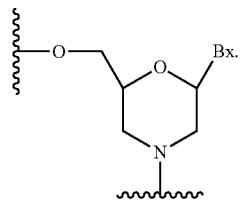

In certain embodiments, morpholinos may be modified, for example by adding or altering various substituent groups from the above morpholino structure. Such sugar surrogates are referred to herein as "modified morpholinos." In certain embodiments, morpholino residues replace a full nucleotide, including the internucleoside linkage, and have the structures shown below, wherein Bx is a heterocyclic base moiety.

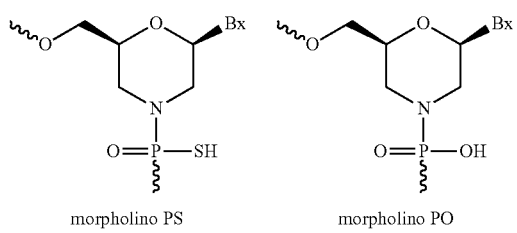

morpholino PS          morpholino PO

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), glycol nucleic acid ("GNA", see Schlegel, et al., J. Am. Chem. Soc. 2017, 139:8537-8546) and nucleosides and oligonucleotides described in Manoharan et al., WO2011/133876.

Many other bicyclic and tricyclic sugar and sugar surrogate ring systems are known in the art that can be used in modified nucleosides. Certain such ring systems are described in Hanessian, et al., J. Org. Chem., 2013, 78: 9051-9063 and include bcDNA and tcDNA. Modifications to bcDNA and tcDNA, such as 6'-fluoro, have also been described (Dogovic and Leumann, J. Org. Chem., 2014, 79: 1271-1279).

In certain embodiments, modified nucleosides are DNA mimics. "DNA mimic" means a nucleoside other than a DNA nucleoside wherein the nucleobase is directly linked to a carbon atom of a ring bound to a second carbon atom within the ring, wherein the second carbon atom comprises a bond to at least one hydrogen atom, wherein the nucleobase and at least one hydrogen atom are trans to one another relative to the bond between the two carbon atoms. In certain embodiments, a DNA mimic comprises a structure represented by the formula below:

Wherein Bx represents a heterocyclic base moiety.

In certain embodiments, a DNA mimic comprises a structure represented by one of the formulas below:

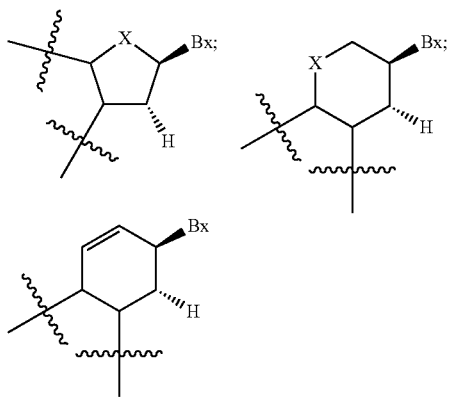

wherein X is O or S and Bx represents a heterocyclic base moiety.

In certain embodiments, a DNA mimic is a sugar surrogate. In certain embodiments, a DNA mimic is a cycohexenyl or hexitol nucleic acid. In certain embodiments, a DNA mimic is described in FIG. 1 of Vester, et. al., "Chemically modified oligonucleotides with efficient RNase H response," *Bioorg. Med. Chem. Letters*, 2008, 18: 2296-2300, incorporated by reference herein. In certain embodiments, a DNA mimic nucleoside has a formula selected from

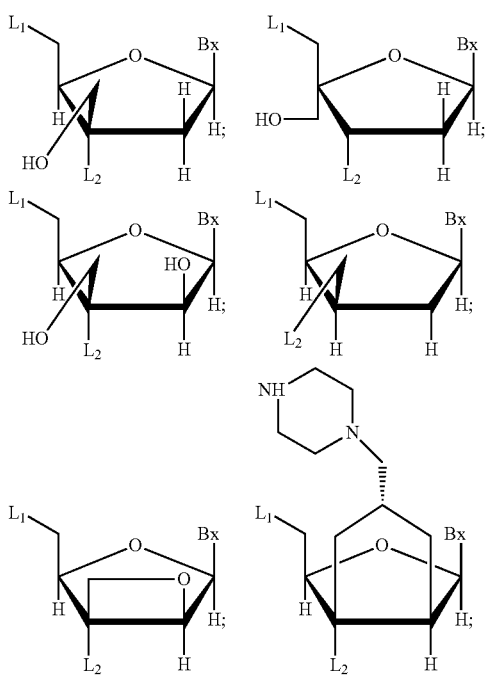

wherein Bx is a heterocyclic base moiety, and $L_1$ and $L_2$ are each, independently, an internucleoside linkage linking the modified THP nucleoside to the remainder of an oligonucleotide or one of $L_1$ and $L_2$ is an internucleoside linkage linking the modified nucleoside to the remainder of an oligonucleotide and the other of $L_1$ and $L_2$ is H, a hydroxyl protecting group, a linked conjugate group, or a 5' or 3'-terminal group. In certain embodiments, a DNA mimic is α,β-constrained nucleic acid (CAN), 2',4'-carbocyclic-LNA, or 2',4'-carbocyclic-ENA. In certain embodiments, a DNA mimic has a sugar moiety selected from among: 4'-C-hydroxymethyl-2'-deoxyribosyl, 3'-C-hydroxymethyl-2'-deoxyribosyl, 3'-C-hydroxymethyl-arabinosyl, 3'-C-2'-O-arabinoxyribosyl, 3'-C-methylene-extended-xyolosyl, 3'-C-2'-O-piperazino-arabinosyl. In certain embodiments, a DNA mimic has a sugar moiety selected from among: 2'-methyl-ribosyl, 2'-S-methylribosyl, 2'-aminoribosyl, 2'-NH(CH$_2$)-ribosyl, 2'-NH(CH$_2$)$_2$-ribosyl, 2'-CH2-F-ribosyl, 2'-CHF2-ribosyl, 2'-CF3-ribosyl, 2'=CF2 ribosyl, 2'-ethylribosyl, 2'-alkenylribosyl, 2'-alkynylribosyl, 2'-O-4'-C-methyleneribosyl, 2'-cyanoarabinosyl, 2'-chloroarabinosyl, 2'-fluoroarabinosyl, 2'-bromoarabinosyl, 2'-azidoarabinosyl, 2'-methoxyarabinosyl, and 2'-arabinosyl. In certain embodiments, a DNA mimic has a sugar moiety selected from 4'-methyl-modified deoxyfuranosyl, 4'-F-deoxyfuranosyl, 4'-OMe-deoxyfuranosyl. In certain embodiments, a DNA mimic has a sugar moiety selected from among: 5'-methyl-2'-β-D-deoxyribosyl, 5'-ethyl-2'-β-D-deoxyribosyl, 5'-allyl-2'-β-D-deoxyribosyl, 2'-fluoro-β-D-arabinofuranosyl. In certain embodiments, DNA mimics are listed on page 32-33 of PCT/US00/267929 as B-form nucleotides, incorporated by reference herein in its entirety.

2. Modified Nucleobases

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443. In certain embodiments, modified nucleosides comprise double-headed nucleosides having two nucleobases. Such compounds are described in detail in Sorinas et al., *J. Org. Chem*, 2014 79: 8020-8030.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

In certain embodiments, compounds comprise or consist of a modified oligonucleotide complementary to an target nucleic acid comprising one or more modified nucleobases. In certain embodiments, the modified nucleobase is 5-methylcytosine. In certain embodiments, each cytosine is a 5-methylcytosine.

B. Modified Internucleoside Linkages

In certain embodiments, compounds described herein having one or more modified internucleoside linkages are selected over compounds having only phosphodiester internucleoside linkages because of desirable properties such as, for example, enhanced cellular uptake, enhanced affinity for target nucleic acids, and increased stability in the presence of nucleases.

In certain embodiments, compounds comprise or consist of a modified oligonucleotide complementary to a target nucleic acid comprising one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, nucleosides of modified oligonucleotides may be linked together using any internucleoside linkage. The two main classes of internucleoside linkages are defined by the presence or absence of a phosphorus atom. Representative phosphorus-containing internucleoside linkages include unmodified phosphodiester internucleoside linkages, modified phosphotriesters such as THP phosphotriester and isopropyl phosphotriester, phosphonates such as methylphosphonate, isopropyl phosphonate, isobutyl phosphonate, and phosphonoacetate, phosphoramidates, phosphorothioate, and phosphorodithioate ("HS-P=S"). Representative non-phosphorus containing internucleoside linkages include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); formacetal, thioacetamido (TANA), alt-thioformacetal, glycine amide, and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. All phosphorothioate linkages described herein are stereorandom unless otherwise specified. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

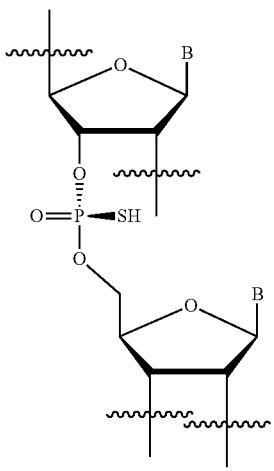

(Rp)

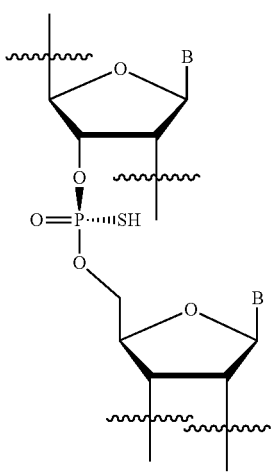

(Sp)

Unless otherwise indicated, chiral internucleoside linkages of modified oligonucleotides described herein can be stereorandom or in a particular stereochemical configuration.

Neutral internucleoside linkages include, without limitation, phosphotriesters, phosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

In certain embodiments, nucleic acids can be linked 2' to 5' rather than the standard 3' to 5' linkage. Such a linkage is illustrated below.

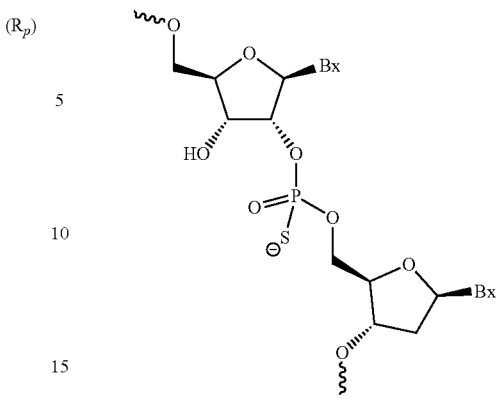

In the context of a nucleoside and/or an oligonucleotide, a non-bicyclic, 2'-linked modified furanosyl sugar moiety is represented by formula IX:

IX

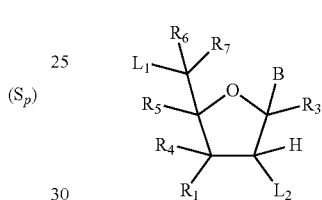

wherein B is a nucleobase; L$_1$ is an internucleoside linkage, a terminal group, a conjugate group, or a hydroxyl group and L$_2$ is an internucleoside linkage. The stereochemistry is not defined unless otherwise noted.

In certain embodiments, nucleosides can be linked by vinicinal 2', 3'-phosphodiester bonds. In certain such embodiments, the nucleosides are threofuranosyl nucleosides (TNA; see Bala, et al., *J Org. Chem.* 2017, 82:5910-5916). A TNA linkage is shown below.

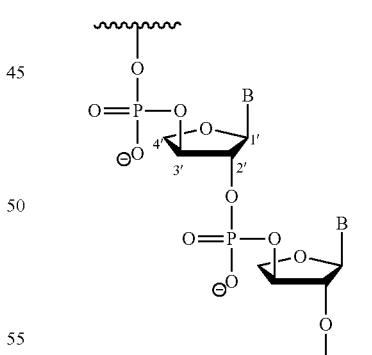

threose nucleic acid (TNA)

Additional modified linkages include α,β-D-CNA type linkages and related conformationally-constrained linkages, shown below. Synthesis of such molecules has been described previously (see Dupouy, et al., *Angew. Chem. Int. Ed. Engl.*, 2014, 45: 3623-3627, Bursting, et al. *Tetrahedron,* 2004, 60:10955-10966; Ostergaard, et al., *ACS Chem. Biol.* 2014, 9: 1975-1979, Dupouy, et al., *Eur. J Org. Chem.,* 2008, U.S. Pat. No. 12,851,294; Martinez, et al., *PLoS One,* 2011, 6:e25510; Dupouy, et al., *Eur. J. Org. Chem.*, 2007, 5256-5264; Boissonnet, et al. *New J. Chem.*, 2011 35: 1528-1533.)

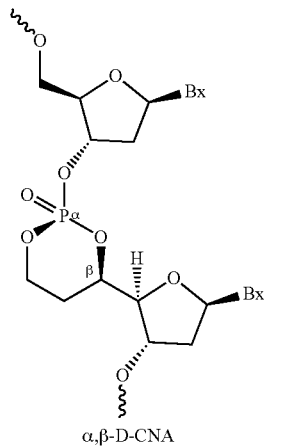

α,β-D-CNA ($R_{C5'}$, $R_P$)

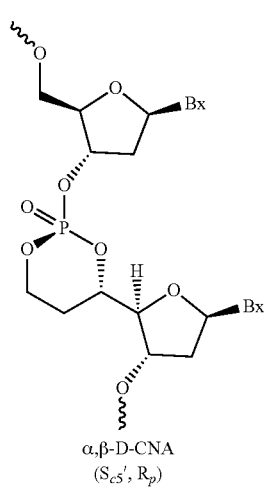

α,β-D-CNA
($S_{C5'}$, $R_p$)

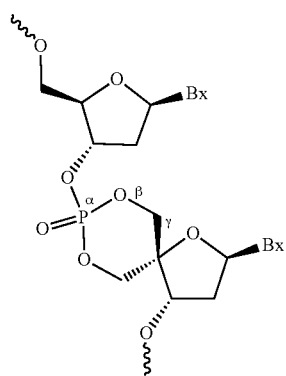

α,β,γ-D-CNA

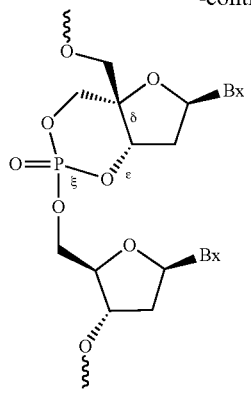

δ,ε,ξ-D-CNA ($R_{C5'}$, $R_P$)

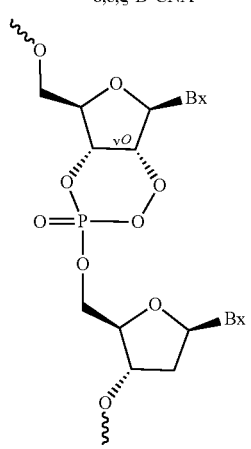

ν°,ε,ξ-D-CNA

II. Certain Motifs

In certain embodiments, oligomeric compounds described herein comprise or consist of oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns or motifs of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

A. Certain Sugar Motifs

In certain embodiments, oligomeric compounds described herein comprise or consist of oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, a modified oligonucleotide comprises or consists of a gapmer. The sugar motif of a gapmer defines the regions of the gapmer: 5'-region, central region, and 3'-region. The positions of the nucleosides within each region are counted beginning at the 5'-end of each region. Each region of a gapmer is connected by an internucleoside linkage, as are the nucleosides within each region. Each nucleoside of the 5'-region and each nucleoside of the 3'-region comprise a 2'-modified furanosyl sugar moiety. The nucleoside at the first position (position 1) of the central region and the nucleoside at the last position of the central region are adjacent to the 5'-region and 3'-region, respectively, and each comprise a sugar moiety independently selected from a 2'-deoxyfuranosyl sugar moiety or a sugar surrogate. Unlike the nucleosides at the first and last positions of the central region, the nucleosides at the other positions within the central region may comprise a 2'-modified furanosyl sugar moiety. In certain embodiments, the 2'-modified furanosyl sugar moiety in the 5' and 3'-regions is a 4'-2'-bicyclic sugar moiety. In certain embodiments, the 2'-modified furanosyl sugar moiety in the 5' and 3' regions is a cEt. In certain embodiments, the 2'-modified furanosyl sugar moiety is a 2'-MOE furanosyl sugar moiety. In certain embodiments, each nucleoside within the gap supports RNase H cleavage. In certain embodiments, a plurality of nucleosides within the gap support RNase H cleavage. In certain embodiments, the nucleoside at the first and last positions of the central region adjacent to the 5' and 3' regions are DNA nucleosides.

Herein, the lengths (number of nucleosides) of the three regions of a gapmer may be provided using the notation [# of nucleosides in the 5'-wing]–[of nucleosides in the gap]–[of nucleosides in the 3'-wing]. Thus, a 3-10-3 gapmer consists of 3 linked nucleosides in each wing and 10 linked nucleosides in the gap. Where such nomenclature is followed by a specific modification, that modification is the modification of each sugar moiety of each wing and the gap nucleosides comprise 2'-β-D-deoxyribosyl sugar moieties. Thus, a 5-10-5 MOE gapmer consists of 5 linked nucleosides comprising 2'-MOE-β-D-ribofuranosyl sugar moieties in the 5'-wing, 10 linked nucleosides comprising a 2'β-D-deoxyribosyl sugar moiety in the gap, and 5 linked nucleosides comprising 2'-MOE-β-D-ribofuranosyl sugar moieties in the 3'-wing. A 3-10-3 cEt gapmer consists of 3 linked nucleosides comprising a cEt in the 5'-wing, 10 linked nucleosides comprising a 2'-β-D-deoxyribosyl sugar moiety in the gap, and 3 linked nucleosides comprising a cEt in the 3'-wing.

In certain embodiments, modified oligonucleotides are 5-10-5 MOE gapmers. In certain embodiments, modified oligonucleotides are 3-10-3 BNA gapmers. In certain embodiments, modified oligonucleotides are 3-10-3 cEt gapmers. In certain embodiments, modified oligonucleotides are 3-10-3 LNA gapmers.

The sugar motif of a 3-10-3 cEt gapmer may also be denoted by the notation kkk-d(10)-kkk, wherein each "k" represents a cEt and each "d" represents a 2'-β-D-deoxyribosyl sugar moiety. This sugar motif is independent of the nucleobase sequence, the internucleoside linkage motif, and any nucleobase modifications. A 5-10-5 MOE gapmer may be denoted by the notation eeeee-d(10)-eeeee or e(5)-d(10)-e(5), wherein each "e" represents a 2'-MOE-β-D-ribofuranosyl sugar moiety, and each "d" represents a 2'-β-D-deoxyribosyl sugar moiety.

B. Certain Nucleobase Motifs

In certain embodiments, oligomeric compounds described herein comprise or consist of oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, one nucleoside comprising a modified nucleobase is in the central region of a modified oligonucleotide. In certain such embodiments, the sugar moiety of said nucleoside is a 2'-β-D-deoxyribosyl moiety. In certain such embodiments, the modified nucleobase is selected from: 5-methyl cytosine, 2-thiopyrimidine, 2-thiothymine, 6-methyladenine, inosine, pseudouracil, or 5-propynepyrimidine.

C. Certain Internucleoside Linkage Motifs

In certain embodiments, oligomeric compounds described herein comprise or consist of oligonucleotides. In certain embodiments, oligonucleotides comprise modified and/or unmodified internucleoside linkages arranged along the oligonucleotide or region thereof in a defined pattern or motif. In certain embodiments, each internucleoside linkage is a phosphodiester internucleoside linkage (P=O). In certain embodiments, each internucleoside linkage of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the internucleoside linkages within the central region of a modified oligonucleotide are all modified. In certain such embodiments, some or all of the internucleoside linkages in the 5'-region and 3'-region are unmodified phosphate linkages. In certain embodiments, the terminal internucleoside linkages are modified. In certain embodiments, the internucleoside linkage motif comprises at least one phosphodiester internucleoside linkage in at least one of the 5'-region and the 3'-region, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the 5'-region and 3'-region are (Sp) phosphorothioates, and the central region comprises at least one Sp, Sp, Rp motif. In certain embodiments, populations of modified oligonucleotides are enriched for modified oligonucleotides comprising such internucleoside linkage motifs.

In certain embodiments, oligonucleotides comprise a region having an alternating internucleoside linkage motif. In certain embodiments, oligonucleotides comprise a region of uniformly modified internucleoside linkages. In certain such embodiments, the internucleoside linkages are phosphorothioate internucleoside linkages. In certain embodiments, all of the internucleoside linkages of the oligonucleotide are phosphorothioate internucleoside linkages. In certain embodiments, each internucleoside linkage of the oligonucleotide is selected from phosphodiester or phosphate and phosphorothioate. In certain embodiments, each internucleoside linkage of the oligonucleotide is selected from phosphodiester or phosphate and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, modified oligonucleotides comprise a linkage motif comprising all phosphorothioate linkages except for one or two methylphosphonate linkages. In certain embodiments, one methylphosphonate linkage is in the central region of an oligonucleotide.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

III. Certain Modified Oligonucleotides

In certain embodiments, oligomeric compounds described herein comprise or consist of modified oligonucleotides. In certain embodiments, the above modifications (sugar, nucleobase, internucleoside linkage) are incorporated into a modified oligonucleotide. In certain embodiments, modified oligonucleotides are characterized by their modifications, motifs, and overall lengths. In certain embodiments, such parameters are each independent of one another. Thus, unless otherwise indicated, each internucleoside linkage of a modified oligonucleotide may be modified or unmodified and may or may not follow the modification pattern of the sugar moieties. Likewise, such modified oligonucleotides may comprise one or more modified nucleobase independent of the pattern of the sugar modifications. Furthermore, in certain instances, a modified oligonucleotide is described by an overall length or range and by lengths or length ranges of two or more regions (e.g., a region of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions or segments, A, B, and C, wherein region or segment A consists of 2-6 linked nucleosides having a specified sugar moiety, region or segment B consists of 6-10 linked nucleosides having a specified sugar moiety, and region or segment C consists of 2-6 linked nucleosides having a specified sugar moiety. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of 20 for the overall length of the modified oligonucleotide. Unless otherwise indicated, all modifications are independent of nucleobase sequence except that the modified nucleobase 5-methylcytosine is necessarily a "C" in an oligonucleotide sequence. In certain embodiments, when a DNA nucleoside or DNA-like nucleoside that comprises a T in a DNA sequence is replaced with a RNA-like nucleoside, including a nucleoside comprising a 2'-OMe modified sugar moiety, the nucleobase T is replaced with the nucleobase U. Each of these compounds has an identical target RNA.

In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

In certain embodiments oligonucleotides have a nucleobase sequence that is complementary to a second oligonucleotide or an identified reference nucleic acid, such as a target nucleic acid. In certain embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 70%, at least 80%, at least 90%, at least 95%, or 100% complementary to the second oligonucleotide or nucleic acid, such as a target nucleic acid.

IV. Certain Conjugated Compounds

In certain embodiments, the oligomeric compounds described herein comprise or consist of an oligonucleotide (modified or unmodified) and optionally one or more conjugate groups and/or terminal groups. Conjugate groups consist of one or more conjugate moiety and a conjugate linker that links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO* 1, 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, i, 923-937), a tocopherol group (Nishina et al., *Molecular Therapy Nucleic Acids,* 2015, 4, e220; doi:10.1038/mtna.2014.72 and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, a conjugate linker is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to oligomeric compounds, such as the oligonucleotides provided herein. In general, a bifunctional linking moiety comprises at least two functional groups. One of the functional groups is selected to bind to a particular site on an oligomeric compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, an oligomeric compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the compound has been taken up, it is desirable that the conjugate group be cleaved to release the unconjugated oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate or phosphodiester linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is a nucleoside comprising a 2'-deoxyfuranosyl that is attached to either the 3' or 5'-terminal nucleoside of an oligonucleotide by a phosphodiester internucleoside linkage and covalently attached to the remainder of the conjugate linker or conjugate moiety by a phosphodiester or phosphorothioate linkage. In certain such embodiments, the cleavable moiety is a nucleoside comprising a 2'β-D-deoxyribosyl sugar moiety. In certain such embodiments, the cleavable moiety is 2'-deoxyadenosine.

3. Certain Cell-Targeting Conjugate Moieties

In certain embodiments, a conjugate group comprises a cell-targeting conjugate moiety. In certain embodiments a conjugate group has the general formula:

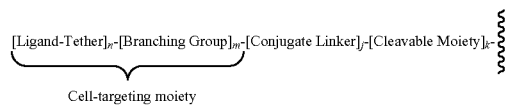

Cell-targeting moiety wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian lung cell.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," *Bioconjugate Chemistry*, 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," *J Med. Chem.* 2004, 47, 5798-5808, which are incorporated herein by reference in their entirety). In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, oligomeric compounds described herein comprise a conjugate group found in any of the following references: Lee, *Carbohydr Res*, 1978, 67, 509-514; Connolly et al., *J Biol Chem*, 1982, 257, 939-945; Pavia et al., *Int J Pep Protein Res*, 1983, 22, 539-548; Lee et al., *Biochem*, 1984, 23, 4255-4261; Lee et al., *Glycoconjugate J*, 1987, 4, 317-328; Toyokuni et al., *Tetrahedron Lett*, 1990, 31, 2673-2676; Biessen et al., *J Med Chem*, 1995, 38, 1538-1546; Valentijn et al., *Tetrahedron*, 1997, 53, 759-770; Kim et al., *Tetrahedron Lett*, 1997, 38, 3487-3490; Lee et al., *Bioconjug Chem*, 1997, 8, 762-765; Kato et al., *Glycobiol*, 2001, 11, 821-829; Rensen et al., *J Biol Chem*, 2001, 276, 37577-37584; Lee et al., *Methods Enzymol*, 2003, 362, 38-43; Westerlind et al., *Glycoconj J*, 2004, 21, 227-241; Lee et al., *Bioorg Med Chem Lett*, 2006, 16(19), 5132-5135; Maierhofer et al., *Bioorg Med Chem*, 2007, 15, 7661-7676; Khorev et al., *Bioorg Med Chem*, 2008, 16, 5216-5231; Lee et al., *Bioorg Med Chem*, 2011, 19, 2494-2500; Kornilova et al., *Analyt Biochem*, 2012, 425, 43-46; Pujol et al., *Angew Chemie Int Ed Engl*, 2012, 51, 7445-7448; Biessen et al., *J Med Chem*, 1995, 38, 1846-1852; Sliedregt et al., *J Med Chem*, 1999, 42, 609-618; Rensen et al., *J Med Chem*, 2004, 47, 5798-5808; Rensen et al., *Arterioscler Thromb Vasc Biol*, 2006, 26, 169-175; van Rossenberg et al., *Gene Ther*, 2004, 11, 457-464; Sato et al., *J Am Chem Soc*, 2004, 126, 14013-14022; Lee et al., *J Org Chem*, 2012, 77, 7564-7571; Biessen et al., *FASEB J*, 2000, 14, 1784-1792; Rajur et al., *Bioconjug Chem*, 1997, 8, 935-940; Duff et al., *Methods Enzymol*, 2000, 313, 297-321; Maier et al., *Bioconjug Chem*, 2003, 14, 18-29; Jayaprakash et al., *Org Lett*, 2010, 12, 5410-5413; Manoharan, Antisense *Nucleic Acid Drug Dev*, 2002, 12, 103-128; Merwin et al., *Bioconjug Chem*, 1994, 5, 612-620; Tomiya et al., *Bioorg Med Chem*, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501, 930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132.

Compositions and Methods for Formulating Pharmaceutical Compositions

Oligomeric compounds described herein may be admixed with pharmaceutically acceptable active or inert substances for the preparation of pharmaceutical compositions. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more oligomeric compounds or a salt thereof. In certain embodiments, the oligomeric compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more oligomeric compound. In certain embodiments, such pharmaceutical composition consists of a sterile saline solution and one or more oligomeric compound. In certain embodiments, the sterile saline is pharmaceutical grade saline. In certain embodiments, a pharmaceutical composition comprises one or more oligomeric compound and sterile water. In certain embodiments, a pharmaceutical composition consists of one oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, a pharmaceutical composition consists of one or more oligomeric compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

An oligomeric compound described herein complementary to a target nucleic acid can be utilized in pharmaceutical compositions by combining the oligomeric compound with a suitable pharmaceutically acceptable diluent or carrier and/or additional components such that the pharmaceutical composition is suitable for injection. In certain embodiments, a pharmaceutically acceptable diluent is phosphate buffered saline. Accordingly, in one embodiment, employed in the methods described herein is a pharmaceutical composition comprising an oligomeric compound complementary to a target nucleic acid and a pharmaceutically acceptable diluent. In certain embodiments, the pharmaceutically acceptable diluent is phosphate buffered saline. In certain embodiments, the oligomeric compound comprises or consists of a modified oligonucleotide provided herein.

Pharmaceutical compositions comprising oligomeric compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the oligomeric compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

Certain Mechanisms

In certain embodiments, oligomeric compounds described herein comprise or consist of modified oligonucleotides. In certain such embodiments, the oligomeric compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Nucleosides that are sufficiently "DNA-like" to elicit RNase H activity are referred to as DNA mimics herein. Further, in certain embodiments, one or more non-DNA-like nucleoside in in the RNA:DNA duplex is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Certain Toxicities

For a compound to be a viable therapeutic agent, it must be safe at therapeutically relevant doses. It has become clear that toxicity of oligonucleotides can arise from one or more of several mechanisms. For example, some oligonucleotides hybridize an unintended RNA (or "off-target RNA") resulting in reduction of the off-target RNA and the protein encoded by that off-target RNA. Such unintended protein reduction may have toxic consequences. The data disclosed herein demonstrate that toxicity can result from oligonucleotides binding certain proteins and subsequent sub-cellular localization of the oligonucleotide/protein complex. Other mechanisms of toxicity may also contribute. Of course, for an oligonucleotide to be a suitable drug for use in therapy, all of the forms or mechanisms of toxicity must be acceptably low.

Since toxicity can result from multiple mechanisms, the observed toxicity for a particular compound will typically be the most toxic mechanism or the mechanism that results in toxicity at the lowest dose for that particular compound (the "limiting toxicity"). Changes to a compound that reduce the limiting toxicity will result in a compound having an observable improvement in toxic profile. Changes that reduce a form of toxicity that is not the limiting toxicity may not result in an observable improvement in toxicity, because the improvement may be masked by the limiting toxicity. In such instances, the improvement to a non-limiting toxicity can nonetheless have value. For example, the limiting toxicity might be controlled through additional changes to the compound or through changes in dose or dose frequency or through use of a separate therapy that mitigates the limiting toxicity; at that point, a previously masked toxicity would become limiting. Alternatively, in certain circumstances, the limiting toxicity might be less relevant (for example, if the drug is intended for delivery to specific tissues not affected by the limiting toxicity or if the compound is for the treatment of severe or life-threatening indications where a certain degree of the limiting toxicity may be acceptable). In such instances, improvements to a non-limiting toxicity can have significant benefit. Further, the various forms and mechanisms of toxicity may have a cumulative effect, particularly over time. Accordingly, the beneficial effects of improvements to a particular mechanism of toxicity might be masked at an early time point where another mechanism is the limiting toxicity, but over time such masked toxicity may contribute or even predominate the overall safety profile.

In certain embodiments, oligomeric compounds of the invention have improved toxicity profiles compared to standard gapmer compounds having a gap comprising only nucleosides having 2'-β-D-deoxyribosyl sugar moieties and the same nucleobase sequence. It should be noted that some standard gapmers are suitable therapeutic agents. Toxicity is driven in part by nucleobase sequence (oligonucleotides having identical chemical modification patterns but different sequences can have vastly different safety profiles). When one attempts to modulate a particular target RNA, one might find an antisense oligonucleotide that has an acceptable safety profile at therapeutic doses. On other occasions, however, the most active/potent oligonucleotides have unacceptable toxicity. In such instances, it is desirable to modify such compounds to reduce their toxicity, ideally with no loss or only modest loss in activity/potency. In certain embodiments, modification motifs described herein reduce toxicity with little or no loss in activity/potency.

Without limitation to any particular mechanism, it is believed that certain modification motifs described herein may reduce interactions between an oligomeric compound and certain proteins. In certain embodiments, such interactions result in the limiting toxicity and so disruption of these interactions results in observable improvements in the toxicity profile. In certain embodiments, the motifs described herein may alter off-target cleavage. In certain embodiments, the disclosed motifs improve toxicity through an undefined mechanism. In certain embodiments, the motifs may improve toxicity through multiple mechanisms, including, but not limited to those described here.

Disclosed herein for comparison are certain gapmer oligonucleotides that are notably more toxic than other gapmers. These toxic gapmer oligonucleotides cause rapid delocalization of paraspeckle proteins, including p54nrb, to nucleoli, possibly due to the binding of these toxic oligonucleotides to the p54nrb protein and/or other paraspeckle proteins. Certain such toxic oligonucleotides have both more global protein binding than their nontoxic (or less toxic) counterparts and have higher binding affinities (i.e., lower Kd values) for key paraspeckle proteins, including p54nrb and RNase H1. Certain such toxic oligonucleotides, but not nontoxic (or less toxic) oligonucleotides, cause the paraspeckle proteins PSF, PSPC1, and FUS to localize to the nucleoli as well, as observed across a number of mouse and human cell types. In certain instances, the nucleolar delocalization of paraspeckle proteins is mediated by RNase H1. Importantly, in some instances, nontoxic (or less toxic) modified oligonucleotides with the same chemical modification pattern (gapmer motif) and a different sequence do not cause the delocalization of p54nrb to nucleoli. This early event leads to nucleolar stress, p53 activation, and apoptotic cell death, both in vitro across a number of mammalian cell types and in vivo in mice. These results were consistent for gapmers with toxic sequences and containing several different commonly-used chemical modifications of modified oligonucleotides, including LNA, cEt, and 2'-MOE.

In certain embodiments, the instant invention is directed towards modified oligonucleotides having chemical modifications that can alleviate the observed toxicity. In certain embodiments, such toxicity is related to protein binding and the resulting nucleolar mislocalization of proteins, such as paraspeckle proteins described above. In certain embodiments, the incorporation of a safety-enhancing nucleoside at position 2, 3 or 4 of the central region (or "gap") of the modified oligonucleotide can reduce both global protein binding and the associated toxicity. In certain embodiments, the safety-enhancing nucleoside is a nucleoside comprising a 2'-OMe β-D-deoxyribosyl sugar moiety at position 2 of the central region. Incorporation of a nucleoside comprising a 2'-OMe-β-D-deoxyribosyl sugar moiety at position 2 of the central region in a toxic 3-10-3, 3-10-4, 4-10-3 cEt gapmer, a 3-10-3 LNA gapmer, a 5-10-5 MOE gapmer, or several cEt/MOE mixed wing gapmers reduced cellular toxicity and apoptosis in vitro and hepatoxicity in vivo across a wide variety of sequences, while having only a modest effect, if any, on antisense activity. In certain embodiments, incorporation of a nucleoside comprising a 2'-OMe-β-D-deoxyribosyl sugar moiety at position 2 of the central region also reduced delayed neurotoxicity, suggesting a common mechanism for delayed neurotoxicity and hepatoxicity. In certain embodiments, the safety-enhancing nucleoside is a nucleoside comprising a 5'-alkyl or 5'-allyl modified β-D-deoxyribosyl sugar moiety at position 3 or position 4 of the central region. In certain instances, incorporation of a nucleoside comprising a 5'-alkyl β-D-deoxyribosyl sugar moiety at position 3 or position 4 of the central region of a 3-10-3 cEt gapmer reduces cellular toxicity and apoptosis in vitro and hepatoxicity in vivo across a variety of sequences, while having a modest effect, if any, on antisense activity. In certain embodiments, the incorporation of a safety-enhancing internucleoside linkage between the nucleosides at positions 2-3 or positions 3-4 of the central region can reduce toxicity. In certain embodiments, one or more of a safety-enhancing linkages linking the nucleosides from positions 2-4 of the central region is a neutral linkage. In certain embodiments, one or more of a safety-enhancing linkages linking the nucleosides from positions 2-4 of the central region is a 2'-5' internucleoside linkage. The instant invention extends to any chemical modification introduced at positions 2, 3 or 4 of the central region, including modifications to nucleosides and to internucleoside linkages. In certain embodiments, such modification reduces in vitro toxicity (compared to the modified oligonucleotide lacking the safety enhancing nucleoside at positions 2, 3 or 4 of the central region or lacking the safety enhancing internucleoside linkage between positions 2-3 or 3-4 of the central region) as measured by the caspase 3/7 assay and/or in vivo hepatotoxicity, as measured by ALT or AST, and/or in vivo neurotoxicity, as measured by an FOB score or accumulation of markers of glial inflammation, Aifl and GFAP.

In certain embodiments, introducing chemical modifications at positions 2, 3 or 4 of the central region can significantly reduce toxicity with only a modest loss in potency, if any. This leads to an improvement in therapeutic index for a given target sequence. In certain cases, such improvements in therapeutic index are large enough to allow further drug development based on a compound targeted to a previously-toxic (but potent) sequence.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain embodiments, a pre-mRNA and corresponding mRNA are both target nucleic acids of a single compound. In certain such embodiments, the target region is entirely within an intron of a target pre-mRNA. In certain embodiments, the target region spans an intron/exon junction. In certain embodiments, the target region is at least 50% within an intron.

Certain Compounds Having Central Region Modifications

In certain embodiments, the oligomeric compounds herein comprise a gapmer comprising one or more an altered nucleotides in the central region of the gapmer. Each of such oligomeric compounds has a corresponding parent oligomeric compound that is identical to the first oligomeric compound except that is lacking the one or more altered nucleotides in the central region of the gapmer. Examples of such parent oligomeric compounds and their corresponding identical oligomeric compounds lacking the altered nucleotide are found in Tables 1 and 2 of Example 1 as well as throughout the Examples section. In Example 1, 558807 is the parent oligonucleotide. In certain embodiments, the central region of a parent oligomeric compound comprises only phosphodiester and/or phosphorothioate internucleoside linkages, unmodified nucleobases and/or 5-methylcytosine, and unmodified, 2'β-D-deoxyribosyl sugar moieties.

In certain embodiments, the present disclosure provides oligomeric compounds that comprise a gapmer comprising one or more altered nucleotides in the central region of the gapmer that have an increased therapeutic index an/or increased tolerability compared to the corresponding parent oligomeric compounds. In certain such embodiments, the modification or modifications of the central region of the oligomeric compounds with increased therapeutic index and/or increased tolerability are particularly useful in providing oligomeric compounds having reduced toxicity without significantly altering the potency. The modifications in the central region described herein can be at any position in the central region, and examples of embodiments comprising modifications at such positions are disclosed in the numbered embodiments and Examples. In certain embodiments, the altered nucleotide is an altered nucleoside attached to a phosphorothioate or phosphodiester internucleoside linkage. In a preferred embodiment, the altered nucleotide is at positions 1-4 of the central region of the modified oligonucleotide. In another preferred embodiment, the altered nucleotide comprises a nucleoside comprising a 2'-modified sugar moiety at position 2 of the central region of the modified oligonucleotide. In another preferred embodiment, the altered nucleotide comprises a nucleoside comprising a 5'-modified sugar moiety at positions 3 or 4 of the central region of the modified oligonucleotide. In another preferred embodiment, the altered nucleotide comprises a neutral internucleoside linkage between positions 2-3 or positions 3-4 of the central region of the modified oligonucleotide.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms. All tautomeric forms of the compounds provided herein are included unless otherwise indicated.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

Non-Limiting Disclosure and Incorporation by Reference

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine nucleobase could be described as a DNA having an RNA sugar, or as an RNA having a DNA nucleobase.

Accordingly, nucleic acid sequences provided herein, including, but not limited to those in the sequence listing, are intended to encompass nucleic acids containing any combination of unmodified or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and compounds having other modified nucleobases, such as "AT$^m$CGAUCG," wherein $^m$C indicates a cytosine base comprising a methyl group at the 5-position. In certain cases, compounds comprising a uridine nucleobase and a 2'-OMe sugar moiety are compared to compounds comprising a thymidine nucleobase with a 2'β-D-deoxyribosyl sugar moiety at the same position. While these compounds have different SEQ ID NO:, they are not considered distinct sequences, and they have identical target RNA. In certain cases, compounds comprising a cytosine nucleobase and a 2'-OMe sugar moiety are compared to compounds comprising a 5-methylcytosine nucleobase and a 2'β-D-deoxyribosyl sugar moiety at the same position.

In the Examples below, modified oligonucleotides are represented by a chemistry notation, always shown in the 5'-to-3' direction, of the format $B_{sl}B_{sl}{}^mB_s$, where "B" or "$^m$B" represents the nucleobase, with a superscript "m" before "B" representing a 5-methyl modification, the subscript in position "s" represents the sugar moiety, and the subscript in position "l" represents the 5'-to-3' internucleoside linkage.

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1 Effect of Position-Specific 2'-Modifications on In Vitro Activity and In Vivo Liver Toxicity of Modified Oligonucleotides Complementary to CXCL12

Modified oligonucleotides were synthesized with kkk-x-d(9)-kkk, kkk-d-x-d(8)-kkk, kkk-dd-x-d(7)-kkk or kkk-d(3)-x-d(6)-kkk sugar motifs, respectively, where "x" represents a sugar moiety having the modification indicated in the table below, "k" represents a cEt, and "d" represents an unmodified, 2'-β-D-deoxyribosyl sugar moiety. These modified oligonucleotides were compared to the otherwise identical modified oligonucleotide lacking an altered nucleotide in the central region, a 3-10-3 cEt gapmer, having three cEt nucleosides in each of the 5' and 3' regions and 10 DNA nucleosides in the central region. Each internucleoside linkage is a phosphorothioate. The compounds in the table below are 100% complementary to mouse CXCL12, GEN-BANK NT_039353.7 truncated from 69/430,515 to 69/445,350 (SEQ ID NO: 1), at position 6877 to 6892.

TABLE 1

Modified oligonucleotides complementary to CXCL12

| Compound ID | position of altered nucleotide in central region | sugar modification of altered nucleotide | Chemistry Notation (5'-3') | SEQ ID NO |
|---|---|---|---|---|
| 558807 | n/a | n/a | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 936049 | 1 | 2'-OMe | $G_{ks}{}^mC_{ks}A_{ks}U_{ms}G_{ds}T_{ds}T_{ds}{}^mC_{ds}T_{ds}{}^mC_{ds}A_{ds}{}^mC_{ds}A_{ds}T_{ks}T_{ks}A_k$ | 19 |
| 828910 | 1 | 2'-MOE | $G_{ks}{}^mC_{ks}A_{ks}T_{es}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 936050 | 1 | cEt | $G_{ks}{}^mC_{ks}A_{ks}T_{ks}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 936054 | 1 | 2'-FANA | $G_{ks}{}^mC_{ks}A_{ks}U_{(FANA)s}G_{ds}T_{ds}T_{ds}{}^mC_{ds}T_{ds}{}^mC_{ds}A_{ds}{}^mC_{ds}A_{ds}T_{ks}T_{ks}A_k$ | 19 |
| 936048 | 1 | 2'-ribo-F | $G_{ks}{}^mC_{ks}A_{ks}U_{fs}G_{ds}T_{ds}T_{ds}{}^mC_{ds}T_{ds}{}^mC_{ds}A_{ds}{}^mC_{ds}A_{ds}T_{ks}T_{ks}A_k$ | 19 |
| 936053 | 2 | 2'-OMe | $G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_k$ | 18 |
| 828911 | 2 | 2'-MOE | $G_{ks}{}^mC_{ks}A_{ks}T_{ds}G_{es}T_{ds}T_{ds}{}^mC_{ds}T_{ds}{}^mC_{ds}A_{ds}{}^mC_{ds}A_{ds}T_{ks}T_{ks}A_k$ | 18 |
| 1070041 | 2 | cEt | $G_{ks}{}^mC_{ks}A_{ks}T_{ds}G_{ks}T_{ds}T_{ds}{}^mC_{ds}T_{ds}{}^mC_{ds}A_{ds}{}^mC_{ds}A_{ds}T_{ks}T_{ks}A_k$ | 18 |
| 1061314 | 2 | 2'-OH (RNA) | $G_{ks}{}^mC_{ks}A_{ks}T_{ds}G_{rs}T_{ds}T_{ds}{}^mC_{ds}T_{ds}{}^mC_{ds}A_{ds}{}^mC_{ds}A_{ds}T_{ks}T_{ks}A_k$ | 18 |
| 936051 | 2 | 2'-FANA | $G_{ks}{}^mC_{ks}A_{ks}T_{ds}G_{(FANA)s}T_{ds}T_{ds}mC_{ds}T_{ds}mC_{ds}A_{ds}mC_{ds}A_{ds}T_{ks}T_{ks}A_k$ | 18 |
| 936052 | 2 | 2'-ribo-F | $G_{ks}{}^mC_{ks}A_{ks}T_{ds}G_{fs}T_{ds}T_{ds}{}^mC_{ds}T_{ds}{}^mC_{ds}A_{ds}{}^mC_{ds}A_{ds}T_{ks}T_{ks}A_k$ | 18 |
| 892826 | 3 | 2'-OMe | $G_{ks}{}^mC_{ks}A_{ks}T_{ds}G_{ds}U_{ms}T_{ds}{}^mC_{ds}T_{ds}{}^mC_{ds}A_{ds}{}^mC_{ds}A_{ds}T_{ks}T_{ks}A_k$ | 20 |
| 828912 | 3 | 2'-MOE | $G_{ks}{}^mC_{ks}A_{ks}T_{ds}G_{ds}T_{es}T_{ds}{}^mC_{ds}T_{ds}{}^mC_{ds}A_{ds}{}^mC_{ds}A_{ds}T_{ks}T_{ks}A_k$ | 18 |
| 892816 | 3 | cEt | $G_{ks}{}^mC_{ks}A_{ks}T_{ds}G_{ds}T_{ks}T_{ds}{}^mC_{ds}T_{ds}{}^mC_{ds}A_{ds}{}^mC_{ds}A_{ds}T_{ks}T_{ks}A_k$ | 18 |
| 895596 | 3 | 2'-FANA | $G_{ks}{}^mC_{ks}A_{ks}T_{ds}G_{ds}U_{(FANA)s}T_{ds}{}^mC_{ds}T_{ds}{}^mC_{ds}A_{ds}{}^mC_{ds}A_{ds}T_{ks}T_{ks}A_k$ | 20 |
| 892821 | 3 | 2'-ribo-F | $G_{ks}{}^mC_{ks}A_{ks}T_{ds}G_{ds}U_{fs}T_{ds}{}^mC_{ds}T_{ds}{}^mC_{ds}A_{ds}{}^mC_{ds}A_{ds}T_{ks}T_{ks}A_k$ | 20 |
| 892819 | 4 | 2'-OMe | $G_{ks}{}^mC_{ks}A_{ks}T_{ds}G_{ds}T_{ds}U_{ms}{}^mC_{ds}T_{ds}{}^mC_{ds}A_{ds}{}^mC_{ds}A_{ds}T_{ks}T_{ks}A_k$ | 21 |

TABLE 1-continued

Modified oligonucleotides complementary to CXCL12

| Compound ID | position of altered nucleotide in central region | sugar modification of altered nucleotide | Chemistry Notation (5'-3') | SEQ ID NO |
|---|---|---|---|---|
| 828913 | 4 | 2'-MOE | $G_{ks}{}^mC_{ks}A_{ks}T_{ds}G_{ds}T_{ds}T_{es}{}^mC_{ds}T_{ds}{}^mC_{ds}A_{ds}{}^mC_{ds}A_{ds}T_{ks}T_{ks}A_k$ | 18 |
| 892817 | 4 | cEt | $G_{ks}{}^mC_{ks}A_{ks}T_{ds}G_{ds}T_{ds}T_{ks}{}^mC_{ds}T_{ds}{}^mC_{ds}A_{ds}{}^mC_{ds}A_{ds}T_{ks}T_{ks}A_k$ | 18 |
| 895595 | 4 | 2'-FANA | $G_{ks}{}^mC_{ks}A_{ks}T_{ds}G_{ds}T_{ds}U_{(FANA)s}{}^mC_{ds}T_{ds}{}^mC_{ds}A_{ds}{}^mC_{ds}A_{ds}T_{ks}T_{ks}A_k$ | 21 |
| 892822 | 4 | 2'-ribo-F | $G_{ks}{}^mC_{ks}A_{ks}T_{ds}G_{ds}T_{ds}U_{fs}{}^mC_{ds}T_{ds}{}^mC_{ds}A_{ds}{}^mC_{ds}T_{ks}T_{ks}A_k$ | 21 |

A subscript "d" indicates an unmodified, 2'-β-D-deoxyribosyl sugar moiety.
A subscript "e" indicates a 2'-MOE-β-D-ribofuranosyl sugar moiety.
A subscript "m" indicates a 2'-O-methyl-β-D-ribofuranosyl sugar moiety.
A subscript "k" indicates a cEt.
A subscript "s" indicates a phosphorothioate internucleoside linkage.
A subscript "f" indicates a 2'-F-β-D-2'-deoxyribosyl sugar moiety.
A subscript "(FANA)" indicates a 2'-F-β-D-arabinofuranosyl modified sugar moiety.
A superscript "m" before a C indicates 5-methyl Cytosine.

For in vitro activity studies, approximately 20,000 mouse 3T3-L1 cells were electroporated with 0, 27 nM, 82 nM, 247 nM, 740 nM, 2,220 nM, 6,660 nM or 20,000 nM antisense oligonucleotide. mRNA was harvested and analyzed by RT-qPCR. CXCL12 mRNA was detected with primer probe set RTS2605 (forward sequence CCAGAGCCAACGT-CAAGCAT, SEQ ID NO: 9; reverse sequence: CAGCCGTGCAACAATCTGAA, SEQ ID NO: 10; probe sequence: TGAAAATCCTCAACACTCCAAACTGTGCC, SEQ ID NO: 11) and RAPTOR mRNA was detected with primer probe set RTS3420 (forward sequence GCCCTCAGAAAGCTCTGGAA, SEQ ID NO: 12; reverse sequence: TAGGGTCGAGGCTCTGCTTGT, SEQ ID NO: 13; probe sequence: CCATCGGTGCAAACCTA-CAGAAGCAGTATG, SEQ ID NO: 14). RAPTOR is a sentinel gene that can be indicative of toxicity, as described in US 20160160280, hereby incorporated by reference.

For acute in vivo toxicity studies, three BALB/C mice per group were administered 150 mg/kg modified oligonucleotide by subcutaneous injection and sacrificed 72 hours later. Three mice were administered an injection of saline as a control. Plasma levels of ALT were measured using an automated clinical chemistry analyzer. Increased ALT is indicative of acute liver toxicity.

TABLE 2

Activity and toxicity of modified oligonucleotides complementary CXCL12

| Compound ID | position of altered nucleotide in central region | sugar modification of altered nucleotide | in vitro CXCL12 $IC_{50}$ (μM) | in vitro RAPTOR $IC_{50}$ (μM) | ALT @ 150 mg/kg (IU/L) |
|---|---|---|---|---|---|
| PBS | n/a | n/a | n/a | n/a | 23 |
| 558807 | n/a | n/a | 0.2 | 1.26 | n.d.** |
| 936049 | 1 | 2'-OMe | 0.17 | 4.8 | 8622 |
| 828910 | 1 | 2'-MOE | 0.12 | 7.2 | 2175 |
| 936050 | 1 | cEt | 0.15 | 6.5 | 912 |
| 936054 | 1 | 2'-FANA | 0.12 | 9.9 | 5755 |
| 936048 | 1 | 2'-ribo-F | 0.15 | 1.9 | death |
| 936053 | 2 | 2'-OMe | 0.17 | >>10 | 46 |

TABLE 2-continued

Activity and toxicity of modified oligonucleotides complementary CXCL12

| Compound ID | position of altered nucleotide in central region | sugar modification of altered nucleotide | in vitro CXCL12 $IC_{50}$ (μM) | in vitro RAPTOR $IC_{50}$ (μM) | ALT @ 150 mg/kg (IU/L) |
|---|---|---|---|---|---|
| 828911 | 2 | 2'-MOE | 0.42 | >>10 | 27 |
| 1070041 | 2 | cEt | 0.52 | n.d. | 96 |
| 1061314 | 2 | 2'-OH (RNA) | n.d. | n.d. | 26 |
| 936051 | 2 | 2'-FANA | 0.12 | 2.34 | death |
| 936052 | 2 | 2'-ribo-F | 0.19 | 13.5 | 1110 |
| 892826 | 3 | 2'-OMe | 0.21 | 7.1 | 10463 |
| 828912 | 3 | 2'-MOE | 0.28 | 10 | 701 |
| 892816 | 3 | cEt | 0.17 | 11 | 278 |
| 895596 | 3 | 2'-FANA | 0.12 | 7.4 | 17369 |
| 892821 | 3 | 2'-ribo-F | 0.18 | 4.5 | 6333 |
| 892819 | 4 | 2'-OMe | 0.18 | >10 | 565 |
| 828913 | 4 | 2'-MOE | 0.22 | 10 | 2474 |
| 892817 | 4 | cEt | 0.23 | 9 | 5264 |
| 895595 | 4 | 2'-FANA | 0.08 | 8.8 | 22082 |
| 892822 | 4 | 2'-ribo-F | 0.04 | 4.85 | 4020 |

**558807 treatment at 16.7 mg/kg leads to an ALT of 586 IU/L in this experiment; mice that are treated with 558807 at 150 mg/kg typically experience death before 72 hours post-treatment.

For the in vitro study reported in the tables below, 3T3-L1 cells were electroporated with 27 nM, 80 nM, 250 nM, 740 nM, 2, 222 nM, 6,667 nM, or 20,000 nM of modified oligonucleotide and levels of P21 and Gadd45a were measured by RT-qPCR. Levels of Gadd45a were analyzed using primer probe set Mm00432802_m1 (ThermoFisher). Levels of P21 were analyzed using primer probe set Mm04207341_m1 (ThermoFisher).

TABLE 2b in vitro P21 Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 558807 | 110 | 98 | 69 | 99 | 117 | 228 | 488 |
| 936049 | 63 | 116 | 96 | 93 | 121 | 151 | 199 |
| 936053 | 151 | 144 | 158 | 160 | 152 | 143 | 155 |
| 892826 | 140 | 104 | 104 | 128 | 138 | 181 | 177 |

TABLE 2c in vitro Gadd45a Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | Expression level of Gadd45a mRNA (% Control) | | | | |
| 558807 | 115 | 120 | 111 | 136 | 155 | 237 | 298 |
| 936049 | 101 | 124 | 131 | 158 | 172 | 212 | 276 |
| 936053 | 144 | 227 | 175 | 203 | 197 | 201 | 193 |
| 892826 | 132 | 114 | 134 | 152 | 147 | 163 | 158 |

For the in vitro study reported in the tables below, b.END cells were electroporated with 27 nM, 80 nM, 250 nM, 740 nM, 2, 222 nM, 6,667 nM, or 20,000 nM of modified oligonucleotide and levels of P21 were measured by RT-qPCR using primer probe set Mm04207341_m1 (ThermoFisher).

TABLE 2d in vitro P21 Expression in b.END cells

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 558807 | 138 | 117 | 93 | 73 | 107 | 160 | 226 |
| 936053 | 108 | 112 | 96 | 90 | 111 | 101 | 118 |
| 892826 | 112 | 112 | 114 | 107 | 117 | 116 | 137 |
| 1061314 | 126 | 128 | 103 | 115 | 128 | 122 | 112 |
| 936051 | 114 | 113 | 109 | 118 | 117 | 123 | 178 |
| 936052 | 109 | 116 | 102 | 100 | 112 | 119 | 138 |
| 828911 | 115 | 108 | 120 | 113 | 114 | 115 | 122 |
| 1070041 | 101 | 100 | 109 | 104 | 104 | 120 | 132 |

TABLE 2e in vitro Gadd45a Expression in b.END cells

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 558807 | 558807 | 86 | 132 | 93 | 101 | 178 | 220 |
| 936053 | 936053 | 111 | n.d. | 148 | 150 | 200 | 215 |
| 892826 | 892826 | 134 | 177 | 160 | 170 | 177 | 162 |
| 1061314 | 1061314 | 135 | 149 | 150 | 197 | 199 | 184 |
| 936051 | 136 | 132 | 152 | 185 | 199 | 193 | 258 |
| 936052 | 125 | 160 | 146 | 173 | 210 | 201 | 228 |
| 828911 | 121 | 154 | 158 | 193 | 190 | 189 | 249 |
| 1070041 | 118 | 139 | 163 | 194 | 225 | 301 | 313 |

For the in vivo activity and toxicity study in the table below, 2 or 3 BALB/C mice per group were administered modified oligonucleotide at 1.8 mg/kg, 5.5 mg/kg, or 16.7 mg/kg by subcutaneous injection and sacrificed after 72 hours.

TABLE 2f in vivo Activity and Toxicity

| Compound ID | position of altered nucleotide in central region | sugar modification of altered nucleotide | in vivo CXCL12 ED50 (mg/kg) | ALT @5.5 mg/kg (IU/L) | ALT @ 16.7 mg/kg (IU/L) |
|---|---|---|---|---|---|
| PBS | n/a | n/a | n/a | 30 (@0 mg/kg) | |
| 558807 | n/a | n/a | 1.6 | 40 | 1721 |
| 936051 | 2 | 2'-FANA | 0.15 | 44 | 4285 |
| 936053 | 2 | 2'-OMe | 5.5 | 27 | 25 |
| 828911 | 2 | 2'-MOE | 14 | 36 | 25 |
| 936052 | 2 | 2'-ribo-F | 2.9 | 26 | 29 |

For in vivo activity and toxicity study in the table below, 3 BALB/C mice per group were administered modified oligonucleotide by subcutaneous injection and sacrificed after 72 hours. Compound 558807 was dosed at 1.8, 5.5, or 16.7 mg/kg, compounds 828911, 936052 and 936053 were dosed at 1.8, 5.5, 16.7 and 50 mg/kg, and compounds 1061315 and 1070041 were dosed at 1.8, 5.5, 16.7, 50 or 150 mg/kg. Tissue were collected and mRNA was isolated and levels of CXCL12 were measured by RT-qPCR with primer probe set RTS2605 as described above. Levels of Gadd45a were analyzed using primer probe set Mm00432802_m1 (ThermoFisher). Levels of P21 were analyzed using primer probe set Mm04207341_m1 (ThermoFisher). Levels of Tnfrsf10b were analyzed using primer probe set Mm00457866_m1 (ThermoFisher). Expression levels were normalized with Ribogreen® and are presented relative to levels in mice treated with PBS.

TABLE 2g

In Vivo Activity and Toxicity of modified oligonucleotides complementary to CXCL12

| Compound ID | position of altered nucleotide in central region | sugar modification of altered nucleotide | in vivo CXCL12 ED50 (mg/kg) | ALT @50 mg/kg (IU/L) | ALT @ 150 mg/kg (IU/L) |
|---|---|---|---|---|---|
| PBS | n/a | n/a | n/a | 28 (@0 mg/kg) | |
| 558807 | n/a | n/a | 2.7 | n.d.** | |
| 936053 | 2 | 2'-OMe | 4.9 | 23 | n.d. |
| 828911 | 2 | 2'-MOE | 14 | 27 | n.d. |
| 1070041 | 2 | cEt | 29 | 25 | 78 |
| 1061314 | 2 | 2'-OH (RNA) | 78 | 21 | 24 |
| 936052 | 2 | 2'-ribo-F | 4.2 | 39 | n.d. |

**558807 treatment at 16.7 mg/kg leads to an ALT of 586 IU/L; mice that are treated with 558807 at 150 mg/kg typically experience death before 72 hours post-treatment.

TABLE 2h

In Vivo Dose-response of Gadd45a mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Gadd45a mRNA (% Control) | | | | |
| 558807 | 100 | 172 | 856 | n/a | n/a |
| 936053 | 61 | 99 | 91 | 92 | n/a |
| 828911 | 80 | 100 | 96 | 100 | n/a |
| 1070041 | 128 | 225 | 139 | 177 | 169 |
| 1061314 | 112 | 84 | 89 | 105 | 180 |
| 936052 | 84 | 80 | 134 | 126 | n/a |

TABLE 2i

In Vivo Dose-response of Tnfrsf10b mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Tnfrsf10b mRNA (% Control) | | | | |
| 558807 | 102 | 267 | 790 | n/a | n/a |
| 936053 | 106 | 111 | 130 | 100 | n/a |
| 828911 | 120 | 116 | 95 | 102 | n/a |
| 1070041 | 106 | 139 | 252 | 483 | 1021 |
| 1061314 | 79 | 66 | 81 | 136 | 220 |
| 936052 | 82 | 101 | 183 | 138 | n/a |

TABLE 2j

In Vivo Dose-response of P21 mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 100 | 61 | 609 | n/a | n/a |
| 936053 | 104 | 94 | 104 | 89 | n/a |
| 828911 | 90 | 145 | 52 | 92 | n/a |
| 1070041 | 28 | 93 | 83 | 132 | 264 |
| 1061314 | 45 | 59 | 30 | 34 | 178 |
| 936052 | 70 | 71 | 51 | 101 | n/a |

For the in vivo activity study in the tables below, 3 BALB/C mice per group were administered 3.37, 11, 33, or 100 mg/kg doses of modified oligonucleotide, as indicated in the table below, by subcutaneous injection and sacrificed 72 hours later. Liver mRNA was isolated an analyzed by RT-PCR as described in above. Expression levels were normalized with Ribogreen® and are expressed relative to PBS-treated control mice.

TABLE 2k

Activity and toxicity of modified oligonucleotides complementary to CXCL12

| Compound ID | position of altered nucleotide in central region | sugar modification of altered nucleotide | ALT (IU/L) at 100 mg/kg | ALT (IU/L) at 33 mg/kg |
|---|---|---|---|---|
| 558807 | n/a | n/a | death | 3740 |
| 936049 | 1 | 2'-OMe | 3060 | 612 |
| 936053 | 2 | 2'-OMe | 42 | 21 |
| 892826 | 3 | 2'-OMe | 1127 | 2281 |

TABLE 2l

In Vivo Dose-response of CXCL12 mRNA upon treatment with modified oligonucleotides complementary to CXCL12

| Compound ID | 3.37 mg/kg | 11 mg/kg | 33 mg/kg | 100 mg/kg |
|---|---|---|---|---|
| | Expression level of CXCL12 mRNA (% Control) | | | |
| 558807 | 95 | 29 | 12 | n.d. |
| 936049 | 102 | 50 | 22 | 14 |

TABLE 21-continued

In Vivo Dose-response of CXCL12 mRNA upon treatment with modified oligonucleotides complementary to CXCL12

| Compound ID | 3.37 mg/kg | 11 mg/kg | 33 mg/kg | 100 mg/kg |
|---|---|---|---|---|
| | Expression level of CXCL12 mRNA (% Control) | | | |
| 936053 | 100 | 70 | 40 | 31 |
| 892826 | 100 | 49 | 16 | 10 |

TABLE 2m

In Vivo Dose-response of P21 mRNA upon treatment with modified oligonucleotides complementary to CXCL12

| Compound ID | 3.37 mg/kg | 11 mg/kg | 33 mg/kg | 100 mg/kg |
|---|---|---|---|---|
| | Expression level of P21 mRNA (% Control) | | | |
| 558807 | 194 | 186 | 32700 | n.d. |
| 936049 | 126 | 127 | 3156 | 21746 |
| 936053 | 100 | 49 | 89 | 185 |
| 892826 | 60 | 60 | 2401 | 12981 |

Example 2 Effect of Position-Specific 5'-Modifications on In Vitro Activity and In Vivo Liver Toxicity of Modified Oligonucleotides Complementary CXCL12

Modified oligonucleotides containing 5'-methyl, 5'-allyl, and 5'-ethyl modifications at various positions were synthesized. Procedures for the synthesis of 5'-methyl and 5'-allyl analogs are detailed in WO2013022967. Procedures for the synthesis of 5'-ethyl analogs are detailed herein below in Example 39. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse CXCL12, GENBANK NT_039353.7 truncated from 69/430,515 to 69/445,350 (SEQ ID NO: 1), at position 6877 to 6892.

TABLE 3

Modified oligonucleotides complementary to CXCL12

| Compound ID | position of altered nucleotide in central region | sugar modification of altered nucleotide | Chemistry Notation (5'-3') | SEQ ID NO |
|---|---|---|---|---|
| 558807 | n/a | n/a | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_{k}$ | 18 |
| 1123320 | 2 | 5'-(S)-Me | $G_{ks}{}^mC_{ks}A_{ks}T_{ds}G_{[(S)-\mu]s}T_{ds}T_{ds}{}^mC_{ds}T_{ds}{}^mC_{ds}A_{ds}{}^mC_{ds}A_{ds}T_{ks}T_{ks}A_{k}$ | 18 |
| 1123322 | 2 | 5'-(R)-Me | $G_{ks}{}^mC_{ks}A_{ks}T_{ds}G_{[(R)-\mu]s}T_{ds}T_{ds}{}^mC_{ds}T_{ds}{}^mC_{ds}A_{ds}{}^mC_{ds}A_{ds}T_{ks}T_{ks}A_{k}$ | 18 |
| 1123479 | 2 | 5'-(R,S)-allyl | $G_{ks}{}^mC_{ks}A_{ks}T_{ds}G_{[\gamma]s}T_{ds}T_{ds}{}^mC_{ds}T_{ds}{}^mC_{ds}A_{ds}{}^mC_{ds}A_{ds}T_{ks}T_{ks}A_{k}$ | 18 |
| 942943 | 3 | 5'-(R)-Me | $G_{ks}{}^mC_{ks}A_{ks}T_{ds}G_{ds}T_{[(R)-\mu]s}T_{ds}{}^mC_{ds}T_{ds}{}^mC_{ds}A_{ds}{}^mC_{ds}A_{ds}T_{ks}T_{ks}A_{k}$ | 18 |
| 957908 | 3 | 5'-(S)-Me | $G_{ks}{}^mC_{ks}A_{ks}T_{ds}G_{ds}T_{[(S)-\mu]s}T_{ds}{}^mC_{ds}T_{ds}{}^mC_{ds}A_{ds}{}^mC_{ds}A_{ds}T_{ks}T_{ks}A_{k}$ | 18 |
| 957910 | 3 | 5'-(R)-allyl | $G_{ks}{}^mC_{ks}A_{ks}T_{ds}G_{ds}T_{[(R)-\gamma]s}T_{ds}{}^mC_{ds}T_{ds}{}^mC_{ds}A_{ds}{}^mC_{ds}A_{ds}T_{ks}T_{ks}A_{k}$ | 18 |
| 957912 | 3 | 5'-(S)-allyl | $G_{ks}{}^mC_{ks}A_{ks}T_{ds}G_{ds}T_{[(S)-\gamma]s}T_{ds}{}^mC_{ds}T_{ds}{}^mC_{ds}A_{ds}{}^mC_{ds}A_{ds}T_{ks}T_{ks}A_{k}$ | 18 |
| 1175787 | 3 | 5'-(R)-Et | $G_{ks}{}^mC_{ks}A_{ks}T_{ds}G_{ds}T_{[(R)-\epsilon]s}T_{ds}{}^mC_{ds}T_{ds}{}^mC_{ds}A_{ds}{}^mC_{ds}A_{ds}T_{ks}T_{ks}A_{k}$ | 18 |
| 1175785 | 3 | 5'-(S)-Et | $G_{ks}{}^mC_{ks}A_{ks}T_{ds}G_{ds}T_{[(S)-\epsilon]s}T_{ds}{}^mC_{ds}T_{ds}{}^mC_{ds}A_{ds}{}^mC_{ds}A_{ds}T_{ks}T_{ks}A_{k}$ | 18 |
| 942944 | 4 | 5'-(R)-Me | $G_{ks}{}^mC_{ks}A_{ks}T_{ds}G_{ds}T_{ds}T_{[(R)-\mu]s}{}^mC_{ds}T_{ds}{}^mC_{ds}A_{ds}{}^mC_{ds}A_{ds}T_{ks}T_{ks}A_{k}$ | 18 |
| 957909 | 4 | 5'-(S)-Me | $G_{ks}{}^mC_{ks}A_{ks}T_{ds}G_{ds}T_{ds}T_{[(S)-\mu]s}{}^mC_{ds}T_{ds}{}^mC_{ds}A_{ds}{}^mC_{ds}A_{ds}T_{ks}T_{ks}A_{k}$ | 18 |
| 957911 | 4 | 5'-(R)-allyl | $G_{ks}{}^mC_{ks}A_{ks}T_{ds}G_{ds}T_{ds}T_{[(R)-\gamma]s}{}^mC_{ds}T_{ds}{}^mC_{ds}A_{ds}{}^mC_{ds}A_{ds}T_{ks}T_{ks}A_{k}$ | 18 |
| 957913 | 4 | 5'-(S)-allyl | $G_{ks}{}^mC_{ks}A_{ks}T_{ds}G_{ds}T_{ds}T_{[(S)-\gamma]s}{}^mC_{ds}T_{ds}{}^mC_{ds}A_{ds}{}^mC_{ds}A_{ds}T_{ks}T_{ks}A_{k}$ | 18 |

TABLE 3-continued

Modified oligonucleotides complementary to CXCL12

| Compound ID | position of altered nucleotide in central region | sugar modification of altered nucleotide | Chemistry Notation (5'-3') | SEQ ID NO |
|---|---|---|---|---|
| 1175786 | 4 | 5'-(R)-Et | $G_{ks}{}^mC_{ks}A_{ks}T_{ds}G_{ds}T_{ds}T_{[(R)-\epsilon]s}{}^mC_{ds}T_{ds}{}^mC_{ds}A_{ds}{}^mC_{ds}A_{ds}T_{ks}T_{ks}A_k$ | 18 |
| 1175782 | 4 | 5'-(S)-Et | $G_{ks}{}^mC_{ks}A_{ks}T_{ds}G_{ds}T_{ds}T_{[(S)-\epsilon]s}{}^mC_{ds}T_{ds}{}^mC_{ds}A_{ds}{}^mC_{ds}A_{ds}T_{ks}T_{ks}A_k$ | 18 |

A subscript "d" indicates an unmodified, 2'-β-D-deoxyribosyl sugar moiety.
A subscript "k" indicates a cEt.
A subscript "s" indicates a phosphorothioate internucleoside linkage.
A subscript "[μ]" indicates a 5'-(R,S)-Me-β-D-2'-deoxyribosyl sugar moiety.
A subscript "[(R)-μ]" indicates a 5'-(R)-Me-β-D-2'-deoxyribosyl sugar moiety.
A subscript "[(S)-μ]" indicates a 5'-(S)-Me-β-D-2'-deoxyribosyl sugar moiety.
A subscript "[γ]" indicates a 5'-(R,S)-allyl-β-D-2'-deoxyribosyl sugar moiety.
A subscript "[(R)-γ]" indicates a 5'-(R)-allyl-β-D-2'-deoxyribosyl sugar moiety.
A subscript "[(S)-γ]" indicates a 5'-(S)-allyl-β-D-2'-deoxyribosyl sugar moiety.
A subscript "[ε]" indicates a 5'-(R,S)-ethyl-β-D-2'-deoxyribosyl sugar moiety.
A subscript "[(R)-ε]" indicates a 5'-(R)-ethyl-β-D-2'-deoxyribosyl sugar moiety.
A subscript "[(S)-ε]" indicates a 5'-(S)-ethyl-β-D-2'-deoxyribosyl sugar moiety.

Experimental Procedures & Results

In vitro activity and in vivo activity and toxicity experiments were performed essentially as described in Example 1. For in vivo toxicity studies, a single BALB/C mouse per modified oligonucleotide was administered 150 mg/kg modified oligonucleotide by subcutaneous injection and sacrificed 72 hours later. For the in vivo activity study in the table below, 2 BALB/C mice per group were administered 1.8 mg/kg, 5.5 mg/kg, 16.7 mg/kg, 50 mg/kg dose of modified oligonucleotide subcutaneously and sacrificed after 72 hours. For 558807, only 1.8 mg/kg, 5.5 mg/kg, and 16.7 mg/kg doses were tested for dose response, due to acute toxicity of higher doses. Tissues were collected and liver mRNA was isolated and levels of CXCL12 were measured by RT-qPCR with primer probe set RTS2605 as described above.

TABLE 4

Activity and toxicity of modified oligonucleotides complementary CXCL12

| Compound ID | position of altered nucleotide in central region | sugar modification of altered nucleotide | In vitro IC50 CXCL12 (μM) | Raptor IC50 (tox marker) | in vivo ED50 (mg/kg) | ALT (at 150 mg/kg) |
|---|---|---|---|---|---|---|
| 558807 | n/a | Parent | 0.11 | 1.3 | 2.9 | n.d.** |
| 942943 | 3 | 5'-(R)-Me | 0.118 | 23 | 2.8 | 2466 |
| 942944 | 4 | 5'-(R)-Me | 0.169 | 22 | 3 | 233 |
| 957908 | 3 | 5'-(S)-Me | 0.193 | 33 | 3.7 | 52 |
| 957909 | 4 | 5'-(S)-Me | 0.159 | 4 | 2.2 | 1267 |
| 957910 | 3 | 5'-(R)-allyl | 0.239 | >>20 | 3.6 | 32 |
| 957911 | 4 | 5'-(R)-allyl | 0.269 | >>20 | 6.4 | 30 |
| 957912 | 3 | 5'-(S)-allyl | 0.234 | >>20 | 5.1 | 30 |
| 957913 | 4 | 5'-(S)-allyl | 0.263 | >>20 | 5.7 | 32 |

**Not tested in this experiment; mice that are treated with 558807 at 150 mg/kg typically experience death before 72 hours post-treatment.

For the in vivo activity and toxicity study reported in the table below, 2 BALB/C mice per group were administered 5 mg/kg or 150 mg/kg modified oligonucleotide subcutaneously and sacrificed 72 hours later. Plasma levels of ALT were measured and liver mRNA was analyzed for target reduction as in example 1 above.

TABLE 5

Activity and toxicity of modified oligonucleotides complementary CXCL12

| Compound ID | position of altered nucleotide in central region | sugar modification of altered nucleotide | CXCL12 mRNA (% control) 5 mg/kg | CXCL12 mRNA (% control) 150 mg/kg | ALT 5 mg/kg (IU/L) | ALT 150 mg/kg (IU/L) |
|---|---|---|---|---|---|---|
| 558807 | n/a | n/a | n.d. | n.d. | n.d. | n.d.** |
| 942943 | 3 | 5'-(R)-Me | 28 | 3 | 27 | 4407 |
| 957910 | 3 | 5'-(R)-allyl | 53 | 7 | 24 | 38 |
| 1175787 | 3 | 5'-(R)-Et | 57 | 6 | 27 | 39 |
| 1175785 | 3 | 5'-(S)-Et | 46 | 8 | 25 | 45 |
| 957909 | 4 | 5'-(S)-Me | 30 | 7 | 22 | 7133 |
| 957913 | 4 | 5'-(S)-allyl | 59 | 10 | 30 | 37 |
| 1175786 | 4 | 5'-(R)-Et | 44 | 35 | 24 | 44 |
| 1175782 | 4 | 5'-(S)-Et | 52 | 7 | 26 | 131 |

**Not tested in this experiment; mice that are treated with 558807 at 150 mg/kg typically experience death before 72 hours post-treatment.

For the results in the tables below, in vivo activity and toxicity experiments were performed essentially as described in Example 1. For in vivo toxicity studies, two BALB/C mice per group was administered 50 or 150 mg/kg modified oligonucleotide by subcutaneous injection and sacrificed 72 hours later. One animal was administered an injection of saline as a control. Plasma levels of ALT were measured using an automated clinical chemistry analyzer.

For the in vivo activity study in the tables below, 2 BALB/C mice per group were administered 1.8 mg/kg, 5.5 mg/kg, 16.7 mg/kg, 50 mg/kg, or 150 mg/kg doses of modified oligonucleotide, as indicated in the table below, by subcutaneous injection and sacrificed 72 hours later. For 558807, only 1.8 mg/kg, 5.5 mg/kg, and 16.7 mg/kg doses were tested for dose response, due to acute toxicity of higher doses. Liver mRNA was isolated an analyzed by RT-PCR as described in Example 1 above. Expression levels were normalized with Ribogreen® and are expressed relative to PBS-treated control mice.

TABLE 6

Activity and toxicity of modified oligonucleotides complementary CXCL12

| Compound ID | position of altered nucleotide in central region | sugar modification of altered nucleotide | in vivo $ED_{50}$ (mg/kg) | ALT (IU/L) at 150 mg/kg | ALT (IU/L) at 50 mg/kg |
|---|---|---|---|---|---|
| 558807 | n/a | n/a | 1.7* | n.d.** | n.d.** |
| 1123320 | 2 | 5'-(R)-Me | 2.8 | 7448 | 3987 |
| 1123322 | 2 | 5'-(S)-Me | 2.1 | 5181 | 1912 |
| 1123479 | 2 | 5'-(R,S)-allyl | 6.1 | 2562 | 56 |

*Compound 558807 was only dosed at 1.8, 5.5, and 16.7 mg/kg
**Not tested in this experiment; mice that are treated with 558807 150 mg/kg typically experience death within 72 hours post-treatment.

TABLE 6b

In Vivo Dose-response of Gadd45a mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Gadd45a mRNA (% Control) | | | | |
| 558807 | 83 | 143 | 188 | n/a | n/a |
| 1123320 | 68 | 80 | 114 | 387 | 683 |
| 1123322 | 105 | 61 | 169 | 141 | 575 |
| 1123479 | 88 | 70 | 75 | 273 | 141 |

TABLE 6c

In Vivo Dose-response of Tnfrsf10b mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Tnfrsf10b mRNA (% Control) | | | | |
| 558807 | 115 | 119 | 195 | n/a | n/a |
| 1123320 | 78 | 115 | 77 | 1,802 | 6,928 |
| 1123322 | 95 | 75 | 231 | 1,036 | 8,281 |
| 1123479 | 174 | 132 | 125 | 303 | 1,423 |

TABLE 6d

In Vivo Dose-response of P21 mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 144 | 123 | 1212 | n/a | n/a |
| 1123320 | 109 | 224 | 114 | 17,332 | 51,431 |
| 1123322 | 218 | 92 | 303 | 10,383 | 75,226 |
| 1123479 | 271 | 209 | 295 | 838 | 12,248 |

TABLE 7

Activity and toxicity of modified oligonucleotides complementary CXCL12

| Compound ID | position of altered nucleotide in central region | sugar modification of altered nucleotide | in vivo $EC_{50}$ (mg/kg) | ALT (IU/L) at 150 mg/kg | ALT (IU/L) at 50 mg/kg |
|---|---|---|---|---|---|
| 936053 | 2 | 2'-OMe | 4.9 | 49 | 23 |
| 1175782 | 4 | 5'-(S)-Et | 3.7 | 153 | 37 |
| 1175785 | 3 | 5'-(S)-Et | 6.6 | 34 | 24 |
| 1175786 | 4 | 5'-(R)-Et | 3.5 | 33 | 26 |
| 1175787 | 3 | 5'-(R)-Et | 5.8 | 39 | 28 |

Example 3 Effect of Position-Specific 2'-Modifications on In Vitro Activity and In Vivo Liver Toxicity of Modified Oligonucleotides Complementary to Factor XI Modified oligonucleotides were synthesized as indicated in the table below, comprising an altered nucleotide at positions 1-3 of the central region. These modified oligonucleotides were compared to the otherwise identical modified oligonucleotide lacking an altered nucleotide in the central region, a 3-10-3 cEt gapmer, containing three cEt nucleosides in each of the 5' and 3' regions and 10 unmodified DNA nucleosides in the central region. Each internucleoside linkage is a phosphorothioate internucleoside linkage. The compounds in the table below are 100% complementary to the complement of mouse Factor XI, GENBANK NT_039460.6 truncated from 6086000 to 6111000 (SEQ ID NO: 2), at position 11699 to 11714.

TABLE 8

Modified oligonucleotides complementary to Factor XI

| Compound ID | position of altered nucleotide in central region | sugar modification of altered nucleotide | Chemistry Notation (5'-3') | SEQ ID NO |
|---|---|---|---|---|
| 464917 | n/a | n/a | $G_{ks}T_{ks}{}^mC_{ks}T_{ds}G_{ds}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 982033 | 1 | 2'-OMe | $G_{ks}T_{ks}{}^mC_{ks}U_{ms}G_{ds}T_{ds}G_{ds}{}^mC_{ds}A_{ds}T_{ds}{}^mC_{ds}T_{ds}{}^mC_{ds}T_{ks}{}^mC_{ks}{}^mC_k$ | 143 |
| 982034 | 2 | 2'-OMe | $G_{ks}T_{ks}{}^mC_{ks}T_{ds}G_{ms}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 985292 | 2 | 2'-MOE | $G_{ks}T_{ks}{}^mC_{ks}T_{ds}G_{es}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 985293 | 2 | cEt | $G_{ks}T_{ks}{}^mC_{ks}T_{ds}G_{ks}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 1011274 | 2 | 2'-FANA | $G_{ks}T_{ks}{}^mC_{ks}T_{ds}G_{(FANA)s}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 604581 | 2 | 2'-ribo-F | $G_{ks}T_{ks}{}^mC_{ks}T_{ds}G_{fs}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 982035 | 3 | 2'-OMe | $G_{ks}T_{ks}{}^mC_{ks}T_{ds}G_{ds}U_{ms}G_{ds}{}^mC_{ds}A_{ds}T_{ds}{}^mC_{ds}T_{ds}{}^mC_{ds}T_{ks}{}^mC_{ks}{}^mC_k$ | 23 |
| 985294 | 3 | 2'-MOE | $G_{ks}T_{ks}{}^mC_{ks}T_{ds}G_{ds}T_{es}G_{ds}{}^mC_{ds}A_{ds}T_{ds}{}^mC_{ds}T_{ds}{}^mC_{ds}T_{ks}{}^mC_{ks}{}^mC_k$ | 22 |
| 985295 | 3 | cEt | $G_{ks}T_{ks}{}^mC_{ks}T_{ds}G_{ds}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 1011276 | 3 | 2'-FANA | $G_{ks}T_{ks}{}^mC_{ks}T_{ds}G_{ds}U_{(FANA)s}G_{ds}{}^mC_{ds}A_{ds}T_{ds}{}^mC_{ds}T_{ds}{}^mC_{ds}T_{ks}{}^mC_{ks}{}^mC_k$ | 23 |
| 605933 | 3 | 2'-ribo-F | $G_{ks}T_{ks}{}^mC_{ks}T_{ds}G_{ds}U_{fs}G_{ds}{}^mC_{ds}A_{ds}T_{ds}{}^mC_{ds}T_{ds}{}^mC_{ds}T_{ks}{}^mC_{ks}{}^mC_k$ | 23 |

A subscript "d" indicates an unmodified, 2'-β-D-deoxyribosyl sugar moiety.
A subscript "e" indicates a 2'-MOE-β-D-ribofuranosyl sugar moiety.
A subscript "m" indicates a 2'-O-methyl-β-D-ribofuranosyl sugar moiety.
A subscript "k" indicates a cEt.
A subscript "s" indicates a phosphorothioate internucleoside linkage.
A subscript "f" indicates a 2'-F-β-D-2'-deoxyribosyl sugar moiety.
A subscript "(FANA)" indicates a 2'-F-β-D-arabinofiiranosyl modified sugar moiety.
A superscript "m" before a C indicates 5-methyl Cytosine.

Experimental Procedures & Results

For in vitro toxicity studies, 3T3-L1 cells were electroporated with 27, 80, 250, 740, 2, 222, 6, 667, or 20,000 nM of modified oligonucleotide and levels of Raptor were measured by RT-qPCR as in Example 1.

For in vivo toxicity studies, two BALB/C mice per group were administered 100 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 8b

Toxicity of modified oligonucleotides complementary Factor XI

| Compound ID | position of altered nucleotide in central region | sugar modification of altered nucleotide | Raptor IC50 (µM) | ALT at 100 mg/kg (IU/L) |
|---|---|---|---|---|
| 464917 | n/a | n/a | 1.6 | 18751 * |
| 982034 | 2 | 2'-OMe | >20 | 1363 |

TABLE 8b-continued

Toxicity of modified oligonucleotides complementary Factor XI

| Compound ID | position of altered nucleotide in central region | sugar modification of altered nucleotide | Raptor IC50 (µM) | ALT at 100 mg/kg (IU/L) |
|---|---|---|---|---|
| 985292 | 2 | 2'-MOE | 15.5 | 2406 |
| 985293 | 2 | cEt | 9.3 | 15141 |
| 1011274 | 2 | 2'-FANA | 2.3 | death |
| 604581 | 2 | 2'-ribo-F | 6 | 14957 |
| 982035 | 3 | 2'-OMe | 1.8 | 6411 |
| 985294 | 3 | 2'-MOE | 6.2 | 2836 |
| 985295 | 3 | cEt | 5.2 | 3669 |
| 1011276 | 3 | 2'-FANA | >20 | death |
| 605933 | 3 | 2'-ribo-F | 4.6 | 18570 |

* ALT for 464917 is for a 50 mg/kg dose

For the in vitro study reported in the tables below, 3T3-L1 cells were electroporated with 27, 80, 250, 740, 2, 222, 6, 667, or 20,000 nM of modified oligonucleotide and levels of P21 and Gadd45a were measured by RT-qPCR. Levels of Gadd45a were analyzed using primer probe set Mm00432802 ml (ThermoFisher). Levels of P21 were analyzed using primer probe set Mm04207341_ml (ThermoFisher).

TABLE 8c in vitro P21 Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | \multicolumn{7}{c}{Expression level of P21 mRNA (% Control)} | | | | | | |
| 464917 | 108 | 124 | 122 | 169 | 228 | 478 | 749 |
| 982033 | 119 | 120 | 128 | 128 | 218 | 498 | 895 |
| 982034 | 115 | 121 | 110 | 102 | 136 | 266 | 840 |
| 982035 | 162 | 157 | 175 | 206 | 466 | 768 | 661 |

TABLE 8d in vitro Gadd45a Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | \multicolumn{7}{c}{Expression level of Gadd45a mRNA (% Control)} | | | | | | |
| 464917 | 130 | 150 | 115 | 179 | 321 | 632 | 633 |
| 982033 | 120 | 117 | 126 | 203 | 331 | 767 | 798 |
| 982034 | 89 | 111 | 103 | 102 | 173 | 678 | 800 |
| 982035 | 161 | 120 | 140 | 181 | 557 | 779 | 497 |

For the in vitro study reported in the tables below, b.END cells were electroporated with 27, 80, 250, 740, 2, 222, 6, 667, or 20,000 nM of modified oligonucleotide and levels of P21 and Gadd45a were measured by RT-qPCR. Levels of Gadd45a were analyzed using primer probe set Mm00432802 ml (ThermoFisher). Levels of P21 were analyzed using primer probe set Mm04207341_ml (ThermoFisher).

TABLE 8e in vitro P21 Expression in b.END cells

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 464917 | 111 | 115 | 124 | 120 | 139 | 192 | 446 |
| 982033 | 105 | 102 | 107 | 110 | 125 | 171 | 414 |
| 982034 | 106 | 102 | 109 | 112 | 120 | 132 | 208 |
| 982035 | 102 | 97 | 111 | 115 | 129 | 168 | 392 |

TABLE 8f in vitro Gadd45a Expression in b.END cells

| Compound ID | 27 nM | 80 nM | 250 nM | 740 nM | 2,222 nM | 6,667 nM | 20,000 nM |
|---|---|---|---|---|---|---|---|
| | | | Expression level of Gadd45a mRNA (% Control) | | | | |
| 464917 | 101 | 83 | 85 | 87 | 129 | 236 | 380 |
| 982033 | 89 | 76 | 101 | 91 | 177 | 347 | 731 |
| 982034 | 58 | 73 | 86 | 88 | 115 | 202 | 373 |
| 982035 | 68 | 72 | 81 | 103 | 166 | 298 | 620 |

For the in vivo activity study in the tables below, 3 BALB/C mice per group were administered 3.37, 11, 33, or 100 mg/kg doses of modified oligonucleotide, as indicated in the table below, by subcutaneous injection and sacrificed 72 hours later. Liver mRNA was isolated an analyzed by RT-PCR as described in Example 1 above. Expression levels were normalized with Ribogreen® and are expressed relative to PBS-treated control mice.

TABLE 8g

Activity and toxicity of modified oligonucleotides complementary FXI

| Compound ID | position of altered nucleotide in central region | sugar modification of altered nucleotide | ALT (IU/L) at 100 mg/kg | ALT (IU/L) at 33 mg/kg |
|---|---|---|---|---|
| 464917 | n/a | n/a | 11816 | 11682 |
| 982033 | 1 | OMe | 26992 | 3951 |
| 982034 | 2 | OMe | 7954 | 920 |
| 982035 | 3 | OMe | 28994 | 3848 |

TABLE 8h

In Vivo Dose-response of FXI mRNA upon treatment with modified oligonucleotides complementary to FXI

| Compound ID | 3.37 mg/kg | 11 mg/kg | 33 mg/kg | 100 mg/kg |
|---|---|---|---|---|
| | Expression level of FXI mRNA (% Control) | | | |
| 464917 | 47 | 12 | 8.0 | 1.8 |
| 982033 | 53 | 18 | 10 | 5.5 |
| 982034 | 53 | 24 | 9.9 | 3.5 |
| 982035 | 36 | 20 | 11 | 5.3 |

TABLE 8i

In Vivo Dose-response of P21 mRNA upon treatment with modified oligonucleotides complementary to FXI

| Compound ID | 3.37 mg/kg | 11 mg/kg | 33 mg/kg | 100 mg/kg |
|---|---|---|---|---|
| | Expression level of P21 mRNA (% Control) | | | |
| 464917 | 230 | 4143 | 4678 | 5289 |
| 982033 | 122 | 1106 | 2926 | 5653 |
| 982034 | 93 | 297 | 1694 | 4294 |
| 982035 | 418 | 1283 | 4759 | 6960 |

Example 4 Effect of Position-Specific 2' and 5'-Modifications on In Vivo Activity and Liver Toxicity of Modified Oligonucleotides Complementary to Factor XI Modified oligonucleotides were synthesized with 2' or 5' modifications as indicated in the table below. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse Factor XI, the complement of GEN-BANK NT_039460.6 truncated from 6086000 to 6111000 (SEQ ID NO: 2), at position 11699 to 11714.

TABLE 9

Modified oligonucleotides complementary to Factor XI

| Compound ID | position of altered nucleotide in central region | sugar modification of altered nucleotide | Chemistry Notation (5'-3') | SEQ ID NO |
|---|---|---|---|---|
| 464917 | n/a | n/a | $G_{ks}T_{ks}{}^mC_{ks}T_{ds}G_{ds}T_{ds}G_{ds}{}^mC_{ds}A_{ds}T_{ds}{}^mC_{ds}T_{ds}{}^mC_{ds}T_{ks}{}^mC_{ks}{}^mC_{k}$ | 22 |
| 443919 | n/a | n/a | $G_{es}T_{es}{}^mC_{es}T_{ds}G_{ds}T_{ds}G_{ds}{}^mC_{ds}A_{ds}T_{ds}{}^mC_{ds}T_{ds}{}^mC_{ds}T_{es}{}^mC_{es}{}^mC_{e}$ | 22 |
| 465977 | n/a | n/a | $G_{ks}T_{ks}{}^mC_{ks}T_{ds}G_{ds}T_{ds}G_{ds}{}^mC_{ds}A_{ds}T_{ds}{}^mC_{ds}T_{ds}{}^mC_{ds}T_{es}{}^mC_{es}{}^mC_{e}$ | 22 |
| 483706 | n/a | n/a | $G_{es}T_{es}{}^mC_{es}T_{ds}G_{ds}T_{ds}G_{ds}{}^mC_{ds}A_{ds}T_{ds}{}^mC_{ds}T_{ds}{}^mC_{ds}T_{ks}{}^mC_{ks}{}^mC_{k}$ | 22 |
| 1183062 | 2 | 5'-(R)-Me | $G_{ks}T_{ks}{}^mC_{ks}T_{ds}G_{[(R)-\mu]s}T_{ds}G_{ds}{}^mC_{ds}A_{ds}T_{ds}{}^mC_{ds}T_{ds}{}^mC_{ds}T_{ks}{}^mC_{ks}{}^mC_{k}$ | 22 |
| 1183059 | 2 | 5'-(S)-Me | $G_{ks}T_{ks}{}^mC_{ks}T_{ds}G_{[(S)-\mu]s}T_{ds}G_{ds}{}^mC_{ds}A_{ds}T_{ds}{}^mC_{ds}T_{ds}{}^mC_{ds}T_{ks}{}^mC_{ks}{}^mC_{k}$ | 22 |
| 1183065 | 2 | 5'-(R)-allyl | $G_{ks}T_{ks}{}^mC_{ks}T_{ds}G_{[(R)-\gamma]s}T_{ds}G_{ds}{}^mC_{ds}A_{ds}T_{ds}{}^mC_{ds}T_{ds}{}^mC_{ds}T_{ks}{}^mC_{ks}{}^mC_{k}$ | 22 |
| 1183063 | 3 | 5'-(R)-Me | $G_{ks}T_{ks}{}^mC_{ks}T_{ds}G_{ds}T_{[(R)-\mu]s}G_{ds}{}^mC_{ds}A_{ds}T_{ds}{}^mC_{ds}T_{ds}{}^mC_{ds}T_{ks}{}^mC_{ks}{}^mC_{k}$ | 22 |
| 1183060 | 3 | 5'-(S)-Me | $G_{ks}T_{ks}{}^mC_{ks}T_{ds}G_{ds}T_{[(S)-\mu]s}G_{ds}{}^mC_{ds}A_{ds}T_{ds}{}^mC_{ds}T_{ds}{}^mC_{ds}T_{ks}{}^mC_{ks}{}^mC_{k}$ | 22 |
| 1183066 | 3 | 5'-(R)-allyl | $G_{ks}T_{ks}{}^mC_{ks}T_{ds}G_{ds}T_{[(R)-\gamma]s}G_{ds}{}^mC_{ds}A_{ds}T_{ds}{}^mC_{ds}T_{ds}{}^mC_{ds}T_{ks}{}^mC_{ks}{}^mC_{k}$ | 22 |
| 1183064 | 4 | 5'-(R)-Me | $G_{ks}T_{ks}{}^mC_{ks}T_{ds}G_{ds}T_{ds}G_{[(R)-\mu]s}{}^mC_{ds}A_{ds}T_{ds}{}^mC_{ds}T_{ds}{}^mC_{ds}T_{ks}{}^mC_{ks}{}^mC_{k}$ | 22 |
| 1183061 | 4 | 5'-(S)-Me | $G_{ks}T_{ks}{}^mC_{ks}T_{ds}G_{ds}T_{ds}G_{[(S)-\mu]s}{}^mC_{ds}A_{ds}T_{ds}{}^mC_{ds}T_{ds}{}^mC_{ds}T_{ks}{}^mC_{ks}{}^mC_{k}$ | 22 |
| 1183067 | 4 | 5'-(R)-allyl | $G_{ks}T_{ks}{}^mC_{ks}T_{ds}G_{ds}T_{ds}G_{[(R)-\gamma]s}{}^mC_{ds}A_{ds}T_{ds}{}^mC_{ds}T_{ds}{}^mC_{ds}T_{ks}{}^mC_{ks}{}^mC_{k}$ | 22 |

A subscript "d" indicates an unmodified, 2'-β-D-deoxyribosyl sugar moiety.
A subscript "k" indicates a cEt.
A subscript "s" indicates a phosphorothioate internucleoside linkage.
A subscript "μ" indicates a 5'-(R,S)-Me-β-D-2'-deoxyribosyl sugar moiety.
A subscript "[(R)-μ]" indicates a 5'-(R)-Me-β-D-2'-deoxyribosyl sugar moiety.
A subscript "[(S)-μ]" indicates a 5'-(S)-Me-β-D-2'-deoxyribosyl sugar moiety.
A subscript "γ" indicates a 5'-(R,S)-allyl-β-D-2'-deoxyribosyl sugar moiety.
A subscript "[(R)-γ]" indicates a 5'-(R)-allyl-P-β-2'-deoxyribosyl sugar moiety.
A subscript "[(S)-γ]" indicates a 5'-(S)-allyl-β-D-2'-deoxyribosyl sugar moiety.
A subscript "ε" indicates a 5'-(R,S)-ethyl-β-D-2'-deoxyribosyl sugar moiety.
A subscript "[(R)-ε]" indicates a 5'-(R)-ethyl-β-D-2'-deoxyribosyl sugar moiety.
A subscript "[(S)-ε]" indicates a 5'-(S)-ethyl-β-D-2'-deoxyribosyl sugar moiety.

Experimental Procedures & Results

For the in vivo activity and toxicity study below, two BALB/C mice per group were administered 33 or 100 mg/kg modified oligonucleotide by subcutaneous injection and sacrificed 72 hours later. Expression levels of FXI were measured by RT-qPCR using primer probe set RTS2898 (forward sequence: ACATGACAGGCGCGATCTCT, SEQ ID NO: 78; reverse sequence: TCTAGGTTCACGTACA-CATCTTTGC, SEQ ID NO: 79; probe sequence: TTCCTT-CAAGCAATGCCCTCAGCAAT, SEQ ID NO: 80). Plasma levels of ALT were measured using an automated clinical chemistry analyzer. Increased ALT is indicative of acute liver toxicity.

TABLE 10

Toxicity and activity of modified oligonucleotides complementary Factor XI

| Compound ID | position of altered nucleotide in central region | sugar modification of altered nucleotide | FXI mRNA (% control) 33 mg/kg | FXI mRNA (% control) 100 mg/kg | ALT (IU/L) at 33 mg/kg | ALT (IU/L) at 100 mg/kg |
|---|---|---|---|---|---|---|
| 464917 | n/a | n/a | 11 | 0.9 | 7511 | 31066* |
| 443919 | n/a | n/a | 27 | 7.9 | 24 | 57 |
| 465977 | n/a | n/a | 5.6 | n.d. | 11575 | death |
| 483706 | n/a | n/a | 20.3 | 4.9 | 52 | 732 |
| 1183062 | 2 | 5'-(R)-Me | 5.7 | n.d. | 12083 | death |
| 1183059 | 2 | 5'-(S)-Me | 4.0 | 2.4 | 662 | 7894 |
| 1183065 | 2 | 5'-(R)-allyl | 5.2 | 1.5 | 4707 | 24000 |
| 1183063 | 3 | 5'-(R)-Me | 4.9 | 2.0 | 2458 | 14891 |
| 1183060 | 3 | 5'-(S)-Me | 8.2 | 2.1 | 8710 | 23995 |
| 1183066 | 3 | 5'-(R)-allyl | 5.1 | 2.0 | 524 | 6473 |

TABLE 10-continued

Toxicity and activity of modified oligonucleotides complementary Factor XI

| Compound ID | position of altered nucleotide in central region | sugar modification of altered nucleotide | FXI mRNA (% control) 33 mg/kg | FXI mRNA (% control) 100 mg/kg | ALT (IU/L) at 33 mg/kg | ALT (IU/L) at 100 mg/kg |
|---|---|---|---|---|---|---|
| 1183064 | 4 | 5'-(R)-Me | 4.0 | 1.5 | 4357 | 11342 |
| 1183061 | 4 | 5'-(S)-Me | 4.1 | 2.3 | 1891 | 20557 |
| 1183067 | 4 | 5'-(R)-allyl | 11 | 3.6 | 184 | 2536 |

*One of two mice died

For the in vitro study reported in the tables below, 3T3-L1 cells were electroporated with 27 nM, 80 nM, 250 nM, 740 nM, 2,222 nM, 6,667 nM, or 20,000 nM of modified oligonucleotide and levels of P21 and Gadd45a were measured by RT-qPCR as described in Example 1 above. Caspase-3 and caspase-7 activation was measured using the Caspase-Glo® 3/7 Assay System (G8090, Promega). Levels of caspase activation correlate with apoptotic cell death.

TABLE 10b in vitro P21 Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 464917 | 100 | 100 | 116 | 139 | 216 | 496 | 1232 |
| 443919 | 122 | 116 | 99 | 86 | 114 | 105 | 184 |
| 465977 | 104 | 117 | 103 | 106 | 139 | 220 | 578 |
| 483706 | 105 | 92 | 116 | 125 | 135 | 165 | 376 |

TABLE 10c in vitro Gadd45a Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | Expression level of Gadd45a mRNA (% Control) | | | | |
| 464917 | 89 | 93 | 106 | 113 | 157 | 324 | 599 |
| 443919 | 163 | 166 | 147 | 129 | 145 | 126 | 178 |
| 465977 | 101 | 110 | 119 | 100 | 135 | 150 | 334 |
| 483706 | 89 | 133 | 185 | 194 | 197 | 217 | 459 |

TABLE 10d in vitro Caspase Activation in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | Caspase Activation | | | | |
| 464917 | 4388 | 4428 | 4656 | 6208 | 20274 | 48106 | 82324 |
| 443919 | 4200 | 4802 | 4986 | 4605 | 4714 | 4552 | 9385 |
| 465977 | 4017 | 4133 | 4253 | 4465 | 6983 | 34156 | 61008 |
| 483706 | 4155 | 4595 | 4020 | 4476 | 4585 | 6565 | 16766 |

For the in vivo study in the table below, three BALB/C mice per group were administered 11 or 33 mg/kg of modified oligonucleotide and sacrificed after 72 hours.

TABLE 10e in vivo Activity and toxicity of modified oligonucleotides complementary FXI

| Compound ID | 2' sugar modification of nucleosides in 5' region | 2' sugar modification of nucleosides in 3' region | P21 mRNA @ 33 mg/kg (% control) | Tnfrsf10b mRNA @ 33 mg/kg (% control) | FXI mRNA @ 33 mg/kg (% control) | ALT@33 mg/kg |
|---|---|---|---|---|---|---|
| 464917 | kkk | kkk | 24040 | 108884 | 1.4 | 18316 |
| 443919 | kkk | eee | 109 | 110 | 16 | 68 |
| 465977 | eee | kkk | n.d. | n.d. | n.d. | death |
| 483706 | eee | eee | 1195 | 733 | 2.7 | 1424 |

Example 5 Effect of Position-Specific 2'-Modifications on In Vitro Activity and In Vivo Liver Toxicity of Modified Oligonucleotides Complementary to PTEN Modified oligonucleotides were synthesized with 2' modifications as indicated in the table below. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse PTEN, GENBANK NC_000085.6, truncated from 32755001 to 32829000 (SEQ ID NO: 3), at position 2635 to 2650.

TABLE 11

Modified oligonucleotides complementary to PTEN

| Compound ID | position of altered nucleotide in central region | sugar modification of altered nucleotide | Chemistry Notation (5'-3') | SEQ ID NO |
|---|---|---|---|---|
| 482050 | n/a | n/a | $A_{ks}T_{ks}{}^mC_{ks}A_{ds}T_{ds}G_{ds}G_{ds}{}^mC_{ds}T_{ds}G_{ds}{}^mC_{ds}A_{ds}G_{ds}{}^mC_{ks}T_{ks}T_k$ | 24 |
| 982036 | 1 | 2'-OMe | $A_{ks}T_{ks}{}^mC_{ks}A_{ms}T_{ds}G_{ds}G_{ds}{}^mC_{ds}T_{ds}G_{ds}{}^mC_{ds}A_{ds}G_{ds}{}^mC_{ks}T_{ks}T_k$ | 24 |
| 982037 | 2 | 2'-OMe | $A_{ks}T_{ks}{}^mC_{ks}A_{ds}U_{ms}G_{ds}G_{ds}{}^mC_{ds}T_{ds}G_{ds}{}^mC_{ds}A_{ds}G_{ds}{}^mC_{ks}T_{ks}T_k$ | 25 |
| 985297 | 2 | 2'-MOE | $A_{ks}T_{ks}{}^mC_{ks}A_{ds}T_{eS}G_{ds}G_{ds}{}^mC_{ds}T_{ds}G_{ds}{}^mC_{ds}A_{ds}G_{ds}{}^mC_{ks}T_{ks}T_k$ | 24 |
| 985298 | 2 | cEt | $A_{ks}T_{ks}{}^mC_{ks}A_{ds}T_{ks}G_{ds}G_{ds}{}^mC_{ds}T_{ds}G_{ds}{}^mC_{ds}A_{ds}G_{ds}{}^mC_{ks}T_{ks}T_k$ | 24 |
| 1011277 | 2 | 2'-FANA | $A_{ks}T_{ks}{}^mC_{ks}A_{ds}U_{(FANA)s}G_{ds}G_{ds}{}^mC_{ds}T_{ds}G_{ds}{}^mC_{ds}A_{ds}G_{ds}{}^mC_{ks}T_{ks}T_k$ | 25 |
| 985296 | 2 | 2'-ribo-F | $A_{ks}T_{ks}{}^mC_{ks}A_{ds}U_{fs}G_{ds}G_{ds}{}^mC_{ds}T_{ds}G_{ds}{}^mC_{ds}A_{ds}G_{ds}{}^mC_{ks}T_{ks}T_k$ | 25 |
| 982038 | 3 | 2'-OMe | $A_{ks}T_{ks}{}^mC_{ks}A_{ds}T_{ds}G_{ms}G_{ds}{}^mC_{ds}T_{ds}G_{ds}{}^mC_{ds}A_{ds}G_{ds}{}^mC_{ks}T_{ks}T_k$ | 24 |
| 985301 | 3 | 2'-MOE | $A_{ks}T_{ks}{}^mC_{ks}A_{ds}T_{ds}G_{es}G_{ds}{}^mC_{ds}T_{ds}G_{ds}{}^mC_{ds}A_{ds}G_{ds}{}^mC_{ks}T_{ks}T_k$ | 24 |
| 985302 | 3 | cEt | $A_{ks}T_{ks}{}^mC_{ks}A_{ds}T_{ds}G_{ks}G_{ds}{}^mC_{ds}T_{ds}G_{ds}{}^mC_{ds}A_{ds}G_{ds}{}^mC_{ks}T_{ks}T_k$ | 24 |
| 1011278 | 3 | 2'-FANA | $A_{ks}T_{ks}{}^mC_{ks}A_{ds}T_{ds}G_{(FANA)s}G_{ds}{}^mC_{ds}T_{ds}G_{ds}{}^mC_{ds}A_{ds}G_{ds}{}^mC_{ks}T_{ks}T_k$ | 24 |
| 985300 | 3 | 2'-ribo-F | $A_{ks}T_{ks}{}^mC_{ks}A_{ds}T_{ds}G_{fs}G_{ds}{}^mC_{ds}T_{ds}G_{ds}{}^mC_{ds}A_{ds}G_{ds}{}^mC_{ks}T_{ks}T_k$ | 24 |

A subscript "d" indicates an unmodified, 2'-β-D-deoxyribosyl sugar moiety.
A subscript "e" indicates a 2'-MOE-β-D-ribofuranosyl sugar moiety.
A subscript "m" indicates a 2'-O-methyl-β-D-ribofiiranosyl sugar moiety.
A subscript "k" indicates a cEt.
A subscript "s" indicates a phosphorothioate internucleoside linkage.
A subscript "f" indicates a 2'-F-β-D-2'-deoxyribosyl sugar moiety.
A subscript "(FANA)" indicates a 2'-F-β-D-arabinofuranosyl modified sugar moiety.
A superscript "m" before a C indicates 5-methyl Cytosine.

For in vitro activity studies, 3T3-L1 cells were plated and transfected with 16, 80, 400, 2,000, and 10,000 nM modified oligonucleotide by electroporation. mRNA was harvested and analyzed by RT-qPCR. PTEN mRNA was detected and RAPTOR mRNA was detected.

For in vivo toxicity studies, 2-4 BALB/C mice per group were administered 200 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 12

Activity and toxicity of modified oligonucleotides complementary PTEN

| Compound ID | position of altered nucleotide in central region | sugar modification of altered nucleotide | PTEN $IC_{50}$ (µM) | RAPTOR $IC_{50}$ (µM) | ALT @ 200 mg/kg (IU/L) |
|---|---|---|---|---|---|
| 482050 | n/a | n/a | 3.9 | 2.4 | 2458 |
| 982037 | 2 | 2'-OMe | 2.7 | 10 | 133 |
| 985297 | 2 | 2'-MOE | 3 | 9.4 | 242 |
| 985298 | 2 | cEt | 1.4 | 2.1 | 890 |
| 1011277 | 2 | 2'-FANA | 3.1 | 3.5 | 1488 |
| 985296 | 2 | 2'-ribo-F | 2.2 | 6 | 1884 |
| 982038 | 3 | 2'-OMe | 1.8 | 3.7 | 327 |
| 985301 | 3 | 2'-MOE | 1.5 | 5 | 261 |
| 985302 | 3 | cEt | 2 | 3.3 | 87 |
| 1011278 | 3 | 2'-FANA | 1.7 | 1.1 | 14073 |
| 985300 | 3 | 2'-ribo-F | 2.2 | 6 | 107 |

For the in vitro study reported in the tables below, 3T3-L1 cells were transfected with 27, 80, 250, 740, 2, 222, 6, 667, or 20,000 nM of modified oligonucleotide by electroporation and levels of P21 and Gadd45a were measured by RT-qPCR as described in example 1.

TABLE 12b in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 482050 | 111 | 107 | 113 | 124 | 113 | 130 | 157 |
| 982036 | 92 | 95 | 93 | 95 | 91 | 110 | 162 |
| 982037 | 112 | 108 | 99 | 105 | 112 | 120 | 113 |
| 982038 | 108 | 105 | 111 | 111 | 114 | 99 | 108 |

TABLE 12c in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 482050 | 65 | 64 | 70 | 67 | 79 | 176 | 276 |
| 982036 | 81 | 62 | 62 | 71 | 113 | 189 | 467 |
| 982037 | 107 | 90 | 79 | 75 | 79 | 100 | 165 |
| 982038 | 110 | 112 | 104 | 131 | 118 | 129 | 266 |

Example 6 Effect of Position-Specific 2'-Modifications on In Vitro Activity and In Vivo Liver Toxicity of Modified Oligonucleotides Complementary to SOD1

Modified oligonucleotides were synthesized with 2' modifications as indicated in the table below. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse SOD1, GENBANK NT_039625.7 truncated from 24924000 to 24933000 (SEQ ID NO: 4), at position 5685 to 5880.

TABLE 13

Modified oligonucleotides complementary to SOD1

| Compound ID | position of altered nucleotide in central region | sugar modification of altered nucleotide | Chemistry Notation (5'-3') | SEQ ID NO |
|---|---|---|---|---|
| 508031 | n/a | n/a | $T_{ks}G_{ks}A_{ks}G_{ds}G_{ds}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 508034 | n/a | n/a | $T_{ks}G_{ks}A_{ks}G_{ds}G_{ds}T_{ds}{}^mC_{ds}{}^mC_{ds}T_{ds}G_{ds}{}^mC_{ds}A_{ds}{}^mC_{ds}T_{es}G_{es}G_{e}$ | 26 |
| 508037 | n/a | n/a | $T_{es}G_{es}A_{es}G_{ds}G_{ds}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 529933 | n/a | n/a | $T_{es}G_{es}A_{es}G_{ds}G_{ds}T_{ds}{}^mC_{ds}{}^mC_{ds}T_{ds}G_{ds}{}^mC_{ds}A_{ds}{}^mC_{ds}T_{es}G_{es}G_{e}$ | 26 |
| 895154 | 1 | 2'-OMe | $T_{ks}G_{ks}A_{ks}G_{ms}G_{ds}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 895155 | 2 | 2'-OMe | $T_{ks}G_{ks}A_{ks}G_{ds}G_{ms}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 985305 | 2 | 2'-MOE | $T_{ks}G_{ks}A_{ks}G_{ds}G_{es}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 985306 | 2 | cEt | $T_{ks}G_{ks}A_{ks}G_{ds}G_{ks}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 1011279 | 2 | 2'-FANA | $T_{ks}G_{ks}A_{ks}G_{ds}G_{(FANA)s}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 985304 | 2 | 2'-ribo-F | $T_{ks}G_{ks}A_{ks}G_{ds}G_{fs}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 895156 | 3 | 2'-OMe | $T_{ks}G_{ks}A_{ks}G_{ds}G_{ds}U_{ms}{}^mC_{ds}{}^mC_{ds}T_{ds}G_{ds}{}^mC_{ds}A_{ds}{}^mC_{ds}T_{ks}G_{ks}G_{k}$ | 27 |
| 985309 | 3 | 2'-MOE | $T_{ks}G_{ks}A_{ks}G_{ds}G_{ds}T_{es}{}^mC_{ds}{}^mC_{ds}T_{ds}G_{ds}{}^mC_{ds}A_{ds}{}^mC_{ds}T_{ks}G_{ks}G_{k}$ | 26 |
| 985310 | 3 | cEt | $T_{ks}G_{ks}A_{ks}G_{ds}G_{ds}T_{ks}{}^mC_{ds}{}^mC_{ds}T_{ds}G_{ds}{}^mC_{ds}A_{ds}{}^mC_{ds}T_{ks}G_{ks}G_{k}$ | 26 |
| 1011280 | 3 | 2'-FANA | $T_{ks}G_{ks}A_{ks}G_{ds}G_{ds}U_{(FANA)s}{}^mC_{ds}{}^mC_{ds}T_{ds}G_{ds}{}^mC_{ds}A_{ds}{}^mC_{ds}T_{ks}G_{ks}G_{k}$ | 27 |
| 985308 | 3 | 2'-ribo-F | $T_{ks}G_{ks}A_{ks}G_{ds}G_{ds}U_{fs}{}^mC_{ds}{}^mC_{ds}T_{ds}G_{ds}{}^mC_{ds}A_{ds}{}^mC_{ds}T_{ks}G_{ks}G_{k}$ | 27 |

A subscript "d" indicates an unmodified, 2'-β-D-deoxyribosyl sugar moiety.
A subscript "e" indicates a 2'-MOE-β-D-ribofuranosyl sugar moiety.
A subscript "m" indicates a 2'-O-methyl-β-D-ribofuranosyl sugar moiety.
A subscript "k" indicates a cEt.
A subscript "s" indicates a phosphorothioate internucleoside linkage.
A subscript "f" indicates a 2'-F-β-D-2'-deoxyribosyl sugar moiety.
A subscript "(FANA)" indicates a 2'-F-β-D-arabinofuranosyl modified sugar moiety.
A superscript "m" before a C indicates 5-methyl Cytosine.

For in vitro activity studies, 3T3-L1 cells were plated at 20,000 cells/well and transfected with 16, 80, 400, 2,000, and 10,000 nM modified oligonucleotide by electroporation. mRNA was harvested and analyzed by RT-qPCR. SOD1 mRNA was detected using primer probe set RTS3025 (forward sequence: TTTTTTGCGCGGTCCTTTC (SEQ ID NO: 119); reverse sequence: GAGGGACCAGAGAGAGCAAGAC (SEQ ID NO: 120); probe sequence: CGCCTTCCGTCCGTCGGCT (SEQ ID NO:121)) and RAPTOR mRNA was detected as in Example 1 above.

For the in vivo toxicity study in the table below, two BALB/C mice per modified oligonucleotide were administered 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 14

Activity and toxicity of modified oligonucleotides complementary SOD1

| Compound ID | position of altered nucleotide in central region | sugar modification of altered nucleotide | SOD1 IC$_{50}$ (μM) | RAPTOR IC$_{50}$ (μM) | ALT @ 150 mg/kg (IU/L) |
|---|---|---|---|---|---|
| 508031 | n/a | n/a | 0.03 | 0.46 | 21934 |
| 895155 | 2 | 2'-OMe | 0.04 | 1 | 112 |
| 985305 | 2 | 2'-MOE | 0.21 | n/a | 63 |
| 985306 | 2 | cEt | 1.61 | 10.2 | 826 |
| 1011279 | 2 | 2'-FANA | 0.28 | 1 | death |
| 985304 | 2 | 2'-ribo-F | 0.04 | 0.8 | 182 |
| 895156 | 3 | 2'-OMe | 0.48 | 4.5 | 1371 |
| 985309 | 3 | 2'-MOE | 0.61 | 6 | 1629 |
| 985310 | 3 | cEt | 1.46 | 11.9 | 178 |
| 1011280 | 3 | 2'-FANA | 0.6 | 4 | death |
| 985308 | 3 | 2'-ribo-F | 0.24 | 0.92 | 887 |

For in vitro activity studies, 3T3-L1 cells were plated at 20,000 cells/well and transfected with 30 nM, 80 nM, 250 nM, 740 nM, 2,222 nM, 6,667 nM, or 20,000 nM modified oligonucleotide by electroporation. P21 and Gadd45a mRNA were analyzed as in Example 1 above and caspase activation was measured as in Example 4 above. Results were normalized with Ribogreen® and are presented relative to the average of untreated control cells.

TABLE 14b in vitro P21 Expression

| Compound ID | 30 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 508031 | 104 | 96 | 104 | 91 | 99 | 180 | 366 |
| 895154 | 94 | 117 | 85 | 93 | 105 | 159 | 181 |
| 895155 | 98 | 110 | 92 | 88 | 88 | 101 | 137 |
| 895156 | 95 | 104 | 74 | 97 | 125 | 139 | 283 |

TABLE 14c in vitro Gadd45a Expression

| Compound ID | 30 nM | 80 nM | 250 nM | 740 nM | 2,222 nM | 6,667 nM | 20,000 nM |
|---|---|---|---|---|---|---|---|
| | | | Expression level of Gadd45a mRNA (% Control) | | | | |
| 508031 | 103 | 99 | 113 | 103 | 139 | 564 | 844 |
| 895154 | 110 | 125 | 114 | 106 | 130 | 297 | 669 |
| 895155 | 129 | 139 | 120 | 126 | 122 | 145 | 340 |
| 895156 | 122 | 132 | 94 | 125 | 223 | 490 | 856 |

TABLE 14d in vitro Caspase Activation in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | Caspase Activation | | | | |
| 508031 | 10871 | 11667 | 12107 | 14458 | 46619 | 101512 | 177873 |
| 895154 | 11681 | 11503 | 11656 | 11422 | 17167 | 70398 | 124774 |
| 895155 | 11669 | 11005 | 11479 | 11156 | 12487 | 20199 | 77630 |
| 895156 | 11980 | 10646 | 10616 | 11178 | 24226 | 72844 | 153302 |

For the in vivo toxicity study in the table below, three BALB/C mice per modified oligonucleotide were administered 100 mg/kg modified oligonucleotide by subcutaneous injection and sacrificed 72 hours later. One animal was administered an injection of saline as a control. Plasma levels of ALT and AST were measured using an automated clinical chemistry analyzer. Increased ALT and AST are indicative of acute liver toxicity.

For the in vivo study in the table below, three BALB/C mice per group were administered 33 or 100 mg/kg of modified oligonucleotide and sacrificed after 24 hours.

TABLE 15

Activity and toxicity of modified oligonucleotides complementary SOD1

| Compound ID | position of altered nucleotide in central region | sugar modification of altered nucleotide | P21 mRNA @ 100 mg/kg (% control) | Tnfrsf10b mRNA @ 100 mg/kg (% control) | Gadd45a mRNA @ 100 mg/kg (% control) | SOD1 mRNA @ 100 mg/kg (% control) |
|---|---|---|---|---|---|---|
| 508031 | n/a | n/a | 823 | 399 | 321 | 36 |
| 895154 | 1 | 2'-OMe | 125 | 176 | 345 | 56 |
| 895155 | 2 | 2'-OMe | 67 | 147 | 365 | 75 |
| 895156 | 3 | 2'-OMe | 538 | 351 | 525 | 51 |

For the in vivo study in the table below, three BALB/C mice per group were administered 33 or 100 mg/kg of modified oligonucleotide and sacrificed after 72 hours.

TABLE 15b

Activity and toxicity of modified oligonucleotides complementary SOD1

| Compound ID | position of altered nucleotide in central region | sugar modification of altered nucleotide | P21 mRNA @ 100 mg/kg (% control) | Tnfrsf10b mRNA @ 100 mg/kg (% control) | Gadd45a mRNA @ 100 mg/kg (% control) | SOD1 mRNA @ 100 mg/kg (% control) | ALT @ 100 mg/kg (IU/L) |
|---|---|---|---|---|---|---|---|
| 508031 | n/a | n/a | 6007 | 9032 | 392 | 13 | 16,317 |
| 895154 | 1 | 2'-OMe | 561 | 1042 | 129 | 19 | 206 |
| 895155 | 2 | 2'-OMe | 165 | 233 | 18 | 26 | 41 |
| 895156 | 3 | 2'-OMe | 3218 | 8189 | 190 | 9.6 | 1,242 |

TABLE 15c

Activity and toxicity of modified oligonucleotides complementary to SOD1

| Compound ID | 2' sugar modification in 5' region | 2' sugar modification in 3' region | P21 mRNA @ 100 mg/kg (% control) | Tnfrsf10b mRNA @ 100 mg/kg (% control) | SOD1 mRNA @ 100 mg/kg (% control) | ALT @ 100 mg/kg (IU/L) |
|---|---|---|---|---|---|---|
| 508031 | kkk | kkk | 3478 | 4593 | 9 | 14526 |
| 508034 | kkk | eee | 11365 | 7288 | 3 | 22396* |
| 508037 | eee | kkk | 130 | 225 | 17 | 20 |
| 529933 | eee | eee | 90 | 142 | 18 | 11 |

*2/3 animals were found dead

For the in vitro study reported in the tables below, 3T3-L1 cells were electroporated with 27 nM, 80 nM, 250 nM, 740 nM, 2, 222 nM, 6,667 nM, or 20,000 nM of modified oligonucleotide and levels of P21 and Gadd45a were measured by RT-qPCR as described in Example 1 above. Caspase-3 and caspase-7 activation was measured using the Caspase-Glo® 3/7 Assay System (G8090, Promega). Levels of caspase activation correlate with apoptotic cell death.

TABLE 15d in vitro Caspase Activation in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | | Caspase Activation | | | |
| 508031 | 5969 | 6550 | 5986 | 8376 | 22499 | 56695 | 91450 |
| 508034 | 5652 | 5258 | 6555 | 7590 | 17098 | 49473 | 73813 |
| 508037 | 4027 | 4000 | 4222 | 4104 | 4208 | 3899 | 7869 |
| 529933 | 5904 | 5393 | 5595 | 5677 | 4772 | 4914 | 11918 |

TABLE 15e in vitro P21 mRNA in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 508031 | 132 | 116 | 119 | 108 | 121 | 185 | 692 |
| 508034 | 119 | 115 | 120 | 117 | 125 | 174 | 344 |
| 508037 | 120 | 119 | 121 | 121 | 117 | 122 | 149 |
| 529933 | 106 | 110 | 101 | 120 | 108 | 108 | 100 |

TABLE 15f in vitro Gadd45a mRNA in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | Expression level of Gadd45a mRNA (% Control) | | | | |
| 508031 | 202 | 132 | 198 | 137 | 215 | 570 | 1046 |
| 508034 | 132 | 132 | 167 | 161 | 185 | 475 | 842 |
| 508037 | 175 | 164 | 181 | 175 | 195 | 215 | 416 |
| 529933 | 136 | 136 | 148 | 167 | 169 | 130 | 155 |

For the in vivo dose-response study in the table below, three BALB/C mice per group were administered 3.7, 11.1, 33, or 100 mg/kg 508031 or 3.7, 11.1, 33, 100, or 300 mg/kg 895155 by subcutaneous injection and sacrificed. Levels of Gadd45a, P21, and Tnfrsf1b mRNA were measured by RT-PCR as described in Example 1.

TABLE 15g

Activity and toxicity of modified oligonucleotides complementary to SOD1

| Compound ID | position of altered nucleotide in central region | sugar modification of altered nucleotide | ED$_{50}$ (mg/kg) |
|---|---|---|---|
| 508031 | n/a | n/a | 13.12 |
| 895155 | 2 | 2'-OMe | 38.8 |

TABLE 15h

In Vivo Dose-response of Tnfrsf10b mRNA upon treatment with modified oligonucleotides complementary to SOD1

| Compound ID | 3.7 mg/kg | 11.1 mg/kg | 33 mg/kg | 100 mg/kg | 300 mg/kg |
|---|---|---|---|---|---|
| | Expression level of Tnfrsf10b mRNA (% Control) | | | | |
| 508031 | 99 | 276 | 3443 | 6446 | n/a |
| 895155 | 81 | 105 | 115 | 193 | 2215 |

TABLE 15i

In Vivo Dose-response of P21 mRNA upon treatment with modified oligonucleotides complementary to SOD1

| Compound ID | 3.7 mg/kg | 11.1 mg/kg | 33 mg/kg | 100 mg/kg | 300 mg/kg |
|---|---|---|---|---|---|
| | Expression level of P21 mRNA (% Control) | | | | |
| 508031 | 163 | 222 | 1867 | 3788 | n/a |
| 895155 | 162 | 167 | 167 | 199 | 1467 |

Example 7 Effect of Position-Specific 2'-Modifications on In Vitro Activity and In Vivo Liver Toxicity of Modified Oligonucleotides Complementary to SRB1

Modified oligonucleotides were synthesized with 2' modifications as indicated in the table below. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleosides in the central region. Each internucleoside linkage is a phosphorothioate. The compounds in the table below are 100% complementary to the complement of mouse SRB1, GENBANK NT_039313.7 truncated from 566000 to 632000 (SEQ ID NO: 5), at position 64840 to 64855.

TABLE 16

Modified oligonucleotides complementary to SRB1

| Compound ID | position of altered nucleotide in central region | sugar modification of altered nucleotide | Chemistry Notation (5'-3') | SEQ ID NO |
|---|---|---|---|---|
| 449093 | n/a | n/a | $T_{ks}T_{ks}{}^mC_{ks}A_{ds}G_{ds}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 982030 | 1 | 2'-OMe | $T_{ks}T_{ks}{}^mC_{ks}A_{ms}G_{ds}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 982031 | 2 | 2'-OMe | $T_{ks}T_{ks}{}^mC_{ks}A_{ds}G_{ms}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 1042573 | 2 | 2'-MOE | $T_{ks}T_{ks}{}^mC_{ks}A_{ds}G_{es}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 1042574 | 2 | cEt | $T_{ks}T_{ks}{}^mC_{ks}A_{ds}G_{ks}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 1042575 | 2 | 2'-FANA | $T_{ks}T_{ks}{}^mC_{ks}A_{ds}G_{(FANA)s}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 1042572 | 2 | 2'-ribo-F | $T_{ks}T_{ks}{}^mC_{ks}A_{ds}G_{fs}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 982032 | 3 | 2'-OMe | $T_{ks}T_{ks}{}^mC_{ks}A_{ds}G_{ds}U_{ms}{}^mC_{ds}A_{ds}T_{ds}G_{ds}A_{ds}{}^mC_{ds}T_{ds}T_{ks}{}^mC_{ks}{}^mC_k$ | 29 |
| 1042577 | 3 | 2'-MOE | $T_{ks}T_{ks}{}^mC_{ks}A_{ds}G_{ds}T_{es}{}^mC_{ds}A_{ds}T_{ds}G_{ds}A_{ds}{}^mC_{ds}T_{ds}T_{ks}{}^mC_{ks}{}^mC_k$ | 28 |
| 1042578 | 3 | cEt | $T_{ks}T_{ks}{}^mC_{ks}A_{ds}G_{ds}T_{ks}{}^mC_{ds}A_{ds}T_{ds}G_{ds}A_{ds}{}^mC_{ds}T_{ds}T_{ks}{}^mC_{ks}{}^mC_k$ | 28 |
| 1042580 | 3 | 2'-FANA | $T_{ks}T_{ks}{}^mC_{ks}A_{ds}G_{ds}U_{(FANA)s}{}^mC_{ds}A_{ds}T_{ds}G_{ds}A_{ds}{}^mC_{ds}T_{ds}T_{ks}{}^mC_{ks}{}^mC_k$ | 29 |
| 1042576 | 3 | 2'-ribo-F | $T_{ks}T_{ks}{}^mC_{ks}A_{ds}G_{ds}U_{fs}{}^mC_{ds}A_{ds}T_{ds}G_{ds}A_{ds}{}^mC_{ds}T_{ds}T_{ks}{}^mC_{ks}{}^mC_k$ | 29 |

A subscript "d" indicates an unmodified, 2'-β-D-deoxyribosyl sugar moiety.
A subscript "e" indicates a 2'-MOE-β-D-ribofuranosyl sugar moiety.
A subscript "m" indicates a 2'-O-methyl-β-D-ribofuranosyl sugar moiety.
A subscript "k" indicates a cEt.
A subscript "s" indicates a phosphorothioate internucleoside linkage.
A subscript "f" indicates a 2'-F-β-D-2'-deoxyribosyl sugar moiety.
A subscript "(FANA)" indicates a 2'-F-β-D-arabinofuranosyl modified sugar moiety.
A superscript "m" before a C indicates 5-methyl Cytosine.

For in vivo toxicity studies, two BALB/C mice per modified oligonucleotide was administered 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 17

Toxicity of modified oligonucleotides complementary SRB1

| Compound ID | position of altered nucleotide in central region | sugar modification of altered nucleotide | ALT @ 150 mg/kg (IU/L) |
|---|---|---|---|
| 449093 | n/a | n/a | 2009 |
| 982031 | 2 | 2'-OMe | 2168 |
| 1042573 | 2 | 2'-MOE | 3368 |
| 1042574 | 2 | cEt | 1972 |
| 1042575 | 2 | 2'-FANA | 16335 |
| 1042572 | 2 | 2'-ribo-F | 3563 |
| 982032 | 3 | 2'-OMe | 1630 |
| 1042577 | 3 | 2'-MOE | 2965 |
| 1042578 | 3 | cEt | 3650 |
| 1042580 | 3 | 2'-FANA | 6622 |
| 1042576 | 3 | 2'-ribo-F | 3521 |

For the in vitro study reported in the tables below, 3T3-L1 cells were transfected with 27, 80, 250, 740, 2, 222, 6, 667, or 20,000 nM of modified oligonucleotide by electroporation and levels of P21 and Gadd45a were measured by RT-qPCR as described in example 1.

TABLE 17b in vitro P21 Expression

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 449093 | 99 | 107 | 101 | 104 | 175 | 212 | 255 |
| 982030 | 102 | 100 | 108 | 125 | 172 | 215 | 288 |
| 982031 | 115 | 116 | 114 | 137 | 174 | 204 | 330 |
| 982032 | 107 | 97 | 106 | 112 | 134 | 183 | 224 |

TABLE 17c in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 449093 | 124 | 105 | 120 | 105 | 122 | 215 | 350 |
| 982030 | 105 | 103 | 107 | 104 | 126 | 249 | 551 |
| 982031 | 88 | 79 | 86 | 80 | 95 | 182 | 447 |
| 982032 | 82 | 69 | 73 | 76 | 89 | 172 | 366 |

Example 8 Effect of Inosine Substitution on In Vitro Activity and In Vivo Liver Toxicity of Modified Oligonucleotides Complementary to CXCL12 and Factor XI

TABLE 18

Modified oligonucleotides

| Compound ID | position of altered nucleotide in central region | nucleobase of altered nucleotide | Chemistry Notation (5'-3') | SEQ ID NO |
|---|---|---|---|---|
| 1061955 | 2 | Inosine | $G_{ks}{}^mC_{ks}A_{ks}T_{ds}I_{ds}T_{ds}T_{ds}{}^mC_{ds}T_{ds}{}^mC_{ds}A_{ds}{}^mC_{ds}A_{ds}T_{ks}T_{ks}A_k$ | 30 |
| 1154233 | 2 | Inosine | $G_{ks}T_{ks}{}^mC_{ks}T_{ds}I_{ds}T_{ds}G_{ds}{}^mC_{ds}A_{ds}T_{ds}C_{ds}T_{ds}{}^mC_{ds}T_{ks}{}^mC_{ks}{}^mC_k$ | 40 |

A subscript "d" indicates a nucleoside comprising an unmodified, 2'-β-D-deoxyribosyl sugar moiety..
A subscript "k" indicates a cEt. A subscript "s" indicates a phosphorothioate internucleoside linkage.
A superscript "m" before C indicates 5-methyl Cytosine.
I indicates inosine.

For in vitro activity studies, 3T3-L1 cells were plated at 20,000 cells/well and transfected with 27 nM, 80 nM, 250 nM, 740 nM, 2,222 nM, 6,667 nM, or 20,000 nM modified oligonucleotide by electroporation. mRNA was harvested and analyzed by RT-qPCR. CXCL12 mRNA and P21 mRNA were analyzed as in example 1.

Caspase-3 and caspase-7 activation was measured using the Caspase-Glo® 3/7 Assay System (G8090, Promega). Levels of caspase activation correlate with apoptotic cell death. Results are presented relative to the caspase activation in control cells not treated with modified oligonucleotide.

For the in vivo activity and toxicity study in the table below, two BALB/C mice per group were administered 16.7, 50, or 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 19

Effect of Inosine on activity and toxicity

| Compound ID | position of altered nucleotide in central region | nucleobase of altered nucleotide | CXCL12 $IC_{50}$ (µM) | in vivo CXCL12 $ED_{50}$ (mg/kg) | ALT @ 16.7 mg/kg (IU/L) | ALT @ 50 mg/kg (IU/L) | ALT @ 150 mg/kg (IU/L) |
|---|---|---|---|---|---|---|---|
| 558807* | n/a | n/a | 0.2 | 1.7 | 209 | death | death |
| 1061955 | 2 | Inosine | 0.3 | 4.2 | 20.5 | 26 | 86 |

*Data presented above in Example 4

TABLE 19b in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 558807 | 102 | 104 | 105 | 101 | 133 | 191 | 301 |
| 1061955 | 117 | 116 | 106 | 104 | 104 | 121 | 149 |

TABLE 19c in vitro Caspase Activation

| Compound ID | 27 nM | 80 nM | 250 nM | 740 nM | 2,222 nM | 6,667 nM | 20,000 nM |
|---|---|---|---|---|---|---|---|
| | | | Relative Caspase Activation (% Control) | | | | |
| 558807 | 135 | 110 | 131 | 115 | 147 | 476 | 462 |
| 1061955 | 75 | 81 | 134 | 120 | 121 | 162 | 170 |

For the study in the tables below, two BALB/C mice per group were administered 1.8 mg/kg, 5.5 mg/kg, 16.7 mg/kg, 50 mg/kg, or 150 mg/kg modified oligonucleotide by subcutaneous injection and sacrificed after 72 hours. 558807 was administered at 1.8 mg/kg, 5.5 mg/kg, 16.7 mg/kg due to acute toxicity at higher doses. Expression levels of Gadd45a, Tnfrsf10b, and P21 mRNA were measured as described in Example 1. Data for 558807 was also presented in Example 2, Tables 6b-6d.

TABLE 19d

In Vivo Dose-response of Gadd45a mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Gadd45a mRNA (% Control) | | | | |
| 558807 | 122 | 211 | 278 | n/a | n/a |
| 1061955 | 109 | 86 | 93 | 84 | 123 |

TABLE 19e

In Vivo Dose-response of Tnfrsf10b mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Tnfrsf10b mRNA (% Control) | | | | |
| 558807 | 160 | 166 | 271 | n/a | n/a |
| 1061955 | 158 | 77 | 126 | 134 | 192 |

TABLE 19f

In Vivo Dose-response of P21 mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 173 | 148 | 1456 | n/a | n/a |
| 1061955 | 36 | 8.6 | 16 | 33 | 72 |

For the in vivo activity and toxicity study in the table below, two BALB/C mice per group were administered 33 or 100 mg/kg modified oligonucleotide by subcutaneous injection and sacrificed 72 hours later. Four mice were administered an injection of saline as a control. FXI mRNA expression was measured by RT-qPCR as described in Example 3. Plasma levels of ALT were measured using an automated clinical chemistry analyzer. Increased ALT is indicative of acute liver toxicity.

TABLE 19g

Effect of Inosine on activity and toxicity

| Compound ID | position of altered nucleotide in central region | nucleobase of altered nucleotide | FXI mRNA @ 33 mg/kg (% control) | FXI mRNA @ 100 mg/kg (% control) | ALT @ 33 mg/kg (IU/L) | ALT @ 100 mg/kg (IU/L) |
|---|---|---|---|---|---|---|
| 464917* | n/a | n/a | 10.9 | 0.9 | 7511 | 31066 |
| 1154233 | 2 | Inosine | 5.0 | 1.2 | 315 | 4553 |

*Data presented above in Example 4

Example 9 Effect of Position-Specific Nucleobase Substitutions on In Vitro Activity and In Vivo Liver Toxicity of Modified Oligonucleotides Complementary to CXCL12

Modified oligonucleotides containing nucleobase modifications at various positions were synthesized. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse CXCL12, GENBANK NT_039353.7 truncated from 69/430,515 to 69/445,350 (SEQ ID NO: 1), at position 6877 to 6892.

Nucleobase Modifications:

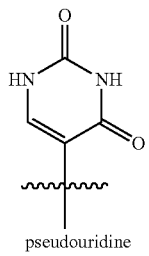

pseudouridine

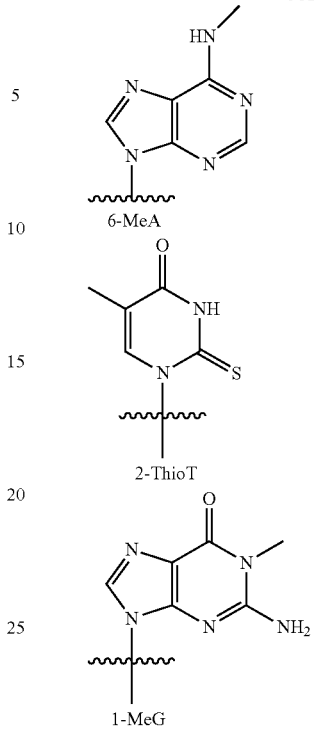

6-MeA

2-ThioT

1-MeG

TABLE 20

Modified oligonucleotides

| Compound ID | position of altered nucleotide in central region | nucleobase of altered nucleotide | Chemistry Notation (5'-3') | SEQ ID NO |
|---|---|---|---|---|
| 1076587 | 2 | 6-MeA, 2'-OH | $G_{ks}{}^mC_{ks}A_{ks}T_{ds}{}^{m6}A_{rs}T_{ds}T_{ds}{}^mC_{ds}T_{ds}{}^mC_{ds}A_{ds}{}^mC_{ds}A_{ds}T_{ks}T_{ks}A_k$ | 31 |
| 1076588 | 3 | 6-MeA, 2'-OH | $G_{ks}{}^mC_{ks}A_{ks}T_{ds}G_{ds}{}^{m6}A_{rs}T_{ds}{}^mC_{ds}T_{ds}{}^mC_{ds}A_{ds}{}^mC_{ds}A_{ds}T_{ks}T_{ks}A_k$ | 32 |
| 1069852 | 2 | pseudouridine, 2'-OH | $G_{ks}{}^mC_{ks}A_{ks}T_{ds}\Psi_{rs}T_{ds}T_{ds}{}^mC_{ds}T_{ds}{}^mC_{ds}A_{ds}{}^mC_{ds}A_{ds}T_{ks}T_{ks}A_k$ | 33 |
| 1061328 | 3 | pseudouridine, 2'-OH | $G_{ks}{}^mC_{ks}A_{ks}T_{ds}G_{ds}\Psi_{rs}T_{ds}{}^mC_{ds}T_{ds}{}^mC_{ds}A_{ds}{}^mC_{ds}A_{ds}T_{ks}T_{ks}A_k$ | 34 |
| 1016673 | 1 | pseudouridine, 2'-H | $G_{ks}{}^mC_{ks}A_{ks}T_{ds}\Psi_{ds}G_{ds}T_{ds}{}^mC_{ds}T_{ds}{}^mC_{ds}A_{ds}{}^mC_{ds}A_{ds}T_{ks}T_{ks}A_k$ | 35 |
| 1004684 | 3 | pseudouridine, 2'-H | $G_{ks}{}^mC_{ks}A_{ks}T_{ds}T_{ds}\Psi_{ds}T_{ds}{}^mC_{ds}T_{ds}{}^mC_{ds}A_{ds}{}^mC_{ds}A_{ds}T_{ks}T_{ks}A_k$ | 36 |
| 1004685 | 4 | pseudouridine, 2'-H | $G_{ks}{}^mC_{ks}A_{ks}T_{ds}G_{ds}T_{ds}\Psi_{ds}{}^mC_{ds}T_{ds}{}^mC_{ds}A_{ds}{}^mC_{ds}A_{ds}T_{ks}T_{ks}A_k$ | 37 |
| 1016674 | 6 | pseudouridine, 2'-H | $G_{ks}{}^mC_{ks}A_{ks}T_{ds}G_{ds}T_{ds}{}^mC_{ds}T_{ds}\Psi_{ds}{}^mC_{ds}A_{ds}{}^mC_{ds}A_{ds}T_{ks}T_{ks}A_k$ | 38 |
| 863089 | 1 | 2-thioT | $G_{ks}{}^mC_{ks}A_{ks}{}^sT_{ds}G_{ds}T_{ds}{}^mC_{ds}T_{ds}{}^mC_{ds}A_{ds}{}^mC_{ds}A_{ds}T_{ks}T_{ks}A_k$ | 18 |
| 863090 | 3 | 2-thioT | $G_{ks}{}^mC_{ks}A_{ks}T_{ds}G_{ds}{}^sT_{ds}T_{ds}{}^mC_{ds}T_{ds}{}^mC_{ds}A_{ds}{}^mC_{ds}A_{ds}T_{ks}T_{ks}A_k$ | 18 |
| 863091 | 4 | 2-thioT | $G_{ks}{}^mC_{ks}A_{ks}T_{ds}G_{ds}T_{ds}{}^sT_{ds}{}^mC_{ds}T_{ds}{}^mC_{ds}A_{ds}{}^mC_{ds}A_{ds}T_{ks}T_{ks}A_k$ | 18 |

TABLE 20-continued

Modified oligonucleotides

| Compound ID | position of altered nucleotide in central region | nucleobase of altered nucleotide | Chemistry Notation (5'-3') | SEQ ID NO |
|---|---|---|---|---|
| 863092 | 6 | 2-thioT | $G_{ks}{}^mC_{ks}A_{ks}T_{ds}G_{ds}T_{ds}T_{ds}{}^mC_{ds}{}^sT_{ds}{}^mC_{ds}A_{ds}{}^mC_{ds}A_{ds}T_{ks}T_{ks}A_k$ | 18 |
| 1061964 | 2 | 1-MeG, 2'-OH | $G_{ks}{}^mC_{ks}A_{ks}T_{ds}{}^{m1}G_{rs}T_{ds}T_{ds}{}^mC_{ds}T_{ds}{}^mC_{ds}A_{ds}{}^mC_{ds}A_{ds}T_{ks}T_{ks}A_k$ | 18 |

A subscript "d" indicates an unmodified, 2'-β-D-deoxyribosyl sugar moiety.
A subscript "r" indicates a unmodified, β-D-ribofuranosyl sugar moiety.
A subscript "k" indicates a cEt.
A subscript "s" indicates a phosphorothioate internucleoside linkage.
A superscript "m" before C indicates 5-methyl Cytosine.
A subscript "s" indicates a phosphorothioate internucleoside linkage.
A superscript "m" before a nucleobase indicator indicates that the nucleobase has a 5-methyl group, such as methyl Cytosine, methyl Adenosine, or methyl Guanosine.
A superscript "m6" before a A indicates 6-methyl Adenosine Ψ represents the nucleobase pseudouridine.
$^s$T represents the nucleobase 2-thiothymidine.

For in vitro activity studies, 3T3-L1 cells were plated at 20,000 cells/well and transfected with 10 nM, 30 nM, 250 nM, 740 nM, 2,220 nM, 6, 667 nM, or 20,000 nM modified oligonucleotide by electroporation. mRNA was harvested and analyzed by RT-qPCR. CXCL12 and RAPTOR mRNA was analyzed as in Example 1. The in vitro caspase assay was performed as described in Example 4.

For the in vivo toxicity study in the table below, two BALB/C mice per modified oligonucleotide were administered 50 or 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 21

Effect of modified nucleobases on activity and toxicity

| Compound ID | position of altered nucleotide in central region | nucleobase of altered nucleotide | CXCL12 IC$_{50}$ (nM) | RAPTOR IC$_{50}$ (nM) | ALT @ 50 mg/kg (IU/L) | ALT @ 150 mg/kg (IU/L) |
|---|---|---|---|---|---|---|
| 558807 | n/a | n/a | 47 | 800 | 6303 | death |
| 1076587 | 2 | 6-MeA | 300 | 18 | n.d. | n.d. |
| 1076588 | 3 | 6-MeA | 1400 | 13 | n.d. | n.d. |
| 1016673 | 1 | pseudouridine, 2'-H | 156 | 3600 | n.d. | n.d. |
| 1004684 | 2 | pseudouridine, 2'-H | 105 | 2600 | n.d. | n.d. |
| 1004685 | 3 | pseudouridine, 2'-H | 157 | 4100 | n.d. | n.d. |
| 1016674 | 4 | pseudouridine, 2'-H | 142 | 3800 | n.d. | n.d. |
| 863089 | 1 | 2-thioT | 48 | 8800 | 390 | 3620 |
| 863090 | 3 | 2-thioT | 130 | 1400 | death | death |
| 863091 | 4 | 2-thioT | 155 | 1700 | 6237 | death |
| 863092 | 6 | 2-thioT | 110 | 1900 | 14514.5 | death |
| 1061964 | 2 | 1-MeG | 5200 | 8600 | n.d. | n.d. |

TABLE 21b in vitro Caspase Activation

| Compound ID | 27 nM | 80 nM | 250 nM | 740 nM | 2222 nM | 6667 nM | 20,000 nM |
|---|---|---|---|---|---|---|---|
| | Relative Caspase Activation (% Control) | | | | | | |
| 558807 | 100 | 100 | 100 | 97 | 110 | 202 | 298 |
| 1076587 | 90 | 86 | 80 | 82 | 81 | 77 | 94 |
| 1076588 | 91 | 91 | 96 | 91 | 96 | 97 | 114 |
| 1069852 | 97 | 87 | 105 | 100 | 89 | 79 | 85 |
| 1061328 | 92 | 95 | 96 | 98 | 102 | 153 | 199 |

TABLE 21c in vitro Caspase Activation

| Compound ID | 27 nM | 80 nM | 250 nM | 740 nM | 2,222 nM | 6,667 nM | 20,000 nM |
|---|---|---|---|---|---|---|---|
| | | | Relative Caspase Activation (% Control) | | | | |
| 558807 | 135 | 110 | 131 | 115 | 147 | 476 | 462 |
| 1061964 | 107 | 142 | 140 | 149 | 135 | 123 | 125 |

TABLE 21d in vitro P21 Expression

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 558807 | 102 | 104 | 105 | 101 | 133 | 191 | 301 |
| 1061964 | 121 | 110 | 115 | 90 | 107 | 102 | 90 |

For in vivo activity and toxicity study in the table below, 2 BALB/C mice per group were administered modified oligonucleotide by subcutaneous injection and sacrificed after 72 hours. Compounds were dosed at 0.6, 1.8, 5.5, 16.7, 50 or 150 mg/kg. Tissue were collected and mRNA was isolated and levels of CXCL12 were measured by RT-qPCR with primer probe set RTS2605 as described above. Levels of Gadd45a were analyzed using primer probe set Mm00432802_ml (ThermoFisher). Levels of P21 were analyzed using primer probe set Mm04207341_ml (ThermoFisher). Levels of Tnfrsf10b were analyzed using primer probe set Mm00457866_ml (ThermoFisher). Expression levels were normalized with Ribogreen® and are presented relative to levels in mice treated with PBS.

TABLE 21e

In Vivo of modified oligonucleotides complementary to CXCL12 containing 2-Thio-T

| Compound ID | 2-Thio-T position in central region | ALT@16.7 mg/kg (IU/L) | ALT @50 mg/kg (IU/L) | ALT @ 150 mg/kg (IU/L) |
|---|---|---|---|---|
| PBS | n/a | | 27 (@0 mg/kg) | |
| 558807 | n/a | 2002 | 6303 | death |
| 863089 | 1 | 60 | 390 | 3620 |
| 863090 | 3 | 4929 | death | death |
| 863091 | 4 | 1894 | 6237 | death |
| 863092 | 6 | 1073 | 14515 | death |

TABLE 21f

In Vivo Activity of modified oligonucleotides complementary to CXCL12 containing 2-Thio-T

| Compound ID | 0.6 mg/kg | 1.8 mg/kg | 5.5 mg/kg | 16.7 mg/kg | 50 mg/kg | 150 mg/kg |
|---|---|---|---|---|---|---|
| | | Expression level of CXCL12 mRNA (% Control) | | | | |
| 558807 | 65 | 34 | 14 | 4 | 7 | n.d. |
| 863089 | 72 | 51 | 33 | 16 | 14 | 8 |
| 863090 | 58 | 31 | 11 | 11 | 0 | 0 |
| 863091 | 66 | 28 | 24 | 12 | 12 | 0 |
| 863092 | 59 | 42 | 20 | 5 | 6 | 0 |

Example 10 Effect of Position-Specific Morpholinos on In Vitro Activity and In Vivo Liver Toxicity of Modified Oligonucleotides Complementary to CXCL12

Modified oligonucleotides containing morpholinos at various positions were synthesized. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse CXCL12, GENBANK NT_039353.7 truncated from 69/430,515 to 69/445,350 (SEQ ID NO: 1), at position 6877 to 6892. Morpholino residues replace a full nucleotide, including the internucleoside linkage, and have the structures shown below.

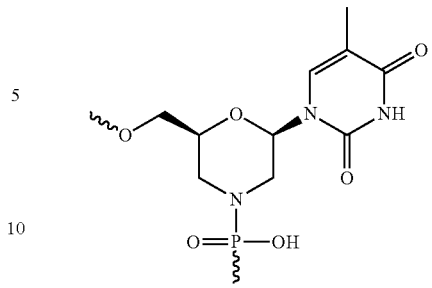

T morpholino PO

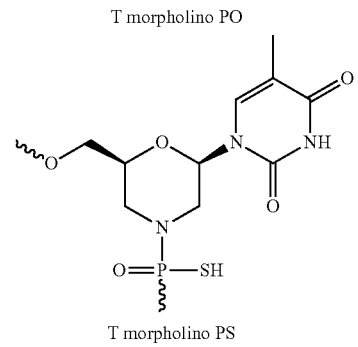

T morpholino PS

TABLE 22

Modified oligonucleotides

| Compound ID | morpholino position in central region | morpholino type | Chemistry Notation (5'-3') | SEQ ID NO |
|---|---|---|---|---|
| 1044689 | 1 | T-PO | $G_{ks}{}^mC_{ks}A_{ks}(MP_o{}^T)G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 1044690 | 3 | T-PO | $G_{ks}{}^mC_{ks}A_{ks}T_{ds}G_{ds}(MP_o{}^T)T_{ds}{}^mC_{ds}T_{ds}{}^mC_{ds}A_{ds}{}^mC_{ds}A_{ds}T_{ks}T_{ks}A_k$ | 18 |
| 1044691 | 4 | T-PO | $G_{ks}{}^mC_{ks}A_{ks}T_{ds}G_{ds}T_{ds}(MP_o{}^T){}^mC_{ds}T_{ds}{}^mC_{ds}A_{ds}{}^mC_{ds}A_{ds}T_{ks}T_{ks}A_k$ | 18 |
| 1044692 | 6 | T-PO | $G_{ks}{}^mC_{ks}A_{ks}T_{ds}G_{ds}T_{ds}T_{ds}{}^mC_{ds}(MP_o{}^T){}^mC_{ds}A_{ds}{}^mC_{ds}A_{ds}T_{ks}T_{ks}A_k$ | 18 |
| 1048416 | 1 | T-PS | $G_{ks}{}^mC_{ks}A_{ks}(MP_o{}^T)G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 1048417 | 3 | T-PS | $G_{ks}{}^mC_{ks}A_{ks}T_{ds}G_{ds}(MP_s{}^T)T_{ds}{}^mC_{ds}T_{ds}{}^mC_{ds}A_{ds}{}^mC_{ds}A_{ds}T_{ks}T_{ks}A_k$ | 18 |
| 1048418 | 4 | T-PS | $G_{ks}{}^mC_{ks}A_{ks}T_{ds}G_{ds}T_{ds}(MP_s{}^T){}^mC_{ds}T_{ds}{}^mC_{ds}A_{ds}{}^mC_{ds}A_{ds}T_{ks}T_{ks}A_k$ | 18 |
| 1048419 | 6 | T-PS | $G_{ks}{}^mC_{ks}A_{ks}T_{ds}G_{ds}T_{ds}T_{ds}{}^mC_{ds}(MP_s{}^T){}^mC_{ds}A_{ds}{}^mC_{ds}A_{ds}T_{ks}T_{ks}A_k$ | 18 |

A subscript "d" indicates a nucleoside comprising an unmodified, 2'-β-D-deoxyribosyl sugar moiety.
A subscript "r" indicates a nucleoside comprising an unmodified, β-D-ribofuranosyl sugar moiety.
A subscript "k" indicates a cEt.
A subscript "s" indicates a phosphorothioate internucleoside linkage.
A superscript "m" before C indicates 5-methyl Cytosine.
A $(MP_o{}^T)$ represents a phosphate thymidine morpholino, while $(MP_s{}^T)$ represents a phosphorothioate thymidine morpholino.

TABLE 22

Effect of morpholinos on in vitro activity and toxicity

| Compound ID | morpholino position in central region | morpholino type | CXCL12 IC$_{50}$ (nM) | RAPTOR IC$_{50}$ (nM) |
|---|---|---|---|---|
| 558807 | n/a | n/a | 47 | 800 |
| 1044689 | 1 | T-PO | 405 | >20000 |
| 1044690 | 3 | T-PO | 182 | 4100 |
| 1044691 | 4 | T-PO | 128 | 4400 |
| 1044692 | 6 | T-PO | 145 | 1900 |
| 1048416 | 1 | T-PS | 333 | >20000 |
| 1048417 | 3 | T-PS | 159 | 3300 |
| 1048418 | 4 | T-PS | 134 | 5200 |
| 1048419 | 6 | T-PS | 119 | 1100 |

Example 11 Effect of Position-Specific MOP on In Vitro Activity and In Vivo Toxicity of Modified Oligonucleotides Complementary CXCL12, Factor XI, PTEN, and SOD-1

Modified oligonucleotides were synthesized with MOP neutral backbone linkages at specific positions in place of phosphorothioate linkages. These modified oligonucleotides were compared to the otherwise identical modified oligonucleotide lacking the altered nucleotide in the central region, a 3-10-3 cEt modified oligonucleotide, containing three cEt nucleosides in each of the 5' and 3' regions and 10 unmodified DNA nucleosides in the central region, and phosphorothioate linkages throughout. The compounds in the table below are 100% complementary to mouse CXCL12, Factor XI, PTEN, or SOD-1, with sequences described above.

MOP
(alkyl phosphonate)

TABLE 23

Modified oligonucleotides containing MOP linkages

| Compound ID | MOP position in central region | Target | Chemistry Notation (5'-3') | SEQ ID NO |
|---|---|---|---|---|
| 766676 | 1 | CXCL12 | G$_{ks}$$^m$C$_{ks}$A$_{ks}$T$_{dx}$G$_{ds}$T$_{ds}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 18 |
| 766677 | 2 | CXCL12 | G$_{ks}$$^m$C$_{ks}$A$_{ks}$T$_{ds}$G$_{dx}$T$_{ds}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 18 |
| 766678 | 3 | CXCL12 | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 18 |
| 766679 | 4 | CXCL12 | G$_{ks}$$^m$C$_{ks}$A$_{ks}$T$_{ds}$G$_{ds}$T$_{ds}$T$_{dx}$$^m$C$_{ds}$T$_{ds}$$^m$C$_{ds}$A$_{ds}$$^m$C$_{ds}$A$_{ds}$T$_{ks}$T$_{ks}$A$_k$ | 18 |
| 766680 | 5 | CXCL12 | G$_{ks}$$^m$C$_{ks}$A$_{ks}$T$_{ds}$G$_{ds}$T$_{ds}$T$_{ds}$$^m$C$_{dx}$T$_{ds}$$^m$C$_{ds}$A$_{ds}$$^m$C$_{ds}$A$_{ds}$T$_{ks}$T$_{ks}$A$_k$ | 18 |
| 766681 | 6 | CXCL12 | G$_{ks}$$^m$C$_{ks}$A$_{ks}$T$_{ds}$G$_{ds}$T$_{ds}$T$_{ds}$$^m$C$_{ds}$T$_{dx}$$^m$C$_{ds}$A$_{ds}$$^m$C$_{ds}$A$_{ds}$T$_{ks}$T$_{ks}$A$_k$ | 18 |
| 766682 | 7 | CXCL12 | G$_{ks}$$^m$C$_{ks}$A$_{ks}$T$_{ds}$G$_{ds}$T$_{ds}$T$_{ds}$$^m$C$_{ds}$T$_{ds}$$^m$C$_{dx}$A$_{ds}$$^m$C$_{ds}$A$_{ds}$T$_{ks}$T$_{ks}$A$_k$ | 18 |
| 766683 | 8 | CXCL12 | G$_{ks}$$^m$C$_{ks}$A$_{ks}$T$_{ds}$G$_{ds}$T$_{ds}$T$_{ds}$$^m$C$_{ds}$T$_{ds}$$^m$C$_{ds}$A$_{dx}$$^m$C$_{ds}$A$_{ds}$T$_{ks}$T$_{ks}$A$_k$ | 18 |
| 766684 | 9 | CXCL12 | G$_{ks}$$^m$C$_{ks}$A$_{ks}$T$_{ds}$G$_{ds}$T$_{ds}$T$_{ds}$$^m$C$_{ds}$T$_{ds}$$^m$C$_{ds}$A$_{ds}$$^m$C$_{dx}$A$_{ds}$T$_{ks}$T$_{ks}$A$_k$ | 18 |
| 766685 | 10 | CXCL12 | G$_{ks}$$^m$C$_{ks}$A$_{ks}$T$_{ds}$G$_{ds}$T$_{ds}$T$_{ds}$$^m$C$_{ds}$T$_{ds}$$^m$C$_{ds}$A$_{ds}$$^m$C$_{ds}$A$_{dx}$T$_{ks}$T$_{ks}$A$_k$ | 18 |
| 965605 | 2 | FactorXI | G$_{ks}$T$_{ks}$$^m$C$_{ks}$T$_{ds}$G$_{dx}$T$_{ds}$G$_{ds}$$^m$C$_{ds}$A$_{ds}$T$_{ds}$$^m$C$_{ds}$T$_{ds}$$^m$C$_{ds}$T$_{ks}$$^m$C$_{ks}$$^m$C$_k$ | 22 |
| 965606 | 3 | FactorXI | G$_{ks}$T$_{ks}$$^m$C$_{ks}$T$_{ds}$G$_{ds}$T$_{dx}$G$_{ds}$$^m$C$_{ds}$A$_{ds}$T$_{ds}$$^m$C$_{ds}$T$_{ds}$$^m$C$_{ds}$T$_{ks}$$^m$C$_{ks}$$^m$C$_k$ | 22 |
| 985299 | 2 | PTEN | A$_{ks}$T$_{ks}$$^m$C$_{ks}$A$_{ds}$T$_{dx}$G$_{ds}$G$_{ds}$$^m$C$_{ds}$T$_{ds}$G$_{ds}$$^m$C$_{ds}$A$_{ds}$G$_{ds}$$^m$C$_{ks}$T$_{ks}$T$_k$ | 24 |
| 985303 | 3 | PTEN | A$_{ks}$T$_{ks}$$^m$C$_{ks}$A$_{ds}$T$_{ds}$G$_{dx}$G$_{ds}$$^m$C$_{ds}$T$_{ds}$G$_{ds}$$^m$C$_{ds}$A$_{ds}$G$_{ds}$$^m$C$_{ks}$T$_{ks}$T$_k$ | 24 |

TABLE 23-continued

Modified oligonucleotides containing MOP linkages

| Compound ID | MOP position in central region | Target | Chemistry Notation (5'-3') | SEQ ID NO |
|---|---|---|---|---|
| 985307 | 2 | SOD1 | $T_{ks}G_{ks}A_{ks}G_{ds}G_{ds}T_{dx}{}^mC_{ds}{}^mC_{ds}T_{ds}G_{ds}{}^mC_{ds}A_{ds}{}^mC_{ds}T_{ks}G_{ks}G_k$ | 26 |
| 985311 | 3 | SOD1 | $T_{ks}G_{ks}A_{ks}G_{ds}G_{ds}T_{dx}{}^mC_{ds}{}^mC_{ds}T_{ds}G_{ds}{}^mC_{ds}A_{ds}{}^mC_{ds}T_{ks}G_{ks}G_k$ | 26 |

A subscript "d" indicates an unmodified, 2'-β-D-deoxyribosyl sugar moiety.
A subscript "k" indicates a cEt.
A subscript "s" indicates a phosphorothioate internucleoside linkage.
A superscript "m" before a C indicates 5-methyl Cytosine.
A subscript "x" indicates a MOP or methoxypropyl internucleoside linkage.
The postion of the internucleoside linkage is designated as the position of the nucleoside that is on the 5' end of the linkage.

For in vitro activity studies for compounds complementary to CXCL12, b.END cells were plated at 20,000 cells/well and transfected with 0, 27 nM, 82 nM, 247 nM, 740 nM, 2,220 nM, 6,660 nM or 20,000 nM antisense oligonucleotide by electroporation. mRNA was harvested and analyzed by RT-qPCR. CXCL12 and raptor mRNA was analyzed as in previous examples.

For in vitro activity studies for compounds complementary to Factor XI, PTEN or SOD1, 3T3-L1 cells were plated at 20,000 cells/well and transfected with 0, 27 nM, 82 nM, 247 nM, 740 nM, 2,220 nM, 6,660 nM or 20,000 nM antisense oligonucleotide by electroporation. mRNA was harvested and analyzed by RT-qPCR. Complementary mRNA and raptor mRNA was analyzed as in previous examples.

For the in vivo toxicity study in the table below, one or two BALB/C mice per modified oligonucleotide were administered modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

For the in vivo activity study in the table below, two to four BALB/C mice per dosing group were administered modified oligonucleotide by subcutaneous injection and sacrificed 24 hours later. Mice were administered 1.9 mg/kg, 5.6 mg/kg, 16.7 mg/kg, 50 mg/k or 150 mg/kg of compound 558807 or 766676-766685. Mice were administered 6.25 mg/kg, 12.5 mg/kg, 25 mg/kg, 50 mg/kg, or 100 mg/kg modified oligonucleotide for compounds 965605 and 965606. Mice were administered 6.25 mg/kg, 12.5 mg/kg, 25 mg/kg, or 100 mg/kg modified oligonucleotide for 464917. Mice were administered 6.25 mg/kg, 12.5 mg/kg, 25 mg/kg, or 150 mg/kg modified oligonucleotide for 482050. Mice were administered 6.25 mg/kg, 12.5 mg/kg, 25 mg/kg, 50 mg/kg or 150 mg/kg modified oligonucleotide for 985299 and 985303. Mice were administered 12.5 mg/kg, 25 mg/kg, 50 mg/kg or 150 mg/kg modified oligonucleotide for 508031, 985307, and 985311. Two animals were administered an injection of saline as a control.

TABLE 24

Effect of MOP backbone modifications on activity and toxicity

| Compound ID | MOP position in central region | Complementary mRNA | Complementary mRNA $IC_{50}$ (μM) | RAPTOR $IC_{50}$ (μM) | in vivo Complementary mRNA $ED_{50}$ (mg/kg) | ALT @ Max dose* (IU/L) |
|---|---|---|---|---|---|---|
| PBS | n/a | n/a | n/a | n/a | n/a | 23 |
| 558807 | n/a | CXCL12 | 0.095 | 1.26 | 2.9 | death |
| 766676 | 1 | CXCL12 | 0.100 | 5.8 | 4.5 | 7764 |
| 766677 | 2 | CXCL12 | 0.110 | >>10 | 6.8 | 46 |
| 766678 | 3 | CXCL12 | 0.115 | >>10 | 6.2 | 44 |
| 766679 | 4 | CXCL12 | 0.080 | 7.2 | 5.7 | 4481 |
| 766680 | 5 | CXCL12 | 0.085 | 3.5 | 5.1 | 9139 |
| 766681 | 6 | CXCL12 | 0.080 | 3.0 | 3.6 | 17846 |
| 766682 | 7 | CXCL12 | 0.090 | 3.8 | 4.4 | 12510 |
| 766683 | 8 | CXCL12 | 0.070 | 2.2 | 4.3 | death |
| 766684 | 9 | CXCL12 | 0.090 | 2.2 | 3.1 | death |
| 766685 | 10 | CXCL12 | 0.090 | 2.0 | 2.1 | death |
| 464917 | n/a | Factor XI | n.d. | 1.6 | 6.9 | 33848 |
| 965605 | 2 | Factor XI | n.d. | 3.7 | 10.2 | 3464 |
| 965606 | 3 | Factor XI | n.d. | 7.7 | 12.3 | 1160 |
| 482050 | n/a | PTEN | 3.9 | 2.4 | 67 | 2458 |
| 985299 | 2 | PTEN | 1.1 | 4 | 120 | 767 |
| 985303 | 3 | PTEN | 1.7 | 3.7 | 194 | 43 |

TABLE 24-continued

Effect of MOP backbone modifications on activity and toxicity

| Compound ID | MOP position in central region | Complementary mRNA | Complementary mRNA IC$_{50}$ (µM) | RAPTOR IC$_{50}$ (µM) | in vivo Complementary mRNA ED$_{50}$ (mg/kg) | ALT @ Max dose* (IU/L) |
|---|---|---|---|---|---|---|
| 508031 | n/a | SOD1 | 0.03 | 0.46 | 63 | 21934 |
| 985307 | 2 | SOD1 | 0.17 | 3.6 | 157 | 57 |
| 985311 | 3 | SOD1 | 0.78 | 5.1 | 173 | 71 |

*ALT at 150 mg/kg for CXCL12 oligonucleotides, 100 mg/kg for Factor XI oligonucleotides, 200 mg/kg for PTEN oligonucleotides 985299 and 985303, 100 mg/kg for PTEN oligonucleotide 482050 and 150 mg/kg for SOD1 oligonucleotides 985307 and 985311, and 100 mg/kg for SOD1 oligonucleotide 508031.
**Value represents the average of two independent experiments Relative caspase activation in 3T3-L1 cells was determined as described in Example 4.

For the in vitro study reported in the tables below, b.END cells were electroporated with 27 nM, 80 nM, 250 nM, 740 nM, 2, 222 nM, 6,667 nM, or 20,000 nM of modified oligonucleotide and levels of P21 were measured by RT-qPCR using primer probe set Mm04207341_m1 (ThermoFisher).

Selected modified nucleotides described in above were tested for their effect on HeLa cells by microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. The number of cells with nucleolar p54nrb and the total number of cells in the images were counted.

TABLE 24a

Effect of MOP backbone modifications on activity and toxicity

| Compound ID | MOP position in central region | Complementary mRNA | Caspase (% mock) | in vitro p21 mRNA (% saline) | % nucleolar p54nrb |
|---|---|---|---|---|---|
| 558807 | n/a | CXCL12 | 313 | 243 | 82 |
| 766676 | 1 | CXCL12 | 243 | 187 | 32 |
| 766677 | 2 | CXCL12 | 121 | 179 | 25 |
| 766678 | 3 | CXCL12 | 136 | 180 | 32 |
| 766679 | 4 | CXCL12 | 240 | 195 | 39 |
| 766680 | 5 | CXCL12 | 351 | 263 | 86 |
| 766681 | 6 | CXCL12 | 315 | 309 | 79 |
| 766682 | 7 | CXCL12 | 345 | 236 | 71 |
| 766683 | 8 | CXCL12 | 257 | 260 | 91 |
| 766684 | 9 | CXCL12 | 314 | 247 | 88 |
| 766685 | 10 | CXCL12 | 308 | 291 | 90 |

For the in vivo toxicity study in the table below, two BALB/C mice per dosing group were administered modified oligonucleotide by subcutaneous injection and sacrificed 72 hours later. Mice were administered 10 mg/kg, 33 mg/kg, or 100 mg/kg modified oligonucleotide for compounds 464917, 965605, and 965606 and 10 mg/kg, 100 mg/kg, or 200 mg/kg for 482050, 985299, and 985303. Two animals were administered an injection of saline as a control. Plasma levels of ALT were measured using an automated clinical chemistry analyzer. Increased ALT is indicative of acute liver toxicity. Therapeutic index was calculated as the ratio of maximum non-toxic dose (MNTD)/ED$_{50}$, where ED$_{50}$ was determined via the in vivo activity study reported in the table above.

TABLE 24b in vivo Toxicity improvement for modified oligonucleotides complementary to Factor XI

| Compound ID | ALT @ 10 mg/kg | ALT @ 33 mg/kg | ALT @ 100 mg/kg | TI (MNTD/ED50) |
|---|---|---|---|---|
| 464917 | 239 | 8199 | 33848 | 1.4 |
| 965605 | 46 | 125 | 3464 | 3.2 |
| 965606 | 55 | 77 | 1160 | 2.7 |

TABLE 24c in vivo Toxicity improvement for modified oligonucleotides complementary to PTEN

| Compound ID | ALT @ 10 mg/kg | ALT @ 100 mg/kg | ALT @ 200 mg/kg | TI (MNTD/ED50) |
|---|---|---|---|---|
| 482050 | 55 | 9496 | 5329 | 0.15 |
| 985299 | 45 | 164 | 767 | 0.8 |
| 985303 | 33 | 39 | 43 | 1.0 |

TABLE 24d in vivo Toxicity improvement for modified oligonucleotides complementary to SOD1

| Compound ID | ALT @ 50 mg/kg | ALT @ 150 mg/kg | TI (MNTD/ED50) |
|---|---|---|---|
| 482050 | 2189 | n.d. | <0.8 |
| 985307 | n.d. | 57 | >1.0 |
| 985311 | n.d. | 71 | >0.9 |

Example 12 Effect of Position-Specific MOP in Combination with 2'-Modifications

Modified oligonucleotides were synthesized with MOP neutral backbone linkages at specific positions in place of phosphorothioate linkages in combination with 2'-FANA or 2'-OMe modified sugar moieties. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleosides in the central region, and phosphorothioate linkages throughout. The compounds in the table below are 100% complementary to mouse CXCL12 or SOD1, with sequences as described above.

3'-HPPO-GalNAc refers to the structure below, wherein the phosphate group is attached to the 3'-oxygen atom of the 3' nucleoside:

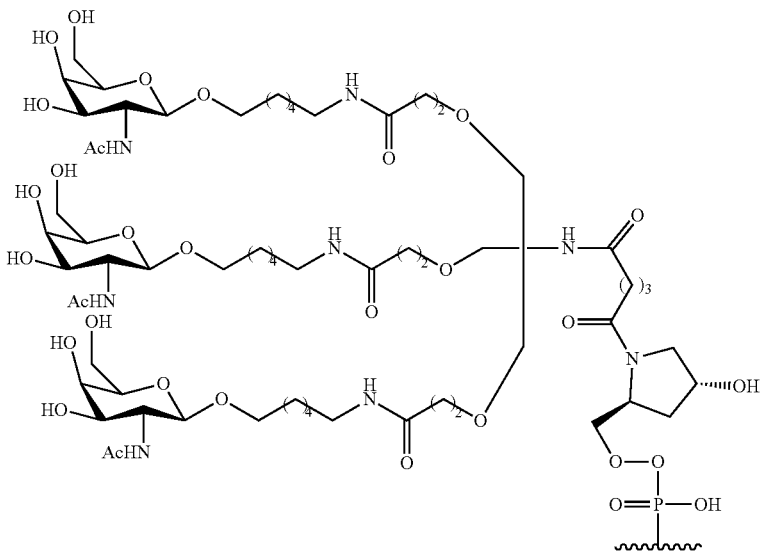

TABLE 25

Modified oligonucleotides containing MOP linkages and 2'-Modifications

| Compound ID | MOP position in central region | 2'-altered nucleotide position in central region | sugar modification of 2'-altered nucleotide | Target | Chemistry Notation (5'-3') | SEQ ID NO |
|---|---|---|---|---|---|---|
| 1061302 | 1 | 1 | 2'-OMe | CXCL12 | $G_{ks}{}^mC_{ks}A_{ks}T_{mx}G_{ds}T_{ds}T_{ds}{}^mC_{ds}T_{ds}{}^mC_{ds}A_{ds}$ ${}^mC_{ds}A_{ds}T_{ks}T_{ks}A_k$ | 18 |
| 1061303 | 2 | 2 | 2'-OMe | CXCL12 | $G_{ks}{}^mC_{ks}A_{ks}T_{ds}G_{mx}T_{ds}T_{ds}{}^mC_{ds}T_{ds}{}^mC_{ds}A_{ds}$ ${}^mC_{ds}A_{ds}T_{kS}T_{ks}A_k$ | 18 |
| 1061304 | 3 | 3 | 2'-OMe | CXCL12 | $G_{ks}{}^mC_{ks}A_{ks}T_{ds}G_{ds}T_{mx}T_{ds}{}^mC_{ds}T_{ds}{}^mC_{ds}A_{ds}$ ${}^mC_{ds}A_{ds}T_{kS}T_{ds}A_k$ | 18 |
| 1061305 | 4 | 4 | 2'-OMe | CXCL12 | $G_{ks}{}^mC_{ks}A_{ks}T_{ds}G_{ds}T_{ds}T_{mx}{}^mC_{ds}T_{ds}{}^mC_{ds}A_{ds}$ ${}^mC_{ds}A_{ds}T_{kS}T_{ds}A_k$ | 18 |
| 1061306 | 1 | 1 | 2'-OMe | SOD1 | $T_{ks}G_{ks}A_{ks}G_{mx}G_{ds}T_{ds}{}^mC_{ds}{}^mC_{ds}{}^mC_{ds}T_{ds}G_{ds}{}^mC_{ds}$ $A_{ds}{}^mC_{ds}T_{ks}G_{ks}G_k$ | 26 |
| 1061307 | 2 | 2 | 2'-OMe | SOD1 | $T_{ks}G_{ks}A_{ks}G_{ds}G_{mx}T_{ds}{}^mC_{ds}{}^mC_{ds}{}^mC_{ds}T_{ds}G_{ds}{}^mC_{ds}$ $A_{ds}{}^mC_{ds}T_{ks}G_{ks}G_k$ | 26 |
| 1061308 | 3 | 3 | 2'-OMe | SOD1 | $T_{ks}G_{ks}A_{ks}G_{ds}G_{ds}T_{mx}{}^mC_{ds}{}^mC_{ds}{}^mC_{ds}T_{ds}G_{ds}{}^mC_{ds}$ $A_{ds}{}^mC_{ds}T_{ks}G_{ks}G_k$ | 26 |
| 955900 | 3 | 1 | 2'-FANA | CXCL12 | $G_{ks}{}^mC{k_S}A{k_S}U_{(FANA)s}G_{ds}T_{dx}$ $T_{ds}{}^mC_{ds}T_{ds}{}^mC_{ds}A_{ds}{}^mC_{ds}A_{ds}T_{ks}T_{ks}A_k$ | 19 |
| 955901 | 3 | 2 | 2'-FANA | CXCL12 | $G_{ks}mC_{ks}A_{ks}T_{ds}G_{(FANA)s}T_{dx}$ $T_{ds}{}^mC_{ds}T_{ds}{}^mC_{ds}A_{ds}{}^mC_{ds}A_{ds}T_{ks}T_{ks}A_k$ | 18 |
| 955902 | 3 | 4 | 2'-FANA | CXCL12 | $G_{ks}mC_{ks}A_{ks}T_{ds}G_{ds}T_{dx}$ $U_{(FANA)s}{}^mC_{ds}T_{ds}{}^mC_{ds}A_{ds}{}^mC_{ds}A_{ds}T_{ks}T_{ks}A_k$ | 21 |
| 955903 | 3 | 5 | 2'-FANA | CXCL12 | $G_{ks}{}^mC_{ks}A_{ks}T_{ds}G_{ds}T_{dx}T_{ds}C_{(FANA)s}T_{ds}{}^mC_{ds}$ $A_{ds}{}^mC_{ds}A_{ds}T_{ks}T_{ks}A_k$ | 18 |
| 955904 | 3 | 6 | 2'-FANA | CXCL12 | $G_{ks}{}^mC_{ks}A_{ks}T_{ds}G_{ds}T_{dx}T_{ds}C_{ds}U_{(FANA)s})$ ${}^mC_{ds}A_{ds}{}^mC_{ds}A_{ds}T_{ks}T_{ks}A_k$ | 39 |
| 955905 | 3 | 7 | 2'-FANA | CXCL12 | $G_{ks}{}^mC_{ks}A_{ks}T_{ds}G_{ds}T_{dx}T_{ds}{}^mC_{ds}T_{ds}C_{(FANA)s}$ $A_{ds}C_{ds}A_{as}T_{ks}T_{ks}A_k$ | 18 |
| 955906 | 3 | 8 | 2'-FANA | CXCL12 | $G_{ks}{}^mC_{kS}A_{ks}T_{ds}G_{ds}T_{dx}T_{ds}{}^mC_{ds}T_{ds}{}^mC_{ds}$ $A_{(FANA)s}C_{ds}A_{ds}T_{ks}T_{ks}A_k$ | 18 |

TABLE 25-continued

Modified oligonucleotides containing MOP linkages and 2'-Modifications

| Compound ID | MOP position in central region | 2'-altered nucleotide position in central region | sugar modification of 2'-altered nucleotide | Target | Chemistry Notation (5'-3') | SEQ ID NO |
|---|---|---|---|---|---|---|
| 955907 | 3 | 9 | 2'-FANA | CXCL12 | $G_{ks}{}^mC_{ks}A_{ks}T_{ds}G_{ds}T_{dx}T_{ds}{}^mC_{ds}T_{ds}{}^mC_{ds}A_{ds}$ $C_{(FANA)s}A_{ds}T_{ks}T_{ks}A_k$ | 18 |
| 955908 | 3 | 10 | 2'-FANA | CXCL12 | $G_{ks}{}^mC_{ks}A_{ks}T_{ds}G_{ds}T_{dx}T_{ds}{}^mC_{ds}T_{ds}{}^mC_{ds}A_{ds}$ ${}^mC_{ds}A_{(FANA)}T_{ks}T_{ks}A_k$ | 18 |
| 855156 | n/a | n/a | n/a | CXCL12 | $G_{ks}{}^mC_{ks}A_{ks}T_{ds}G_{ds}T_{ds}T_{ds}{}^mC_{ds}T_{ds}{}^mC_{ds}A_{ds}$ ${}^mC_{ds}A_{ds}T_{ks}T_{ks}A_k$-HPPO-GalNac | 18 |
| 855161 | 3 | n/a | n/a | CXCL12 | $G_{ks}mC_{ks}A_{ks}T_{ds}G_{ds}T_{dx}$ $T_{ds}{}^mC_{ds}T_{ds}{}^mC_{ds}A_{ds}{}^mC_{ds}A_{ds}T_{ks}T_{ks}A_k$-HPPO-GalNac | 18 |
| 855160 | 1, 2 | n/a | n/a | CXCL12 | $G_{ks}{}^mC_{ks}A_{ks}T_{dx}G_{dx}T_{ds}$ $T_{ds}{}^mC_{ds}T_{ds}{}^mC_{ds}A_{ds}{}^mC_{ds}A_{ds}T_{ks}T_{ks}A_k$-HPPO-GalNac | 18 |
| 895571 | n/a | 3 | 2'-MOE | CXCL12 | $G_{ks}{}^mC_{ks}A_{ks}T_{ds}G_{ds}T_{es}T_{ds}{}^mC_{ds}T_{ds}{}^mC_{ds}A_{ds}$ ${}^mC_{ds}A_{ds}T_{ks}T_{ks}A_k$-HPPO-GalNac | 18 |
| 978782 | 3 | 2 | 2'-FANA | CXCL12 | $G_{ks}{}^mC_{ks}A_{ks}T_{ds}G_{(FANA)s}T_{dx}$ $T_{ds}{}^mC_{ds}T_{ds}{}^mC_{ds}A_{ds}{}^mC_{ds}A_{ds}T_{ks}T_{ks}A_k$-HPPO-GalNac | 18 |
| 978783 | 3 | 4 | 2'-FANA | CXCL12 | $G_{ks}{}^mC_{ks}A_{ks}T_{ds}G_{ds}T_{dx}$ $U_{(FANA)s}{}^mC_{ds}T_{ds}{}^mC_{ds}A_{ds}{}^mC_{ds}A_{ds}T_{ks}T_{ks}A_k$-HPPO-GalNac | 21 |
| 978784 | 3 | 5 | 2'-FANA | CXCL12 | $G_{ks}mC_{ks}A_{ks}T_{ds}G_{ds}T_{dx}$ $T_{ds}C_{(FANA)s}T_{ds}mC_{ds}A_{ds}{}^mC_{ds}A_{ds}T_{ks}T_{ks}A_k$-HPPO-GalNac | 18 |
| 978785 | 3 | 6 | 2'-FANA | CXCL12 | $G_{ks}{}^mC_{ks}A_{ks}T_{ds}G_{ds}T_{dx}$ $T_{ds}{}^mC_{ds}U_{(FANA)s}{}^mC_{ds}A_{ds}{}^mC_{ds}A_{ds}T_{ks}T_{ks}A_k$-HPPO-GalNac | 39 |
| 978786 | 3 | 10 | 2'-FANA | CXCL12 | $G_{ks}{}^mC_{ks}A_{ks}T_{ds}G_{ds}T_{dx}$ $T_{ds}{}^mC_{ds}T_{ds}{}^mC_{ds}A_{ds}{}^mC_{ds}A_{(FANA)s}T_{ks}T_{ks}A_k$-HPPO-GalNac | 18 |

A subscript "d" indicates an unmodified, 2'-β-D-(eoxyribosyl sugar moiety.
A subscript "e" indicates a 2'-MOE-β-D-ribofuranosyl sugar moiety.
A subscript "m" indicates a 2'-O-methyl-β-D-ribofuranosyl sugar moiety.
A subscript "k" indicates a cEt.
A subscript "s" indicates a phosphorothioate internucleoside linkage.
A subscript "f" indicates a 2'-F-β-D-2'-deoxyribosyl sugar moiety.
A subscript "(FANA)" indicates a 2'-F-β-D-arabinofuranosyl modified sugar moiety.
A superscript "m" before a C indicates 5-methyl Cytosine.

For in vitro activity studies, 3T3-L1 cells were plated at 20,000 cells/well and transfected with 0, 27 nM, 82 nM, 247 nM, 740 nM, 2,220 nM, 6,660 nM or 20,000 nM of modified oligonucleotide by electroporation. After X hours, mRNA was harvested and analyzed by RT-qPCR. Target and raptor mRNA was analyzed as previous examples.

TABLE 26

Effect of MOP backbone modifications combined with ara-F modifications on in vitro activity and toxicity

| Compound ID | MOP position in central region | FANA position in central region | Target IC$_{50}$ (nM) | RAPTOR IC$_{50}$ (nM) |
|---|---|---|---|---|
| 558807 | n/a | n/a | 34 | 1000 |
| 766678 | 3 | n/a | 67 | >20,000 |
| 955900 | 3 | 1 | 58 | >20,000 |
| 955901 | 3 | 2 | 43 | >20,000 |
| 955902 | 3 | 4 | 27 | >20,000 |
| 955903 | 3 | 5 | 27 | >20,000 |
| 955904 | 3 | 6 | 65 | >20,000 |
| 955905 | 3 | 7 | 93 | 16000 |
| 955906 | 3 | 8 | 99 | >20,000 |
| 955907 | 3 | 9 | 154 | >20,000 |
| 955908 | 3 | 10 | 171 | >20,000 |

For the in vivo toxicity study in the table below, three male BALB/C mice per modified oligonucleotide were administered 0.2, 0.6, 1.8 or 50 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 27

Effect of MOP backbone modifications combined with 2' modifications on in vivo activity and toxicity

| Compound ID | MOP position in central region | position of 2'-altered nucleotide in central region | sugar modification of 2'-altered nucleotide | in vivo CXCL12 ED$_{50}$ (mg/kg) | ALT @ 50 mg/kg |
|---|---|---|---|---|---|
| 855156 | n/a | n/a | n/a | 0.13 | 2938* |
| 855161 | 3 | n/a | n/a | 0.36 | 40 |
| 855160 | 2, 3 | n/a | n/a | 0.37 | 28 |
| 895571 | n/a | 3 | 2'-MOE | 0.43 | 319 |
| 978782 | 3 | 2 | 2'-FANA | 0.47 | 56 |
| 978783 | 3 | 4 | 2'-FANA | 0.43 | 39 |

*Value represents the ALT at 1.8 mg/kg

For the in vivo toxicity study in the table below, male BALB/C mice per modified oligonucleotide were administered 5, 50, or 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity. The caspase assay was performed in vitro as described in Example 8.

TABLE 28

Effect of MOP backbone modifications combined with 2'-OMe modified sugar moieties

| Compound ID | MOP position in central region | 2'-OMe position in central region | CXCL12 IC$_{50}$ (μM) | in vivo CXCL12 ED$_{50}$ (mg/kg) | ALT @ 50 mg/kg (IU/L) | ALT @ 150 mg/kg (IU/L) |
|---|---|---|---|---|---|---|
| 558807 | n/a | n/a | 0.18 | 2.88 | 8329 | death |
| 936053 | n/a | 2 | 0.17 | 1.75 | 75 | 40 |
| 1061302 | 1 | 1 | 0.09 | 0.39 | 101 | 2253 |
| 1061303 | 2 | 2 | 0.13 | 11 | 49 | 34 |
| 1061304 | 3 | 3 | 0.09 | 4.6 | 31 | 52 |
| 1061305 | 4 | 4 | 0.09 | 15.4 | 22 | 31 |

TABLE 28b in vitro Caspase Activation

| Compound ID | 27 nM | 80 nM | 250 nM | 740 nM | 2,222 nM | 6,667 nM | 20,000 nM |
|---|---|---|---|---|---|---|---|
| | Relative Caspase Activation (% Control) | | | | | | |
| 558807 | 98 | 106 | 112 | 139 | 288 | 587 | 1977 |
| 936053 | 106 | 111 | 113 | 91 | 98 | 107 | 153 |
| 1061302 | 98 | 90 | 106 | 111 | 149 | 456 | 1555 |
| 1061303 | 104 | 99 | 104 | 84 | 102 | 86 | 125 |
| 1061304 | 91 | 97 | 82 | 96 | 85 | 105 | 269 |
| 1061305 | 90 | 96 | 72 | 91 | 84 | 103 | 348 |

TABLE 28c

In Vivo Dose-response of Gadd45a mRNA upon treatment with modified oligonucleotides complementary to CXCL12

| Compound ID | 5.0 mg/kg | 50 mg/kg | 150 mg/kg |
|---|---|---|---|
| | Expression level of Gadd45a mRNA (% Control) | | |
| 558807 | 120 | 473 | n.d. |
| 936053 | 76 | 169 | 219 |
| 1061302 | 188 | 178 | 357 |
| 1061303 | 55 | 66 | 66 |
| 1061304 | 58 | 66 | 97 |
| 1061305 | 67 | 18 | 20 |

TABLE 28d

In Vivo Dose-response of Tnfrsf10b mRNA upon treatment with modified oligonucleotides complementary to CXCL12

| Compound ID | 5.0 mg/kg | 50 mg/kg | 150 mg/kg |
|---|---|---|---|
| | Expression level of Tnfrsf10b mRNA (% Control) | | |
| 558807 | 137 | 8022 | n.d. |
| 936053 | 91 | 104 | 180 |
| 1061302 | 104 | 137 | 1217 |
| 1061303 | 90 | 92 | 110 |
| 1061304 | 70 | 75 | 149 |
| 1061305 | 79 | 60 | 50 |

TABLE 28e

In Vivo Dose-response of P21 mRNA upon treatment with modified oligonucleotides complementary to CXCL12

| Compound ID | 5.0 mg/kg | 50 mg/kg | 150 mg/kg |
|---|---|---|---|
| | Expression level of P21 mRNA (% Control) | | |
| 558807 | 84 | 58138 | n.d. |
| 936053 | 239 | 81 | 299 |
| 1061302 | 87 | 315 | 14680 |
| 1061303 | 293 | 495 | 480 |
| 1061304 | 182 | 400 | 353 |
| 1061305 | 353 | 321 | 223 |

Example 13 Effect of Position-Specific 2'-OMe on In Vitro Activity and Toxicity of Modified Oligonucleotides with a Variety of Sequences Modified oligonucleotides were synthesized as indicated in the table below. The compounds have the sugar motif kkk-d(10)-kkk or kkk-d-m-d(8)-kkk, where "k" represents a cEt, "d" represents an unmodified, 2'-β-D-deoxyribosyl sugar moiety, and "m" represents a 2'-OMe-β-D-ribofuranosyl sugar moiety. For sequences with a T at position 5 (from the 5' end) in the parent kkk-d(10)-kkk oligonucleotide, the kkk-d-m-d(8)-kkk contains a 2'-OMe modified U at this position. For sequences with a $^m$C at position 5 (from the 5' end) in the parent kkk-d(10)-kkk oligonucleotide, the kkk-d-m-d(8)-kkk contains a 2'-OMe modified C at this position, with no 5-Me group.

For the in vivo toxicity study in the table below, two male BALB/C mice per modified oligonucleotide were administered 150 mg/kg modified oligonucleotide by subcutaneous injection and sacrificed 72 hours later. One animal was administered an injection of saline as a control. Plasma levels of ALT was measured using an automated clinical chemistry analyzer. Increased ALT is indicative of acute liver toxicity.

For a subset of compounds, on-target activity was measured in the liver. RNA was isolated from the liver and measured by RT-qPCR using the primer probe sets described in Table 30 below. Results were normalized with Ribogreen® and are reported normalized to PBS-treated animals.

Levels of mRNA for Gadd45a, P21, and Tnfrsf10b were analyzed as in Example 1 for mice administered 150 mg/kg modified oligonucleotide. Results are normalized with Ribogreen® and presented relative to PBS-treated control animals.

The caspase assay was performed in vitro as described in Example 8.

TABLE 29

Targets and Sequences

| Parent Compound ID | Corresponding compound with 2'-OMe at position 2 of the central region | Complementary mRNA | Sequence | SEQ ID NO |
|---|---|---|---|---|
| 546006 | 1133071 | HDAC2 | GAGGATGGCAAGCACA | 41 |
| 549334 | | AR | CACCTGCGGGAAGCTC | 42 |
| | 1200896 | AR | CACCUGCGGGAAGCTC | 126 |
| 562920 | 1201379 | VWF | TGTGCCCCAGCCCATT | 43 |
| 572912 | 1200898 | PABPN1 | CTTCCACAGTATATCT | 44 |
| 576095 | 1200899 | EGLN2 | TACTGGTAGTGTTGCT | 45 |
| 597605 | 1200900 | HEGFL | TTGACACAAAGGGAGT | 46 |
| 601840 | 1201381 | MTDH | GAATCTCCTTTTCCAG | 47 |
| 640599 | 1201862 | EZH2 | TTTACACGCTTCCGCC | 48 |
| 694804 | | DNM2 | AGACTCTCGGTTCCGA | 49 |
| | 1202810 | | AGACUCTCGGTTCCGA | 127 |

TABLE 29-continued

Targets and Sequences

| Parent Compound ID | Corresponding compound with 2'-OMe at position 2 of the central region | Complementary mRNA | Sequence | SEQ ID NO |
|---|---|---|---|---|
| 738431 | 1200905 | Nestin | CTTTTCTATCAGTCTC | 51 |
| 739428 | 1201694 | WWTR1/TNS | CTTCTTGATGTCTTTC<br>CTTCUTGATGTCTTTC | 52<br>129 |
| 747137 | 1200907 | FOXO1A | AAGTGTCACTAAAACC | 53 |
| 747149 | 1203759 | FOXO1A | GGACTGAAATAGCAGA<br>GGACUGAAATAGCAGA | 54<br>130 |
| 747190 | 1203759 | FOXO1A | AGGCTGGCCCCCACTG<br>AGGCUGGCCCCCACTG | 55<br>131 |
| 758252 | 1203759 | CHOP/DDIT3 | GGTTTTTGATTCTTCC<br>GGTTUTTGATTCTTCC | 56<br>132 |
| 797793 | 1201073 | DLL4 | GCATGCCGCCCCGTCC | 57 |
| 808013 | 1203761 | CYBB | TCTTCATACAATAGCA | 58 |
| 813942 | 1203762 | CDK9 | CGTTCAAATTCCGTCT | 59 |
| 832311 | 1201199 | PEMT | TCCGGCTGCGGCTCAG | 60 |

TABLE 30

Primer Probe Sets

| Transcript | PP Set Name | Primer | Sequence | SEQ ID NO: |
|---|---|---|---|---|
| HDAC2 | RTS3500 | Forward<br>Reverse<br>Probe | TGATGGTGTTGAGGAAGCTTTTT<br>TCCCTCAAGTCTCCTGTTCCA<br>ACAACAGATCGCGTGATGACCGTCTC | 15<br>16<br>17 |
| DNM2 | RTS36436 | Forward<br>Reverse<br>Probe | AGAGGAGACCGAGCGAAT<br>CATGGTTTGTGTTGATGTACGAC<br>CCTACATCAGGGAGCGAGAAGGGA | 61<br>62<br>63 |
| FOXO1A | RTS4973 | Forward<br>Reverse<br>Probe | GTCAAGACTACAACACACAGC<br>AAAACTATAAGGAGGGGTGAAGG<br>CTGAAGGACTTTTAAATGTAGCCTGCTCACTAA | 64<br>65<br>66 |
| PABPN1 | n/a | Forward<br>Reverse<br>Probe | CCGGAGCTAGAAGCGATCAA<br>CCTTTAGCTTCTCAGCCTCTTCCT<br>CTCGAGTCAGGGAGATG | 70<br>71<br>72 |

TABLE 31

Toxicity and Activity

| Compound ID | Position of 2'-altered nucleotide in central region | sugar modification of altered nucleotide | Gadd45a mRNA (% Control) | Tnfrsf10b mRNA (% Control) | P21 mRNA (% Control) | ALT @ 150 mg/kg | Relative Caspase Activation (% Control) @ 20 μM | Complementary mRNA* (% Control) |
|---|---|---|---|---|---|---|---|---|
| PBS | n/a | n/a | 100 | 100 | 111 | 28 @ 0 | n.d. | 100 |
| 546006 | n/a | n/a | 1885 | 4660 | 6556 | 131 | 291 | 38 |
| 1133071 | 2 | 2'-OMe | 1357 | 5569 | 6541 | 245 | 279 | 37 |
| 549334 | n/a | n/a | 187 | 225 | 182 | 30 | n.d. | n.d. |

TABLE 31-continued

Toxicity and Activity

| Compound ID | Position of 2'-altered nucleotide in central region | sugar modification of altered nucleotide | Gadd45a mRNA (% Control) | Tnfrsf10b mRNA (% Control) | P21 mRNA (% Control) | ALT @ 150 mg/kg | Relative Caspase Activation (% Control) @ 20 µM | Complementary mRNA* (% Control) |
|---|---|---|---|---|---|---|---|---|
| 1200896 | 2 | 2'-OMe | 165 | 126 | 130 | 28 | n.d. | n.d. |
| 562920 | n/a | n/a | 498 | 568 | 1336 | 109 | 473 | n.d. |
| 1201379 | 2 | 2'-OMe | 171 | 200 | 402 | 32 | 473 | n.d. |
| 572912 | n/a | n/a | 357 | 7503 | 5043 | 3883 | 205 | n.d. |
| 1200898 | 2 | 2'-OMe | 155 | 170 | 301 | 41 | 84 | n.d. |
| 576095 | n/a | n/a | 147 | 121 | 154 | 39 | n.d. | n.d. |
| 1200899 | 2 | 2'-OMe | 401 | 154 | 169 | 32 | n.d. | n.d. |
| 597605 | n/a | n/a | 353 | 1965 | 2263 | 488 | 328 | n.d. |
| 1200900 | 2 | 2'-OMe | 121 | 227 | 228 | 32 | 126 | n.d. |
| 601840 | n/a | n/a | 221 | 365 | 840 | 98 | 287 | n.d. |
| 1201381 | 2 | 2'-OMe | 103 | 123 | 72 | 24 | 274 | n.d. |
| 640599 | n/a | n/a | 111 | 286 | 376 | 26 | 184 | n.d. |
| 1201862 | 2 | 2'-OMe | 96 | 262 | 276 | 22 | 99 | n.d. |
| 694804 | n/a | n/a | 336 | 916 | 1297 | 1090 | 257 | 6 |
| 1202810 | 2 | 2'-OMe | 106 | 238 | 257 | 36 | 166 | 16 |
| 715415 | n/a | n/a | 186 | 1211 | 1249 | 420 | 137 | n.d. |
| 1203758 | 2 | 2'-OMe | 78 | 150 | 115 | 41 | 141 | n.d. |
| 738431 | n/a | n/a | 229 | 507 | 448 | 608 | 220 | n.d. |
| 1200905 | 2 | 2'-OMe | 141 | 193 | 197 | 69 | 181 | n.d. |
| 739428 | n/a | n/a | 234 | 1975 | 2107 | 533 | 269 | n.d. |
| 1201694 | 2 | 2'-OMe | 154 | 593 | 388 | 42 | 114 | n.d. |
| 747137 | n/a | n/a | 155 | 1379 | 1851 | 50 | 512 | 19 |
| 1200907 | 2 | 2'-OMe | 99 | 716 | 824 | 39 | 168 | 27 |
| 747149 | n/a | n/a | 454 | 5765 | 4892 | 606 | 166 | 9 |
| 1203759 | 2 | 2'-OMe | 105 | 119 | 211 | 33 | 109 | 22 |
| 747190 | n/a | n/a | 162 | 2856 | 4677 | 1315 | 393 | 2 |
| 1200961 | 2 | 2'-OMe | 129 | 237 | 345 | 71 | 305 | 7 |
| 758252 | n/a | n/a | 158 | 989 | 861 | 725 | 355 | n.d. |
| 1233760 | 2 | 2'-OMe | 94 | 106 | 182 | 47 | 187 | n.d. |
| 797793 | n/a | n/a | 190 | 1175 | 1181 | 1318 | 229 | n.d. |
| 1201073 | 2 | 2'-OMe | 184 | 230 | 201 | 78 | 125 | n.d. |
| 808013 | n/a | n/a | 126 | 2153 | 4617 | 169 | 437 | n.d. |
| 1203761 | 2 | 2'-OMe | 154 | 163 | 147 | 25 | 113 | n.d. |
| 813942 | n/a | n/a | 351 | 3758 | 4638 | 127 | 340 | n.d. |
| 1203762 | 2 | 2'-OMe | 103 | 89 | 257 | 28 | 88 | n.d. |
| 832311 | n/a | n/a | 305 | 1059 | 878 | 739 | 288 | n.d. |
| 1201199 | 2 | 2'-OMe | 294 | 720 | 597 | 208 | 256 | n.d. |

*Value represents the reduction of the mRNA that is complementary to the modified oligonucleotide as indicated in Table 29 above.

Example 14 Dose-Response of Position-Specific 2'-OMe on In Vitro and In Vivo Activity and Toxicity of Modified Oligonucleotides with a Variety of Sequences On target in vivo activity and toxicity was measured for a subset of compounds described in Example 13 above. Two male BALB/c mice per group were administered 1.85, 5.55, 16.67, 50, or 150 mg/kg modified oligonucleotide once via subcutaneous injection, as indicated in the tables below. Mice were sacrificed after 1 week and mRNA was isolated from the liver and measured by RT-qPCR using the primer probe sets described in Table 30 above. Levels of mRNA for Gadd45a, P21, and Tnfrsf10b were analyzed as in Example 1. Results were normalized with Ribogreen and are reported normalized to PBS-treated animals. Plasma levels of ALT was measured using an automated clinical chemistry analyzer. Increased ALT is indicative of acute liver toxicity. The therapeutic index is calculated as a ratio of the maximum non-toxic dose divided by the in vivo ED50. The maximum non-toxic dose is the highest dose at which the ALT value remains less than 5× increased compared to PBS-treated mice, typically 150 IU/L.

TABLE 33 in vivo dose response activity

| | Target Expression (% Control) | | | | | |
|---|---|---|---|---|---|---|
| Compound Number | 1.9 mg/kg | 5.6 mg/kg | 16.7 mg/kg | 50 mg/kg | 150 mg/kg | ED50 (µg/g) |
| 546006 | 86.8 | 75.6 | 78.1 | 56.2 | 41.4 | 87.9 |
| 1133071 | 81.6 | 74.5 | 61.4 | 52.9 | 37.6 | 53.9 |
| 572912 | 80.7 | 58.2 | 34.6 | 26.2 | 21.7 | 10.0 |
| 1200898 | 84.8 | 80.2 | 67.4 | 42.4 | 16.3 | 31.5 |
| 694804 | 62.8 | 38.2 | 15.3 | 7.8 | 7.6 | 3.2 |
| 1202810 | 71.0 | 46.7 | 33.2 | 21.0 | 10.1 | 5.8 |
| 747137 | 45.3 | 42.5 | 28.7 | 21.4 | 14.0 | 1.5 |
| 1200907 | 42.1 | 35.3 | 40.2 | 30.6 | 18.8 | 0.53 |
| 747149 | 72.8 | 42.2 | 23.6 | 14.6 | 7.3 | 6.0 |
| 1203759 | 52.9 | 40.6 | 24.4 | 21.5 | 18.3 | 2.1 |
| 715415 | 61.5 | 56.9 | 41.9 | 19.9 | 12.0 | 6.5 |
| 1203758 | 71.6 | 68.8 | 61.1 | 34.8 | 20.9 | 20.0 |

TABLE 34 in vivo dose response toxicity (ALT)

| Compound Number | ALT (IU/L) | | | | |
|---|---|---|---|---|---|
| | 1.9 mg/kg | 5.6 mg/kg | 16.7 mg/kg | 50 mg/kg | 150 mg/kg |
| 546006 | 29 | 29 | 22 | 26 | 173 |
| 1133071 | 24 | 25 | 25 | 44 | 356 |
| 572912 | 23 | 27 | 112 | 730 | 4674 |
| 1200898 | 23 | 24 | 25 | 28 | 32 |
| 694804 | 29 | 24 | 24 | 143 | 2160 |
| 1202810 | 22 | 24 | 24 | 23 | 61 |
| 747137 | 24 | 22 | 24 | 25 | 86 |
| 1200907 | 23 | 21 | 21 | 31 | 32 |
| 747149 | 26 | 26 | 38 | 157 | 1867 |
| 1203759 | 25 | 21 | 23 | 27 | 27 |
| 715415 | 23 | 21 | 25 | 77 | 1384 |
| 1203758 | 25 | 23 | 23 | 23 | 54 |

TABLE 34b

In Vivo Dose-response of Gadd45a mRNA upon treatment with modified oligonucleotides complementary to HDAC2

| | 1.9 mg/kg | 5.6 mg/kg | 16.7 mg/kg | 50 mg/kg | 150 mg/kg |
|---|---|---|---|---|---|
| | Expression level of Gadd45a mRNA (% Control) | | | | |
| 546006 | 122 | 112 | 77 | 302 | 1070 |
| 1133071 | 94 | 134 | 154 | 396 | 873 |
| 572912 | 94 | 95 | 187 | 196 | 227 |
| 1200898 | 103 | 80 | 112 | 109 | 99 |
| 694804 | 126 | 106 | 161 | 163 | 459 |
| 1202810 | 115 | 93 | 91 | 188 | 169 |
| 747137 | 94 | 67 | 80 | 96 | 153 |
| 1200907 | 79 | 86 | 142 | 88 | 140 |
| 747149 | 123 | 172 | 146 | 283 | 575 |
| 1203759 | 100 | 147 | 102 | 172 | 154 |
| 715415 | 91 | 118 | 201 | 159 | 393 |
| 1203758 | 143 | 114 | 206 | 162 | 197 |

TABLE 34c

In Vivo Dose-response of Tnfrsf10b mRNA upon treatment with modified oligonucleotides

| Compound ID | 1.9 mg/kg | 5.6 mg/kg | 16.7 mg/kg | 50 mg/kg | 150 mg/kg |
|---|---|---|---|---|---|
| | Expression level of Tnfrsf10b mRNA (% Control) | | | | |
| 546006 | 87 | 78 | 161 | 248 | 4235 |
| 1133071 | 95 | 96 | 157 | 622 | 5166 |
| 572912 | 210 | 190 | 551 | 4070 | 5847 |
| 1200898 | 135 | 116 | 105 | 170 | 179 |
| 694804 | 81 | 98 | 116 | 284 | 1775 |
| 1202810 | 88 | 110 | 88 | 128 | 241 |
| 747137 | 56 | 74 | 115 | 273 | 1013 |
| 1200907 | 99 | 86 | 15 | 239 | 453 |
| 747149 | 73 | 70 | 116 | 636 | 6027 |
| 1203759 | 87 | 55 | 57 | 97 | 105 |
| 715415 | 62 | 57 | 111 | 259 | 999 |
| 1203758 | 67 | 72 | 64 | 79 | 126 |

TABLE 34d

In Vivo Dose-response of P21 mRNA upon treatment with modified oligonucleotides

| Compound ID | 1.9 mg/kg | 5.6 mg/kg | 16.7 mg/kg | 50 mg/kg | 150 mg/kg |
|---|---|---|---|---|---|
| | Expression level of P21 mRNA (% Control) | | | | |
| 546006 | 103 | 90 | 172 | 342 | 5193 |
| 1133071 | 97 | 68 | 197 | 773 | 6571 |
| 572912 | 224 | 228 | 762 | 2787 | 3182 |
| 1200898 | 98 | 106 | 70 | 164 | 172 |
| 694804 | 108 | 76 | 72 | 172 | 2212 |
| 1202810 | 91 | 125 | 245 | 51 | 162 |
| 747137 | 43 | 59 | 122 | 294 | 1220 |
| 1200907 | 108 | 97 | 110 | 383 | 708 |
| 747149 | 95 | 44 | 207 | 985 | 3869 |
| 1203759 | 61 | 30 | 47 | 71 | 95 |
| 715415 | 46 | 24 | 45 | 213 | 757 |
| 1203758 | 36 | 34 | 18 | 26 | 35 |

TABLE 34e

Therapeutic Index

| Compound ID | 2'-altered nucleotide position in central region | sugar modification of altered nucleotide | MNTD (mg/kg) | TI (MNTD/ED$_{50}$) | Fold-TI improvement |
|---|---|---|---|---|---|
| 546006 | n/a | n/a | 50 | 0.6 | 1.5 |
| 1133071 | 2 | 2'-OMe | 50 | 0.9 | |
| 572912 | n/a | n/a | 16.7 | 2 | >2.4 |
| 1200898 | 2 | 2'-OMe | >150 | >4.8 | |
| 694804 | n/a | n/a | 50 | 16 | >1.6 |
| 1202810 | 2 | 2'-OMe | >150 | >26 | |
| 747137 | n/a | n/a | >150 | >99 | ~2.9 |
| 1200907 | 2 | 2'-OMe | >150 | >284 | |
| 747149 | n/a | n/a | 50 | 11 | >6.5 |
| 1203759 | 2 | 2'-OMe | >150 | >72 | |
| 715415 | n/a | n/a | 50 | 8 | n/a |
| 1203758 | 2 | 2'-OMe | >150 | >7.5 | |

Example 15 Effect of Modified Oligonucleotides on Nucleolar Localization of p54nrb Selected modified nucleotides described in above were tested for their effect on HeLa cells by microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. The number of cells with nucleolar p54nrb and the total number of cells in the images were counted. ALT data presented were previously described in Example 13 above.

TABLE 35

Nucleolar mislocalization of p54nrb and correlation with hepatoxicity

| Compound ID | 2'-altered nucleotide position in central region | sugar modification of altered nucleotide | % cells with mislocalization of p54nrb | ALT @ 150 mg/kg |
|---|---|---|---|---|
| 546006 | n/a | n/a | 56 | 131 |
| 1133071 | 2 | 2'-OMe | 67 | 245 |
| 572912 | n/a | n/a | 75 | 3883 |

TABLE 35-continued

Nucleolar mislocalization of p54nrb and correlation with hepatoxicity

| Compound ID | 2'-altered nucleotide position in central region | sugar modification of altered nucleotide | % cells with mislocalization of p54nrb | ALT @ 150 mg/kg |
|---|---|---|---|---|
| 1200898 | 2 | 2'-OMe | 3 | 41 |
| 758252 | n/a | n/a | 71 | 725 |
| 1233760 | 2 | 2'-OMe | 4 | 47 |

Example 16 Effect of Position-Specific 2'-OMe on In Vitro Activity and Toxicity of Modified Oligonucleotides with Various Sequences Modified oligonucleotides with the sugar motifs lll-d(10)-lll and lll-d-m-d(8)-lll were synthesized, where "l" indicates a β-D-locked nucleic acid β-D-LNA), "d" represents a 2'-β-D-deoxyribosyl sugar moiety and "m" represents a 2'-OMe-β-D-ribofuranosyl sugar moiety. Each internucleoside linkage is a phosphorothioate internucleoside linkage. For sequences with a T at position 5 (from the 5' end) in the parent lll-d(10)-lll oligonucleotide, the lll-d-m-d(8)-lll contains a 2'-OMe modified U at this position. For sequences with a $^m$C at position 5 (from the 5' end) in the parent lll-d(10)-lll oligonucleotide, the lll-d-m-d(8)-lll contains a 2'-OMe modified C at this position lacking a 5-Me group.

TABLE 36

Modified Oligonucleotides

| lll-d(10)-lll compound ID | lll-d-m-d(8)-lll compound ID | Complementary mRNA | Sequence (5'-3') | SEQ ID NO |
|---|---|---|---|---|
| 1247569 | 1247570 | HDAC2 | GAGGATGGCAAGCACA | 41 |
| 1247571 | 1247572 | PABPN1 | CTTCCACAGTATATCT | 44 |
| 1247573 | | DNM2 | AGACTCTCGGTTCCGA | 49 |
| | 1247574 | | AGACUCTCGGTTCCGA | 127 |
| 1247575 | 1247576 | FOXO1A | AAGTGTCACTAAAACC | 53 |
| 1247577 | 1247578 | FOXO1A | GGACTGAAATAGCAGA | 54 |
| | 1247578 | | GGACUGAAAUAGCAGA | 130 |

In vivo toxicity and on target in vivo activity was measured for the compounds described above. Two male balb/c mice per group were administered 16.67 or 150 mg/kg modified oligonucleotide once via subcutaneous injection, as indicated in the tables below. Mice were sacrificed after 72 hours and mRNA was isolated from the liver and measured by RT-qPCR using the primer probe sets described in Table 30 above. Levels of mRNA for P21, and Tnfrsf10b were analyzed as in Example 1. Results were normalized with Ribogreen and are reported normalized to PBS-treated animals.

TABLE 37 in vivo activity and toxicity

| | Complementary mRNA Expression (% Control) | | ALT (IU/L) | | P21 mRNA (% Control) | | Tnfrsf10b mRNA (% Control) | |
|---|---|---|---|---|---|---|---|---|
| Compound Number | 16.7 mg/kg | 150 mg/kg | 16.7 mg/kg | 150 mg/kg | 16.7 mg/kg | 150 mg/kg | 16.7 mg/kg | 150 mg/kg |
| 1247569 | 70 | 35 | 37 | 2368 | 163 | 12778 | 158 | 7046 |
| 1247570 | 72 | 46 | 34 | 867 | 444 | 11860 | 320 | 6772 |
| 1247571 | 40 | 26 | 460 | 10838 | 3061 | 7588 | 2216 | 8133 |
| 1247572 | 54 | 16 | 26 | 330 | 90 | 928 | 124 | 679 |
| 1247573 | 7 | 19 | 59 | 20665 | 153 | 10379 | 157 | 4858 |
| 1247574 | 19 | 6 | 25 | 284 | 139 | 839 | 123 | 575 |
| 1247575 | 51 | 30 | 50 | 2404 | 390 | 11275 | 334 | 6365 |
| 1247576 | 57 | 27 | 25 | 85 | 142 | 1850 | 218 | 2033 |
| 1247577 | 52 | 25 | 34 | 2460 | 256 | 11736 | 193 | 14610 |
| 1247578 | 60 | 21 | 25 | 39 | 124 | 133 | 178 | 143 |
| 1247579 | 48 | 14 | 23 | 1696 | 95 | 3704 | 176 | 108 |
| 1247580 | 77 | 21 | 28 | 232 | 78 | 265 | 2850 | 307 |

Example 17 Effect of Position-Specific 2'-Modifications on In Vitro Activity and In Vivo Liver Toxicity of Modified Oligonucleotides Complementary to CPT1A Modified oligonucleotides were synthesized as indicated in the table below. These modified oligonucleotides were compared to the otherwise identical modified oligonucleotide lacking an altered nucleotide in the central region, a 5-10-5 MOE modified oligonucleotide, containing five nucleosides each comprising a 2'-MOE-β-D-ribofuranosyl sugar moiety in each of the 5' and 3' regions and 10 unmodified DNA nucleosides in the central region. Each internucleoside linkage is a phosphorothioate internucleoside linkage. The compounds in the table below are 100% complementary to mouse CPT1A, GENBANK NC_000085.6 truncated from 3319001 to 3389000 (SEQ ID NO: 6), at position 49870 to 49889. In certain instances, a modified oligonucleotide comprising a T at position 5 is compared to a modified oligonucleotide comprising a 2'-OMe U at position 5.

TABLE 38

Modified oligonucleotides complementary to CPT1A

| Compound ID | position of altered nucleotide in central region | sugar modification of altered nucleotide | Chemistry Notation | SEQ ID NO |
|---|---|---|---|---|
| 147420 | n/a | n/a | $A_{es}A_{es}T_{es}G_{es}T_{es}G_{ds}{}^mC_{ds}{}^mC_{ds}T_{ds}G_{ds}{}^mC_{ds}T_{ds}$ $G_{ds}T_{ds}{}^mC_{ds}{}^mC_{es}T_{es}T_{es}G_{es}A_e$ | 73 |
| 994947 | n/a | OMe | $A_{es}A_{es}T_{es}G_{ms}T_{es}G_{ds}{}^mC_{ds}{}^mC_{ds}T_{ds}G_{ds}{}^mC_{ds}T_{ds}$ $G_{ds}T_{ds}{}^mC_{ds}{}^mC_{es}T_{es}T_{es}G_{es}A_e$ | 73 |
| 994948 | n/a | OMe | $A_{es}A_{es}T_{es}G_{es}U_{ms}G_{ds}{}^mC_{ds}{}^mC_{ds}T_{ds}G_{ds}{}^mC_{ds}T_{ds}$ $G_{ds}T_{ds}{}^mC_{ds}{}^mC_{es}T_{es}T_{es}G_{es}A_e$ | 74 |
| 994949 | 1 | OMe | $A_{es}A_{es}T_{es}G_{es}T_{es}G_{ms}{}^mC_{ds}{}^mC_{ds}T_{ds}G_{ds}{}^mC_{ds}T_{ds}$ $G_{ds}T_{ds}{}^mC_{ds}{}^mC_{es}T_{es}T_{es}G_{es}A_e$ | 73 |
| 994950 | 2 | OMe | $A_{es}A_{es}T_{es}G_{es}T_{es}G_{ds}C_{ms}{}^mC_{ds}T_{ds}G_{ds}{}^mC_{ds}T_{ds}$ $G_{ds}T_{ds}{}^mC_{ds}{}^mC_{es}T_{es}T_{es}G_{es}A_e$ | 73 |
| 994951 | 3 | OMe | $A_{es}A_{es}T_{es}G_{es}T_{es}G_{ds}{}^mC_{ds}C_{ms}T_{ds}G_{ds}{}^mC_{ds}T_{ds}$ $G_{ds}T_{ds}{}^mC_{ds}{}^mC_{es}T_{es}T_{es}G_{es}A_e$ | 73 |

A subscript "d" indicates an unmodified, 2'-β-D-deoxyribosyl sugar moiety.
A subscript "e" indicates a 2'-MOE-β-D-ribofuranosyl sugar moiety.
A subscript "m" indicates a 2'-O-methyl-β-D-ribofuranosyl sugar moiety.
A subscript "k" indicates a cEt. A subscript "s" indicates a phosphorothioate internucleoside linkage.
A superscript "m" before a C indicates 5-methyl Cytosine..
A subscript "x" indicates a MOP internucleoside linkage.
A subscript "(FANA)" indicates a nucleoside comprising an ara 2'-F modified sugar moiety.

For the in vivo toxicity and activity study in the table below, BALB/C mice per modified oligonucleotide were administered 200 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity. Liver mRNA was harvested and analyzed by RT-qPCR. Cpt1a mRNA was detected using primer probe setRTS40014 (forward sequence: AGATCAATCGGACCCTAGACA, SEQ ID NO: 75; reverse sequence: CAGCACCTTCAGCGAGTA; SEQ ID NO: 76; probe sequence: AAGAGGACGCCACTCACGATGTTC, SEQ ID NO: 77) and P21 and Tnfrsf10b mRNA were detected as described in Example 1.

TABLE 39

Activity and toxicity of modified oligonucleotides complementary CPT1A

| Compound ID | position of altered nucleotide in central region | sugar modification of altered nucleotide | Cpt1a (% control) | P21 (% control) | Tnfrsf10b (% control) | ALT @ 200 mg/kg (IU/L) |
|---|---|---|---|---|---|---|
| 147420 | n/a | n/a | 6.42 | 6616 | 8796 | 15308 |
| 994947 | n/a | 2'-OMe | 6.49 | 6984 | 11499 | 18395 |
| 994948 | n/a | 2'-OMe | 8.99 | 7085 | 10520 | 10535 |
| 994949 | 1 | 2'-OMe | 5.90 | 6370 | 9595 | 12370 |
| 994950 | 2 | 2'-OMe | 12.19 | 2219 | 2146 | 52 |
| 994951 | 3 | 2'-OMe | 6.72 | 6275 | 10555 | 2991 |

For the in vivo activity study in the table below, three BALB/C mice per modified oligonucleotide were administered 2.5, 7.4, 22.2, 66.7, 200 mg/kg 147420 or 994950 by subcutaneous injection and sacrificed after 72 hours. Plasma levels of ALT were measured using an automated clinical chemistry analyzer. Increased ALT is indicative of acute liver toxicity. Cpt1a mRNA was detected using RT-qPCR as described above.

TABLE 40

In Vivo Toxicity of modified oligonucleotides complementary CPT1A

| | ALT (IU/L) | | | | |
|---|---|---|---|---|---|
| Compound Number | 2.5 mg/kg | 7.4 mg/kg | 22.2 mg/kg | 66.7 mg/kg | 200 mg/kg |
| 147420 | 51 | 23 | 23 | 106 | 7794 |
| 994950 | 25 | 25 | 21 | 23 | 53 |

TABLE 41

In Vivo Activity of modified oligonucleotides complementary CPT1A

| | CPT1 mRNA (% Control) | | | | |
|---|---|---|---|---|---|
| Compound Number | 2.5 mg/kg | 7.4 mg/kg | 22.2 mg/kg | 66.7 mg/kg | 200 mg/kg |
| 147420 | 115.9 | 93.1 | 78.2 | 33.7 | 4.6 |
| 994950 | 116.0 | 117.2 | 105.6 | 55.9 | 21.9 |

TABLE 42

In Vivo Dose-response of Tnfrsf10b mRNA upon treatment with modified oligonucleotides

| | Tnfrsf10b mRNA (% Control) | | | | |
|---|---|---|---|---|---|
| Compound Number | 2.5 mg/kg | 7.4 mg/kg | 22.2 mg/kg | 66.7 mg/kg | 200 mg/kg |
| 147420 | 132 | 141 | 162 | 2341 | 8622 |
| 994950 | 119 | 133 | 125 | 153 | 1026 |

TABLE 43

In Vivo Dose-response of P21 mRNA upon treatment with modified oligonucleotides

| | P21 mRNA (% Control) | | | | |
|---|---|---|---|---|---|
| Compound Number | 2.5 mg/kg | 7.4 mg/kg | 22.2 mg/kg | 66.7 mg/kg | 200 mg/kg |
| 147420 | 141 | 94 | 240 | 4305 | 15334 |
| 994950 | 105 | 89 | 103 | 208 | 2413 |

Example 18 Effect of 2'-OMe Modification in Modified Oligonucleotides Complementary to Factor XI Modified oligonucleotides were synthesized as indicated in the table below. The compounds have the sugar motif kkk-d(10)-kkk ("parent") or kkk-d-m-d(8)-kkk, where "k" represents a cEt, "d" represents an unmodified, 2'-β-D-deoxyribosyl sugar moiety, and "m" represents a 2'-OMe-ribofuranosyl sugar moiety. For sequences with a Tat position 5 (from the 5' end) in the parent kkk-d(10)-kkk oligonucleotide, the kkk-d-m-d(8)-kkk contains a 2'-OMe modified U at this position. For sequences with a $^m$C at position 5 (from the 5' end) in the kkk-d(10)-kkk oligonucleotide, the kkk-d-m-d(8)-kkk contains a 2'-OMe modified C at this position, lacking the 5-Me group. Each internucleoside linkage is a phosphorothioate internucleoside linkage.

For the in vitro activity study in the table below, primary mouse hepatocytes were isolated from male balb/c mice and transfected with 0.9, 2.7, 8.2, 24.7, 74.0, 222, 667, or 2,000 nM modified oligonucleotide. After 24 hrs, mRNA was harvested and analyzed for FXI and RAPTOR as described above.

For the in vivo toxicity study in the table below, two male BALB/C mice per modified oligonucleotide were administered 150 mg/kg modified oligonucleotide by subcutaneous injection and sacrificed 72 hours later. One animal was administered an injection of saline as a control. Plasma levels of ALT was measured using an automated clinical chemistry analyzer. Increased ALT is indicative of acute liver toxicity.

For a subset of compounds, on-target activity was measured in the liver. RNA was isolated from the liver and measured by RT-qPCR using the primer probe set RTS2898, described in Example 4 above. Results were normalized with Ribogreen® and are reported normalized to PBS-treated animals.

TABLE 44

Sequences

| kkk-d(10)-kkk compound ID | kkk-d-m-d(8)-kkk compound ID | Sequence (5'-3') | SEQ ID NO |
|---|---|---|---|
| 464917 | 982034 | GTCTGTGCATCTCTCC | 22 |
| 464924 | | GTTATTGTGGTTGGCG | 81 |
| | 1133247 | GTTAUTGTGGTTGGCG | 133 |
| 465156 | | ATTCTGTGTGCACTGC | 82 |
| | 1133310 | ATTCUGTGTGCACTGC | 134 |
| 465162 | 1133316 | TCTTGTCTGACATTCT | 83 |
| 465163 | 1133317 | TTTTGTGTCTTCTGTA | 84 |
| 465172 | | CTGTTTGAGTTTTCTC | 85 |
| | 1133326 | CTGTUTGAGTTTTCTC | 135 |
| 465174 | 1133328 | CAAAGTGATACCAGTT | 86 |
| 465175 | | AATCTTCCAGGGCCAC | 87 |
| | 1133329 | AATCUTCCAGGGCCAC | 136 |
| 465176 | | TCATTTCTATGGAATA | 88 |
| | 1133330 | TCATUTCTATGGAATA | 137 |
| 465178 | 1133332 | GTCAGTATCCCAGTGT | 89 |
| 465179 | 1133333 | GGTTACAGTGGAAGAG | 90 |
| 465181 | 1133335 | TCTGGGTGTTCTTACG | 91 |
| 465186 | 1133340 | TTTCCTTGAGTAGTAG | 92 |
| 465187 | 1133341 | TCTCCTTGCTGTATTT | 93 |

TABLE 45

Activity and Toxicity of Modified oligonucleotides complementary to Factor XI

| Compound ID | altered nucleotide position in central region | sugar modification of altered nucleotide | in vitro FXI IC$_{50}$ (nM) | in vitro RAPTOR IC$_{50}$ (nM) | Relative Caspase Activation (% Control) @20 μM | p21 @150 mg/kg | FXI @ 10 mg/kg | ALT @ 150 mg/kg (IU/L) |
|---|---|---|---|---|---|---|---|---|
| 464917 | n/a | n/a | 101 | 44 | 700 | death | 25.4 | death |
| 982034 | 2 | 2'-OMe | 221 | 119 | 122 | 31922 | 40.8 | 13172 |
| 464924 | n/a | n/a | 115 | >2000 | 332 | 19340 | 8.6 | 5365 |
| 1133247 | 2 | 2'-OMe | 189 | >2000 | 190 | 753 | 12.1 | 33 |
| 465156 | n/a | n/a | 98 | 129 | 934 | 82279 | 14.4 | 24858 |
| 1133310 | 2 | 2'-OMe | 354 | 465 | 603 | 127 | 14.7 | 7034 |
| 465162 | n/a | n/a | 99 | >2000 | 758 | death | 15.1 | death |
| 1133316 | 2 | 2'-OMe | 144 | >2000 | 189 | 4660 | 34.2 | 60 |
| 465163 | n/a | n/a | 163 | >2000 | 115 | 34117 | 41.5 | 2347 |
| 1133317 | 2 | 2'-OMe | 272 | >2000 | 67 | 11844 | 79.4 | 478 |
| 465172 | n/a | n/a | 106 | >2000 | 429 | 512 | 57.6 | 23 |
| 1133326 | 2 | 2'-OMe | 176 | >2000 | 157 | 237 | 64.8 | 20 |
| 465174 | n/a | n/a | 69 | >2000 | 130 | 276 | 21.7 | 21 |
| 1133328 | 2 | 2'-OMe | 393 | >2000 | 113 | 167 | 33.8 | 23 |
| 465175 | n/a | n/a | 50 | 125 | 523 | 6957 | 37.8 | 1564 |
| 1133329 | 2 | 2'-OMe | 99 | 170 | 501 | 1564 | 59.8 | 60 |
| 465176 | n/a | n/a | 111 | >2000 | 219 | 344 | 98.6 | 27 |
| 1133330 | 2 | 2'-OMe | 89 | >2000 | 135 | 190 | 95.1 | 22 |
| 465178 | n/a | n/a | 11 | 115 | 364 | 900086 | 8.1 | 13168 |
| 1133332 | 2 | 2'-OMe | 24 | 1653 | 247 | 5982 | 27.0 | 75 |
| 465179 | n/a | n/a | 74 | >2000 | 188 | 4046 | 23.0 | 344 |
| 1133333 | 2 | 2'-OMe | 82 | >2000 | 102 | 122 | 62.4 | 23 |
| 465181 | n/a | n/a | 75 | 1571 | 487 | 17469 | 25.4 | 7087 |
| 1133335 | 2 | 2'-OMe | 56 | >2000 | 214 | 929 | 61.7 | 26 |
| 465186 | n/a | n/a | 75 | >2000 | 200 | 42551 | 17.3 | 3709 |
| 1133340 | 2 | 2'-OMe | 208 | >2000 | 125 | 513 | 42.8 | 34 |
| 465187 | n/a | n/a | 35 | 475 | 393 | 778834 * | 10.4 | 11752 * |
| 1133341 | 2 | 2'-OMe | 28 | >2000 | 167 | 1984 | 38.6 | 36 |

*½ animals were found dead

Example 19 Effect of 2'-OMe Incorporation on Toxicity of Modified Oligonucleotides Complementary to HDAC2

Modified oligonucleotides were synthesized as indicated in the table below. The compounds have the sugar motif kkk-d(10)-kkk ("parent") or kkk-d-m-d(8)-kkk, where "k" represents a cEt, "d" represents an unmodified, 2'-β-D-deoxyribosyl sugar moiety, and "m" represents a 2'-OMe-β-D-ribofuranosylsugar moiety. For sequences with a T at position 5 (from the 5' end) in the parent kkk-d(10)-kkk oligonucleotide, the kkk-d-m-d(8)-kkk contains a 2'-OMe modified U at this position. For sequences with a $^mC$ at position 5 (from the 5' end) in the kkk-d(10)-kkk oligonucleotide, the kkk-d-m-d(8)-kkk contains a 2'-OMe modified C at this position, lacking the 5-Me group. Each internucleoside linkage is a phosphorothioate internucleoside linkage.

For the in vitro activity study in the table below, primary mouse hepatocytes were isolated from male balb/c mice and transfected with 0.9, 2.7, 8.2, 24.7, 74.0, 222, 667, or 2,000 nM modified oligonucleotide. After 24 hrs, mRNA was harvested and analyzed for HDAC2 and RAPTOR as described above. For the in vivo toxicity study in the table below, two male BALB/C mice per modified oligonucleotide were administered 10 or 150 mg/kg modified oligonucleotide by subcutaneous injection and sacrificed 72 hours later. One animal was administered an injection of saline as a control. Plasma levels of ALT was measured using an automated clinical chemistry analyzer. Increased ALT is indicative of acute liver toxicity.

For a subset of compounds, on-target activity was measured in the liver. RNA was isolated from the liver and measured by RT-qPCR using the primer probe set RTS3500 described above in Example 13. Results were normalized with Ribogreen® and are reported normalized to PBS-treated animals.

TABLE 46

| | Sequences | | |
|---|---|---|---|
| kkk-d(10)-kkk compound ID | kkk-d-m-d(8)-kkk compound ID | Sequence (5'-3') | SEQ ID NO |
| 545984 | 1133060 | TTGCCAATATCACCAT | 94 |
| 545996 | | CAACUGAACCACCCGT | 95 |
| | 1133066 | CAACTGAACCACCCGT | 138 |
| 546004 | 1133070 | GCACAATATCATTAAC | 96 |
| 546009 | 1132933 | GACTCTCTGATGATAC | 97 |
| 546023 | 1132940 | CTATACCATCTCTCAT | 98 |
| 546024 | 1133080 | CATCATCTATACCATC | 99 |
| 546034 | 1133085 | ACACATTTAGCATGAC | 100 |
| 546045 | | ATTATATGGCAACTCA | 101 |
| | 1132951 | ATTAUATGGCAACTCA | 139 |
| 546049 | 1132953 | GACTAATATGCAGTTT | 102 |
| 546075 | 1132966 | GTCAAATTCAAGGGTT | 103 |
| 546095 | 1132976 | CATAAAGCATGGTGGA | 104 |
| 546108 | 1133122 | TAGTCTCTGTCAGTTA | 105 |
| 546109 | 1132983 | GTACCTATAGTCTCTG | 106 |
| 546110 | 1133123 | TCATGTACCTATAGTC | 107 |
| 546112 | 1133124 | TCTTAATTTCATGTAC | 108 |
| 546118 | 1133127 | ACCCTCAAGTCTCCTG | 109 |

TABLE 47

In vitro Activity and Toxicity of Modified oligonucleotides complementary to HDAC2

| Compound ID | altered nucleotide position in central region | sugar modification of altered nucleotide | in vitro HDAC 2 IC$_{50}$ (nM) | in vitro RAPTOR IC$_{50}$ (nM) | Relative Caspase Activation (% Control) @20 μM |
|---|---|---|---|---|---|
| 546009 | n/a | n/a | 44 | 773 | 632 |
| 1132933 | 2 | 2'-OMe | 89 | >2000 | 193 |
| 546023 | n/a | n/a | 79 | 1643 | 825 |
| 1132940 | 2 | 2'-OMe | 156 | >2000 | 980 |
| 546045 | n/a | n/a | 72 | 460 | 469 |
| 1132951 | 2 | 2'-OMe | 98 | >2000 | 326 |
| 546049 | n/a | n/a | 82 | >2000 | 127 |
| 1132953 | 2 | 2'-OMe | 144 | >2000 | 132 |
| 546075 | n/a | n/a | 81 | >2000 | 149 |
| 1132966 | 2 | 2'-OMe | 135 | >2000 | 143 |
| 546095 | n/a | n/a | 78 | >2000 | 126 |
| 1132976 | 2 | 2'-OMe | 128 | >2000 | 98 |
| 546109 | n/a | n/a | 30 | >2000 | 396 |
| 1132983 | 2 | 2'-OMe | 44 | >2000 | 117 |
| 545984 | n/a | n/a | 89 | 452 | 1235 |
| 1133060 | 2 | 2'-OMe | 126 | >2000 | 270 |
| 545996 | n/a | n/a | 297 | >2000 | 776 |
| 1133066 | 2 | 2'-OMe | 111 | >2000 | 327 |
| 546004 | n/a | n/a | 181 | >2000 | 124 |
| 1133070 | 2 | 2'-OMe | 164 | >2000 | 90 |
| 546024 | n/a | n/a | 85 | >2000 | 124 |
| 1133080 | 2 | 2'-OMe | 45 | >2000 | 123 |
| 546034 | n/a | n/a | 125 | >2000 | 107 |
| 1133085 | 2 | 2'-OMe | 125 | >2000 | 104 |
| 546108 | n/a | n/a | 21 | 144 | 1265 |
| 1133122 | 2 | 2'-OMe | 34 | >2000 | 176 |
| 546110 | n/a | n/a | 17 | >2000 | 82 |
| 1133123 | 2 | 2'-OMe | 30 | >2000 | 95 |
| 546112 | n/a | n/a | 178 | >2000 | 106 |
| 1133124 | 2 | 2'-OMe | 106 | >2000 | 98 |
| 546118 | n/a | n/a | 6 | 181 | 425 |
| 1133127 | 2 | 2'-OMe | 11 | >2000 | 158 |

TABLE 48

In vivo Activity and Toxicity of Modified oligonucleotides complementary to HDAC2

| Compound ID | HDAC2 @ 10 mg/kg | HDAC2 @ 150 mg/kg | P21 mRNA @ 150 mg/kg | Tnfrsf10b @ 150 mg/kg | ALT @ 150 mg/kg (IU/L) |
|---|---|---|---|---|---|
| 546009 | 22 | 7.5 | 5739 | 7162 | 14907 |
| 1132933 | 40 | 7.5 | 98 | 176 | 31 |
| 546023 | 57 | 9.9 | 1586 | 754 | 820 |
| 1132940 | 61 | 12.7 | 1348 | 565 | 224 |
| 546045 | 68 | 17.2 | 5601 | 2362 | 1031 |
| 1132951 | 60 | 15.3 | 1726 | 970 | 183 |
| 546049 | 50 | 8.9 | 294 | 133 | 29 |

TABLE 48-continued

In vivo Activity and Toxicity of Modified oligonucleotides complementary to HDAC2

| Compound ID | HDAC2 @ 10 mg/kg | HDAC2 @ 150 mg/kg | P21 mRNA @ 150 mg/kg | Tnfrsf10b @ 150 mg/kg | ALT @ 150 mg/kg (IU/L) |
|---|---|---|---|---|---|
| 1132953 | 71 | 15.2 | 282 | 150 | 27 |
| 546075 | 71 | 16.2 | 282 | 232 | 21 |
| 1132966 | 61 | 27.7 | 741 | 621 | 86 |
| 546095 | 39 | 12.7 | 3303 | 2314 | 1063 |
| 1132976 | 50 | 15.3 | 685 | 512 | 94 |
| 546109 | 29 | 4.3 | 684 | 706 | 182 |
| 1132983 | 37 | 5.2 | 217 | 190 | 34 |
| 545984 | 31 | 4.9 | 14070 | 10327 | 37277 |
| 1133060 | 42 | 9.0 | 183 | 138 | 39 |
| 545996 | 56 | 14.7 | 613 | 458 | 433 |
| 1133066 | 60 | 24.2 | 215 | 156 | 28 |
| 546004 | 64 | 13.4 | 499 | 203 | 35 |
| 1133070 | 69 | 17.6 | 286 | 192 | 30 |
| 546024 | 34 | 6.2 | 381 | 169 | 25 |
| 1133080 | 41 | 8.1 | 452 | 201 | 26 |
| 546034 | 52 | 7.5 | 181 | 140 | 32 |
| 1133085 | 68 | 10.6 | 127 | 143 | 27 |
| 546108 | 3 | n.d. | n.d. | n.d. | death |
| 1133122 | 7 | 1.9 | 1524 | 1353 | 131 |
| 546110 | 15 | 6.2 | 23642 | 6298 | 5132 |
| 1133123 | 35 | 3.3 | 221 | 155 | 29 |
| 546112 | 52 | 14.3 | 817 | 350 | 34 |
| 1133124 | 59 | 13.9 | 822 | 571 | 29 |
| 546118 | 13 | 5.7 | 3853 | 3854 | 3894 |
| 1133127 | 15 | 4.8 | 470 | 473 | 139 |

For the FOB scores reported in the table below, mice per group were administered 100 μg modified oligonucleotide by intracerebroventricular (ICV) injection. At 3 hours and 2 weeks post-injection, mice were evaluated according to 7 different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing For each of the 7 criteria, a mouse was given a subscore of 0 if it met the criteria and 1 if it did not. After all 7 criteria were evaluated, the FOB scores were summed for each mouse and averaged within each treatment group. The results are presented in the table below.

Two weeks after injection of modified oligonucleotide, mice were sacrificed and levels of HDAC, p21 and Aifl were measured in the cortex and the spinal cord by RT-PCR as described above. Aifl is a marker for inflammation. Results are presented below relative to control animals.

TABLE 48b

In vivo Activity and Toxicity of Modified oligonucleotides complementary to HDAC2

| Compound ID | 3 hr FOB | 2 week FOB | HDAC mRNA Cortex | HDAC mRNA Spinal Cord | p21 mRNA Cortex | p21 mRNA Spinal Cord | Aif1 mRNA Cortex | Aif1 mRNA Spinal cord |
|---|---|---|---|---|---|---|---|---|
| 546009 | 5.5 | 5.5 | n.d. | n.d. | n.d. | n.d. | n.d. | n.d. |
| 1132933 | 3.5 | 0 | 45.3 | 45.3 | 148 | 227 | 96 | 129 |
| 546023 | 0 | 0 | 36.3 | 31.3 | 120 | 144 | 117 | 156 |
| 1132940 | 0 | 0 | 59.2 | 39.3 | 135 | 166 | 94 | 174 |
| 546045 | 4.5 | 0 | 43.4 | 39.2 | 136 | 284 | 113 | 161 |
| 1132951 | 3 | 0 | 61.4 | 42.6 | 128 | 200 | 86 | 121 |
| 546049 | 1 | 0 | 95.3 | 68.8 | 111 | 116 | 90 | 110 |
| 1132953 | 3 | 0 | 67.1 | 47.8 | 126 | 138 | 82 | 103 |
| 546075 | 7 | 7 | n.d. | n.d. | n.d. | n.d. | n.d. | n.d. |
| 1132966 | 2.5 | 0 | 39.9 | 40.9 | 129 | 174 | 116 | 130 |
| 546095 | 5.5 | 0 | 66.7 | 44.2 | 124 | 321 | 90 | 189 |
| 1132976 | 6 | 0 | 55 | 36 | 132 | 427 | 87 | 248 |
| 546109 | 7 | 7 | n.d. | n.d. | n.d. | n.d. | n.d. | n.d. |
| 1132983 | 7 | 7 | n.d. | n.d. | n.d. | n.d. | n.d. | n.d. |
| 545984 | 2.5 | 6.5 | n.d. | n.d. | n.d. | n.d. | n.d. | n.d. |
| 1133060 | 1 | 0 | 71.0 | 39.8 | 107 | 130 | 92 | 112 |
| 545996 | 3 | 0 | 59.1 | 48.9 | 122 | 220 | 104 | 171 |
| 1133066 | 7 | 7 | n.d. | n.d. | n.d. | n.d. | n.d. | n.d. |
| 546004 | 0 | 0 | 55.3 | 47.6 | 136 | 261 | 116 | 176 |
| 1133070 | 0 | 0 | 58.7 | 50.0 | 127 | 173 | 81 | 99 |
| 546024 | 6.5 | 0 | 20.2 | 20.5 | 134 | 211 | 115 | 140 |
| 1133080 | 1 | 0 | 34.6 | 18.4 | 109 | 139 | 88 | 112 |
| 546034 | 3 | 0 | 58.9 | 46.6 | 96 | 149 | 98 | 146 |
| 1133085 | 3 | 0 | 79.0 | 42.0 | 114 | 126 | 101 | 137 |
| 546108 | 2 | 6.5 | n.d. | n.d. | n.d. | n.d. | n.d. | n.d. |
| 1133122 | 3.5 | 1 | 25.4 | 17.7 | 97 | 166 | 120 | 178 |
| 546110 | 2.5 | 3 | 55.0 | 23.5 | 88 | 294 | 93 | 342 |
| 1133123 | 0 | 0 | 57.4 | 49.8 | 112 | 149 | 85 | 105 |
| 546112 | 3 | 0 | 68.5 | 46.6 | 108 | 119 | 97 | 420 |
| 1133124 | 1.5 | 0 | 70.8 | 52.8 | 122 | 107 | 157 | 873 |
| 546118 | 7 | 7 | n.d. | n.d. | n.d. | n.d. | n.d. | n.d. |
| 1133127 | 7 | 7 | n.d. | n.d. | n.d. | n.d. | n.d. | n.d. |

Example 20 Incorporation of 2'-OMe at Various Positions

Modified oligonucleotides were synthesized with kkk-m-d(9)-kkk, kkk-d-m-d(8)-kkk, kkk-dd-m-d(7)-kkk or kkk-d(3)-m-d(6)-kkk sugar motifs, respectively, where "m" represents a 2'-OMe-β-D-ribofuranosylsugar moiety, "k" represents a cEt, and "d" represents an unmodified, 2'-β-D-deoxyribosyl sugar moiety. In certain instances, 2'-OMeU replaces 2'-deoxyT. These modified oligonucleotides were compared to the otherwise identical modified oligonucleotide lacking an altered nucleotide in the central region, a 3-10-3 cEt modified oligonucleotide, containing three cEt nucleosides in each of the 5' and 3' regions and 10 unmodified DNA nucleosides in the central region. Each internucleoside linkage is a phosphorothioate internucleoside linkage. The compounds in the table below are 100% complementary to mouse CXCL12, GENBANK NT_039353.7 truncated from 69/430,515 to 69/445,350 (SEQ ID NO: 1), at position 6877 to 6892.

TABLE 49

Modified Oligonucleotides

| Compound ID | altered nucleotide position in central region | sugar moiety of altered nucleotide | Chemistry Notation | SEQ ID NO |
|---|---|---|---|---|
| 558807 | n/a | n/a | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 1061877 | 1 | 2'-OMe | $G_{ks}{}^mC_{ks}A_{ks}U_{ms}G_{ds}T_{ds}T_{ds}{}^mC_{ds}T_{ds}{}^mC_{ds}A_{ds}{}^mC_{ds}A_{ds}T_{ks}T_{ks}A_k$ | 19 |
| 936053 | 2 | 2'-OMe | $G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_k$ | 18 |
| 1061879 | 3 | 2'-OMe | $G_{ks}{}^mC_{ks}A_{ks}T_{ds}G_{ds}U_{ms}T_{ds}{}^mC_{ds}T_{ds}{}^mC_{ds}A_{ds}{}^mC_{ds}A_{ds}T_{ks}T_{ks}A_k$ | 20 |
| 1061981 | 4 | 2'-OMe | $G_{ks}{}^mC_{ks}A_{ks}T_{ds}G_{ds}T_{ds}U_{ms}{}^mC_{ds}T_{ds}{}^mC_{ds}A_{ds}{}^mC_{ds}A_{ds}T_{ks}T_{ks}A_k$ | 21 |
| 1244110 | 5 | 2'-OMe | $G_{ks}{}^mC_{ks}A_{ks}T_{ds}G_{ds}T_{ds}T_{ds}C_{ms}T_{ds}{}^mC_{ds}A_{ds}{}^mC_{ds}A_{ds}T_{ks}T_{ks}A_k$ | 18 |
| 1244111 | 6 | 2'-OMe | $G_{ks}mC_{ks}A_{ks}T_{ds}G_{ds}T_{ds}T_{ds}mC_{ds}U_{ms}mC_{ds}A_{ds}{}^mC_{ds}A_{ds}T_{ks}T_{ks}A_k$ | 39 |
| 1244112 | 7 | 2'-OMe | $G_{ks}{}^mC_{ks}A_{ks}T_{ds}G_{ds}T_{ds}T_{ds}{}^mC_{ds}T_{ds}C_{ms}A_{ds}{}^mC_{ds}A_{ds}T_{ks}T_{ks}A_k$ | 18 |
| 1244113 | 8 | 2'-OMe | $G_{ks}{}^mC_{ks}A_{ks}T_{ds}G_{ds}T_{ds}T_{ds}{}^mC_{ds}T_{ds}{}^mC_{ds}A_{ms}{}^mC_{ds}A_{ds}T_{ks}T_{ks}A_k$ | 18 |
| 1244114 | 9 | 2'-OMe | $G_{ks}{}^mC_{ks}A_{ks}T_{ds}G_{ds}T_{ds}T_{ds}{}^mC_{ds}T_{ds}{}^mC_{ds}A_{ds}C_{ms}A_{ds}T_{ks}T_{ks}A_k$ | 18 |
| 1244115 | 10 | 2'-OMe | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ms}T_{ks}T_{ks}A_k$ | 18 |

A subscript "d" indicates an unmodified, 2'-β-D-deoxyribosyl sugar moiety.
A subscript "m" indicates a 2'-O-methyl-β-D-ribofuranosyl sugar moiety.
A subscript "k" indicates a cEt.
A subscript "s" indicates a phosphorothioate internucleoside linkage..
A superscript "m" before a C indicates 5-methyl Cytosine.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2,222 nM, 6,667 nM, or 20,000 nM of modified oligonucleotide by electroporation and levels of p21 were measured by RT-qPCR as described in Example 1 above. The caspase assay was performed as described in Example 8 above in 3T3-L1 cells. Localization of p54nrb in HeLa cells was quantitated as described in Example 15.

TABLE 50

In vitro activity and toxicity of modified oligonucleotides complementary to CXCL12

| Compound ID | in vitro CXCL12 IC$_{50}$ (nM) | in vitro Caspase (% control) @ 20 µM | in vitro p21 (% control) @ 20 µM | % nucleolar p54nrb |
|---|---|---|---|---|
| 558807 | 47 | 641 | 307 | 92 |
| 1061877 | 13 | 519 | 266 | 43 |
| 936053 | 67 | 173 | 143 | 8 |
| 1061879 | 59 | 416 | 192 | 59 |
| 1061981 | 112 | 325 | 129 | 46 |
| 1244110 | 21 | 386 | 390 | 60 |
| 1244111 | 53 | 380 | 430 | 69 |
| 1244112 | 42 | 345 | 344 | 92 |
| 1244113 | 114 | 361 | 373 | 54 |
| 1244114 | 17 | 399 | 440 | 78 |
| 1244115 | 70 | 372 | 400 | 67 |

Example 21 Stereochemical Isomers of Nucleosides

Modified oligonucleotides containing modified nucleotides with various stereochemical configurations at positions 1', 3', and 5' of the 2'-deoxyfuranosyl sugar were synthesized. Amidites for the synthesis of β-L-DNA-containing nucleotides are commercially available (ChemGenes) and the synthesis of both α-L and β-L dT phosphoramidites has been reported (Morvan, *Biochem and Biophys Research Comm*, 172(2): 537-543, 1990). The altered nucleotides were contained within the central region of the oligonucleotide.

These modified oligonucleotides were compared to the otherwise identical modified oligonucleotide lacking a an altered nucleotide in the central region, 558807, described in Table 1, Example 1 above. The compounds in Table 51 each comprise a 5' wing and a 3' wing each consisting of three linked cEt nucleosides and a central region comprising nucleosides each comprising 2'β-D-deoxyribosyl sugar moieties aside from the altered nucleotide, as indicated. Each internucleoside linkage is a phosphodiester internucleoside linkage. The compounds in the table below are 100% complementary to mouse CXCL12, GENBANK NT_039353.7 truncated from 69/430,515 to 69/445,350 (SEQ ID NO: 1), at position 6877 to 6892.

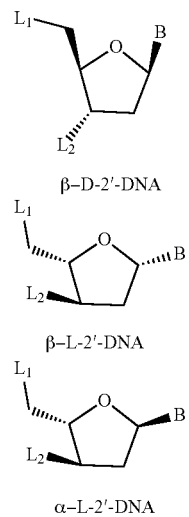

β–D-2'-DNA

β–L-2'-DNA

α–L-2'-DNA

B is any nucleobase and L$_1$ and L$_2$ are internucleoside linkages

TABLE 51 modified oligonucleotides with stereochemical modifications

| Compound ID | position of altered nucleotide in central region | stereochemical configuration of altered nucleotide | Chemistry Notation (5' to 3') | SEQ ID NO |
|---|---|---|---|---|
| 1215458 | 2 | β-L-DNA | G$_{ks}$$^m$C$_{ks}$A$_{ks}$T$_{ds}$[$_{β-L}$G$_{ds}$]T$_{ds}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 18 |
| 1215459 | 3 | β-L-DNA | G$_{ks}$$^m$C$_{ks}$A$_{ks}$T$_{ds}$G$_{ds}$[$_{β-L}$T$_{ds}$]T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 18 |
| 1215460 | 4 | β-L-DNA | G$_{ks}$$^m$C$_{ks}$A$_{ks}$T$_{ds}$G$_{ds}$T$_{ds}$[$_{β-L}$T$_{ds}$]$^m$C$_{ds}$T$_{ds}$$^m$C$_{ds}$A$_{ds}$$^m$C$_{ds}$A$_{ds}$T$_{ks}$T$_{ks}$A$_k$ | 18 |
| 1215461 | 3 | α-L-DNA | G$_{ks}$$^m$C$_{ks}$A$_{ks}$T$_{ds}$G$_{ds}$[$_{α-L}$T$_{ds}$]T$_{ds}$$^m$C$_{ds}$T$_{ds}$$^m$C$_{ds}$A$_{ds}$$^m$C$_{ds}$A$_{ds}$T$_{ks}$T$_{ks}$A$_k$ | 18 |
| 1215462 | 4 | α-L-DNA | G$_{ks}$$^m$C$_{ks}$A$_{ks}$T$_{ds}$G$_{ds}$T$_{ds}$[$_{α-L}$T$_{ds}$]$^m$C$_{ds}$T$_{ds}$$^m$C$_{ds}$A$_{ds}$$^m$C$_{ds}$A$_{ds}$T$_{ks}$T$_{ks}$A$_k$ | 18 |

A subscript "d" indicates an unmodified, 2'-β-D-deoxyribosyl sugar moiety.
A subscript "k" incicates a cEt.
A subscript "s" indicates a phosphorothioate internucleoside linkage.
[$_{β-L}$B$_{ds}$] indicates a modified β-L-DNA nucleotide with a 2'-deoxyribosyl moiety, a phosphorothioate linkage, and base B.
[$_{α-L}$B$_{ds}$] indicates a modified, a-L DNA nucleotide with a 2'-deoxyribosyl sugar moiety, a phosphorothioate linkage, and base B.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2,222 nM, 6,667 nM, or 20,000 nM of modified oligonucleotide by electroporation and levels of P21 and Gadd45a and Tnfrsf10b were measured by RT-qPCR as described in Example 1 above. The caspase assay was performed as described in Example 8 above in 3T3-L1 cells.

For the in vivo activity study in the tables below, 2 BALB/C mice per group were administered 1.8 mg/kg, 5.5 mg/kg, 16.7 mg/kg, 50 mg/kg, or 150 mg/kg doses of modified oligonucleotide, as indicated in the table below, by subcutaneous injection and sacrificed 72 hours later. For 558807, only 1.8 mg/kg, 5.5 mg/kg, and 16.7 mg/kg doses were tested for dose response, due to acute toxicity of higher doses. Liver mRNA was isolated an analyzed by RT-PCR as described in Example 1 above. Expression levels were normalized with Ribogreen® and are expressed relative to PBS-treated control mice.

TABLE 52

Activity and toxicity of modified oligonucleotides complementary CXCL12

| Compound ID | in vitro CXCL12 $IC_{50}$ (µM) | in vitro RAPTOR $IC_{50}$ (µM) | in vivo CXCL12 $ED_{50}$ (mg/kg) | ALT @ 50 mg/kg (IU/L) | ALT @ 150 mg/kg (IU/L) |
|---|---|---|---|---|---|
| PBS | n/a | n/a | n/a | 25 @ 0 mg/kg | |
| 558807 | 0.10 | 1 | 2.9 | n.d.** | |
| 1215458 | 0.41 | >20 | 11 | 32 | 42 |
| 1215459 | 0.44 | >20 | 13 | 31 | 37 |
| 1215460 | 0.41 | >20 | 13 | 29 | 43 |
| 1215461 | 0.14 | 3 | 2.8 | 1725 | 6301 |
| 1215462 | 0.13 | 3 | 3.6 | 45 | 3652 |

**558807 treatment at 16.7 mg/kg leads to an ALT of 586 IU/L; mice that are treated with 558807 at 150 mg/kg typically experience death before 72 hours post-treatment.

TABLE 53 in vitro Caspase Activation

| Compound ID | 27 nM | 80 nM | 250 nM | 740 nM | 2,222 nM | 6,667 nM | 20,000 nM |
|---|---|---|---|---|---|---|---|
| | | | Relative Caspase Activation (% Control) | | | | |
| 558807 | 106 | 113 | 117 | 169 | 250 | 396 | 343 |
| 1215458 | 81 | 88 | 98 | 95 | 74 | 78 | 95 |
| 1215459 | 96 | 88 | 111 | 98 | 98 | 81 | 102 |
| 1215460 | 89 | 98 | 96 | 111 | 91 | 113 | 130 |
| 1215461 | 90 | 94 | 89 | 117 | 142 | 201 | 250 |
| 1215462 | 96 | 93 | 95 | 119 | 150 | 192 | 240 |

TABLE 53b in vitro P21 Expression

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 558807 | 98 | 116 | 122 | 115 | 115 | 135 | 184 |
| 1215458 | 104 | 127 | 135 | 153 | 139 | 140 | 130 |
| 1215459 | 99 | 116 | 134 | 154 | 158 | 141 | 147 |
| 1215460 | 85 | 109 | 118 | 120 | 118 | 122 | 109 |
| 1215461 | 105 | 107 | 128 | 136 | 139 | 147 | 153 |
| 1215462 | 110 | 127 | 143 | 150 | 139 | 124 | 143 |

TABLE 53c in vitro Tnfrsf10b Expression

| Compound ID | 27 nM | 80 nM | 250 nM | 740 nM | 2,222 nM | 6,667 nM | 20,000 nM |
|---|---|---|---|---|---|---|---|
| | | | Expression level of Tnfrsf10b mRNA (% Control) | | | | |
| 558807 | 107 | 108 | 105 | 99 | 113 | 102 | 68 |
| 1215458 | 90 | 88 | 92 | 87 | 81 | 78 | 80 |
| 1215459 | 97 | 108 | 108 | 100 | 103 | 94 | 83 |
| 1215460 | 92 | 100 | 99 | 102 | 95 | 95 | 84 |
| 1215461 | 86 | 91 | 99 | 98 | 97 | 97 | 114 |
| 1215462 | 101 | 97 | 98 | 56 | 82 | 101 | 108 |

TABLE 53d

| | in vitro Gadd45a Expression | | | | | | |
|---|---|---|---|---|---|---|---|
| Compound ID | 27 nM | 80 nM | 250 nM | 740 nM | 2,222 nM | 6,667 nM | 20,000 nM |
| | Expression level of Gadd45a mRNA (% Control) | | | | | | |
| 558807 | 123 | 134 | 135 | 136 | 164 | 180 | 223 |
| 1215458 | 132 | 142 | 141 | 135 | 125 | 104 | 87 |
| 1215459 | 163 | 167 | 183 | 190 | 179 | 150 | 110 |
| 1215460 | 127 | 142 | 140 | 141 | 143 | 120 | 95 |
| 1215461 | 117 | 141 | 150 | 165 | 168 | 167 | 128 |
| 1215462 | 110 | 139 | 143 | 138 | 133 | 150 | 137 |

Example 22 Stereochemical Isomers of Nucleosides

Modified oligonucleotides containing β-L-DNA nucleotides (described in Example 21 above) at various positions were synthesized. These modified oligonucleotides were compared to compound 558807, described in Table 1, Example 1 above. Compound 558807 contains 5-methyl cytosine for all cytosine nucleosides, as do compounds 1215458-1215460 described in the table below. The compounds in Table 54 each comprise a 5' wing and a 3' wing each consisting of three linked cEt nucleosides and a central region comprising nucleosides each comprising 2'-β-D-deoxyribosyl sugar moieties aside from the altered nucleotide, as indicated. Each internucleoside linkage is a phosphodiester internucleoside linkage. Compounds 1244441-1244447 in the table below contain unmethylated cytosine in the central region of the compounds. The compounds in the table below are 100% complementary to mouse CXCL12, GENBANK NT_039353.7 truncated from 69/430,515 to 69/445,350 (SEQ ID NO: 1), at position 6877 to 6892.

TABLE 54 modified oligonucleotides with stereochemical modifications

| Compound ID | position of altered nucleotide in central region | stereochemical configuration of altered nucleotide | Chemistry Notation | SEQ ID NO |
|---|---|---|---|---|
| 1244441 | 1 | β-L-DNA | $G_{ks}{}^mC_{ks}A_{ks}[_{β-L}T_{ds}]G_{ds}T_{ds}T_{ds}C_{ds}T_{ds}C_{ds}A_{ds}C_{ds}A_{ds}A_{ks}T_{ks}A_k$ | 18 |
| 1215458 | 2 | β-L-DNA | $G_{ks}{}^mC_{ks}A_{ks}T_{ds}$ $[_{β-L}G_{ds}]T_{ds}T_{ds}{}^mC_{ds}T_{ds}{}^mC_{ds}A_{ds}{}^mC_{ds}A_{ds}T_{ks}T_{ks}A_k$ | 18 |
| 1215459 | 3 | β-L-DNA | $G_{ks}{}^mC_{ks}A_{ks}T_{ds}G_{ds}$ $[_{β-L}T_{ds}]T_{ds}{}^mC_{ds}T_{ds}{}^mC_{ds}A_{ds}{}^mC_{ds}A_{ds}T_{ks}T_{ks}A_k$ | 18 |
| 1215460 | 4 | β-L-DNA | $G_{ks}{}^mC_{ks}A_{ks}T_{ds}G_{ds}T_{ds}$ $[_{β-L}T_{ds}]{}^mC_{ds}T_{ds}{}^mC_{ds}A_{ds}{}^mC_{ds}A_{ds}T_{ks}T_{ks}A_k$ | 18 |
| 1244442 | 5 | β-L-DNA | $G_{ks}{}^mC_{ks}A_{ks}T_{ds}G_{ds}T_{ds}T_{ds}[_{β-L}C_{ds}]T_{ds}C_{ds}A_{ds}C_{ds}A_{ds}T_{ks}T_{ks}A_k$ | 18 |
| 1244443 | 6 | β-L-DNA | $G_{ks}{}^mC_{ks}A_{ks}T_{ds}G_{ds}T_{ds}T_{ds}C_{ds}[_{β-L}T_{ds}]C_{ds}A_{ds}C_{ds}A_{ds}T_{ks}T_{ks}A_k$ | 18 |
| 1244444 | 7 | β-L-DNA | $G_{ks}{}^mC_{ks}A_{ks}T_{ds}G_{ds}T_{ds}T_{ds}C_{ds}T_{ds}[_{β-L}C_{ds}]A_{ds}C_{ds}A_{ds}T_{ks}T_{ks}A_k$ | 18 |
| 1244445 | 8 | β-L-DNA | $G_{ks}mC_{ks}A_{ks}T_{ds}G_{ds}T_{ds}T_{ds}C_{ds}T_{ds}C_{ds}[_{β-L}A_{ds}]C_{ds}A_{ds}T_{ks}T_{ks}A_k$ | 18 |
| 1244446 | 9 | β-L-DNA | $G_{ks}{}^mC_{ks}A_{ks}T_{ds}G_{ds}T_{ds}T_{ds}C_{ds}T_{ds}C_{ds}A_{ds}[_{β-L}C_{ds}]A_{ds}T_{ks}T_{ks}A_k$ | 18 |
| 1244447 | 10 | β-L-DNA | $G_{ks}{}^mC_{ks}A_{ks}T_{ds}G_{ds}T_{ds}T_{ds}C_{ds}T_{ds}C_{ds}A_{ds}C_{ds}[_{β-L}A_{ds}]T_{ks}T_{ks}A_k$ | 18 |

A subscript "c" indicates a nucleoside comprising an n unmodified, 2'-β-D-deoxyribosyl sugar moiety.

A subscript "k" indicates a cEt.

A subscript "s" indicates a phosphorothioate internucleoside linkage.

[β-LB_ds] indicates a modified β-L-DNA nucleotide with a 2'-deoxyribosyl sugar moiety, a phosphorothioate linkage, and base B.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2, 222 nM, 6,667 nM, or 20,000 nM of modified oligonucleotide by electroporation and levels of P21 and Gadd45a and Tnfrsf10b were measured by RT-qPCR as described in Example 1 above. The caspase assay was performed as described in Example 8 above in 3T3-L1 cells. Localization of p54nrb in HeLa cells was quantitated as described in Example 15.

TABLE 55

In vitro activity and toxicity of modified oligonucleotides complementary to CXCL12

| Compound ID | in vitro CXCL12 $IC_{50}$ (nM) | in vitro Caspase (% control) @ 20 μM |
|---|---|---|
| 558807 | 0.029 | 321 |
| 1244441 | 0.471 | 108 |
| 1215458 | 0.200 | 104 |
| 1215459 | 0.191 | 111 |
| 1215460 | 0.130 | 133 |
| 1244442 | 0.134 | 185 |
| 1244443 | 0.083 | 279 |
| 1244444 | 0.109 | 213 |
| 1244445 | 0.198 | 249 |
| 1244446 | 0.127 | 243 |
| 1244447 | 0.080 | 333 |

Example 23 Stereochemical Isomers of Nucleosides

Modified oligonucleotides containing α-D-DNA nucleotides (see below) at various positions were synthesized. These modified oligonucleotides were compared to the otherwise identical modified oligonucleotide lacking an altered nucleotide in the central region. The compounds in Table 54 each comprise a 5' wing and a 3' wing each consisting of three linked cEt nucleosides and a central region comprising nucleosides each comprising 2'-β-D-deoxyribosyl sugar moieties aside from the altered nucleotide, as indicated. Each internucleoside linkage is a phosphodiester internucleoside linkage. The compounds in the table below are 100% complementary to mouse CXCL12, GENBANK NT_039353.7 truncated from 69/430,515 to 69/445,350 (SEQ ID NO: 1), at position 6877 to 6892.

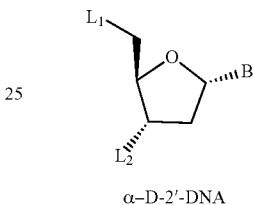

α–D-2'-DNA

TABLE 56 modified oligonucleotides with stereochemical modifications

| Compound ID | position of altered nucleotide in central region | stereochemical configuration of altered nucleotide | Chemistry Notation | SEQ ID NO |
|---|---|---|---|---|
| 1244458 | none | none | $G_{ks}{}^mC_{ks}A_{ks}T_{ds}G_{ds}T_{ds}T_{ds}C_{ds}T_{ds}C_{ds}A_{ds}C_{ds}A_{ds}T_{ds}T_{ds}A_k$ | 18 |
| 1244448 | 1 | α-D-DNA | $G_{ks}{}^mC_{ks}A_{ks}T_{ds}[_{\alpha\text{-}D}T_{ds}]G_{ds}T_{ds}T_{ds}C_{ds}T_{ds}C_{ds}A_{ds}C_{ds}A_{ds}T_{ks}T_{ks}A_k$ | 18 |
| 1244449 | 2 | α-D-DNA | $G_{ks}{}^mC_{ks}A_{ks}T_{ds}[_{\alpha\text{-}D}G_{ds}]T_{ds}T_{ds}C_{ds}T_{ds}C_{ds}A_{ds}C_{ds}A_{ds}T_{ks}T_{ks}A_k$ | 18 |
| 1244450 | 3 | α-D-DNA | $G_{ks}{}^mC_{ks}A_{ks}T_{ds}G_{ds}[_{\alpha\text{-}D}T_{ds}]T_{ds}C_{ds}T_{ds}C_{ds}A_{ds}C_{ds}A_{ds}T_{ks}T_{ks}A_k$ | 18 |
| 1244451 | 4 | α-D-DNA | $G_{ks}{}^mC_{ks}A_{ks}T_{ds}G_{ds}T_{ds}[_{\alpha\text{-}D}T_{ds}]C_{ds}T_{ds}C_{ds}A_{ds}C_{ds}A_{ds}T_{ks}T_{ks}A_k$ | 18 |
| 1244452 | 5 | α-D-DNA | $G_{ks}{}^mC_{ks}A_{ks}T_{ds}G_{ds}T_{ds}T_{ds}[_{\alpha\text{-}D}C_{ds}]T_{ds}C_{ds}A_{ds}C_{ds}A_{ds}T_{ks}T_{ks}A_k$ | 18 |
| 1244453 | 6 | α-D-DNA | $G_{ks}{}^mC_{ks}A_{ks}T_{ds}G_{ds}T_{ds}T_{ds}C_{ds}[_{\alpha\text{-}D}T_{ds}]C_{ds}A_{ds}C_{ds}A_{ds}T_{ks}T_{ks}A_k$ | 18 |
| 1244454 | 7 | α-D-DNA | $G_{ks}{}^mC_{ks}A_{ks}T_{ds}G_{ds}T_{ds}T_{ds}C_{ds}T_{ds}[_{\alpha\text{-}D}C_{ds}]A_{ds}C_{ds}A_{ds}T_{ks}T_{ks}A_k$ | 18 |
| 1244455 | 8 | α-D-DNA | $G_{ks}{}^mC_{ks}A_{ks}T_{ds}G_{ds}T_{ds}T_{ds}C_{ds}T_{ds}C_{ds}[_{\alpha\text{-}D}A_{ds}]C_{ds}A_{ds}T_{ks}T_{ks}A_k$ | 18 |
| 1244456 | 9 | α-D-DNA | $G_{ks}{}^mC_{ks}A_{ks}T_{ds}G_{ds}T_{ds}T_{ds}C_{ds}T_{ds}C_{ds}A_{ds}[_{\alpha\text{-}D}C_{ds}]A_{ds}T_{ks}T_{ks}A_k$ | 18 |
| 1244457 | 10 | α-D-DNA | $G_{ks}{}^mC_{ks}A_{ks}T_{ds}G_{ds}T_{ds}T_{ds}C_{ds}T_{ds}C_{ds}A_{ds}C_{ds}[_{\alpha\text{-}D}C_{ds}]T_{ks}T_{ks}A_k$ | 18 |

A subscript "d" indicates a nucleoside comprising an n unmodified, 2'-β-D-deoxyribosyl sugar moiety.
A subscript "k" indicates a cEt.
A subscript "s" indicates a phosphorothioate internucleoside linkage.
[$_{\alpha\text{-}D}$-B$_{ds}$] indicates a modified, α-D-DNA nucleotide with a 2'-deoxyribosyl sugar moiety, a phosphorothioate linkage, and base B.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2, 222 nM, 6,667 nM, or 20,000 nM of modified oligonucleotide by electroporation and levels of p21 were measured by RT-qPCR as described in Example 1 above. The caspase assay was performed as described in Example 8 above in 3T3-L1 cells. Localization of p54nrb in HeLa cells was quantitated as described in Example 15.

TABLE 57

In vitro activity and toxicity of modified oligonucleotides complementary CXCL12

| Compound ID | in vitro CXCL12 $IC_{50}$ (nM) | in vitro Caspase (% control) @ 20 μM | in vitro p21 (% control) @ 20 μM | % nucleolar p54nrb |
|---|---|---|---|---|
| 1244458 | 19 | 785 | 327 | 86 |
| 1244448 | 35 | 269 | 135 | 66 |
| 1244449 | 169 | 111 | 101 | 8 |
| 1244450 | 103 | 96 | 169 | 11 |
| 1244451 | 45 | 261 | 206 | 78 |
| 1244452 | 393 | 295 | 146 | 83 |
| 1244453 | 80 | 417 | 255 | 92 |
| 1244454 | 512 | 287 | 240 | 65 |
| 1244455 | 125 | 409 | 310 | 83 |
| 1244456 | 247 | 233 | 269 | 96 |
| 1244457 | 31 | 854 | 400 | 100 |

Example 24 4'-methyl and Xylo DNA

Modified oligonucleotides containing an altered nucleotide with a 4'-methyl modified sugar moiety or a 2'-deoxy-β-D-xylofuranosyl (2'deoxy-β-D-XNA) sugar moiety at various positions were synthesized (see Table 58 below).

Synthesis of oligonucleotides comprising 2'deoxy-β-D-XNA nucleosides has been described previously (Wang, et. al., *Biochemistry*, 56(29): 3725-3732, 2017). Synthesis of oligonucleotides comprising 4'-methyl modified nucleosides has been described previously (e.g., Detmer et. al., *European J. Org. Chem*, 1837-1846, 2003). The compounds in Table 58 each comprise a 5' wing and a 3' wing each consisting of three linked cEt nucleosides and a central region comprising nucleosides each comprising 2'-β-D-deoxyribosyl sugar moieties aside from the altered nucleotide, as indicated. Each internucleoside linkage is a phosphodiester internucleoside linkage. These compounds were compared to a compound comprising a 2'-OMe modified sugar moiety at position 2 of the central region, 936053, described in Example 1 above. The compounds in the table below are 100% complementary to mouse CXCL12, GENBANK NT_039353.7 truncated from 69/430,515 to 69/445,350 (SEQ ID NO: 1), at position 6877 to 6892.

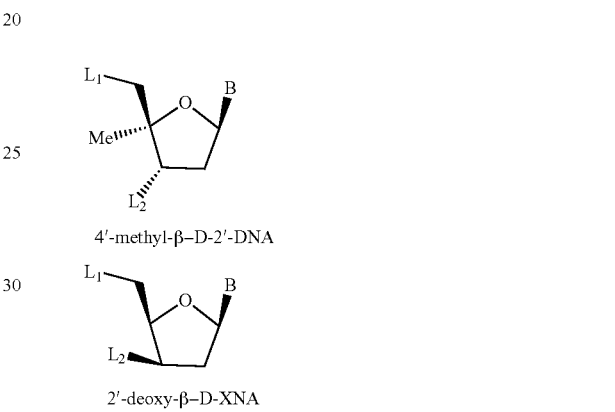

4'-methyl-β–D-2'-DNA

2'-deoxy-β–D-XNA

TABLE 58 modified oligonucleotides with stereochemical modifications

| Compound ID | position of altered nucleotide in central region | modification of altered nucleotide | Chemistry Notation | SEQ ID NO |
|---|---|---|---|---|
| 936053 | 2 | 2'-OMe | $G_{ks}{}^mC_{ks}A_{ks}T_{ds}G_{ms}T_{ds}T_{ds}{}^mC_{ds}T_{ds}mC_{ds}A_{ds}{}^mC_{ds}A_{ds}T_{ks}T_{ks}A_k$ | 18 |
| 1244461 | 3 | 4'-Me | $G_{ks}{}^mC_{ks}A_{ks}T_{ds}G_{ds}T_{[4m]s}T_{ds}{}^mC_{ds}T_{ds}{}^mC_{ds}A_{ds}{}^mC_{ds}A_{ds}T_{ks}T_{ks}A_k$ | 18 |
| 1244462 | 4 | 4'-Me | $G_{ks}{}^mC_{ks}A_{ks}T_{ds}G_{ds}T_{ds}T_{[4m]s}{}^mC_{ds}T_{ds}{}^mC_{ds}A_{ds}{}^mC_{ds}A_{ds}T_{ks}T_{ks}A_k$ | 18 |
| 1263776 | 3 | β-D-XNA | $G_{ks}{}^mC_{ks}A_{ks}T_{ds}G_{ds[\beta\text{-}D}T_{xs]}T_{ds}{}^mC_{ds}T_{ds}{}^mC_{ds}A_{ds}{}^mC_{ds}A_{ds}T_{ks}T_{ks}A_k$ | 18 |
| 1263777 | 4 | β-D-XNA | $G_{ks}{}^mC_{ks}A_{ks}T_{ds}G_{ds}T_{ds[\beta\text{-}D}T_{xs]}{}^mC_{ds}T_{ds}{}^mC_{ds}A_{ds}{}^mC_{ds}A_{ds}T_{ks}T_{ks}A_k$ | 18 |

A subscript "d" indicates an unmodified, 2'-β-D-deoxyribosyl sugar moiety.

A subscript "k" indicates a cEt.

A subscript "s" indicates a phosphorothioate internucleoside linkage.

A superscript "m" indicates 5-methyl Cytosine.

A subscript "[4m]" indicates a 4'-methyl-2'-β-D-deoxyribosyl sugar moiety.

$[\beta\text{-}D\text{-}B_{xs}]$ indicates a modified, β-D-XNA (xylo) nucleotide with a 2'-deoxyxylosyl sugar moiety, a phosphorothioate linkage, and base B.

For in vivo activity and toxicity studies, 3 BALB/c mice per group were administered 10 or 150 mg/kg modified oligonucleotide by subcutaneous injection and sacrificed after 72 hours. Four animals were administered saline to serve as a control. RT-PCR was performed as described in Example 1 to determine mRNA levels of CXCL12, P21, Tnfrsf10b, and Gadd45a. Plasma levels of ALT was measured using an automated clinical chemistry analyzer. Increased ALT is indicative of acute liver toxicity.

TABLE 59

In vivo activity and toxicity of modified oligonucleotides complementary to CXCL12

| Compound ID | in vivo CXCL12 @ 10 mg/kg (% control) | in vivo CXCL12 @ 150 mg/kg (% control) | in vivo P21 @ 150 mg/kg (% control) | in vivo Tnfrsf10b @ 150 mg/kg (% control) | in vivo Gadd45a @ 150 mg/kg (% control) | in vivo ALT @ 10 mg/kg (IU/L) | in vivo ALT @ 150 mg/kg (IU/L) |
|---|---|---|---|---|---|---|---|
| PBS | 100 | 100 | 100 | 100 | 100 | 26 (@ 0 mg/kg) | |
| 936053 | 37 | 13 | 175 | 448 | 216 | 23 | 83 |
| 1244461 | 22 | 5 | 2994 | 4663 | 1124 | 31 | 5080 |
| 1244462 | 30 | 7* | 1038 | 717* | 407* | 28 | 1789* |
| 1263776 | 19 | 11 | 4846 | 10686 | 1032 | 27 | 9234 |
| 1263777 | 13 | n.d. | n.d. | n.d. | n.d. | 58 | death |

*Value represents the average of 2 samples.

Example 25 Microscopy

Selected modified nucleotides described in the Examples above were tested for their effect on HeLa cells by microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells.

For experiments reported in the tables below, the number of cells with nucleolar p54nrb and the total number of cells in the images were counted and a percentage of cells with mislocalization of p54nrb was calculated. Where the same compound appears in multiple tables, these represent the results from independent experiments.

TABLE 60

Nucleolar mislocalization of p54nrb

| Compound ID | Cells with nucleolar p54nrb | Total cells | % cells with mislocalization |
|---|---|---|---|
| Mock | 0 | 74 | 0 |
| 558807 | 45 | 51 | 88 |

TABLE 61

Nucleolar mislocalization of p54nrb

| Compound ID | Sugar Motif | % cells with mislocalization | ALT @ 150 mg/kg (IU/L) |
|---|---|---|---|
| 464917 | kkk-d(10)-kkk | 75 | death |
| 982034 | kkk-d-m-(8)-kkk | <7 | 13,172 |
| 465175 | kkk-d(10)-kkk | 57 | 1,564 |
| 1133329 | kkk-d-m-(8)-kkk | 48 | 60 |
| 465181 | kkk-d(10)-kkk | 58 | 7,087 |
| 1133335 | kkk-d-m-(8)-kkk | <1 | 26 |
| 545984 | kkk-d(10)-kkk | 98 | 37,277 |
| 1133060 | kkk-d-m-(8)-kkk | 0 | 39 |

For experiments reported in the tables below, selected images were qualitatively analyzed and assigned a score of (−), indicating that no p54nrb mislocalization to the nucleolus was observed, or a score of (+) indicating that mislocalization of p54nrb to the nucleolus was observed in some cells, or (++) indicating that p54nrb mislocalization to the nucleolus was observed in most or all cells.

TABLE 62

Nucleolar mislocalization of p54nrb and correlation with toxicity

| Compound ID | Complementary mRNA | Mislocalization of p54nrb | ALT @ max dose* |
|---|---|---|---|
| 558807 | CXCL12 | ++ | death |
| 936049 | CXCL12 | ++ | 8,622 |
| 936053 | CXCL12 | − | 46 |
| 892826 | CXCL12 | − | 10,463 |
| 766677 | CXCL12 | − | 23 |
| 828911 | CXCL12 | − | 27 |
| 936051 | CXCL12 | + | death |
| 936052 | CXCL12 | − | 1,110 |
| 1070041 | CXCL12 | + | 96 |
| 1061314 | CXCL12 | − | 26 |
| 1061302 | CXCL12 | + | 2,253 |
| 1061303 | CXCL12 | − | 34 |
| 1061304 | CXCL12 | − | 52 |
| 1061305 | CXCL12 | − | 31 |
| 1076587 | CXCL12 | − | n.d. |
| 1076588 | CXCL12 | + | n.d. |
| 1069852 | CXCL12 | − | n.d. |
| 1061328 | CXCL12 | + | n.d. |
| 1061955 | CXCL12 | − | 86 |
| 1061964 | CXCL12 | − | n.d. |
| 1244441 | CXCL12 | − | n.d. |
| 1215458 | CXCL12 | − | n.d. |
| 1215459 | CXCL12 | − | n.d. |
| 1215460 | CXCL12 | − | n.d. |
| 1244442 | CXCL12 | − | n.d. |
| 1244443 | CXCL12 | + | n.d. |
| 1244444 | CXCL12 | ++ | n.d. |
| 1244445 | CXCL12 | ++ | n.d. |
| 1244446 | CXCL12 | ++ | n.d. |
| 1244447 | CXCL12 | ++ | n.d. |
| 464917 | FXI | + | 18,316 |
| 465977 | FXI | + | death |
| 483706 | FXI | + | 1,424 |
| 443919 | FXI | − | 68 |
| 820685** | FXI | − | 59 |
| 508031 | SOD1 | ++ | 16,317 |

TABLE 62-continued

Nucleolar mislocalization of p54nrb and correlation with toxicity

| Compound ID | Complementary mRNA | Mislocalization of p54nrb | ALT @ max dose* |
|---|---|---|---|
| 895154 | SOD1 | + | 206 |
| 895155 | SOD1 | − | 41 |
| 895156 | SOD1 | + | 1,242 |
| 508034 | SOD1 | + | 22,396 |
| 508037 | SOD1 | − | 20 |
| 529933 | SOD1 | − | 11 |

*Data presented in previous examples; maximum administered dose is 150 mg/kg for modified oligonucleotides complementary to CXCL12, 100 mg/kg for modified oligonucleotides complementary to SOD1, and 33 mg/kg for compounds complementary to FXI, except that the ALT for 820685 is at 100 mg/kg.

**820685 has the same sequence as 464917 and a sugar motif of kkk-m(10)-kkk.

Example 26 Nucleolar Mislocalization of p54nrb with Fluorescently-Labeled Modified Oligonucleotides Modified oligonucleotides described in the tables above were conjugated to Cy3 or FAM on the 3'-end via a phosphorothioate linker or on the 5'-end via a phosphorothioate linker to generate a compound comprising a conjugate group that comprises a fluorophore, resulting in a fluorescently labeled modified oligonucleotide. Fluorescently labeled modified oligonucleotides were incubated with HeLa cells at 200 nM for 2 hours and cells were imaged by fluorescent microscopy. Cellular protein p54nrb was stained by mP54 antibody (Santa Cruz Biotech, sc-376865) and DAPI was used to stain for the nucleus of cells. For experiments reported in the tables below, images were qualitatively analyzed and assigned a score of (−), indicating that no p54nrb mislocalization to the nucleolus was observed, or a score of (+) indicating that mislocalization of p54nrb to the nucleolus was observed in some cells, or (++) indicating that p54nrb mislocalization to the nucleolus was observed in most or all cells.

TABLE 63

Fluorescently Labeled Modified Oligonucleotides

| Unlabelled compound ID | Fluorescently-labelled compound ID | Chemistry notation for Fluorescently-labelled compound | SEQ ID NO: |
|---|---|---|---|
| 558807 | 925819 | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_{ks}$-Cy3 | 18 |
| 766676 | 925820 | $G_{ks}{}^mC_{ks}A_{ks}T_{dx}G_{ds}T_{ds}T_{ds}{}^mC_{ds}T_{ds}{}^mC_{ds}A_{ds}{}^mC_{ds}A_{ds}T_{ks}T_{ks}A_{ks}$-Cy3 | 18 |
| 766677 | 925821 | $G_{ks}{}^mC_{ks}A_{ks}T_{ds}G_{dx}T_{ds}T_{ds}{}^mC_{ds}T_{ds}{}^mC_{ds}A_{ds}{}^mC_{ds}A_{ds}T_{ks}T_{ks}A_{ks}$-Cy3 | 18 |
| 766678 | 925822 | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_{ks}$-Cy3 | 18 |
| 766679 | 925826 | $G_{ks}{}^mC_{ks}A_{ks}T_{ds}G_{ds}T_{ds}T_{dx}{}^mC_{ds}T_{ds}{}^mC_{ds}A_{ds}{}^mC_{ds}A_{ds}T_{ks}T_{ks}A_{ks}$-Cy3 | 18 |
| 766684 | 925824 | $G_{ks}{}^mC_{ks}A_{ks}T_{ds}G_{ds}T_{ds}T_{ds}{}^mC_{ds}T_{ds}{}^mC_{ds}A_{ds}{}^mC_{dx}A_{ds}T_{ks}T_{ks}A_{ks}$-Cy3 | 18 |
| 936049 | 958339 | Cy3-$G_{ks}{}^mC_{ks}A_{ks}U_{ms}G_{ds}T_{ds}T_{ds}{}^mC_{ds}T_{ds}{}^mC_{ds}A_{ds}{}^mC_{ds}A_{ds}T_{ks}T_{ks}A_{k}$ | 19 |
| 936053 | 958340 | Cy3-$G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_{k}$ | 18 |
| 892826 | 958341 | Cy3-$G_{ks}{}^mC_{ks}A_{ks}T_{ds}G_{ds}U_{ms}T_{ds}{}^mC_{ds}T_{ds}{}^mC_{ds}A_{ds}{}^mC_{ds}A_{ds}T_{ks}T_{ks}A_{k}$ | 20 |
| 558807 | 1189295 | FAM-$G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_{ks}$ | 18 |
| 1061955 | 1189310 | FAM-$G_{ks}{}^mC_{ks}A_{ks}T_{ds}I_{ds}T_{ds}T_{ds}{}^mC_{ds}T_{ds}{}^mC_{ds}A_{ds}{}^mC_{ds}A_{ds}T_{ks}T_{ks}A_{ks}$ | 30 |
| 766677 | 1215929 | FAM-$G_{ks}{}^mC_{ks}A_{ks}T_{ds}G_dxT_{ds}T_{ds}{}^mC_{ds}T_{ds}{}^mC_{ds}A_{ds}{}^mC_{ds}A_{ds}T_{ks}T_{ks}A_{ks}$ | 18 |
| 936053 | 1189369 | FAM-$G_{ks}{}^mC_{ks}A_{ks}T_{ds}GmsT_{ds}T_{ds}{}^mC_{ds}T_{ds}{}^mC_{ds}A_{ds}{}^mC_{ds}A_{ds}T_{ks}T_{ks}A_{k}$ | 18 |
| 942944 | 1215928 | FAM-$G_{ks}{}^mC_{ks}A_{ks}T_{ds}G_{ds}T_{ds}{}^{(R)-m}T_{ds}{}^mC_{ds}T_{ds}{}^mC_{ds}A_{ds}{}^mC_{ds}A_{ds}T_{ks}T_{ks}A_{k}$ | 18 |
| 464917 | 813223 | CY3-$G_{ks}T_{ks}{}^mC_{ks}T_{ds}G_{ds}T_{ds}G_{ds}{}^mC_{ds}A_{ds}T_{ds}{}^mC_{ds}T_{ds}{}^mC_{ds}T_{ks}{}^mC_{ks}{}^mC_{k}$ | 22 |
| 508031 | 828939 | Cy3-$T_{ks}G_{ks}A_{ks}G_{ds}G_{ds}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 482050 | 841864 | Cy3-$A_{ks}T_{ks}{}^mC_{ks}A_{ds}T_{ds}G_{ds}G_{ds}{}^mC_{ds}T_{ds}G_{ds}{}^mC_{ds}A_{ds}G_{ds}{}^mC_{ks}T_{ks}T_{k}$ | 24 |
| 449093 | 489982 | FAM-$T_{ks}T_{ks}{}^mC_{ks}A_{ds}G_{ds}T_{ds}{}^mC_{ds}A_{ds}T_{ds}G_{ds}A_{ds}{}^mC_{ds}T_{ds}T_{ks}{}^mC_{ks}{}^mC_{k}$ | 28 |
| 465178 | 869208 | Cy3-$G_{ks}T_{ks}{}^mC_{ks}A_{ds}G_{ds}T_{ds}A_{ds}T_{ds}{}^mC_{ds}{}^mC_{ds}{}^mC_{ds}A_{ds}A_{ds}G_{ds}T_{ks}G_{ks}T_{k}$ | 89 |
| 575013 | 869198 | Cy3-${}^mC_{ks}A_{ks}G_{ks}A_{ds}T_{ds}A_{ds}T_{ds}A_{ds}G_{ds}G_{ds}A_{ds}{}^mC_{ds}T_{ds}G_{ks}G_{ks}A_{k}$ | 110 |
| 549139 | 869199 | Cy3-$G_{ks}A_{ks}{}^mC_{ks}G_{ds}{}^mC_{ds}G_{ds}{}^mC_{ds}{}^mC_{ds}T_{ds}G_{ds}A_{ds}A_{ds}G_{ds}G_{ks}T_{ks}T_{k}$ | 111 |

TABLE 63-continued

Fluorescently Labeled Modified Oligonucleotides

| Unlabelled compound ID | Fluorescently-labelled compound ID | Chemistry notation for Fluorescently-labelled compound | SEQ ID NO: |
|---|---|---|---|
| 508032 | 869200 | Cy3-$G_{ks}G_{ks}A_{ks}{}^mC_{ds}A_{ds}{}^mC_{ds}A_{ds}T_{ds}T_{ds}G_{ds}G_{ds}{}^mC_{ds}{}^mC_{ds}A_{ks}{}^mC_{ks}A_k$ | 112 |
| 464932 | 869201 | Cy3-$G_{ks}G_{ks}{}^mC_{ks}{}^mC_{ds}A_{ds}{}^mC_{ds}{}^mC_{ds}A_{ds}{}^mC_{ds}G_{ds}{}^mC_{ds}T_{ds}G_{ds}T_{ks}{}^mC_{ks}A_k$ | 113 |
| 465131 | 869202 | Cy3-$T_{ks}G_{ks}{}^mC_{ks}{}^mC_{ds}A_{ds}{}^mC_{ds}{}^mC_{ds}G_{ds}T_{ds}A_{ds}G_{ds}A_{ds}{}^mC_{ds}A_{ks}{}^mC_{ks}G_k$ | 114 |
| 147420 | 841863 | Cy3-$A_{es}A_{es}T_{es}G_{es}T_{es}G_{ds}{}^mC_{ds}{}^mC_{ds}T_{ds}G_{ds}{}^mC_{ds}T_{ds}G_{ds}T_{ds}{}^mC_{ds}{}^mC_{es}T_{es}T_{es}G_{es}A_e$ | 73 |

A subscript "d" indicates an unmodified, 2'-β-D-deoxyribosyl sugar moiety.
A subscript "e" indicates a 2'-MOE-β-D-ribofuranosyl sugar moiety.
A subscript "m" indicates a 2'-O-methyl-β-D-ribofuranosyl sugar moiety.
A subscript "k" indicates a cEt.
A subscript "s" indicates a phosphorothioate internucleoside linkage.
A superscript "m" before a C indicates 5-methyl Cytosine..
A subscript "x" indicates a MOP internucleoside linkage.

TABLE 64

Nucleolar mislocalization of p54nrb

| Unlabelled compound ID | Fluorescently-labelled Compound ID | Complementary mRNA | Mislocalization of p54nrb | ALT @ 150 mg/kg of unlabelled modified oligonucleotide |
|---|---|---|---|---|
| 558807 | 925819 | CXCL12 | ++ | death |
| 766676 | 925820 | CXCL12 | ++ | 5,475 |
| 766677 | 925821 | CXCL12 | − | 23 |
| 766678 | 925822 | CXCL12 | − | 67 |
| 766679 | 925823 | CXCL12 | + | 3,347 |
| 766684 | 925824 | CXCL12 | ++ | death |
| 936049 | 958339 | CXCL12 | ++ | 8,622 |
| 936053 | 958340 | CXCL12 | − | 46 |
| 892826 | 958341 | CXCL12 | + | 10,463 |
| 558807 | 1189295 | CXCL12 | ++ | death |
| 1061955 | 1189310 | CXCL12 | − | 86 |
| 766677 | 1215929 | CXCL12 | − | 23 |
| 936053 | 1189369 | CXCL12 | − | 46 |
| 942944 | 1215928 | CXCL12 | + | 233 |

TABLE 65

Nucleolar mislocalization of p54nrb

| Unlabelled compound ID | Fluorescently-labelled Compound ID | Complementary mRNA | Mislocalization of p54nrb | ALT @ 200 mg/kg of unlabelled modified oligonucleotide |
|---|---|---|---|---|
| 147420 | 841863 | CPT1A | ++ | 7,794 |

TABLE 67

Nucleolar mislocalization of p54nrb

| Unlabelled compound ID | Fluorescently-labelled compound ID | Complementary mRNA | Mislocalization of p54nrb, labelled modified oligonucleotide | Maximum tolerated dose unlabelled modified oligonucleotide (mg/kg, mouse) |
|---|---|---|---|---|
| 464917 | 813223 | FXI | + | 11 |
| 508031 | 828939 | SOD1 | ++ | 33 |
| 482050 | 841864 | PTEN | ++ | 33 |
| 449093 | 489982 | SRB1 | ++ | 33 |
| 465178 | 869208 | FXI | + | 100 |
| 575013 | 869198 | FXII | − | >300 |
| 549139 | 869199 | none | − | >300 |
| 508032 | 869200 | SOD1 | − | >300 |
| 464932 | 869201 | FXI | − | >300 |
| 465131 | 869202 | FXI | − | >300 |

TABLE 68

Nucleolar mislocalization of p54nrb

| Unlabelled compound ID | Fluorescently-labelled compound ID | Cells with nucleolar p54nrb | Total cells | % cells with p54nrb mis-localization |
|---|---|---|---|---|
| 558807 | 925819 | 57 | 74 | 77 |
| 936049 | 958339 | 51 | 72 | 71 |
| 936053 | 958340 | 6 | 65 | 9 |
| 892826 | 958341 | 30 | 53 | 57 |

For in vivo maximum tolerated doses reported in the table below, 2-4 BALB/C mice per group were administered modified oligonucleotide at 3.7, 11, 33, 100, or 300 mg/kg by subcutaneous injection and sacrificed after 72 hours. Maximum tolerated dose is the highest dose at which ALT is below 5× that in PBS-treated control mice, or ~150 IU/L.

Example 27 In Vivo and In Vitro Toxicity of LNA-Containing Modified Oligonucleotides Modified oligonucleotides in the table below have a 3-10-3 sugar motif with LNA nucleosides on the 5' and 3' ends and DNA nucleosides in the central region.

TABLE 69

Modified Oligonucleotides

| Compound ID | Chemistry notation | SEQ ID NO: |
|---|---|---|
| 569713 | $G_{ls}A_{ls}{}^mC_{ls}G_{ds}{}^mC_{ds}G_{ds}G_{ds}{}^mC_{ds}{}^mC_{ds}T_{ds}G_{ds}A_{ds}A_{ds}G_{ds}G_{ls}T_{ls}T_l$ | 111 |
| 569717 | $A_{ls}T_{ls}{}^mC_{ls}A_{ds}T_{ds}G_{ds}G_{ds}{}^mC_{ds}T_{ds}G_{ds}{}^mC_{ds}A_{ds}G_{ds}{}^mC_{ls}T_{ls}T_l$ | 24 |
| 569719 | $G_{ls}T_{ls}{}^mC_{ls}T_{ds}G_{ds}T_{ds}G_{ds}{}^mC_{ds}A_{ds}T_{ds}{}^mC_{ds}T_{ds}{}^mC_{ds}T_{ls}{}^mC_{ls}{}^mC_l$ | 22 |
| 569721 | $T_{ls}G_{ls}A_{ls}G_{ds}G_{ds}T_{ds}{}^mC_{ds}{}^mC_{ds}T_{ds}G_{ds}{}^mC_{ds}A_{ds}{}^mC_{ds}T_{ls}G_{ls}G_l$ | 26 |
| 814336 | $G_{ls}{}^mC_{ls}A_{ls}T_{ds}G_{ds}T_{ds}T_{ds}{}^mC_{ds}T_{ds}{}^mC_{ds}A_{ds}{}^mC_{ds}A_{ds}T_{ls}T_{ls}A_l$ | 18 |

A subscript "d" indicates an unmodified, 2'-β-D-deoxyribosyl sugar moiety.
A subscript "l" indicates a β-D-LNA sugar moiety.
A subscript "s" indicates a phosphorothioate internucleoside linkage.
A superscript "m" before a C indicates 5-methyl Cytosine.

Modified nucleotides with 3-10-3111-d(10)-lll sugar motifs were tested for their effect on 3T3 cells by microscopy. 3T3 cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. For experiments reported in the tables below, images were qualitatively analyzed and assigned a score of (−), indicating that no p54nrb mislocalization to the nucleolus was observed, or a scale of (+) indicating that mislocalization of p54nrb to the nucleolus was observed in some cells, or (++) indicating that p54nrb mislocalization to the nucleolus was observed in most or all cells. Modified nucleotides with 3-10-3 lll-d(10)-lll or kkk-d(10)-kkk sugar motifs were tested in vivo. For in vivo toxicity data, 2-4 BALB/C mice were administered modified oligonucleotide by subcutaneous injection at the doses indicated in the table below. Mice were sacrificed after 72 hours and mRNA was isolated and analyzed as described in Example 1 above. ALT values in plasma were obtained using a clinical chemistry analyzer.

TABLE 70

Modified oligonucleotide dosages administered to mice

| Compound ID | Dose 1 (mg/kg) | Dose 2 (mg/kg) (Maximum dose) |
|---|---|---|
| 549139 | 300 | n/a |
| 569713 | 300 | n/a |
| 482050 | 33 | 100 |
| 569717 | 33 | 100 |
| 464917 | 11 | 33 |
| 569719 | 11 | 33 |
| 508031 | 33 | 100 |
| 569721 | 33 | 100 |
| 558807 | 17 | 51 |
| 814336 | 17 | 51 |

TABLE 71

In vitro p54nrb localization and in vitro toxicity

| Compound ID | Complementary mRNA | Mislocalization of p54nrb | ALT @ maximum dose | P21 mRNA at maximum dose (% control) | Tnfrsf10b mRNA at maximum dose (% control) |
|---|---|---|---|---|---|
| 549139 | none | − | 35 | 306 | 252 |
| 569713 | none | − | 44 | 449 | 241 |
| 482050 | PTEN | n.d. | 6555 | 10,430 | 4,232 |
| 569717 | PTEN | n.d. | 270 | 17,295 | 9,568 |
| 464917 | FXI | ++ | 13,920 | 9,590 | 7,731 |
| 569719 | FXI | + | 14,449 | 13,020 | 6,569 |
| 508031 | SOD1 | ++ | 18,550 | 8,909 | 6,678 |
| 569721 | SOD1 | + | 33,246 | 12,193 | 9,169 |
| 558807 | CXCL12 | ++ | 9,510 | 11,904 | 6,831 |
| 814336 | CXCL12 | ++ | death* | n.d. | n.d. |

*At 17 mg/kg, ALT was 4725, P21 mRNA was 11,567, and Tnfrsf10b mRNA was 8,636.

For the in vitro study reported in the tables below, 3T3-L1 cells were electroporated with 27 nM, 80 nM, 250 nM, 740 nM, 2,222 nM, 6,667 nM, or 20,000 nM of modified oligonucleotide and levels of P21 and Gadd45a were measured by RT-qPCR as described in Example 1 above. Caspase-3 and caspase-7 activation was measured using the Caspase-Glo® 3/7 Assay System (G8090, Promega). Levels of caspase activation correlate with apoptotic cell death.

TABLE 72 in vitro Caspase Activation

| Compound ID | 27 nM | 80 nM | 250 nM | 740 nM | 2,222 nM | 6,667 nM | 20,000 nM |
|---|---|---|---|---|---|---|---|
| | | | | Caspase Activation | | | |
| 549139 | 2693 | 2272 | 2536 | 2170 | 2664 | 2128 | 2406 |
| 569713 | 2219 | 1988 | 1996 | 1892 | 2099 | 2178 | 3202 |
| 464917 | 1988 | 2116 | 1907 | 2365 | 6580 | 13268 | 24228 |

TABLE 72-continued in vitro Caspase Activation

| Compound ID | 27 nM | 80 nM | 250 nM | 740 nM | 2,222 nM | 6,667 nM | 20,000 nM |
|---|---|---|---|---|---|---|---|
| | | | | Caspase Activation | | | |
| 569719 | 2080 | 2183 | 2610 | 4225 | 10773 | 14199 | 20524 |
| 508031 | 7082 | 6602 | 7123 | 8876 | 14962 | 20060 | 29955 |
| 569721 | 7905 | 7741 | 8508 | 10364 | 20715 | 24370 | 49476 |
| 558807 | 7272 | 7887 | 8672 | 12555 | 19397 | 25124 | 28133 |
| 814336 | 7308 | 7975 | 9150 | 12927 | 21327 | 26992 | 26794 |

TABLE 73 in vitro P21 Expression

| Compound ID | 27 nM | 80 nM | 250 nM | 740 nM | 2,222 nM | 6,667 nM | 20,000 nM |
|---|---|---|---|---|---|---|---|
| | | | | Expression level of P21 mRNA (% Control) | | | |
| 549139 | 108 | 104 | 93 | 97 | 97 | 88 | 99 |
| 569713 | 116 | 105 | 94 | 127 | 129 | 139 | 166 |
| 464917 | 129 | 132 | 145 | 149 | 275 | 595 | 1044 |
| 569719 | 120 | 118 | 144 | 160 | 332 | 731 | 922 |
| 508031 | 100 | 90 | 99 | 102 | 100 | 124 | 247 |
| 569721 | 116 | 104 | 123 | 119 | 148 | 123 | 470 |
| 558807 | 95 | 126 | 123 | 123 | 104 | 119 | 193 |
| 814336 | 86 | 100 | 96 | 85 | 119 | 170 | 254 |

TABLE 74 in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | | | | Expression level of Gadd45a mRNA (% Control) | | | |
| 549139 | 113 | 125 | 105 | 83 | 72 | 61 | 35 |
| 569713 | 168 | 139 | 116 | 154 | 135 | 162 | 147 |
| 464917 | 153 | 170 | 187 | 210 | 376 | 906 | 933 |
| 569719 | 165 | 168 | 217 | 220 | 514 | 1223 | 1086 |
| 508031 | 106 | 115 | 111 | 112 | 114 | 211 | 345 |
| 569721 | 165 | 168 | 158 | 136 | 212 | 326 | 451 |
| 558807 | 200 | 198 | 222 | 216 | 200 | 235 | 263 |
| 814336 | 117 | 113 | 139 | 148 | 169 | 198 | 278 |

TABLE 75 in vitro Tnfrsf10b Expression

| Compound ID | 27 nM | 80 nM | 250 nM | 740 nM | 2,222 nM | 6,667 nM | 20,000 nM |
|---|---|---|---|---|---|---|---|
| | | | | Expression level of Tnfrsf10b mRNA (% Control) | | | |
| 549139 | 93 | 96 | 87 | 87 | 89 | 98 | 96 |
| 569713 | 116 | 111 | 79 | 119 | 115 | 128 | 114 |
| 464917 | 122 | 127 | 129 | 93 | 116 | 186 | 125 |
| 569719 | 105 | 107 | 117 | 88 | 119 | 151 | 36 |

Example 28 Total Protein Binding of Modified Oligonucleotides Complementary to SOD1

Modified oligonucleotides described in the examples above were evaluated for their total protein binding in HeLa nuclear lysate. Cellular proteins were captured with the biotin-conjugated modified oligonucleotide 791136, which has a 5'-biotin-TEG, the sugar motif kkk-d(10)-kkk and the same sequence as 464917, GTCTGTGCATCTCTCC (SEQ ID NO: 22) and eluted with increasing concentrations of 508031, 895154, 895155, and 895156, described in Example 6 above. Eluted proteins were run on an SDS-PAGE gel. Increased total protein binding is observed for compound 508031 and 895154 compared to compound 895155 and 895156.

Example 29 Total Protein Binding of Modified Oligonucleotides Complementary to FXI Modified oligonucleotides described in the examples above were evaluated for their total protein binding in HeLa nuclear lysate. Cellular proteins were captured with the biotin-conjugated modified oligonucleotide 791136, which has a 5'-biotin-TEG, the sugar motif kkk-d(10)-kkk and the same sequence as 464917, GTCTGTGCATCTCTCC (SEQ ID NO: 22) and eluted with increasing concentrations of 464917, 465977, 483706, and 820685, described in Examples 4 and 25 above. Eluted proteins were run on an SDS-PAGE gel. Increased total protein binding is observed for compound 464917 and 465977 compared to compounds 483706 and 820685. A series of western blots was done to detect SSBP1, NCL1, PCNA, p54nrb, RNase H1, and PSF.

In an independent experiment, cellular proteins were captured with 791136 and eluted with increasing concentrations of 464917, 465178, 464392, and 465131. Increased total protein binding is observed for compound 464917 compared to 465178, 464932, and 465131.

Example 30 Total Protein Binding, Activity and Toxicity with MOP Linkages

Modified oligonucleotides were evaluated for their total protein binding in cells. Cellular proteins were captured with the biotin-conjugated modified oligonucleotide 592590, which has a 5'-biotin-TEG, the sugar motif kkk-d(10)-kkk and the sequence GCTAGCCTCTGGATTT (SEQ ID NO:115) and eluted with the modified oligonucleotides described in the table below. Eluted proteins were run on an SDS-PAGE gel and visualized. Decreased protein binding is observed for compounds with decreased toxicity compared to 558807, in particular for compounds 766654, 766655, and 766666.

In vitro activity and in vivo activity and toxicity experiments were performed essentially as described in Example 1. For in vivo toxicity studies, a single BALB/C mouse per dose of modified oligonucleotide was administered 16.7 mg/kg, 50 mg/kg, or 150 mg/kg modified oligonucleotide by subcutaneous injection and sacrificed 72 hours later. ALT levels were measured using an automated clinical chemistry analyzer. For the in vivo activity study in the table below, 1 BALB/C mouse per group was administered 1.8 mg/kg, 5.5 mg/kg, 16.7 mg/kg, 50 mg/kg or 150 mg/kg modified oligonucleotide subcutaneously and sacrificed after 24 hours.

TABLE 77 in vivo Activity and Toxicity

| Compound ID | MOP linkage positions | in vivo CXCL12 ED50 (mg/kg) | ALT @ 50 mg/kg (IU/L) | ALT @ 150 mg/kg (IU/L) |
|---|---|---|---|---|
| PBS | n/a | n/a | 26 (@0 mg/kg) | |
| 558807 | n/a | 2.9 | 19,806 | death |
| 766653 | 1, 2 | 23.6 | 32 | 33 |
| 766654 | 2, 3 | 31.6 | 28 | 30 |
| 766655 | 3, 4 | 32.7 | 28 | 27 |
| 766656 | 4, 5 | 26.7 | 25 | 29 |
| 766657 | 5, 6 | 7.0 | 213 | 5,503 |
| 766658 | 6, 7 | 6.2 | 64 | 1,380 |
| 766659 | 7, 8 | 10.6 | 51 | 3,423 |
| 766665 | 8, 9 | 5.5 | 3,437 | 11,954 |
| 766664 | 9, 10 | 6.2 | 4,045 | death |

Example 31 Self-Structure of Modified Oligonucleotides Complementary to CXCL12

Tm was determined for self-structures of modified oligonucleotides described in the examples above. Compounds in the table below are complementary to CXCL12 and have sequences corresponding to SEQ ID NO: 18-21. Tm was

TABLE 76

Modified oligonucleotides containing Two MOP linkages

| Compound ID | Linkage Mod position in central region | Target | Chemistry Notation | SEQ ID NO |
|---|---|---|---|---|
| 766653 | 1, 2 | CXCL12 | $G_{ks}{}^mC_{ks}A_{ks}T_{dx}G_{dx}T_{ds}T_{ds}{}^mC_{ds}T_{ds}{}^mC_{ds}A_{ds}{}^mC_{ds}A_{ds}T_{ks}T_{ks}A_k$ | 18 |
| 766654 | 2, 3 | CXCL12 | $G_{ks}{}^mC_{ks}A_{ks}T_{ds}G_{dx}T_{dx}T_{ds}{}^mC_{ds}T_{ds}{}^mC_{ds}A_{ds}{}^mC_{ds}A_{ds}T_{ks}T_{ks}A_k$ | 18 |
| 766655 | 3, 4 | CXCL12 | $G_{ks}{}^mC_{ks}A_{ks}T_{ds}G_{ds}T_{dx}T_{dx}{}^mC_{ds}T_{ds}{}^mC_{ds}A_{ds}{}^mC_{ds}A_{ds}T_{ks}T_{ks}A_k$ | 18 |
| 766656 | 4, 5 | CXCL12 | $G_{ks}{}^mC_{ks}A_{ks}T_{ds}G_{ds}T_{ds}T_{dx}{}^mC_{dx}T_{ds}{}^mC_{ds}A_{ds}{}^mC_{ds}A_{ds}T_{ks}T_{ks}A_k$ | 18 |
| 766657 | 5, 6 | CXCL12 | $G_{ks}{}^mC_{ks}A_{ks}T_{ds}G_{ds}T_{ds}T_{ds}{}^mC_{dx}T_{dx}{}^mC_{ds}A_{ds}{}^mC_{ds}A_{ds}T_{ks}T_{ks}A_k$ | 18 |
| 766658 | 6, 7 | CXCL12 | $G_{ks}{}^mC_{ks}A_{ks}T_{ds}G_{ds}T_{ds}T_{ds}{}^mC_{ds}T_{dx}{}^mC_{dx}A_{ds}{}^mC_{ds}A_{ds}T_{ks}T_{ks}A_k$ | 18 |
| 766659 | 7, 8 | CXCL12 | $G_{ks}{}^mC_{ks}A_{ks}T_{ds}G_{ds}T_{ds}T_{ds}{}^mC_{ds}T_{ds}{}^mC_{dx}A_{dx}{}^mC_{ds}A_{ds}T_{ks}T_{ks}A_k$ | 18 |
| 766665 | 8, 9 | CXCL12 | $G_{ks}{}^mC_{ks}A_{ks}T_{ds}G_{ds}T_{ds}T_{ds}{}^mC_{ds}T_{ds}{}^mC_{ds}A_{dx}{}^mC_{dx}A_{ds}T_{ks}T_{ks}A_k$ | 18 |
| 766664 | 9, 10 | CXCL12 | $G_{ks}{}^mC_{ks}A_{ks}T_{ds}G_{ds}T_{ds}T_{ds}{}^mC_{ds}T_{ds}{}^mC_{ds}A_{ds}{}^mC_{dx}A_{dx}T_{ks}T_{ks}A_k$ | 18 |

A subscript "d" indicates an unmodified, 2'-β-D-deoxyribosyl sugar moiety.
A subscript "k" indicates a cEt.
A subscript "s" indicates a phosphorothioate internucleoside linkage.
A superscript "m" before a C indicates 5-methyl Cytosine.
A subscript "x" indicates a MOP internucleoside linkage.

also determined for duplexes of the modified oligonucleotides described in the examples above in complex with a RNA 20-mer with the sequence GAUAAUGUGAGAACAUGCCU (SEQ ID NO: 116).

TABLE 78

Tm of Modified Oligonucleotides complementary to CXCL12, Self-Structure and Duplex

| Compound ID | linkage-altered nucleotide (position in central region) | Sugar-modification of altered nucleotide (position in central region) | Tm (° C.) Self structure | Tm (° C.) duplex |
|---|---|---|---|---|
| 558807 | none | none | 48.6 | 65.1 |
| 1061955 | none | inosine (2) | 32.9 | 57.5 |
| 766676 | MOP(1) | none | 44.6 | 63.3 |
| 766677 | MOP(2) | none | 45.3 | 63.5 |
| 766678 | MOP(3) | none | 47.9 | 63.1 |
| 766679 | MOP(4) | none | 47.1 | 62.6 |
| 766680 | MOP(5) | none | n.d. | 63 |
| 766681 | MOP(6) | none | n.d. | 62.9 |
| 766682 | MOP(7) | none | n.d. | 63.8 |
| 766683 | MOP(8) | none | n.d. | 63.3 |
| 766684 | MOP(9) | none | n.d. | 64.1 |
| 766685 | MOP(10) | none | n.d. | 63.9 |
| 936053 | none | 2'-OMe (2) | 49.0 | 67.0 |
| 828911 | none | 2'-MOE (2) | 48.2 | 66.8 |
| 1070041 | none | cEt (2) | 52.7 | 69.5 |
| 936051 | none | 2'-FANA (2) | 46.1 | 64.8 |
| 936052 | none | 2'-ribo-F (2) | 47.2 | 66.0 |
| 1123320 | none | 5'-(R)—Me (2) | 49.4 | 65.5 |
| 1123322 | none | 5'-(S)—Me (2) | 43.0 | 62.0 |
| 942943 | none | 5'-(R)—Me (3) | 47.3 | 62.3 |
| 957908 | none | 5'-(S)—Me (3) | 45.1 | 65.1 |
| 942944 | none | 5'-(R)—Me (4) | 49.5 | 62.3 |
| 957909 | none | 5'-(S)—Me (4) | 46.2 | 66.3 |
| 957910 | none | 5'-(R)-allyl (3) | 44.4 | 62.1 |
| 957911 | none | 5'-(R)-allyl (4) | 47.3 | 62.4 |
| 957912 | none | 5'-(S)-allyl (3) | 41.7 | 64.0 |
| 957913 | none | 5'-(S)-allyl (4) | 47.1 | 64.6 |
| 1069852 | none | pseudoU (2) | 24.4 | 54.4 |
| 1061328 | none | pseudoU (3) | 44.6 | 55.3 |
| 1215458 | none | β-L-DNA (2) | n.d. | 58 |
| 1215459 | none | β-L-DNA (3) | 43 | 59 |
| 1215460 | none | β-L-DNA (4) | 45 | 62 |
| 1215461 | none | α-L-DNA (3) | 41 | 63 |
| 1215462 | none | α-L-DNA (4) | 49 | 65 |

TABLE 79

Tm of Modified Oligonucleotide Self-Structure

| Compound ID | Target | Tm (° C.) |
|---|---|---|
| 449093 | SRB1 | <40 |
| 464917 | FXI | <40 |
| 482050 | PTEN | 33.4 |
| 508031 | SOD-1 | 58.9 |

Example 32 2'-Modifications in 5' and 3'-Regions of Modified Oligonucleotides Modified oligonucleotides containing various sugar modification motifs were synthesized as indicated in the table below. The compounds in the table below are 100% complementary to mouse CXCL12, GENBANK NT_039353.7 truncated from 69/430,515 to 69/445,350 (SEQ ID NO: 1) at positions 6877 to 6892 (16-mers) or 6875 to 6894 (20-mers).

TABLE 80 modified oligonucleotides with 2'-sugar modifications

| Compound ID | 2'-modified sugars on 5'-end | 2'-modified sugars on 3'-end | Chemistry Notation | SEQ ID NO |
|---|---|---|---|---|
| 558807 | kkk | kkk | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 1035522 | kkk | eee | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{es}T_{es}A_e$ | 18 |
| 1035523 | eee | kkk | $G_{es}{}^mC_{es}A_{es}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 985648 | eee | eee | $G_{es}{}^mC_{es}A_{es}T_{ds}G_{ds}T_{ds}T_{ds}{}^mC_{ds}T_{ds}{}^mC_{ds}A_{ds}{}^mC_{ds}A_{ds}T_{es}T_{es}A_e$ | 18 |
| 1069842 | kkeee | eeekk | $A_{ks}G_{ks}G_{es}{}^mC_{es}A_{es}T_{ds}G_{ds}T_{ds}T_{ds}{}^mC_{ds}T_{ds}{}^mC_{ds}A_{ds}{}^mC_{ds}A_{ds}T_{es}T_{es}A_{es}T_{ks}{}^mC_k$ | 117 |
| 1069843 | kkeee | kkkkk | $A_{ks}G_{ks}G_{es}{}^mC_{es}A_{es}T_{ds}G_{ds}T_{ds}T_{ds}{}^mC_{ds}T_{ds}{}^mC_{ds}A_{ds}{}^mC_{ds}A_{ds}T_{ks}T_{ks}A_{ks}T_{ks}{}^mC_k$ | 117 |
| 1069844 | kkkkk | eeekk | $A_{ks}G_{ks}G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{es}T_{es}A_{es}T_{ks}{}^mC_k$ | 117 |
| 386864 | eeeee | eeeee | $A_{es}G_{es}G_{es}{}^mC_{es}A_{es}T_{ds}G_{ds}T_{ds}T_{ds}{}^mC_{ds}T_{ds}{}^mC_{ds}A_{ds}{}^mC_{ds}A_{ds}T_{es}T_{es}A_{es}T_{es}{}^mC_e$ | 117 |
| 1069845 | kkkkk | kkkkk | $A_{ks}G_{ks}G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_{ks}T_{ks}{}^mC_k$ | 117 |
| 1069846 | eekkkk | kkkkk | $A_{eS}G_{eS}G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_{ks}T_{ks}{}^mC_k$ | 117 |
| 1069847 | kkkkk | kkkee | $A_{kS}G_{ks}G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{kS}T_{kS}A_{kS}T_{eS}{}^mC_e$ | 117 |

A subscript "d" indicates an unmodified, 2'-β-D-deoxyribosyl sugar moiety.
A subscript "k" indicates a cEt.
A subscript "s" indicates a phosphorothioate internucleoside linkage.
A superscript "m" before a C indicates 5-methyl Cytosine.
A subscript "e" indicates a 2'-MOE-β-D-ribofuranosyl sugar moiety.
A subscript "m" indicates a 2'-O-methyl-β-D-ribofuranosyl sugar moiety.

For the in vitro study reported in the tables below, 3T3-L1 cells were electroporated with 27 nM, 80 nM, 250 nM, 740 nM, 2, 222 nM, 6,667 nM, or 20,000 nM of modified oligonucleotide and levels of CXCL12 were measured by RT-qPCR as described in Example 1 above. Caspase activation was measured as described in Example 4 above. Results are presented relative to the caspase activation in control cells not treated with modified oligonucleotide. Mislocalization of p54nrb was analyzed as described in Example 15 above. For experiments reported in the tables below, selected images were qualitatively analyzed and assigned a score of (−), indicating that no p54nrb mislocalization to the nucleolus was observed, or a score of (+) indicating that mislocalization of p54nrb to the nucleolus was observed in some cells, or (++) indicating that p54nrb mislocalization to the nucleolus was observed in most or all cells. Treatment of HeLa cells with certain modified oligonucleotides caused a filamentous appearance of p54nrb in cells. This is indicated by a "f" in the table below.

TABLE 81 in vitro Activity and Toxicity

| Compound ID | Caspase (% control) | CXCL12 IC$_{50}$ (nM) | p54nrb mislocalization |
|---|---|---|---|
| 558807 | 1135 | 30 | ++ |
| 1035522 | 1261 | 35 | +, f |
| 1035523 | 244 | 100 | +, f |
| 985648 | 207 | 200 | −, f |
| 1069842 | 353 | 350 | +, f |
| 1069843 | 670 | 100 | ++ |
| 1069844 | 748 | 350 | + |
| 386864 | 1104 | 200 | −, f |
| 1069845 | 213 | 350 | ++ |
| 1069846 | 963 | 100 | + |
| 1069847 | 923 | 250 | + |

Example 33 Effect of Treatment of b.END Cells with Modified Oligonucleotides

For the in vitro study reported in the tables below, b.END.3 cells were electroporated with 3.125, 6.25, 12.5, 25, or 50 nM of modified oligonucleotide 464917 (heptatotoxic) or 549148 (nontoxic). 549148 is a 3-10-3 cEt modified oligonucleotide with the sequence GGCTACTACGCCGTCA (SEQ ID NO: 118), which is not complementary to any known mouse gene. Expression levels of p21 and Gadd45a mRNA were measured after 0, 1, 2, 4, and 6 hours by RT-qPCR as described in Example 1.

TABLE 82

Relative mp21 mRNA dose response/time course in b.END cells

| Compound | Dose (nM) | % Control mp21 mRNA | | | |
|---|---|---|---|---|---|
| | | 1 hrs | 2 hrs | 4 hrs | 6 hrs |
| 464917 | 0 | 100 | 100 | 100 | 100 |
| 464917 | 3.125 | 102 | 134 | 147 | 174 |
| 464917 | 6.25 | 113 | 149 | 169 | 242 |
| 464917 | 12.50 | 107 | 141 | 199 | 250 |
| 464917 | 25.0 | 122 | 183 | 330 | 394 |
| 464917 | 50.0 | 113 | 210 | 399 | 427 |
| 549148 | 0 | 100 | 100 | 100 | 100 |
| 549148 | 3.125 | 111 | 42 | 140 | 107 |
| 549148 | 6.25 | 88 | 90 | 128 | 126 |
| 549148 | 12.50 | 120 | 86 | 119 | 109 |
| 549148 | 25.0 | 114 | 111 | 147 | 107 |
| 549148 | 50.0 | 111 | 94 | 126 | 119 |

TABLE 82a

Relative mGadd45a mRNA dose response/time course in b.END cells

| Compound | Dose (nM) | % Control mGadd45a mRNA | | | |
|---|---|---|---|---|---|
| | | 1 hrs | 2 hrs | 4 hrs | 6 hrs |
| 464917 | 0 | 100 | 100 | 100 | 100 |
| 464917 | 3.125 | 87 | 88 | 203 | 396 |
| 464917 | 6.25 | 81 | 154 | 259 | 565 |
| 464917 | 12.50 | 85 | 173 | 331 | 905 |
| 464917 | 25.0 | 102 | 247 | 715 | 1586 |
| 464917 | 50.0 | 132 | 420 | 1376 | 3339 |
| 549148 | 0 | 100 | 100 | 100 | 100 |
| 549148 | 3.125 | 85 | 31 | 106 | 109 |
| 549148 | 6.25 | 72 | 95 | 103 | 125 |
| 549148 | 12.50 | 85 | 87 | 106 | 127 |
| 549148 | 25.0 | 85 | 103 | 144 | 123 |
| 549148 | 50.0 | 97 | 107 | 131 | 198 |

Example 34 Nucleolar Delocalization of p54nrb in Various Cell Lines

Cells were plated at 20,000 cells/well and transfected with Lipofectamine 2,000 and 60 nM of modified oligonucleotide 791143, compound 464917 labeled on the 3'-end with Cy3. Cells were visualized 6 hours after transfection.

TABLE 83 p54nrb nucleolar mislocalization

| Compound ID | Cell line | p54nrb nucleolar mislocalization |
|---|---|---|
| 791143 | U2OS | + |
| 791143 | NIH3T3 | ++ |

Cells were plated at 20,000 cells/well and transfected by free uptake with modified oligonucleotide 791143 as indicated in the table below. Cells were visualized 5 hours after transfection.

TABLE 84 p54nrb nucleolar mislocalization

| Compound ID | Cell line | p54nrb nucleolar mislocalization |
|---|---|---|
| 791143 | MHT | + |
| 791143 | HeLa | ++ |

Cells were plated at 20,000 cells/well and transfected by NEON electroporation at 1400V, 20 ms, 2 pulses with 60 nM modified oligonucleotide 813223, compound 464917 labeled on the 5'-end with Cy3. Cells were visualized 5 hours after transfection.

TABLE 85 p54nrb nucleolar mislocalization

| Compound ID | Cell line | p54nrb nucleolar mislocalization |
|---|---|---|
| 813223 | HeLa | ++ |

Cells were transfected with 60 nM modified oligonucleotide 813223 or compound 813225. Compound 813225 is the control oligonucleotide 549148 described above labeled on the 5'-end with Cy3. Cells were visualized 4 hours after transfection

TABLE 85b p54nrb nucleolar mislocalization

| Compound ID | Cell line | p54nrb nucleolar mislocalization |
|---|---|---|
| 813223 | b.END3 | ++ |
| 813225 | b.END3 | − |
| 813223 | NIH3T3 | + |
| 813223 | primary neuron | + |
| 813223 | primary hepatocyte | ++ |

Example 35 Effect of Depletion of RNaseH1 on Toxicity of Modified Oligonucleotides HeLa cells were plated at 150,000 cells/well and transfected with control siRNA targeting luciferase or siRNA targeted to RNaseH1 (s48357 or s48358 from ThermoFisher) at a final concentration of 3 nM using Lipofectamine RNAiMAX for 48 hours. Modified oligonucleotides 464917 and 549148 were added to the cells by free uptake. 549148 is a 3-10-3 cEt modified oligonucleotide with the sequence GGCTACTACGCCGTCA (SEQ ID NO: 118), which is not complementary to any known mouse gene. Confocal microscopy was used to visualize p54nrb localization as described in Example 15 above.

TABLE 86 in vitro p54nrb mislocalization

| Compound ID | siRNA | p54nrb nucleolar mislocalization |
|---|---|---|
| 464917 | mock | ++ |
| 464917 | RNaseH1a | − |
| 464917 | RNaseH1b | − |

TABLE 87 in vitro P21 Expression in HeLa cells

| Compound ID | siRNA | 0 nM | 3.125 nM | 6.25 nM | 12.5 nM | 25 nM | 50 nM |
|---|---|---|---|---|---|---|---|
| | | \multicolumn{6}{c}{Expression level of P21 mRNA (% Control)} | | | | | |
| 464917 | Luci | 90 | 134 | 141 | 143 | 171 | 201 |
| 464917 | H1 | 78 | 79 | 82 | 83 | 84 | 95 |
| 549148 | Luci | 100 | 119 | 105 | 84 | 94 | 82 |
| 549148 | H1 | 99 | 86 | 92 | 81 | 79 | 85 |

TABLE 88 in vitro Gadd45a Expression in HeLa cells

| Compound ID | siRNA | 0 nM | 3.125 nM | 6.25 nM | 12.5 nM | 25 nM | 50 nM |
|---|---|---|---|---|---|---|---|
| | | \multicolumn{6}{c}{Expression level of P21 mRNA (% Control)} | | | | | |
| 464917 | Luci | 73 | 119 | 126 | 179 | 270 | 463 |
| 464917 | H1 | 65 | 82 | 110 | 117 | 154 | 260 |
| 549148 | Luci | 100 | 89 | 107 | 102 | 97 | 83 |
| 549148 | H1 | 72 | 83 | 103 | 103 | 105 | 96 |

Example 36 Protein Binding of Modified Oligonucleotides

Modified oligonucleotides described in the examples above were evaluated for their protein binding in cells. Cellular proteins were captured with the biotin-conjugated modified oligonucleotide 791136, which has a 5'-biotin-TEG, the sugar motif kkk-d(10)-kkk, a full phosphorothioate backbone, and the same sequence as 464917, GTCTGTG-CATCTCTCC (SEQ ID NO: 22). Proteins were eluted with increasing concentrations of 464917 or 549148. Eluted proteins were run on an SDS-PAGE gel and analyzed by western blot for p54nrb, FUS, RNaseH1, SSBP1, Ku70, PSPC1, SND1, FUBP, NCL1, and Ku80. Band intensities are represented in the table below: −, no band; +, faint band; ++, medium band; +++, intense band.

TABLE 89

Protein binding of modified oligonucleotides

| Protein | Relative band intensity 464917 | | Relative band intensity 549148 | |
|---|---|---|---|---|
| | 0.625 µM | 5 µM | 0.625 µM | 5 µM |
| p54nrb | − | +++ | − | + |
| FUS | − | ++ | − | − |
| RNaseH1 | − | ++ | − | + |
| SSBP1 | ++ | ++ | + | + |
| Ku70 | + | ++ | + | + |
| PSPC1 | − | + | − | + |
| SND1 | ++ | +++ | + | ++ |
| FUBP | + | ++ | + | + |
| NCL1 | + | ++ | + | + |
| Ku80 | + | ++ | ++ | ++ |

Total protein binding to 464917 and 549418 was tested using biotin-464917 or biotin-549148 to capture cellular proteins, which were then eluted with increasing concentrations of 464917 or 549148. The hepatotoxic compound 464917 shows increased global protein binding compared to 549148.

Example 37 In Vitro Activity and Toxicity of Modified Oligonucleotides Comprising Modified Internucleoside Linkages Modified oligonucleotides were designed based on the control oligonucleotide 558807, described in Example 1 herein and synthesized using standard procedures. Modified internucleoside linkages (1 or 2) were positioned at various positions within the central region of the oligonucleotides as illustrated below. The resulting modified oligonucleotides were tested for their ability to inhibit CXCL12 (Chemokine ligand 12) and Raptor expression levels. The potency of the modified oligonucleotides was evaluated and compared to the control oligonucleotide.

The modified oligonucleotides were tested in vitro in mouse b.END cells by electroporation. Cells at a density of 20,000 cells per well are transfected using electroporation with 0.027, 0.082, 0.25, 0.74, 2.22, 6.67 and 20 uM concentrations of each of the oligonucleotides listed below. After a treatment period of approximately 24 hours, RNA is isolated from the cells and mRNA levels are measured by quantitative real-time PCR and the CXCL12 mRNA and Raptor mRNA levels are adjusted according to total RNA content, as measured by RIBOGREEN®.

TABLE 90

Modified Oligonucleotides

| Compound ID | Linkage-altered nucleotide position in central region | Linkage mod "x" | Chemistry Notation | SEQ ID NO |
|---|---|---|---|---|
| 558807 | n/a | n/a | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 857528 | 3 | THP phosphotriester | $G_{ks}{}^mC_{ks}A_{ks}T_{ds}G_{ds}T_xT_{ds}{}^mC_{ds}T_{ds}{}^mC_{ds}A_{ds}{}^mC_{ds}A_{ds}T_{ks}T_{ks}A_k$ | 18 |
| 857529 | 3 | isopropylphosphotriester | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$ | 18 |
| 857530 | 3 | isobutylphosphonate | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$ | 18 |
| 857505 | 3 | isopropylphosphonate | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$ | 18 |
| 883401 | 3 | amide-3 | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 883521 | 3 | formacetal | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 857532 | 4 | THP phosphotriester | $G_{ks}{}^mC_{ks}A_{ks}T_{ds}G_{ds}T_{ds}T_x{}^mC_{ds}T_{ds}{}^mC_{ds}A_{ds}{}^mC_{ds}A_{ds}T_{ks}T_{ks}A_k$ | 18 |
| 857533 | 4 | isopropylphosphotriester | $G_{ks}{}^mC_{ks}A_{ks}T_{ds}G_{ds}T_{ds}T_x{}^mC_{ds}T_{ds}{}^mC_{ds}A_{ds}{}^mC_{ds}A_{ds}T_{ks}T_{ks}A_k$ | 18 |
| 857531 | 4 | isopropylphosphonate | $G_{ks}{}^mC_{ks}A_{ks}T_{ds}G_{ds}T_{ds}T_{dx}{}^mC_{ds}T_{ds}{}^mC_{ds}A_{ds}{}^mC_{ds}A_{ds}T_{ks}T_{ks}A_k$ | 18 |
| 857534 | 4 | isobutylphosphonate | $G_{ks}{}^mC_{ks}A_{ks}T_{ds}G_{ds}T_{ds}T_{dx}{}^mC_{ds}T_{ds}{}^mC_{ds}A_{ds}{}^mC_{ds}A_{ds}T_{ks}T_{ks}A_k$ | 18 |
| 857537 | 3, 4 | isopropylphosphonate | $G_{ks}{}^mC_{ks}A_{ks}T_{ds}G_{ds}T_{dx}T_{dx}{}^mC_{ds}T_{ds}{}^mC_{ds}A_{ds}{}^mC_{ds}A_{ds}T_{ks}T_{ks}A_k$ | 18 |
| 857540 | 3, 4 | isobutylphosphonate | $G_{ks}{}^mC_{ks}A_{ks}T_{ds}G_{ds}T_{dx}T_{dx}{}^mC_{ds}T_{ds}{}^mC_{ds}A_{ds}{}^mC_{ds}A_{ds}T_{ks}T_{ks}A_k$ | 18 |
| 857538 | 3, 4 | THP phosphotriester | $G_{ks}{}^mC_{ks}A_{ks}T_{ds}G_{ds}T_{dx}T_{dx}{}^mC_{ds}T_{ds}{}^mC_{ds}A_{ds}{}^mC_{ds}A_{ds}T_{ks}T_{ks}A_k$ | 18 |

A subscript "d" indicates a an unmodified, 2'-β-D-deoxyribosyl sugar moiety.
A subscript "k" indicates a cEt.
A subscript "s" indicates a phosphorothioate internucleoside linkage.
A superscript "m" before a C indicates 5-methyl Cytosine.
A subscript "x" indicates a modified internucleoside linkage as indicated in the "linkage mod x" column.
These linkages are illustrated below.

TABLE 90-continued

Modified Oligonucleotides

| Compound ID | Linkage-altered nucleotide position in central region | Linkage mod "x" | Chemistry Notation | SEQ ID NO |
|---|---|---|---|---| isopropylphosphonate isobutylphosphonate

THP phosphotriester isopropylphosphotriester amide-3 formacetal

The half maximal inhibitory concentration ($IC_{50}$) of each oligonucleotide listed above was calculated by plotting the concentration of oligonucleotide versus the percent inhibition of CXCL12 mRNA or Raptor mRNA expression achieved at each concentration, and noting the concentration of oligonucleotide at which 50% inhibition of CXCL12 mRNA expression is achieved compared to the control. The results are presented in the table below.

TABLE 91

In vitro Activity and Toxicity

| Compound ID | $IC_{50}$ (µM) CXCL12 | Raptor % Control (4 µM) | Raptor IC50* (µM) |
|---|---|---|---|
| 558807 | 0.17 | 47 | 3.7 |
| 857505 | 0.15 | 82 | >4 |
| 857530 | 0.32 | 87 | >4 |
| 857528 | 0.23 | 110 | >4 |
| 857529 | 1.09 | 74 | >4 |
| 883401 | 30 | 65 | >4 |
| 883521 | 0.40 | 94 | >4 |
| 857531 | 0.27 | 99 | >4 |
| 857534 | 0.12 | 57 | >4 |
| 857532 | 0.16 | 69 | >4 |
| 857533 | 0.10 | 61 | >4 |
| 857537 | 1.4 | 82 | >4 |
| 857540 | 0.48 | 65 | >4 |
| 857538 | 0.33 | 110 | >4 |
| 857539 | 0.13 | 74 | >4 |

*IC50 values can only be calculated when less than the highest dose in the experiment, in this case, 4 µM Example 38

Modified oligonucleotides were designed based on 558807. Each modified oligonucleotide has a modified internucleoside linkage positioned between nucleosides 3 and 4 counting from the 5'-gap junction (not including the 3 cEt modified nucleosides in the 5'-wing) as illustrated below. Each of the modified oligonucleotides is conjugated with a HPPO-GalNAc conjugate group at the 3'-end as illustrated below. The oligonucleotides were evaluated for reduction in CXCL12 (Chemokine ligand 12) mRNA expression levels in vivo. The transaminase levels (ALT and AST) for each dose were also measured.

Six week old BALB/C mice (purchased from Charles River) were injected subcutaneously once at dosage 0.2, 0.6, 1.8 or 50 mg/kg with the modified oligonucleotides shown below or with saline control. For compound 855156, mice were injected with 0.21, 0.62, 1.85, or 5.56 mg/kg modified oligonucleotide. Each treatment group consisted of 3 animals. The mice were sacrificed 72 hours following administration, and organs and plasma were harvested for further analysis.

TABLE 92

Modified Oligonucleotides

| Compound ID | Linkage-altered nucleotide position in central region | Linkage mod "x" | Chemistry Notation | SEQ ID NO |
|---|---|---|---|---|
| 895566 | 3 | isopropylphosphonate | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 895567 | 3 | THP phosphotriester | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 895568 | 3 | isopropylphosphotriester | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 895569 | 3 | isobutylphosphonate | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 895570 | 3 | formacetal | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 913196 | 3 | amide-3 | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 920046 | 3 | TANA | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 951972 | 3 | (R)-MOP | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 951973 | 3 | (S)-MOP | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 974343 | 3 | alt-thioformacetal | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 974344 | 3 | glycine amide | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 1011295 | 3 | thioformacetal | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |
| 1011296 | 3 | MMI | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNAc | 18 |

A subscript "d" indicates an unmodified, 2'-β-D-deoxyribosyl sugar moiety.
A subscript "k" indicates a cEt.
A subscript "s" indicates a phosphorothioate internucleoside linkage.
A superscript "m" before a C indicates 5-methyl Cytosine.
A subscript "x" indicates a modified internucleoside linkage as indicated in the "linkage mod x" column.
These linkages are illustrated below.

TABLE 92-continued

Modified Oligonucleotides

| Compound ID | Linkage-altered nucleotide position in central region | Linkage mod "x" | Chemistry Notation | SEQ ID NO |
|---|---|---|---|---|

TANA alt-thioformacetal glycine amide thioformacetal

MMI

Each modified oligonucleotide in the study includes a 3'-HPPO-GalNAc conjugate group which is attached to the 3'-oxygen of the oligomeric compound. The 3'-HPPO-GalNAc conjugate group is illustrated below wherein the phosphate group is attached to the 3'-oxygen atom:

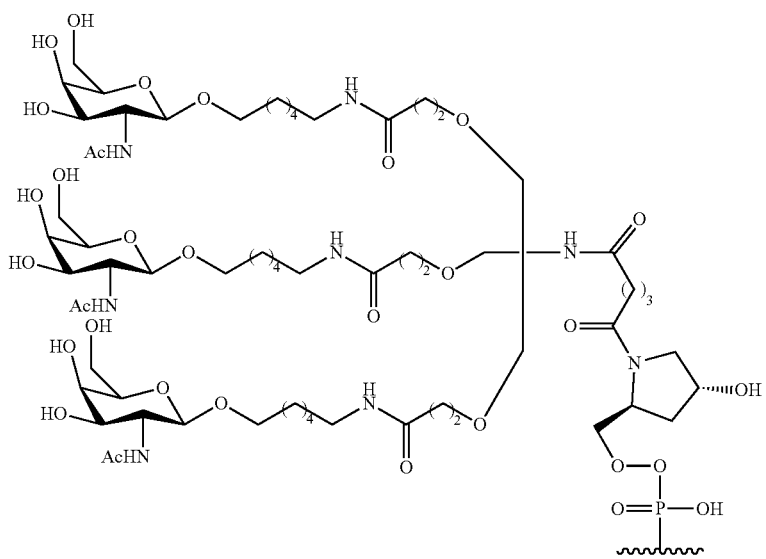

Liver tissues were homogenized and mRNA levels were quantitated using real-time PCR and normalized to RIBOGREEN as described herein. Plasma chemistry markers such as liver transaminase levels, alanine aminotransferase (ALT) in serum were measured relative to saline injected mice.

The $ED_{50}$ values were calculated by plotting the concentrations of oligonucleotides used versus the percent inhibition of CXCL12 mRNA expression achieved at each concentration, and noting the concentration of oligonucleotide at which 50% inhibition of CXCL12 mRNA expression was achieved compared to the control.

TABLE 93

In vivo Toxicity

| Compound ID | Linkage-altered nucleotide position in Central region | Linkage Mod | ALT (at 50 mg/kg) |
|---|---|---|---|
| 855156* | n/a | n/a | 4298** |
| 855161 | 3 | MOP | 31 |
| 895566 | 3 | isopropylphosphonate | 24 |
| 895567 | 3 | THP phosphotriester | 25 |
| 895568 | 3 | isopropylphosphotriester | 38 |
| 895569 | 3 | isobutylphosphonate | 28 |
| 895570 | 3 | formacetal | 31 |
| 913196 | 3 | amide-3 | 29 |
| 920046 | 3 | TANA | 24 |
| 951972 | 3 | (R)-MOP | 47 |
| 951973 | 3 | (S)-MOP | 45 |
| 974343 | 3 | alt-thioacetal | 39 |
| 974344 | 3 | glycine amide | 30 |
| 1011295 | 3 | thioacetal | 38 |
| 1011296 | 3 | MMI | 56 |

*Described in Table 25 above

**Values determined in an independent experiment and shown for comparison; ALT value is at 5.56 mg/kg modified oligonucleotide TABLE 93b In Vivo CXCL12 mRNA levels

| Compound ID | 0.21 mg/kg | 0.62 mg/kg | 1.85 mg/kg | 5.56 mg/kg | 50 mg/kg |
|---|---|---|---|---|---|
| | Expression level of CXCL12 mRNA (% Control) | | | | |
| 855156* | 81 | 63 | 45 | 31 | n.d. |
| 895566 | 68 | 55 | 42 | n.d. | 22 |
| 895567 | 59 | 50 | 36 | n.d. | 18 |
| 895568 | 69 | 49 | 37 | n.d. | 17 |
| 895569 | 72 | 51 | 41 | n.d. | 18 |
| 895570 | 68 | 50 | 38 | n.d. | 17 |
| 913196 | 62 | 48 | 44 | n.d. | 19 |
| 920046 | 80 | 58 | 58 | n.d. | 25 |
| 855161 | 67 | 51 | 38 | 32 | 21 |
| 951972 | 77 | 61 | 39 | 29 | 20 |
| 951973 | 81 | 59 | 37 | 32 | 19 |
| 974343 | 86 | 56 | 37 | 27 | 16 |
| 974344 | 79 | 69 | 44 | 34 | 23 |
| 1011295 | 78 | 62 | 44 | 31 | 30 |
| 1011296 | 77 | 63 | 49 | 51 | 29 |

Example 39 Synthesis of 5'-(R)-Ethyl and 5'-(S)-Ethyl Phosphoramidites

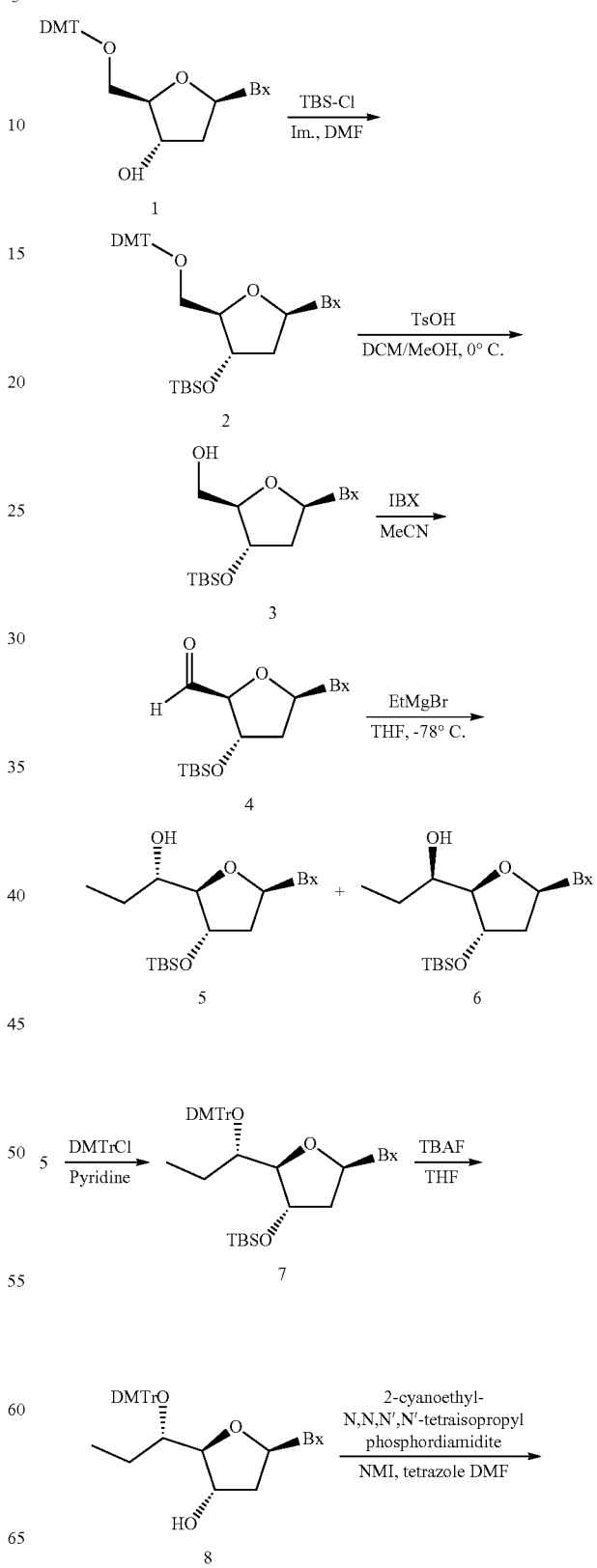

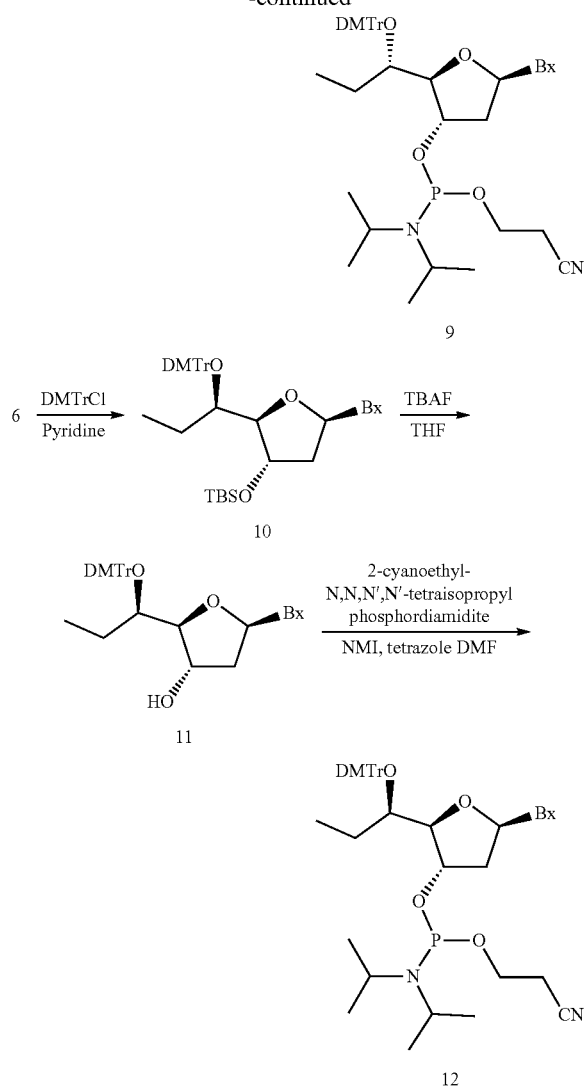

1 was synthesized by The National Institutes of Pharmaceutical R&D

Bx=N(Bz)-A, N(iBu)-G, N(Bz)MeC, T

5'-(R)-ethyl and 5'-(S)-ethyl phosphordiamidates were prepared as per the scheme illustrated above.

Example 40 Time Course of Modified Oligonucleotides in HeLa Cells

HeLa cells were transfected with a modified oligonucleotide listed in the tables below. At 0, 0.5, 1, 2, 4, and 6 hours after transfection, cells were lysed and mRNA was isolated and analyzed by RT-qPCR. Primer probe set HTS3934 (forward sequence: TGGAGACTCTCAGGGTCGAAA, SEQ ID NO: 122; reverse sequence: GGCGTTTG-GAGTGGTAGAAATC, SEQ ID NO: 123; probe sequence: CGGCGGCAGACCAGCATGAC, SEQ ID NO: 124) was used to detect human p21 mRNA, and primer probe set HS00169255_m1 (ThermoFisher)) was used to detect human Gadd45a mRNA. Results are normalized to untreated cells.

TABLE 94

Relative hp21 mRNA timecourse in HeLa cells

| | % Control human p21 mRNA | | | | | |
|---|---|---|---|---|---|---|
| Compound | 0 hrs | 0.5 hrs | 1 hrs | 2 hrs | 4 hrs | 6 hrs |
| 464917 | 100 | 123 | 133 | 241 | 259 | 557 |
| 558807 | 97.8 | 113 | 135 | 187 | 253 | 528 |
| 549148 | 120 | 120 | 129 | 187 | 138 | 147 |
| 549139 | 102 | 125 | 124 | 143 | 133 | 213 |

TABLE 95

Relative hGadd45a mRNA timecourse in HeLa cells

| | % Control human Gadd45a mRNA | | | | | |
|---|---|---|---|---|---|---|
| Compound | 0 hrs | 0.5 hrs | 1 hrs | 2 hrs | 4 hrs | 6 hrs |
| 464917 | 100 | 157 | 281 | 375 | 632 | 746 |
| 558807 | 105 | 188 | 227 | 297 | 261 | 412 |
| 549148 | 106 | 156 | 200 | 231 | 156 | 180 |
| 549139 | 94 | 157 | 213 | 229 | 167 | 237 |

HeLa cells were transfected with various concentrations of modified oligonucleotide as indicated in the table below. At 0, 1, 2, 4, 6, and 8 hours after transfection, cells were lysed and mRNA was isolated and analyzed by RT-qPCR as described above.

TABLE 96

Relative hp21 mRNA dose response/time course in HeLa cells

| | | % Control human p21 mRNA | | | | | |
|---|---|---|---|---|---|---|---|
| Compound | Dose (nM) | 0 hrs | 1 hrs | 2 hrs | 4 hrs | 6 hrs | 8 hrs |
| 464917 | 0 | 100 | 114 | 87 | 105 | 107 | 97 |
| 464917 | 3.125 | 100 | 109 | 76 | 111 | 179 | 126 |
| 464917 | 6.25 | 100 | 110 | 86 | 113 | 219 | 159 |
| 464917 | 12.50 | 100 | 112 | 86 | 126 | 287 | 239 |
| 464917 | 25.0 | 100 | 110 | 98 | 153 | 313 | 399 |
| 464917 | 50.0 | 100 | 96 | 94 | 165 | 392 | 490 |
| 464917 | 100.0 | 100 | 108 | 106 | 191 | 450 | 600 |
| 464917 | 200.0 | 100 | 99 | 100 | 230 | 510 | 660 |
| 549148 | 0 | 100 | 89 | 106 | 113 | 106 | 79 |
| 549148 | 3.125 | 100 | 105 | 100 | 117 | 126 | 96 |
| 549148 | 6.25 | 100 | 88 | 99 | 128 | 115 | 84 |
| 549148 | 12.50 | 100 | 95 | 108 | 107 | 115 | 107 |
| 549148 | 25.0 | 100 | 95 | 123 | 130 | 140 | 111 |
| 549148 | 50.0 | 100 | 101 | 111 | 122 | 131 | 114 |
| 549148 | 100.0 | 100 | 98 | 89 | 131 | 104 | 100 |
| 549148 | 200.0 | 100 | 93 | 95 | 163 | 102 | 99 |

TABLE 97

Relative hGadd45a mRNA dose response/time course in HeLa cells

| | | % Control human p21 mRNA | | | | | |
|---|---|---|---|---|---|---|---|
| Compound | Dose (nM) | 0 hrs | 1 hrs | 2 hrs | 4 hrs | 6 hrs | 8 hrs |
| 464917 | 0 | 100 | 97 | 80 | 109 | 110 | 88 |
| 464917 | 3.125 | 100 | 117 | 95 | 156 | 208 | 170 |
| 464917 | 6.25 | 100 | 121 | 111 | 176 | 176 | 205 |
| 464917 | 12.50 | 100 | 139 | 126 | 165 | 271 | 261 |
| 464917 | 25.0 | 100 | 147 | 136 | 176 | 279 | 420 |
| 464917 | 50.0 | 100 | 130 | 171 | 203 | 368 | 700 |
| 464917 | 100.0 | 100 | 143 | 194 | 261 | 835 | 1234 |
| 464917 | 200.0 | 100 | 113 | 198 | 213 | 890 | 1111 |

TABLE 97-continued

Relative hGadd45a mRNA dose response/time course in HeLa cells

| Compound | Dose (nM) | % Control human p21 mRNA | | | | | |
|---|---|---|---|---|---|---|---|
| | | 0 hrs | 1 hrs | 2 hrs | 4 hrs | 6 hrs | 8 hrs |
| 549148 | 0 | 100 | 98 | 104 | 104 | 111 | 99 |
| 549148 | 3.125 | 100 | 124 | 133 | 120 | 132 | 133 |
| 549148 | 6.25 | 100 | 151 | 140 | 155 | 160 | 142 |
| 549148 | 12.50 | 100 | 159 | 159 | 131 | 120 | 144 |
| 549148 | 25.0 | 100 | 173 | 172 | 148 | 156 | 180 |
| 549148 | 50.0 | 100 | 155 | 170 | 164 | 104 | 164 |
| 549148 | 100.0 | 100 | 140 | 129 | 141 | 160 | 190 |
| 549148 | 200.0 | 100 | 121 | 115 | 128 | 107 | 185 |

Example 41 Time Course of Toxicity of Modified Oligonucleotide 464917 In Vivo

The modified oligonucleotide 464917 was administered subcutaneously at 11, 33, or 100 mg/kg to 9 BALB/C mice per dosing group. Three mice from each group were sacrificed at 24 hours, three at 48 hours, and the last three at 72 hours after dosing. mRNA was isolated and analyzed as described in Example 1. ALT values in plasma were obtained using a clinical chemistry analyzer.

TABLE 98

Time Course of Activity and Toxicity in mice

| Compound | Dose (mg/kg) | 24 hrs | 48 hrs ALT | 72 hrs | 24 hrs | 48 hrs mFXI mRNA | 72 hrs |
|---|---|---|---|---|---|---|---|
| 464917 | 0 | 44 | 58 | 29 | 100 | 100 | 100 |
| 464917 | 11 | 40 | 132 | 311* | 20 | 17 | 11* |
| 464917 | 33 | 98 | 2015 | 8072 | 2.7 | 2.6 | 5.7 |
| 464917 | 100 | 168 | 12261 | 26659* | 1.7 | 0.5 | 0.07** |

*Data represents a single mouse
**Data represents the average of two mice

TABLE 99

Time Course of Toxicity in mice

| Compound | Dose (mg/kg) | 24 hrs | 48 hrs mP21 mRNA | 72 hrs | 24 hrs | 48 hrs mTnfrsf10b mR | 72 hrs NA |
|---|---|---|---|---|---|---|---|
| 464917 | 0 | 100 | 100 | 100 | 100 | 100 | 100 |
| 464917 | 11 | 518 | 607 | 2060* | 272 | 845 | 3401* |
| 464917 | 33 | 6451 | 1846 | 5221 | 2071 | 5333 | 7013 |
| 464917 | 100 | 163667 | 4067 | 4910** | 5451 | 12293 | 7402** |

*Data represents a single mouse
**Data represents the average of two mice

Example 42 Nucleolar Delocalization of p54nrb In Vivo

Compound 959265 is compound 464917 conjugated to a Cy3 on the 5'-end and HPPO-GalNAc on the 3'-end. Balb/c mice were administered 15 mg/kg of 959265 by subcutaneous injection. Hepatocytes were isolated and purified 40 hours after administration of modified oligonucleotide and plated on a confocal dish for 6-7 hours. After 6-7 hours, cells were fixed with formaldehyde and stained for p54nrb with immunofluorescent staining for p54nrb. Levels of FXI and p21 were detected by RT-qPCR as described above.

A single dose of 959265 at 15 mg/kg reduced FXI to 10.6% of control values. Levels of p21 mRNA were upregulated 1,046%. Isolated hepatocytes were observed to contain p54nrb that had been localized to the nucleolus or no detectable p54nrb.

Example 43 Nucleolar Delocalization of p54nrb In Vivo

Balb/c mice were administered 100 mg/kg of 464917 or 549148 by subcutaneous injection. Hepatocytes were isolated and purified 16 hours after administration of modified oligonucleotide and plated on a confocal dish for 1-2 hours. After 1-2 hours, cells were fixed with formaldehyde and stained for p54nrb with immunofluorescent staining for p54nrb.

Localization of p54nrb to the nucleolus of hepatocytes was observed for compound 464917 but not for compound 549148.

Example 44 In Vivo Activity and Toxicity of Compounds Containing a MOP Neutral Linkage Six week old BALB/C mice (purchased from Charles River) were injected subcutaneously once at dosage 0.2, 0.6, 1.8 5.4, or 50 mg/kg with the modified oligonucleotides shown below or with saline control. For compound 855156, mice were injected with 0.2, 0.6, 1.8, 5.4, or 15 mg/kg modified oligonucleotide. Each treatment group consisted of 3 animals. The mice were sacrificed 72 hours following administration, and organs and plasma were harvested for further analysis.

Liver tissues were homogenized and mRNA levels were quantitated using real-time PCR and normalized to RIBOGREEN as described herein. Plasma chemistry markers such as liver transaminase levels, alanine aminotranferase (ALT) in serum were measured relative to saline injected mice.

The $ED_{50}$ values were calculated by plotting the concentrations of oligonucleotides used versus the percent inhibition of CXCL12 mRNA expression achieved at each concentration, and noting the concentration of oligonucleotide at which 50% inhibition of CXCL12 mRNA expression was achieved compared to the control.

TABLE 100

Modified Oligonucleotides

| Compound ID | position of linkage-altered nucleotide in central region | Linkage mod | Chemistry Notation | SEQ ID NO |
|---|---|---|---|---|
| 869742 | n/a | n/a | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}T_k$-HPPO-GalNAc | 125 |
| 898384 | 3 | MOP | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}T_k$-HPPO-GalNAc | 125 |
| 898385 | 2, 3 | MOP | $G_{ks}{}^mC_{ks}A_{ks}T_{ds}G_{dx}T_{dx}T_{ds}{}^mC_{ds}T_{ds}{}^mC_{ds}A_{ds}{}^mC_{ds}A_{ds}T_{ks}T_{ks}T_k$-HPPO-GalNAc | 125 |

A subscript "d" indicates an unmodified, 2'-β-D-deoxyribosyl sugar moiety.
A subscript "k" indicates a cEt.
A subscript "s" indicates a phosphorothioate internucleoside linkage.
A superscript "m" before a C indicates 5-methyl Cytosine.
A subscript "x" indicates a MOP internucleoside linkage.

TABLE 101

In vivo Toxicity

| Compound ID | Linkage Mod position in Central region | Linkage Mod | ALT at 15 mg/kg | ALT at 50 mg/kg |
|---|---|---|---|---|
| 855156 | n/a | n/a | 9,639 | n/a |
| 869742 | n/a | n/a | 2,001 | n/a |
| 898384 | 3 | MOP | 30 | 32 |
| 898385 | 2, 3 | MOP | 32 | 30 |

TABLE 102

In Vivo CXCL12 mRNA levels

| Compound ID | 0.2 mg/kg | 0.6 mg/kg | 1.8 mg/kg | 5.4 mg/kg | 15 mg/kg | 50 mg/kg |
|---|---|---|---|---|---|---|
| | Expression level of CXCL12 mRNA (% Control) | | | | | |
| 855156 | 64 | 42 | 23 | 19 | 16 | n/a |
| 869742 | 87 | 58 | 32 | 23 | 18 | n/a |
| 898384 | 87 | 91 | 49 | 40 | 36 | 31 |
| 898385 | 91 | 90 | 64 | 64 | 55 | 41 |

Example 45

Modified oligonucleotides were tested for toxicity in vivo in Balb/c mice.

TABLE 103

Modified Oligonucleotides

| Compound ID | Chemistry notation | SEQ ID NO: |
|---|---|---|
| 575013 | ${}^mC_{ks}A_{ks}G_{ks}A_{ds}T_{ds}A_{ds}T_{ds}A_{ds}G_{ds}G_{ds}A_{ds}{}^mC_{ds}T_{ds}G_{ks}G_{ks}A_k$ | 110 |
| 465131 | $T_{ks}G_{ks}{}^mC_{ks}{}^mC_{ds}A_{ds}{}^mC_{ds}{}^mC_{ds}G_{ds}T_{ds}A_{ds}G_{ds}A_{ds}{}^mC_{ds}A_{ks}{}^mC_{ks}G_k$ | 114 |
| 549139 | $G_{ks}A_{ks}{}^mC_{ks}G_{ds}{}^mC_{ds}G_{ds}{}^mC_{ds}{}^mC_{ds}T_{ds}G_{ds}A_{ds}A_{ds}G_{ds}G_{ks}T_{ks}T_k$ | 111 |
| 464932 | $G_{ks}G_{ks}A_{ks}{}^mC_{ds}A_{ds}{}^mC_{ds}A_{ds}T_{ds}T_{ds}G_{ds}G_{ds}{}^mC_{ds}{}^mC_{ds}A_{ks}{}^mC_{ks}A_k$ | 112 |

A subscript "d" indicates an unmodified, 2'-β-D-deoxyribosyl sugar moiety.
A subscript "k" indicates a cEt modified sugar moiety.
A subscript "s" indicates a phosphorothioate internucleoside linkage.
A superscript "m" before a C indicates 5-methyl Cytosine.

For in vivo toxicity studies, 3 BALB/c mice per group were administered the indicated dose of modified oligonucleotide by subcutaneous injection and sacrificed after 72 hours. Four animals were administered saline to serve as a control. RT-PCR was performed as described in Example 1 to determine mRNA levels of CXCL12, P21, Tnfrsf10b, and Gadd45a. Plasma levels of ALT were measured using an automated clinical chemistry analyzer. Increased ALT is indicative of acute liver toxicity.

For the in vitro toxicity study in the table below, the caspase assay was performed essentially as described in Example 8 in 3T3-L1 cells. The caspase assay was performed in HeLa cells by free uptake at 2 μM modified oligonucleotide and in b.END3 cells by free uptake at 50 μM modified oligonucleotide.

TABLE 104

In vivo and in vitro toxicity of modified oligonucleotides

| Compound ID | in vivo Dose (mg/kg) | ALT (IU/L) | in vivo P21 (% control) | in vivo Tnfrsf10b (% control) | in vitro caspase @20 μM, 3T3-L1 (% control) | in vitro caspase @2 μM, HeLa (% control) | in vitro caspase @50 μM, b.END (% control) |
|---|---|---|---|---|---|---|---|
| 575013 | 100 | 12 | 54 | 105 | 237 | 100 | 140 |
| 465131 | 100 | 21 | 111 | 164 | 114 | 119 | n.d. |
| 549139 | 100 | 24 | 118 | 135 | 125 | 111 | 113 |
| 549148 | 100 | 24 | 72 | 83 | 184 | 121 | 159 |
| 464932 | 100 | 5 | 150 | 180 | 280 | 113 | 187 |
| 449093 | 33 | 2324 | 42802 | 3835 | 2703 | 306 | 783 |
|  | 100 | 9983 | 150994 | 3744 |  |  |  |
| 482050 | 33 | 1470 | 7890 | 4725 | 1502 | 203 | 439 |
|  | 100 | 6555 | 10430 | 4232 |  |  |  |
| 508031 | 33 | 648 | 2980 | 2239 | 1082 | 255 | 357 |
|  | 100 | 18550 | 8909 | 6678 |  |  |  |
| 558807 | 17 | 1877 | 2763 | 1168 | 910 | 408 | 413 |
|  | 51 | 9510 | 11904 | 6831 |  |  |  |
| 464917 | 11 | 601 | 6098 | 3516 | 1724 | 219 | 552 |
|  | 33 | 13920 | 9590 | 7731 |  |  |  |

Example 46 Time Course of Toxicity and Activity of Modified Oligonucleotide 464932 or 464917 In Vivo The modified oligonucleotide 464932, described in Example 45 above, or 464917, described in Example 4 above, was administered subcutaneously at 33 mg/kg to BALB/C mice. Three mice from each dosing group were sacrificed at each indicated time point and mRNA was isolated and analyzed as described in Example 1. ALT values in plasma were obtained using a clinical chemistry analyzer and were normalized to saline-treated animals.

TABLE 105

Time Course of Activity and Toxicity in mice

| Treatment | Measurement | 8 hrs | 12 hrs | 16 hrs | 24 hrs | 48 hrs | 72 hrs |
|---|---|---|---|---|---|---|---|
| PBS | ALT | 20 | 41 | 40 | 40 | 44 | 41 |
| 464932 | ALT | 49 | 64 | 58 | 47 | 39 | 108 |
|  | mFXI | 174 | 104 | 40 | 53 | 19 | 12 |
|  | mP21 | 94 | 115 | 71 | 182 | 47 | 185 |
|  | mTnfrsf10b | 133 | 101 | 112 | 108 | 117 | 140 |
| 464917 | ALT | 39 | 49 | 53 | 41 | 1903 | 13917 |
|  | mFXI | 100 | 56 | 12 | 19 | 4 | 5 |
|  | mP21 | 138 | 391 | 829 | 3751 | 1854 | 12716 |
|  | mTnfrsf10b | 118 | 221 | 714 | 1250 | 6369 | 8781 |

Example 47 Time Course of Toxicity and Activity of Modified Oligonucleotide 558807 or 558765 In Vivo Modified oligonucleotide 558765 is a 3-10-3 cEt gapmer with a full phosphorothioate backbone and the sequence A<sup>m</sup>CAT<sup>m</sup>CTT<sup>m</sup>CAGAT<sup>m</sup>CATT (SEQ ID NO: 144). The modified oligonucleotide 558807 or 558765 was administered subcutaneously at 51 mg/kg to BALB/C mice. Three mice from each dosing group were sacrificed at each indicated time point and mRNA was isolated and analyzed as described in Example 1. ALT values in plasma were obtained using a clinical chemistry analyzer and were normalized to saline-treated animals.

TABLE 106

Time Course of Activity and Toxicity in mice

| Treatment | Measurement | 8 hrs | 12 hrs | 16 hrs | 24 hrs | 48 hrs | 72 hrs |
|---|---|---|---|---|---|---|---|
| PBS | ALT | 21 | 42 | 40 | 40 | 44 | 41 |
| 558765 | ALT | 34 | 53 | 46 | 92 | 33 | 36 |
|  | mCXCL12 | 109 | 94 | 20 | 54 | 29 | 26 |
|  | mP21 | 143 | 116 | 92 | 209 | 48 | 404 |
|  | mTnfrsf10b | 106 | 70 | 118 | 98 | 154 | 215 |
| 558807 | ALT | 36 | 50 | 53 | 36 | 1888 | 7272 |
|  | mCXCL12 | 43 | 18 | 5 | 10 | 3 | 3 |
|  | mP21 | 136 | 142 | 86 | 580 | 1573 | 1642 |
|  | mTnfrsf10b | 101 | 148 | 236 | 292 | 3375 | 7454 |

Example 48 Toxicity Improvement In Vivo with Incorporation 2'-OMe Modified-Nucleoside in the Central Region BALB/c mice were administered 1.8, 5.5, 16.7, or 50 mg/kg of 558807 or 1.8, 5.5, 16.7, 50, 100, 200, or 300 mg/kg of 936053 and sacrificed after 72 hours. Plasma levels of ALT were measured with a clinical chemistry analyzer and mRNA was isolated and analyzed as described in Example 1. Therapeutic index (TI) was calculated as the maximum non-toxic dose divided by the ED50. Compound 936053 differs from compound 558807 only in the presence of a 2'-OMe group at position 5 from the 5' end of the compound, or position 2 of the central region.

TABLE 107 in vivo dose response

| Compound ID | Dose (mg/kg) | ALT (IU/L) | in vivo P21 (% control) | in vivo Tnfrsf10b (% control) | in vivo Gadd45a (% control) | CXCL12 mRNA (% control) | ED50 (mg/kg) | MTND (mg/kg) | Therapeutic Index |
|---|---|---|---|---|---|---|---|---|---|
| 558807 | 1.8 | 24 | 118 | 120 | 147 | 67.5 | 2.75 | 5.5 | 2 |
|  | 5.5 | 27 | 63 | 103 | 176 | 20.3 |  |  |  |
|  | 16.7 | 586 | 625 | 788 | 879 | 9.7 |  |  |  |
|  | 50 | death | n.d. | n.d. | n.d. | n.d. |  |  |  |
| 936053 | 1.8 | 34 | 104 | 78 | 61 | 65.3 | 4.86 | 200 | 41 |
|  | 5.5 | 26 | 94 | 137 | 99 | 47.4 |  |  |  |
|  | 16.7 | 23 | 104 | 110 | 91 | 32.7 |  |  |  |
|  | 50 | 23 | 89 | 122 | 90 | 14.4 |  |  |  |
|  | 100 | 42 | n.d. | n.d. | n.d. | n.d. |  |  |  |
|  | 200 | 109 | n.d. | n.d. | n.d. | n.d. |  |  |  |
|  | 300 | 231 | n.d. | n.d. | n.d. | n.d. |  |  |  |

Example 49 Toxicity Improvement of Modified Oligonucleotides Targeted to FXI

BALB/c mice were administered 1.8, 5.5, 16.7, 50 or 150 mg/kg of modified oligonucleotide by subcutaneous injection. Each group contained 3 mice. A group of 4 mice was administered PBS as a control. Plasma levels of ALT were measured with a clinical chemistry analyzer and mRNA was isolated and analyzed as described in Example 1. Modified oligonucleotides are described in Example 18. Each pair of compounds, presented adjacent to each other in the table below, represents a compound with the motif kkk-d(10)-kkk (464xxx) and the same sequence with the motif kkk-d-m-d (8)-kkk (1133xxx). In instances where position 5 in the original sequence is a T, this nucleoside is a 2'-OMeU in the kkk-d-m-d(8)-kkk sequence.

TABLE 108 in vivo dose response

| Compound ID | Dose (mg/kg) | ALT (IU/L) | in vivo P21 (% control) | FXI mRNA (% control) | ED50 (mg/kg) | MTND (mg/kg) | Therapeutic Index |
|---|---|---|---|---|---|---|---|
| 464924 | 1.8 | 27 | 136 | 59.7 | 2.4 | 16.7 | 7.0 |
|  | 5.5 | 27 | 144 | 20.4 |  |  |  |
|  | 16.7 | 31 | 167 | 2.5 |  |  |  |
|  | 50 | 646 | 551 | 0.4 |  |  |  |
|  | 150 | 4509 | 1160 | 0.4 |  |  |  |
| 1133247 | 1.8 | 32 | 130 | 75.0 | 3.4 | >150 | >44 |
|  | 5.5 | 30 | 67 | 29.3 |  |  |  |
|  | 16.7 | 30 | 94 | 5.4 |  |  |  |
|  | 50 | 37 | 123 | 1.9 |  |  |  |
|  | 150 | 53 | 304 | 1.4 |  |  |  |
| 465172 | 1.8 | 26 | 131 | 73.5 | 6.7 | >150 | >22 |
|  | 5.5 | 22 | 102 | 57.8 |  |  |  |
|  | 16.7 | 23 | 99 | 28.8 |  |  |  |
|  | 50 | 25 | 102 | 13.8 |  |  |  |
|  | 150 | 33 | 177 | 6.2 |  |  |  |
| 1133326 | 1.8 | 25 | 51 | 81.1 | 16.3 | >150 | >9 |
|  | 5.5 | 25 | 64 | 81.8 |  |  |  |
|  | 16.7 | 24 | 55 | 49.0 |  |  |  |
|  | 50 | 24 | 78 | 21.1 |  |  |  |
|  | 150 | 22 | 90 | 11.8 |  |  |  |
| 465174 | 1.8 | 25 | 192 | 67.5 | 4.2 | >150 | >36 |
|  | 5.5 | 29 | 172 | 46.8 |  |  |  |
|  | 16.7 | 22 | 31 | 18.0 |  |  |  |
|  | 50 | 20 | 49 | 7.5 |  |  |  |
|  | 150 | 29 | 83 | 5.7 |  |  |  |
| 1133328 | 1.8 | 21 | 40 | 74.8 | 4.8 | >150 | >32 |
|  | 5.5 | 23 | 38 | 44.3 |  |  |  |
|  | 16.7 | 28 | 42 | 18.6 |  |  |  |
|  | 50 | 26 | 25 | 13.0 |  |  |  |
|  | 150 | 31 | 38 | 10.7 |  |  |  |
| 465178 | 1.8 | 26 | 43 | 47.2 | 1.7 | 16.7 | 10 |
|  | 5.5 | 35 | 119 | 18.4 |  |  |  |
|  | 16.7 | 73 | 627 | 4.3 |  |  |  |
|  | 50 | 1067 | 3509 | 0.7 |  |  |  |
|  | 150 | 11596 | 4849 | 0.4 |  |  |  |

TABLE 108-continued in vivo dose response

| Compound ID | Dose (mg/kg) | ALT (IU/L) | in vivo P21 (% control) | FXI mRNA (% control) | ED50 (mg/kg) | MTND (mg/kg) | Therapeutic Index |
|---|---|---|---|---|---|---|---|
| 1133332 | 1.8 | 23 | 101 | 47.8 | 1.8 | 150 | 83 |
|  | 5.5 | 35 | 42 | 30.7 |  |  |  |
|  | 16.7 | 33 | 136 | 13.1 |  |  |  |
|  | 50 | 41 | 600 | 3.7 |  |  |  |
|  | 150 | 117 | 1414 | 1.3 |  |  |  |

Example 50 Toxicity Improvement of Modified Oligonucleotides Targeted to HDAC2

BALB/c mice were administered 1.8, 5.5, 16.7, 50 or 150 mg/kg of modified oligonucleotide by subcutaneous injection. Each group contained 3 mice. A group of 4 mice was administered PBS as a control. Plasma levels of ALT were measured with a clinical chemistry analyzer and mRNA was isolated and analyzed as described in Example 1. Modified oligonucleotides are described in Example 19. Each pair of compounds, presented adjacent to each other in the table below, represents a compound with the motif kkk-d(10)-kkk (546xxx) and the same sequence with the motif kkk-d-m-d(8)-kkk (1133xxx). In instances where position 5 in the original sequence is a T, this nucleoside is a 2'-OMeU in the kkk-d-m-d(8)-kkk sequence.

TABLE 109 in vivo dose response

| Compound ID | Dose (mg/kg) | ALT (IU/L) | HDAC2 mRNA (% control) | ED50 (mg/kg) | MTND (mg/kg) | Therapeutic Index |
|---|---|---|---|---|---|---|
| 546108 | 1.8 | 33 | 74 | 3.2 | 16.7 | 5.2 |
|  | 5.5 | 47 | 26.2 |  |  |  |
|  | 16.7 | 168 | 3.8 |  |  |  |
|  | 50 | 1713 | 4.8 |  |  |  |
|  | 150 | 17844 | 4.5 |  |  |  |
| 1133122 | 1.8 | 29 | 91.6 | 5.5 | >150 | >27 |
|  | 5.5 | 25 | 48.3 |  |  |  |
|  | 16.7 | 2 | 11.0 |  |  |  |
|  | 50 | 43 | 1.1 |  |  |  |
|  | 150 | 78 | 1.1 |  |  |  |
| 546110 | 1.8 | 25 | 72.9 | 6.4 | 16.7 | 2.6 |
|  | 5.5 | 27 | 57.4 |  |  |  |
|  | 16.7 | 37 | 29.4 |  |  |  |
|  | 50 | 416 | 6.7 |  |  |  |
|  | 150 | 2817 | 6.0 |  |  |  |
| 1133123 | 1.8 | 24 | 71.0 | 6.8 | >150 | >22 |
|  | 5.5 | 80 | 49.6 |  |  |  |
|  | 16.7 | 25 | 47.8 |  |  |  |
|  | 50 | 25 | 8.0 |  |  |  |
|  | 150 | 28 | 3.0 |  |  |  |
| 546118 | 1.8 | 30 | 69.9 | 23.8 | 16.7 | 0.7 |
|  | 5.5 | 29 | 70.1 |  |  |  |
|  | 16.7 | 40 | 50.8 |  |  |  |
|  | 50 | 365 | 39.1 |  |  |  |
|  | 150 | 1681 | 36.0 |  |  |  |
| 1133127 | 1.8 | 35 | 77.2 | 24.9 | >150 | >6 |
|  | 5.5 | 25 | 60.6 |  |  |  |
|  | 16.7 | 26 | 57.1 |  |  |  |
|  | 50 | 25 | 39.9 |  |  |  |
|  | 150 | 33 | 34.4 |  |  |  |

Example 51 Toxicity Improvement of Modified Oligonucleotides

Modified oligonucleotides were tested for toxicity in vivo in Balb/c mice. Compound 865060 has the motif kkk-d(10)-kkkk and compound 865061 has the motif kkkk-d(10)-kkk. Compounds 1269430 and 1269431 are otherwise identical compounds to 865060 and 865061, respectively, containing a 2'-OMe modified sugar moiety at the second position in the central region.

TABLE 110

Modified Oligonucleotides

| Compound ID | Chemistry notation | SEQ ID NO: |
|---|---|---|
| 865060 | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{kS}T_{ks}A_{ks}T_k$ | 125 |
| 865061 | $G_{ks}G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{kS}T_{ks}A_k$ | 141 |
| 1269430 | $G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_{ks}T_k$ | 125 |
| 1269431 | $G_{ks}G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_k$ | 141 |

A subscript "d" indicates an unmodified, 2'-β-D-deoxyribosyl sugar moiety.
A subscript "k" indicates a cEt.
A subscript "m" indicates a 2'-O-methyl-β-D-ribofuranosyl sugar moiety.
A subscript "s" indicates a phosphorothioate internucleoside linkage.
A superscript "m" before a C indicates 5-methyl Cytosine.

For in vivo toxicity studies, 3 BALB/c mice per group were administered the indicated dose of modified oligonucleotide by subcutaneous injection and sacrificed after 72 hours. Four animals were administered saline to serve as a control. RT-PCR was performed as described in Example 1 to determine mRNA levels of CXCL12, P21, Tnfrsf10b, and Gadd45a. Plasma levels of ALT was measured using an automated clinical chemistry analyzer. Increased ALT is indicative of acute liver toxicity.

For the in vitro toxicity study in the table below, the caspase assay was performed essentially as described in Example 8 in 3T3-L1 cells, the percent nucleolar p54nrb was visualized as described in Example 11, and the p21 mRNA levels were determined as described in Example 11.

TABLE 111

In vivo and in vitro toxicity of modified oligonucleotides

| Compound ID | in vitro CXCL12 IC$_{50}$ (nM) | Relative Caspase Activation (% Control) @20 μM | in vitro p21 mRNA (% Control) @20 μM | in vitro % nucleolar p54nrb | in vivo p21 @150 mg/kg | in vivo Tnfrsf10b mRNA @ 150 mg/kg | ALT @ 150 mg/kg (IU/L) |
|---|---|---|---|---|---|---|---|
| 558807 | 183 | 432 | 285 | 82 | 7152* | 5504* | 9928* |
| 936053 | 259 | 114 | 114 | 0 | 166 | 204 | 12 |
| 865060 | 310 | 355 | 224 | 64 | 7604* | 9339* | 11058* |
| 1269430 | 308 | 110 | 127 | 0 | 209 | 350 | 10 |
| 865061 | 510 | 738 | 198 | 75 | 12531 | 6351 | 9014 |
| 1269431 | 849 | 116 | 134 | 0 | 376 | 661 | 52 |

*Value at 50 mg/kg dose; mice administered 150 mg/kg did not survive

Example 52 Long-Term Toxicity Improvement of Modified Oligonucleotides

Modified oligonucleotides were tested for toxicity in vivo in Balb/c mice. Mice were administered 50 mg/kg modified oligonucleotide once a week for six weeks and ALT was measured using an automated clinical chemistry analyzer. Compounds in the table below are described in Example 13. Each pair of compounds represents an oligonucleotide with the sugar motif kkk-d(10)-kkk (upper) and an oligonucleotide with the same sequence having the sugar motif kkk-d-m-d(8)-kkk (lower).

TABLE 112

Long-term Toxicity

| Compound ID | Week of Dosing | | | | | |
|---|---|---|---|---|---|---|
| | 1 | 2 | 3 | 4 | 5 | 6 |
| | ALT (IU/L) | | | | | |
| PBS | 35 | 65 | 27 | 45 | 55 | 23 |
| 572912 | 398 | 1036 | 2667 | 2787 | n.d. | n.d. |
| 1200898 | 36 | 53 | 70 | 112 | 187 | 513 |
| 797793 | 1210 | 972 | 1674 | 2703 | 3831 | 3635 |
| 1201073 | 99 | 143 | 165 | 178 | 217 | 330 |
| 576095 | 46 | 83 | 1017 | 1763 | 2886 | 4118 |
| 1200899 | 50 | 57 | 129 | 550 | 1225 | 1392 | n.d. indicates that the mice were sacrificed prior to the measurement date.

Example 53

Modified oligonucleotides were designed based on 546118. Each of the modified oligonucleotides is conjugated with a THA-GalNAc conjugate group at the 3'-end. THA-GalNac refers to this structure:

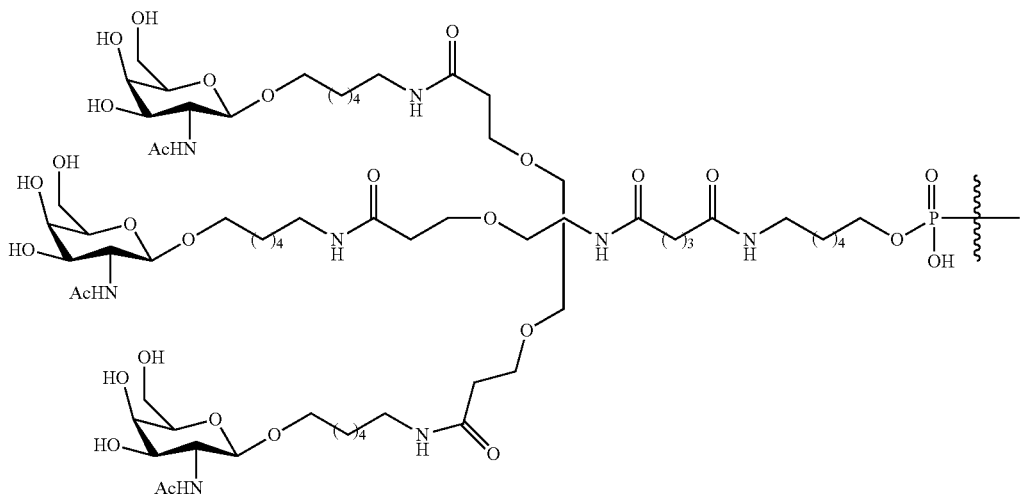

wherein the phosphate group is attached to the 3'-oxygen atom of the 3' nucleoside.

The oligonucleotides were evaluated for reduction in HDAC2 mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.023, 0.067, 0.2, 0.6, 1.8, 5.4, 15, or 50 mg/kg with the modified oligonucleotides shown below or with saline control. Each treatment group consisted of 3 animals. The mice were sacrificed 72 hours following administration, and organs and plasma were harvested for further analysis.

TABLE 113

Modified Oligonucleotides

| Compound ID | position of altered nucleotide in central region | modification of altered nucleotide | Chemistry Notation | SEQ ID NO |
|---|---|---|---|---|
| 1270732 | N/A | N/A | $A_{ks}{}^mC_{ks}{}^mC_{ks}{}^mC_{ds}T_{ds}$ ${}^mC_{ds}A_{ds}A_{ds}G_{ds}T_{ds}$ ${}^mC_{ds}T_{ds}{}^mC_{ds}{}^mC_{ks}T_{ks}$ $G_k$-THAGalNAc | 109 |
| 1270733 | 2 | 2'-OMe | $A_{ks}{}^mC_{ks}{}^mC_{ks}{}^mC_{ds}U_{ms}$ ${}^mC_{ds}A_{ds}A_{dsds}T_{ds}$ ${}^mC_{ds}T_{ds}{}^mC_{ds}{}^mC_{ks}$ $T_{ks}G_k$-THAGalNAc | 140 |
| 1270734 | 2 | MOP | $A_{ks}{}^mC_{ks}{}^mC_{ks}{}^mC_{ds}T_{dx}$ ${}^mC_{ds}A_{ds}A_{ds}A_{ds}T_{ds}$ ${}^mC_{ds}T_{ds}{}^mC_{ds}{}^mC_{ks}$ $T_{ks}G_k$-THAGalNAc | 109 |

A subscript "d" indicates an unmodified, 2'-β-D-deoxyribosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage.

TABLE 114

In vivo Activity and Toxicity of Modified Oligonucleotides

| Compound ID | Dose (mg/kg) | ALT (IU/L) | P21 mRNA (% Control) | Tnfrsf10b mRNA (% Control) | HDAC2 ED50 (mg/kg) |
|---|---|---|---|---|---|
| 1270732 | 0.023 | 34 | 106 | n.d. | 0.060 |
| | 0.067 | 7 | 74 | n.d. | |
| | 0.2 | 15 | 113 | 80 | |
| | 0.6 | 13 | 112 | 76 | |
| | 1.8 | 33 | 537 | 118 | |
| | 5.4 | 122 | 688 | 271 | |
| | 15 | 1467 | 2606 | 1418 | |
| | 50 | 3429 | 5197 | 3064 | |
| 1270733 | 0.023 | 22 | 71 | n.d. | 0.066 |
| | 0.067 | 43 | 91 | n.d. | |
| | 0.2 | 18 | 89 | 80 | |
| | 0.6 | 20 | 103 | 104 | |
| | 1.8 | 17 | 81 | 81 | |
| | 5.4 | 23 | 154 | 81 | |
| | 15 | 11 | 172 | 110 | |
| | 50 | 22 | 988 | 353 | |
| 1270734 | 0.023 | 13 | 64 | n.d. | 0.084 |
| | 0.067 | 22 | 65 | n.d. | |
| | 0.2 | 31 | 158 | 93 | |
| | 0.6 | 7 | 230 | 149 | |
| | 1.8 | 12 | 64 | 93 | |
| | 5.4 | 20 | 169 | 110 | |
| | 15 | 318 | 1513 | 608 | |
| | 50 | 1650 | 2894 | 1368 | | n.d. means a value was not determined.

Example 54

Modified oligonucleotides were designed based on 546110, described in Example 19 above. Each of the modified oligonucleotides is conjugated with a THA-GalNAc conjugate group at the 3'-end as described in Example 53 above. The oligonucleotides were evaluated for reduction in HDAC2 mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.016, 0.08, 0.40, 2.0, or 50 mg/kg with the modified oligonucleotides shown below or with saline control. Each treatment group consisted of 3 animals. The mice were sacrificed 72 hours following administration, and organs and plasma were harvested for further analysis.

TABLE 115

Modified Oligonucleotides

| Compound ID | position of altered nucleotide in central region | modification of altered nucleotide | Chemistry Notation (5' to 3') | SEQ ID NO |
|---|---|---|---|---|
| 1270729 | n/a | n/a | $T_{ks}{}^mC_{ks}A_{ks}T_{ds}G_{ds}T_{ds}A_{ds}$ ${}^mC_{ds}{}^mC_{ds}T_{ds}A_{ds}T_{ds}A_{ds}$ $G_{ks}T_{ks}{}^mC_k$-THA-GalNAc | 107 |
| 1270733 | 2 | 2'-OMe | $T_{ks}{}^mC_{ks}A_{ks}T_{ds}G_{ms}T_{ds}A_{ds}$ ${}^mC_{ds}{}^mC_{ds}T_{ds}A_{ds}T_{ds}A_{ds}$ $T_{ds}A_{ds}G_{ks}T_{ks}{}^mC_k$-THA-GalNAc | 107 |
| 1270734 | 2 | MOP | $T_{ks}{}^mC_{ks}A_{ks}T_{ds}G_{dx}T_{ds}A_{ds}$ ${}^mC_{ds}{}^mC_{ds}T_{ds}A_{ds}T_{ds}A_{ds}$ $G_{ks}T_{ks}{}^mC_k$-THA-GalNAc | 107 |

A subscript "d" indicates an unmodified, 2'-β-D-deoxyribosyl sugar moiety.
A subscript "k" indicates a cEt.
A subscript "m" indicates a 2'-O-methyl-β-D-ribofuranosyl sugar moiety.
A subscript "s" indicates a phosphorothioate internucleoside linkage.
A superscript "m" before a C indicates 5-methyl Cytosine.
A subscript "x" indicates a MOP internucleoside linkage.

TABLE 116

In vivo Activity and Toxicity of Modified Oligonucleotides

| Compound ID | Dose (mg/kg) | ALT (IU/L) | P21 mRNA (% Control) | Tnfrsf10b mRNA (% Control) | HDAC2 ED50 (mg/kg) |
|---|---|---|---|---|---|
| 1270729 | 0.016 | 6 | 69 | 123 | 0.76 |
|  | 0.08 | 14 | 61 | 136 |  |
|  | 0.40 | 13 | 71 | 142 |  |
|  | 2.0 | 17 | 174 | 154 |  |
|  | 50 | 3655 | 7927 | 5297 |  |
| 1270730 | 0.016 | 31 | 107 | 124 | 1.05 |
|  | 0.08 | 10 | 144 | 132 |  |
|  | 0.40 | 17 | 65 | 99 |  |
|  | 2.0 | 9 | 88 | 123 |  |
|  | 50 | 11 | 110 | 164 |  |
| 1270731 | 0.016 | 22 | 88 | 135 | 1.28 |
|  | 0.08 | 13 | 86 | 101 |  |
|  | 0.40 | 20 | 135 | 138 |  |
|  | 2.0 | 13 | 66 | 137 |  |
|  | 50 | 6 | 76 | 164 |  | n.d. means a value was not determined.

Example 55

Modified oligonucleotides were designed based on 747149, described in Example 13 above. Each of the modified oligonucleotides is conjugated with a THA-GalNAc conjugate group at the 3'-end as described in Example 53 above. The oligonucleotides were evaluated for reduction in FBO1A mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.025, 0.10, 0.40, 1.6, 6.4, or 50 mg/kg with the modified oligonucleotides shown below or with saline control. Each treatment group consisted of 3 animals. The mice were sacrificed 72 hours following administration, and organs and plasma were harvested for further analysis.

TABLE 117

Modified Oligonucleotides

| Compound ID | position of altered nucleotide in central region | modification of altered nucleotide | Chemistry Notation (5' to 3') | SEQ ID NO |
|---|---|---|---|---|
| 1270738 | N/A | N/A | $G_{ks}G_{ks}A_{ks}{}^mC_{ds}T_{ds}G_{ds}A_{ds}$ $A_{ds}A_{ds}T_{ds}A_{ds}G_{ds}{}^mC_{ds}$ $A_{ks}G_{ks}A_k$-THA-GalNAc | 54 |
| 1270739 | 2 | 2'-OMe | $G_{ks}G_{ks}A_{ks}{}^mC_{ds}U_{ms}G_{ds}A_{ds}$ $A_{ds}A_{ds}T_{ds}A_{ds}G_{ds}{}^mC_{ds}A_{ks}$ $G_{ks}A_k$-THA-GalNAc | 130 |
| 1270740 | 2 | MOP | $G_{ks}G_{ks}A_{ks}{}^mC_{ds}T_{dx}G_{ds}A_{ds}$ $A_{ds}A_{ds}T_{ds}A_{ds}G_{ds}{}^mC_{ds}A_{ks}$ $G_{ks}A_k$-THA-GalNAc | 54 |

A subscript "d" indicates an unmodified, 2'-β-D-deoxyribosyl sugar moiety.
A subscript "k" indicates a cEt.
A subscript "s" indicates a phosphorothioate internucleoside linkage.
A superscript "m" before a C indicates 5-methyl Cytosine.
A subscript "x" indicates a MOP internucleoside linkage.
A subscript "m" indicates a 2'-O-methyl-β-D-ribofuranosyl sugar moiety.

TABLE 118

In vivo Activity and Toxicity of Modified Oligonucleotides

| Compound ID | Dose (mg/kg) | ALT (IU/L) | P21 mRNA (% Control) | Tnfrsf10b mRNA (% Control) | FBO1A ED50 (mg/kg) |
|---|---|---|---|---|---|
| 1270738 | 0.025 | 29 | 49 | 114 | 1.23 |
|  | 0.10 | 18 | 46 | 119 |  |
|  | 0.40 | 30 | 156 | 133 |  |
|  | 1.6 | 62 | 273 | 258 |  |
|  | 6.4 | 177 | 1020 | 1426 |  |
|  | 50 | 1467 | 4296 | 10211 |  |
| 1270739 | 0.025 | 10 | 66 | 115 | 5.16 |
|  | 0.10 | 14 | 54 | 120 |  |
|  | 0.40 | 9 | 39 | 93 |  |
|  | 1.6 | 16 | 34 | 98 |  |
|  | 6.4 | 12 | 88 | 116 |  |
|  | 50 | 26 | 163 | 115 |  |
| 1270740 | 0.025 | 25 | 59 | 94 | 3.33 |
|  | 0.10 | 20 | 79 | 143 |  |
|  | 0.40 | 22 | 81 | 110 |  |
|  | 1.6 | 7 | 68 | 146 |  |
|  | 6.4 | 27 | 195 | 165 |  |
|  | 50 | 102 | 1378 | 439 |  |

Example 56

Modified oligonucleotides were designed based on 464924, described in Example 18 above. Each of the modified oligonucleotides is conjugated with a THA-GalNAc conjugate group at the 3'-end as described in Example 53 above. The oligonucleotides were evaluated for reduction in FXI mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.025, 0.10, 0.40, 1.6, 6.4, or 50 mg/kg with the modified oligonucleotides shown below or with saline control. Each treatment group consisted of 3 animals. The mice were sacrificed 72 hours following administration, and organs and plasma were harvested for further analysis.

TABLE 119

Modified Oligonucleotides

| Compound ID | position of altered nucleotide in central region | modification of altered nucleotide | Chemistry Notation (5' to 3') | SEQ ID NO |
|---|---|---|---|---|
| 1270735 | N/A | N/A | $G_{ks}T_{ks}T_{ks}A_{ds}T_{dS}T_{ds}G_{ds}$ $T_{ds}G_{ds}G_{ds}T_{ds}T_{ds}G_{ds}$ $G_{ks}{}^mC_{ks}G_k$-THA-GalNAc | 81 |
| 1270736 | 2 | 2'-OMe | $G_{ks}T_{ks}T_{ks}A_{ds}U_{ms}T_{ds}G_{ds}$ $T_{ds}G_{ds}G_{ds}T_{ds}T_{ds}G_{ds}$ $G_{ks}{}^mC_{ks}G_k$-THA-GalNAc | 133 |
| 1270737 | 2 | MOP | $G_{ks}T_{ks}T_{ks}A_{ds}T_{ds}T_{ds}G_{ds}$ $T_{ds}G_{ds}G_{ds}T_{ds}T_{ds}G_{ds}$ $G_{ks}{}^mC_{kS}G_k$-THA-GalNAc | 81 |

A subscript "d" indicates an unmodified, 2'-β-D-deoxyribosyl sugar moiety.
A subscript "k" indicates a cEt.
A subscript "m" indicates a 2'-O-methyl-β-D-ribofuranosyl sugar moiety.
A subscript "s" indicates a phosphorothioate internucleoside linkage.
A superscript "m" before a C indicates 5-methyl Cytosine.
A subscript "x" indicates a MOP internucleoside linkage.

TABLE 120

In vivo Activity and Toxicity of Modified Oligonucleotides

| Compound ID | Dose (mg/kg) | ALT (IU/L) | P21 mRNA (% Control) | Tnfrsf10b mRNA (% Control) | FBO1A ED50 (mg/kg) |
|---|---|---|---|---|---|
| 1270735 | 0.025 | 9 | 86 | 93 | 0.86 |
| | 0.10 | 8 | 26 | 66 | |
| | 0.40 | 10 | 94 | 81 | |
| | 1.6 | 22 | 69 | 95 | |
| | 6.4 | 3 | 114 | 137 | |
| | 50 | 30 | 266 | 308 | |
| 1270736 | 0.025 | 17 | 95 | 70 | 0.81 |
| | 0.10 | 26 | 53 | 65 | |
| | 0.40 | 29 | 77 | 58 | |
| | 1.6 | 11 | 53 | 93 | |
| | 6.4 | 12 | 64 | 90 | |
| | 50 | 28 | 92 | 125 | |
| 1270740 | 0.025 | 17 | 63 | 77 | 1.47 |
| | 0.10 | 14 | 83 | 101 | |
| | 0.40 | 9 | 62 | 72 | |
| | 1.6 | 21 | 98 | 105 | |
| | 6.4 | 12 | 33 | 104 | |
| | 50 | 11 | 168 | 214 | |

Example 57 Introduction of 5'-Alkyl Modifications In Vivo

Modified oligonucleotides containing a 5'-alkyl modified nucleoside in the central region were synthesized.

The oligonucleotides were evaluated for reduction in target mRNA expression levels in vivo. The transaminase levels (ALT and AST) for each dose were measured.

For the in vitro toxicity study in the table below, the caspase assay was performed essentially as described in Example 8 in Hepa1-6 cells.

Fr the in vivo toxicity and activity study in the table below, six week old BALB/C mice (purchased from Charles River) were injected subcutaneously once at dosage 1.8, 5.5, 16.7, 50, or 150 mg/kg with the modified oligonucleotides shown below or with saline control. Each treatment group consisted of 3 animals. The mice were sacrificed 72 hours following administration, and organs and plasma were harvested for further analysis.

TABLE 121

Modified Oligonucleotides

| Compound ID | Chemistry notation | SEQ ID NO: |
|---|---|---|
| 546108 | $T_{ks}A_{ks}G_{ks}T_{ds}{}^mC_{ds}T_{ds}{}^mC_{ds}T_{ds}G_{ds}T_{ds}{}^mC_{ds}A_{ds}G_{ds}T_{ks}T_{ks}A_k$ | 105 |
| 1133122 | $T_{ks}A_{ks}G_{ks}T_{ds}C_{ms}T_{ds}{}^mC_{ds}T_{ds}G_{ds}T_{ds}{}^mC_{ds}A_{ds}G_{ds}T_{ks}T_{ks}A_k$ | 105 |
| 1280765 | $T_{ks}A_{ks}G_{ks}T_{ds}{}^mC_{dx}T_{ds}{}^mC_{ds}T_{ds}G_{ds}T_{ds}{}^mC_{ds}A_{ds}G_{ds}T_{ks}T_{ks}A_k$ | 105 |
| 1280766 | $T_{ks}A_{ks}G_{ks}T_{ds}{}^mC_{ds}T_{[(R)-\text{и}]s}{}^mC_{ds}T_{ds}G_{ds}T_{ds}{}^mC_{ds}A_{ds}G_{ds}T_{ks}T_{ks}A_k$ | 105 |
| 1280767 | $T_{ks}A_{ks}G_{ks}T_{ds}{}^mC_{ds}T_{ds}{}^mC_{[(R)-\text{и}]s}{}^mT_{ds}G_{ds}T_{ds}{}^mC_{ds}A_{ds}G_{ds}T_{ks}T_{ks}A_k$ | 105 |
| 1280768 | $T_{ks}A_{ks}G_{ks}T_{ds}{}^mC_{ds}T_{[(R)-\varepsilon]s}{}^mC_{ds}T_{ds}G_{ds}T_{ds}{}^mC_{ds}A_{ds}G_{ds}T_{ks}T_{ks}A_k$ | 105 |
| 1280769 | $T_{ks}A_{ks}G_{ks}T_{ds}{}^mC_{ds}T_{ds}{}^mC_{[(R)-\varepsilon]s}{}^mT_{ds}G_{ds}T_{ds}{}^mC_{ds}A_{ds}G_{ds}T_{ks}T_{ks}A_k$ | 105 |
| 694804 | $A_{ks}G_{ks}A_{ks}{}^mC_{ds}T_{ds}{}^mC_{ds}T_{ds}{}^mC_{ds}G_{ds}G_{ds}T_{ds}T_{ds}{}^mC_{ds}{}^mC_{ks}G_{ks}A_k$ | 49 |
| 1202810 | $A_{ks}G_{ks}A_{ks}{}^mC_{ds}U_{ms}{}^mC_{ds}T_{ds}{}^mC_{ds}G_{ds}G_{ds}T_{ds}T_{ds}{}^mC_{ds}{}^mC_{ks}G_{ks}A_k$ | 127 |

TABLE 121-continued

Modified Oligonucleotides

| Compound ID | Chemistry notation | SEQ ID NO: |
|---|---|---|
| 1280776 | $A_{ks}G_{ks}A_{ks}{}^mC_{ds}T_{ds}{}^mC_{ds}T_{dx}{}^mC_{ds}T_{ds}{}^mC_{ds}G_{ds}G_{ds}T_{ds}T_{ds}{}^mC_{ds}{}^mC_{ks}G_{ks}A_k$ | 49 |
| 1280785 | $A_{ks}G_{ks}A_{ks}{}^mC_{ds}T_{ds}{}^mC_{ds}{}^mC_{[(R)-\mu]s}T_{ds}{}^mC_{ds}G_{ds}G_{ds}T_{ds}T_{ds}{}^mC_{ds}{}^mC_{ks}G_{ks}A_k$ | 49 |
| 1280795 | $A_{ks}G_{ks}A_{ks}{}^mC_{ds}T_{ds}{}^mC_{ds}{}^mC_{ds}T_{[(R)-\mu]s}{}^mC_{ds}G_{ds}G_{ds}T_{ds}T_{ds}{}^mC_{ds}{}^mC_{ks}G_{ks}A_k$ | 49 |
| 1280804 | $A_{ks}G_{ks}A_{ks}{}^mC_{ds}T_{ds}{}^mC_{ds}{}^mC_{[(R)-\epsilon]s}T_{ds}{}^mC_{ds}G_{ds}G_{ds}T_{ds}T_{ds}{}^mC_{ds}{}^mC_{ks}G_{ks}A_k$ | 49 |
| 1280810 | $A_{ks}G_{ks}A_{ks}{}^mC_{ds}T_{ds}{}^mC_{ds}{}^mC_{ds}T_{[(R)-\epsilon]s}{}^mC_{ds}G_{ds}G_{ds}T_{ds}T_{ds}{}^mC_{ds}{}^mC_{ks}G_{ks}A_k$ | 49 |
| 465178 | $G_{ks}T_{ks}{}^mC_{ks}A_{ds}G_{ds}T_{ds}A_{ds}T_{ds}{}^mC_{ds}{}^mC_{ds}{}^mC_{ds}A_{ds}G_{ds}T_{ks}G_{ks}T_k$ | 89 |
| 1133332 | $G_{ks}T_{ks}{}^mC_{ks}A_{ds}G_{ms}T_{ds}A_{ds}T_{ds}{}^mC_{ds}{}^mC_{ds}{}^mC_{ds}A_{ds}G_{ds}T_{ks}G_{ks}T_k$ | 89 |
| 1280775 | $G_{ks}T_{ks}{}^mC_{ks}A_{ds}G_{dx}T_{ds}A_{ds}T_{ds}{}^mC_{ds}{}^mC_{ds}{}^mC_{ds}A_{ds}G_{ds}T_{ks}G_{ks}T_k$ | 89 |
| 1280784 | $G_{ks}T_{ks}{}^mC_{ks}A_{ds}G_{ds}T_{[(R)-\mu]s}A_{ds}T_{ds}{}^mC_{ds}{}^mC_{ds}{}^mC_{ds}A_{ds}G_{ds}T_{ks}G_{ks}T_k$ | 89 |
| 1280794 | $G_{ks}T_{ks}{}^mC_{ks}A_{ds}G_{ds}T_{ds}A_{[(R)-\mu]s}T_{ds}{}^mC_{ds}{}^mC_{ds}{}^mC_{ds}A_{ds}G_{ds}T_{ks}G_{ks}T_k$ | 89 |
| 1280803 | $G_{ks}T_{ks}{}^mC_{ks}A_{ds}G_{ds}T_{[(R)-\epsilon]s}A_{ds}T_{ds}{}^mC_{ds}{}^mC_{ds}{}^mC_{ds}A_{ds}G_{ds}T_{ks}G_{ks}T_k$ | 89 |
| 1281809 | $G_{ks}T_{ks}{}^mC_{ks}A_{ds}G_{ds}T_{ds}A_{[(R)-\epsilon]s}T_{ds}{}^mC_{ds}{}^mC_{ds}{}^mC_{ds}A_{ds}G_{ds}T_{ks}G_{ks}T_k$ | 89 |
| 546110 | $T_{ks}{}^mC_{ks}A_{ks}T_{ds}G_{ds}T_{ds}A_{ds}{}^mC_{ds}{}^mC_{ds}T_{ds}A_{ds}T_{ds}A_{ds}G_{ks}T_{ks}{}^mC_k$ | 107 |
| 1133201 | $T_{ks}{}^mC_{ks}A_{ks}T_{ds}G_{ms}T_{ds}A_{ds}{}^mC_{ds}{}^mC_{ds}T_{ds}A_{ds}T_{ds}A_{ds}G_{ks}T_{ks}{}^mC_k$ | 107 |
| 1280778 | $T_{ks}{}^mC_{ks}A_{ks}T_{ds}G_{dx}T_{ds}A_{ds}{}^mC_{ds}{}^mC_{ds}T_{ds}A_{ds}T_{ds}A_{ds}G_{ks}T_{ks}{}^mC_k$ | 107 |
| 1280779 | $T_{ks}{}^mC_{ks}A_{ks}T_{ds}G_{ds}T_{[(R)-\mu]s}A_{ds}{}^mC_{ds}{}^mC_{ds}T_{ds}A_{ds}T_{ds}A_{ds}G_{ks}T_{ks}{}^mC_k$ | 107 |
| 1280789 | $T_{ks}{}^mC_{ks}A_{ks}T_{ds}G_{ds}T_{ds}A_{[(R)-\mu]s}{}^mC_{ds}{}^mC_{ds}T_{ds}A_{ds}T_{ds}A_{ds}G_{ks}T_{ks}{}^mC_k$ | 107 |
| 1280798 | $T_{ks}{}^mC_{ks}A_{ks}T_{ds}G_{ds}T_{[(R)-\epsilon]s}A_{ds}{}^mC_{ds}{}^mC_{ds}T_{ds}A_{ds}T_{ds}A_{ds}G_{ks}T_{ks}{}^mC_k$ | 107 |
| 1281804 | $T_{ks}{}^mC_{ks}A_{ks}T_{ds}G_{ds}T_{ds}A_{[(R)-\epsilon]s}{}^mC_{ds}{}^mC_{ds}T_{ds}A_{ds}T_{ds}A_{ds}G_{ks}T_{ks}{}^mC_k$ | 107 |
| 464924 | $G_{ks}T_{ks}T_{ks}A_{ds}T_{ds}T_{ds}G_{ds}T_{ds}G_{ds}G_{ds}T_{ds}T_{ds}G_{ds}G_{ks}{}^mC_{ks}G_k$ | 81 |
| 1133247 | $G_{ks}T_{ks}T_{ks}A_{ds}U_{ms}T_{ds}G_{ds}T_{ds}G_{ds}G_{ds}T_{ds}T_{ds}G_{ds}G_{ks}{}^mC_{ks}G_k$ | 133 |
| 1280774 | $G_{ks}T_{ks}T_{ks}A_{ds}T_{dx}T_{ds}G_{ds}T_{ds}G_{ds}G_{ds}T_{ds}T_{ds}G_{ds}G_{ks}{}^mC_{ks}G_k$ | 81 |
| 1280783 | $G_{ks}T_{ks}T_{ks}A_{ds}T_{ds}T_{[(R)-\mu]s}G_{ds}T_{ds}G_{ds}G_{ds}T_{ds}T_{ds}G_{ds}G_{ks}{}^mC_{ks}G_k$ | 81 |
| 1280793 | $G_{ks}T_{ks}T_{ks}A_{ds}T_{ds}T_{ds}G_{[(R)-\mu]s}T_{ds}G_{ds}G_{ds}T_{ds}T_{ds}G_{ds}G_{ks}{}^mC_{ks}G_k$ | 81 |
| 747149 | $G_{ks}G_{ks}A_{ks}{}^mC_{ds}T_{ds}G_{ds}A_{ds}A_{ds}A_{ds}T_{ds}A_{ds}G_{ds}{}^mC_{ds}A_{ks}G_{ks}A_k$ | 54 |
| 1203759 | $G_{ks}G_{ks}A_{ks}{}^mC_{ds}U_{ms}G_{ds}A_{ds}A_{ds}A_{ds}T_{ds}A_{ds}G_{ds}{}^mC_{ds}A_{ks}G_{ks}A_k$ | 130 |
| 1280778 | $G_{ks}G_{ks}A_{ks}{}^mC_{ds}T_{dx}G_{ds}A_{ds}A_{ds}A_{ds}T_{ds}A_{ds}G_{ds}{}^mC_{ds}A_{ks}G_{ks}A_k$ | 54 |
| 1280787 | $G_{ks}G_{ks}A_{ks}{}^mC_{ds}T_{ds}G_{[(R)-\mu]s}A_{ds}A_{ds}A_{ds}T_{ds}A_{ds}G_{ds}{}^mC_{ds}A_{ks}G_{ks}A_k$ | 54 |
| 1280797 | $G_{ks}G_{ks}A_{ks}{}^mC_{ds}T_{ds}G_{ds}A_{[(R)-\mu]s}A_{ds}A_{ds}T_{ds}A_{ds}G_{ds}{}^mC_{ds}A_{ks}G_{ks}A_k$ | 54 |

A subscript "d" indicates an unmodified, 2'-β-D-deoxyribosyl sugar moiety. A subscript "k" indicates a cEt. A subscript "s" indicates a phosphorothioate internucleoside linkage. A subscript "[(R)-μ]" indicates a 5'-(R)-Me-β-D-2'-deoxyribosyl sugar moiety. A subscript "[(R)-ε]" indicates a 5'-(R)-ethyl-β-D-2'-deoxyribosyl sugar moiety.

TABLE 122

Activity and Toxicity in vitro and in vivo

| Compound ID | Target | position of altered nucleoside in central region | modification of altered nucleoside | in vivo Target $ED_{50}$ (mg/kg) | in vivo ALT @150 mg/kg | Relative Caspase Activation (% Control) @20 µM |
|---|---|---|---|---|---|---|
| 546108 | HDAC2 | N/A | N/A | n.d. | n.d. | 2436 |
| 1133122 | HDAC2 | 2 | 2'-OMe | 6.1 | 127 | 103 |
| 1280765 | HDAC2 | 2 | MOP | 7.7 | 29 | 157 |
| 1280766 | HDAC2 | 3 | 5'-(R)-Me | 4.5 | 61 | 158 |
| 1280767 | HDAC2 | 4 | 5'-(R)-Me | 5.9 | 79 | 122 |
| 1280768 | HDAC2 | 3 | 5'-(R)-Et | 8.6 | 39 | 70 |
| 1280769 | HDAC2 | 4 | 5'-(R)-Et | 9.6 | 55 | 90 |
| 694804 | DMN2 | N/A | N/A | n.d. | n.d. | 1443 |
| 1202810 | DMN2 | 2 | 2'-OMe | 14.7 | 50 | 70 |
| 1280776 | DMN2 | 2 | MOP | 8.6 | 24 | 214 |
| 1280785 | DMN2 | 3 | 5'-(R)-Me | 6.2 | 92 | 285 |
| 1280795 | DMN2 | 4 | 5'-(R)-Me | 7.3 | 27 | 113 |
| 1280804 | DMN2 | 3 | 5'-(R)-Et | 14.9 | 36 | 135 |
| 1280810 | DMN2 | 4 | 5'-(R)-Et | 16.2 | 26 | 211 |
| 465178 | FXI | N/A | N/A | n.d. | n.d. | 506 |
| 1133332 | FXI | 2 | 2'-OMe | 2.0 | 119 | 168 |
| 1280775 | FXI | 2 | MOP | 2.5 | 153 | 136 |
| 1280784 | FXI | 3 | 5'-(R)-Me | 1.7 | 260 | 145 |
| 1280794 | FXI | 4 | 5'-(R)-Me | 2.3 | 358 | 165 |
| 1280803 | FXI | 3 | 5'-(R)-Et | 4.9 | 122 | 104 |
| 1281809 | FXI | 4 | 5'-(R)-Et | 21.2 | 56 | 93 |
| 546110 | FXI | N/A | N/A | n.d. | n.d. | 404 |
| 1133201 | FXI | 2 | 2'-OMe | 10.6 | 127 | 96 |
| 1280778 | FXI | 2 | MOP | 26.6 | 29 | 105 |
| 1280779 | FXI | 3 | 5'-(R)-Me | 10.9 | 61 | 84 |
| 1280789 | FXI | 4 | 5'-(R)-Me | 11.7 | 79 | 74 |
| 1280798 | FXI | 3 | 5'-(R)-Et | 30.5 | 39 | 78 |
| 1281804 | FXI | 4 | 5'-(R)-Et | 31.5 | 55 | 80 |
| 464924 | FXI | N/A | N/A | n.d. | n.d. | n.d. |
| 1133247 | FXI | 2 | 2'-OMe | 4.6 | 51 | n.d. |
| 1280774 | FXI | 2 | MOP | 3.7 | 37 | n.d. |
| 1280783 | FXI | 3 | 5'-(R)-Me | 3.6 | 48 | n.d. |
| 1280793 | FXI | 4 | 5'-(R)-Me | 2.3 | 351 | n.d. |
| 747149 | FOXO1A | N/A | N/A | n.d. | n.d. | n.d. |
| 1203759 | FOXO1A | 2 | 2'-OMe | 24.9 | 30 | n.d. |
| 1280778 | FOXO1A | 2 | MOP | 8.5 | 35 | n.d. |
| 1280787 | FOXO1A | 3 | 5'-(R)-Me | 65.9 | 62 | n.d. |
| 1280797 | FOXO1A | 4 | 5'-(R)-Me | 20.4 | 22 | n.d. |

Example 58 Nucleosides with Chiral Phosphorothioate Linkages

Modified oligonucleotides containing chirally-controlled phosphorothioate linkages in the central region were synthesized. The compounds in the table below are 100% complementary to mouse CXCL12, GENBANK NT_039353.7 truncated from 69/430,515 to 69/445,350 (SEQ ID NO: 1), at position 6877 to 6892. Each compound has the kkk-d(10)-kkk sugar motif, wherein each "k" represents a 2'-constrained ethyl modified sugar moiety and each "d" represents a 2'-deoxy sugar moiety. Internucleoside linkages 1, 2, 3, 14, and 15 are stereorandom phosphorothioate linkages. Internucleoside linkages 4-13 have the stereochemistry indicated in the table below, wherein a subscript "s" indicates a stereorandom phosphorothioate internucleoside linkage, a subscript "r" indicates a phosphorothioate internucleoside linkage having the (Rp) configuration and a subscript "q" indicates a phosphorothioate internucleoside linkage having the (Sp) configuration.

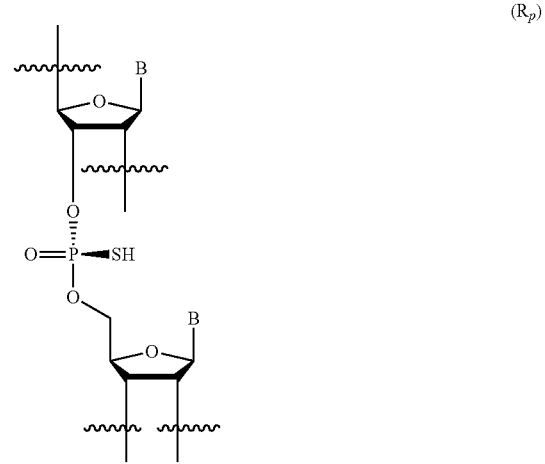

(Rp)

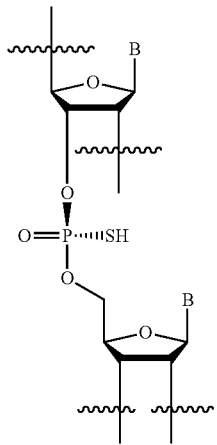

(S_p)

TABLE 123 modified oligonucleotides with stereochemically-controlled phosphorothioate linkages

| Compound ID | Chemistry Notation | SEQ ID NO |
|---|---|---|
| 558807 | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 1220041 | $G_{ks}{}^mC_{ks}A_{ks}T_{dq}G_{dq}T_{dq}T_{dq}{}^mC_{dq}T_{dq}{}^mC_{dq}A_{dq}{}^mC_{dq}A_{dq}T_{ks}T_{ks}A_k$ | 18 |
| 1220042 | $G_{ks}{}^mC_{ks}A_{ks}T_{dr}G_{dq}T_{dq}T_{dq}{}^mC_{dq}T_{dq}{}^mC_{dq}A_{dq}{}^mC_{dq}A_{dq}T_{ks}T_{ks}A_k$ | 18 |
| 1220043 | $G_{ks}{}^mC_{ks}A_{ks}T_{dq}G_{dr}T_{dq}T_{dq}{}^mC_{dq}T_{dq}{}^mC_{dq}A_{dq}{}^mC_{dq}A_{dq}T_{ks}T_{ks}A_k$ | 18 |
| 1220044 | $G_{ks}{}^mC_{ks}A_{ks}T_{dq}G_{dq}T_{dr}T_{dq}{}^mC_{dq}T_{dq}{}^mC_{dq}A_{dq}{}^mC_{dq}A_{dq}T_{ks}T_{ks}A_k$ | 18 |
| 1220045 | $G_{ks}{}^mC_{ks}A_{ks}T_{dq}G_{dq}T_{dq}T_{dr}{}^mC_{dq}T_{dq}{}^mC_{dq}A_{dq}{}^mC_{dq}A_{dq}T_{ks}T_{ks}A_k$ | 18 |
| 1220046 | $G_{ks}{}^mC_{ks}A_{ks}T_{dq}G_{dq}T_{dq}T_{dq}{}^mC_{dr}T_{dq}{}^mC_{dq}A_{dq}{}^mC_{dq}A_{dq}T_{ks}T_{ks}A_k$ | 18 |
| 1220051 | $G_{ks}{}^mC_{ks}A_{ks}T_{dq}G_{dq}T_{dq}T_{dq}{}^mC_{dq}T_{dr}{}^mC_{dq}A_{dq}{}^mC_{dq}A_{dq}T_{ks}T_{ks}A_k$ | 18 |
| 1220047 | $G_{ks}{}^mC_{ks}A_{ks}T_{dq}G_{dq}T_{dq}T_{dq}{}^mC_{dq}T_{dq}{}^mC_{dr}A_{dq}{}^mC_{dq}A_{dq}T_{ks}T_{ks}A_k$ | 18 |
| 1220048 | $G_{ks}{}^mC_{ks}A_{ks}T_{dq}G_{dq}T_{dq}T_{dq}{}^mC_{dq}T_{dq}{}^mC_{dq}A_{dr}{}^mC_{dq}A_{dq}T_{ks}T_{ks}A_k$ | 18 |
| 1220049 | $G_{ks}{}^mC_{ks}A_{ks}T_{dq}G_{dq}T_{dq}T_{dq}{}^mC_{dq}T_{dq}{}^mC_{dq}A_{dq}{}^mC_{dr}A_{dq}T_{ks}T_{ks}A_k$ | 18 |
| 1220050 | $G_{ks}{}^mC_{ks}A_{ks}T_{dq}G_{dq}T_{dq}T_{dq}{}^mC_{dq}T_{dq}{}^mC_{dq}A_{dq}{}^mC_{dq}A_{dr}T_{ks}T_{ks}A_k$ | 18 |
| 1237987 | $G_{ks}{}^mC_{ks}A_{ks}T_{dq}G_{dq}T_{dq}T_{dq}{}^mC_{dq}T_{dq}{}^mC_{dq}A_{dq}{}^mC_{dr}A_{dr}T_{ks}T_{ks}A_k$ | 18 |
| 1237988 | $G_{ks}{}^mC_{ks}A_{ks}T_{dq}G_{dq}T_{dq}T_{dq}{}^mC_{dq}T_{dq}{}^mC_{dr}A_{dr}{}^mC_{dq}A_{dq}T_{ks}T_{ks}A_k$ | 18 |
| 1237989 | $G_{ks}{}^mC_{ks}A_{ks}T_{dq}G_{dq}T_{dq}T_{dq}{}^mC_{dq}T_{dr}{}^mC_{dq}A_{dq}{}^mC_{dq}A_{dq}T_{ks}T_{ks}A_k$ | 18 |
| 1237990 | $G_{ks}{}^mC_{ks}A_{ks}T_{dq}G_{dq}T_{dr}T_{dr}{}^mC_{dq}T_{dq}{}^mC_{dq}A_{dq}{}^mC_{dq}A_{dq}T_{ks}T_{ks}A_k$ | 18 |
| 1237991 | $G_{ks}{}^mC_{ks}A_{ks}T_{dr}G_{dr}T_{dq}T_{dq}{}^mC_{dq}T_{dq}{}^mC_{dq}A_{dq}{}^mC_{dq}A_{dq}T_{ks}T_{ks}A_k$ | 18 |
| 1220052 | $G_{ks}{}^mC_{ks}A_{ks}T_{dr}G_{dr}T_{dr}T_{dr}{}^mC_{dr}T_{dr}{}^mC_{dr}A_{dr}{}^mC_{dr}A_{dr}T_{ks}T_{ks}A_k$ | 18 |
| 1220053 | $G_{ks}{}^mC_{ks}A_{ks}T_{dq}G_{dr}T_{dr}T_{dr}{}^mC_{dr}T_{dr}{}^mC_{dr}A_{dr}{}^mC_{dr}A_{dr}T_{ks}T_{ks}A_k$ | 18 |
| 1220054 | $G_{ks}{}^mC_{ks}A_{ks}T_{dr}G_{dq}T_{dr}T_{dr}{}^mC_{dr}T_{dr}{}^mC_{dr}A_{dr}{}^mC_{dr}A_{dr}T_{ks}T_{ks}A_k$ | 18 |
| 1220055 | $G_{ks}{}^mC_{ks}A_{ks}T_{dr}G_{dr}T_{dq}T_{dr}{}^mC_{dr}T_{dr}{}^mC_{dr}A_{dr}{}^mC_{dr}A_{dr}T_{ks}T_{ks}A_k$ | 18 |
| 1220056 | $G_{ks}{}^mC_{ks}A_{ks}T_{dr}G_{dr}T_{dr}T_{dq}{}^mC_{dr}T_{dr}{}^mC_{dr}A_{dr}{}^mC_{dr}A_{dr}T_{ks}T_{ks}A_k$ | 18 |
| 1220057 | $G_{ks}{}^mC_{ks}A_{ks}T_{dr}G_{dr}T_{dr}T_{dr}{}^mC_{dq}T_{dr}{}^mC_{dr}A_{dr}{}^mC_{dr}A_{dr}T_{ks}T_{ks}A_k$ | 18 |

TABLE 123-continued modified oligonucleotides with stereochemically-
controlled phosphorothioate linkages

| Compound ID | Chemistry Notation | SEQ ID NO |
|---|---|---|
| 1220058 | $G_{ks}{}^mC_{ks}A_{ks}T_{dr}G_{dr}T_{dr}T_{dr}{}^mC_{dr}T_{dr}{}^mC_{dq}{}^mC_{dr}A_{dr}{}^mC_{dr}A_{dr}T_{ks}T_{ks}A_k$ | 18 |
| 1220059 | $G_{ks}{}^mC_{ks}A_{ks}T_{dr}G_{dr}T_{dr}T_{dr}{}^mC_{dr}T_{dr}{}^mC_{dq}A_{dr}{}^mC_{dr}A_{dr}T_{ks}T_{ks}A_k$ | 18 |
| 1220060 | $G_{ks}{}^mC_{ks}A_{ks}T_{dr}G_{dr}T_{dr}T_{dr}{}^mC_{dr}T_{dr}{}^mC_{dr}A_{dq}{}^mC_{dr}A_{dr}T_{ks}T_{ks}A_k$ | 18 |
| 1220061 | $G_{ks}{}^mC_{ks}A_{ks}T_{dr}G_{dr}T_{dr}T_{dr}{}^mC_{dr}T_{dr}{}^mC_{dr}A_{dr}{}^mC_{dq}A_{dr}T_{ks}T_{ks}A_k$ | 18 |
| 1220062 | $G_{ks}{}^mC_{ks}A_{ks}T_{dr}G_{dr}T_{dr}T_{dr}{}^mC_{dr}T_{dr}{}^mC_{dr}A_{dr}{}^mC_{dr}A_{dq}T_{ks}T_{ks}A_k$ | 18 |
| 1220063 | $G_{ks}{}^mC_{ks}A_{ks}T_{dq}G_{dq}T_{dq}T_{dq}{}^mC_{dq}T_{dq}{}^mC_{dq}A_{dq}{}^mC_{dq}A_{dq}T_{ks}T_{ks}A_k$ | 18 |
| 1220064 | $G_{ks}{}^mC_{ks}A_{ks}T_{dr}G_{dr}T_{dr}T_{dr}{}^mC_{dr}T_{dq}{}^mC_{dr}A_{dr}{}^mC_{dq}A_{dq}T_{ks}T_{ks}A_k$ | 18 |

A subscript "d" an unmodified, 2'-β-D-deoxyribosyl sugar moiety.
A subscript "k" indicates a cEt.
A superscript "m" before a C indicates 5-methyl Cytosine.
A subscript "s" indicates a stereorandom phosphorothioate internucleoside linkage,
a subscript "r" indicates a phosphorothioate internucleoside linkage having the (Rp) configuration, and a subscript "q" indicates a phosphorothioate internucleoside linkage having the (Sp) configuration.

For in vitro activity studies, 3T3-L1 cells were plated at 20,000 cells/well and transfected with 27 nM, 80 nM, 250 nM, 740 nM, 2,222 nM, 6,667 nM, or 20,000 nMnM modified oligonucleotide by electroporation. mRNA was harvested and analyzed by RT-qPCR. CXCL12 mRNA was detected with primer probe set RTS 2605 (forward sequence CCAGAGCCAACGTCAAGCAT, SEQ ID NO: 9; reverse sequence: CAGCCGTGCAACAATCTGAA, SEQ ID NO: 10; probe sequence: TGAAAATCCTCAACACTC-CAAACTGTGCC, SEQ ID NO: 11) and P21 mRNA was detected with primer probe set Mm04207341_ml (ThermoFisher).

Caspase-3 and caspase-7 activation was measured using the Caspase-Glo® 3/7 Assay System (G8090, Promega). Levels of caspase activation correlate with apoptotic cell death. Results are presented relative to the caspase activation in control cells not treated with modified oligonucleotide. Localization of p54nrb in HeLa cells was visualized with confocal microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. The number of cells with nucleolar p54nrb and the total number of cells in the images were counted. The self-structure Tm of each compound was determined.

TABLE 124

In vitro activity, toxicity, and Tm of modified oligonucleotides complementary to CXCL12

| Compound ID | in vitro CXCL12 IC$_{50}$ (nM) | in vitro Caspase (% control) @ 20 μM | P21 mRNA (% control) @ 20 μM | % nucleolar p54nrb | Tm (° C.) |
|---|---|---|---|---|---|
| 558807 | 39 | 1437 | 353 | 90 | 64.4 |
| 1220041 | 388 | 223 | 182 | 0 | 61.3 |
| 1220042 | 159 | 584 | 431 | 32 | 62.1 |
| 1220043 | 114 | 838 | 488 | 88 | 62 |
| 1220044 | 181 | 489 | 251 | 18 | 61.5 |
| 1220045 | 222 | 321 | 259 | 9.7 | 61.9 |
| 1220046 | 145 | 572 | 635 | 28 | 61.7 |

TABLE 124-continued

In vitro activity, toxicity, and Tm of modified oligonucleotides complementary to CXCL12

| Compound ID | in vitro CXCL12 IC$_{50}$ (nM) | in vitro Caspase (% control) @ 20 μM | P21 mRNA (% control) @ 20 μM | % nucleolar p54nrb | Tm (° C.) |
|---|---|---|---|---|---|
| 1220051 | 237 | 310 | 167 | 20 | 61.6 |
| 1220047 | 60 | 814 | 238 | 38 | 61.5 |
| 1220048 | 74 | 287 | 174 | 38 | 61.3 |
| 1220049 | 77 | 323 | 243 | 17 | 61.6 |
| 1220050 | 132 | 174 | 121 | 6.4 | 61.5 |
| 1237987 | 26 | 317 | 273 | 3.9 | 62.2 |
| 1237988 | 20 | 336 | 236 | 23 | 62.1 |
| 1237989 | 72 | 300 | 394 | 28 | 62.2 |
| 1237990 | 186 | 299 | 355 | 14 | 62.5 |
| 1237991 | 35 | 562 | 585 | 77 | 63 |

TABLE 125

In vitro activity, toxicity, and Tm of modified oligonucleotides complementary to CXCL12

| Compound ID | in vitro CXCL12 IC$_{50}$ (nM) | in vitro Caspase (% control) (a), 20 μM | P21 mRNA (% control) @ 20 μM | % nucleolar p54nrb | Tm |
|---|---|---|---|---|---|
| 558807 | 95 | 647 | 235 | 93 | 64.4 |
| 1220052 | 63 | 484 | 272 | 98 | 67.4 |
| 1220053 | 99 | 621 | 261 | 95 | 66.2 |
| 1220054 | 197 | 495 | 192 | 96 | 66.8 |
| 1220055 | 51 | 606 | 370 | 100 | 66.9 |
| 1220056 | 103 | 569 | 369 | 97 | 67 |
| 1220057 | 104 | 593 | 330 | 92 | 67.1 |
| 1220058 | 125 | 578 | 273 | 100 | 67.3 |
| 1220059 | 109 | 525 | 351 | 62 | 66.7 |
| 1220060 | 61 | 553 | 328 | 100 | 67.3 |
| 1220061 | 84 | 409 | 329 | 100 | 67.1 |
| 1220062 | 123 | 550 | 394 | 100 | 67.1 |
| 1220063 | 111 | 138 | 128 | 12 | 63.1 |
| 1220064 | 53 | 160 | 218 | 100 | 65.3 |

Example 59 Nucleosides with Chiral Phosphorothioate Linkages and 3'-GalNAc

Modified oligonucleotides containing chirally-controlled phosphorothioate linkages in the central region and a 3'-THA-GalNAc were synthesized. The compounds in the table below are 100% complementary to mouse CXCL12, GENBANK NT_039353.7 truncated from 69/430,515 to 69/445,350 (SEQ ID NO: 1), at position 6877 to 6892. Each compound has the kkk-d(10)-kkk sugar motif, wherein each "k" represents a 2'-constrained ethyl modified sugar moiety and each "d" represents a 2'-deoxy sugar moiety. Internucleoside linkages 1, 2, 3, 14, and 15 are stereorandom phosphorothioate linkages. Internucleoside linkages 4-13 have the stereochemistry indicated in the table below, wherein a subscript "s" indicates a stereorandom phosphorothioate internucleoside linkage, a subscript "r" indicates a phosphorothioate internucleoside linkage having the (Rp) configuration and a subscript "q" indicates a phosphorothioate internucleoside linkage having the (Sp) configuration. THA-GalNAc refers to this structure at the 3' end of the molecule:

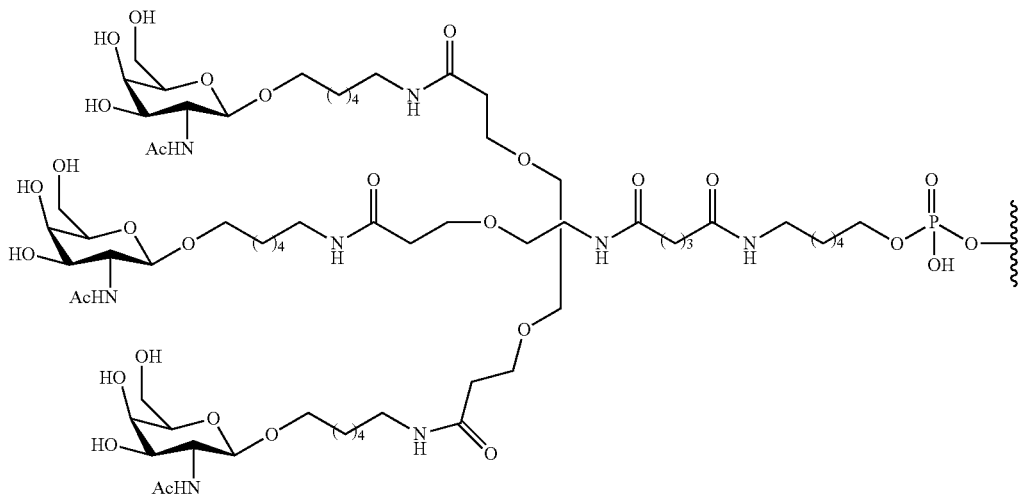

wherein the phosphate group is attached to the 3'-oxygen atom of the 3' nucleoside.

TABLE 126

Modified oligonucleotides

| Compound ID | Chemistry Notation | SEQ ID NO |
|---|---|---|
| 558807 | $G_{ks}{}^mC_{ks}A_{ks}T_{ds}G_{ds}T_{ds}T_{ds}{}^mC_{ds}$ $T_{ds}{}^mC_{ds}A_{ds}{}^mC_{ds}A_{ds}T_{ks}T_{ks}A_k$ | 18 |
| 855156 | $G_{ks}{}^mC_{ks}A_{ks}T_{ds}G_{ds}T_{ds}T_{ds}{}^mC_{ds}$ $T_{ds}{}^mC_{ds}A_{ds}{}^mC_{ds}A_{ds}T_{ks}T_{ks}A_k$-THA-GalNAc | 18 |
| 1220050 | $G_{ks}{}^mC_{ks}A_{ks}T_{dq}G_{dq}T_{dq}T_{dq}{}^mC_{dq}$ $T_{dq}{}^mC_{dq}A_{dq}{}^mC_{dq}A_{dr}T_{ks}T_{ks}A_k$ | 18 |
| 1277251 | $G_{ks}{}^mC_{ks}A_{ks}T_{dq}G_{dq}T_{dq}T_{dq}{}^mC_{dq}$ $T_{dq}{}^mC_{dq}A_{dq}{}^mC_{dq}A_{dr}T_{ks}T_{ks}A_k$-THA-GalNAc | 18 |

TABLE 126-continued

Modified oligonucleotides

| Compound ID | Chemistry Notation | SEQ ID NO |
|---|---|---|
| 1220059 | $Gks{}^mC_{ks}A_{ks}T_{dr}G_{dr}T_{dr}T_{dr}{}^mC_{dr}$ $T_{dr}{}^mC_{dq}A_{dr}{}^mC_{dr}A_{dr}T_{ks}T_{ks}A_k$ | 18 |
| 1277252 | $G_{ks}{}^mC_{ks}A_{ks}T_{dr}G_{dr}T_{dr}T_{dr}{}^mC_{dr}$ $T_{dr}{}^mC_{dq}A_{dr}{}^mC_{dr}A_{dr}T_{ks}T_{ks}A_k$-THA-GalNAc | 18 |
| 1220063 | $G_{ks}{}^mC_{ks}A_{ks}T_{dq}G_{dq}T_{dr}T_{dq}{}^mC_{dq}$ $T_{dr}{}^mC_{dq}A_{dq}{}^mC_{dr}A_{dr}T_{ks}T_{ks}A_k$ | 18 |
| 1277253 | $G_{ks}{}^mC_{ks}A_{ks}T_{dq}G_{dq}T_{dr}T_{dq}{}^mC_{dq}$ $T_{dr}{}^mC_{dq}A_{dq}{}^mC_{dr}A_{dr}T_{ks}T_{ks}A_k$-THA-GalNAc | 18 |
| 1237988 | $G_{ks}{}^mC_{ks}A_{ks}T_{dq}G_{dq}T_{dq}T_{dq}{}^mC_{dq}$ $T_{dq}{}^mC_{dr}A_{dr}{}^mC_{dq}A_{dr}T_{ks}T_{ks}A_k$ | 18 |

TABLE 126-continued

Modified oligonucleotides

| Compound ID | Chemistry Notation | SEQ ID NO |
|---|---|---|
| 1277254 | $G_{ks}{}^mC_{ks}A_{ks}T_{dq}G_{dq}T_{dq}T_{dq}{}^mC_{dq}$ $T_{dq}{}^mC_{dr}A_{dr}{}^mC_{dq}A_{dr}T_{ks}T_{ks}A_k$-THA-GalNAc | 18 |

A subscript "d" indicates an unmodified, 2'-β-D-deoxyribosyl sugar moiety..

A subscript "k" indicates a cEt.

A superscript "m" indicates 5-methyl Cytosine.

A subscript "s" indicates a stereorandom phosphorothioate internucleoside linkage, a subscript "r" indicates a phosphorothioate internucleoside linkage having the (Rp) configuration, and a subscript "q" indicates a phosphorothioate internucleoside linkage having the (Sp) configuration.

TABLE 127

In vitro toxicity and activity of modified oligonucleotides

| Compound ID | in vitro CXCL12 IC$_{50}$ (nM) | in vitro Caspase (% control) @ 20 μM | % nucleolar p54nrb |
|---|---|---|---|
| 855156 | 40 | 1437 | 90 |
| 1277251 | 130 | 174 | 6.4 |
| 1277252 | 111 | 525 | 62 |
| 1277253 | 111 | 138 | 12 |
| 1277254 | 20 | 336 | 24 |

Example 60 Nucleosides with Two Chiral Phosphate Linkages in an Otherwise Stereorandom Phosphorthioate Nucleotide Modified oligonucleotides containing chirally-controlled phosphorothioate linkages at two positions of the central region were synthesized. The compounds in the table below are 100% complementary to mouse CXCL12, GENBANK NT_039353.7 truncated from 69/430,515 to 69/445,350 (SEQ ID NO: 1), at position 6877 to 6892. Each compound with an ID in the range of 1273959-1273967 has a kkk-d(10)-kkk sugar motif, wherein each "k" represents a 2'-constrained ethyl modified sugar moiety and each "d" represents a 2'-deoxy sugar moiety. Each compound with an ID in the range of 1276491-1276497 has a kkk-d-m-d(8)-kkk sugar motif, wherein each "k" represents a cEt and each "d" represents a nucleoside comprising an unmodified, 2'-β-D-deoxyribosyl sugar moiety and each "m" represents nucleoside comprising a 2'-Omethyl modified sugar moiety. Internucleoside linkages are as indicated in the table below, wherein a subscript "s" indicates a stereorandom phosphorothioate internucleoside linkage, a subscript "r" indicates a phosphorothioate internucleoside linkage having the (Rp) configuration and a subscript "q" indicates a phosphorothioate internucleoside linkage having the (Sp) configuration. Each compound contains an "Rp/Sp" unit comprising an internucleoside linkage having the (Rp) configuration followed by an internucleoside linkage having the (Sp) configuration, from 5'-3'.

Compounds were tested in 3T3-L1 cells for caspase activation as described in Example 1 above.

TABLE 128

Modified oligonucleotides

| Compound ID | Chemistry Notation | SEQ ID NO |
|---|---|---|
| 1273959 | G$_{ks}$$^m$C$_{ks}$A$_{ks}$T$_{dr}$G$_{dq}$T$_{ds}$T$_{ds}$$^m$C$_{ds}$T$_{ds}$$^m$C$_{ds}$A$_{ds}$$^m$C$_{ds}$A$_{ds}$T$_{ks}$T$_{ks}$A$_{k}$ | 18 |
| 1273960 | G$_{ks}$$^m$C$_{ks}$A$_{ks}$T$_{ds}$G$_{dr}$T$_{ds}$T$_{ds}$$^m$C$_{ds}$T$_{ds}$$^m$C$_{ds}$A$_{ds}$$^m$C$_{ds}$A$_{ds}$T$_{ks}$T$_{ks}$A$_{k}$ | 18 |
| 1273961 | G$_{ks}$$^m$C$_{ks}$A$_{ks}$T$_{ds}$G$_{ds}$T$_{dr}$T$_{ds}$$^m$C$_{ds}$T$_{ds}$$^m$C$_{ds}$A$_{ds}$$^m$C$_{ds}$A$_{ds}$T$_{ks}$T$_{ks}$A$_{k}$ | 18 |
| 1273962 | G$_{ks}$$^m$C$_{ks}$A$_{ks}$T$_{ds}$G$_{ds}$T$_{ds}$T$_{dr}$$^m$C$_{dq}$T$_{ds}$$^m$C$_{ds}$A$_{ds}$$^m$C$_{ds}$A$_{ds}$T$_{ks}$T$_{ks}$A$_{k}$ | 18 |
| 1273963 | G$_{ks}$$^m$C$_{ks}$A$_{ks}$T$_{ds}$G$_{ds}$T$_{ds}$T$_{ds}$$^m$C$_{dr}$T$_{dq}$$^m$C$_{ds}$A$_{ds}$$^m$C$_{ds}$A$_{ds}$T$_{ks}$T$_{ks}$A$_{k}$ | 18 |
| 1273964 | G$_{ks}$$^m$C$_{ks}$A$_{ks}$T$_{ds}$G$_{ds}$T$_{ds}$T$_{ds}$$^m$C$_{ds}$T$_{dq}$$^m$C$_{dq}$A$_{ds}$$^m$C$_{ds}$A$_{ds}$T$_{ks}$T$_{ks}$A$_{k}$ | 18 |
| 1273965 | G$_{ks}$$^m$C$_{ks}$A$_{ks}$T$_{ds}$G$_{ds}$T$_{ds}$T$_{ds}$$^m$C$_{ds}$T$_{dr}$$^m$C$_{dq}$A$_{ds}$$^m$C$_{ds}$A$_{ds}$T$_{ks}$T$_{ks}$A$_{k}$ | 18 |
| 1273966 | G$_{ks}$$^m$C$_{ks}$A$_{ks}$T$_{ds}$G$_{ds}$T$_{ds}$T$_{ds}$$^m$C$_{ds}$T$_{ds}$$^m$C$_{dr}$A$_{dq}$$^m$C$_{ds}$A$_{ds}$T$_{ks}$T$_{ks}$A$_{k}$ | 18 |
| 1273967 | G$_{ks}$$^m$C$_{ks}$A$_{ks}$T$_{ds}$G$_{ds}$T$_{ds}$T$_{ds}$$^m$C$_{ds}$T$_{ds}$$^m$C$_{ds}$A$_{dr}$$^m$C$_{dq}$A$_{ds}$T$_{ks}$T$_{ks}$A$_{k}$ | 18 |
| 1276491 | G$_{ks}$$^m$C$_{ks}$A$_{ks}$T$_{ds}$G$_{ms}$T$_{dr}$T$_{dq}$$^m$C$_{ds}$T$_{ds}$$^m$C$_{ds}$A$_{ds}$$^m$C$_{dr}$A$_{dq}$T$_{ks}$T$_{ks}$A$_{k}$ | 18 |
| 1276492 | G$_{ks}$$^m$C$_{ks}$A$_{ks}$T$_{ds}$G$_{ms}$T$_{ds}$T$_{dr}$$^m$C$_{dq}$T$_{ds}$$^m$C$_{ds}$A$_{ds}$$^m$C$_{ds}$A$_{ds}$T$_{ks}$T$_{ks}$A$_{k}$ | 18 |
| 1276493 | G$_{ks}$$^m$C$_{ks}$A$_{ks}$T$_{ds}$G$_{ms}$T$_{ds}$T$_{ds}$$^m$C$_{dr}$T$_{dq}$$^m$C$_{ds}$A$_{ds}$$^m$C$_{ds}$A$_{ds}$T$_{ks}$T$_{ks}$A$_{k}$ | 18 |
| 1276494 | G$_{ks}$$^m$C$_{ks}$A$_{ks}$T$_{ds}$G$_{ms}$T$_{ds}$T$_{ds}$$^m$C$_{ds}$T$_{dr}$$^m$C$_{dq}$A$_{ds}$$^m$C$_{ds}$A$_{ds}$T$_{ks}$T$_{ks}$A$_{k}$ | 18 |
| 1276495 | G$_{ks}$$^m$C$_{ks}$A$_{ks}$T$_{ds}$G$_{ms}$T$_{ds}$T$_{ds}$$^m$C$_{ds}$T$_{ds}$$^m$C$_{dr}$A$_{dq}$$^m$C$_{ds}$A$_{ds}$T$_{ks}$T$_{ks}$A$_{k}$ | 18 |
| 1276496 | G$_{ks}$$^m$C$_{ks}$A$_{ks}$T$_{ds}$G$_{ms}$T$_{ds}$T$_{ds}$$^m$C$_{ds}$T$_{ds}$$^m$C$_{ds}$A$_{dr}$$^m$C$_{dq}$A$_{ds}$T$_{ks}$T$_{ks}$A$_{k}$ | 18 |
| 1276497 | G$_{ks}$$^m$C$_{ks}$A$_{ks}$T$_{ds}$G$_{ms}$T$_{ds}$T$_{ds}$$^m$C$_{ds}$T$_{ds}$$^m$C$_{ds}$A$_{ds}$$^m$C$_{dr}$A$_{dq}$T$_{ks}$T$_{ks}$A$_{k}$ | 18 |

A subscript "d" indicates an unmodified, 2'-β-D-deoxyribosyl sugar moiety.
A subscript "k" indicates a cEt.
A superscript "m" before a C indicates 5-methyl Cytosine.
A subscript "s" indicates a stereorandom phosphorothioate internucleoside linkage, a subscript "r" indicates a phosphorothioate internucleoside linkage having the (Rp) configuration, and a subscript "q" indicates a phosphorothioate internucleoside linkage having the (Sp) configuration.
A subscript "m" represents a 2'-O-methyl modified sugar moiety.

TABLE 129

Caspase activation in 3T3L1 cells

| Compound ID | in vitro Caspase (% control) @ 20 μM |
|---|---|
| 1273959 | 1138 |
| 1273960 | 654 |
| 1273961 | 1036 |
| 1273962 | 752 |
| 1273963 | 1349 |
| 1273964 | 907 |
| 1273965 | 984 |
| 1273966 | 750 |
| 1273967 | 785 |
| 1276491 | 116 |
| 1276492 | 450 |
| 1276493 | 234 |
| 1276494 | 85 |
| 1276495 | 214 |
| 1276496 | 165 |
| 1276497 | 148 |

Example 61

Modified oligonucleotides were designed based on compounds 546108, 546118, 465178, and 694804, described in Examples 18, 18, 19, and 13, respectively. For sequences with a T at position 5 (from the 5' end) in the parent kkk-d(10)-kkk oligonucleotide, the kkk-d-m-d(8)-kkk contains a 2'-OMe modified U at this position. For sequences with a mC at position 5 (from the 5' end) in the parent kkk-d(10)-kkk oligonucleotide, the kkk-d-m-d(8)-kkk contains a 2'-OMe modified C at this position, lacking the 5-methyl group. Each of the modified oligonucleotides is conjugated with a THA-GalNAc conjugate group at the 3'-end. The oligonucleotides were evaluated for in vivo toxicity at a single dose after 72 hours.

Six week old BALB/C mice (purchased from Charles River) were injected subcutaneously once at 50 mg/kg with the modified oligonucleotides shown below or with saline control. Each treatment group consisted of 3 animals. The mice were sacrificed 72 hours following administration, and organs and plasma were harvested for further analysis.

TABLE 130

Modified Oligonucleotides

| Compound ID | Target | position of altered nucleotide in central region | modification of altered nucleotide | Chemistry Notation (5' to 3') | SEQ ID NO |
|---|---|---|---|---|---|
| 1306441 | HDAC | N/A | N/A | $T_{ks}A_{ks}G_{ks}T_{ds}{}^mC_{ds}T_{ds}{}^mC_{ds}T_{ds}G_{ds}T_{ds}{}^mC_{ds}A_{ds}G_{ds}T_{ks}T_{ks}A_k$-THA-GalNAc | 105 |
| 1306442 | HDAC | 2 | 2'-OMe | $T_{ks}A_{ks}G_{ks}T_{ds}C_{ms}T_{ds}{}^mC_{ds}T_{ds}G_{ds}T_{ds}{}^mC_{ds}A_{ds}G_{ds}T_{ks}T_{ks}A_k$-THA-GalNAc | 105 |
| 1306443 | HDAC | 2 | MOP | $T_{ks}A_{ks}G_{ks}T_{ds}{}^mC_{dx}T_{ds}{}^mC_{ds}T_{ds}G_{ds}T_{ds}{}^mC_{ds}A_{ds}G_{ds}T_{ks}T_{ks}A_k$-THA-GalNAc | 105 |
| 1306444 | HDAC | 3 | MOP | $T_{ks}A_{ks}G_{ks}T_{ds}{}^mC_{ds}T_{dx}{}^mC_{ds}T_{ds}G_{ds}T_{ds}{}^mC_{ds}A_{ds}G_{ds}T_{ks}T_{ks}A_k$-THA-GalNAc | 105 |
| 1306445 | HDAC | 3 | MOP | $A_{ks}{}^mC_{kS}{}^mC_{ks}{}^mC_{ds}T_{ds}{}^mC_{dx}A_{ds}A_{ds}G_{ds}T_{ds}{}^mC_{ds}T_{ds}{}^mC_{ds}{}^mC_{kS}T_{ks}G_k$-THA-GalNAc | 109 |
| 1306446 | FXI | N/A | N/A | $G_{ks}T_{ks}{}^mC_{ks}A_{ds}G_{ds}T_{ds}A_{ds}T_{ds}{}^mC_{ds}{}^mC_{ds}T{}^mC_{ds}A_{ds}G_{dsks}G_{ks}T_k$-THA-GalNAc | 89 |
| 1306447 | FXI | 2 | 2'-OMe | $G_{ks}T_{ks}{}^mC_{ks}A_{ds}G_{ms}T_{ds}A_{ds}T_{ds}{}^mC_{ds}{}^mC_{ds}{}^mC_{ds}A_{ds}G_{ds}T_{ks}G_{ks}T_k$-THA-GalNAc | 89 |
| 1306448 | FXI | 2 | MOP | $G_{ks}T_{ks}{}^mC_{ks}A_{ds}G_{dx}T_{ds}A_{ds}T_{ds}{}^mC_{ds}{}^mC_{ds}{}^mC_{ds}A_{ds}G_{ds}T_{ks}G_{ks}T_k$-THA-GalNAc | 89 |
| 1306449 | FXI | 3 | MOP | $G_{ks}T_{ks}{}^mC_{ks}A_{ds}G_{ds}T_{dx}A_{ds}T_{ds}{}^mC_{ds}{}^mC_{ds}{}^mC_{ds}A_{ds}G_{ds}T_{ks}G_{ks}T_k$-THA-GalNAc | 89 |
| 1306450 | DMN2 | N/A | N/A | $A_{ks}G_{ks}A_{ks}{}^mC_{ds}T_{ds}mC_{ds}T_{ds}mC_{ds}G_{ds}G_{ds}T_{ds}T_{ds}{}^mC_{ds}mC_{ks}G_{ks}A_k$-THA-GalNAc | 49 |
| 1306451 | DMN2 | 2 | 2'-OMe | $A_{ks}G_{ks}A_{ks}mC_{ds}U_{ms}mC_{ds}T_{ds}mC_{ds}G_{ds}G_{ds}T_{ds}T_{ds}mC_{ds}mC_{ks}G_{ks}A_k$-THA-GalNAc | 127 |

TABLE 130-continued

Modified Oligonucleotides

| Compound ID | Target | position of altered nucleotide in central region | modification of altered nucleotide | Chemistry Notation (5' to 3') | SEQ ID NO |
|---|---|---|---|---|---|
| 1306452 | DMN2 | 2 | MOP | $A_{ks}G_{ks}A_{ks}{}^mC_{ds}T_{dx}{}^mC_{ds}T_{ds}mC_{ds}G_{ds}G_{ds}T_{ds}T_{ds}mC_{ds}{}^mC_{ks}G_{ks}A_k$-THA-GalNAc | 49 |
| 1306453 | DMN2 | 3 | MOP | $A_{ks}G_{ks}A_{ks}{}^mC_{ds}T_{ds}{}^mC_{dx}T_{ds}mC_{ds}G_{ds}G_{ds}T_{ds}T_{ds}mC_{ds}{}^mC_{ks}G_{ks}A_k$-THA-GalNAc | 49 |

A subscript "d" indicates an unmodified, 2'-β-D-deoxyribosyl sugar moiety.
A subscript "k" indicates a cEt.
A subscript "s" indicates a phosphorothioate internucleoside linkage.
A superscript "m" before a C indicates 5-methyl Cytosine.
A subscript "x" indicates a MOP internucleoside linkage..
A subscript "m" indicates a 2'-O-methyl-β-D-ribofuranosyl sugar moiety.

TABLE 131

In vivo Toxicity of Modified Oligonucleotides

| Compound ID | position of altered nucleotide in central region | modification of altered nucleotide | ALT (IU/L) |
|---|---|---|---|
| PBS | N/A | N/A | 28 |
| 1306441 | N/A | N/A | 2371 |
| 1306442 | 2 | 2'-OMe | 37 |
| 1306443 | 2 | MOP | 30 |
| 1306444 | 3 | MOP | 38 |
| 1306445 | 3 | MOP | 51 |
| 1306446 | N/A | N/A | 1555 |
| 1306447 | 2 | 2'-OMe | 53 |
| 1306448 | 2 | MOP | 43 |
| 1306449 | 3 | MOP | 43 |
| 1306450 | N/A | N/A | 1058 |
| 1306451 | 2 | 2'-OMe | 34 |
| 1306452 | 2 | MOP | 25 |
| 1306453 | 3 | MOP | 23 |

Example 62 Effect of 2'-OMe Incorporation on Delayed Toxicity of Modified Oligonucleotides Complementary to HDAC2

Modified oligonucleotides were synthesized with 2' modifications as indicated in the table below. The compounds have the sugar motif kkk-d(10)-kkk ("parent") or kkk-d-m-d(8)-kkk, where "k" represents a cEt, "d" represents an unmodified, 2'β-D-deoxyribosyl sugar moiety, and "m" represents 2'-OMe-β-D-ribofuranosyl sugar moiety. For sequences with a T at position 5 (from the 5' end) in the parent kkk-d(10)-kkk oligonucleotide, the kkk-d-m-d(8)-kkk contains a 2'-OMe modified U at this position. For sequences with a $^mC$ at position 5 (from the 5' end) in the parent kkk-d(10)-kkk oligonucleotide, the kkk-d-m-d(8)-kkk contains a 2'-OMe modified C at this position, lacking the 5-methyl group. The modified oligonucleotides in the table below have a mixed backbone motif sooosssssssssos or sooosossssssssos, wherein each "s" represents a phosphorothioate internucleoside linkage and each "o" represents a phosphodiester internucleoside linkage, as indicated by the chemistry notation in the table.

For the in vivo toxicity study in the table below, four female $C_{57}/B16$ mice per group were administered 300 μg modified oligonucleotide by intracerebroventricular (ICV) injection. At 8 weeks post-injection, mice were evaluated according to 7 different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing For each of the 7 criteria, a mouse was given a subscore of 0 if it met the criteria and 1 if it did not. After all 7 criteria were evaluated, the FOB scores were summed for each mouse and averaged within each treatment group. The results are presented in the table below.

TABLE 132

In vivo Activity and Toxicity of Modified oligonucleotides complementary to HDAC2

| Compound ID | Chemistry notation | HDAC2 mRNA (% control) Cortex | 8 week FOB | SER ID NO: |
|---|---|---|---|---|
| 1282276 | $G_{ks}A_{ko}{}^mC_{ko}T_{ds}{}^mC_{ds}T_{ds}{}^mC_{ds}T_{ds}G_{ds}A_{ds}T_{ds}G_{ds}A_{ds}T_{ko}A_{ks}{}^mC_k$ | 86 | 5 | 97 |
| 1282277 | $G_{ks}A_{ko}{}^mC_{ko}T_{ds}C_{ms}T_{ds}{}^mC_{ds}T_{ds}G_{ds}A_{ds}T_{ds}G_{ds}A_{ds}T_{ko}A_{ks}{}^mC_k$ | n.d. | 7 | 97 |
| 1282278 | $G_{ks}A_{ko}{}^mC_{ko}T_{ds}C_{mo}T_{ds}{}^mC_{ds}T_{ds}G_{ds}A_{ds}T_{ds}G_{ds}A_{ds}T_{ko}A_{ks}{}^mC_k$ | 72 | 6 | 97 |
| 1282280 | ${}^mC_{ks}T_{ko}A_{kg}T_{ds}A_{ds}T_{ds}{}^mC_{ds}A_{ds}T_{ds}{}^mC_{ds}T_{ds}{}^mC_{ds}T_{ds}{}^mC_{ko}A_{ks}T_k$ | 44 | 2 | 98 |
| 1282296 | ${}^mC_{ks}T_{ko}A_{ko}T_{ds}A_{ms}{}^mC_{ds}{}^mC_{ds}A_{ds}T_{ds}{}^mC_{ds}T_{ds}{}^mC_{ds}T_{ds}{}^mC$-$_{ko}A_{ks}T_k$ | n.d. | 7 | 98 |
| 1282622 | ${}^mC_{ks}T_{ko}A_{ko}T_{ds}A_{mo}{}^mC_{ds}{}^mC_{ds}A_{ds}T_{ds}{}^mC_{ds}T_{ds}{}^mC_{ds}T_{ds}{}^mC$-$_{ko}A_{ks}T_k$ | 68 | 0 | 98 |
| 1282281 | $A_{ks}T_{ko}T_{ko}A_{ds}T_{ds}A_{ds}T_{ds}G_{ds}G_{ds}{}^mC_{ds}A_{ds}A_{ds}{}^mC_{ds}T_{ks}{}^mC_{ks}A_k$ | 70 | 4 | 101 |
| 1282627 | $A_{ks}T_{ko}T_{ko}A_{ds}U_{ms}A_{ds}T_{ds}G_{ds}G_{ds}{}^mC_{ds}A_{ds}A_{ds}{}^mC_{ds}T_{ks}{}^mC_{ks}A_k$ | 50 | 0 | 139 |

TABLE 132-continued

In vivo Activity and Toxicity of Modified oligonucleotides complementary to HDAC2

| Compound ID | Chemistry notation | HDAC2 mRNA(% control) Cortex | 8 week FOB | SEQ ID NO: |
|---|---|---|---|---|
| 1282282 | $G_{ks}A_{ko}{}^mC_{ko}T_{ds}A_{ds}A_{ds}T_{ds}A_{ds}T_{ds}G_{ds}{}^mC_{ds}A_{ds}G_{ds}T_{ko}T_{ks}T_k$ | 107 | 0 | 102 |
| 1282628 | $G_{ks}A_{ko}{}^mC_{ko}T_{ds}A_{ms}A_{ds}T_{ds}A_{ds}T_{ds}G_{ds}{}^mC_{ds}A_{ds}G_{ds}T_{ko}T_{ks}T_k$ | 86 | 0 | 102 |
| 1282283 | $G_{ks}T_{ks}{}^mC_{ko}A_{ds}A_{ds}A_{ds}T_{ds}T_{ds}{}^mC_{ds}A_{ds}A_{ds}G_{ds}G_{ds}G_{ko}T_{ks}T_k$ | n.d. | 7 | 103 |
| 1282629 | $G_{ks}T_{ks}{}^mC_{ko}A_{ds}A_{ms}A_{ds}T_{ds}T_{ds}{}^mC_{ds}A_{ds}A_{ds}G_{ds}G_{ds}G_{ko}T_{ks}T_k$ | n.d. | 7 | 103 |
| 1282284 | ${}^mC_{ks}A_{ko}T_{ko}A_{ds}A_{ds}A_{ds}G_{ds}{}^mC_{ds}A_{ds}T_{ds}G_{ds}G_{ds}T_{ds}G_{ko}G_{ks}A_k$ | n.d. | 7 | 104 |
| 1282630 | ${}^mC_{ks}A_{ko}T_{ko}A_{ds}A_{ms}A_{ds}G_{ds}{}^mC_{ds}A_{ds}T_{ds}G_{ds}G_{ds}T_{ds}G_{ko}G_{ks}A_k$ | n.d. | 7 | 104 |
| 1224264 | $G_{ks}T_{ko}A_{ko}{}^mC_{ds}{}^mC_{ds}T_{ds}A_{ds}T_{ds}A_{ds}G_{ds}T_{ds}{}^mC_{ds}T_{ds}{}^mC_{ko}T_{ks}G_k$ | n.d. | 7 | 106 |
| 1282631 | $G_{ks}T_{ko}A_{ko}T_{ds}C_{ms}T_{ds}A_{ds}T_{ds}A_{ds}G_{ds}T_{ds}T_{ds}T_{ds}T_{ko}T_{ks}G_k$ | n.d. | 7 | 106 |
| 1282285 | $T_{ks}T_{ko}G_{ko}{}^mC_{ds}{}^mC_{ds}A_{ds}A_{ds}T_{ds}A_{ds}T_{ds}{}^mC_{ds}A_{ds}{}^mC_{ds}{}^mC_{ko}A_{ks}T_k$ | n.d. | 7 | 94 |
| 1282632 | $T_{ks}T_{ko}G_{ko}{}^mC_{ds}C_{ms}A_{ds}A_{ds}T_{ds}A_{ds}T_{ds}{}^mC_{ds}A_{ds}{}^mC_{ds}{}^mC_{ko}A_{ks}T_k$ | 59 | 0 | 94 |
| 1282623 | $T_{ks}T_{ko}G_{ko}{}^mC_{ds}C_{mo}A_{ds}A_{ds}T_{ds}A_{ds}T_{ds}{}^mC_{ds}A_{ds}{}^mC_{ds}{}^mC_{ko}A_{ks}T_k$ | 88 | 0 | 94 |
| 1282286 | ${}^mC_{ks}A_{ko}A_{ko}{}^mC_{ds}T_{ds}G_{ds}A_{ds}A_{ds}{}^mC_{ds}{}^mC_{ds}A_{ds}{}^mC_{ds}{}^mC_{ds}{}^mC\text{-}{}_{ko}G_{ks}T_k$ | 68 | 3 | 95 |
| 1282633 | ${}^mC_{ks}A_{ko}A_{ko}{}^mC_{ds}U_{ms}G_{ds}A_{ds}A_{ds}{}^mC_{ds}{}^mC_{ds}A_{ds}{}^mC_{ds}{}^mC_{ds}{}^mC\text{-}{}_{ko}G_{ks}T_k$ | 71 | 0 | 138 |
| 1282287 | $G_{ks}{}^mC_{ko}A_{ko}{}^mC_{ds}A_{ds}A_{ds}T_{ds}A_{ds}T_{ds}{}^mC_{ds}A_{ds}T_{ds}T_{ds}A_{ko}A_{ks}{}^mC_k$ | 74 | 0 | 96 |
| 1282634 | $G_{ks}{}^mC_{ko}A_{ko}{}^mC_{ds}A_{ms}A_{ds}T_{ds}A_{ds}T_{ds}{}^mC_{ds}A_{ds}T_{ds}T_{ds}A_{ko}A_{ks}{}^mC_k$ | 70 | 0 | 96 |
| 1282288 | ${}^mC_{ks}A_{ko}T_{ko}{}^mC_{ds}A_{ds}T_{ds}{}^mC_{ds}T_{ds}A_{ds}T_{ds}A_{ds}{}^mC_{ds}{}^mC_{ds}A_{ko}T_{ks}{}^mC_k$ | 16 | 2 | 99 |
| 1282298 | ${}^mC_{ks}A_{ko}T_{ko}{}^mC_{ds}A_{ms}T_{ds}{}^mC_{ds}T_{ds}A_{ds}T_{ds}A_{ds}{}^mC_{ds}{}^mC_{ds}A\text{-}{}_{ko}T_{ks}{}^mC_k$ | 18 | 4 | 99 |
| 1282624 | ${}^mC_{ks}A_{ko}T_{ko}{}^mC_{ds}A_{mo}T_{ds}{}^mC_{ds}T_{ds}A_{ds}T_{ds}A_{ds}{}^mC_{ds}{}^mC_{ds}A\text{-}{}_{ko}T_{ks}{}^mC_k$ | 70 | 0 | 99 |
| 1224263 | $A_{ks}{}^mC_{ko}A_{ko}{}^mC_{ds}A_{ds}T_{ds}T_{ds}T_{ds}A_{ds}G_{ds}{}^mC_{ds}A_{ds}T_{ds}G_{ko}A_{ks}{}^mC_k$ | n.d. | 2 | 100 |
| 1282635 | $A_{ks}{}^mC_{ko}A_{ko}{}^mC_{ds}A_{ms}T_{ds}T_{ds}T_{ds}A_{ds}G_{ds}{}^mC_{ds}A_{ds}T_{ds}G_{ko}A_{ks}{}^mC_k$ | 61 | 0 | 100 |
| 1282289 | $T_{ks}A_{ko}G_{ko}T_{ds}{}^mC_{ds}T_{ds}{}^mC_{ds}T_{ds}G_{ds}T_{ds}{}^mC_{ds}A_{ds}G_{ds}T_{ko}T_{ks}A_k$ | n.d. | 7 | 105 |
| 1282621 | $T_{ks}A_{ko}G_{ko}T_{ds}C_{ms}T_{ds}{}^mC_{ds}T_{ds}G_{ds}T_{ds}{}^mC_{ds}A_{ds}G_{ds}T_{ko}T_{ks}A_k$ | n.d. | 7 | 105 |
| 1282625 | $T_{ks}A_{ko}G_{ko}T_{ds}C_{mo}T_{ds}{}^mC_{ds}T_{ds}G_{ds}T_{ds}{}^mC_{ds}A_{ds}G_{ds}T_{ko}T_{ks}A_k$ | n.d | 6 | 105 |
| 1282290 | $T_{ks}{}^mC_{ko}A_{ko}T_{ds}G_{ds}T_{ds}A_{ds}{}^mC_{ds}{}^mC_{ds}T_{ds}A_{ds}A_{ds}G_{ko}T_{ks}{}^mC_k$ | 22 | 6 | 107 |
| 1282300 | $T_{ks}{}^mC_{ko}A_{ko}T_{ds}GJ_{ds}A_{ds}{}^mC_{ds}{}^mC_{ds}T_{ds}A_{ds}T_{ds}A_{ds}G_{ko}T_{ks}{}^mC_k$ | 60 | 0 | 107 |
| 1282626 | $T_{ks}{}^mC_{ko}A_{ko}T_{ds}G_{mo}T_{ds}A_{ds}{}^mC_{ds}{}^mC_{ds}T_{ds}A_{ds}T_{ds}A_{ds}G_{ko}T_{ks}{}^mC_k$ | 107 | 0 | 107 |
| 1282291 | $T_{ks}{}^mC_{ko}T_{ko}T_{ds}A_{ds}A_{ds}T_{ds}T_{ds}T_{ds}{}^mC_{ds}A_{ds}T_{ds}G_{ds}T_{ko}A_{ks}{}^mC_k$ | 64 | 0 | 108 |
| 1282636 | $T_{ks}{}^mC_{ko}T_{ko}T_{ds}A_{ms}A_{ds}T_{ds}T_{ds}T_{ds}{}^mC_{ds}A_{ds}T_{ds}G_{ds}T_{ko}A_{ks}{}^mC_k$ | 65 | 0 | 108 |
| 1282292 | $A_{ks}{}^mC_{ko}{}^mC_{ko}{}^mC_{ds}T_{ds}{}^mC_{ds}A_{ds}A_{ds}G_{ds}T_{ds}{}^mC_{ds}T_{ds}{}^mC_{ds}{}^mC\text{-}{}_{ko}T_{ks}G_k$ | n.d. | 6 | 109 |
| 1282637 | $A_{ks}{}^mC_{ko}{}^mC_{ko}{}^mC_{ds}U_{ms}{}^mC_{ds}A_{ds}A_{ds}G_{ds}T_{ds}{}^mC_{ds}T_{ds}{}^mC_{ds}{}^mCk\text{-}{}_OT_{ks}Gk$ | n.d. | 7 | 109 |

A subscript "d" indicates an unmodified, 2'-β-D-deoxyribosyl sugar moiety.
A subscript "e" indicates a 2'-MOE-β-D-ribofuranosyl sugar moiety.
A subscript "m" indicates a 2'-O-methyl-β-D-ribofuranosyl sugar moiety.
A subscript "k" indicates a cEt.
A subscript "s" indicates a phosphorothioate internucleoside linkage.
A superscript "m" before a C indicates 5-methyl Cytosine.
A subscript "x" indicates a MOP internucleoside linkage.

Example 63 Effect of Incorporation of 2'-OMe at Various Positions

Modified oligonucleotides were synthesized with 2' modifications as indicated in the table below. The compounds have the sugar motif of kkk-d-m-d(8)-kkk, kkk-d(8)-m-d-kkk, or kkk-mm-d(8)-kkk where "k" represents a cEt, "d" represents an unmodified, 2'-β-D-deoxyribosyl sugar moiety, and "m" represents a 2'-OMe-β-D-ribofuranosyl sugar moiety. For parent sequences with a T at the 2'-OMe-modified position, modified sequences contain a 2'-OMe modified U at this position. For parent sequences with a mC at the 2'-OMe-modified position, modified sequences contain a 2'-OMe modified C at this position, lacking the 5-methyl group.

TABLE 133

Modified Oligonucleotides

| Compound ID | Target | position of altered nucleotide in central region | modification of altered nucleotide | Chemistry Notation (5' to 3') | SEQ ID NO |
|---|---|---|---|---|---|
| 936053 | CXCL12 | 2 | 2'-OMe | $G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_k$ | 18 |
| 1244114 | CXCL12 | 9 | 2'-OMe | $G_{ks}{}^mC_{ks}A_{ks}T_{ds}G_{ds}T_{ds}T_{ds}{}^mC_{ds}T_{ds}{}^mC_{ds}A_{ds}C_{ms}A_{ds}T_{ks}T_{ks}A_k$ | 18 |

TABLE 133-continued

Modified Oligonucleotides

| Compound ID | Target | position of altered nucleotide in central region | modification of altered nucleotide | Chemistry Notation (5' to 3') | SEQ ID NO |
|---|---|---|---|---|---|
| 1306760 | CXCL12 | 1, 2 | 2'-OMe | $G_{ks}{}^mC_{ks}A_{ks}U_{ms}G_{ms}T_{ds}T_{ds}{}^mC_{ds}$ $T_{ds}{}^mC_{ds}A_{ds}{}^mC_{ds}A_{ds}T_{ks}T_{ks}A_k$ | 19 |
| 895155 | SOD-1 | 2 | 2'-OMe | $T_{ks}G_{ks}A_{ks}G_{ds}G_{ms}T_{ds}{}^mC_{ds}{}^mC_{ds}$ $T_{ds}G_{ds}{}^mC_{ds}A_{ds}{}^mC_{ds}T_{ks}G_{ks}G_k$ | 26 |
| 1308544 | SOD-1 | 9 | 2'-OMe | $T_{ks}G_{ks}A_{ks}G_{ds}G_{ds}T_{ds}{}^mC_{ds}{}^mC_{ds}$ $T_{ds}G_{ds}{}^mC_{ds}A_{ms}{}^mC_{ds}T_{ks}G_{ks}G_k$ | 26 |
| 1309002 | SOD-1 | 1, 2 | 2'-OMe | $T_{ks}G_{ks}A_{ks}G_{ms}G_{ms}T_{ds}{}^mC_{ds}{}^mC_{ds}$ $T_{ds}G_{ds}{}^mC_{ds}A_{ds}{}^mC_{ds}T_{ks}G_{ks}G_k$ | 26 |
| 1133122 | HDAC2 | 2 | 2'-OMe | $T_{ks}A_{ks}G_{ks}T_{ds}C_{ms}T_{ds}{}^mC_{ds}T_{ds}$ $G_{ds}T_{ds}{}^mC_{ds}A_{ds}G_{ds}T_{ks}T_{ks}A_k$ | 105 |
| 1308545 | HDAC2 | 9 | 2'-OMe | $T_{ks}A_{ks}G_{ks}T_{ds}T_{ds}T_{ds}{}^mC_{ds}T_{ds}$ $G_{ds}T_{ds}{}^mC_{ds}A_{ms}G_{ds}T_{ks}T_{ks}A_k$ | 105 |
| 1309073 | HDAC2 | 1, 2 | 2'-OMe | $T_{ks}A_{ks}G_{ks}U_{ms}C_{ms}T_{ds}{}^mC_{ds}T_{ds}$ $G_{ds}T_{ds}{}^mC_{ds}A_{ds}G_{ds}T_{ks}T_{ks}A_k$ | 145 |

A subscript "d" indicates an unmodified, 2'-β-D-deoxyribosyl sugar moiety.
A subscript "e" indicates a 2'-MOE-β-D-ribofuranosyl sugar moiety.
A subscript "m" indicates a 2'-O-methyl-β-D-ribofuranosyl sugar moiety.
A subscript "k" indicates a cEt.
A subscript "s" indicates a phosphorothioate internucleoside linkage.
A superscript "m" before a C indicates 5-methyl Cytosine.

Six week old BALB/C mice (purchased from Charles River) were injected subcutaneously once at dosage 1.8, 5.5, 16.7, 50, or 150 mg/kg with the modified oligonucleotides shown below or with saline control. Each treatment group consisted of 3 animals. The mice were sacrificed 72 hours following administration, and organs and plasma were harvested for further analysis. The oligonucleotides were evaluated for reduction in target mRNA expression levels in vivo. P21 and Tnfrsf10b mRNA levels were also measured. The transaminase levels (ALT and AST) for each dose were also measured.

TABLE 134

In vivo Activity and Toxicity of Modified Oligonucleotides

| Compound ID | position of altered nucleotide in central region | ALT (IU/L) @ 50 mg/kg | ALT (IU/L) @150 mg/kg | ED50 (mg/kg) for target |
|---|---|---|---|---|
| 936053 | 2 | 11 | 109 | 3.5 |
| 1244114 | 9 | 9092 | death | 1.0 |
| 1306760 | 1, 2 | 16 | 436 | 3.0 |
| 895155 | 2 | 29 | 110 | 11.0 |
| 1308544 | 9 | 2054 | 14507 | 27.7 |
| 1309002 | 1, 2 | 6 | 64 | 47.6 |
| 1133122 | 2 | 31 | 76 | 2.7 |
| 1308545 | 9 | 24695 | death | 0.9 |
| 1309073 | 1, 2 | 28 | 128 | 3.1 |

Example 63 Effect of Incorporation of 2'-OMe in a Modified Oligonucleotide with 11 Nucleosides in the Central Region Modified oligonucleotides were synthesized with 2' modifications as indicated in the table below. The compounds have the sugar motif of kkk-d(11)-kkk, kkk-d-m-d(9)-kkk, or kkk-dd-m-d(8)-kkk, where "k" represents a cEt, "d" represents an unmodified, 2'β-D-deoxyribosyl sugar moiety, and "m" represents a 2'-OMe-β-D-ribofuranosyl modified sugar moiety. For parent sequences with a T at the 2'-OMe-modified position, modified sequences contain a 2'-OMe modified U at this position.

TABLE 135

Modified Oligonucleotides

| Compound ID | Target | position of altered nucleoside in central region | modification of altered nucleoside | Chemistry Notation (5' to 3') | SEQ ID NO |
|---|---|---|---|---|---|
| 1280764 | CXCL12 | N/A | 2'-OMe | $G_{ks}{}^mC_{ks}A_{ks}T_{ds}G_{ms}$ $T_{dS}T_{ds}{}^mC_{dS}T_{ds}{}^mC_{ds}A_{ds}$ ${}^mC_{ds}A_{ds}T_{dS}T_{ks}A_{ks}T_k$ | 125 |
| 1280763 | CXCL12 | 2 | 2'-OMe | $G_{ks}{}^mC_{ks}A_{ks}T_{ds}G_{ds}T_{ds}$ $Td_s{}^mC_{ds}T_{ds}{}^mC_{ds}A_{ds}C_{ms}$ $A_{ds}T_{ds}T_{ks}A_{ks}T_k$ | 125 |

TABLE 135-continued

Modified Oligonucleotides

| Compound ID | Target | position of altered nucleoside in central region | modification of altered nculeoside | Chemistry Notation (5' to 3') | SEQ ID NO |
|---|---|---|---|---|---|
| 1306440 | CXCL12 | 3 | 2'-OMe | $G_{ks}{}^mC_{ks}A_{ks}T_{ds}G_{ds}U_{ms}$ $T_{ds}{}^mC_{ds}T_{ds}{}^mC_{ds}A_{ds}$ ${}^mC_{ds}A_{ds}T_{ds}T_{ks}A_{ks}T_k$ | 146 |

A subscript "d" indicates an unmodified, 2'-β-D-deoxyribosyl sugar moiety.
A subscript "e" indicates a 2'-MOE-β-D-ribofuranosyl sugar moiety.
A subscript "m" indicates a 2'-O-methyl-β-D-ribofuranosyl sugar moiety.
A subscript "k" indicates a cEt.
A subscript "s" indicates a phosphorothioate internucleoside linkage.
A superscript "m" before a C indicates 5-methyl Cytosine.

Six week old BALB/C mice (purchased from Charles River) were injected subcutaneously once at dosage 50 or 150 mg/kg with the modified oligonucleotides shown below or with saline control. Each treatment group consisted of 3 animals. The mice were sacrificed 72 hours following administration, and organs and plasma were harvested for further analysis. P21 and Tnfrsf10b mRNA levels were measured. The transaminase levels (ALT and AST) for each dose were also measured.

TABLE 136

In vivo Activity and Toxicity of Modified Oligonucleotides with an 11-base central region

| Compound ID | position of 2'-OMe nucleotide in central region | ALT (IU/L) @ 50 mg/kg | ALT (IU/L) @150 mg/kg | P21 mRNA @150 mg/kg | Tnfrsf10b mRNA @ 150 mg/kg |
|---|---|---|---|---|---|
| 1280764 | N/A | death | death | death | death |
| 1280763 | 2 | 109 | 112 | 236 | 460 |
| 1306440 | 3 | 5109 | 7614 | 7022 | 13361 |

Example 65 Effect of Incorporation of 2'-OMe in a Modified Oligonucleotide on Kidney Toxicity Modified oligonucleotides were synthesized as indicated in the table below. The compounds have the sugar motif of kkk-d(10)-kkk or kkk-d-m-d(8)-kkk, where "k" represents a cEt, "d" represents an unmodified, 2'-β-D-deoxyribosyl sugar moiety, and "m" represents a 2'-OMe-β-D-ribofuranosyl sugar moiety.

TABLE 137

Modified Oligonucleotides

| Compound ID | position of altered nucleotide in central region | modification of altered nucleotide | Chemistry Notation (5' to 3') | SEQ ID NO |
|---|---|---|---|---|
| 683702 | N/A | N/A | $A_{ks}C_{ks}A_{ks}A_{ds}G_{ds}G_{ds}A_{ds}{}^mC_{ds}A_{ds}$ ${}^mC_{ds}{}^mC_{ds}A_{ds}A_{ds}G_{ks}A_{ks}T_{ks}$ | 147 |
| 1295373 | 2 | 2'-OMe | $A_{ks}C_{ks}A_{ks}A_{ds}G_{ms}G_{ds}A_{ds}{}^mC_{ds}A_{ds}$ ${}^mC_{ds}{}^mC_{ds}A_{ds}A_{ds}G_{ks}A_{ks}T_{ks}$ | 147 |

A subscript "d" indicates an unmodified, 2'-β-D-deoxyribosyl sugar moiety.
A subscript "k" indicates a cEt.
A subscript "m" indicates a 2'-O-methyl-β-D-ribofuranosyl sugar moiety.
A subscript "s" indicates a phosphorothioate internucleoside linkage.
A superscript "m" before a C indicates 5-methyl Cytosine.
A subscript "x" indicates a MOP internucleoside linkage.

8-10 week old Sprague Dawley rats were injected subcutaneously at dosage 50 mg/kg/week for two weeks (3 total injections) with the modified oligonucleotides shown below or with saline control. Each treatment group consisted of 3 animals. The mice were sacrificed 72 hours following administration, and organs and plasma were harvested for further analysis. KIM-1, NGAL, P21 and Tnfrsf10b mRNA levels were measured. Primer probe set rHAVCR1 (forward sequence: GGGATTACAGAGATCGTGACTGATT (SEQ ID NO: 148), reverse sequence: TGCAGCTGGAAGAAC-CAAAA (SEQ ID NO:149), probe sequence CAGAGTAAAATACCCATTCCAGCTCCTGGG (SEQ ID NO: 150)) was used to measure KIM-1 and primer probe set RTS4389 (forward sequence: GATTCGTCAGCTTTGC-CAAGT (SEQ ID NO: 151), reverse sequence: CGTCTGTTCAGTTGTCAATGCA (SEQ ID NO:152), probe sequence TCTGGGCCTCAAGGATAACAA-CATCGTTT (SEQ ID NO: 153)) was used to measure NGAL. The transaminase levels (ALT and AST) for each dose were also measured.

TABLE 138

In vivo Toxicity of Modified Oligonucleotides in kidney

| Compound ID | 2'-OMe position in central region | ALT (IU/L) | P21 mRNA (liver) | KIM-1 mRNA (kidney) | NGAL mRNA (kidney) | P21 mRNA (kidney) |
|---|---|---|---|---|---|---|
| 683702 | N/A | 393 | 1243 | 3449 | 741 | 439 |
| 1295373 | 2 | 39 | 92 | 122 | 142 | 98 |

Example 66 Nucleosides with Various Chemistries at Position 2 and 3 of the Central Region Modified oligonucleotides containing altered nucleotides at position 2 of the central region were synthesized. The compounds in the table below are 100% complementary to mouse FXI. The sequence of the oligonucleotides is GTT-ATTGTGGTTGGCG (SEQ ID NO: 81), GTTAUT-GTGGTTGGCG (SEQ ID NO: 133), or GTTATUGTGGTTGGCG (SEQ ID NO: 154) as indicated in the table below. The compounds have the sugar motif kkk-d-Z-d(8)-kkk or kkk-dd-Z-d(7)-kkk, where "k" represents a cEt, "d" represents an unmodified, 2'-β-D-deoxyribosyl sugar moiety, and "Z" represents a nucleotide comprising a modification as indicated in Table 139 below. Compounds were tested in 3T3-L1 cells for caspase activation essentially as described in Example 1 above.

TABLE 139

Modified oligonucleotides and in vitro toxicity

| Compound ID | position of altered nucleotide in central region | Modification of altered nucleotide | SEQ ID NO | in vitro Caspase (% control) @ 40 μM |
|---|---|---|---|---|
| 464924 | N/A | N/A | 81 | 246 |
| 1326529 | 2 | cEt | 81 | 593 |
| 1326530 | 3 | cEt | 81 | 376 |
| 1326531 | 2 | 2'-MOE | 81 | 146 |
| 1326532 | 3 | 2'-MOE | 81 | 121 |
| 1133247 | 2 | 2'-OMe | 133 | 133 |
| 1326533 | 3 | 2'-OMe | 154 | 126 |
| 1326534 | 2 | 2'-FANA | 133 | 65 |
| 1326535 | 3 | 2'-FANA | 154 | 158 |
| 1326536 | 2 | 2'-ribo-F | 133 | 116 |
| 1326537 | 3 | 2'-ribo-F | 154 | 103 |
| 1326538 | 2 | F-HNA | 81 | 115 |
| 1326539 | 3 | F-HNA | 81 | 298 |
| 1351257 | 2 | LNA | 81 | 665 |
| 1351258 | 3 | LNA | 81 | 136 |
| 1351259 | 2 | α-L-LNA | 133 | 217 |
| 1351260 | 3 | α-L-LNA | 154 | 114 |
| 1351261 | 2 | ENA | 81 | 175 |
| 1351262 | 3 | ENA | 81 | 209 |

"cEt" has the meaning set forth herein.
"2'-MOE" has the meaning set forth herein.
"2'-OMe" has the meaning set forth herein.
"2'-FANA" indicates a 2'-F-β-D-arabinofuranosyl modified sugar moiety.
"F-HNA" has the meaning set forth herein.
"2'-ribo-F" indicates a 2'-fluororibose.
"LNA" has the meaning set forth herein.
"α-L-LNA" has the meaning set forth herein.
"ENA" has the meaning set forth herein.

Example 67 Nucleosides with Various Chemistries at Position 2 and 3 of the Central Region Modified oligonucleotides with 2'-5' internucleoside linkages in the central region were synthesized as indicated in the table below, "k" represents a cEt, and "d" represents an unmodified, 2'β-D-deoxyribosyl sugar moiety, and "25s" represents a 2'-5' internucleoside linkage. An example of a 2'-5' internucleoside linkage is shown below:

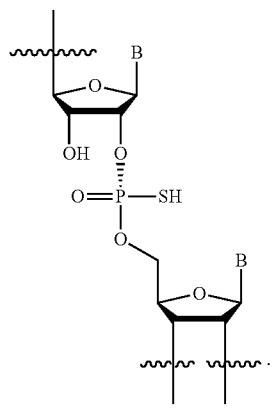

These modified oligonucleotides were compared to the otherwise identical modified oligonucleotide lacking an altered internucleoside linkage nucleotide in the central region, a 3-10-3 cEt gapmer, having three cEt nucleosides in each of the 5' and 3' regions and 10 DNA nucleosides in the central region (compound 558807). The modified oligonucleotides were also compared to a modified oligonucleotide having a 2'OMe at position 2 of the central region (Compound 936053). As demonstrated by the caspase activity, placement of a 2'-5' internucleoside linkage at certain positions in the central region reduces caspase activity compared to the otherwise identical modified oligonucleotide lacking an altered internucleoside linkage. The compounds in the table below are 100% complementary to mouse CXCL12, GENBANK NT_039353.7 truncated from 69/430,515 to 69/445,350 (SEQ ID NO: 1), at position 6877 to 6892.

The compounds were tested in Hepa1-6 cells for caspase activation essentially as described in Example 1 above and the results are shown in the table below.

TABLE 140

Modified oligonucleotides complementary to CXCL12

| Compound ID | position of altered linkage in central region | Chemistry Notation (5'-3') | in vitro Caspase (% control) @ 20 μM | SEQ ID NO |
|---|---|---|---|---|
| 558807 | n/a | $G_{ks}{}^mC_{ks}A_{ks}T_{ds}G_{ds}T_{ds}T_{ds}{}^mC_{ds}$ $T_{ds}{}^mC_{ds}A_{ds}{}^mC_{ds}A_{ds}T_{ks}T_{ks}A_k$ | 3843 | 18 |
| 936053 | n/a | $G_{ks}{}^mC_{ks}A_{ks}T_{ds}G_{ms}T_{ds}T_{ds}{}^mC_{ds}$ $T_{ds}{}^mC_{ds}A_{ds}{}^mC_{ds}A_{ds}T_{ks}T_{ks}A_k$ | 148 | 18 |
| 1273969 | 1 | $G_{ks}{}^mC_{ks}A_{ks}U_{d25s}G_{ms}T_{ds}T_{ds}$ ${}^mC_{ds}T_{ds}{}^mC_{ds}A_{ds}{}^mC_{ds}A_{ds}T_{ks}$ $T_{ks}A_k$ | 538 | 19 |
| 1306771 | 2 | $G_{ks}{}^mC_{ks}A_{ks}T_{ds}G_{m25s}T_{ds}T_{ds}$ ${}^mC_{ds}T_{ds}{}^mC_{ds}A_{ds}{}^mC_{ds}A_{ds}T_{ks}$ $T_{ks}A_k$ | 526 | 18 |
| 1307546 | 3 | $G_{ks}{}^mC_{ks}A_{ks}T_{ds}G_{ms}U_{d25s}T_{ds}$ ${}^mC_{ds}T_{ds}{}^mC_{ds}A_{ds}{}^mC_{ds}A_{ds}T_{ks}$ $T_{ks}A_k$ | 164 | 20 |
| 1306773 | 4 | $G_{ks}{}^mC_{ks}A_{ks}T_{ds}G_{ms}T_{ds}U_{d25s}$ ${}^mC_{ds}T_{ds}{}^mC_{ds}A_{ds}{}^mC_{ds}A_{ds}T_{ks}$ $T_{ks}A_k$ | 210 | 21 |
| 1306777 | 5 | $G_{ks}{}^mC_{ks}A_{ks}T_{ds}G_{ms}T_{ds}T_{ds}$ ${}^mC_{d25s}T_{ds}{}^mC_{ds}A_{ds}{}^mC_{ds}A_{ds}$ $T_{ks}T_{ks}A_k$ | 4293 | 18 |
| 1309496 | 6 | $G_{ks}{}^mC_{ks}A_{ks}T_{ds}G_{ms}T_{ds}T_{ds}$ ${}^mC_{ds}U_{d25s}{}^mC_{ds}A_{ds}{}^mC_{ds}A_{ds}$ $T_{ks}T_{ks}A_k$ | 3744 | 39 |
| 1306759 | 7 | $G_{ks}{}^mC_{ks}A_{ks}T_{ds}G^m{}_sT_{ds}T_{ds}$ ${}^mC_{ds}T_{ds}{}^mC_{d25s}A_{ds}{}^mC_{ds}A_{ds}$ $T_{ks}T_{ks}A_k$ | 3408 | 18 |

TABLE 140-continued

Modified oligonucleotides complementary to CXCL12

| Compound ID | position of altered linkage in central region | Chemistry Notation (5'-3') | in vitro Caspase (% control) @ 20 µM | SER ID NO |
|---|---|---|---|---|
| 1306738 | 8 | $G_{ks}{}^mC_{ks}A_{ks}T_{dS}G_{ms}T_{dS}T_{dS}$ $^mC_{dS}T_{ds}{}^mC_{ds}A_{d2s}{}^mC_{ds}A_{ds}$ $T_{ks}T_{ks}A_k$ | 2162 | 18 |
| 1306931 | 9 | $G_{ks}{}^mC_{ks}A_{ks}T_{ds}G_{ms}T_{ds}T_{ds}$ $^mC_{ds}T_{ds}{}^mC_{ds}A_{ds}{}^mC_{d2s}A_{ds}$ $T_{ks}T_{ks}A_k$ | 4384 | 18 |
| 1306769 | 10 | $G_{ks}{}^mC_{ks}A_{ks}T_{ds}G_{ms}T_{ds}T_{ds}$ $^mC_{ds}T_{ds}{}^mC_{ds}A_{ds}{}^mC_{ds}A_{d2s}$ $T_{ks}T_{ks}A_k$ | 4769 | 18 |

What is claimed:

1. An oligomeric compound comprising a modified oligonucleotide consisting of 16-20 linked nucleosides, wherein the modified oligonucleotide has a 5'-region, a central region, and a 3'-region, wherein:
   the 5'-region consists of 3-5 linked nucleosides, each comprising modified sugar moiety;
   the 3' region consists of 3-5 linked nucleosides, each comprising a modified sugar moiety;
   and the central region consists of 8-10 linked nucleosides, wherein the central region has the following formula:

$(N_d)(N_x)(N_d)_n$ wherein $N_x$ is a nucleoside comprising a 2'-OMe-β-D-ribofuranosyl sugar moiety and each $N_d$ is a nucleoside comprising a 2'-β-D-deoxyribosyl sugar moiety;
   and n is 6-8.

2. The oligomeric compound of claim 1, wherein each modified sugar moiety is selected from a 2'-substituted sugar moiety and a 4'-to-2' linked bicyclic sugar moiety.

3. The oligomeric compound of claim 2, wherein each 4'-to-2' linked bicyclic sugar moiety is independently selected from cEt, LNA, and ENA.

4. The oligomeric compound of claim 2, wherein each 4'-to-2' linked bicyclic sugar moiety is cEt.

5. The oligomeric compound of claim 2, wherein each 2'-substituted sugar moiety has a 2'-substituent independently selected from 2'-MOE, 2'-OMe, and 2'-NMA.

6. The oligomeric compound of claim 2, wherein each 2'-substituted sugar moiety has a 2'-MOE substituent.

7. The oligomeric compound of claim 1, wherein each nucleobase of each nucleoside of the modified oligonucleotide is independently selected from thymine, uracil, guanine, cytosine, 5-methylcytosine, and adenine.

8. The oligomeric compound of claim 1, wherein each internucleoside linkage is independently selected from phosphodiester and phosphorothioate internucleoside linkages.

9. The oligomeric compound of claim 1, wherein at least one internucleoside linkage within the central region is a modified internucleoside linkage other than phosphorothioate and each remaining internucleoside linkage in the modified oligonucleotide is independently selected from phosphodiester and phosphorothioate internucleoside linkages.

10. The oligomeric compound of claim 9, wherein the central region contains exactly one modified internucleoside linkage other than phosphorothioate.

11. The oligomeric compound of claim 1, wherein the nucleobase sequence of the modified oligonucleotide is at least 85%, at least 90%, at least 95%, or 100% complementary to a target RNA.

12. The oligomeric compound of claim 11, wherein the target RNA is a target mRNA or a target pre-mRNA.

13. The oligomeric compound of claim 12, wherein the target RNA is expressed in the liver, in the central nervous system, and/or in muscle cells.

14. The oligomeric compound of claim 1, comprising a conjugate group.

15. The oligomeric compound of claim 14, wherein the conjugate group comprises GalNAc.

16. A method comprising administering the oligomeric compound of claim 1 to a subject.

17. The oligomeric compound of claim 1, wherein the modified oligonucleotide consists of the motif eeeee-d-m-d (8)-eeeee, wherein each e is a nucleoside comprising a 2'-MOE sugar moiety, wherein each d is a nucleoside comprising a 2'-β-D-deoxyribosyl sugar moiety, and wherein m is a nucleoside comprising a 2'-OMe-β-D-ribofuranosyl sugar moiety.

18. The oligomeric compound of claim 17, wherein each internucleoside linkage is independently selected from phosphodiester and phosphorothioate internucleoside linkages.

19. The oligomeric compound of claim 17, comprising a conjugate group.

20. The oligomeric compound of claim 19, wherein the conjugate group comprises GalNAc.

21. A method comprising administering the oligomeric compound of claim 17 to a subject.

* * * * *